United States Patent
Jiang et al.

(10) Patent No.: US 11,993,574 B2
(45) Date of Patent: May 28, 2024

(54) PYRAZOLE AND IMIDAZOLE COMPOUNDS FOR INHIBITION OF IL-17 AND RORGAMMA

(71) Applicant: REATA PHARMACEUTICALS, INC., Irving, TX (US)

(72) Inventors: Xin Jiang, Irving, TX (US); Melean Visnick, Irving, TX (US); Christopher F. Bender, Irving, TX (US); Gary Bolton, Irving, TX (US); Bradley Caprathe, Irving, TX (US); Chitase Lee, Irving, TX (US); Brian Kornberg, Irving, TX (US); Patrick O'Brien, Irving, TX (US); Martha R. Hotema, Irving, TX (US)

(73) Assignee: REATA PHARMACEUTICALS, INC, Irving, TX (US)

( * ) Notice: Subject to any disclaimer, the term of this patent is extended or adjusted under 35 U.S.C. 154(b) by 0 days.

(21) Appl. No.: 17/251,295

(22) PCT Filed: Jun. 17, 2019

(86) PCT No.: PCT/US2019/037543
§ 371 (c)(1),
(2) Date: Dec. 11, 2020

(87) PCT Pub. No.: WO2019/241796
PCT Pub. Date: Dec. 19, 2019

(65) Prior Publication Data
US 2021/0292281 A1  Sep. 23, 2021

Related U.S. Application Data

(60) Provisional application No. 62/687,602, filed on Jun. 20, 2018, provisional application No. 62/685,742, filed on Jun. 15, 2018.

(51) Int. Cl.
| | |
|---|---|
| C07D 231/54 | (2006.01) |
| C07D 235/02 | (2006.01) |
| C07D 401/04 | (2006.01) |
| C07D 401/06 | (2006.01) |
| C07D 401/10 | (2006.01) |
| C07D 401/14 | (2006.01) |
| C07D 403/04 | (2006.01) |
| C07D 403/10 | (2006.01) |
| C07D 403/14 | (2006.01) |
| C07D 405/04 | (2006.01) |
| C07D 409/04 | (2006.01) |
| C07D 413/10 | (2006.01) |
| C07D 413/14 | (2006.01) |
| C07D 417/04 | (2006.01) |
| C07D 417/14 | (2006.01) |

(52) U.S. Cl.
CPC ......... *C07D 231/54* (2013.01); *C07D 235/02* (2013.01); *C07D 401/04* (2013.01); *C07D 401/06* (2013.01); *C07D 401/10* (2013.01); *C07D 401/14* (2013.01); *C07D 403/04* (2013.01); *C07D 403/10* (2013.01); *C07D 403/14* (2013.01); *C07D 405/04* (2013.01); *C07D 409/04* (2013.01); *C07D 413/10* (2013.01); *C07D 413/14* (2013.01); *C07D 417/04* (2013.01); *C07D 417/14* (2013.01)

(58) Field of Classification Search
CPC ... C07D 231/54; C07D 403/10; A61K 31/416
See application file for complete search history.

(56) References Cited

U.S. PATENT DOCUMENTS

| | | | |
|---|---|---|---|
| 6,326,507 | B1 | 12/2001 | Gribble et al. |
| 6,552,075 | B2 | 4/2003 | Gribble et al. |

(Continued)

FOREIGN PATENT DOCUMENTS

| | | |
|---|---|---|
| JP | 2018-510135 | 4/2018 |
| JP | 2018-515494 | 6/2018 |

(Continued)

OTHER PUBLICATIONS

Simone, Oncology: Introduction, Cecil Textbook of Medicine, 20th Edition, vol. 1, pp. 1004-1010, 1996.*
Acute Leukemia, Merck Manual (Online Edition) 6 pages, pp. 1-6 (2013).*
Pearce et al., Failure modes in anticancer drug discovery and development, Cancer Drug Design and Discovery Edited by Stephen Neidle, Chapter 18, pp. 424-435 (2008).*

(Continued)

*Primary Examiner* — Deepak R Rao
(74) *Attorney, Agent, or Firm* — Parker Highlander PLLC

(57) ABSTRACT

Disclosed herein are compounds of the formula: as well as analogs thereof, wherein the variables are defined herein. Also provided are pharmaceutical compositions thereof. In some aspects, the compounds and compositions provided herein may be used to modulate the activity of IL-17 and RORγ. Also provided are methods of administering compounds and composition provided herein to a patient in need thereof, for example, for the treatment or prevention of diseases or disorders associated with inflammation or for autoimmune disorders.

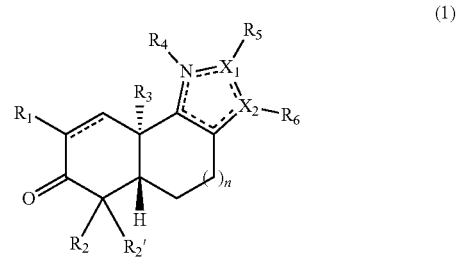

(1)

37 Claims, No Drawings

(56) References Cited

U.S. PATENT DOCUMENTS

| | | |
|---|---|---|
| 6,974,801 B2 | 12/2005 | Honda et al. |
| 7,176,237 B2 | 2/2007 | Honda et al. |
| 7,288,568 B2 | 10/2007 | Gribble et al. |
| 7,435,755 B2 | 10/2008 | Konopleva et al. |
| 7,678,830 B2 | 3/2010 | Honda et al. |
| 7,714,012 B2 | 5/2010 | Honda et al. |
| 7,795,305 B2 | 9/2010 | Konopleva et al. |
| 7,863,327 B2 | 1/2011 | Gribble et al. |
| 7,915,402 B2 | 3/2011 | Anderson et al. |
| 7,943,778 B2 | 5/2011 | Jiang et al. |
| 8,034,955 B2 | 10/2011 | Gribble et al. |
| 8,067,394 B2 | 11/2011 | Honda et al. |
| 8,067,465 B2 | 11/2011 | Honda et al. |
| 8,071,632 B2 | 12/2011 | Jiang et al. |
| 8,088,824 B2 | 1/2012 | Walling et al. |
| 8,124,656 B2 | 2/2012 | Anderson et al. |
| 8,124,799 B2 | 2/2012 | Anderson et al. |
| 8,129,429 B2 | 3/2012 | Sporn et al. |
| 8,258,329 B2 | 9/2012 | Anderson et al. |
| 8,299,046 B2 | 10/2012 | Sporn et al. |
| 8,309,601 B2 | 11/2012 | Walling et al. |
| 8,314,137 B2 | 11/2012 | Honda et al. |
| 8,338,618 B2 | 12/2012 | Jiang et al. |
| 8,394,967 B2 | 3/2013 | Jiang et al. |
| 8,440,820 B2 | 5/2013 | Anderson et al. |
| 8,440,854 B2 | 5/2013 | Anderson et al. |
| 8,455,544 B2 | 6/2013 | Sporn et al. |
| 8,513,436 B2 | 8/2013 | Anderson et al. |
| 8,586,775 B2 | 11/2013 | Gribble et al. |
| RE45,288 E | 12/2014 | Anderson et al. |
| 8,921,340 B2 | 12/2014 | Sporn et al. |
| RE45,325 E | 1/2015 | Anderson et al. |
| 8,993,640 B2 | 3/2015 | Anderson et al. |
| 9,000,188 B2 | 4/2015 | Honda et al. |
| 9,090,574 B2 | 7/2015 | Anderson et al. |
| 9,102,681 B2 | 8/2015 | Anderson et al. |
| 9,174,941 B2 | 11/2015 | Anderson et al. |
| 9,233,998 B2 | 1/2016 | Anderson et al. |
| 9,249,089 B2 | 2/2016 | Jiang et al. |
| 9,278,912 B2 | 3/2016 | Jiang et al. |
| 9,290,536 B2 | 3/2016 | Anderson et al. |
| 9,464,082 B2 | 10/2016 | Donner et al. |
| 9,796,668 B2 | 10/2017 | Anderson et al. |
| 9,884,809 B2 | 2/2018 | Anderson et al. |
| 2002/0042535 A1 | 4/2002 | Gribble et al. |
| 2002/0115856 A1 | 8/2002 | Sakya |
| 2003/0119732 A1 | 1/2003 | Konopleva et al. |
| 2003/0125361 A1 | 7/2003 | Clare et al. |
| 2003/0232786 A1 | 12/2003 | Honda et al. |
| 2003/0236303 A1 | 12/2003 | Gribble et al. |
| 2004/0002463 A1 | 1/2004 | Honda et al. |
| 2004/0138187 A1 | 7/2004 | Reading et al. |
| 2005/0288363 A1 | 12/2005 | Gribble et al. |
| 2007/0155742 A1 | 7/2007 | Honda et al. |
| 2008/0220057 A1 | 9/2008 | Gribble et al. |
| 2008/0233195 A1 | 9/2008 | Sporn et al. |
| 2008/0261985 A1 | 10/2008 | Honda et al. |
| 2009/0048204 A1 | 2/2009 | Walling et al. |
| 2009/0048205 A1 | 2/2009 | Meyer et al. |
| 2009/0060873 A1 | 3/2009 | Sporn et al. |
| 2009/0093447 A1 | 4/2009 | Konopleva et al. |
| 2009/0270364 A1 | 10/2009 | Liu et al. |
| 2009/0326063 A1 | 12/2009 | Sporn et al. |
| 2010/0041904 A1 | 2/2010 | Jiang et al. |
| 2010/0048887 A1 | 2/2010 | Anderson et al. |
| 2010/0048892 A1 | 2/2010 | Anderson et al. |
| 2010/0048911 A1 | 2/2010 | Jiang et al. |
| 2010/0056777 A1 | 3/2010 | Anderson et al. |
| 2010/0261930 A1 | 10/2010 | Honda et al. |
| 2011/0009363 A1 | 1/2011 | Honda et al. |
| 2011/0196007 A1 | 8/2011 | Honda et al. |
| 2011/0245206 A1 | 10/2011 | Jiang et al. |
| 2011/0245233 A1 | 10/2011 | Anderson et al. |
| 2011/0281955 A1 | 11/2011 | Meyer et al. |
| 2012/0071684 A1 | 3/2012 | Walling et al. |
| 2012/0101149 A1 | 4/2012 | Honda et al. |
| 2012/0196880 A1 | 8/2012 | Anderson et al. |
| 2012/0214814 A1 | 8/2012 | Anderson et al. |
| 2012/0220652 A1 | 8/2012 | Sporn et al. |
| 2012/0238767 A1 | 9/2012 | Jiang et al. |
| 2012/0245374 A1 | 9/2012 | Anderson et al. |
| 2012/0252776 A1 | 10/2012 | Anderson et al. |
| 2012/0283450 A1 | 11/2012 | Anderson et al. |
| 2013/0089526 A1 | 4/2013 | Sporn et al. |
| 2013/0122053 A1 | 5/2013 | Sporn et al. |
| 2013/0237721 A1 | 9/2013 | Gribble et al. |
| 2013/0274480 A1 | 10/2013 | Honda et al. |
| 2013/0317007 A1 | 11/2013 | Anderson et al. |
| 2013/0324599 A1 | 12/2013 | Anderson et al. |
| 2013/0345276 A1 | 12/2013 | Sporn et al. |
| 2014/0051739 A1 | 2/2014 | Anderson et al. |
| 2014/0066408 A1 | 3/2014 | Jiang et al. |
| 2014/0088163 A1 | 3/2014 | Jiang et al. |
| 2014/0088188 A1 | 3/2014 | Jiang et al. |
| 2014/0100227 A1 | 4/2014 | Bender et al. |
| 2014/0179928 A1 | 6/2014 | Anderson et al. |
| 2014/0275618 A1 | 9/2014 | Gribble et al. |
| 2014/0377235 A1 | 12/2014 | Sporn et al. |
| 2015/0080465 A1 | 3/2015 | Chin et al. |
| 2015/0148384 A1 | 5/2015 | Anderson et al. |
| 2015/0152071 A1 | 6/2015 | Jiang et al. |
| 2015/0225397 A1 | 8/2015 | Donner et al. |
| 2015/0259377 A1 | 9/2015 | Anderson et al. |
| 2016/0130220 A1 | 5/2016 | Anderson et al. |
| 2016/0145200 A1 | 5/2016 | Anderson et al. |
| 2018/0111931 A1 | 4/2018 | Barlaam et al. |
| 2018/0127380 A1 | 5/2018 | Jiang et al. |
| 2018/0170908 A1 | 6/2018 | Aspnes et al. |
| 2018/0170931 A1 | 6/2018 | Koudriakova et al. |
| 2019/0322665 A1 | 10/2019 | Bacani et al. |
| 2020/0077658 A1 | 3/2020 | Sambasivan et al. |
| 2020/0131148 A1 | 4/2020 | Jiang et al. |

FOREIGN PATENT DOCUMENTS

| | | |
|---|---|---|
| WO | WO 1999/065478 | 12/1999 |
| WO | WO 2002/047611 | 6/2002 |
| WO | WO 2003/059339 | 7/2003 |
| WO | WO 2004/064723 | 8/2004 |
| WO | WO 2006/089406 | 8/2006 |
| WO | WO 2008/064132 | 5/2008 |
| WO | WO 2008/064133 | 5/2008 |
| WO | WO 2008/136838 | 11/2008 |
| WO | WO 2009/023232 | 2/2009 |
| WO | WO 2009/023845 | 2/2009 |
| WO | WO 2009/089545 | 7/2009 |
| WO | WO 2009/129545 | 10/2009 |
| WO | WO 2009/129546 | 10/2009 |
| WO | WO 2009/129548 | 10/2009 |
| WO | WO 2009/146216 | 12/2009 |
| WO | WO 2009/146218 | 12/2009 |
| WO | WO 2010/011782 | 1/2010 |
| WO | WO 2010/053817 | 5/2010 |
| WO | WO 2010/093944 | 8/2010 |
| WO | WO 2011/130302 | 10/2011 |
| WO | WO 2012/083306 | 6/2012 |
| WO | WO 2012/125488 | 9/2012 |
| WO | WO 2013/163344 | 10/2013 |
| WO | WO 2013/188818 | 12/2013 |
| WO | WO 2014/040056 | 3/2014 |
| WO | WO 2014/040060 | 3/2014 |
| WO | WO 2014/040073 | 3/2014 |
| WO | WO 2015/027206 | 2/2015 |
| WO | WO 2015/112792 | 7/2015 |
| WO | WO 2016/130818 | 8/2016 |
| WO | WO 2016/130927 | 8/2016 |
| WO | WO 2016/179460 | 11/2016 |

| | | | |
|---|---|---|---|
| WO | WO 2018/111315 | 6/2018 | |
| WO | WO 2019/246461 | 12/2019 | |

OTHER PUBLICATIONS

Gura et al., Systems for identifying new drugs are often faulty, Science, 278:1041-1042, 1997.*

Johnson et al., Relationships between drug activity in NCI preclinical in vitro and in vivo models and early clinical trials, British Journal of Cancer, 84(10):1424-1431, 2001.*

Damasio, Alzheimer's Disease and related dementias, Cecil Textbook of Medicine, 20th Edition, vol. 2, pp. 1992-1996, 1996.*

Layzer, Degenerative diseases of the nervous system, Cecil Textbook of Medicine, 20th Edition, vol. 2, pp. 2050-2057, 1996.*

Douglas, Jr., Introduction to Viral Diseases, Cecil Textbook of Medicine, 20th Edition, vol. 2, pp. 1739-1747, 1996.*

Bosseray et al., PubMed Abstract (Pathol Biol (Paris) 50(8):483-92), 2002.*

Razonable et al., PubMed Abstract (Herpes 10(3):60-5), 2003.*

Goff, PubMed Abstract (J Gene Med. 3(6):517-28), 2001.*

Albini and Sporn, "Opinion: the tumour microenvironment as a target for chemoprevention," *Nature Reviews Cancer*, 7: 139-447, 2007.

Andresen and Margaretha, "Preparation of Dialkyl 2-Cyanocycloalk-2-en-1-ones," *J. Chem. Research (S)*, 332, 1994.

Caron et al., "Versatile Strategy to access tricycles related to quassinoids and triterpenes," *Org. Letters*, 12(3) 508-511, 2010.

Chadalapaka, et al., "Structure-dependent inhibition of bladder and pancreatic cancer cell growth by 2-substituted glycyrrhetinic and ursolic acid derivatives," *Bioorganic & Medicinal Chemistry Letters*, 18:2633-2639, 2008.

Chintharlapalli et al., "Structure-dependent activity of glycyrrhetinic acid derivatives as peroxisome proliferator-activated receptor γ agonists in colon cancer cells," *Molecular Cancer Therapeutics*, 6 (5): 1588-1598, 2007.

Clinton et al., "Steroidal [3,2-c]pyrazoles. II. Androstanes, 19-norandrostanes and their unsaturated analogs," *J. Am Chem Soc.*, 83:1478-1491, 1961.

Connolly et al., "Grandiofolione: a novel tetranortriterpenoid," *Chemical Communications*, 23:867-568, 1966.

De Ruggieri et al., "Deidrogenazione e bromurazione di beta-chetonitrili steroidali," *Il Farmaco*, 20: 358-388, 1964. (English summary).

Dinkova-Kostova et al., "Extremely potent triterpenoid inducers of the phase 2 response: correlations of protection against oxidant and inflammatory stress," *Proc. Natl. Acad. Sci.*, 102(12): 4584-4589, 2005.

Duan et al., "Immunosuppressive terpenoids from extracts of *Tripterygium wilfordii*," *Tetrahedron*, 57 (40): 8413-8424, 2001.

Favaloro et al., "Design and synthesis of tricyclic compounds with enone functionalities in rings A and C: a novel class of highly active inhibitors of nitric oxide production in mouse macrophages," *J. Med. Chem.*, 45:4801-4805, 2002.

Ferreira et al., "Phytochemistry of the mopane, *Colophosperum mopane*," *Phytochemistry*, 64 (1): 31-51, 2003.

Finlay et al., "Novel A-ring cleaved analogs of oleanolic and ursolic acids which affect growth regulation in NRP.152 prostate cells," *Biorg. Med. Chem. Lett.*, 7(13): 1769-1772, 1997.

Finlay et al., "The Effects of A and C Ring Modification of Oleanolic and Ursolic Acid on the Inhibition of Nitric Oxide Formation in Mouse Macrophages," 213th American Chemical Society National Meeting, Abstract: 084, 1997.

Hatcher et al., "Curcumin Cellular and Molecular from ancient medicine to current clinical trials," *CMLS Cellular and Molecular Sciences*, 65 (11): 1631-1652, 2008.

Honda et al., "A novel dicyanotriterpenoid, 2-cyano-3,12-dioxooleana-1,9(11)-dien-28-onitrile, active at picomolar concentrations for inhibition of nitric oxide production," *Bioorg. Med. Chem. Lett.*, 12:1027-1030, 2002.

Honda et al., "An efficient synthesis of tricyclic compounds (+)-(4αβ, 8αβ, 10aα)-1,2,3,4,4a,6,7,8,8a,9,10,10a-Dodecahydro-1,1,4a-Trimethyl-2-OXophenanthrene-8a-Carboxolic acid, its methyl ester, and (+)-(4αβ,8αβ,10aα)-3,4,4a,6,7,8,8a,9,10,10a-Decahydro-8a-hydroxymethyl-1,1,4a-trimethylphenanthren-2(1H)-one," *Org. Prep. Proced. Int.*, 37(6): 546-550, 2005.

Honda et al., "Design and synthesis of 23, 24-dinoroleanolic acid derivatives, novel triterpenoid-steroid hybrid molecules," *J. Org. Chem.*, 63:4846-4849, 1998.

Honda et al., "Design and synthesis of 2-cyano-3,12-dioxoolean-1,9-dien-28-oic acid, a novel and highly active inhibitor of nitric oxide production in mouse macrophages," *Bioorg Med Chem Lett.*, 8(19):2711-2714, 1998.

Honda et al., "Design, synthesis, and biological evaluation of biotin conjugates of 2-cyano-3,12-dioxooleana-1,9(11)-dien-28-oic acid for the isolation of the protein targets," *J. Med. Chem.*, 47 (20): 4923-4932, 2004.

Honda et al., "Efficient synthesis of (−)- and (+)-tricyclic compounds with enome functionalities in rings A and C. A novel class of orally active anti-inflammatory and cancer chemopreventive agents," *Org Biomol Chem.*, 1:4384-4391, 2003.

Honda et al., "New enone derivatives of oleanolic acid and ursolic acid as inhibitors of nitric oxide production in mouse macrophages," *Bioorg. Med. Chem. Lett.*, 7:1623-1628, 1997.

Honda et al., "New synthetic oleanane and ursane triterpenoids as inhibitors of nitric oxide production in mouse macrophages," The Fifth Chemical Congress of North America, Cancun, Mexico, Abstract 552 and slides for oral presentation, Nov. 1997.

Honda et al., "Novel synthetic oleanane and ursane triterpenoids with various enone functionalities in ring A as inhibitors of nitric oxide production in mouse macrophages," *J. Med. Chem.*, 43:1866-1877, 2000.

Honda et al., "Novel synthetic oleanane triterpenoids: a series of highly active inhibitors of nitric oxide production in mouse macrophages," *Bioorg Med Chem Lett*, 9(24):3429-3434, 1999.

Honda et al., "Novel tricyclic compounds having acetylene groups at C-8a and cyano enones in rings A and C: highly potent anti-inflammatory and cytoprotective agents," *J. Med. Chem.*, 50:1731-1734, 2007.

Honda et al., "Revision and confirmation of the regiochemistry of isoxazoles derived from methyl oleanonate and lanost-8-en-3-one. Synthesis of a new lanostane triterpenoid with a cyano-enone functionality in ring A," *J. Org. Chem.*, 68:4991-4993, 2003.

Honda et al., "Synthesis of (±)-3,3-ethylenedioxy-14α-hydroxy-5-picrasene-11,16-dione, a 14αH-picrasane derivative," *Chem. Lett.*, 299-302, 1981.

Honda et al., "Synthesis of a novel dicyano abietane analogue: a potential antiinflammatory agent," *J. Org. Chem.*, 71:3314-3316, 2006.

Honda et al., "Synthetic oleanane and ursane triterpenoids with modified rings A and C: A series of highly active inhibitors of nitric oxide production in mouse macrophages," *J. Med. Chem.*, 43:4233-4246, 2000.

Honda et al., "Tricyclic Compounds Containing Nonenolizable Cyano Enones. A Novel Class of Highly Potent Anti-Inflammatory and Cytoprotective Agents," *J. Med. Chem.*, 54(6):1762-1778, 2011.

Huerta et al., "Characterization of novel small-molecule NRF2 activators: Structural and biochemical validation of stereospecific KEAP1 binding", *Biochem. Biophys. Acta*, 1860(11):2537-2552, 2016.

Hybertson, et al., "Oxidative stress in health and disease: The therapeutic potential of Nrf2 activation", *Molecular Aspects of Medicine*, 2011, 32:234-246.

International Preliminary Report on Patentability issued in corresponding PCT Application No. PCT/US2015/012579, dated Jul. 26, 2016.

International Preliminary Report on Patentability issued in corresponding PCT Application No. PCT/US2017/000094, dated Jun. 27, 2019.

International Preliminary Report on Patentability issued in corresponding PCT Application No. PCT/US2016/017769, dated Aug. 15, 2017.

International Preliminary Report on Patentability issued in corresponding PCT Application No. PCT/US2011/065897, dated Jun. 27, 2013.

International Preliminary Report on Patentability issued in corresponding PCT Application No. PCT/US2019/037543, dated Sep. 28, 2020.
International Search Report and Written Opinion issued in corresponding PCT Application No. PCT/US2015/012579, dated Mar. 19, 2015.
International Search Report and Written Opinion issued in corresponding PCT Application No. PCT/US2017/000094, dated Mar. 26, 2018.
International Search Report and Written Opinion issued in corresponding PCT Application No. PCT/US2016/017769, dated Apr. 15, 2016.
International Search Report and Written Opinion issued in corresponding PCT Application No. PCT/US2011/065897, dated Jul. 27, 2012.
International Search Report and Written Opinion issued in corresponding PCT Application No. PCT/US2019/037543, dated Sep. 2, 2019.
Kincl et al., "Pituitary gonadotropin inhibitory action of neutral steroids," *Acta. Endocrinologica*, 46: 300-306, 1964.
Kobayashi et al., "The antioxidant defense system Keap1-Nrf2 comprises a multiple sensing mechanism for responding to a wide range of chemical compounds," *Mol. Cell Biol.*, 29(2):493-502, 2009.
Konopleva et al., "Activation of nuclear transcription factor PPARγ by the novel triterpenoid CDDO as targeted therapy in breast cancer," 2002 Keystone Symposium, Abstract No. 539, 2002.
Konopleva et al., "Mechanisms and Activity of PPARγ-Active Triterpenoids CDDO and CDDO-Me in Leukemias," *Blood*, 106:2460, 2005.
Konopleva et al., "Novel synthetic triterpenoid CDDO-Me: potent antiproliferative, proapoptotic and differentiating agent in AML," *Blood*, 96(11), Part 1: 121A, abstract #522, 2000.
Konopleva et al., "Novel synthetic triterpenoid, CDDO, and its methyl ester: Potent antiproliferative, proapoptotic and differentiating agents in AML" *Blood*, 94(Suppl 1):479a, Abstract #2140, 1999.
Konopleva et al., "Novel triterpenoid CDDO-Me is a potent inducer of apoptosis and differentiation in acute myelogenous leukemia," *Blood*, 99(1):326-335, 2002.
Konopleva et al., "Peroxisome proliferator-activated receptor gamma and retinoid X receptor ligands are potent inducers of differentiation and apoptosis in leukemias," *Mol. Cancer Ther.*, 3:1249-1262, 2004.
Konopleva et al., "PPARγ Ligand CDDO Induces Apoptosis in Leukemias Via Multiple Apoptosis Pathways," Abstracts of the 44th Annual Meeting of the American Society of Hematology, Abstract No. 2209, 2002.
Konopleva et al., "PPARγ Ligands Are Potent Inducers of Apoptosis in Leukemias and Lymphomas," American Society of Hematology 43rd Annual Meeting and Exposition, Abstract No. 501, 2001.
Konopleva et al., "PPARγ Nuclear Receptor as a Novel Molecular Target in Leukemia Therapy," *Proc. Amer. Assoc. Cancer Res.*, 43:4730, 2002.
Konopleva et al., "PPARγ nuclear receptor as a novel therapeutic target in AML," *Blood*, 96(11):460a, Abstract #1982, 2000.
Konopleva et al., "PPARγ nuclear receptor as a novel therapeutic target in AML," *Proc. of the AACR*, 42, Abstract #4458, 2001.
Konopleva et al., "Suppression of ERK Activation is Required for Triterpenoid Methyl-CDDO-Induced Apoptosis in AML," *Blood*, 102(11):1404, 2003.
Konopleva et al., "Synthetic triterpenoid 2-cyano-3,12-dioxooleana-1,9-dien-28-oic acid induces growth arrest in HER2-overexpressing breast cancer cells," *Mol. Cancer Ther.*, 5:317-328, 2006.
Konopleva et al., "Synthetic triterpenoid CDDO as a novel therapy for resistant breast cancer," *Proc. Amer. Assoc. Cancer Res.*, 44:2726, 2003.
Konopleva et al., "The novel triterpenoid CDDO-Me suppresses MAPK pathways and promotes p38 activation in acute myeloid leukemia cells," *Leukemia*, 19:1350-1354, 2005.

Konopleva et al., "The synthetic triterpenoid 2-cyano-3,12-dioxooleana-1,9-dien-28-oic acid induces caspase-dependent and -independent apoptosis in acute myelogenous leukemia," *Cancer Res.*, 64:7927-7935, 2004.
Liby et al., "A novel acetylenic tricyclic bis-(cyano enone) potently induces phase 2 cytoprotective pathways and blocks liver carcinogenesis induced by aflatoxin," *Cancer Res.*, 68:6727-6733, 2008.
Liby et al., "Novel semisynthetic analogues of betulinic acid with diverse cytoprotective, antiproliferative, and proapoptotic activities," *Mol. Cancer. Ther.*, 6(7): 2113-2119, 2007.
Liby et al., "The rexinoid LG100268 and the synthetic triterpenoid CDDO-methyl amide are more potent than erlotinib for prevention of mouse lung carcinogenesis," *Mol. Cancer Ther.*, 7:1251-1257, 2008.
Liby et al., "The synthetic triterpenoid CDDO-Imidazolide suppresses STAT phosphorylation and induces apoptosis in myeloma and lung cancer cells," *Clinical Cancer Research*, 12 (14 Part 1): 4288-4293, 2006.
Liby et al., "The synthetic triterpenoids CDDO-Methyl ester and CDDO-ethyl amide prevent lung cancer induced by vinyl carbamate in A/J mice," *Cancer Research*, 67 (6): 1-7, 2007.
Liby et al., "The synthetic triterpenoids, CDDO and CDDO-imidazolide, are potent inducers of heme oxygenase-1 and Nrf2/ARE signaling," *Cancer Res.*, 65:4789-4798, 2005.
Liby et al., "Triterpenoids and rexinoids as multifunctional agents for the prevention and treatment of cancer," *Nat. Rev. Cancer*, 7 (5): 357-369, 2007.
Orr et al, "Steroids. CCLXV. Studies in cyano steroids. 3. Unsaturated 2-cyano steroids," *J. Org. Chem.*, 29(11): 3300-3303, 1964.
Ribo et al., "Synthesis of methyl 1,11-dioxooleanan-2,12-dien-30-oate and its 24-nor derivative," *Afinidad*, 38(373): 197-200, 1981.
Satoh et al., "Activation of the Keap1/Nrf2 pathway for neuroprotection by electrophilic phase II inducers," *PNAS*, 103 (3): 768-773, 2006.
Second Written Opinion issued in corresponding PCT Application No. PCT/US2019/037543, dated May 13, 2020.
Shin et al., "Inhibitory roles of NRF2 and an oleanolic triterpenoid on adipocyte differentiation and obesity," dissertation submitted to John Hopkins University in conformity with the requirements for the degree of Doctor of Philosophy, Mar. 2009.
Shin et al., "NRF2 modulates aryl hydrocarbon receptor signaling: influence on adipogenesis," *Molecular and Cellular Biology*, 27 (20): 7188-7197, 2007.
Soufli et al., "Overview of cytokines and nitric oxide involvement in immuno-pathogenesis of inflammatory bowel diseases", *World J. Gastrointest. Pharmacol. Ther.*, 7(3):353-360, 2016.
Sporn et al., "New Synthetic Triterpenoids: Potent Agents for Prevention and Treatment of Tissue Injury Caused by Inflammatory and Oxidative Stress," *J. Nat. Prod.*, 74(3):537-545, 2011.
Subba Rao, et al., "Chemical modifications of natural triterpenes—glycyrrhetinic and boswellic acids: evaluation of their biological activity," *Tetrahedron*, 64(51):11541-11548, 2008.
Suh et al., "A novel synthetic oleanane triterpenoid, 2-cyano-3,12-dioxoolean-1,9-dien-28-oic acid (CDDO), induces cell differentiation in human myeloid leukemias," Proceedings of the American Association for Cancer Research Annual Meeting, 40:300, abstract 1988, 1999.
Suh et al., "A novel synthetic oleanane triterpenoid, 2-cyano-3,12-dioxoolean-1,9-dien-28-oic acid, with potent differentiating, antiproliferative, and anti-inflammatory activity," *Cancer Res.*, 59(2):336-341, 1999.
Suh et al., "New triterpenoids as cancer preventive and anti-inflammatory agents," Proceedings of the American Association for Cancer Research, Abstract No. 1457, 38: 216, 1997.
Suh et al., "Novel triterpenoids suppress inducible nitlic oxide synthase (iNOS) and inducible cyclooxygenase (COX-2) in mouse macrophages," *Cancer Res.*, 58:717-723, 1998.
Suh et al., "Novel triterpenoids suppress inducible nitric oxide synthase (iNOS) and inducible cyclooxygenase (COX-2)," Proceedings of the American Association for Cancer Research Annual Meeting, 39: Abstract No. 1821, 1998.

Suh et al., "Synthetic triterpenoids activate a pathway for apoptosis in AML cells involving downregulation of FLIP and sensitization to TRAIL," *Leukemia*, 17:2122-2129, 2003.

Suh et al., "Synthetic triterpenoids enhance transforming growth factor β/Smad signaling," *Cancer Res.*, 63:1371-1376, 2003.

Suh et al., "Triterpenoids CDDO and CDDO-Me Down-Regulate FLIP Expression and Sensitize AML Cells to Trail-Induced Apoptosis," American Society of Hematology 43rd Annual Meeting and Exposition, Abstract No. 498, 2001.

Sun et al., "Structure-activity relationships of oleanan-and ursane-type triterpenoids," *Botanical Studies*, 47:339-368, 2006.

Xu et al., "The role of nitric oxide in cancer", *Cell Res.*, 12:311-320, 2002.

Yates et al., "Potent protection against aflatoxin-induced tumorigenesis through induction of Nrf2-regulated pathways by the triterpenoid 1-[2-cyano-3-,12-dioxooleana-1,9(11)-dien-28-oyl]imidazole," *Cancer Res.*, 66 (4): 2488-2494, 2007.

You et al., "Synthesis and cytotoxic activity of a-ring modified betulinic acid derivatives," *Bioorganic and Medicinal Chemistry Letters*, 13 (19): 3137-3140, 2003.

U.S. Appl. No. 15/791,677, filed Oct. 24, 2017.
U.S. Appl. No. 16/701,585, filed Dec. 3, 2019.
U.S. Appl. No. 15/548,909, filed Aug. 4, 2017.
U.S. Appl. No. 16/468,054, filed Jun. 10, 2019.

Office Communication issued in U.S. Appl. No. 17/252,841, dated Mar. 20, 2023.

Office Communication issued in Japanese Application No. 2020-569890, dated Jun. 14, 2023. English Translation Appended.

Office Communication issued in Chinese Application No. 2020-569890, dated Mar. 25, 2023. English Translation Appended.

Seelige et al., "The ancient cytokine IL-17D is regulated by Nrf2 and mediates tumor and virus surveillance" *Cytokine*, 91:10-12, 2016.

Office Communication issued in European Application No. 19746552.9 dated Jul. 14, 2023.

Rauhamäki et al., "Discover of Retinoic Acid-Related Orphan Receptor γt Inverse Agonists via Docking and Negative Image-Based Screening" *ACS Omega*, 3:6259-266, 2018.

* cited by examiner

PYRAZOLE AND IMIDAZOLE COMPOUNDS FOR INHIBITION OF IL-17 AND RORGAMMA

This application is a national phase application under 35 U.S.C. § 371 of International Application No. PCT/US2019/037543, filed Jun. 17, 2019, which claims the benefit of U.S. Provisional Application No. 62/685,742, filed on Jun. 15, 2018 and U.S. Provisional Application No. 62/687,602, filed on Jun. 20, 2018, the entire contents of each are hereby incorporated by reference.

BACKGROUND OF THE INVENTION

I. Field of the Invention

The present invention relates generally to the fields of biology and medicine. More particularly, it concerns compounds, compositions, and methods for the treatment and prevention of diseases such as those associated with RAR-related orphan receptor γ (RORγ) and excess production of IL-17.

II. Description of Related Art

Inflammatory diseases, particularly autoimmune diseases, such as rheumatoid arthritis, osteoarthritis, psoriasis, and multiple sclerosis, frequently have severe and long-term adverse effects on physical well-being and quality of life. In many patients these diseases cause significant disability, and in some cases (e.g., lupus and multiple sclerosis) they may be life-threatening. Recent advances in therapeutic options, such as the development of therapeutic antibodies against tumor necrosis factor (TNF), have improved outcomes and quality of life for many patients. However, significant numbers of patients do not achieve adequate relief of symptoms from these therapies or cannot tolerate them. Even in patients who do respond, side effects can be significant and may be life-threatening due to immune suppression or other complications.

Recent research on chronic inflammation and autoimmunity has revealed an important role played by a subpopulation of T lymphocytes known as Th17 cells. These cells produce the inflammatory cytokine interleukin 17 (IL-17). Excessive levels of IL-17 have been reported in a variety of autoimmune diseases including multiple sclerosis, rheumatoid arthritis, psoriasis, inflammatory bowel diseases, vitiligo, Sjögren syndrome, and ankylosing spondylitis (Miossec and Kolls, 2012; Yang et al., 2014; Gaffen et al., 2014). Evidence suggests that IL-17 also plays a significant role in the pathology of vasculitis, atherosclerosis, and inflammatory lung diseases, such as cystic fibrosis and chronic obstructive pulmonary disorder (COPD). IL-17 is also implicated in the pathophysiology of epilepsy and neurodegenerative diseases including Alzheimer's disease, Parkinson's disease, and ALS. Elevated levels of IL-17 or Th17 cells have been reported in patients with psychiatric and neuropsychiatric conditions including schizophrenia, obsessive-compulsive disorder, bipolar disorder, post-traumatic stress disorder, major depression, and autism. Elevations in IL-17 have been implicated in other conditions involving dysregulated inflammatory signaling, including obesity, insulin resistance, and fatty liver disease.

Although Th17 cells are not the only source of IL-17, it has been reported that these cells are a major source of this cytokine in tissues undergoing damage from autoimmune disease, such as arthritic joints. And elevated levels of IL-17 have been reported to promote tissue degradation, e.g., by stimulating the production of matrix metalloproteinases, which is a source of damage to connective tissue and cartilage, and increasing the expression of receptor activator of NF-κB ligand (RANKL), which stimulates osteoclast activity and promotes bone damage.

Inappropriate activity of Th17 cells, including overproduction of IL-17, has also been implicated in the pathologies associated with certain viral and parasitic infections. For example, IL-17 has been implicated in the development of severe neuroinflammation associated with *Toxoplasma gondii* infection and increased severity of lesions associated with *Leishmania* infection. In these and other cases, IL-17 appears to play a role in perpetuating the infection, promoting an excessive inflammatory response, and inhibiting clearance of the infectious agent (Waite and Skokos, 2011). Accordingly, therapies that prevent or inhibit excess production of IL-17, or otherwise reduce circulating levels of IL-17, would have significant potential in a wide range of diseases or disorders, including those with inflammatory and autoimmune-related components.

Both the differentiation of Th17 cells and their production of IL-17 are regulated to a significant degree by the retinoid orphan receptor RORγt, a member of the nuclear hormone receptor family. Expression of RORγt is common to all types of Th17 cells and plays a significant role in their differentiation as well as their activity. RORγ also regulates the production of IL-17 in other cell types, including gamma delta T cells, innate lymphoid cells, and lymphoid tissue inducer cells (Bronner et al, 2017). Inhibition of RORγt activity has been shown to result in reduced expression of IL-17. As such, the identification of small molecule inhibitors of RORγt is of great interest.

SUMMARY OF THE INVENTION

The present disclosure provides novel compounds, including pyrazole and imidazole derivatives with anti-inflammatory and/or antioxidant properties, pharmaceutical compositions thereof, methods for their manufacture, and methods for their use. In some embodiments, the compounds are further defined as:

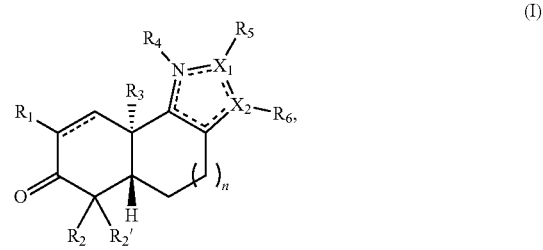

(I)

wherein:
n is 0, 1, or 2;
$R_1$ is cyano, fluoro, —$CF_3$, or —$C(O)R_a$, wherein:
 $R_a$ is hydroxy or amino; or
  alkoxy$_{(C\leq 6)}$, alkylamino$_{(C\leq 6)}$, dialkylamino$_{(C\leq 6)}$, or a substituted version of any of these groups;
$R_2$ and $R_2'$ are each independently hydrogen; or
 alkyl$_{(C\leq 12)}$, cycloalkyl$_{(C\leq 12)}$, alkenyl$_{(C\leq 12)}$, alkynyl$_{(C\leq 12)}$, aryl$_{(C\leq 18)}$, aralkyl$_{(C\leq 18)}$, heteroaryl$_{(C\leq 18)}$, heteroaralkyl$_{(C\leq 18)}$, or a substituted version of any of these groups; or $R_2$ and $R_2'$ are taken together and are alkanediyl$_{(C\le 8)}$, alkenediyl$_{(C\le 8)}$, or a substituted version of either of these groups;

$R_3$ is alkyl$_{(C\le 12)}$, alkenyl$_{(C\le 12)}$, aryl$_{(C\le 12)}$, aralkyl$_{(C\le 12)}$, or a substituted version of any of these groups;

$R_4$ and $R_5$ are each independently absent or hydrogen; or alkyl$_{(C\le 12)}$, cycloalkyl$_{(C\le 12)}$, heterocycloalkyl$_{(C\le 12)}$, aryl$_{(C\le 12)}$, aralkyl$_{(C\le 12)}$, heteroaryl$_{(C\le 12)}$, heteroaralkyl$_{(C\le 12)}$, -arenediyl$_{(C\le 12)}$-alkyl$_{(C\le 12)}$, -arenediyl$_{(C\le 12)}$-aryl$_{(C\le 12)}$, -arenediyl$_{(C\le 12)}$-heteroaryl$_{(C\le 12)}$, -arenediyl$_{(C\le 12)}$-heterocycloalkyl$_{(C\le 12)}$, -arenediyl$_{(C\le 12)}$-cycloalkyl$_{(C\le 12)}$, -heteroarenediyl$_{(C\le 12)}$-alkyl$_{(C\le 12)}$, -heteroarenediyl$_{(C\le 12)}$-aryl$_{(C\le 12)}$, -hetero-arenediyl$_{(C\le 12)}$-heteroaryl$_{(C\le 12)}$, -heteroarenediyl$_{(C\le 12)}$-heterocycloalkyl$_{(C\le 12)}$, -heteroarenediyl$_{(C\le 12)}$-cycloalkyl$_{(C\le 12)}$, -heterocycloalkanediyl$_{(C\le 12)}$-aryl$_{(C\le 12)}$, -heterocycloalkanediyl$_{(C\le 12)}$-heteroaryl$_{(C\le 12)}$, or a substituted version of any of these groups; or a group of the formula:

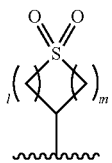

wherein l and m are each 0, 1, 2, or 3;

$R_6$ is absent, hydrogen, or amino; or alkylamino$_{(C\le 12)}$, dialkylamino$_{(C\le 12)}$, cycloalkylamino$_{(C\le 12)}$, dicycloalkylamino$_{(C\le)}$, alkyl(cycloalkyl)amino$_{(C\le 12)}$, arylamino$_{(C\le 12)}$, diarylamino$_{(C\le 12)}$, alkyl$_{(C\le 12)}$, cycloalkyl$_{(C\le 12)}$, -alkanediyl$_{(C\le 12)}$-cycloalkyl$_{(C\le 12)}$, -alkanediyl$_{(C\le 18)}$-aralkoxy$_{(C\le 18)}$, heterocycloalkyl$_{(C\le 12)}$, aryl$_{(C\le 18)}$, -arenediyl$_{(C\le 12)}$-alkyl$_{(C\le 12)}$, aralkyl$_{(C\le 18)}$, -arenediyl$_{(C\le 18)}$-heterocycloalkyl$_{(C\le 12)}$, heteroaryl$_{(C\le 18)}$, -heteroarenediyl$_{(C\le 12)}$-alkyl$_{(C\le 12)}$, heteroaralkyl$_{(C\le 18)}$, acyl$_{(C\le 12)}$, alkoxy$_{(C\le 12)}$, or a substituted version of any of these groups; and $X_1$ and $X_2$ are each independently C or N, provided that $X_2$ is C when $R_6$ is amino, alkylamino$_{(C\le 12)}$, dialkylamino$_{(C\le 12)}$, cycloalkylamino$_{(C\le 12)}$, dicycloalkylamino$_{(C\le 12)}$, alkyl(cycloalkyl)amino$_{(C\le 12)}$, arylamino$_{(C\le 12)}$, or diarylamino$_{(C\le 12)}$;

or a pharmaceutically acceptable salt thereof.

In some embodiments, the compounds are further defined as:

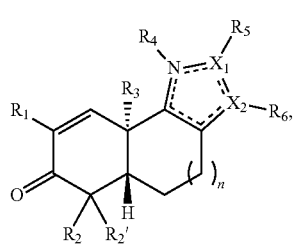

(II)

wherein:

n is 0, 1, or 2;

$R_1$ is cyano, fluoro, —CF$_3$, or —C(O)R$_a$, wherein

R$_a$ is hydroxy or amino; or alkoxy$_{(C\le 6)}$, alkylamino$_{(C\le 6)}$, dialkylamino$_{(C\le 6)}$, or a substituted version of any of these groups;

$R_2$ and $R_2'$ are each independently hydrogen; or alkyl$_{(C\le 12)}$, cycloalkyl$_{(C\le 12)}$, alkenyl$_{(C\le 12)}$, alkynyl$_{(C\le 12)}$, aryl$_{(C\le 18)}$, aralkyl$_{(C\le 18)}$, heteroaryl$_{(C\le 18)}$, heteroaralkyl$_{(C\le 18)}$, or a substituted version of any of these groups; or $R_2$ and $R_2'$ are taken together and are alkanediyl$_{(C\le 8)}$, alkenediyl$_{(C\le 8)}$, or a substituted version of either of these groups;

$R_3$ is alkyl$_{(C\le 12)}$, alkenyl$_{(C\le 12)}$, aryl$_{(C\le 12)}$, aralkyl$_{(C\le 12)}$, or a substituted version of any of these groups;

$R_4$ and $R_5$ are each independently absent or hydrogen; or alkyl$_{(C\le 12)}$, cycloalkyl$_{(C\le 12)}$, heterocycloalkyl$_{(C\le 12)}$, aryl$_{(C\le 12)}$, aralkyl$_{(C\le 12)}$, heteroaryl$_{(C\le 12)}$, heteroaralkyl$_{(C\le 12)}$, -arenediyl$_{(C\le 12)}$-alkyl$_{(C\le 12)}$, -arenediyl$_{(C\le 12)}$-aryl$_{(C\le 12)}$, -arenediyl$_{(C\le 12)}$-heteroaryl$_{(C\le 12)}$, -arenediyl$_{(C\le 12)}$-heterocycloalkyl$_{(C\le 12)}$-arenediyl$_{(C\le 12)}$-cycloalkyl$_{(C\le 12)}$, -heteroarenediyl$_{(C\le 12)}$-alkyl$_{(C\le 12)}$-heteroarenediyl$_{(C\le 12)}$-aryl$_{(C\le 12)}$, -hetero-arenediyl$_{(C\le 12)}$-heteroaryl$_{(C\le 12)}$, -heteroarenediyl$_{(C\le 12)}$-heterocycloalkyl$_{(C\le 12)}$, -heteroarenediyl$_{(C\le 12)}$-cycloalkyl$_{(C\le 12)}$, -heterocycloalkanediyl$_{(C\le 12)}$-aryl$_{(C\le)}$, -heterocycloalkanediyl$_{(C\le 12)}$-heteroaryl$_{(C\le 12)}$, or a substituted version of any of these groups; or a group of the formula:

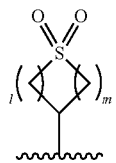

wherein l and m are each 0, 1, 2, or 3;

$R_6$ is absent, hydrogen, or amino; or alkylamino$_{(C\le 12)}$, dialkylamino$_{(C\le 12)}$, cycloalkylamino$_{(C\le 12)}$, dicycloalkylamino$_{(C\le 12)}$, alkyl(cycloalkyl)amino$_{(C\le 12)}$, arylamino$_{(C\le 12)}$, diarylamino$_{(C\le 12)}$, alkyl$_{(C\le 12)}$, cycloalkyl$_{(C\le 12)}$, -alkanediyl$_{(C\le 12)}$-cycloalkyl$_{(C\le 12)}$, -alkanediyl$_{(C\le 18)}$-aralkoxy$_{(C\le 18)}$, heterocycloalkyl$_{(C\le 12)}$, aryl$_{(C\le 18)}$, -arenediyl$_{(C\le 12)}$-alkyl$_{(C\le 12)}$, aralkyl$_{(C\le 18)}$, -arenediyl$_{(C\le 18)}$-heterocycloalkyl$_{(C\le 12)}$, heteroaryl$_{(C\le 18)}$, -heteroarenediyl$_{(C\le 12)}$-alkyl$_{(C\le 12)}$, heteroaralkyl$_{(C\le 18)}$, acyl$_{(C\le 12)}$, alkoxy$_{(C\le 12)}$, or a substituted version of any of these groups;

and $X_1$ and $X_2$ are each independently C or N provided that $X_2$ is C when $R_6$ is amino, alkylamino$_{(C\le 12)}$, dialkylamino$_{(C\le 12)}$, cycloalkylamino$_{(C\le 12)}$, dicycloalkylamino$_{(C\le 12)}$, alkyl(cycloalkyl)amino$_{(C\le 12)}$, arylamino$_{(C\le 12)}$, or diarylamino$_{(C\le 12)}$;

or a pharmaceutically acceptable salt thereof.

In some embodiments, the compounds are further defined as:

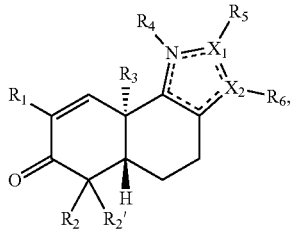

(III)

wherein:
R$_1$ is cyano, fluoro, —CF$_3$, or —C(O)R$_a$, wherein
R$_a$ is hydroxy or amino; or
alkoxy$_{(C≤6)}$, alkylamino$_{(C≤6)}$, dialkylamino$_{(C≤6)}$, or a substituted version of any of these groups;
R$_2$ and R$_2$' are each independently hydrogen; or
alkyl$_{(C≤12)}$, cycloalkyl$_{(C≤12)}$, alkenyl$_{(C≤12)}$, alkynyl$_{(C≤12)}$, aryl$_{(C≤18)}$, aralkyl$_{(C≤18)}$, heteroaryl$_{(C≤18)}$, heteroaralkyl$_{(C≤18)}$, or a substituted version of any of these groups; or
R$_2$ and R$_2$' are taken together and are alkanediyl$_{(C≤8)}$, alkenediyl$_{(C≤8)}$, or a substituted version of either of these groups;
R$_3$ is alkyl$_{(C≤12)}$, alkenyl$_{(C≤12)}$, aryl$_{(C≤12)}$, aralkyl$_{(C≤12)}$, or a substituted version of any of these groups;
R$_4$ and R$_5$ are each independently absent or hydrogen; or
alkyl$_{(C≤12)}$, cycloalkyl$_{(C≤12)}$, heterocycloalkyl$_{(C≤12)}$, aryl$_{(C≤12)}$, aralkyl$_{(C≤12)}$, heteroaryl$_{(C≤12)}$, heteroaralkyl$_{(C≤12)}$, -arenediyl$_{(C≤12)}$-alkyl$_{(C≤12)}$, -arenediyl$_{(C≤12)}$-aryl$_{(C≤12)}$, -arenediyl$_{(C≤12)}$-heteroaryl$_{(C≤12)}$, -arenediyl$_{(C≤12)}$-heterocycloalkyl$_{(C≤12)}$, -arenediyl$_{(C≤12)}$-cycloalkyl$_{(C≤12)}$, -heteroarenediyl$_{(C≤12)}$-alkyl$_{(C≤12)}$, -heteroarenediyl$_{(C≤12)}$-aryl$_{(C≤12)}$, -hetero-arenediyl$_{(C≤12)}$-heteroaryl$_{(C≤12)}$, -heteroarenediyl$_{(C≤12)}$-heterocycloalkyl$_{(C≤12)}$, -heteroarenediyl$_{(C≤12)}$-cycloalkyl$_{(C≤12)}$, -heterocycloalkanediyl$_{(C≤12)}$-aryl$_{(C≤12)}$, -heterocycloalkanediyl$_{(C≤12)}$-heteroaryl$_{(C≤12)}$, or a substituted version of any of these groups; or
a group of the formula:

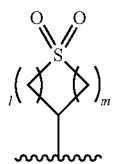

wherein l and m are each 0, 1, 2, or 3;
R$_6$ is absent, hydrogen, or amino; or
alkylamino$_{(C≤12)}$, dialkylamino$_{(C≤12)}$, cycloalkylamino$_{(C≤12)}$, dicycloalkylamino$_{(C≤12)}$, alkyl(cycloalkyl)amino$_{(C≤12)}$, arylamino$_{(C≤12)}$, diarylamino$_{(C≤12)}$, alkyl$_{(C≤12)}$, cycloalkyl$_{(C≤12)}$, -alkanediyl$_{(C≤12)}$-cycloalkyl$_{(C≤12)}$, -alkanediyl$_{(C≤18)}$-aralkoxy$_{(C≤18)}$, heterocycloalkyl$_{(C≤12)}$, aryl$_{(C≤18)}$, -arenediyl$_{(C≤12)}$-alkyl$_{(C≤12)}$, aralkyl$_{(C≤18)}$, -arenediyl$_{(C≤18)}$-heterocycloalkyl$_{(C≤12)}$, heteroaryl$_{(C≤18)}$, -heteroarenediyl$_{(C≤12)}$-alkyl$_{(C≤12)}$, heteroaralkyl$_{(C≤18)}$, acyl$_{(C≤12)}$, alkoxy$_{(C≤12)}$, or a substituted version of any of these groups; and X$_1$ and X$_2$ are each independently C or N, provided that X$_2$ is C when R$_6$ is amino, alkylamino$_{(C≤12)}$, dialkylamino$_{(C≤12)}$, cycloalkylamino$_{(C≤12)}$, dicycloalkylamino$_{(C≤12)}$, alkyl(cycloalkyl)amino$_{(C≤12)}$, arylamino$_{(C≤12)}$, or diarylamino$_{(C≤12)}$;
or a pharmaceutically acceptable salt thereof.

In some embodiments, the compounds are further defined as:

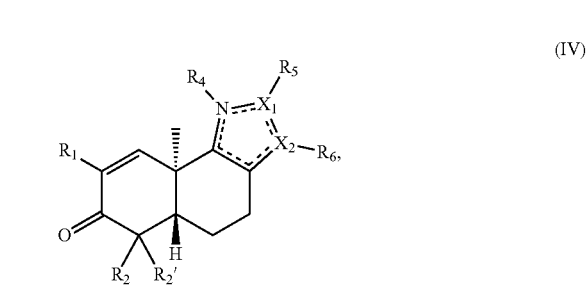

(IV)

wherein:
R$_1$ is cyano, fluoro, —CF$_3$, or —C(O)R$_a$, wherein
R$_a$ is hydroxy or amino; or
alkoxy$_{(C≤6)}$, alkylamino$_{(C≤6)}$, dialkylamino$_{(C≤6)}$, or a substituted version of any of these groups;
R$_2$ and R$_2$' are each independently hydrogen; or
alkyl$_{(C≤12)}$, cycloalkyl$_{(C≤12)}$, alkenyl$_{(C≤12)}$, alkynyl$_{(C≤12)}$, aryl$_{(C≤18)}$, aralkyl$_{(C≤18)}$, heteroaryl$_{(C≤18)}$, heteroaralkyl$_{(C≤18)}$, or a substituted version of any of these groups; or
R$_2$ and R$_2$' are taken together and are alkanediyl$_{(C≤8)}$, alkenediyl$_{(C≤8)}$, or a substituted version of either of these groups;
R$_4$ and R$_5$ are each independently absent or hydrogen; or
alkyl$_{(C≤12)}$, cycloalkyl$_{(C≤12)}$, heterocycloalkyl$_{(C≤12)}$, aryl$_{(C≤12)}$, aralkyl$_{(C≤12)}$, heteroaryl$_{(C≤12)}$, heteroaralkyl$_{(C≤12)}$, -arenediyl$_{(C≤12)}$-alkyl$_{(C≤12)}$, -arenediyl$_{(C≤12)}$-aryl$_{(C≤12)}$, -arenediyl$_{(C≤12)}$-heteroaryl$_{(C≤12)}$, -arenediyl$_{(C≤12)}$-heterocycloalkyl$_{(C≤12)}$, -arenediyl$_{(C≤12)}$-cycloalkyl$_{(C≤12)}$, -heteroarenediyl$_{(C≤12)}$-alkyl$_{(C≤12)}$, -heteroarenediyl$_{(C≤12)}$-aryl$_{(C≤12)}$, -heteroarenediyl$_{(C≤12)}$-heteroaryl$_{(C≤12)}$, -heteroarenediyl$_{(C≤12)}$-hetero-cycloalkyl$_{(C≤12)}$, -heteroarenediyl$_{(C≤12)}$-cycloalkyl$_{(C≤12)}$, -heterocycloalkanediyl$_{(C≤12)}$-aryl$_{(C≤12)}$, -heterocycloalkanediyl$_{(C≤12)}$-heteroaryl$_{(C≤12)}$, or a substituted version of any of these groups; or
a group of the formula:

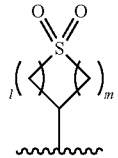

wherein:
l and m are each 0, 1, 2, or 3;
R$_6$ is absent, hydrogen, or amino; or
alkylamino$_{(C≤12)}$, dialkylamino$_{(C≤12)}$, cycloalkylamino$_{(C≤12)}$, dicycloalkylamino$_{(C≤12)}$, alkyl(cycloalkyl)amino$_{(C≤12)}$, arylamino$_{(C≤12)}$, diarylamino$_{(C≤12)}$, alkyl$_{(C≤12)}$, cycloalkyl$_{(C≤12)}$, -alkanediyl$_{(C≤12)}$-cycloalkyl$_{(C≤12)}$, -alkanediyl$_{(C≤18)}$-aralkoxy$_{(C≤18)}$, heterocycloalkyl$_{(C \leq 12)}$, aryl$_{(C \leq 18)}$, -arenediyl$_{(C \leq 12)}$-alkyl$_{(C \leq 12)}$, aralkyl$_{(C \leq 18)}$, -arenediyl$_{(C \leq 18)}$-heterocycloalkyl$_{(C \leq 12)}$, heteroaryl$_{(C \leq 18)}$, -heteroarenediyl$_{(C \leq 12)}$-alkyl$_{(C \leq 12)}$, heteroaralkyl$_{(C \leq 18)}$, acyl$_{(C \leq 12)}$, alkoxy$_{(C \leq 12)}$, or a substituted version of any of these groups; and $X_1$ and $X_2$ are each independently C or N, provided that $X_2$ is C when $R_6$ is amino, alkylamino$_{(C \leq 12)}$, dialkylamino$_{(C \leq 12)}$, cycloalkylamino$_{(C \leq 12)}$, dicycloalkylamino$_{(C \leq 12)}$, alkyl(cycloalkyl)amino$_{(C \leq 12)}$, arylamino$_{(C \leq 12)}$, or diarylamino$_{(C \leq 12)}$;

or a pharmaceutically acceptable salt thereof.

In some embodiments, the compounds are further defined as:

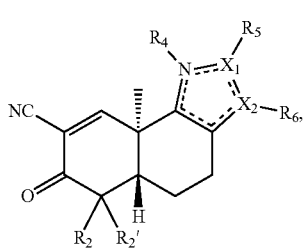

(V)

wherein:

$R_2$ and $R_2'$ are each independently hydrogen; or
alkyl$_{(C \leq 12)}$, cycloalkyl$_{(C \leq 12)}$, alkenyl$_{(C \leq 12)}$, alkynyl$_{(C \leq 12)}$, aryl$_{(C \leq 18)}$, aralkyl$_{(C \leq 18)}$, heteroaryl$_{(C \leq 18)}$, heteroaralkyl$_{(C \leq 18)}$, or a substituted version of any of these groups; or $R_2$ and $R_2$ are taken together and are alkanediyl$_{(C \leq 8)}$, alkenediyl$_{(C \leq 8)}$, or a substituted version of either of these groups;

$R_4$ and $R_5$ are each independently absent or hydrogen; or
alkyl$_{(C \leq 12)}$, cycloalkyl$_{(C \leq 12)}$, heterocycloalkyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, -arenediyl$_{(C \leq 12)}$-alkyl$_{(C \leq 12)}$, -arenediyl$_{(C \leq 12)}$-aryl$_{(C \leq 12)}$, -arenediyl$_{(C \leq 12)}$-heteroaryl$_{(C \leq 12)}$, -arenediyl$_{(C \leq 12)}$-heterocycloalkyl$_{(C \leq 12)}$, -arenediyl$_{(C \leq 12)}$-cycloalkyl$_{(C \leq 12)}$, -heteroarenediyl$_{(C \leq 12)}$-alkyl$_{(C \leq 12)}$, -heteroarenediyl$_{(C \leq 12)}$-aryl$_{(C \leq 12)}$, -hetero-arenediyl$_{(C \leq 12)}$-heteroaryl$_{(C \leq 12)}$, -heteroarenediyl$_{(C \leq 12)}$-heterocycloalkyl$_{(C \leq 12)}$, -heteroarenediyl$_{(C \leq 12)}$-cycloalkyl$_{(C \leq 12)}$, -heterocycloalkanediyl$_{(C \leq 12)}$-aryl$_{(C \leq 12)}$, -heterocycloalkanediyl$_{(C \leq 12)}$-heteroaryl$_{(C \leq 12)}$, or a substituted version of any of these groups; or
a group of the formula:

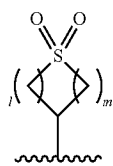

wherein l and m are each 0, 1, 2, or 3;
$R_6$ is absent, hydrogen, or amino; or
alkylamino$_{(C \leq 12)}$, dialkylamino$_{(C \leq 12)}$, cycloalkylamino$_{(C \leq 12)}$, dicycloalkylamino$_{(C \leq 12)}$, alkyl(cycloalkyl)amino$_{(C \leq 12)}$, arylamino$_{(C \leq 12)}$, diarylamino$_{(C \leq 12)}$, alkyl$_{(C \leq 12)}$, cycloalkyl$_{(C \leq 12)}$, -alkanediyl$_{(C \leq 12)}$-cycloalkyl$_{(C \leq 12)}$, -alkanediyl$_{(C \leq 18)}$-aralkoxy$_{(C \leq 18)}$, heterocycloalkyl$_{(C \leq 12)}$, aryl$_{(C \leq 12)}$, -arenediyl$_{(C \leq 12)}$-alkyl$_{(C \leq 12)}$, aralkyl$_{(C \leq 18)}$, -arenediyl$_{(C \leq 18)}$-heterocycloalkyl$_{(C \leq 12)}$, heteroaryl$_{(C \leq 18)}$, -heteroarenediyl$_{(C \leq 12)}$-alkyl$_{(C \leq 12)}$, heteroaralkyl$_{(C \leq 18)}$, acyl$_{(C \leq 12)}$, alkoxy$_{(C \leq 12)}$, or a substituted version of any of these groups; and $X_1$ and $X_2$ are each independently C or N, provided that $X_2$ is C when $R_6$ is amino, alkylamino$_{(C \leq 12)}$, dialkylamino$_{(C \leq 12)}$, cycloalkylamino$_{(C \leq 12)}$, dicycloalkylamino$_{(C \leq 12)}$, alkyl(cycloalkyl)amino$_{(C \leq 12)}$, arylamino$_{(C \leq 12)}$, or diarylamino$_{(C \leq 12)}$;

or a pharmaceutically acceptable salt thereof.

In some embodiments, the compounds are further defined as:

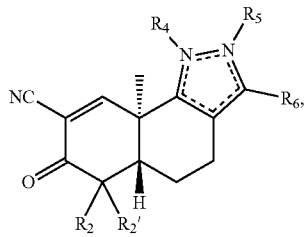

(VI)

wherein:

$R_2$ and $R_2'$ are each independently hydrogen; or
alkyl$_{(C \leq 12)}$, cycloalkyl$_{(C \leq 12)}$, alkenyl$_{(C \leq 12)}$, alkynyl$_{(C \leq 12)}$, aryl$_{(C \leq 18)}$, aralkyl$_{(C \leq 18)}$, heteroaryl$_{(C \leq 18)}$, heteroaralkyl$_{(C \leq 18)}$, or a substituted version of any of these groups; or $R_2$ and $R_2'$ are taken together and are alkanediyl$_{(C \leq 8)}$, alkenediyl$_{(C \leq 8)}$, or a substituted version of either of these groups;

$R_4$ and $R_5$ are each independently absent, hydrogen; or
alkyl$_{(C \leq 12)}$, cycloalkyl$_{(C \leq 12)}$, heterocycloalkyl$_{(C \leq 12)}$, aryl$_{(C \leq 12)}$, aralkyl$_{(C \leq 12)}$, heteroaryl$_{(C \leq 23)}$, heteroaralkyl$_{(C \leq 12)}$, -arenediyl$_{(C \leq 12)}$-alkyl$_{(C \leq 12)}$, -arenediyl$_{(C \leq 12)}$-aryl$_{(C \leq 12)}$, -arenediyl$_{(C \leq 12)}$-heteroaryl$_{(C \leq 12)}$, -arenediyl$_{(C \leq 12)}$-heterocycloalkyl$_{(C \leq 12)}$, -arenediyl$_{(C \leq 12)}$-cycloalkyl$_{(C \leq 12)}$, -heteroarenediyl$_{(C \leq 12)}$-alkyl$_{(C \leq 12)}$, -heteroarenediyl$_{(C \leq 12)}$-aryl$_{(C \leq 12)}$, -heteroarenediyl$_{(C \leq 12)}$-heteroaryl$_{(C \leq 12)}$, -heteroarenediyl$_{(C \leq 12)}$-hetero-cycloalkyl$_{(C \leq 12)}$, -heteroarenediyl$_{(C \leq 12)}$-cycloalkyl$_{(C \leq 12)}$, -heterocyclo-alkanediyl$_{(C \leq 12)}$-aryl$_{(C \leq 12)}$, -heterocycloalkanediyl$_{(C \leq 12)}$-heteroaryl$_{(C \leq 12)}$, or a substituted version of any of these groups; or
a group of the formula:

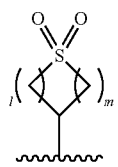

wherein l and m are each 0, 1, 2, or 3;
$R_6$ is absent, hydrogen; or
alkylamino$_{(C \leq 12)}$, dialkylamino$_{(C \leq 12)}$, cycloalkylamino$_{(C \leq 12)}$, dicycloalkylamino$_{(C \leq 12)}$, alky(cycloalkyl)amino$_{(C \leq 12)}$, arylamino$_{(C \leq 12)}$, diarylamino$_{(C \leq 12)}$, alkyl$_{(C\leq12)}$, cycloalkyl$_{(C\leq12)}$, -alkanediyl$_{(C\leq12)}$-cycloalkyl$_{(C\leq12)}$, -alkanediyl$_{(C\leq18)}$-aralkoxy$_{(C\leq18)}$, heterocycloalkyl$_{(C\leq12)}$, aryl$_{(C\leq18)}$, -arenediyl$_{(C\leq12)}$-alkyl$_{(C\leq12)}$, aralkyl$_{(C\leq18)}$, -arenediyl$_{(C\leq18)}$-heterocycloalkyl$_{(C\leq12)}$, heteroaryl$_{(C\leq18)}$, -heteroarenediyl$_{(C\leq12)}$-alkyl$_{(C\leq12)}$, heteroaralkyl$_{(C\leq18)}$, acyl$_{(C\leq12)}$, alkoxy$_{(C\leq12)}$, or a substituted version of any of these groups;

or a pharmaceutically acceptable salt thereof.

In some embodiments, the compounds are further defined as:

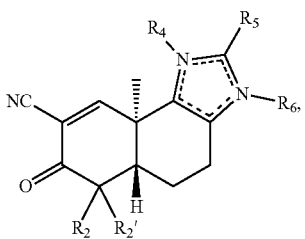

(VII)

wherein:
$R_2$ and $R_2'$ are each independently hydrogen; or
alkyl$_{(C\leq12)}$, cycloalkyl$_{(C\leq12)}$, alkenyl$_{(C\leq12)}$, alkynyl$_{(C\leq12)}$, aryl$_{(C\leq18)}$, aralkyl$_{(C\leq18)}$, heteroaryl$_{(C\leq18)}$, heteroaralkyl$_{(C\leq18)}$, or a substituted version of any of these groups; or
$R_2$ and $R_2'$ are taken together and are alkanediyl$_{(C\leq8)}$, alkenediyl$_{(C\leq8)}$, or a substituted version of either of these groups;
$R_4$ and $R_5$ are each independently absent, hydrogen; or
alkyl$_{(C\leq12)}$, cycloalkyl$_{(C\leq12)}$, heterocycloalkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, -arenediyl$_{(C\leq12)}$-alkyl$_{(C\leq12)}$, -arenediyl$_{(C\leq12)}$-aryl$_{(C\leq12)}$, -arenediyl$_{(C\leq12)}$-heteroaryl$_{(C\leq12)}$, -arenediyl$_{(C\leq12)}$-heterocycloalkyl$_{(C\leq12)}$, -arenediyl$_{(C\leq12)}$-cycloalkyl$_{(C\leq12)}$, -heteroarenediyl$_{(C\leq12)}$-alkyl$_{(C\leq)}$, -heteroarenediyl$_{(C\leq12)}$-aryl$_{(C\leq12)}$, -heteroarenediyl$_{(C\leq12)}$-heteroaryl$_{(C\leq12)}$, -heteroarenediyl$_{(C\leq12)}$-hetero-cycloalkyl$_{(C\leq12)}$, -heteroarenediyl$_{(C\leq12)}$-cycloalkyl$_{(C\leq12)}$, -heterocycloalkanediyl$_{(C\leq12)}$-aryl$_{(C\leq12)}$, -heterocycloalkanediyl$_{(C\leq12)}$-heteroaryl$_{(C\leq12)}$, or a substituted version of any of these groups; or
a group of the formula:

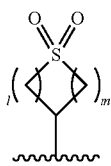

wherein l and m are each 0, 1, 2, or 3; and
$R_6$ is absent, hydrogen; or
alkylamino$_{(C\leq12)}$, dialkylamino$_{(C\leq12)}$, cycloalkylamino$_{(C\leq12)}$, dicycloalkylamino$_{(C\leq12)}$, alkyl(cycloalkyl)amino$_{(C\leq12)}$, arylamino$_{(C\leq12)}$, diarylamino$_{(C\leq12)}$, alkyl$_{(C\leq12)}$, cycloalkyl$_{(C\leq12)}$, -alkanediyl$_{(C\leq12)}$-cycloalkyl$_{(C\leq12)}$, -alkanediyl$_{(C\leq18)}$-aralkoxy$_{(C\leq18)}$, heterocycloalkyl$_{(C\leq12)}$, aryl$_{(C\leq18)}$, -arenediyl$_{(C\leq12)}$-alkyl$_{(C\leq12)}$, aralkyl$_{(C\leq18)}$, -arenediyl$_{(C\leq18)}$-heterocycloalkyl$_{(C\leq12)}$, heteroaryl$_{(C\leq18)}$, -heteroarenediyl$_{(C\leq12)}$-alkyl$_{(C\leq18)}$, heteroaralkyl$_{(C\leq18)}$, acyl$_{(C\leq12)}$, alkoxy$_{(C\leq12)}$, or a substituted version of any of these groups; wherein:

or a pharmaceutically acceptable salt thereof.

In some embodiments, the compounds are further defined as:

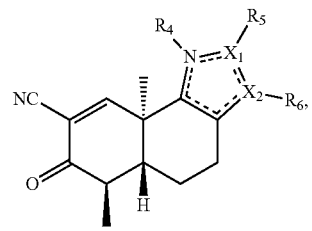

(VIII)

wherein:
$R_4$ and $R_5$ are each independently absent, hydrogen; or
alkyl$_{(C\leq12)}$, cycloalkyl$_{(C\leq12)}$, heterocycloalkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, -arenediyl$_{(C\leq12)}$-alkyl$_{(C\leq12)}$, -arenediyl$_{(C\leq12)}$-aryl$_{(C\leq12)}$, -arenediyl$_{(C\leq12)}$-heteroaryl$_{(C\leq12)}$, -arenediyl$_{(C\leq12)}$-heterocycloalkyl$_{(C\leq12)}$, -arenediyl$_{(C\leq12)}$-cycloalkyl$_{(C\leq12)}$, -heteroarenediyl$_{(C\leq12)}$-alkyl$_{(C\leq12)}$, -heteroarenediyl$_{(C\leq12)}$-aryl$_{(C\leq12)}$, -heteroarenediyl$_{(C\leq12)}$-heteroaryl$_{(C\leq12)}$, -heteroarenediyl$_{(C\leq12)}$-hetero-cycloalkyl$_{(C\leq12)}$, -heteroarenediyl$_{(C\leq12)}$-cycloalkyl$_{(C\leq12)}$, -heterocycloalkanediyl$_{(C\leq12)}$-aryl$_{(C\leq12)}$, -heterocycloalkanediyl$_{(C\leq12)}$-heteroaryl$_{(C\leq12)}$, or a substituted version of any of these groups; or
a group of the formula:

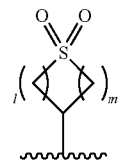

wherein l and m are each 0, 1, 2, or 3; and
$R_6$ is absent, hydrogen; or
alkylamino$_{(C\leq12)}$, dialkylamino$_{(C\leq12)}$, cycloalkylamino$_{(C\leq12)}$, dicycloalkylamino$_{(C\leq12)}$, alkyl(cycloalkyl)amino$_{(C\leq12)}$, arylamino$_{(C\leq12)}$, diarylamino$_{(C\leq12)}$, alkyl$_{(C\leq12)}$, cycloalkyl$_{(C\leq12)}$, -alkanediyl$_{(C\leq12)}$-cycloalkyl$_{(C\leq12)}$, -alkanediyl$_{(C\leq18)}$-aralkoxy$_{(C\leq18)}$, heterocycloalkyl$_{(C\leq12)}$, aryl$_{(C\leq18)}$, -arenediyl$_{(C\leq12)}$-alkyl$_{(C\leq12)}$, aralkyl$_{(C\leq18)}$, -arenediyl$_{(C\leq18)}$-heterocycloalkyl$_{(C\leq12)}$, heteroaryl$_{(C\leq18)}$, -heteroarenediyl$_{(C\leq12)}$-alkyl$_{(C\leq12)}$, heteroaralkyl$_{(C\leq18)}$, acyl$_{(C\leq12)}$, alkoxy$_{(C\leq12)}$, or a substituted version of any of these groups; and
$X_1$ and $X_2$ are each independently C or N, provided that $X_2$ is C when $R_6$ is amino, alkylamino$_{(C\leq12)}$, dialkylamino$_{(C\leq12)}$, cycloalkylamino$_{(C\leq12)}$, dicycloalkylamino$_{(C\leq12)}$, alkyl(cycloalkyl)amino$_{(C\leq12)}$, arylamino$_{(C\leq12)}$, or diarylamino$_{(C\leq12)}$;

or a pharmaceutically acceptable salt thereof.

In other embodiments, the compounds are further defined as:

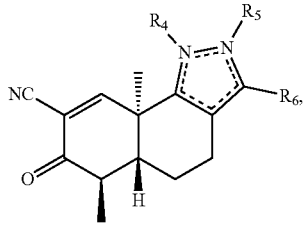

(IX)

wherein:
R₄ and R₅ are each independently absent, hydrogen; or
alkyl$_{(C≤12)}$, cycloalkyl$_{(C≤12)}$, heterocycloalkyl$_{(C≤12)}$, aryl$_{(C≤12)}$, aralkyl$_{(C≤12)}$, heteroaryl$_{(C≤12)}$, heteroaralkyl$_{(C≤12)}$, -arenediyl$_{(C≤12)}$-alkyl$_{(C≤12)}$, -arenediyl$_{(C≤12)}$-aryl$_{(C≤12)}$, -arenediyl$_{(C≤12)}$-heteroaryl$_{(C≤12)}$, -arenediyl$_{(C≤12)}$-heterocycloalkyl$_{(C≤12)}$, -arenediyl$_{(C≤12)}$-cycloalkyl$_{(C≤12)}$, -heteroarenediyl$_{(C≤12)}$-alkyl$_{(C≤12)}$, -heteroarenediyl$_{(C≤12)}$-heteroaryl$_{(C≤12)}$, -heteroarenediyl$_{(C≤12)}$-hetero-cycloalkyl$_{(C≤12)}$, -heteroarenediyl$_{(C≤12)}$-cycloalkyl$_{(C≤12)}$, -heterocyclo-alkanediyl$_{(C≤12)}$-aryl$_{(C≤12)}$, -heterocycloalkanediyl$_{(C≤12)}$-heteroaryl$_{(C≤12)}$, or a substituted version of any of these groups; or
a group of the formula:

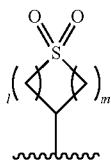

wherein l and m are each 0, 1, 2, or 3; and
R₆ is absent, hydrogen; or
alkylamino$_{(C≤12)}$, dialkylamino$_{(C≤12)}$, cycloalkylamino$_{(C≤12)}$, dicycloalkylamino$_{(C≤12)}$, alkyl(cycloalkyl)amino$_{(C≤12)}$, arylamino$_{(C≤12)}$, diarylamino$_{(C≤12)}$, alkyl$_{(C≤12)}$, cycloalkyl$_{(C≤12)}$, -alkanediyl$_{(C≤12)}$-cycloalkyl$_{(C≤12)}$, -alkanediyl$_{(C≤18)}$-aralkoxy$_{(C≤18)}$, heterocycloalkyl$_{(C≤12)}$, aryl$_{(C≤18)}$, -arenediyl$_{(C≤12)}$-alkyl$_{(C≤12)}$, aralkyl$_{(C≤18)}$, -arenediyl$_{(C≤18)}$-heterocycloalkyl$_{(C≤12)}$, heteroaryl$_{(C≤18)}$, -heteroarenediyl$_{(C≤12)}$-alkyl$_{(C≤12)}$, heteroaralkyl$_{(C≤18)}$, acyl$_{(C≤12)}$, alkoxy$_{(C≤12)}$, or a substituted version of any of these groups; wherein:
or a pharmaceutically acceptable salt thereof.

In other embodiments, the compounds are further defined as:

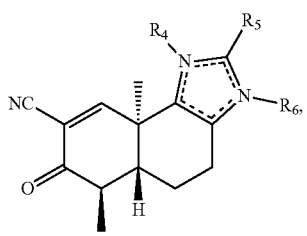

(X)

wherein:
R₄ and R₅ are each independently absent, hydrogen; or
alkyl$_{(C≤12)}$, cycloalkyl$_{(C≤12)}$, heterocycloalkyl$_{(C≤12)}$, aryl$_{(C≤12)}$, aralkyl$_{(C≤12)}$, heteroaryl$_{(C≤12)}$, heteroaralkyl$_{(C≤12)}$, -arenediyl$_{(C≤12)}$-alkyl$_{(C≤12)}$, -arenediyl$_{(C≤12)}$-aryl$_{(C≤12)}$, -arenediyl$_{(C≤12)}$-heteroaryl$_{(C≤12)}$, -arenediyl$_{(C≤12)}$-heterocycloalkyl$_{(C≤12)}$, -arenediyl$_{(C≤12)}$-cycloalkyl$_{(C≤12)}$, -heteroarenediyl$_{(C≤12)}$-alkyl$_{(C≤12)}$, -heteroarenediyl$_{(C≤12)}$-aryl$_{(C≤12)}$, -heteroarenediyl$_{(C≤12)}$-heteroaryl$_{(C≤12)}$, -heteroarenediyl$_{(C≤12)}$-hetero-cycloalkyl$_{(C≤12)}$, -heteroarenediyl$_{(C≤12)}$-cycloalkyl$_{(C≤12)}$, -heterocyclo-alkanediyl$_{(C≤12)}$-aryl$_{(C≤12)}$, -heterocycloalkanediyl$_{(C≤12)}$-heteroaryl$_{(C≤12)}$, or a substituted version of any of these groups; or
a group of the formula:

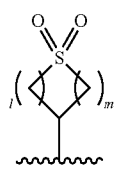

wherein l and m are each 0, 1, 2, or 3; and
R₆ is absent, hydrogen; or
alkylamino$_{(C≤12)}$, dialkylamino$_{(C≤12)}$, cycloalkylamino$_{(C≤12)}$, dicycloalkylamino$_{(C≤12)}$, alky(cycloalkyl)amino$_{(C≤12)}$, arylamino$_{(C≤12)}$, diarylamino$_{(C≤12)}$, alkyl$_{(C≤12)}$, cycloalkyl$_{(C≤12)}$, -alkanediyl$_{(C≤12)}$-cycloalkyl$_{(C≤12)}$, -alkanediyl$_{(C≤18)}$-aralkoxy$_{(C≤18)}$, heterocycloalkyl$_{(C≤12)}$, aryl$_{(C≤18)}$, -arenediyl$_{(C≤12)}$-alkyl$_{(C≤12)}$, aralkyl$_{(C≤18)}$, -arenediyl$_{(C≤18)}$-heterocycloalkyl$_{(C≤12)}$, heteroaryl$_{(C≤18)}$, -heteroarenediyl$_{(C≤12)}$-alkyl$_{(C≤12)}$, heteroaralkyl$_{(C≤18)}$, acyl$_{(C≤12)}$, alkoxy$_{(C≤12)}$, or a substituted version of any of these groups;
or a pharmaceutically acceptable salt thereof.

In some embodiments, X₁ and X₂ are both N. In other embodiments, X₁ and X₂ are not both N. In other embodiments, either X₁ or X₂ is N. In some embodiments, X₁ is N. In some embodiments, X₂ is N.

In some embodiments, R₃ is alkyl$_{(C≤12)}$ or substituted alkyl$_{(C≤12)}$. In some embodiments, R₃ alkyl$_{(C≤12)}$ such as methyl. In some embodiments, R₁ is cyano. In other embodiments, R₁ is —C(O)R$_a$. In some embodiments, R$_a$ is alkoxy$_{(C≤6)}$ such as methoxy. In other embodiments, R$_a$ is amino.

In some embodiments. R₂' is hydrogen. In some embodiments, R₂ is hydrogen. In other embodiments, R₂' and R₂ are both hydrogen. In other embodiments, R₂ is alkyl$_{(C≤12)}$ or substituted alkyl$_{(C≤12)}$. In some embodiments, R₂ is alkyl$_{(C≤12)}$, such as methyl. In some embodiments, R₄ is absent. In other embodiments, R₄ is hydrogen. In other embodiments, R₄ is alkyl$_{(C≤12)}$ or substituted alkyl$_{(C≤12)}$. In some embodiments, R₄ is substituted alkyl$_{(C≤12)}$ such as 2,2,2-trifluoroethyl. In other embodiments, R₄ is cycloalkyl$_{(C≤12)}$ or substituted cycloalkyl$_{(C≤12)}$. In some embodiments, R₄ is cycloalkyl$_{(C≤12)}$ such as cyclohexyl. In other embodiments, R₄ is heterocycloalkyl$_{(C≤12)}$ or substituted heterocycloalkyl$_{(C≤12)}$. In some embodiments, R₄ is heterocycloalkyl$_{(C≤12)}$ such as tetrahydro-2H-pyran-4-yl or 1,1-dioxidotetrahydrothiophen-3-yl. In other embodiments. R₄ is:

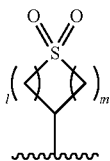

wherein l and m are each 0, 1, 2, or 3. In some embodiments, l is 1 or 2. In some embodiments, m is 1 or 2.

In other embodiments, $R_4$ is aryl$_{(C≤18)}$ or substituted aryl$_{(C≤18)}$. In some embodiments. $R_4$ is aryl$_{(C≤18)}$ such as phenyl, o-tolyl, p-tolyl, [1,1'-biphenyl]-4-yl, 4-isopropylphenyl, naphthalen-1-yl, 4'-methyl-[1,1'-biphenyl]-4-yl, or 2'-methyl-[1,1'-biphenyl]-4-yl. In other embodiments, $R_4$ is substituted aryl$_{(C≤18)}$ such as 4-(trifluoromethyl)phenyl, 4-cyanophenyl, 2-fluorophenyl, 4-fluorophenyl, 4-chlorophenyl, 3,4-dichlorophenyl, 4-methoxyphenyl, 4-(trifluoromethoxy)phenyl, 4-carboxyphenyl, 4'-methoxy-[1,1'-biphenyl]-4-yl, 4'-(dimethyliminio)-[1,1'-biphenyl]-4-yl, 2'-fluoro-[1,1'-biphenyl]-4-yl, 3'-fluoro-[1,1'-biphenyl]-4-yl, 2'-(hydroxymethyl)-[1,1'-biphenyl]-4-yl, 3'-(hydroxymethyl)-[1,1'-biphenyl]-4-yl, 4'-(hydroxymethyl)-[1,1'-biphenyl]-4-yl, or 5-(3-(hydroxymethyl)phenyl. In other embodiments, $R_4$ is aralkyl$_{(C≤18)}$ or substituted aralkyl$_{(C≤18)}$. In some embodiments, $R_4$ is aralkyl$_{(C≤18)}$ such as benzyl. In other embodiments, $R_4$ is -arenediyl$_{(C≤12)}$-heterocycloalkyl$_{(C≤12)}$ or substituted -arenediyl$_{(C≤12)}$-heterocycloalkyl$_{(C≤12)}$. In some embodiments, $R_4$ is -arenediyl$_{(C≤12)}$-heterocycloalkyl$_{(C≤12)}$ such as 4-morpholinophenyl. In other embodiments, $R_4$ is heteroaryl$_{(C≤18)}$ or substituted heteroaryl$_{(C≤18)}$. In some embodiments, $R_4$ is heteroaryl$_{(C≤18)}$ such as pyridin-4-yl, quinolin-4-yl, 5-methylpyridin-2-yl, 6-methylpyridin-3-yl, (pyridin-3-yl)phenyl, (pyridin-4-yl)phenyl, 4-(3,5-dimethylisoxazol-4-yl)phenyl, 4-(pyrimidin-4-yl)phenyl, 4-(pyrimidin-5-yl)phenyl, 4-(pyridin-3-yl)phenyl, 4-(pyridin-4-yl)phenyl, 5-phenylpyridin-2-yl, [3,3'-bipyridin]-6-yl, 5-cyclopropylpyridin-2-yl, 6-phenylpyridin-3-yl, 4-(6-methylpyridazin-4-yl)phenyl, 5-methyl-1,2,4-oxadiazol-3-yl, 3-methyl-1,2,4-oxadiazol-5-yl, 4-methyl-5-phenyl-4H-1,2,4-triazol-3-yl, 1-phenylpiperidin-4-yl, 4-phenyloxazol-2-yl, 4-(6-methylpyridazin-4-yl)phenyl, 4-(5-methyl-1,2,4-oxadiazol-3-yl)phenyl, 4-(3-methyl-1,2,4-oxadiazol-5-yl)phenyl, 4-(1,2,4-oxadiazol-3-yl)phenyl, 4-(pyridazin-3-yl)phenyl, 4-(5-methylpyridazin-3-yl)phenyl, 1-methyl-1H-benzo[d]imidazol-2-yl, or benzo[d]thiazol-2-yl. In other embodiments, $R_4$ is substituted heteroaryl$_{(C≤18)}$ such as 2-fluoro-4-(pyridin-3-yl)phenyl, 5-(trifluoromethyl)pyridin-2-yl, 5-(3-fluorophenyl)pyridin-2-yl, 5-(4-fluorophenyl)pyridin-2-yl, 4-(2-(hydroxymethyl)pyridine-4-yl)phenyl, 4-(2-(fluoromethyl)pyridine-4-yl)phenyl, 5-(trifluoromethyl)benzo[d]oxazol-2-yl, 6-chlorobenzo[d]thiazol-2-yl, or 4-(5-fluoropyridin-3-yl)phenyl.

In some embodiments, $R_5$ is hydrogen. In other embodiments, $R_5$ is alkyl$_{(C≤12)}$ or substituted alkyl$_{(C≤12)}$. In some embodiments, $R_5$ is alkyl$_{(C≤12)}$ such as methyl. In other embodiments, $R_5$ is cycloalkyl$_{(C≤12)}$ or substituted cycloalkyl$_{(C≤12)}$. In some embodiments, $R_5$ is cycloalkyl$_{(C≤12)}$ such as cyclohexyl. In other embodiments, $R_5$ is heterocycloalkyl$_{(C≤12)}$ or substituted heterocycloalkyl$_{(C≤12)}$. In some embodiments, $R_5$ is heterocycloalkyl$_{(C≤18)}$ such as tetrahydro-2H-pyran-4-yl. In other embodiments, $R_5$ is aryl$_{(C≤18)}$ or substituted aryl$_{(C≤18)}$. In some embodiments, $R_5$ is aryl$_{(C≤18)}$ such as phenyl, o-tolyl, p-tolyl, [1,1'-biphenyl]-4-yl, 4-isopropylphenyl, naphthalen-1-yl, [1,1'-biphenyl]-3-yl, or 3-isopropylphenyl. In other embodiments, $R_5$ is substituted aryl$_{(C≤18)}$ such as 4-chlorophenyl, 3,4-dichlorophenyl, 4-methoxyphenyl, 4-(trifluoromethoxy)phenyl, 3-bromophenyl, 3-chlorophenyl, 4-(dimethylamino)phenyl. In other embodiments, $R_5$ is aralkyl$_{(C≤18)}$ or substituted aralkyl$_{(C≤18)}$. In some embodiments, $R_5$ is aralkyl$_{(C≤18)}$ such as benzyl. In other embodiments, $R_5$ is -arenediyl$_{(C≤12)}$-heterocycloalkyl$_{(≤12)}$ or substituted -arenediyl$_{(C≤12)}$-heterocycloalkyl$_{(C≤12)}$. In some embodiments, $R_5$ is -arenediyl$_{(C≤12)}$-heterocycloalkyl$_{(C≤12)}$ such as 3-morpholinophenyl. In other embodiments, $R_5$ is heteroaryl$_{(C≤18)}$ or substituted heteroaryl$_{(C≤18)}$. In some embodiments, $R_5$ is heteroaryl$_{(C≤18)}$ such as pyridin-4-yl, quinolin-4-yl, quinolin-3-yl, quinolin-5-yl, 3-(pyridin-4-yl)phenyl, 3-(pyrimidin-5-yl)phenyl, 2-isopropylpyrimidin-5-yl, 6-cyclopropylpyridin-3-yl, 3-(1-methyl-1H-pyrazol-4-yl)phenyl, 1-methyl-1H-pyrazol-4-yl, 3-(3,5-dimethylisoxazol-4-yl)phenyl, 3-(1-methyl-1H-pyrazol-5-yl)phenyl, or 2-cyclopropylpyridin-4-yl. In other embodiments, $R_5$ is substituted heteroaryl$_{(C≤18)}$ such as 2-(trifluoromethyl)pyridin-4-yl or 3-(5-fluoropyridin-3-yl)phenyl. In other embodiments, $R_5$ is -heteroarenediyl$_{(C≤12)}$-heterocycloalkyl$_{(C≤12)}$ or substituted -heteroarenediyl$_{(C≤12)}$-heterocycloalkyl$_{(C≤12)}$. In some embodiments, $R_5$ is -heteroarenediyl$_{(C≤12)}$-heterocycloalkyl$_{(C≤12)}$ such as 2-morpholinopyridin-4-yl.

In some embodiments, $R_6$ is hydrogen. In other embodiments, $R_6$ is amino. In other embodiments, $R_6$ is alkylamino$_{(C≤12)}$ or substituted alkylamino$_{(C≤12)}$. In some embodiments, $R_6$ is alkylamino$_{(C≤12)}$ such as methylamino. In other embodiments, $R_6$ is cycloalkylamino$_{(C≤12)}$ or substituted cycloalkylamino$_{(C≤12)}$. In some embodiments, $R_6$ is cycloalkylamino$_{(C≤12)}$ such as cyclobutylamino. In other embodiments, $R_6$ is alkyl(cycloalkyl)amino$_{(C≤12)}$ or substituted alkyl(cycloalkyl)amino$_{(C≤12)}$. In some embodiments. $R_6$ is alkyl(cycloalkyl)amino$_{(C≤12)}$ such as methyl(cyclobutyl)amino. In other embodiments, $R_6$ is arylamino$_{(C≤12)}$ or substituted arylamino$_{(C≤12)}$. In some embodiments, $R_6$ is arylamino$_{(C≤12)}$ such as phenylamino. In other embodiments, $R_6$ is alkyl$_{(C≤12)}$ or substituted alkyl$_{(C≤12)}$. In some embodiments, $R_6$ is alkyl$_{(C≤12)}$ such as methyl. In other embodiments, $R_6$ is substituted alkyl$_{(C≤12)}$ such as 2-hydroxyethyl or 2-methoxyethyl. In other embodiments, $R_6$ is acyl$_{(C≤6)}$ or substituted acyl$_{(C≤6)}$. In some embodiments, $R_6$ is acyl$_{(C≤6)}$ such as —C(O)CH$_3$. In other embodiments, $R_6$ is cycloalkyl$_{(C≤12)}$ or substituted cycloalkyl$_{(C≤12)}$. In some embodiments, $R_6$ is cycloalkyl$_{(C≤12)}$ such as cyclopropyl or cyclohexyl. In other embodiments, $R_6$ is -alkanediyl$_{(C≤18)}$-cycloalkyl$_{(C≤18)}$ or substituted -alkanediyl$_{(C≤18)}$-cycloalkyl$_{(C≤18)}$. In some embodiments, $R_6$ is -alkanediyl$_{(C≤18)}$-cycloalkyl$_{(C≤18)}$ such as cyclobutylmethyl. In other embodiments, $R_6$ is aryl$_{(C≤18)}$ or substituted aryl$_{(C≤18)}$. In some embodiments, $R_6$ is aryl$_{(C≤18)}$ such as phenyl, o-tolyl, p-tolyl, or 3-isopropylphenyl. In other embodiments, $R_6$ is substituted aryl$_{(C≤18)}$ such as 2-fluorophenyl, 4-fluorophenyl, 4-(hydroxymethyl)phenyl, 3-fluorophenyl, or 4-(fluoromethyl)phenyl. In other embodiments, $R_6$ is aralkyl$_{(C≤18)}$ or substituted aralkyl$_{(C≤18)}$. In some embodiments, $R_6$ is aralkyl$_{(C≤18)}$ such as benzyl. In other embodiments $R_6$ is substituted aralkyl$_{(C≤18)}$ such as 2-fluorobenzyl, 4-fluorobenzyl, or 4-chlorobenzyl. In other embodiments. $R_6$ is -arenediyl$_{(C≤18)}$-heterocycloalkyl$_{(C≤12)}$ or substituted -arenediyl$_{(C≤18)}$-heterocycloalkyl$_{(C≤12)}$. In some embodiments, $R_6$ is -arenediyl$_{(C≤18)}$-heterocycloalkyl$_{(C≤12)}$ such as 4-morpholinophenyl. In other embodiments, $R_6$ is heteroaryl$_{(C≤18)}$s or substituted heteroaryl$_{(C≤18)}$. In some embodiments, $R_6$ is heteroaryl$_{(C≤18)}$ such as pyridin-2-yl, pyridin-3-yl, pyridin-4-yl, 2-methyl-2H-tetrazol-5-yl, 1-methyl-1H-pyrazol-4-yl, pyrimidin-4-yl, pyrimidin-5-yl, 3-methyl-1,2,4-oxadiazol-5-yl)phenyl, pyridin-2-ylmethyl, 3-methyl-1,2,4-oxadiazol-5-yl, or 5-methyl-1,2,4-oxadiazol-3-yl. In other embodiments, $R_6$ is heteroaralkyl$_{(C \leq 18)}$ or heteroaralkyl$_{(C \leq 18)}$. In some embodiments, $R_6$ is heteroaralkyl$_{(C \leq 18)}$ such as 2-pyridinylmethyl or 4-pyridinylmethyl. In other embodiments, $R_6$ is -alkanediyl$_{(C \leq 18)}$-aralkoxy$_{(C \leq 18)}$ or substituted -alkanediyl$_{(C \leq 18)}$-aralkoxy$_{(C \leq 18)}$. In some embodiments. $R_6$ is -alkanediyl$_{(C \leq 18)}$-aralkoxy$_{(C \leq 18)}$ such as 2-(benzyloxy)ethyl.

In some embodiments, the compounds are further defined as:

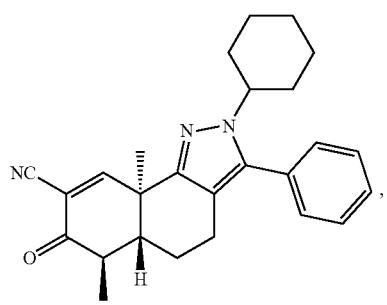,

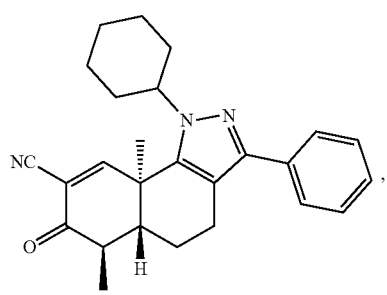,

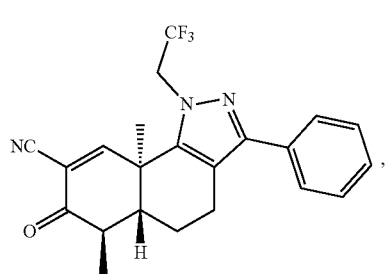,

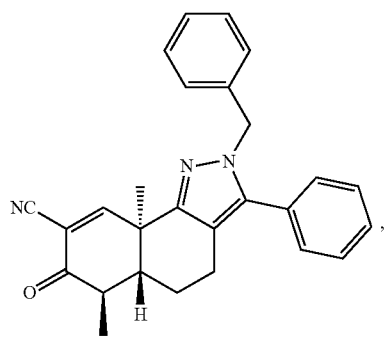,

-continued

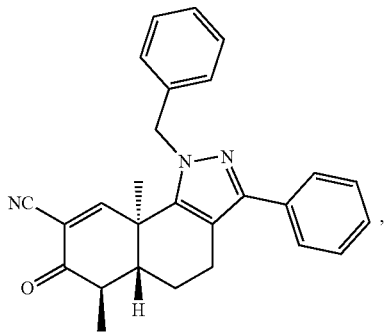,

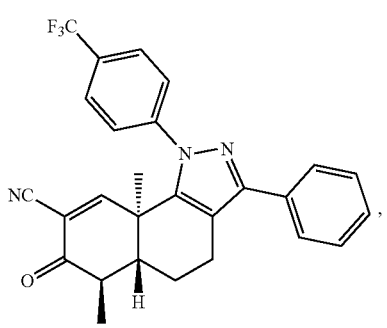,

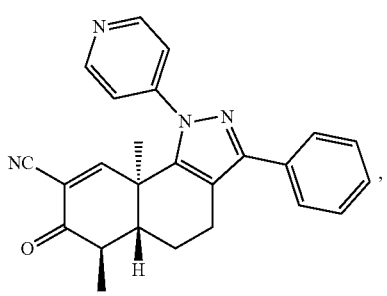,

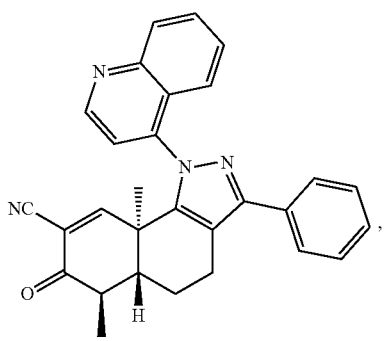,

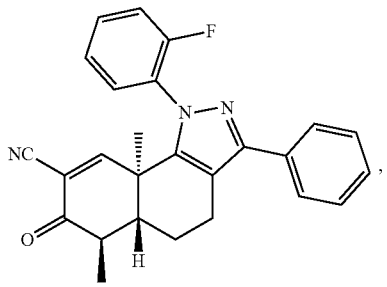,

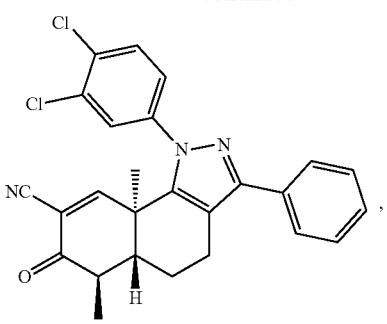,
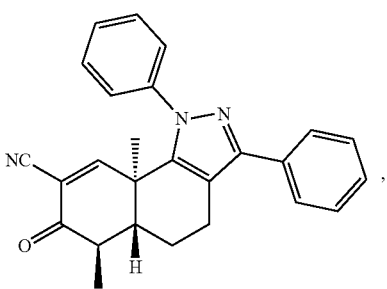,
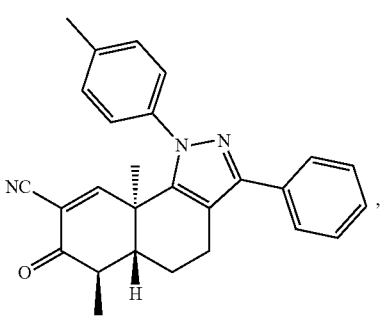,
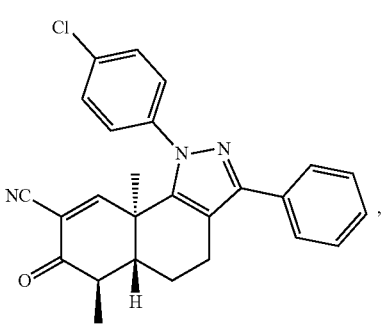,
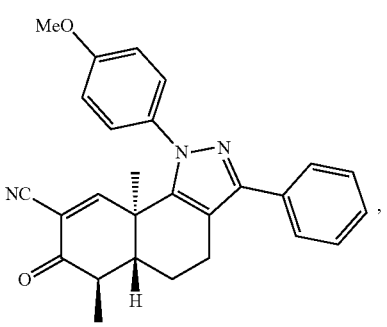,
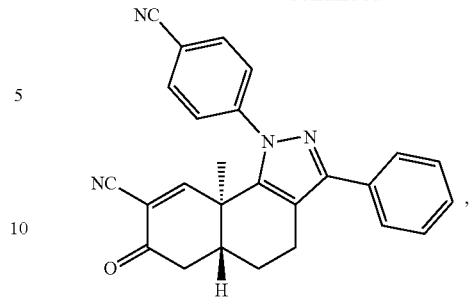,
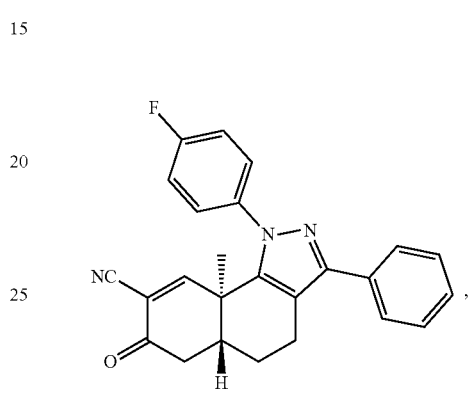,
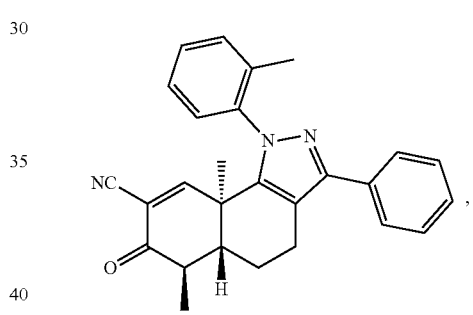,
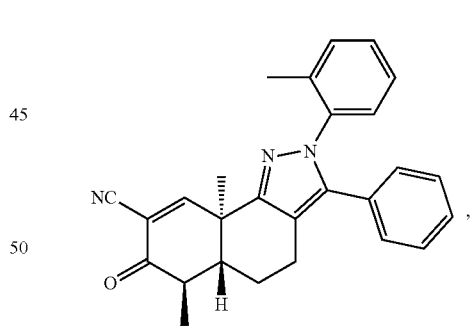,
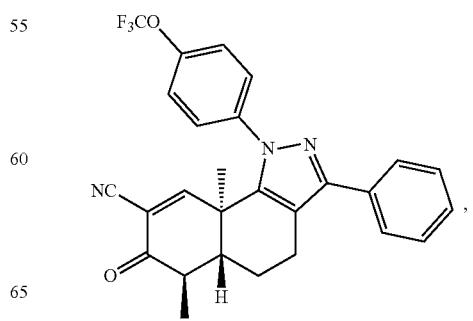, -continued
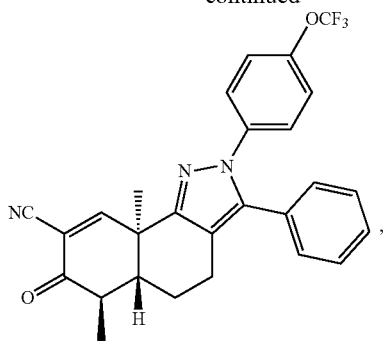
,
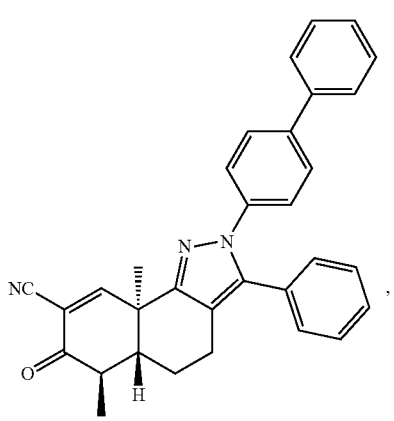
,
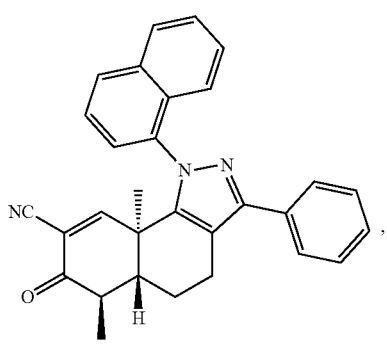
,
-continued
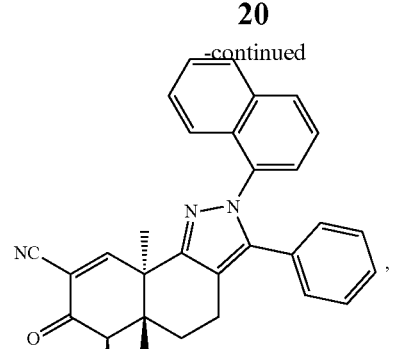
,
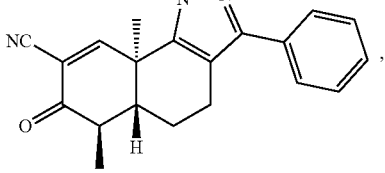
,
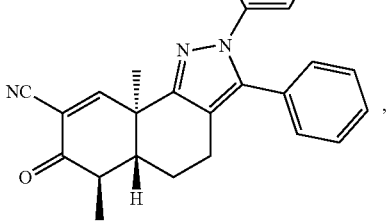
,
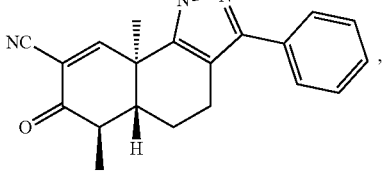
,
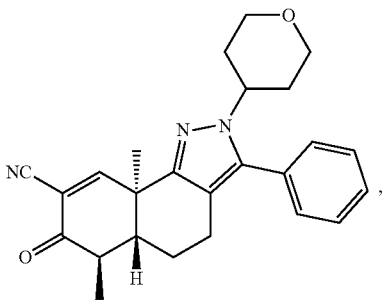
, -continued
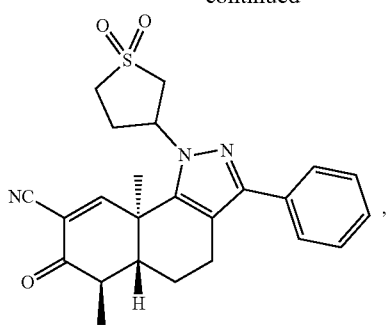
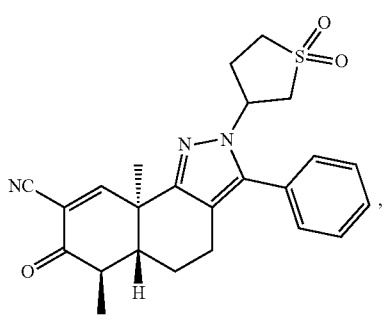
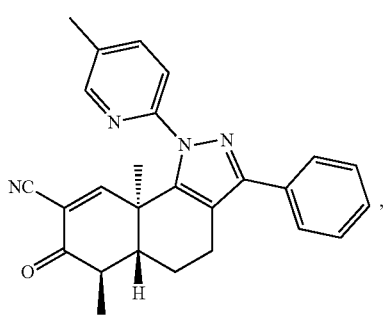
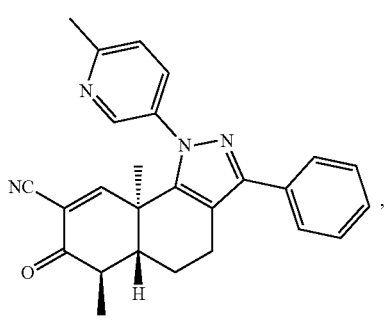
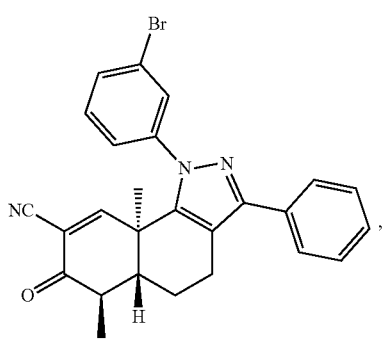
-continued
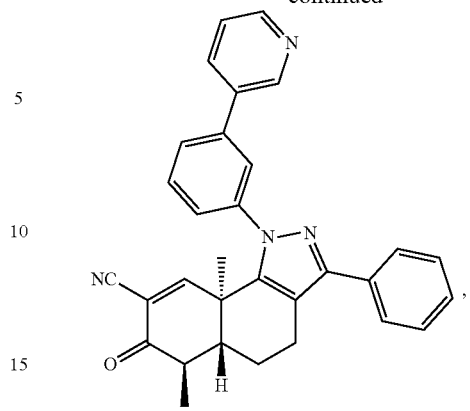
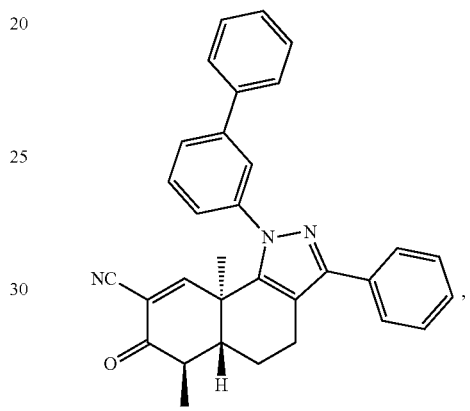
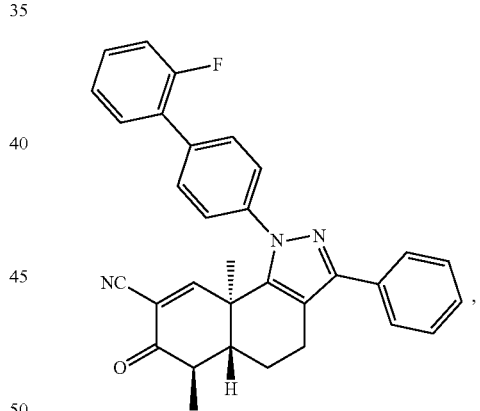
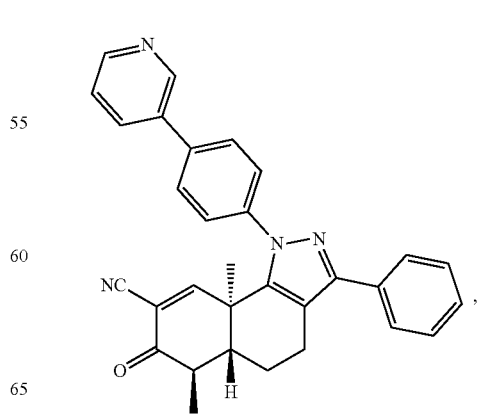

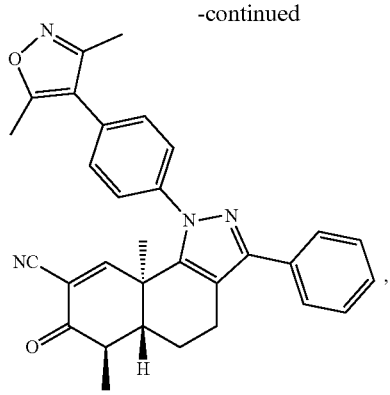
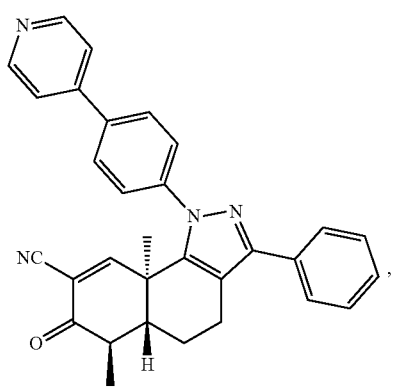
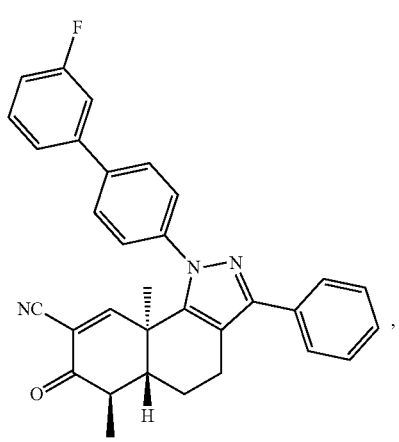
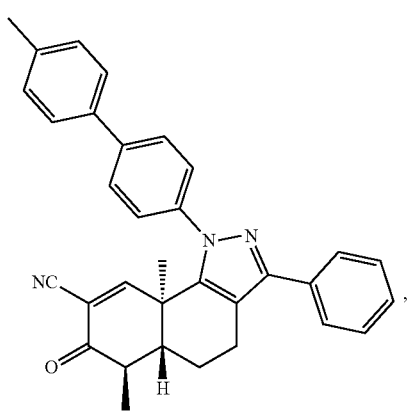
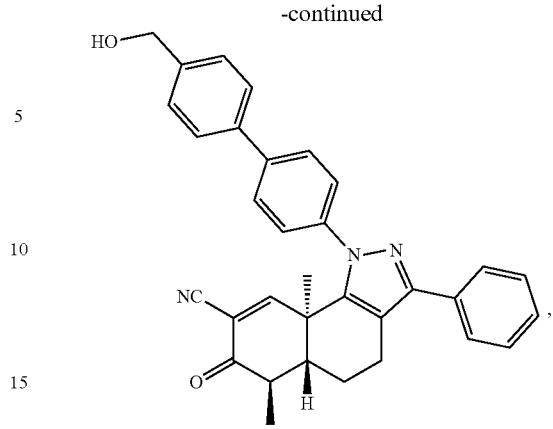
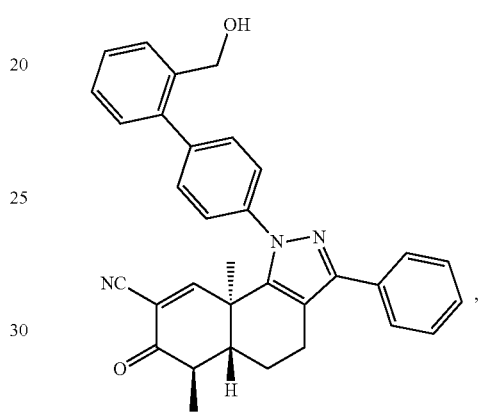
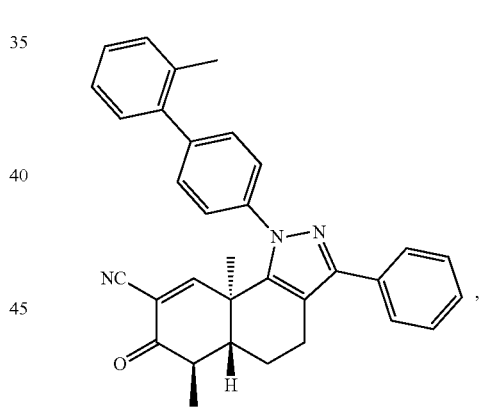
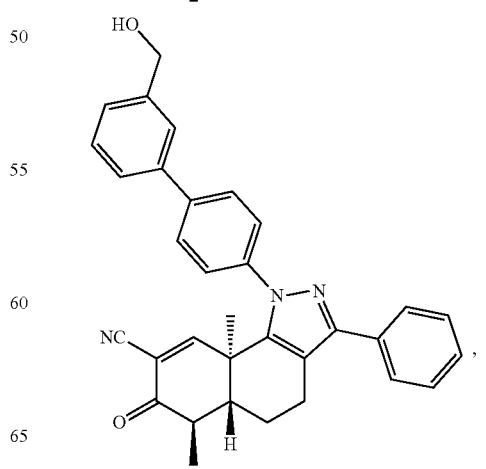

25
-continued
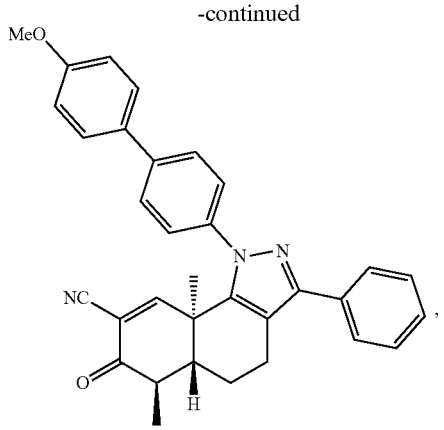
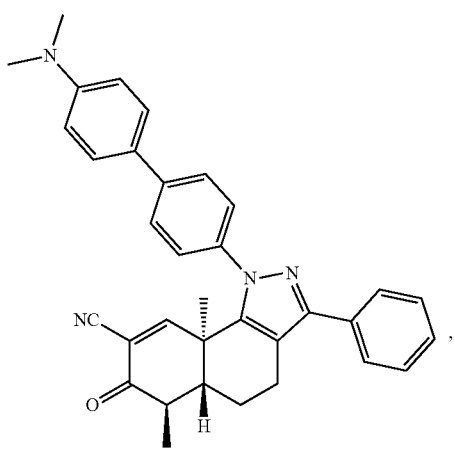
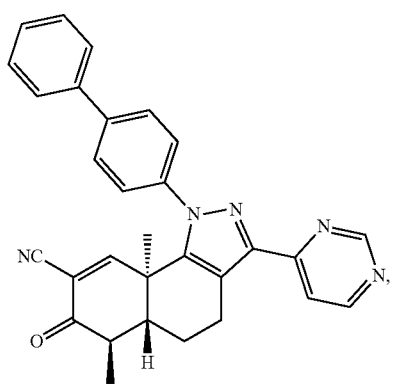
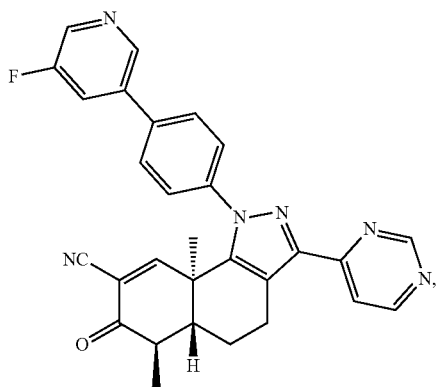
26
-continued
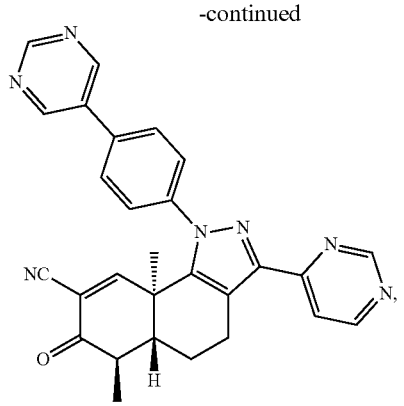
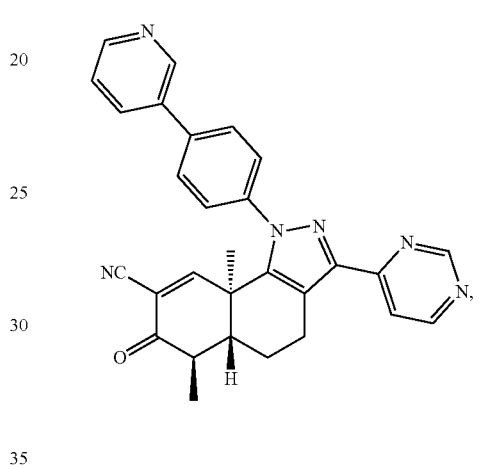
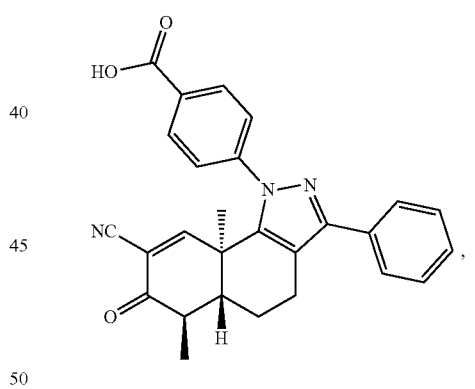
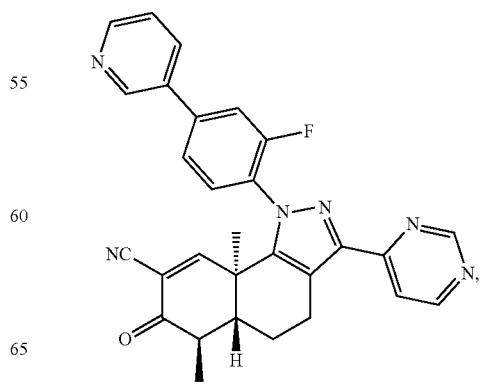

27
-continued
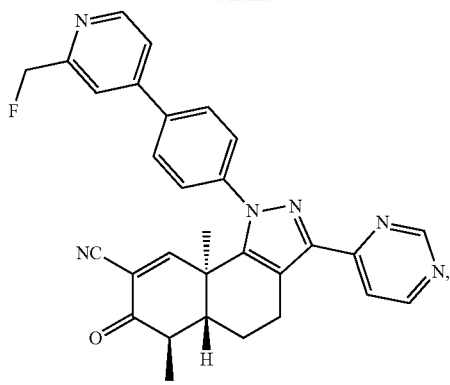
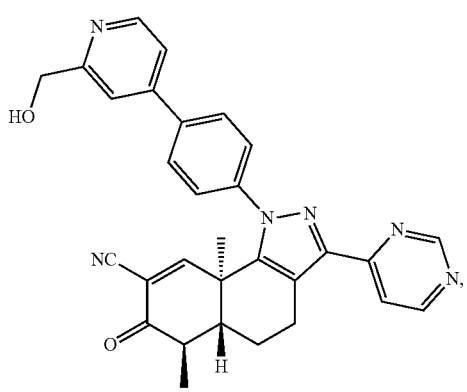
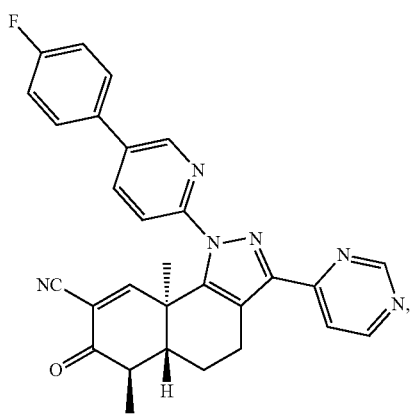
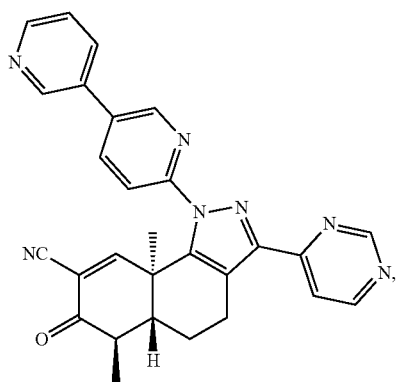
28
-continued
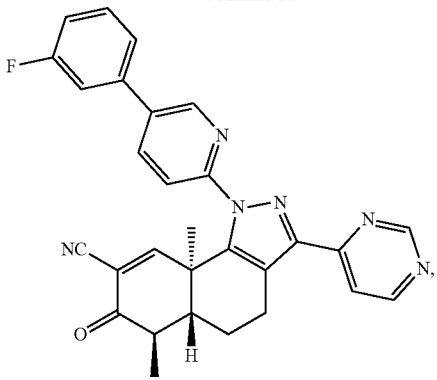
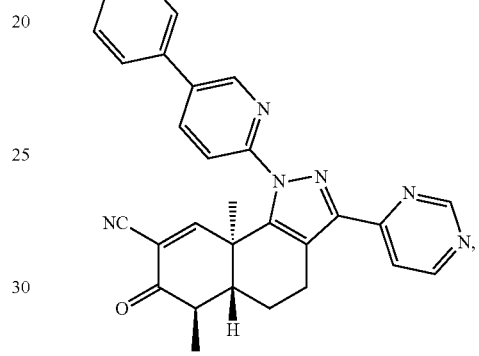
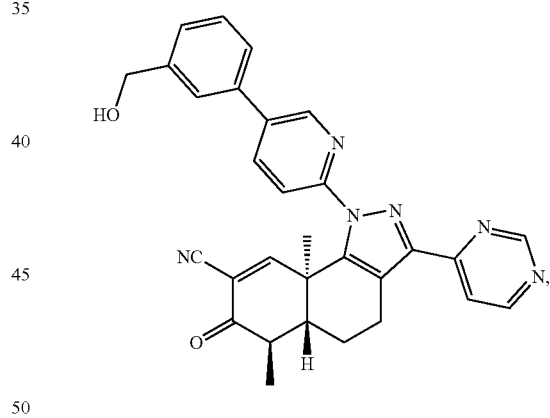
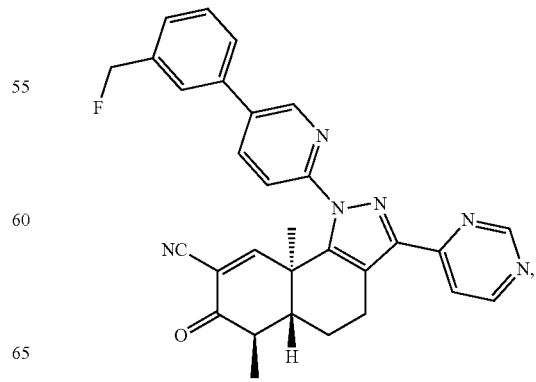

-continued
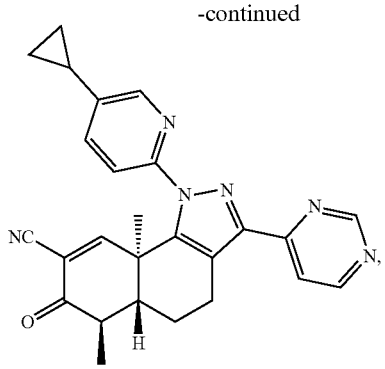
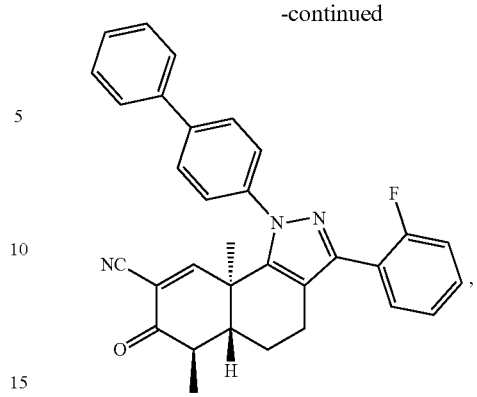
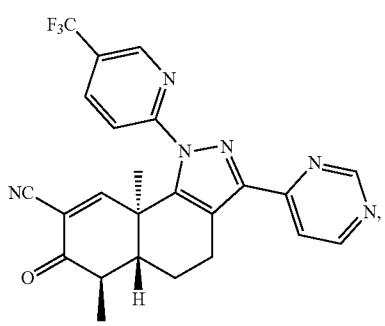
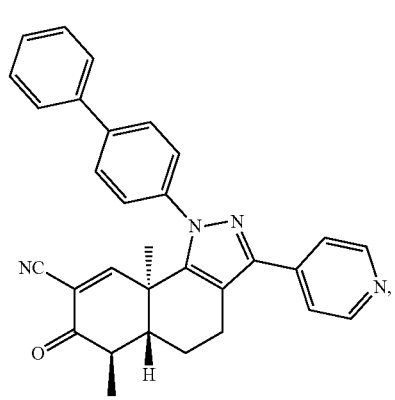
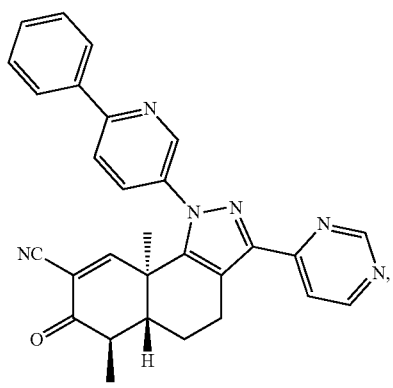
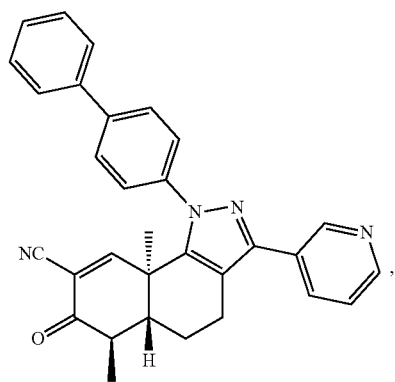
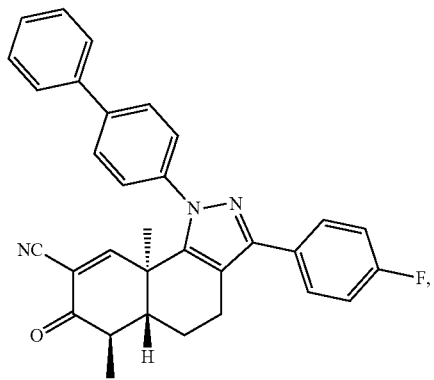
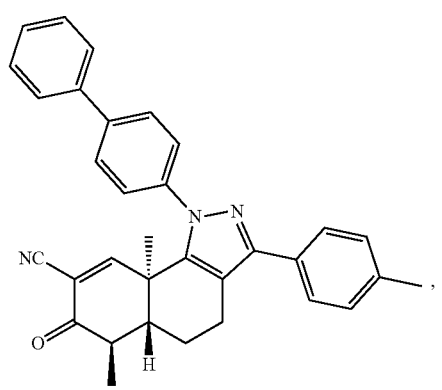

31
-continued
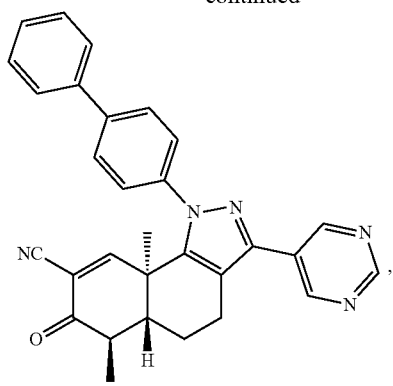
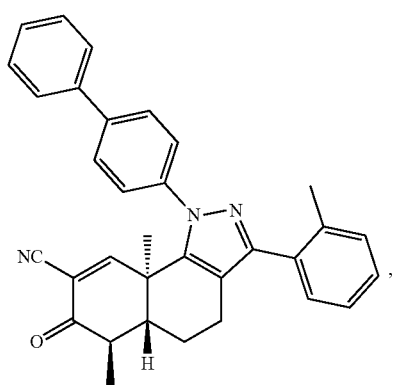
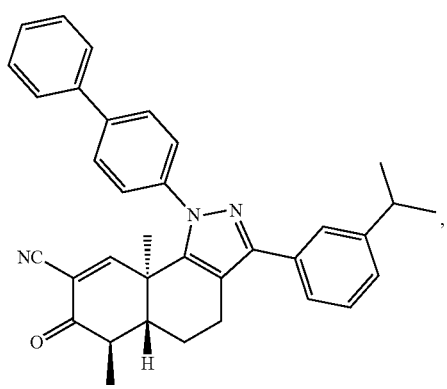
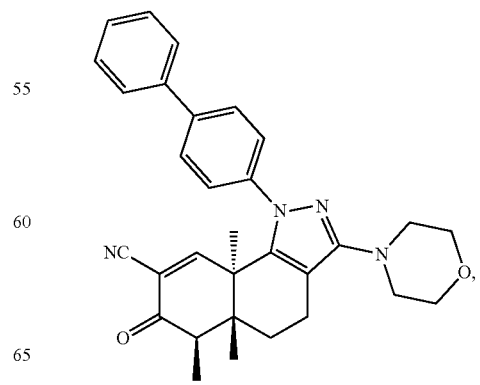
32
-continued
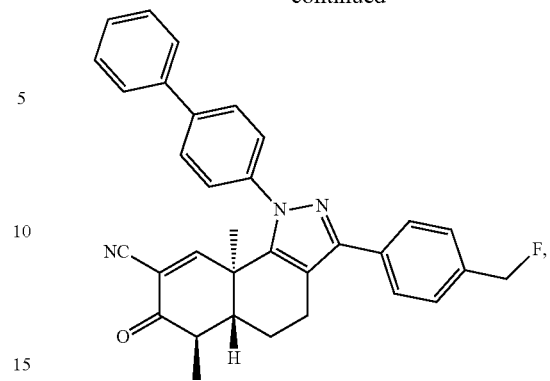
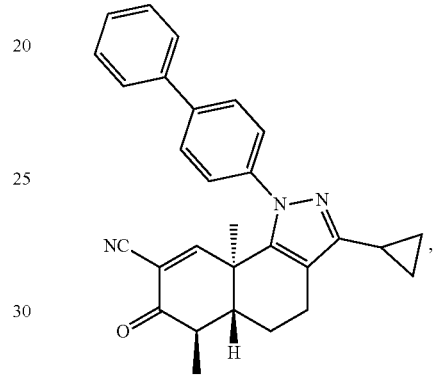
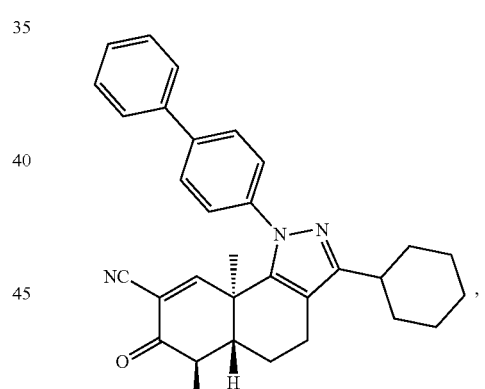

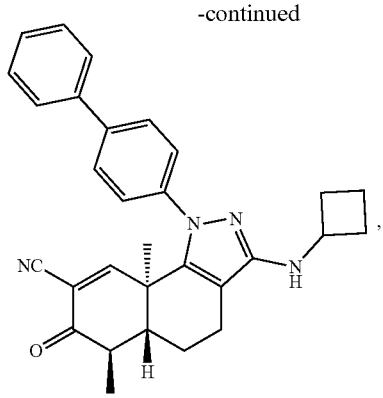
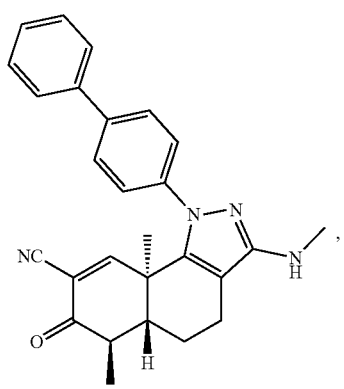
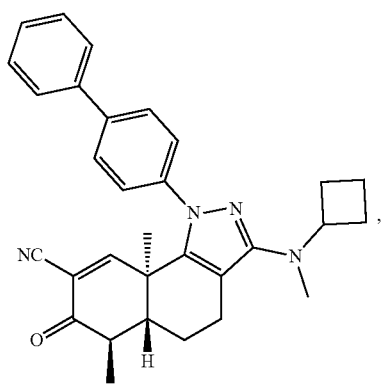
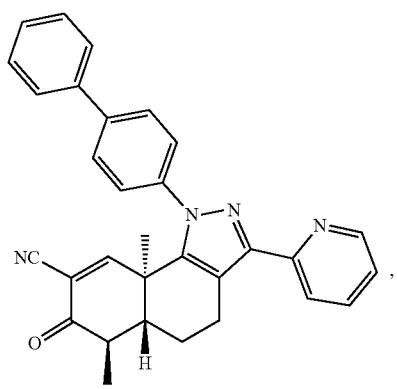
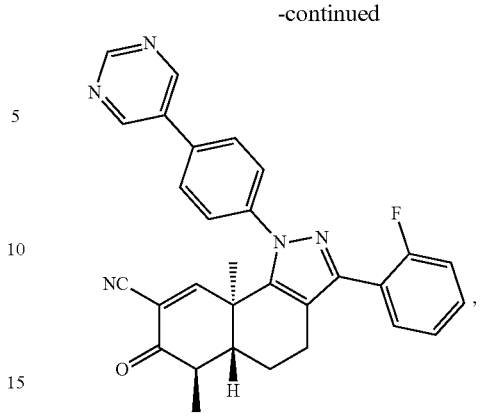
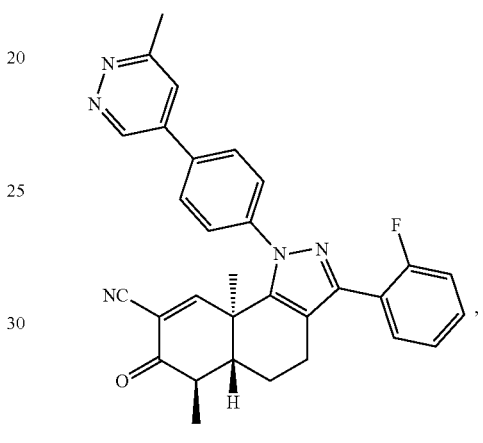
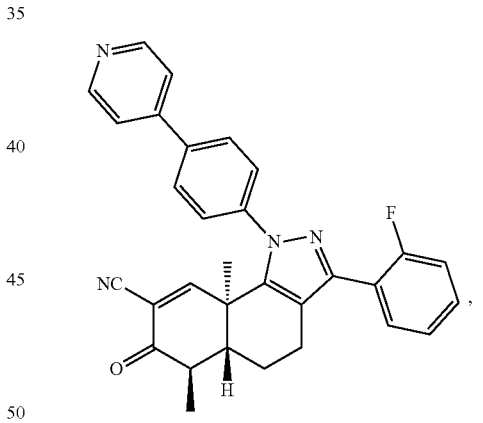
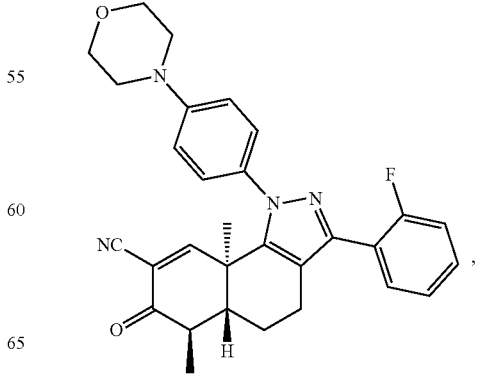

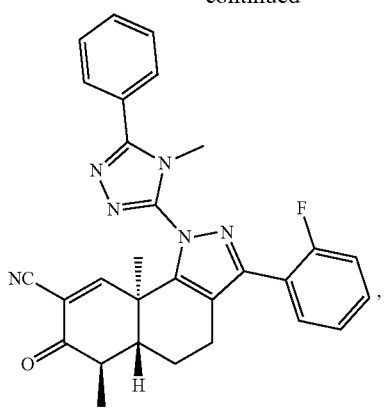
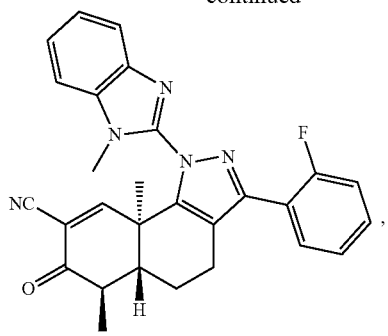
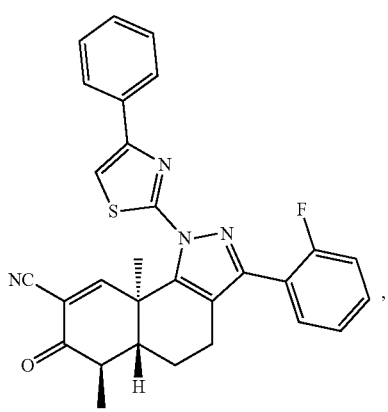
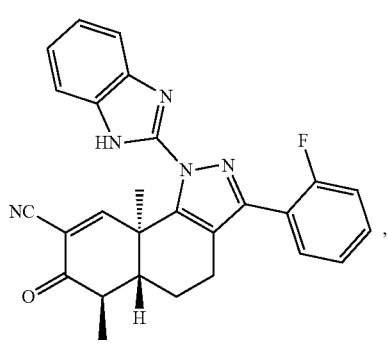
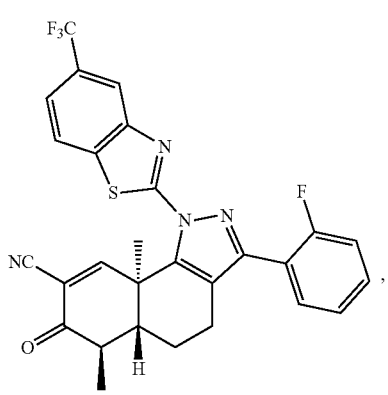
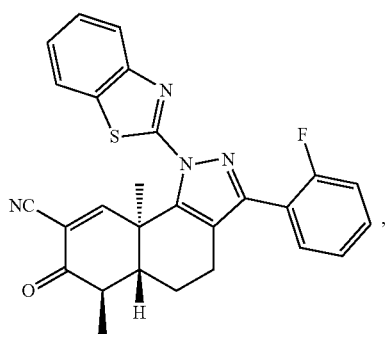
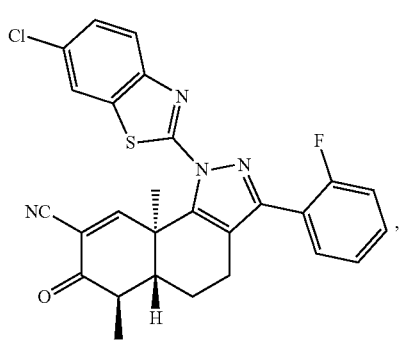
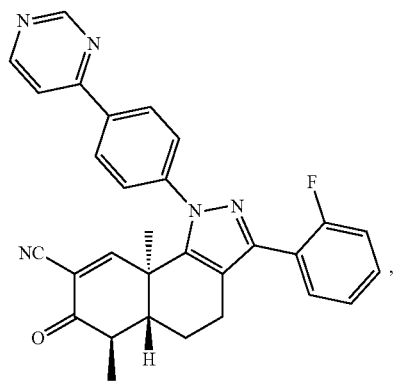

37
-continued
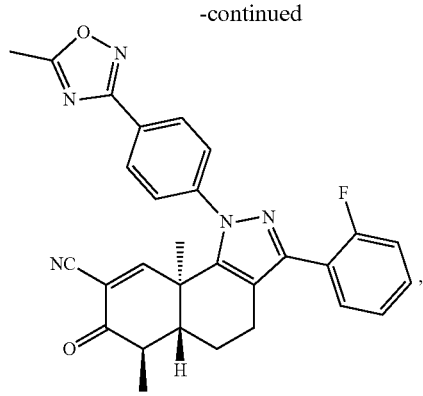
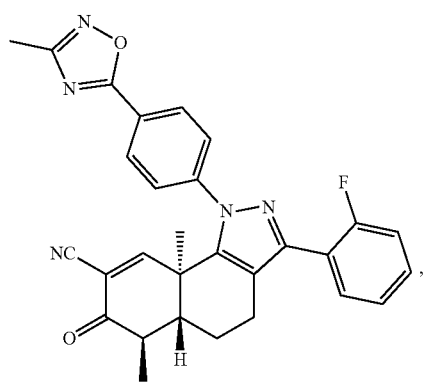
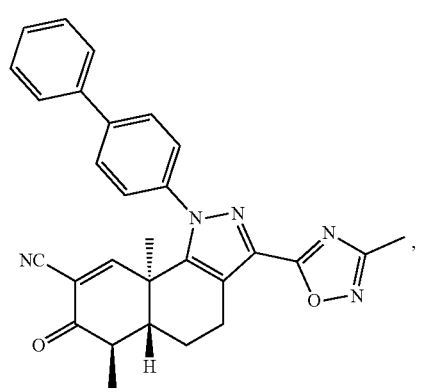
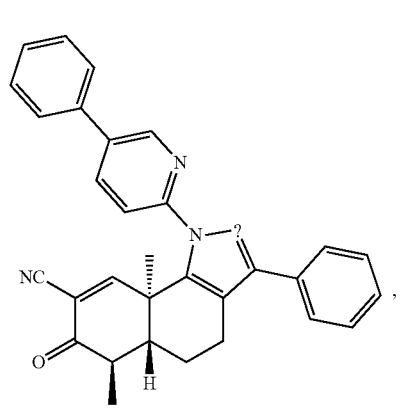
38
-continued
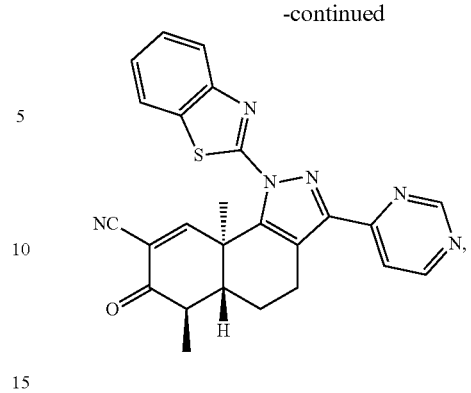
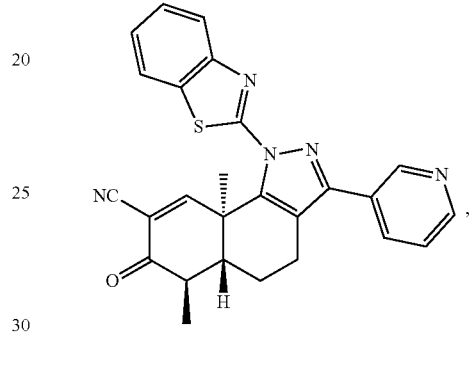
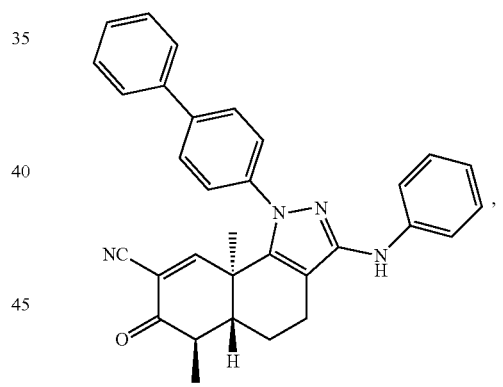
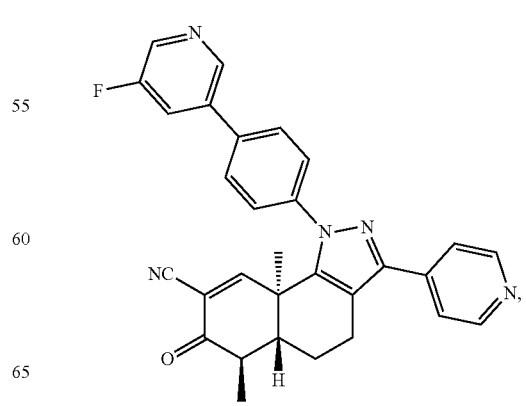

39
-continued
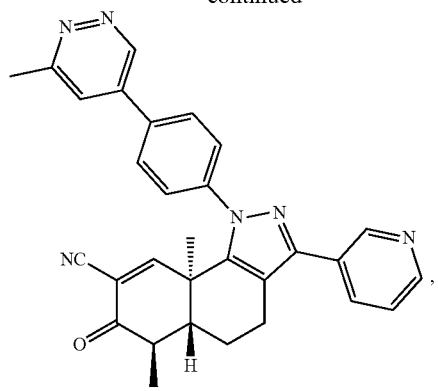
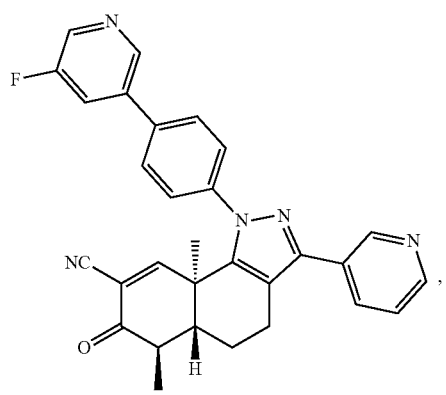
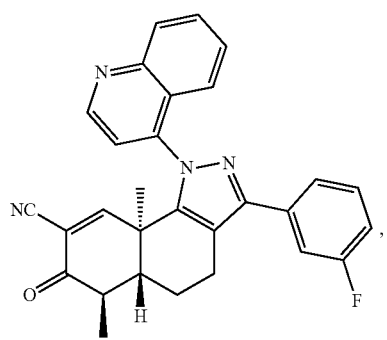
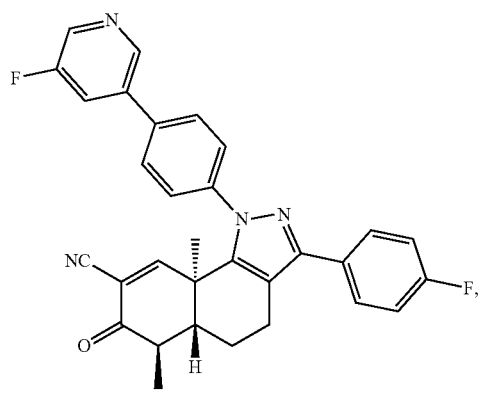
40
-continued
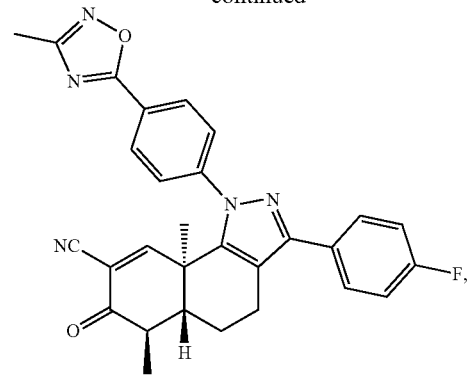
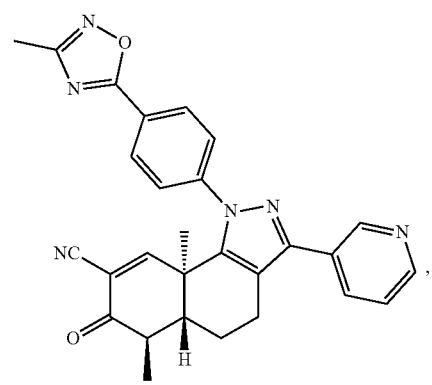
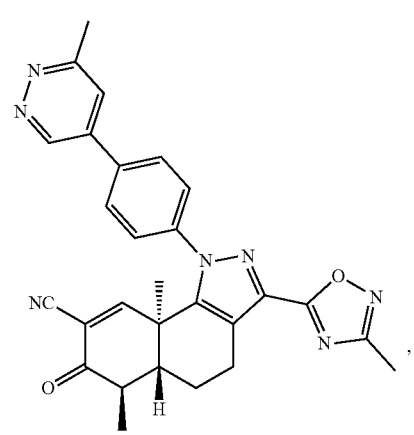
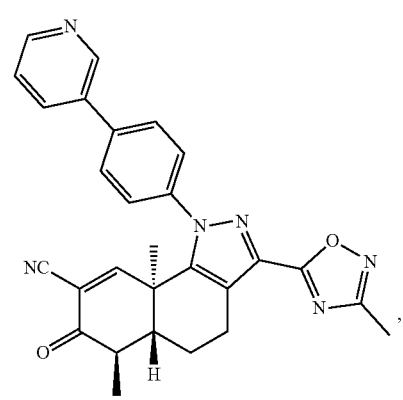

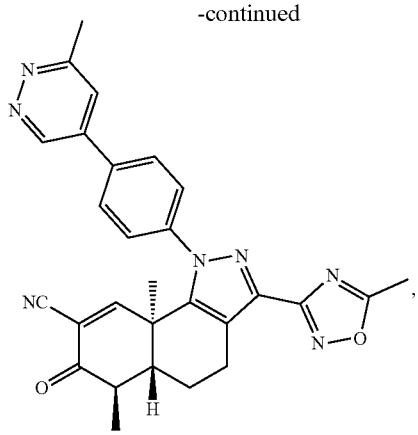
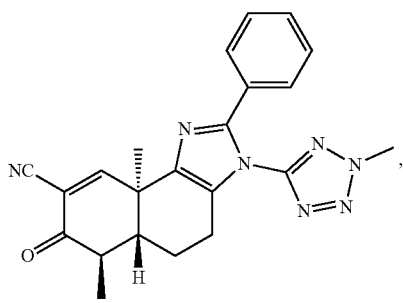
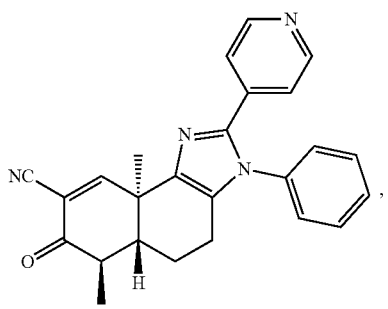
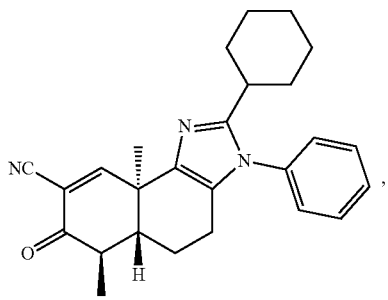
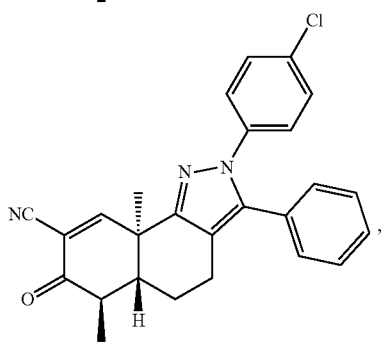
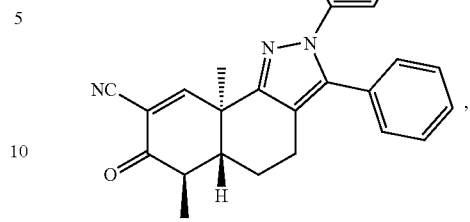
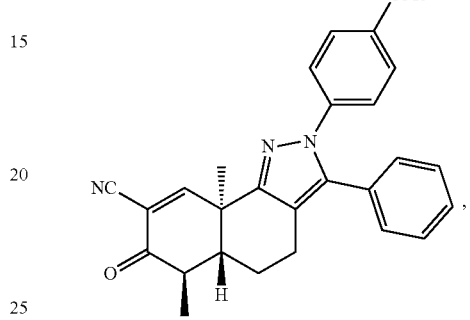
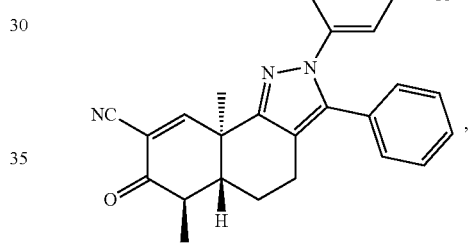
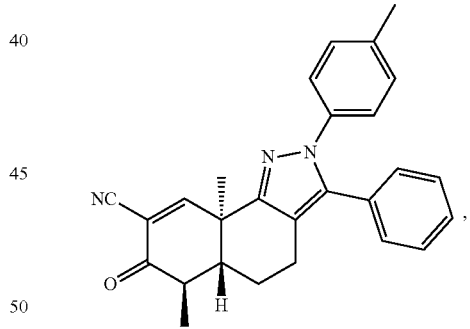
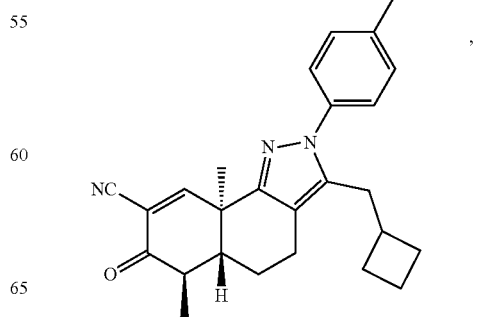

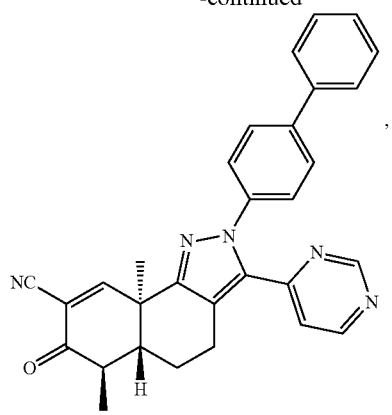
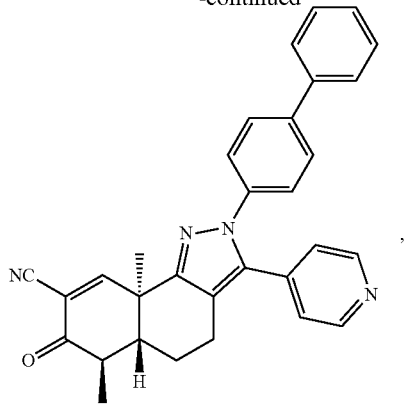
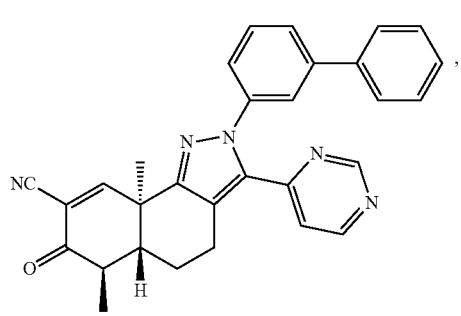
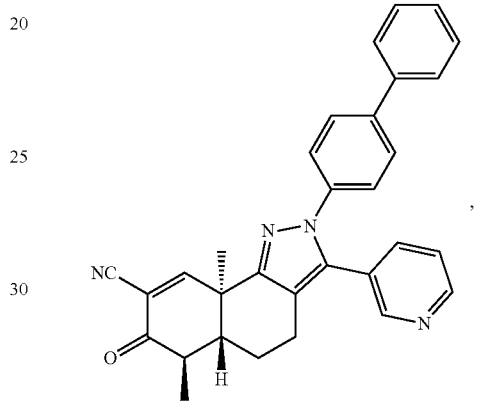
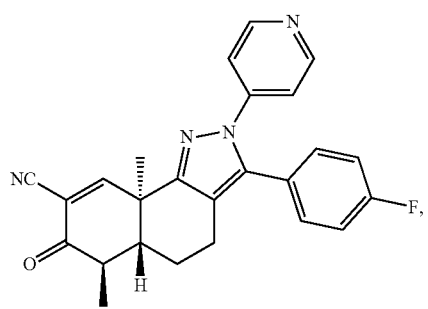
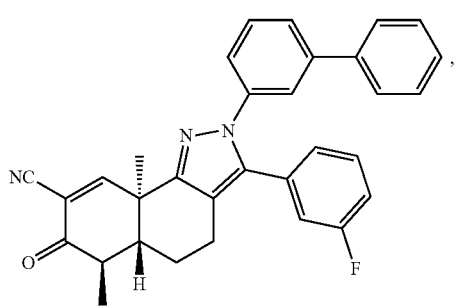
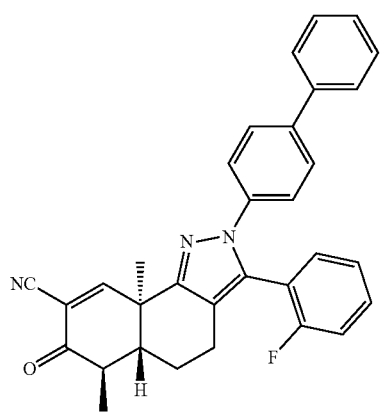
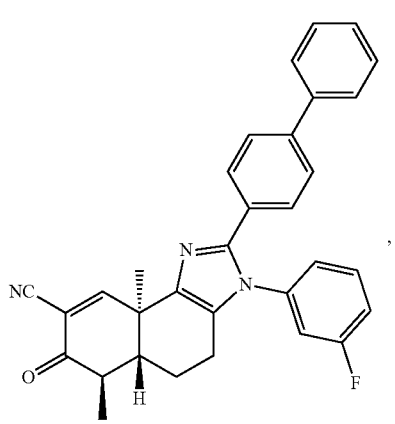

-continued
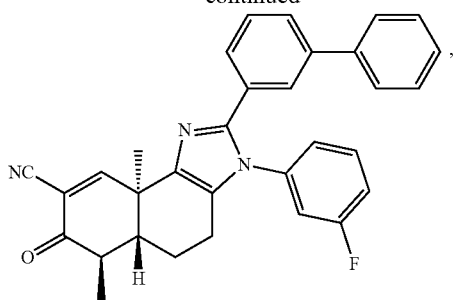,
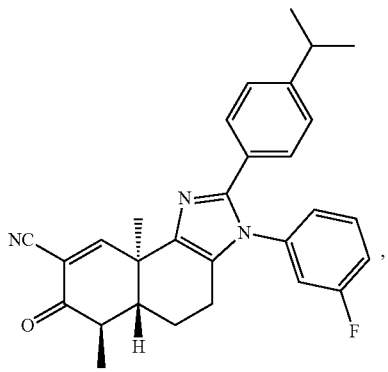,
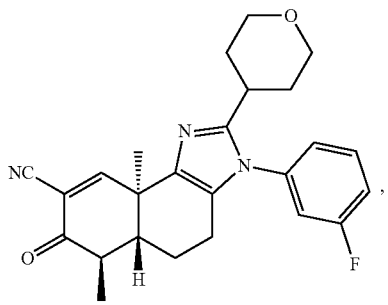,
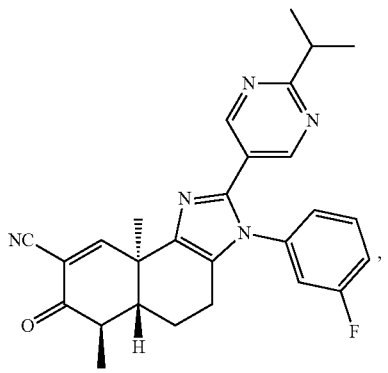,
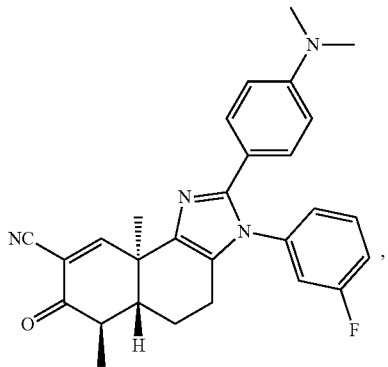,
-continued
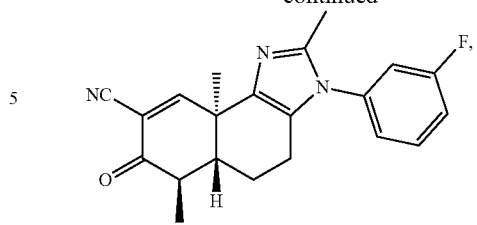,
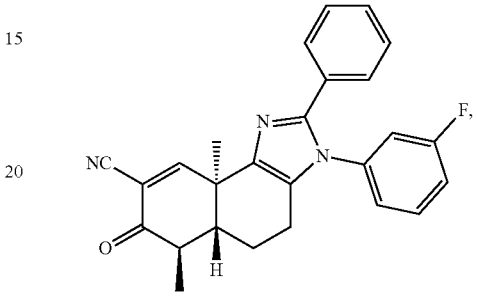,
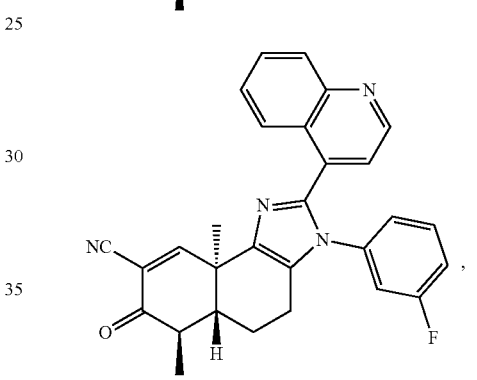,
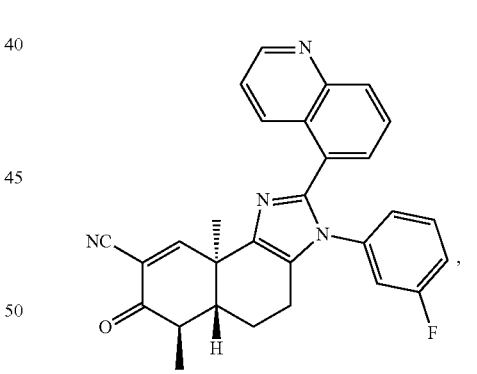,
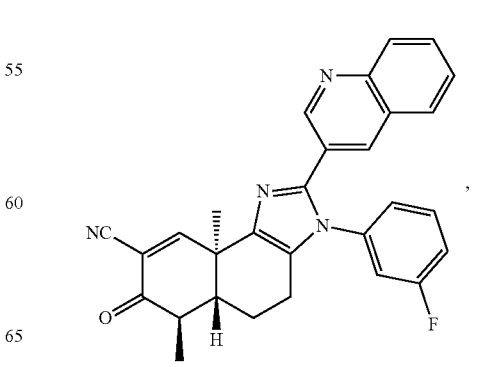, -continued
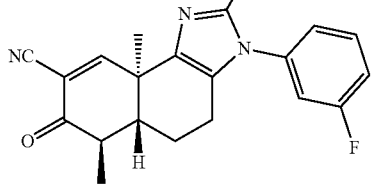
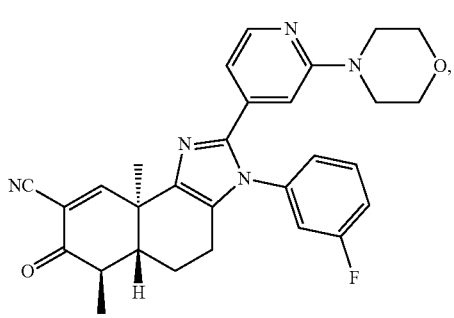
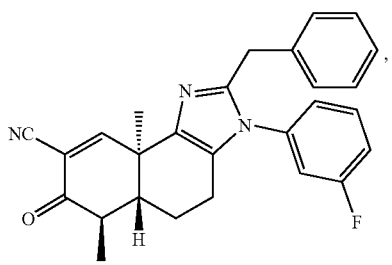
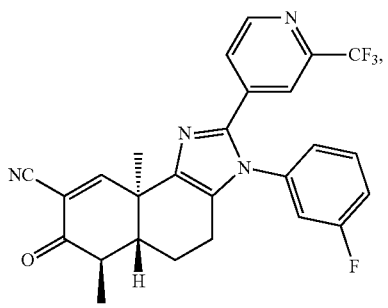
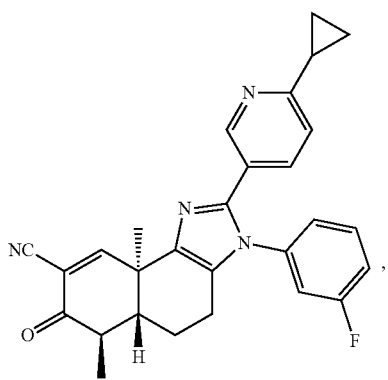
-continued
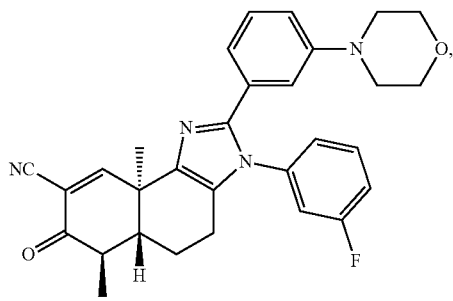
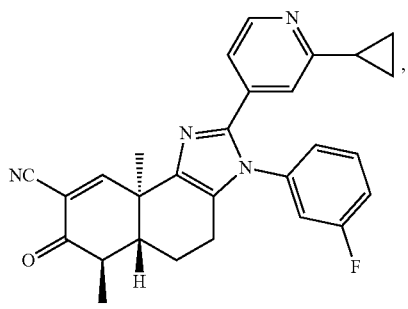
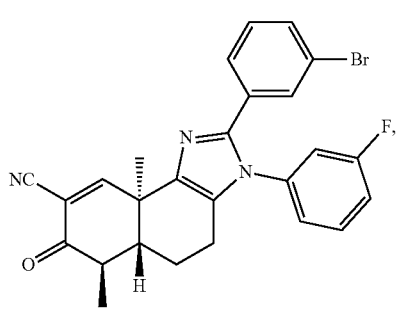
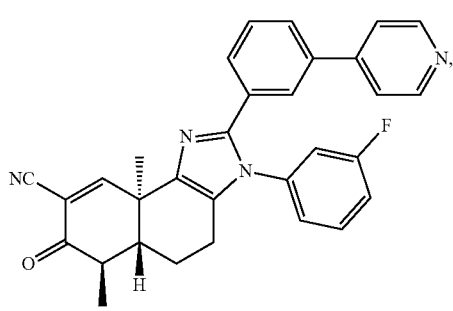
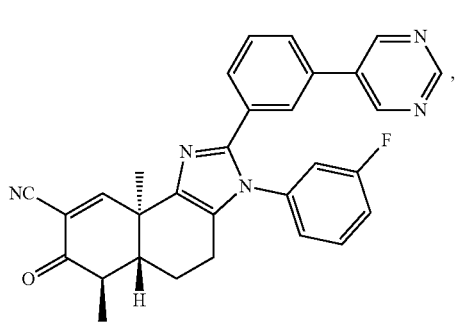

-continued

51
-continued
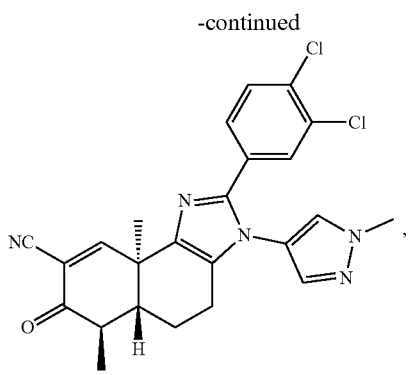
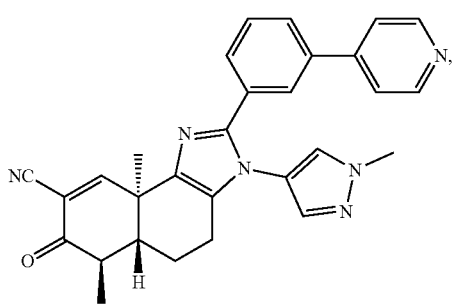
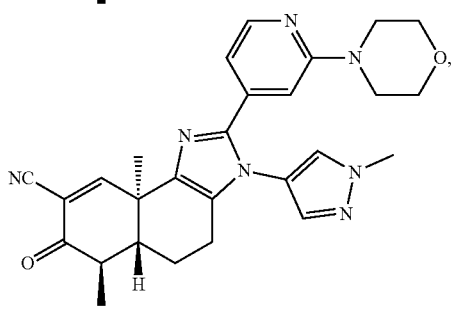
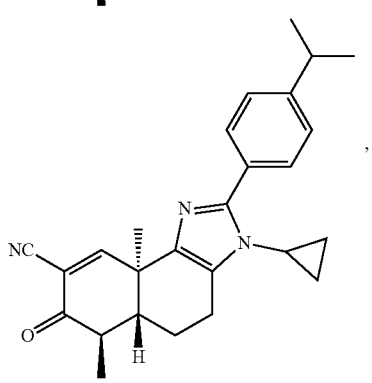
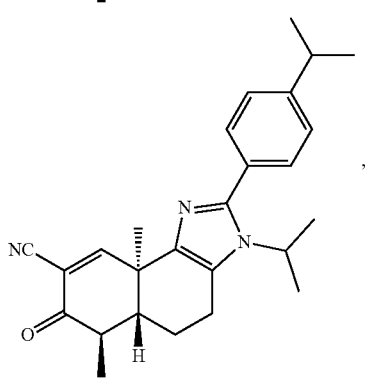
52
-continued
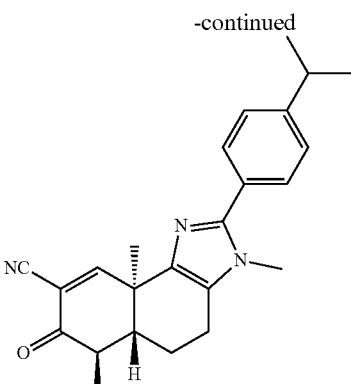
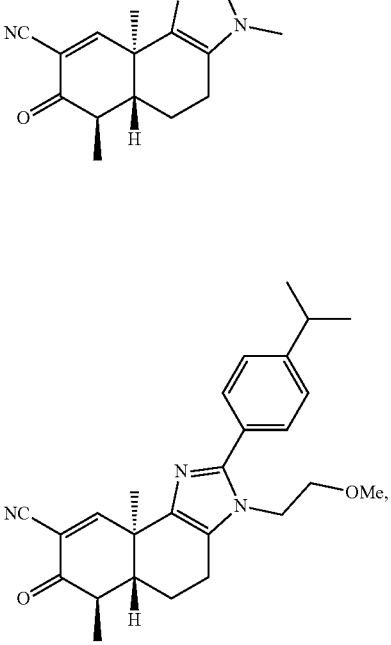
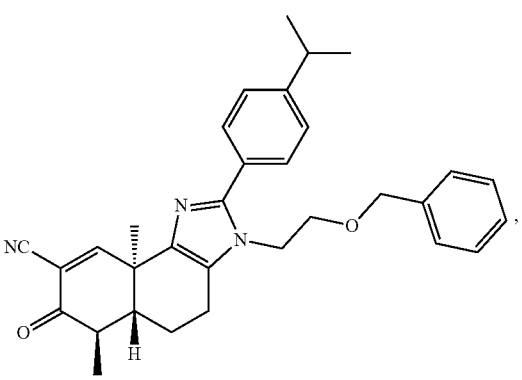
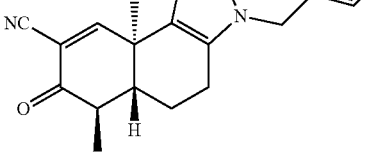

-continued
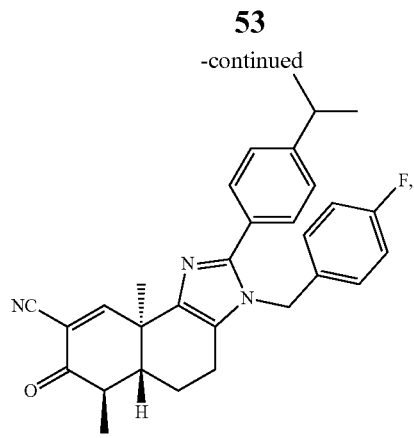
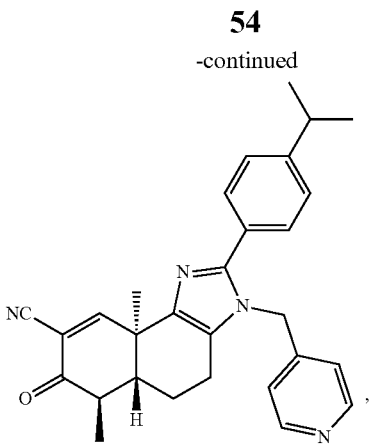
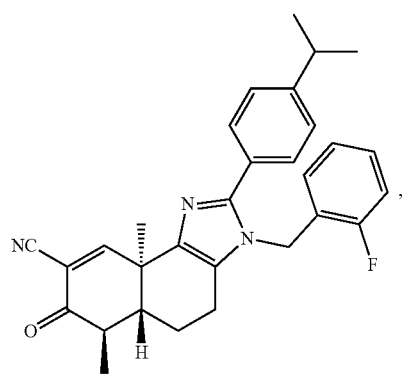
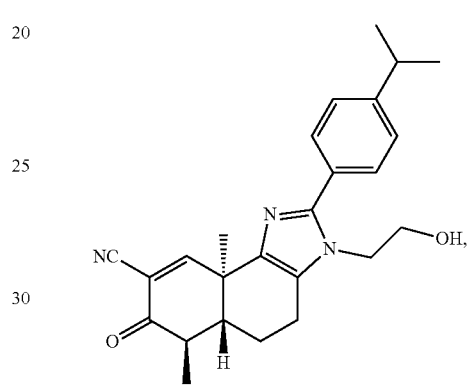
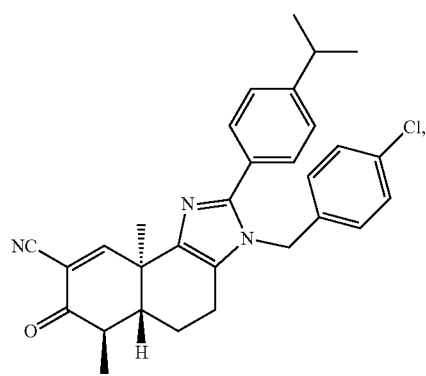
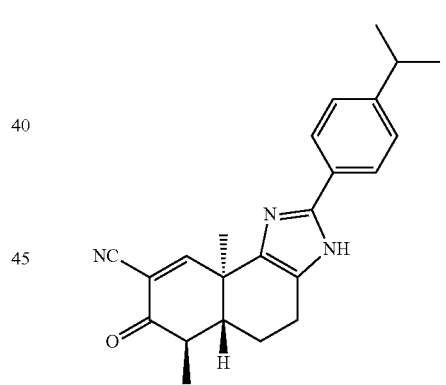
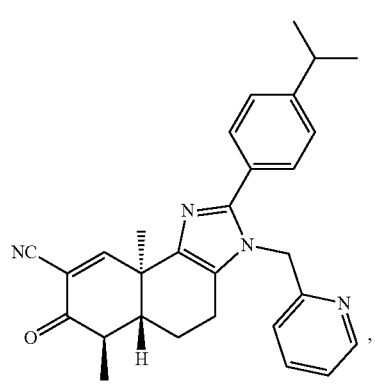
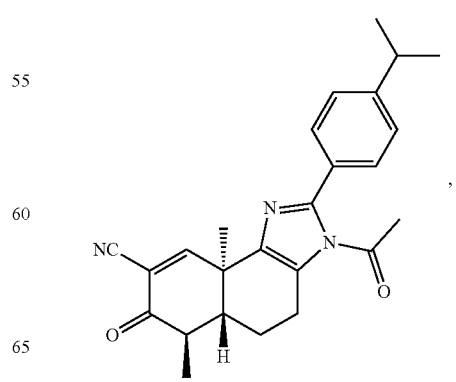

-continued
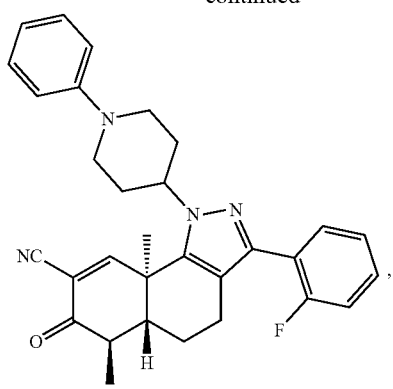
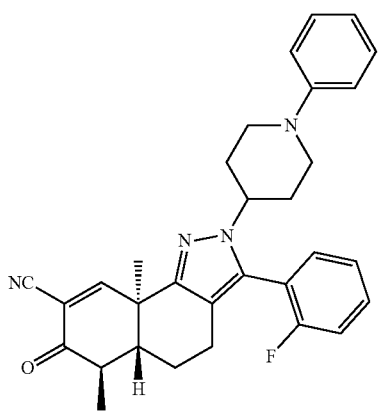
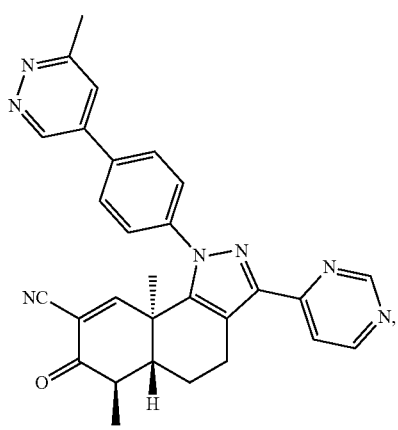
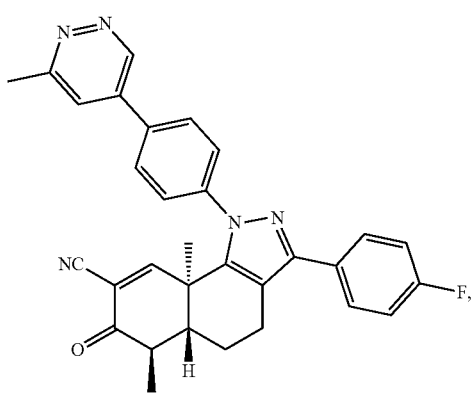
-continued
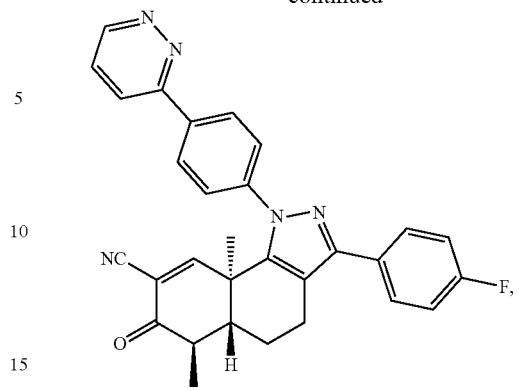
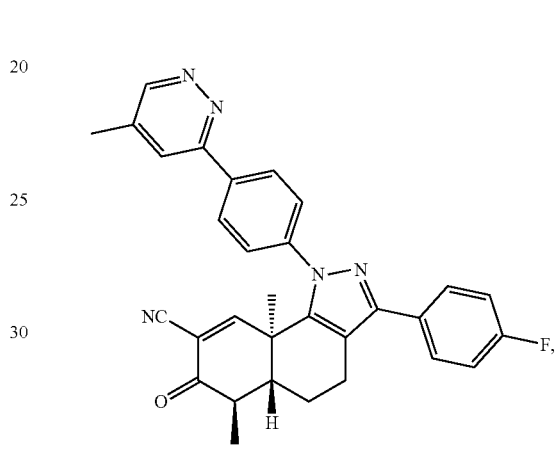
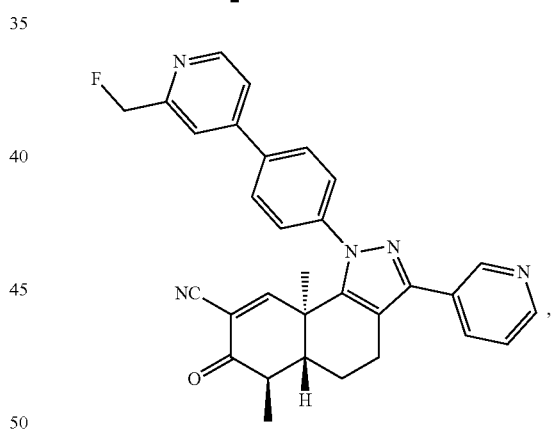
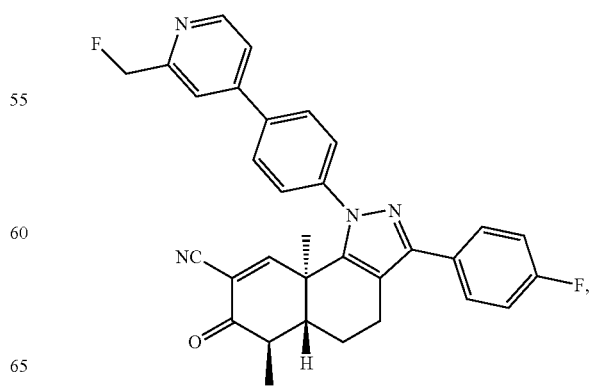

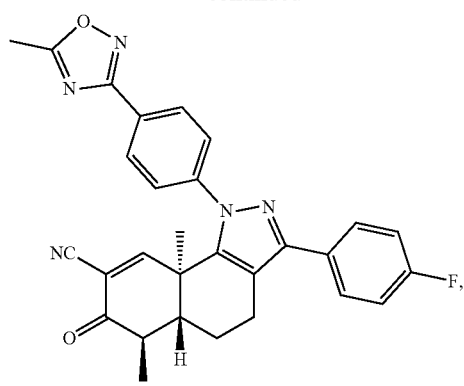
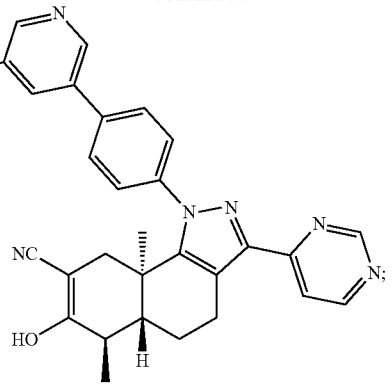
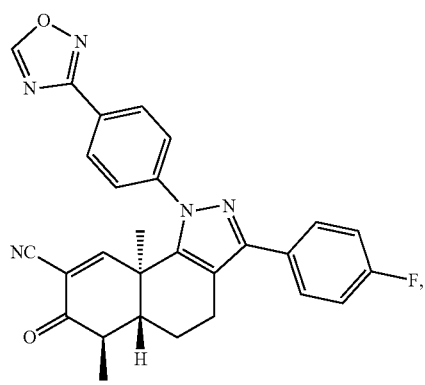
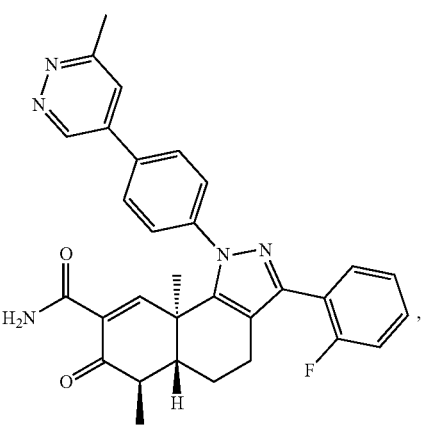
or a pharmaceutically acceptable salt of any of the above formulas.
In some embodiments, the compounds may be further defined as:
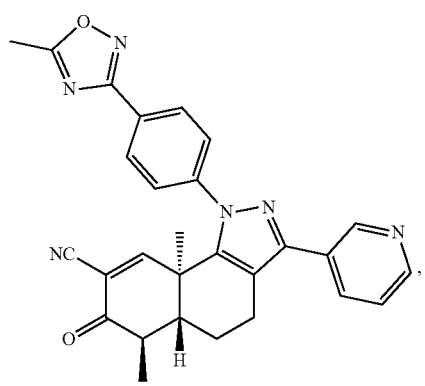
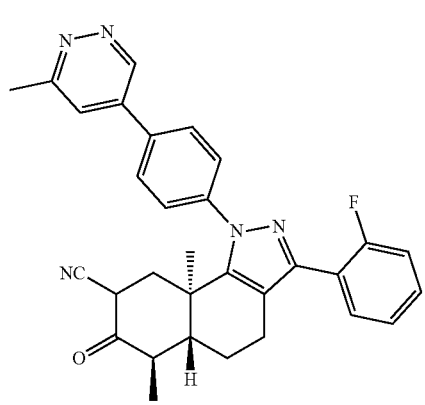
or
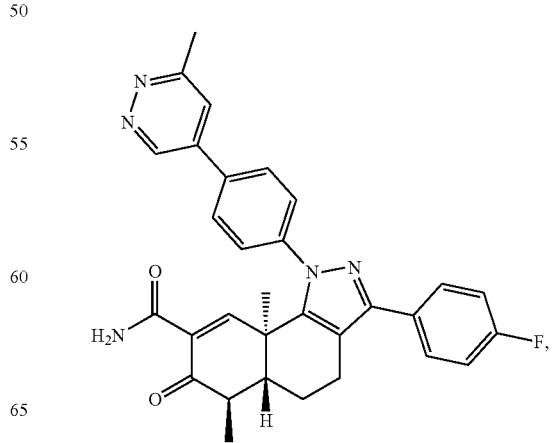

-continued

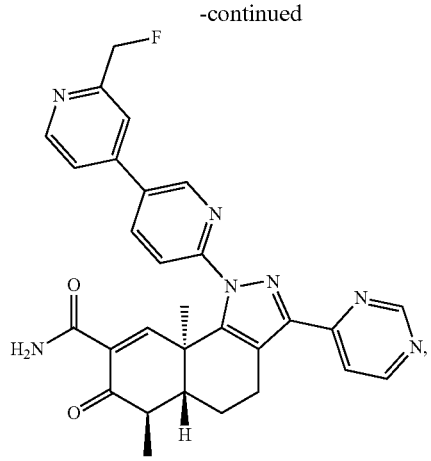

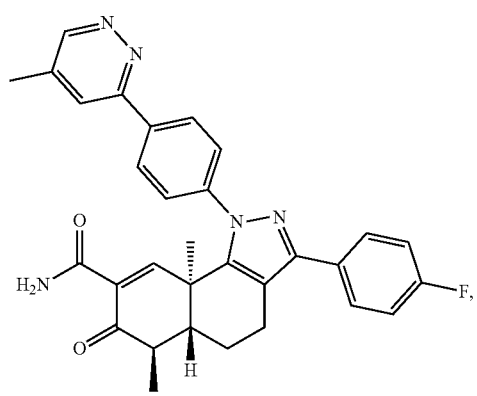

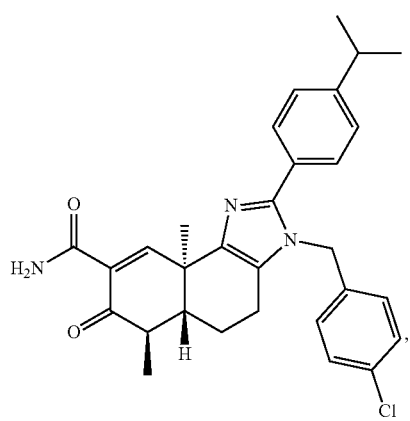

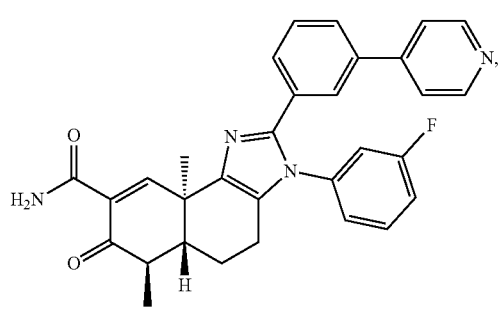

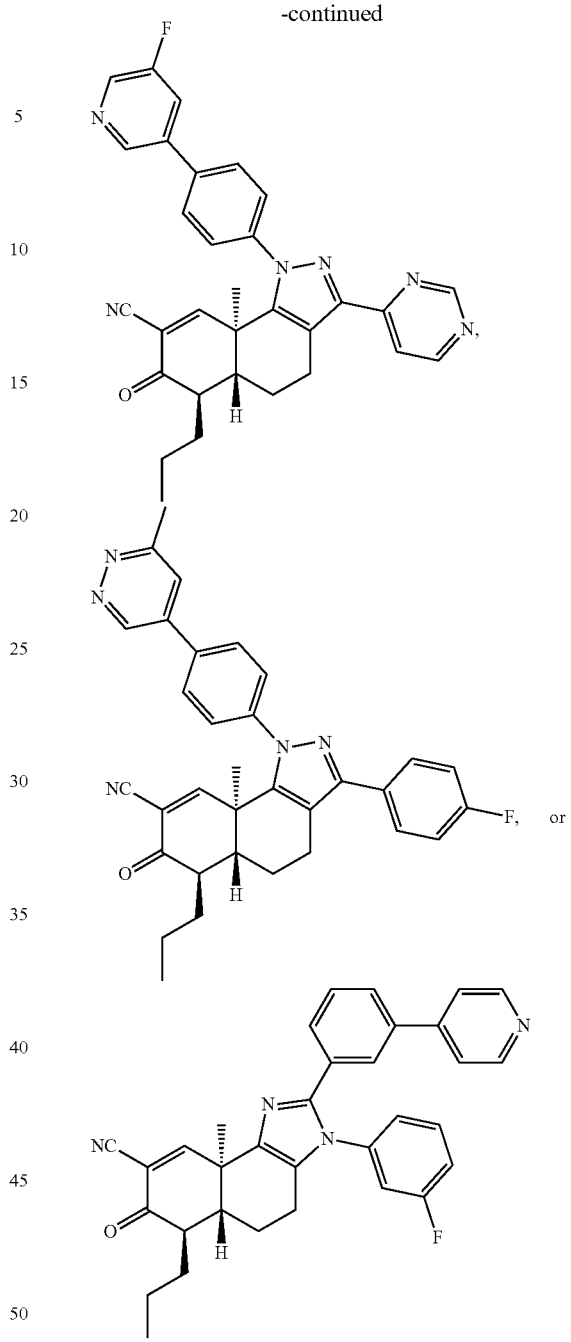

or a pharmaceutically acceptable salt of any of the above formulas.

In some aspects, the present disclosure provides compounds of the formula:

(5aR,6R,9aS)-2-cyclohexyl-6,9a-dimethyl-7-oxo-3-phenyl-4,5,5a,6,7,9a-hexahydro-2H-benzo[g]indazole-8-carbonitrile;

(5aR,6R,9aS)-1-cyclohexyl-6,9a-dimethyl-7-oxo-3-phenyl-4,5,5a,6,7,9a-hexahydro-1H-benzo[g]indazole-8-carbonitrile;

(5aR,6R,9aS)-6,9a-dimethyl-7-oxo-3-phenyl-1-(2,2,2-trifluoroethyl)-4,5,5a,6,7,9a-hexahydro-1H-benzo[g]indazole-8-carbonitrile;

(5aR,6R,9aS)-2-benzyl-6,9a-dimethyl-7-oxo-3-phenyl-4,5,5a,6,7,9a-hexahydro-2H-benzo[g]indazole-8-carbonitrile;

(5aR,6R,9a)-1-benzyl-6,9a-dimethyl-7-oxo-3-phenyl-4,5,5a,6,7,9a-hexahydro-1H-benzo[g]indazole-8-carbonitrile;

(5aR,6R,9aS)-6,9a-dimethyl-7-oxo-3-phenyl-1-(4-(trifluoromethyl)phenyl)-4,5,5a,6,7,9a-hexahydro-1H-benzo[g]indazole-8-carbonitrile;

(5aR,6R,9aS)-6,9a-dimethyl-7-oxo-3-phenyl-1-(pyridin-4-yl)-4,55a,6,7,9a-hexahydro-1H-benzo[g]indazole-8-carbonitrile;

(5aR,6R,9aS)-6,9a-dimethyl-7-oxo-3-phenyl-1-(quinolin-4-yl)-4,5,5a,6,7,9a-hexahydro-1H-benzo[g]indazole-8-carbonitrile;

(5aR,6R,9aS)-1-(2-fluorophenyl)-6,9a-dimethyl-7-oxo-3-phenyl-4,5,5a,6,7,9a-hexahydro-1H-benzo[g]indazole-8-carbonitrile;

(5aR,6R,9aS)-1-(3,4-dichlorophenyl)-6,9a-dimethyl-7-oxo-3-phenyl-4,5,5a,6,7,9a-hexahydro-1H-benzo[g]indazole-8-carbonitrile;

(5aR,6R,9aS)-6,9a-dimethyl-7-oxo-1,3-diphenyl-4,5,5a,6,7,9a-hexahydro-1H-benzo[g]indazole-8-carbonitrile;

(5aR,6R,9aS)-6,9a-dimethyl-7-oxo-3-phenyl-1-(p-tolyl)-4,5,5a,6,7,9a-hexahydro-1H-benzo[g]indazole-8-carbonitrile;

(5aR,6R,9aS)-1-(4-chlorophenyl)-6,9a-dimethyl-7-oxo-3-phenyl-4,5,5a,6,7,9a-hexahydro-1H-benzo[g]indazole-8-carbonitrile;

(5aR,6R,9aS)-1-(4-methoxyphenyl)-6,9a-dimethyl-7-oxo-3-phenyl-4,5,5a,6,7,9a-hexahydro-1H-benzo[g]indazole-8-carbonitrile;

(5aR,9aS)-1-(4-cyanophenyl)-9a-methyl-7-oxo-3-phenyl-4,5,5a,6,7,9a-hexahydro-1H-benzo[g]indazole-8-carbonitrile;

(5aR,9aS)-1-(4-fluorophenyl)-9a-methyl-7-oxo-3-phenyl-4,5,5a,6,7,9a-hexahydro-1H-benzo[g]indazole-8-carbonitrile;

(5aR,6R,9aS)-6,9a-dimethyl-7-oxo-3-phenyl-1-(o-tolyl)-4,5,5a,6,7,9a-hexahydro-1H-benzo[g]indazole-8-carbonitrile;

(5aR,6R,9aS)-6,9a-dimethyl-7-oxo-3-phenyl-2-(o-tolyl)-4,5,5a,6,7,9a-hexahydro-2H-benzo[g]indazole-8-carbonitrile;

(5aR,6R,9aS)-6,9a-dimethyl-7-oxo-3-phenyl-1-(4-(trifluoromethoxy)phenyl)-4,5,5a,6,7,9a-hexahydro-1H-benzo[g]indazole-8-carbonitrile;

(5aR,6R,9aS)-6,9a-dimethyl-7-oxo-3-phenyl-2-(4-(trifluoromethoxy)phenyl)-4,5,5a,6,7,9a-hexahydro-2H-benzo[g]indazole-8-carbonitrile;

(5aR,6R,9aS)-1-([1,1'-biphenyl]-4-yl)-6,9a-dimethyl-7-oxo-3-phenyl-4,5,5a,6,7,9a-hexahydro-1H-benzo[g]indazole-8-carbonitrile;

(5aR,6R,9aS)-2-([1,1'-biphenyl]-4-yl)-6,9a-dimethyl-7-oxo-3-phenyl-4,5,5a,6,7,9a-hexahydro-2H-benzo[g]indazole-8-carbonitrile;

(5aR,6R,9aS)-6,9a-dimethyl-1-(naphthalen-1-yl)-7-oxo-3-phenyl-4,5,5a,6,7,9a-hexahydro-1H-benzo[g]indazole-8-carbonitrile;

(5aR,6R,9aS)-6,9a-dimethyl-2-(naphthalen-1-yl)-7-oxo-3-phenyl-4,5,5a,6,7,9a-hexahydro-2H-benzo[g]indazole-8-carbonitrile;

(5aR,6R,9aS)-1-(4-isopropylphenyl)-6,9a-dimethyl-7-oxo-3-phenyl-4,5,5a,6,7,9a-hexahydro-11H-benzo[g]indazole-8-carbonitrile;

(5aR,6R,9aS)-2-(4-isopropylphenyl)-6,9a-dimethyl-7-oxo-3-phenyl-4,5,5a,6,7,9a-hexahydro-2H-benzo[g]indazole-8-carbonitrile;

(5aR,9aS)-6,9a-dimethyl-7-oxo-3-phenyl-1-(tetrahydro-2H-pyran-4-yl)-4,5,5a,6,7,9a-hexahydro-1H-benzo[g]indazole-8-carbonitrile;

(5aR,6R,9aS)-6,9a-dimethyl-7-oxo-3-phenyl-2-(tetrahydro-2H-pyran-4-yl)-4,5,5a,6,7,9a-hexahydro-2H-benzo[lg]indazole-8-carbonitrile;

(5aR,6R,9aS)-1-(1,1-dioxidotetrahydrothiophen-3-yl)-6,9a-dimethyl-7-oxo-3-phenyl-4,5,5a,6,7,9a-hexahydro-1H-benzo[g]indazole-8-carbonitrile;

(5aR,6R,9aS)-2-(1,1-dioxidotetrahydrothiophen-3-yl)-6,9a-dimethyl-7-oxo-3-phenyl-4,5,5a,6,7,9a-hexahydro-2H-benzo[g]imidazole-8-carbonitrile;

(5aR,6R,9aS)-6,9a-dimethyl-1-(5-methylpyridin-2-yl)-7-oxo-3-phenyl-4,5,5a,6,7,9a-hexahydro-1H-benzo[g]indazole-8-carbonitrile;

(5aR,6R,9aS)-6,9a-dimethyl-1-(6-methylpyridin-3-yl)-7-oxo-3-phenyl-4,5,5a,6,7,9a-hexahydro-1H-benzo[g]indazole-8-carbonitrile;

(5aR,6R,9aS)-1-(3-bromophenyl)-6,9a-dimethyl-7-oxo-3-phenyl-4,5,5a,6,7,9a-hexahydro-1H-benzo[g]indazole-8-carbonitrile;

(5aR,6R,9aS)-6,9a-dimethyl-7-oxo-3-phenyl-1-(3-(pyridin-3-yl)phenyl)-4,5,5a,6,7,9a-hexahydro-1H-benzo[g]indazole-8-carbonitrile;

(5aR,6R,9aS)-1-([1,1'-biphenyl]-3-yl)-6,9a-dimethyl-7-oxo-3-phenyl-4,5,5a,6,7,9a-hexahydro-1H-benzo[g]indazole-8-carbonitrile;

(5aR,6R,9aS)-1-(2'-fluoro-[1,1'-biphenyl]-4-yl)-6,9a-dimethyl-7-oxo-3-phenyl-4,5,5a,6,7,9a-hexahydro-1H-benzo[g]indazole-8-carbonitrile;

(5aR,6R,9aS)-6,9a-dimethyl-7-oxo-3-phenyl-1-(4-(pyridin-3-yl)phenyl)-4,5,5a,6,7,9a-hexahydro-1H-benzo[g]indazole-8-carbonitrile;

(5aR,6R,9aS)-1-(4-(3,5-dimethylisoxazol-4-yl)phenyl)-6,9a-dimethyl-7-oxo-3-phenyl-4,5,5a,6,7,9a-hexahydro-1H-benzo[g]indazole-8-carbonitrile;

(5aR,6R,9aS)-6,9a-dimethyl-7-oxo-3-phenyl-1-(4-(pyridin-4-yl)phenyl)-4,5,5a,6,7,9a-hexahydro-1H-benzo[g]indazole-8-carbonitrile;

(5aR,6R,9aS)-1-(3'-fluoro-[1,1'-biphenyl]-4-yl)-6,9a-dimethyl-7-oxo-3-phenyl-4,5,5a,6,7,9a-hexahydro-1H-benzo[g]indazole-8-carbonitrile;

(5aR,6R,9aS)-6,9a-dimethyl-1-(4'-methyl-[1,1'-biphenyl]-4-yl)-7-oxo-3-phenyl-4,5,5a,6,7,9a-hexahydro-1H-benzo[g]indazole-8-carbonitrile;

(5aR,6R,9aS)-1-(4'-(hydroxymethyl)-[1,1'-biphenyl]-4-yl)-6,9a-dimethyl-7-oxo-3-phenyl-4,5,5a,6,7,9a-hexahydro-1H-benzo[g]indazole-8-carbonitrile;

(5aR,6R,9aS)-1-(2'-(hydroxymethyl)-[1,1'-biphenyl]-4-yl)-6,9a-dimethyl-7-oxo-3-phenyl-4,5,5a,6,7,9a-hexahydro-1H-benzo[g]indazole-8-carbonitrile;

(5aR,6R,9aS)-6,9a-dimethyl-1-(2'-methyl-[1,1'-biphenyl]-4-yl)-7-oxo-3-phenyl-4,5,5a,6,7,9a-hexahydro-1H-benzo[g]indazole-8-carbonitrile;

(5aR,6R,9aS)-1-(3'-(hydroxymethyl)-[1,1'-biphenyl]-4-yl)-6,9a-dimethyl-7-oxo-3-phenyl-4,5,5a,6,7,9a-hexahydro-1H-benzo[g]indazole-8-carbonitrile;

(5aR,6R,9aS)-1-(4'-methoxy-[1,1'-biphenyl]-4-yl)-6,9a-dimethyl-7-oxo-3-phenyl-4,5,5a,6,7,9a-hexahydro-1H-benzo[g]indazole-8-carbonitrile;

(5aR,6R,9aS)-1-(4'-(dimethylamino)-[1,1'-biphenyl]-4-yl)-6,9a-dimethyl-7-oxo-3-phenyl-4,5,5a,6,7,9a-hexahydro-1H-benzo[g]indazole-8-carbonitrile;

(5aR,6R,9aS)-1-([1,1'-biphenyl]-4-yl)-6,9a-dimethyl-7-oxo-3-(pyrimidin-4-yl)-4,5,5a,6,7,9a-hexahydro-1H-benzo[g]indazole-8-carbonitrile;

(5aR,6R,9aS)-1-(4-(5-fluoropyridin-3-yl)phenyl)-6,9a-dimethyl-7-oxo-3-(pyrimidin-4-yl)-4,5,5a,6,7,9a-hexahydro-1H-benzo[g]indazole-8-carbonitrile;

(5aR,6R,9aS)-6,9a-dimethyl-7-oxo-3-(pyrimidin-4-yl)-1-(4-(pyrimidin-5-yl)phenyl)-4,5,5a,6,7,9a-hexahydro-1H-benzo[g]indazole-8-carbonitrile;

(5aR,6R,9aS)-6,9a-dimethyl-7-oxo-1-(4-(pyridin-3-yl)phenyl)-3-(pyrimidin-4-yl)-4,5,5a,6,7,9a-hexahydro-1H-benzo[g]indazole-8-carbonitrile;

4-((5aR,6R,9aS)-8-cyano-6,9a-dimethyl-7-oxo-3-phenyl-4,5,5a,6,7,9a-hexahydro-1H-benzo[g]indazol-1-yl)benzoic acid;

(5aR,6R,9aS)-1-(2-oxo-4-(pyridin-3-yl)phenyl)-6,9a-dimethyl-7-oxo-3-(pyrimidin-4-yl)-4,5,5a,6,7,9a-hexahyrdo-1H-benzo[g]indazole-8-carbonitrile;

(5aR,6R,9aS)-1-(4-(2-(fluoromethyl)pyridin-4-yl)phenyl)-6,9a-dimethyl-7-oxo-3-(pyrimidin-4-yl)-4,5,5a,6,7,9a-hexahydro-1H-benzo[g]indazole-8-carbonitrile;

(5aR,6R,9aS)-1-(4-(2-(hydroxymethyl)pyridin-4-yl)phenyl)-6,9a-dimethyl-7-oxo-3-(pyrimidin-4-yl)-4,5,5a,6,7,9a-hexahydro-1H-benzo[g]indazole-8-carbonitrile;

(5aR,6R,9aS)-1-(5-(4-fluorophenyl)pyridin-2-yl)-6,9a-dimethyl-7-oxo-3-(pyrimidin-4-yl)-4,5,5a,6,7,9a-hexahydro-1H-benzo[g]indazole-8-carbonitrile;

(5aR,6R,9aS)-1-([3,3'-bipyridin]-6-yl)-6,9a-dimethyl-7-oxo-3-(pyrimidin-4-yl)-4,5,5a,6,7,9a-hexahydro-1H-benzo[g]indazole-8-carbonitrile;

(5aR,6R,9aS)-1-(5-(3-fluorophenyl)pyridin-2-yl)-6,9a-dimethyl-7-oxo-3-(pyrimidin-4-yl)-4,5,5a,6,7,9a-hexahydro-1H-benzo[g]indazole-8-carbonitrile;

(5aR,6R,9aS)-6,9a-dimethyl-7-oxo-1-(5-phenylpyridin-2-yl)-3-(pyrimidin-4-yl)-4,5,5a,6,7,9a-hexahydro-1H-benzo[g]indazole-8-carbonitrile;

(5aR,6R,9aS)-1-(5-(3-(hydroxymethyl)phenyl)pyridin-2-yl)-6,9a-dimethyl-7-oxo-3-(pyrimidin-4-yl)-4,5,5a,6,7,9a-hexahydro-1H-benzo[g]indazole-8-carbonitrile;

(5aR,6R,9aS)-1-(5-(3-(fluoromethyl)phenyl)pyridin-2-yl)-6,9a-dimethyl-7-oxo-3-(pyrimidin-4-yl)-4,5,5a,6,7,9a-hexahydro-1H-benzo[g]indazole-8-carbonitrile;

(5aR,6R,9aS)-1-(5-cyclopropylpyridin-2-yl)-6,9a-dimethyl-7-oxo-3-(pyrimidin-4-yl)-4,5,5a,6,7,9a-hexahydro-1H-benzo[g]indazole-8-carbonitrile;

(5aR,6R,9aS)-6,9a-dimethyl-7-oxo-3-(pyrimidin-4-yl)-1-(5-(trifluoromethyl)pyridin-2-yl)-4,5,5a,6,7,9a-hexahydro-1H-benzo[g]indazole-8-carbonitrile;

(5aR,6R,9aS)-6,9a-dimethyl-7-oxo-1-(6-phenylpyridin-3-yl)-3-(pyrimidin-4-yl)-4,5,5a,6,7,9a-hexahydro-1H-benzo[g]indazole-8-carbonitrile;

(5aR,6R,9aS)-1-([1,1'-biphenyl]-4-yl)-3-(4-fluorophenyl)-6,9a-dimethyl-7-oxo-4,5,5a,6,7,9a-hexahydro-1H-benzo[g]indazole-8-carbonitrile;

(5aR,6R,9aS)-1-([1,1'-biphenyl]-4-yl)-3-(2-fluorophenyl)-6,9a-dimethyl-7-oxo-4,5,5a,6,7,9a-hexahydro-1H-benzo[g]indazole-8-carbonitrile;

(5aR,6R,9aS)-1-([1,1'-biphenyl]-4-yl)-6,9a-dimethyl-7-oxo-3-(pyridin-4-yl)-4,5,5a,6,7,9a-hexahydro-1H-1-benzo[g]indazole-8-carbonitrile;

(5aR,6R,9aS)-1-([1,1'-biphenyl]-4-yl)-6,9a-dimethyl-7-oxo-3-(pyridin-3-yl)-4,5,5a,6,7,9a-hexahydro-1H-benzo[g]indazole-8-carbonitrile;

(5aR,6R,9aS)-1-([1,1'-biphenyl]-4-yl)-6,9a-dimethyl-7-oxo-3-(p-tolyl)-4,5,5a,6,7,9a-hexahydro-1H-benzo[g]indazole-8-carbonitrile;

(5aR,6R,9aS)-1-([1,1'-biphenyl]-4-yl)-6,9a-dimethyl-7-oxo-3-(pyrimidin-5-yl)-4,5,5a,6,7,9a-hexahydro-1H-benzo[g]indazole-8-carbonitrile;

(5aR,6R,9aS)-1-([1,1'-biphenyl]-4-yl)-3-(3-isopropylphenyl)-6,9a-dimethyl-7-oxo-4,5,5a,6,7,9a-hexahydro-1H-benzo[g]indazole-8-carbonitrile;

(5aR,6R,9aS)-1-([1,1'-biphenyl]-4-yl)-6,9a-dimethyl-7-oxo-3-(o-tolyl)-4,5,5a,6,7,9a-hexahydro-1H-benzo[g]indazole-8-carbonitrile;

(5aR,6R,9aS)-1-([1,1'-biphenyl]-4-yl)-3-(4-(hydroxymethyl)phenyl)-6,9a-dimethyl-7-oxo-4,5,5a,6,7,9a-hexahydro-1H-benzo[g]indazole-8-carbonitrile;

(5aR,6R,9S)-1-([1,1'-biphenyl]-4-yl)-3-(4-(fluoromethyl)phenyl)-6,9a-dimethyl-7-oxo-4,5,5a,6,7,9a-hexahydro-1H-benzo[g]indazole-8-carbonitrile;

(5aR,6R,9aS)-1-([1,1'-biphenyl]-4-yl)-3-cyclopropyl-6,9a-dimethyl-7-oxo-4,5,5a,6,7,9a-hexahydro-1H-benzo[g]indazole-8-carbonitrile;

(5aR,6R,9aS)-1-([1,1'-biphenyl]-4-yl)-3-cyclohexyl-6,9a-dimethyl-7-oxo-4,5,5a,6,7,9a-hexahydro-1H-benzo[g]indazole-8-carbonitrile;

(5aR,6R,9aS-1-([1,1'-biphenyl]-4-yl)-6,9a-dimethyl-3-morpholino-7-oxo-4,5,5a,6,7,9a-hexahydro-1H-benzo[g]indazole-8-carbonitrile;

(5aR,6R,9aS)-1-([1,1'-biphenyl]-4-yl)-3-(cyclobutylamino)-6,9a-dimethyl-7-oxo-4,5,5a,6,7,9a-hexahydro-1H-benzo[g]indazole-8-carbonitrile;

(5aR,6R,9aS)-1-([1,1'-biphenyl]-4-yl)-6,9a-dimethyl-3-(methylamino)-7-oxo-4,5,5a,6,7,9a-hexahydro-1H-benzo[g]indazole-8-carbonitrile;

(5aR,6R,9aS)-1-([1,1'-biphenyl]-4-yl)-3-(cyclobutyl(methyl)amino)-6,9a-dimethyl-7-oxo-4,5,5a,6,7,9a-hexahydro-1H-benzo[g]indazole-8-carbonitrile;

(5aR,6R,9aS)-1-([1,1'-biphenyl]-4-yl)-6,9a-dimethyl-7-oxo-3-(pyridin-2-yl)-4,5,5a,6,7,9a-hexahydro-1H-benzo[g]indazole-8-carbonitrile;

(5aR,6R,9aS)-3-(2-fluorophenyl)-6,9a-dimethyl-7-oxo-1-(4-(pyrimidin-5-yl)phenyl)-4,5,5a,6,7,9a-hexahydro-1H-benzo[g]indazole-8-carbonitrile;

(5aR,6R,9aS)-3-(2-fluorophenyl)-6,9a-dimethyl-1-(4-(6-methylpyridazin-4-yl)phenyl)-7-oxo-4,55a,6,7,9a-hexahydro-1H-benzo[g]imidazole-8-carbonitrile;

(5aR,6R,9aS)-3-(2-fluorophenyl)-6,9a-dimethyl-7-oxo-1-(4-(pyridin-4-yl)phenyl)-4,5,5a,6,7,9a-hexahydro-1H-benzo[g]indazole-8-carbonitrile;

(5aR,6R,9aS)-3-(2-fluorophenyl)-6,9a-dimethyl-1-(4-morpholinophenyl)-7-oxo-4,5,5a,6,7,9a-hexahydro-1H-benzo[g]indazole-8-carbonitrile;

(5aR,6R,9aS)-3-(2-fluorophenyl)-6,9a-dimethyl-1-(4-methyl-5-phenyl-4H-1,2,4-triazol-3-yl)-7-oxo-4,5,5a,6,7,9a-hexahydro-1H-benzo[g]indazole-8-carbonitrile;

(5aR,6R,9aS)-3-(2-fluorophenyl)-6,9a-dimethyl-7-oxo-1-(4-phenylthiazol-2-yl)-4,5,5a,6,7,9a-hexahydro-1H-benzo[g]indazole-8-carbonitrile;

(5aR,6R,9aS)-3-(2-fluorophenyl)-6,9a-dimethyl-7-oxo-1-(5-(trifluoromethyl)benzo[d]thiazol-2-yl)-4,5,5a,6,7,9a-hexahydro-1H-benzo[g]indazole-8-carbonitrile;

(5aR,6R,9aS)-1-(6-chlorobenzo[d]thiazol-2-yl)-3-(2-fluorophenyl)-6,9a-dimethyl-7-oxo-4,5,5a,6,7,9a-hexahydro-1H-benzo[g]indazole-8-carbonitrile;

(5aR,6R,9aS)-3-(2-fluorophenyl)-6,9a-dimethyl-1-(1-methyl-1-benzo[d]imidazol-2-yl)-7-oxo-4,5,5a,6,7,9a-hexahydro-1H-benzo[g]indazole-8-carbonitrile;

(5aR,6R,9aS)-1-(1H-benzo[d]imidazol-2-yl)-3-(2-fluorophenyl)-6,9a-dimethyl-7-oxo-4,5,5a,6,7,9a-hexahydro-1H-benzo[g]indazole-8-carbonitrile;

(5aR,6R,9a)-1-(benzo[d]thiazol-2-yl)-3-(2-fluorophenyl)-6,9a-dimethyl-7-oxo-4,5,5a,6,7,9a-hexahydro-1H-benzo[g]indazole-8-carbonitrile;

(5aR,6R,9aS)-3-(2-fluorophenyl)-6,9a-dimethyl-7-oxo-1-(4-(pyrimidin-4-yl)phenyl)-4,5,5a,6,7,9a-hexahydro-1H-benzo[g]indazole-8-carbonitrile;

(5aR,6R,9aS)-3-(2-fluorophenyl)-6,9a-dimethyl-1-(4-(5-methyl-1,2,4-oxadiazol-1-yl)phenyl)-7-oxo-4,5,5a,6,7,9a-hexahydro-1H-benzo[g]indazole-8-carbonitrile (5aR,6R,9aS)-3-(2-fluorophenyl)-6,9a-dimethyl-1-(4-(3-methyl-1,2,4-oxadiazol-5-yl)phenyl)-7-oxo-4,5,5a,6,7,9a-hexahydro-1H-benzo[g]indazole-8-carbonitrile (5aR,6R,9aS)-1-([1,1'-biphenyl]-4-yl)-6,9a-dimethyl-3-(3-methyl-1,2,4-oxadiazol-5-yl)-7-oxo-4,5,5a,6,7,9a-hexahydro-1H-benzo[g]indazole-8-carbonitrile (5aR,6R,9a)-6,9a-dimethyl-7-oxo-3-phenyl-1-(5-phenylpyridin-2-yl)-4,5,5a,6,7,9a-hexahydro-1H-benzo[g]indazole-8-carbonitrile;

(5aR,6R,9aS)-1-(benzo[d]thiazol-2-yl)-6,9a-dimethyl-7-oxo-3-(pyrimidin-4-yl)-4,5,5a,6,7,9a-hexahydro-1H-benzo[g]indazole-8-carbonitrile;

(5aR,6R,9aS)-1-(benzo[d]thiazol-2-yl)-6,9a-dimethyl-7-oxo-3-(pyridin-3-yl)-4,5,5a,6,7,9a-hexahydro-1H-benzo[g]indazole-8-carbonitrile;

(5aR,6R,9aS)-1-([1,1'-biphenyl]-4-yl)-6,9a-dimethyl-7-oxo-3-(phenylamino)-4,5,5a,6,7,9a-hexahydro-1H-benzo[g]indazole-8-carbonitrile;

(5aR,6R,9aS)-1-(4-(5-fluoropyridin-3-yl)phenyl)-6,9a-dimethyl-7-oxo-3-(pyridin-4-yl)-4,5,5a,6,7,9a-hexahydro-1H-benzo[g]indazole-8-carbonitrile;

(5aR,6R,9aS)-6,9a-dimethyl-1-(4-(6-methylpyridazin-4-yl)phenyl)-7-oxo-3-(pyridin-3-yl)-4,5,5a,6,7,9a-hexahydro-1H-benzo[g]indazole-8-carbonitrile;

(5aR,6R,9aS)-1-(4-(5-fluoropyridin-3-yl)phenyl)-6,9a-dimethyl-7-oxo-3-(pyridin-3-yl)-4,5,5a,6,7,9a-hexahydro-1H-benzo[g]indazole-8-carbonitrile;

(5aR,6R,9aS)-3-(3-fluorophenyl)-6,9a-dimethyl-7-oxo-1-(quinolin-4-yl)-4,5,5a,6,7,9a-hexahydro-1H-benzo[g]indazole-8-carbonitrile;

(5aR,6R,9aS)-3-(4-fluorophenyl)-1-(4-(5-fluoropyridin-3-yl)phenyl)-6,9a-dimethyl-7-oxo-4,5,5a,6,7,9a-hexahydro-1H-benzo[g]indazole-8-carbonitrile;

(5aR,6R,9aS)-3-(4-fluorophenyl)-6,9a-dimethyl-1-(4-(3-menthyl-1,2,4-oxadiazol-5-yl)phenyl)-7-oxo-4,5,5a,6,7,9a-hexahydro-1-benzo[g]indazole-8-carbonitrile;

(5aR,6R,9aS)-6,9a-dimethyl-1-(4-(3-methyl-1,2,4-oxadiazol-5-yl)phenyl)-7-oxo-3-(pyridin-3-yl)-4,5,5a,6,7,9a-hexahydro-1-benzo[g]indazole-8-carbonitrile;

(5aR,6R,9aS)-6,9a-dimethyl-3-(3-methyl-1,2,4-oxadiazol-5-yl)-1-(4-(6-methylpyridazin-4-yl)phenyl)-7-oxo-4,5,5a,6,7,9a-hexahydro-1-benzo[g]indazole-8-carbonitrile;

(5aR,6R,9aS)-6,9a-dimethyl-3-(3-methyl-1,2,4-oxadiazol-5-yl)-7-oxo-1-(4-(pyridin-3-yl)phenyl)-4,5,5a,6,7,9a-hexahydro-1H-benzo[g]indazole-8-carbonitrile;

(5aR,6R,9aS)-6,9a-dimethyl-3-(5-methyl-1,2,4-oxadiazol-3-yl)-1-(4-(6-methylpyridazin-4-yl)phenyl)-7-oxo-4,5,5a,6,7,9a-hexahydro-1H-benzo[g]indazole-8-carbonitrile;

(5aR,6R,9aS)-6,9a-dimethyl-3-(2-methyl-2-tetrazol-5-yl)-7-oxo-2-phenyl-4,5,5a,6,7,9a-hexahydro-3H-naphtho[1,2-d]imidazole-8-carbonitrile;

(5aR,6R,9aS)-6,9a-dimethyl-7-oxo-3-phenyl-2-(pyridin-4-yl)-4,5,5a,6,7,9a-hexahydro-3H-naphtho[1,2-d]imidazole-8-carbonitrile;

(5aR,6R,9aS)-2-cyclohexyl-6,9a-dimethyl-7-oxo-3-phenyl-4,5,5a,6,7,9a-hexahydro-3H-naphtho[1,2-d]imidazole-8-carbonitrile;

(5aR,6R,9aS)-2-(4-chlorophenyl)-6,9a-dimethyl-7-oxo-3-phenyl-4,5,5a,6,7,9a-hexahydro-2H-benzo[g]indazole-8-carbonitrile;

(5aR,6R,9aS)-6,9a-dimethyl-7-oxo-2,3-diphenyl-4,5,5a,6,7,9a-hexahydro-2H-benzo[g]indazole-8-carbonitrile;

(5aR,6R,9aS)-2-(4-methoxyphenyl)-6,9a-dimethyl-7-oxo-3-phenyl-4,5,5a,6,7,9a-hexahydro-2H-benzo[g]indazole-8-carbonitrile;

(5aR,6R,9aS)-2-(3,4-dichlorophenyl)-6,9a-dimethyl-7-oxo-3-phenyl-4,5,5a,6,7,9a-hexahydro-2H-benzo[g]indazole-8-carbonitrile;

(5aR,6R,9aS)-6,9a-dimethyl-7-oxo-3-phenyl-2-(p-tolyl)-4,5,5a,6,7,9a-hexahydro-2H-benzo[g]indazole-8-carbonitrile;

(5aR,6R,9aS)-2-([1,1'-biphenyl]-4-yl)-3-(cyclobutylmethyl)-6,9a-dimethyl-7-oxo-4,5,5a,6,7,9a-hexahydro-2H-benzo[g]indazole-8-carbonitrile;

(5aR,6R,9aS)-2-([1,1'-biphenyl]-4-yl)-6,9a-dimethyl-7-oxo-3-(pyrimidin-4-yl)-4,5,5a,6,7,9a-hexahydro-2H-benzo[g]indazole-8-carbonitrile;

(5aR,6R,9aS)-2-([1,1'-biphenyl]-3-yl)-6,9a-dimethyl-7-oxo-3-(pyrimidin-4-yl)-4,5,5a,6,7,9a-hexahydro-2H-benzo[g]indazole-8-carbonitrile;

(5aR,6R,9aS)-3-(4-fluorophenyl)-6,9a-dimethyl-7-oxo-2-(pyridin-4-yl)-4,5,5a,6,7,9a-hexahydro-2H-benzo[g]indazole-8-carbonitrile;

(5aR,6R,9aS)-2-([1,1'-biphenyl]-4-yl)-3-(2-fluorophenyl)-6,9a-dimethyl-7-oxo-4,5,5a,6,7,9a-hexahydro-2H-benzo[g]indazole-8-carbonitrile;

(5aR,6R,9aS)-2-([1,1'-biphenyl]-4-yl)-6,9a-dimethyl-7-oxo-3-(pyridin-4-yl)-4,5,5a,6,7,9a-hexahydro-2H-benzo[g]indazole-8-carbonitrile;

(5aR,6R,9aS)-2-([1,1'-biphenyl]-4-yl)-6,9a-dimethyl-7-oxo-3-(pyridin-3-yl)-4,5,5a,6,7,9a-hexahydro-2H-benzo[g]indazole-8-carbonitrile;

(5aR,6R,9aS)-2-([1,1'-biphenyl]-3-yl)-3-(3-fluorophenyl)-6,9a-dimethyl-7-oxo-4,5,5a,6,7,9a-hexahydro-2H-benzo[g]indazole-8-carbonitrile;

(5aR,6R,9aS)-2-([1,1'-biphenyl]-4-yl)-3-(3-fluorophenyl)-6,9a-dimethyl-7-oxo-4,5,5a,6,7,9a-hexahydro-3H-naphtho[1,2-d]imidazole-8-carbonitrile;

(5aR,6R,9aS)-2-([1,1'-biphenyl]-3-yl)-3-(3-fluorophenyl)-6,9a-dimethyl-7-oxo-4,5,5a,6,7,9a-hexahydro-3H-naphtho[1,2-d]imidazole-8-carbonitrile;

(5aR,6R,9a)-3-(3-fluorophenyl)-2-(4-isopropylphenyl)-6,9a-dimethyl-7-oxo-4,5,5a,6,7,9a-hexahydro-3H-naphtho[1,2-d]imidazole-8-carbonitrile;

(5aR,6R,9aS)-3-(3-fluorophenyl)-6,9a-dimethyl-7-oxo-2-(tetrahydro-2H-pyran-4-yl)-4,5,5a,6,7,9a-hexahydro-3H-naphtho[1,2-d]imidazole-8-carbonitrile;

(5aR,6R,9aS)-3-(3-fluorophenyl)-2-(2-isopropylpyrimidin-5-yl)-6,9a-dimethyl-7-oxo-4,5,5a,6,7,9a-hexahydro-3H-naphtho[1,2-d]imidazole-8-carbonitrile;

(5aR,6R,9aS)-2-(4-(dimethylamino)phenyl)-3-(3-fluorophenyl)-6,9a-dimethyl-7-oxo-4,5,5a,6,7,9a-hexahydro-3H-naphtho[1,2-d]imidazole-8-carbonitrile;

(5aR,6R,9aS)-3-(3-fluorophenyl)-2,6,9a-trimethyl-7-oxo-4,5,5a,6,7,9a-hexahydro-3H-naphtho[1,2-d]imidazole-8-carbonitrile;

(5aR,6R,9aS)-3-(3-fluorophenyl)-6,9a-dimethyl-7-oxo-2-phenyl-4,5,5a,6,7,9a-hexahydro-3H-naphtho[1,2-d]imidazole-8-carbonitrile;

(5aR,6R,9aS)-3-(3-fluorophenyl)-6,9a-dimethyl-7-oxo-2-(quinolin-4-yl)-4,5,5a,6,7,9a-hexahydro-3H-naphtho[1,2-d]imidazole-8-carbonitrile;

(5aR,6R,9aS)-3-(3-fluorophenyl)-6,9a-dimethyl-7-oxo-2-(quinolin-5-yl)-4,5,5a,6,7,9a-hexahydro-3H-naphtho[1,2-d]imidazole-8-carbonitrile;

(5aR,6R,9S)-3-(3-fluorophenyl)-6,9a-dimethyl-7-oxo-2-(quinolin-3-yl)-4,5,5a,6,7,9a-hexahydro-3H-naphtho[1,2-d]imidazole-8-carbonitrile;

(5aR,6R,9aS)-3-(3-fluorophenyl)-2-(3-isopropylphenyl)-6,9a-dimethyl-7-oxo-4,5,5a,6,7,9a-hexahydro-3H-naphtho[1,2-d]imidazole-8-carbonitrile;

(5aR,6R,9a)-3-(3-fluorophenyl)-6,9a-dimethyl-2-(2-morpholinopyridin-4-yl)-7-oxo-4,5,5a,6,7,9a-hexahydro-3H-naphtho[1,2-d]imidazole-8-carbonitrile;

(5aR,6R,9a)-2-benzyl-3-(3-fluorophenyl)-6,9a-dimethyl-7-oxo-4,5,5a,6,7,9a-hexahydro-3H-naphtho[1,2-d]imidazole-8-carbonitrile;

(5aR,6R,9aS)-3-(3-fluorophenyl)-6,9a-dimethyl-7-oxo-2-(2-(trifluoromethyl)pyridin-4-yl)-4,5,5a,6,7,9a-hexahydro-3H-naphtho[1,2-d]imidazole-8-carbonitrile;

(5aR,6R,9aS)-2-(6-cyclopropylpyridin-3-yl)-3-(3-fluorophenyl)-6,9a-dimethyl-7-oxo-4,5,5a,6,7,9a-hexahydro-3H-naphtho[1,2-d]imidazole-8-carbonitrile;

(5aR,6R,9a)-3-(3-fluorophenyl)-6,9a-dimethyl-2-(3-morpholinophenyl)-7-oxo-4,5,5a,6,7,9a-hexahydro-3H-naphtho[1,2-d]imidazole-8-carbonitrile;

(5aR,6R,9aS)-2-(2-cyclopropylpyridin-4-yl)-3-(3-fluorophenyl)-6,9a-dimethyl-7-oxo-4,5,5a,6,7,9a-hexahydro-3H-naphtho[1,2-d]imidazole-8-carbonitrile;

(5aR,6R,9aS)-2-(3-bromophenyl)-3-(3-fluorophenyl)-6,9a-dimethyl-7-oxo-4,5,5a,6,7,9a-hexahydro-3H-naphtho[1,2-d]imidazole-8-carbonitrile;

(5aR,6R,9aS)-3-(3-fluorophenyl)-6,9a-dimethyl-7-oxo-2-(3-(pyridin-4-yl)phenyl)-4,5,5a,6,7,9a-hexahydro-3H-naphtho[1,2-d]imidazole-8-carbonitrile;

(5aR,6R,9aS)-3-(3-fluorophenyl)-6,9a-dimenthyl-7-oxo-2-(3-(pyrimidin-5-yl)phenyl)-4,5,5a,6,7,9a-hexahydro-3H-naphtho[1,2-d]imidazole-8-carbonitrile;

(5aR,6R,9a)-3-(3-fluorophenyl)-2-(3-(5-fluoropyridin-3-yl)phenyl)-6,9a-dimethyl-7-oxo-4,5,5a,6,7,9a-hexahydro-3H-naphtho[1,2-d]imidazole-8-carbonitrile;

(5aR,6R,9aS)-3-(3-fluorophenyl)-6,9a-dimethyl-2-(3-(1-methyl-1H-pyrazol-4-yl)phenyl)-7-oxo-4,5,5a,6,7,9a-hexahydro-3H-naphtho[1,2-d]imidazole-8-carbonitrile;

(5aR,6R,9aS)-2-(3-(3,5-dimethylisoxazol-4-yl)phenyl)-3-(3-fluorophenyl)-6,9a-dimethyl-7-oxo-4,5,5a,6,7,9a-hexahydro-3H-naphtho[1,2-d]imidazole-8-carbonitrile;

(5aR,6R,9aS)-3-(3-fluorophenyl)-6,9a-dimethyl-2-(3-(1-methyl-1H-pyrazol-5-yl)phenyl)-7-oxo-4,5,5a,6,7,9a-hexahydro-3H-naphtho[1,2-d]imidazole-8-carbonitrile;

(5aR,6R,9aS)-2-([1,1'-biphenyl]-4-yl)-6,9a-dimethyl-7-oxo-3-(pyridin-3-yl)-4,5,5a,6,7,9a-hexahydro-3H-naphtho[1,2-d]imidazole-8-carbonitrile;

(5aR,6R,9aS)-2-(4-isopropylphenyl)-6,9a-dimethyl-7-oxo-3-(pyridin-3-yl)-4,5,5a,6,7,9a-hexahydro-3H-naphtho[1,2-d]imidazole-8-carbonitrile;

(5aR,6R,9aS)-6,9a-dimethyl-7-oxo-3-(pyridin-3-yl)-2-(quinolin-4-yl)-4,5,5a,6,7,9a-hexahydro-3H-naphtho[1,2-d]imidazole-8-carbonitrile;

(5aR,6R,9aS)-2-([1,1'-biphenyl]-3-yl)-6,9a-dimethyl-7-oxo-3-(pyridin-3-yl)-4,5,5a,6,7,9a-hexahydro-3H-naphtho[1,2-d]imidazole-8-carbonitrile;

(5aR,6R,9a)-2-(4-isopropylphenyl)-6,9a-dimethyl-3-(1-methyl-1H-pyrazol-4-yl)-7-oxo-4,5,5a,6,7,9a-hexahydro-3-naphtho[1,2-d]imidazole-8-carbonitrile;

(5aR,6R,9aS)-2-(3-chlorophenyl)-6,9a-dimethyl-3-(1-methyl-1H-pyrazol-4-yl)-7-oxo-4,5,5a,6,7,9a-hexahydro-3H-naphtho[1,2-d]imidazole-8-carbonitrile;

(5aR,6R,9aS)-2-(3,4-dichlorophenyl)-6,9a-dimethyl-3-(1-methyl-1H-pyrazol-4-yl)-7-oxo-4,5,5a,6,7,9a-hexahydro-3H-naphtho[1,2-d]imidazole-8-carbonitrile;

(5aR,6R,9aS)-6,9a-dimethyl-3-(1-methyl-1-pyrazol-4-yl)-7-oxo-2-(3-(pyridin-4-yl)phenyl)-4,5,5a,6,7,9a-hexahydro-3H-naphtho[1,2-d]imidazole-8-carbonitrile;

(5aR,6R,9aS)-6,9a-dimethyl-3-(1-methyl-1H-pyrazol-4-yl)-2-(2-morpholinopyridin-4-yl)-7-oxo-4,5,5a,6,7,9a-hexahydro-3H-naphtho[1,2-d]imidazole-8-carbonitrile;

(5aR,6R,9aS)-3-cyclopropyl-2-(4-isopropylphenyl)-6,9a-dimethyl-7-oxo-4,5,5a,6,7,9a-hexahydro-3H-naphtho[1,2-d]imidazole-8-carbonitrile;

(5aR,6R,9aS)-3-isopropyl-2-(4-isopropylphenyl)-6,9a-dimethyl-7-oxo-4,5,5a,6,7,9a-hexahydro-3H-naphtho[1,2-d]imidazole-8-carbonitrile;

(5aR,6R,9a)-2-(4-isopropylphenyl)-3,6,9a-trimethyl-7-oxo-4,5,5a,6,7,9a-hexahydro-3H-naphtho[1,2-d]imidazole-8-carbonitrile;

(5aR,6R,9aS)-2-(4-isopropylphenyl)-3-(2-methoxyethyl)-6,9a-dimethyl-7-oxo-4,5,5a,6,7,9a-hexahydro-3H-naphtho[1,2-a]imidazole-8-carbonitrile;

(5aR,6R,9aS)-3-(2-(benzyloxy)ethyl)-2-(4-isopropylphenyl)-6,9a-dimethyl-7-oxo-4,5,5a,6,7,9a-hexahydro-3H-naphtho[1,2-d]imidazole-8-carbonitrile;

(5aR,6R,9aS)-3-benzyl-2-(4-isopropylphenyl)-6,9a-dimethyl-7-oxo-4,5,5a,6,7,9a-hexahydro-3H-naphtho[1,2-d]imidazole-8-carbonitrile;

(5aR,6R,9aS)-3-(4-fluorobenzyl)-2-(4-isopropylphenyl)-6,9a-dimethyl-7-oxo-4,5,5a,6,7,9a-hexahydro-3H-naphtho[1,2-d]imidazole-8-carbonitrile;

(5aR,6R,9aS)-3-(2-fluorobenzyl)-2-(4-isopropylphenyl)-6,9a-dimethyl-7-oxo-4,5,5a,6,7,9a-hexahydro-3H-naphtho[1,2-d]imidazole-8-carbonitrile;

(5aR,6R,9aS)-3-(4-chlorobenzyl)-2-(4-isopropylphenyl)-6,9a-dimethyl-7-oxo-4,5,5a,6,7,9a-hexahydro-3H-naphtho[1,2-d]imidazole-8-carbonitrile;

(5aR,6R,9a)-2-(4-isopropylphenyl)-6,9a-dimethyl-7-oxo-3-(pyridin-2-ylmethyl)-4,5,5a,6,7,9a-hexahydro-3H-naphtho[1,2-d]imidazole-8-carbonitrile;

(5aR,6R,9aS)-2-(4-isopropylphenyl)-6,9a-dimethyl-7-oxo-3-(pyridin-4-ylmethyl)-4,5,5a,6,7,9a-hexahydro-3H-naphtho[1,2-d]imidazole-8-carbonitrile;

(5aR,6R,9aS)-3-(2-hydroxyethyl)-2-(4-isopropylphenyl)-6,9a-dimethyl-7-oxo-4,5,5a,6,7,9a-hexahydro-3H-naphtho[1,2-d]imidazole-8-carbonitrile;

(5aR,6R,9aS)-2-(4-isopropylphenyl)-6,9a-dimethyl-7-oxo-4,5,5a,6,7,9a-hexahydro-3H-naphtho[1,2-d]imidazole-8-carbonitrile;

(5aR,6R,9aS)-3-acetyl-2-(4-isopropylphenyl)-6,9a-dimethyl-7-oxo-4,5,5a,6,7,9a-hexahydro-3H-naphtho[1,2-d]imidazole-8-carbonitrile;

(5aR,9aS)-3-(2-fluorophenyl)-6,9a-dimethyl-7-oxo-1-(1-phenylpiperidin-4-yl)-4,5,5a,6,7,9a-hexahydro-1H-benzo[g]indazole-8-carbonitrile;

(5aR,6R,9aS)-3-(2-fluorophenyl)-6,9a-dimethyl-7-oxo-2-(1-phenylpiperidin-4-yl)-4,5,5a,6,7,9a-hexahydro-2H-benzo[g]indazole-8-carbonitrile (5aR,6R,9aS)-6,9a-dimethyl-1-(4-(6-methylpyridazin-4-yl)phenyl)-7-oxo-3-(pyrimidin-4-yl)-4,5,5a,6,7,9a-hexahydro-1H-benzo[g]indazole-8-carbonitrile;

(5aR,6R,9aS)-3-(4-fluorophenyl)-6,9a-dimethyl-1-(4-(6-methylpyridazin-4-yl)phenyl)-7-oxo-4,5,5a,6,7,9a-hexahydro-1H-benzo[g]indazole-8-carbonitrile;

(5aR,6R,9aS)-3-(4-fluorophenyl)-6,9a-dimethyl-7-oxo-1-(4-(pyridazin-3-yl)phenyl)-4,5,5a,6,7,9a-hexahydro-1H-benzo[g]indazole-8-carbonitrile;

(5aR,6R,9aS)-3-(4-fluorophenyl)-6,9a-dimethyl-1-(4-(5-methylpyridazin-3-yl)phenyl)-7-oxo-4,5,5a,6,7,9a-hexahydro-1H-benzo[g]indazole-8-carbonitrile;
(5aR,6R,9aS)-1-(4-(2-(fluoromethyl)pyridin-4-yl)phenyl)-6,9a-dimethyl-7-oxo-3-(pyridin-3-yl)-4,5,5a,6,7,9a-hexahydro-1-benzo[g]indazole-8-carbonitrile;
(5aR,6R,9aS)-1-(4-(2-(fluoromethyl)pyridin-4-yl)phenyl)-3-(4-fluorophenyl)-6,9a-dimethyl-7-oxo-4,5,5a,6,7,9a-hexahydro-1H-benzo[g]indazole-8-carbonitrile;
(5aR,6R,9aS)-3-(4-fluorophenyl)-6,9a-dimethyl-1-(4-(5-methyl-1,2,4-oxadiazol-3-yl)phenyl)-7-oxo-4,5,5a,6,7,9a-hexahydro-1H-benzo[g]indazole-8-carbonitrile;
(5aR,6R,9aS)-1-(4-(1,2,4-oxadiazol-3-yl)phenyl)-3-(4-fluorophenyl)-6,9a-dimethyl-7-oxo-4,5,5a,6,7,9a-hexahydro-1H-benzo[g]indazole-8-carbonitrile;
(5aR,6R,9aS)-6,9a-dimethyl-1-(4-(5-methyl-1,2,4-oxadiazol-3-yl)phenyl)-7-oxo-3-(pyridin-3-yl)-4,5,5a,6,7,9a-hexahydro-1H-benzo[g]indazole-8-carbonitrile;
(5aR,6R,9aS)-1-(4-(5-fluoropyridin-3-yl)phenyl)-6,9a-dimethyl-7-oxo-3-(pyrimidin-4-yl)-4,5,5a,6,7,8,9,9a-octahydro-1H-benzo[g]indazole-8-carbonitrile; or
(5aR,6R,9aR)-3-(2-fluorophenyl)-6,9a-dimethyl-1-(4-(6-methylpyridazin-4-yl)phenyl)-7-oxo-4,5,5a,6,7,8,9,9a-octahydro-1H-benzo[g]indazole-8-carbonitrile;
or a pharmaceutically acceptable salt thereof.

In still yet another aspect, the present disclosure provides pharmaceutical compositions comprising:
(A) a compound described herein or shown above; and
(B) an excipient.

In some embodiments, the pharmaceutical composition is formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally intravenously, intravascularly, intravitreally, liposomally, locally, mucosally, parenterally, rectally, subconjunctival, subcutaneously, sublingually, topically, transbuccally, transdermally, vaginally, in crèmes, in lipid compositions, via a catheter, via a lavage, via continuous infusion, via infusion, via inhalation, via injection, via local delivery, or via localized perfusion. In some embodiments, the pharmaceutical composition is formulated for oral administration. In other embodiments, the pharmaceutical composition is formulated for administration via injection. In some embodiments, the pharmaceutical composition is formulated for intraarterial administration, intramuscular administration, intraperitoneal administration, or intravenous administration. In other embodiments, the pharmaceutical composition is formulated for administration topically. In some embodiments, the pharmaceutical composition is formulated for topical administration to the skin or to the eye. In some embodiments, the pharmaceutical composition is formulated as a unit dose.

In still another aspect, the present disclosure provides methods of treating or preventing, a disease or disorder in a patient in need thereof comprising administering to the patient a pharmaceutically effective amount of a compound or composition described herein. In some embodiments, the patient is a mammal such as a human. In some embodiments, the disease or disorder is associated with increased production of cytokine IL-17. In some embodiments, the disease or disorder is associated with dysregulated angiogenesis.

In some embodiments, the disease or disorder is an autoimmune disease, organ rejection, asthma, cancer, a neurological disorder, a psychiatric disorder, a neuropsychiatric disorder, chronic pain syndrome, an inflammatory condition, a retinal disorder, or a cardiovascular disease. In some embodiments, the disease or disorder is cancer. In other embodiments, the autoimmune disease is psoriasis, multiple sclerosis, scleroderma, rheumatoid arthritis, lupus, psoriatic arthritis, ankylosing spondylitis, Sjögren syndrome, vitiligo, uveitis, dry eye syndrome, systemic sclerosis, type 1 diabetes, myasthenia gravis, and inflammatory bowel disease. In other embodiments, the cardiovascular disease is vasculitis, atherosclerosis, myocardial infarction, myocarditis, heart failure, pulmonary hypertension, or stroke. In other embodiments, the neurological disorder is epilepsy, multiple sclerosis, spinal cord injury, Guillain-Barre syndrome, or another neurological disorder involving dysregulated inflammatory signaling or oxidative stress. In other embodiments, the neurodegenerative disorder is Alzheimer's disease, Parkinson's disease, amyotrophic lateral sclerosis, or Huntington's disease. In other embodiments, the inflammatory condition is pancreatitis, hepatitis, pulmonary fibrosis, cystic fibrosis, chronic obstructive pulmonary disease, asthma, dermatitis, gastritis, esophagitis, irritable bowel syndrome, inflammatory bowel disease, nephritis, muscle wasting, or osteoarthritis. In other embodiments, the chronic pain syndrome is fibromyalgia or neuropathic pain. In some embodiments, the disease or disorder is a severe inflammatory response to a pathogen such as from encephalitis, meningitis, *H. pylori, Toxoplasma gondii*, or *Leishmania* spp. In other embodiments, the disease or disorder is obesity or a condition associated with obesity. In some embodiments, the condition associated with obesity is insulin resistance or fatty liver disease. In some embodiments, the retinal disorder is macular degeneration or another disorder of the retina.

In some embodiments, the disease or disorder is associated with inflammation. In some embodiments, the disease or disorder associated with inflammation is obesity, Type 2 diabetes, or a complication of Type 1 or Type 2 diabetes. In some embodiments, the complication of Type 1 or Type 2 diabetes is neuropathy, reduced kidney function or chronic kidney disease, retinopathy, diabetic ulcers, or cardiovascular disease. In other embodiments, the disease or disorder associated with inflammation is chronic kidney disease. In some embodiments, the chronic kidney disease is hereditary. In other embodiments, the chronic kidney disease is due to a non-hereditary cause. In some embodiments, the method comprises administering the compound once. In other embodiments, the method comprises administering the compound two or more times.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula doesn't mean that it cannot also belong to another generic formula.

DESCRIPTION OF ILLUSTRATIVE EMBODIMENTS

Disclosed herein are new compounds and compositions that may be used to inhibit the activity of the RORγ nuclear receptor and/or IL-17 and thus useful in the treatment of a wide variety of different indications such as autoimmune disease, metabolic diseases, cancer, and infections. In some embodiments, these compounds are used to modulate the expression of one or more downstream compound such as interleukin-17 (IL-17).

I. Compounds and Synthetic Methods

The compounds of the present invention (also referred to as "compounds of the present disclosure") are shown, for example, above, in the summary of the invention section, and in the claims below. They may be made using the synthetic methods outlined in the Examples section. These methods can be further modified and optimized using the principles and techniques of organic chemistry as applied by a person skilled in the art. Such principles and techniques are taught, for example, in Smith, *March's Advanced Organic Chemistry: Reactions, Mechanisms, and Structure*, (2013), which is incorporated by reference herein. In addition, the synthetic methods may be further modified and optimized for preparative, pilot- or large-scale production, either batch or continuous, using the principles and techniques of process chemistry as applied by a person skilled in the art. Such principles and techniques are taught, for example, in Anderson, *Practical Process Research & Development—A Guide for Organic Chemists* (2012), which is incorporated by reference herein.

All the compounds of the present invention may in some embodiments be used for the prevention and treatment of one or more diseases or disorders discussed herein or otherwise. In some embodiments, one or more of the compounds characterized or exemplified herein as an intermediate, a metabolite, and/or prodrug, may nevertheless also be useful for the prevention and treatment of one or more diseases or disorders. As such, unless explicitly stated to the contrary, all the compounds of the present invention are deemed "active compounds" and "therapeutic compounds" that are contemplated for use as active pharmaceutical ingredients (APIs). Actual suitability for human or veterinary use is typically determined using a combination of clinical trial protocols and regulatory procedures, such as those administered by the Food and Drug Administration (FDA). In the United States, the FDA is responsible for protecting the public health by assuring the safety, effectiveness, quality, and security of human and veterinary drugs, vaccines and other biological products, and medical devices.

In some embodiments, the compounds of the present invention have the advantage that they may be more efficacious than, be less toxic than, be longer acting than, be more potent than, produce fewer side effects than, be more easily absorbed than, more metabolically stable than, more lipophilic than, more hydrophilic than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

Compounds of the present invention may contain one or more asymmetrically-substituted carbon or nitrogen atom and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can have the S or the R configuration. In some embodiments, the present compounds may contain two or more atoms which have a defined stereochemical orientation.

Chemical formulas used to represent compounds of the present invention will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}$C and $^{14}$C.

In some embodiments, compounds of the present invention function as prodrugs or can be derivatized to function as prodrugs. Since prodrugs are known to enhance numerous desirable properties of pharmaceuticals (e.g., solubility, bioavailability, manufacturing, etc.), the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a patient, cleaves to form a hydroxy, amino, or carboxylic acid, respectively.

In some embodiments, compounds of the present invention exist in salt or non-salt form. With regard to the salt form(s), in some embodiments the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

It will be appreciated that many organic compounds can form complexes with solvents in which they are reacted or from which they are precipitated or crystallized. These complexes are known as "solvates." Where the solvent is water, the complex is known as a "hydrate." It will also be appreciated that many organic compounds can exist in more than one solid form, including crystalline and amorphous forms. All solid forms of the compounds provided herein, including any solvates thereof are within the scope of the present invention.

II. Diseases Associated with Inflammatory Cytokine IL-17

Various reports have implicated the inflammatory cytokine IL-17 in the pathogenesis of many autoimmune diseases, including rheumatoid arthritis, psoriasis and psoriatic arthritis, inflammatory bowel diseases (including but not limited to Crohn's disease), multiple sclerosis, autoimmune nephritis, autoimmune uveitis, Type 1 diabetes, and ankylosing spondylitis. In some embodiments, the compounds provided herein may be administered to a patient in order to treat or prevent one or more of these diseases or disorders. A type of T lymphocyte known as a Th17 cell is a primary source of IL-17. There are multiple members of the IL-17 family. The first identified member, IL-17A, is commonly referred to as IL-17. IL-17 is composed of two monomers linked by disulfide bonds to form a homodimer (Miossec and Kolls, 2012). Aside from IL-17A, the other principal family member is IL-17F. Some evidence suggests that IL-17F and IL-17A, though they have many effects in common, may have different effects in certain settings such as lung inflammation. The IL-17 cytokines bind to IL-17 receptors (IL-17R) located in the membrane of select cell types. Although there are multiple subtypes of the IL-17 receptor, the IL-17RA/IL-17RC complex is required for the activity of IL-17A and IL-17F. IL-17RA has the unusual property of signaling through a pathway that involves an adaptor protein (ACTI) rather than the Janus kinase/signal transducer and activator of transcription (JAK/STAT) pathway employed by most interleukin receptors. Binding of IL-17A to IL-17RA activates the pro-inflammatory nuclear factor-kappa B (NF-κB) pathway and pro-inflammatory elements of the mitogen-activated protein kinase (MAPK) pathway such as JUN N-terminal kinase (JNK), p38 and extracellular signal-related kinase (ERK). IL-17 activity stimulates secretion of IL-6 and IL-8 from mesenchymal cells and leads to fever along with the accumulation of neutrophils in blood and tissue. In some embodiments, the compounds provided herein may be used to inhibit the secretion of IL-6 and IL-8 from mesenchymal cells. In some embodiments, the compounds provided herein may be administered to a patient in order to prevent or inhibit fever in a patient. In some embodiments, the compounds provided herein may be administered to a patient in order to prevent the accumulation of neutrophils in the blood or tissue of the patient.

Aside from its contribution to acute inflammation, IL-17 also contributes to chronic inflammation (Miossec and Kolls, 2012). In some embodiments, the compounds provided herein may be administered to a patient in order to prevent or treat chronic inflammation. IL-17 stimulates the production of matrix metalloproteinases (MMPs), which among other effects can degrade cartilage in joints. In some embodiments, the compounds provided herein may be administered to a patient in order to prevent or treat degradation of the patient's cartilage. IL-17 also increases the expression of receptor activator of NF-κB ligand (RANKL) in osteoblasts, leading to differentiation and activation of osteoclasts and bone degradation. In some embodiments, the compounds provided herein may be administered to a patient in order to prevent or treat degradation of the patient's bone. Depending on the target cell that is exposed to it, IL-17 may stimulate the production of IL-6, IL-8, IL-1, tumor necrosis factor (TNF), MMPs, nitric oxide, or several other proteins that are implicated in inflammatory conditions (e.g., tissue factor, CCL20, G-CSF and GM-CSF). In some embodiments, the compounds provided herein may be administered to a patient in order to inhibit the production of IL-6. IL-8, IL-1, tumor necrosis factor (TNF), MMPs, nitric oxide, or several other proteins that are implicated in inflammatory conditions (e.g., tissue factor, CCL20, G-CSF and GM-CSF).

Although IL-17 plays a role in the immune response to invading pathogens, excessive IL-17 activity has been implicated in pathologies associated with an excessive immune response to an infection. In some embodiments, the compounds provided herein may be administered to a patient in order to prevent or treat excessive immune response to an infection. For example, IL-17 has been implicated in the severe neuroinflammation associated with *Toxoplasma gondii* infection and increased severity of lesions associated with *Leishmania* infection. In some embodiments, the compounds provided herein may be administered to a patient in order to treat or prevent neuroinflammation, for example, neuroinflammation associated with *Toxoplasma gondii* infection. In some embodiments, the compounds provided herein may be administered to a patient in order to treat or prevent lesions associated with *Leishmania* infection. In these and other cases, IL-17 appears to play a role in perpetuating the infection, promoting an excessive inflammatory response, and inhibiting clearance of the infectious agent (Waite and Skokos, 2012). In some embodiments, the compounds provided herein may be administered to a patient in order to prevent an excessive inflammatory response and/or promote the clearance of an infectious agent.

Drugs targeting IL-17 have entered clinical trials for a wide variety of inflammatory conditions, including psoriasis, rheumatoid arthritis, ankylosing spondylitis, uveitis. Behcet's disease, psoriatic arthritis, Crohn's disease, polymyalgia rheumatica, dry eye syndrome, multiple sclerosis, graft-versus-host disease, and asthma. In some embodiments, the compounds provided herein may be administered to a patient in order to treat or prevent one or more of these diseases or disorders. Preclinical evidence also implicates IL-17 in the pathology of type 1 diabetes, and Th17 cells are elevated in patients with adult onset Still's disorder, another autoimmune disease. In some embodiments, the compounds provided herein may be administered to a patient in order to treat type 1 diabetes. In some embodiments, the compounds provided herein may be administered to a patient in order to treat or prevent adult onset Still's disorder. Activity of Th17 cells has been implicated in the development of graft-versus-host disease following allogeneic stem cell (e.g., bone marrow) transplantation (Fujiwara, et al, 2014). In some embodiments, the compounds provided herein may be administered to a patient in order to treat or prevent graft-versus-host disease, for example, following allogeneic stein cell (e.g., bone marrow) transplantation. Given the large body of evidence to date, it is likely that therapies reducing the expression of IL-17 or otherwise reducing its levels in circulation or target tissues (e.g., anti-IL17 monoclonal antibodies) could have broad applications in the treatment of autoimmune diseases and other inflammatory conditions. In some embodiments, the compounds provided herein may be administered to a patient in order to reduce the expression of IL-17 or its levels in circulation or target tissues (e.g., anti-IL17 monoclonal antibodies). In some embodiments, the compounds provided herein may be administered to a patient in order to treat autoimmune diseases or other inflammatory conditions.

Overproduction of IL-17 or elevated numbers of Th17 cells have been reported in patient studies or animal models of a large number of conditions, including autoimmune diseases, neurological disorders, cardiovascular diseases, cancer, psychiatric and neuropsychiatric disorders, acute and chronic inflammatory conditions, chronic pain syndromes, organ rejection or graft-versus-host disease, or asthma and other allergic conditions. In some embodiments, the compounds provided herein may be administered to a patient in order to treat or prevent one or more of these diseases or disorders.

Both the differentiation of Th17 cells and their production of IL-17 are regulated to a significant degree by the retinoid orphan receptor RORγt, a member of the nuclear hormone receptor family. Expression of RORγt is common to all types of Th17 cells. RORγ also regulates the production of IL-17 in other cell types, including γδ T cells, innate lymphoid cells, and lymphoid tissue inducer cells (Bronner et al., 2017). Inhibition of RORγt activity results in reduced expression of IL-17. In some embodiments, the compounds provided herein may be administered to a patient in order to inhibit RORγt activity.

Compounds and compositions provided herein may be used to suppress IL-17 production in cultures of human T cells that are exposed to a mixture of cytokines known to induce differentiation into Th17 cells. In some embodiments, the ability to act as inverse agonists of RORγt is also demonstrated. Without wishing to be bound by any theory, it is believed that, for example, RORγt-independent mechanisms appear to contribute to the suppression of IL-17 production. Thus, the compounds and compositions provided herein may be used for inhibiting differentiation of T cells into Th17 cells, as well as inhibiting production of IL-17 by mature Th17 cells. In some of these embodiments, the net result is a reduction in IL-17 levels. In some embodiments, the compounds provided herein may be administered to a patient in order to suppress IL-17 production in one or more of the patient's tissues or organs.

III. Pharmaceutical Formulations and Routes of Administration

In another aspect, for administration to a patient in need of such treatment, pharmaceutical formulations (also referred to as a pharmaceutical preparations, pharmaceutical compositions, pharmaceutical products, medicinal products, medicines, medications, or medicaments) comprise a therapeutically effective amount of a compound disclosed herein formulated with one or more excipients and/or drug carriers appropriate to the indicated route of administration. In some embodiments, the compounds disclosed herein are formulated in a manner amenable for the treatment of human and/or veterinary patients. In some embodiments, formulation comprises admixing or combining one or more of the compounds disclosed herein with one or more of the following excipients: lactose, sucrose, starch powder, cellulose esters of alkanoic acids, cellulose alkyl esters, talc, stearic acid, magnesium stearate, magnesium oxide, silicon dioxide, sodium and calcium salts of phosphoric and sulfuric acids, sodium lauryl sulfate, gelatin, acacia, sodium alginate, polyvinylpyrrolidone, and/or polyvinyl alcohol. In some embodiments, e.g., for oral administration, the pharmaceutical formulation may be tableted or encapsulated. In some embodiments, the compounds may be dissolved or slurried in water, polyethylene glycol, propylene glycol, ethanol, corn oil, cottonseed oil, peanut oil, sesame oil, benzyl alcohol, sodium chloride, and/or various buffers. In some embodiments, the pharmaceutical formulations may be subjected to pharmaceutical operations, such as sterilization, and/or may contain drug carriers and/or excipients such as preservatives, stabilizers, wetting agents, emulsifiers, encapsulating agents such as lipids, dendrimers, polymers, proteins such as albumin, nucleic acids, and buffers.

Pharmaceutical formulations may be administered by a variety of methods, e.g., orally or by injection (e.g. subcutaneous, intravenous, and intraperitoneal). Depending on the route of administration, the compounds disclosed herein may be coated in a material to protect the compound from the action of acids and other natural conditions which may inactivate the compound. To administer the active compound by other than parenteral administration, it may be necessary to coat the compound with, or co-administer the compound with, a material to prevent its inactivation. In some embodiments, the active compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes.

The compounds disclosed herein may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

The compounds disclosed herein can be administered orally, for example, with an inert diluent or an assimilable edible carrier. The compounds and other ingredients may also be enclosed in a hard or soft-shell gelatin capsule, encapsulated in HPMC capsules, compressed into tablets, or incorporated directly into the patient's diet. For oral therapeutic administration, the compounds disclosed herein may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such pharmaceutical formulations is such that a suitable dosage will be obtained.

The therapeutic compound may also be administered topically to the skin, eye, ear, or mucosal membranes. Administration of the therapeutic compound topically may include formulations of the compounds as a topical solution, lotion, cream, ointment, gel, foam, transdermal patch, or tincture. When the therapeutic compound is formulated for topical administration, the compound may be combined with one or more agents that increase the permeability of the compound through the tissue to which it is administered. In other embodiments, it is contemplated that the topical administration is administered to the eye. Such administration may be applied to the surface of the cornea, conjunctiva, or sclera. Without wishing to be bound by any theory, it is believed that administration to the surface of the eye allows the therapeutic compound to reach the posterior portion of the eye. Ophthalmic topical administration can be formulated as a solution, suspension, ointment, gel, or emulsion. Finally, topical administration may also include administration to the mucosa membranes such as the inside of the mouth. Such administration can be directly to a particular location within the mucosal membrane such as a tooth, a sore, or an ulcer. Alternatively, if local delivery to the lungs is desired the therapeutic compound may be administered by inhalation in a dry powder or aerosol formulation.

In some embodiments, it may be advantageous to formulate parenteral compositions in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical carrier. In some embodiments, the specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient. In some embodiments, active compounds are administered at a therapeutically effective dosage sufficient to treat a condition associated with a condition in a patient. For example, the efficacy of a compound can be evaluated in an animal model system that may be predictive of efficacy in treating the disease in a human or another animal.

In some embodiments, the effective dose range for the therapeutic compound can be extrapolated from effective doses determined in animal studies for a variety of different animals. In some embodiments, the human equivalent dose (HED) in mg/kg can be calculated in accordance with the following formula (see, e.g., Reagan-Shaw et al., *FASEB J.*, 22(3):659-661, 2008, which is incorporated herein by reference):

HED (mg/kg)=Animal dose (mg/kg)×(Animal $K_m$/Human $K_m$)

Use of the $K_m$ factors in conversion results in HED values based on body surface area (BSA) rather than only on body mass. $K_m$ values for humans and various animals are well known. For example, the $K_m$ for an average 60 kg human (with a BSA of 1.6 m$^2$) is 37, whereas a 20 kg child (BSA 0.8 m$^2$) would have a $K_m$ of 25. $K_m$ for some relevant animal models are also well known, including: mice $K_m$ of 3 (given a weight of 0.02 kg and BSA of 0.007); hamster $K_m$ of 5 (given a weight of 0.08 kg and BSA of 0.02); rat $K_m$ of 6 (given a weight of 0.15 kg and BSA of 0.025) and monkey $K_m$ of 12 (given a weight of 3 kg and BSA of 0.24).

Precise amounts of the therapeutic composition depend on the judgment of the practitioner and are specific to each individual. Nonetheless, a calculated HED dose provides a general guide. Other factors affecting the dose include the physical and clinical state of the patient, the route of administration, the intended goal of treatment and the potency, stability and toxicity of the particular therapeutic formulation.

The actual dosage amount of a compound of the present disclosure or composition comprising a compound of the present disclosure administered to a patient may be determined by physical and physiological factors such as type of animal treated, age, sex, body weight, severity of condition, the type of disease being treated, previous or concurrent therapeutic interventions, idiopathy of the patient and on the route of administration. These factors may be determined by a skilled artisan. The practitioner responsible for administration will typically determine the concentration of active ingredient(s) in a composition and appropriate dose(s) for the individual patient. The dosage may be adjusted by the individual physician in the event of any complication.

In some embodiments, the therapeutically effective amount typically will vary from about 0.001 mg/kg to about 1000 mg/kg, from about 0.01 mg/kg to about 750 mg/kg, from about 100 mg/kg to about 500 mg/kg, from about 1 mg/kg to about 250 mg/kg, from about 10 mg/kg to about 150 mg/kg in one or more dose administrations daily, for one or several day s (depending of course of the mode of administration and the factors discussed above). Other suitable dose ranges include 1 mg to 10,000 mg per day, 100 mg to 10,000 mg per day, 500 mg to 10,000 mg per day, and 500 mg to 1,000 mg per day. In some embodiments, the amount is less than 10,000 mg per day with a range of 750 mg to 9,000 mg per day.

In some embodiments, the amount of the active compound in the pharmaceutical formulation is from about 1 to about 100 weight percent. In some embodiments, the amount of the active compound in the pharmaceutical formulation is from about 10 to about 90, from about 25 to about 75, or about 50 weight percent.

Single or multiple doses of the agents are contemplated. Desired time intervals for delivery of multiple doses can be determined by one of ordinary skill in the art employing no more than routine experimentation. As an example, patients may be administered two doses daily at approximately 12-hour intervals. In some embodiments, the agent is administered once a day.

The agent(s) may be administered on a routine schedule. As used herein a routine schedule refers to a predetermined designated period of time. The routine schedule may encompass periods of time which are identical, or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may be taken orally and that the timing of which is or is not dependent upon food intake. Thus, for example, the agent can be taken every morning and/or every evening, regardless of when the patient has eaten or will eat.

IV. Combination Therapy

In addition to being used as a monotherapy, the compounds of the present invention may also find use in combination therapies. Effective combination therapy may be achieved with a single composition or pharmacological formulation that includes both agents, or with two distinct compositions or formulations, administered at the same time, wherein one composition includes a compound of this invention, and the other includes the second agent(s). Alternatively, the therapy may precede or follow the other agent treatment by intervals ranging from minutes to months.

Non-limiting examples of such combination therapy include combination of one or more compounds of the invention with another anti-inflammatory agent, a chemotherapeutic agent, radiation therapy, an antidepressant, an antipsychotic agent, an anticonvulsant, a mood stabilizer, an anti-infective agent, an antihypertensive agent, a cholesterol-lowering agent or other modulator of blood lipids, an agent for promoting weight loss, an antithrombotic agent, an agent for treating or preventing cardiovascular events such as myocardial infarction or stroke, an antidiabetic agent, an agent for reducing transplant rejection or graft-versus-host disease, an anti-arthritic agent, an analgesic agent, an anti-asthmatic agent or other treatment for respiratory diseases, or an agent for treatment or prevention of skin disorders. Compounds of the invention may be combined with agents designed to improve a patient's immune response to cancer, including (but not limited to) cancer vaccines. See Lu et al. (2011), which is incorporated herein by reference.

V. Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanyl" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$_2$—; and "sulfinyl" means —S(O)—.

In the context of chemical formulas, the symbol "—" means a single bond, "=" means a double bond, and "≡" means triple bond. The symbol "-----" represents an optional bond, which if present is either single or double. The symbol "===" represents a single bond or a double bond. Thus, the formula

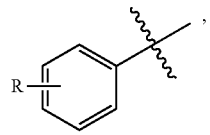

covers, for example,

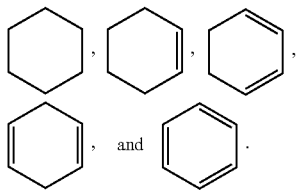

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol "⁓" when drawn perpendicularly across a bond (e.g.,

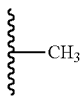

for methyl) indicates a point of attachment of the group. It is noted that the point of attachment is typically only identified in this manner for larger groups in order to assist the reader in unambiguously identifying a point of attachment. The symbol "◥" means a single bond where the group attached to the thick end of the wedge is "out of the page." The symbol "◨" means a single bond where the group attached to the thick end of the wedge is "into the page". The symbol "⁓" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a variable is depicted as a "floating group" on a ring system, for example, the group "R" in the formula:

then the variable may replace any hydrogen atom attached to any of the ring atoms, including a depicted, implied, or expressly defined hydrogen, so long as a stable structure is formed. When a variable is depicted as a "floating group" on a fused ring system, as for example the group "R" in the formula:

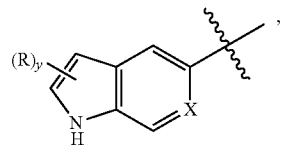

then the variable may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the R enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" defines the exact number (n) of carbon atoms in the group/class. "C≤n" defines the maximum number (n) of carbon atoms that can be in the group/class, with the minimum number as small as possible for the group/class in question. For example, it is understood that the minimum number of carbon atoms in the groups "alkyl$_{(C≤8)}$", "cycloalkanediyl$_{(C≤8)}$", "heteroaryl$_{(C≤8)}$", and "acyl$_{(C≤8)}$" is one, the minimum number of carbon atoms in the groups "alkenyl$_{(C≤8)}$", "alkynyl$_{(C≤8)}$", and "heterocycloalkyl$_{(C≤8)}$" is two, the minimum number of carbon atoms in the group "cycloalkyl$_{(C≤8)}$" is three, and the minimum number of carbon atoms in the groups "aryl$_{(C≤8)}$" and "arenediyl$_{(C≤8)}$" is six. "Cn-n'" defines both the minimum (n) and maximum number (n') of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefin$_{C5}$" are all synonymous. When any of the chemical groups or compound classes defined herein is modified by the term "substituted", any carbon atom in the moiety replacing the hydrogen atom is not counted. Thus methoxyhexyl, which has a total of seven carbon atoms, is an example of a substituted alkyl$_{(C1-6)}$. Unless specified otherwise, any chemical group or compound class listed in a claim set without a carbon atom limit has a carbon atom limit of less than or equal to twelve.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" signifies that the compound or chemical group so modified is an acyclic or cyclic, but non-aromatic compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" signifies that the compound or chemical group so modified has a planar unsaturated ring of atoms with 4n+2 electrons in a fully conjugated cyclic π system.

The term "alkyl" refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (—Pr, $^i$Pr or isopropyl), —CH$_2$CH$_2$CH$_2$CH$_3$ (n-Bu). —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkylidene" refers to the divalent group =CRR' in which R and R' are independently hydrogen, alkyl, aryl, or heteroaryl. Non-limiting examples of alkylidene groups include: =CH$_2$, =CH(CH$_2$CH$_3$), and =C(CH$_3$)$_2$. An "alkane" refers to the class of compounds having the formula H—R, wherein R is alkyl as this term is defined above.

The term "cycloalkyl" refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —CH(CH$_2$)$_2$ (cyclopropyl), cyclobutyl, cyclopentyl, or cyclohexyl (Cy). As used herein, the term does not preclude the presence of one or more alkyl groups (carbon number limitation permitting) attached to a carbon atom of the non-aromatic ring structure. The term "cycloalkanediyl" refers to a divalent saturated aliphatic group with two carbon atoms as points of attachment, no carbon-carbon double or triple bonds, and no atoms other than carbon and hydrogen. The group

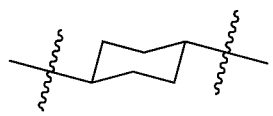 [SMILES: *C1CCC(*)CC1]

is a non-limiting example of cycloalkanediyl group. A "cycloalkane" refers to the class of compounds having the formula H—R, wherein R is cycloalkyl as this term is defined above.

The term "alkenyl" refers to a monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" refers to a divalent unsaturated aliphatic group, with two carbon atoms as points of attachment, a linear or branched acyclic structure, at least one nonaromatic carbon-carbon double bond, no carbon-carbon triple bonds, and no atoms other than carbon and hydrogen. The groups —CH=CH—, —CH=C(CH$_3$)CH$_2$—, —CH=CHCH$_2$—, and —CH$_2$CH=CHCH$_2$— are non-limiting examples of alkenediyl groups. It is noted that while the alkenediyl group is aliphatic, once connected at both ends, this group is not precluded from forming part of an aromatic structure. The terms "alkene" and "olefin" are synonymous and refer to the class of compounds having the formula H—R, wherein R is alkenyl as this term is defined above. Similarly, the terms "terminal alkene" and "α-olefin" are synonymous and refer to an alkene having just one carbon-carbon double bond, wherein that bond is part of a vinyl group at an end of the molecule.

The term "alkynyl" refers to a monovalent unsaturated aliphatic group with a carbon atom as the point of attachment, a linear or branched acyclic structure, at least one carbon-carbon triple bond, and no atoms other than carbon and hydrogen. As used herein, the term alkynyl does not preclude the presence of one or more non-aromatic carbon-carbon double bonds. The groups —C≡CH, —C≡CCH$_3$, and —CH$_2$C≡CCH$_3$ are non-limiting examples of alkynyl groups. An "alkyne" refers to the class of compounds having the formula H—R, wherein R is alkynyl. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aryl" refers to a monovalent unsaturated aromatic group with an aromatic carbon atom as the point of attachment, said carbon atom forming part of a one or more aromatic ring structures, each with six ring atoms that are all carbon, and wherein the group consists of no atoms other than carbon and hydrogen. If more than one ring is present, the rings may be fused or unfused. Unfused rings are connected with a covalent bond. As used herein, the term aryl does not preclude the presence of one or more alkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl (e.g., 4-phenylphenyl). The term "arenediyl" refers to a divalent aromatic group with two aromatic carbon atoms as points of attachment, said carbon atoms forming part of one or more six-membered aromatic ring structures, each with six ring atoms that are all carbon, and wherein the divalent group consists of no atoms other than carbon and hydrogen. As used herein, the term arenediyl does not preclude the presence of one or more alkyl groups (carbon number limitation permitting) attached to the first aromatic ring or any additional aromatic ring present. If more than one ring is present, the rings may be fused or unfused. Unfused rings are connected with a covalent bond. Non-limiting examples of arenediyl groups include:

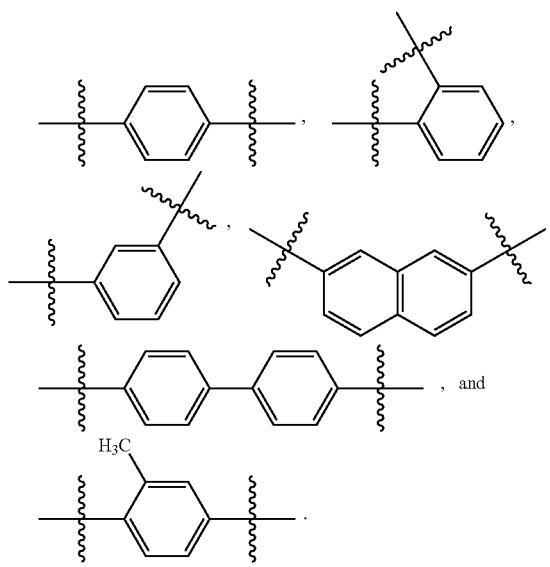

An "arene" refers to the class of compounds having the formula H—R, wherein R is aryl as that term is defined above. Benzene and toluene are non-limiting examples of arenes.

The term "aralkyl" refers to the monovalent group -alkanediyl-aryl, in which the terms alkanediyl and aryl are each used in a manner consistent with the definitions provided above. Non-limiting examples are: phenylmethyl (benzyl, Bn) and 2-phenyl-ethyl.

The term "heteroaryl" refers to a monovalent aromatic group with an aromatic carbon atom or nitrogen atom as the point of attachment, said carbon atom or nitrogen atom forming part of one or more aromatic ring structures, each with three to eight ring atoms, wherein at least one of the ring atoms of the aromatic ring structure(s) is nitrogen, oxygen or sulfur, and wherein the heteroaryl group consists of no atoms other than carbon, hydrogen, aromatic nitrogen, aromatic oxygen and aromatic sulfur. If more than one ring is present, the rings are fused. The term heteroaryl does not preclude the presence of one or more alkyl or aryl groups (carbon number limitation permitting) attached to one or more ring atoms. Non-limiting examples of heteroaryl groups include benzoxazolyl, benzimidazolyl, furanyl, imidazolyl (Im), indolyl, indazolyl (Im), isoxazolyl, methylpyridinyl, oxazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl.

The term "heteroarenediyl" refers to a divalent aromatic group, with two aromatic carbon atoms, two aromatic nitrogen atoms, or one aromatic carbon atom and one aromatic nitrogen atom as the two points of attachment, said atoms forming part of one or more aromatic ring structures, each with three to eight ring atoms, wherein at least one of the ring atoms of the aromatic ring structure(s) is nitrogen, oxygen or sulfur, and wherein the divalent group consists of no atoms other than carbon, hydrogen, aromatic nitrogen, aromatic oxygen and aromatic sulfur. If more than one ring is present, the rings are fused; however, the term heteroarenediyl does not preclude the presence of one or more alkyl or aryl groups (carbon number limitation permitting) attached to one or more ring atoms. Non-limiting examples of heteroarenediyl groups include:

The term "N-heteroaryl" refers to a heteroaryl group with a nitrogen atom as the point of attachment. A "heteroarene" refers to the class of compounds having the formula H—R, wherein R is heteroaryl. Pyridine and quinoline are non-limiting examples of heteroarenes.

The term "heteroaralkyl" refers to the monovalent group -alkanediyl-heteroaryl, in which the terms alkanediyl and heteroaryl are each used in a manner consistent with the definitions provided above. Non-limiting examples are: pyridinylmethyl and 2-quinolinyl-ethyl.

The term "heterocycloalkyl" refers to a monovalent non-aromatic group with a carbon atom or nitrogen atom as the point of attachment, said carbon atom or nitrogen atom forming part of one or more non-aromatic ring structures, each with three to eight ring atoms, wherein at least one of the ring atoms of the non-aromatic ring structure(s) is nitrogen, oxygen or sulfur, and wherein the heterocycloalkyl group consists of no atoms other than carbon, hydrogen, nitrogen, oxygen and sulfur. If more than one ring is present, the rings are fused. As used herein, the term does not preclude the presence of one or more alkyl groups (carbon number limitation permitting) attached to one or more ring atoms. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl.

The term "heterocycloalkanediyl" refers to a divalent cyclic group, with two carbon atoms, two nitrogen atoms, or one carbon atom and one nitrogen atom as the two points of attachment, said atoms forming part of one or more ring structure(s) wherein at least one of the ring atoms of the non-aromatic ring structure(s) is nitrogen, oxygen or sulfur, and wherein the divalent group consists of no atoms other than carbon, hydrogen, nitrogen, oxygen and sulfur. If more than one ring is present, the rings are fused. As used herein, the term heterocycloalkanediyl does not preclude the presence of one or more alkyl groups (carbon number limitation permitting) attached to one or more ring atoms. Also, the term does not preclude the presence of one or more double bonds in the ring or ring system, provided that the resulting group remains non-aromatic. Non-limiting examples of heterocycloalkanediyl groups include:

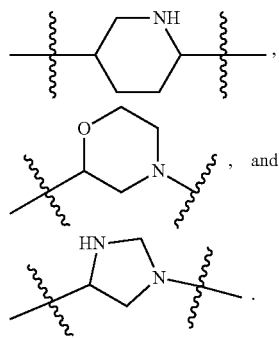

The term "N-heterocycloalkyl" refers to a heterocycloalkyl group with a nitrogen atom as the point of attachment. N-pyrrolidinyl is an example of such a group.

The term "acyl" refers to the group —C(O)R, in which R is a hydrogen, alkyl, cycloalkyl, or aryl as those terms are defined above. The groups, —CHO, —C(O)CH₃ (acetyl, Ac), —C(O)CH₂CH₃, —C(O)CH(CH₃)₂, —C(O)CH(CH₂)₂, —C(O)C₆H₅, and —C(O)C₆H₄CH₃ are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkyl group, as defined above, attached to a —CHO group.

The term "alkoxy" refers to the group —OR, in which R is an alkyl, as that term is defined above. Non-limiting examples include: —OCH₃ (methoxy), —OCH₂CH₃ (ethoxy), —OCH₂CH₂CH₃, —OCH(CH₃)₂ (isopropoxy), or —OC(CH₃)₃ (tert-butoxy). The terms "cycloalkoxy", "alkenyloxy", "alkynyloxy", "aryloxy" "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkylthio" and "acylthio" refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group.

The term "alkylamino" refers to the group —NHR, in which R is an alkyl, as that term is defined above. Non-limiting examples include: —NHCH₃ and —NHCH₂CH₃. The term "dialkylamino" refers to the group —NRR', in which R and R' can be the same or different alkyl groups. Non-limiting examples of dialkylamino groups include: —N(CH₃)₂ and —N(CH₃)(CH₂CH). The terms "cycloalkylamino", "alkenylamino", "alkynylamino", "arylamino", "aralkylamino", "heteroarylamino", "heterocycloalkylamino", and "alkoxyamino" when used without the "substituted" modifier, refers to groups, defined as —NHR, in which R is cycloalkyl, alkenyl, alkynyl, aryl, aralkyl, heteroaryl, heterocycloalkyl, and alkoxy, respectively. A non-limiting example of an arylamino group is —NHC₆H₅. The terms "dicycloalkylamino", "dialkenylamino", "dialkylamino", "diarylamino", "diaralkylamino", "dihcteroarylamino", "diheterocycloalkylamino", and "dialkoxyamino", refers to groups, defined as —NRR', in which R and R' are both cycloalkyl, alkenyl, alkynyl, aryl, aralkyl, heteroaryl, heterocycloalkyl, and alkoxy, respectively. Similarly, the term alkyl(cycloalkyl)amino refers to a group defined as —NRR', in which R is alkyl and R' is cycloalkyl. The term "amido" (acylamino), when used without the "substituted" modifier, refers to the group —NHR, in which R is acyl, as that term is defined above. A non-limiting example of an amido group is —NHC(O)CH₃.

When a chemical group is used with the "substituted" modifier, one or more hydrogen atom has been replaced, independently at each instance, by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂. For example, the following groups are non-limiting examples of substituted alkyl groups: —CH₂OH, —CH₂Cl, —CF₃, —CH₂CN, —CH₂C(O)OH, —CH₂C(O)OCH₃, —CH₂C(O)NH₂, —CH₂C(O)CH₃, —CH₂OCH₃, —CH₂OC(O)CH₃, —CH₂NH₂, —CH₂N(CH₃)₂, and —CH₂CH₂Cl. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH₂Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH₂F, —CF₃, and —CH₂CF₃ are non-limiting examples of fluoroalkyl groups. Non-limiting examples of substituted aralkyls are: (3-chlorophenyl)-methyl, and 2-chloro-2-phenyl-eth-1-yl. The groups, —C(O)CH₂CF₃, —CO₂H (carboxyl), —CO₂CH₃ (methylcarbonyl), —CO₂CH₂CH₃, —C(O)NH₂ (carbamoyl), and —CON(CH₃)₂, are non-limiting examples of substituted acyl groups. The groups —NHC(O)OCH₃ and —NHC(O)NHCH₃ are non-limiting examples of substituted amido groups.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects or patients.

An "active ingredient" (AI) or active pharmaceutical ingredient (API) (also referred to as an active compound, active substance, active agent, pharmaceutical agent, agent, biologically active molecule, or a therapeutic compound) is the ingredient in a pharmaceutical drug that is biologically active.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating or preventing a disease, is an amount sufficient to effect such treatment or prevention of the disease.

An "excipient" is a pharmaceutically acceptable substance formulated along with the active ingredient(s) of a medication, pharmaceutical composition, formulation, or drug delivery system. Excipients may be used, for example, to stabilize the composition, to bulk up the composition (thus often referred to as "bulking agents," "fillers," or "diluents" when used for this purpose), or to confer a therapeutic enhancement on the active ingredient in the final dosage form, such as facilitating drug absorption, reducing viscosity, or enhancing solubility. Excipients include pharmaceutically acceptable versions of antiadherents, binders, coatings, colors, disintegrants, flavors, glidants, lubricants, preservatives, sorbents, sweeteners, and vehicles. The main excipient that serves as a medium for conveying the active ingredient is usually called the vehicle. Excipients may also be used in the manufacturing process, for example, to aid in the handling of the active substance, such as by facilitating powder flowability or non-stick properties, in addition to aiding in vitro stability such as prevention of denaturation or aggregation over the expected shelf life. The suitability of an excipient will typically vary depending on the route of administration, the dosage form, the active ingredient, as well as other factors.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "$IC_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human patients are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio. One example of compounds which are pharmaceutically acceptable include those compounds, materials, compositions, and/or dosage forms have been designated by the United States Food and Drug Administration (US FDA) as having a status of generally regarded as safe (GRAS).

"Pharmaceutically acceptable salts" means salts of compounds disclosed herein which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

A "pharmaceutically acceptable carrier," "drug carrier," or simply "carrier" is a pharmaceutically acceptable substance formulated along with the active ingredient medication that is involved in carrying, delivering and/or transporting a chemical agent. Drug carriers may be used to improve the delivery and the effectiveness of drugs, including for example, controlled-release technology to modulate drug bioavailability, decrease drug metabolism, and/or reduce drug toxicity. Some drug carriers may increase the effectiveness of drug delivery to the specific target sites. Examples of carriers include: liposomes, microspheres (e.g., made of poly(lactic-co-glycolic) acid), albumin microspheres, synthetic polymers, nanofibers, protein-DNA complexes, protein conjugates, erythrocytes, virosomes, and dendrimers.

A "pharmaceutical drug" (also referred to as a pharmaceutical, pharmaceutical preparation, pharmaceutical composition, pharmaceutical formulation, pharmaceutical product, medicinal product, medicine, medication, medicament, or simply a drug, agent, or preparation) is a composition used to diagnose, cure, treat, or prevent disease, which comprises an active pharmaceutical ingredient (API) (defined above) and optionally contains one or more inactive ingredients, which are also referred to as excipients (defined above).

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Non-limiting examples of suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-β-toluoyltartrates, methanesulfonates, ethanesulfonates, benzenesulfonates, p-toluenesulfonates, cyclohexylsulfamates, quinates, and esters of amino acids. Similarly, a compound comprising an amine group may be administered as an amide that is converted by hydrolysis in vivo to the amine compound.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease or symptom thereof in a subject or patient that is experiencing or displaying the pathology or symptomatology of the disease.

The term "unit dose" refers to a formulation of the compound or composition such that the formulation is prepared in a manner sufficient to provide a single therapeutically effective dose of the active ingredient to a patient in a single administration. Such unit dose formulations that may be used include but are not limited to a single tablet, capsule, or other oral formulations, or a single vial with a syringeable liquid or other injectable formulations.

The above definitions supersede any conflicting definition in any reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

VI. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: Synthesis and Characterization
i. Synthetic Routes to Compounds
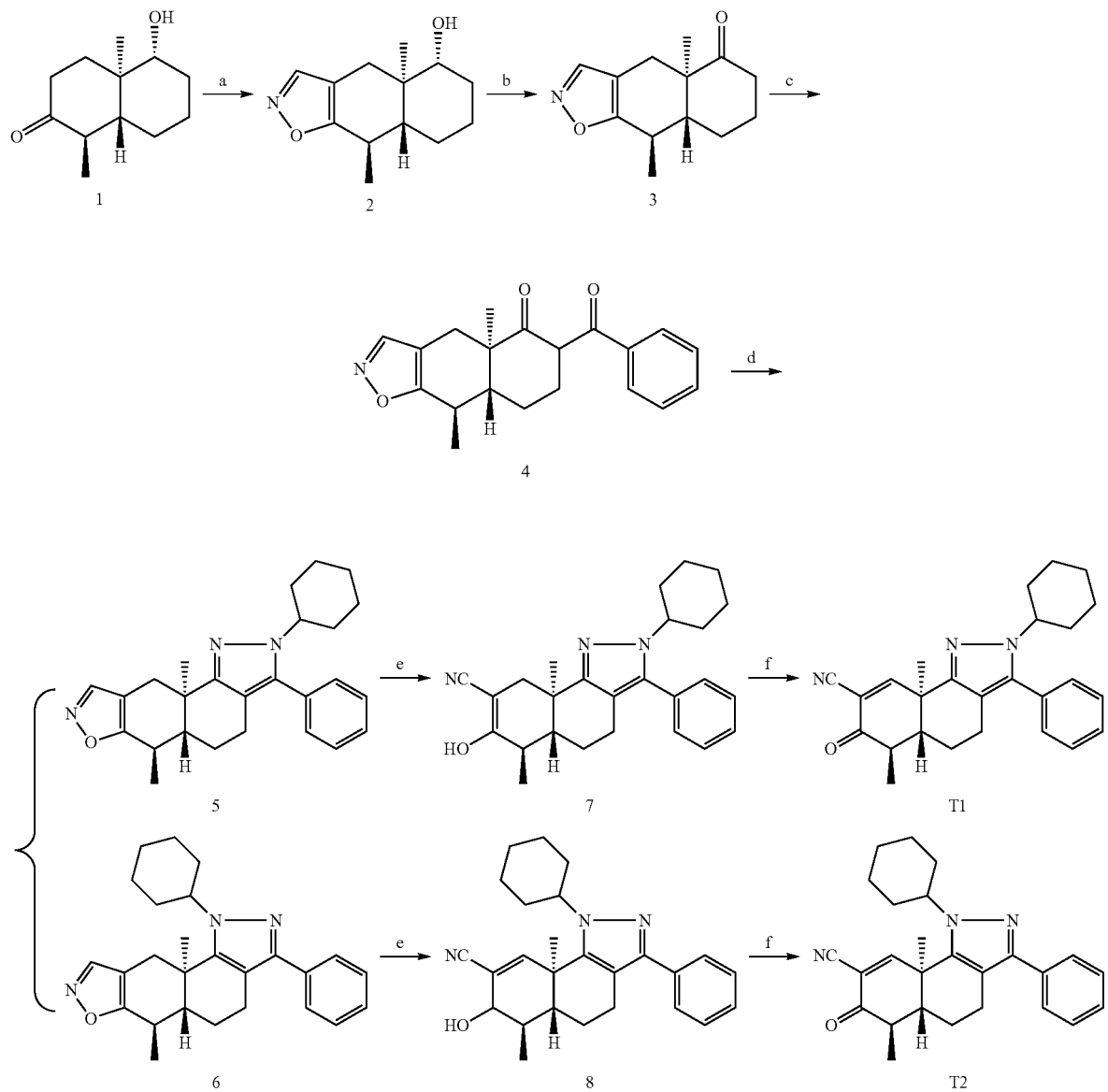
Reagents and conditions: a) i) HCO₂Et, NaOMe, MeOH, 0° C. to rt; ii) NH₂OH•HCl, EtOH, H₂O, 55° C.; b) Jones' reagent, acetone, 0° C.; c) MgBr₂•Et₂O, DIPEA, PhCOCl, CH₂Cl₂, rt d) cyclohexylhydrazine hydrochloride, EtOH, microwave, 110° C.; e) NaOMe, MeOH, 55° C.; f) DDQ, toluene, 85° C. (for T1); or DBDMH, DMF, 0° C.; pyridine, 55° C. (for T2).
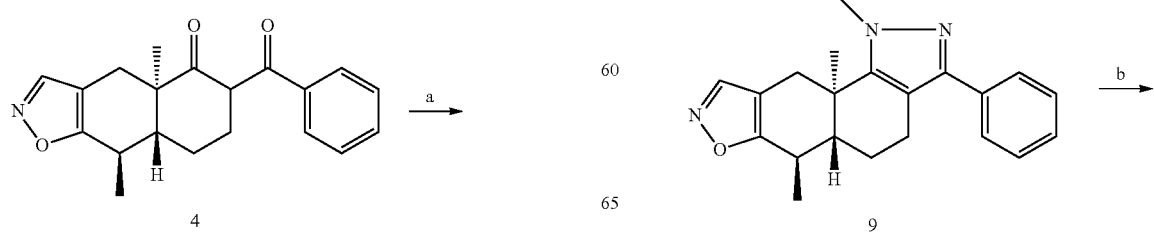

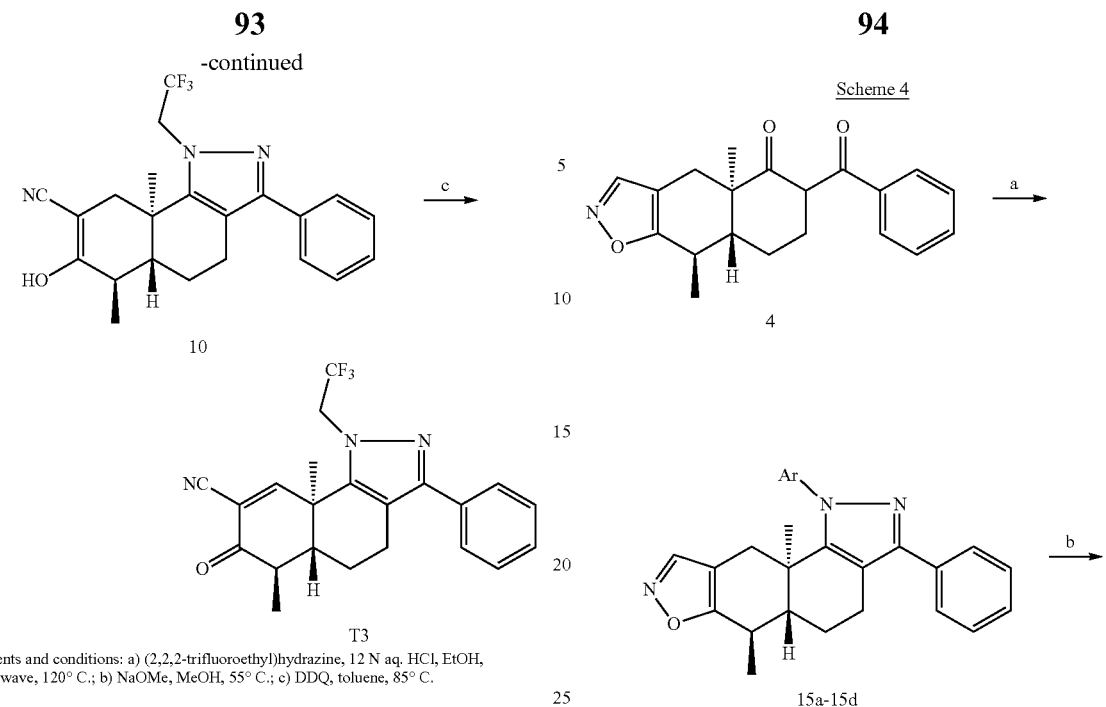
Reagents and conditions: a) (2,2,2-trifluoroethyl)hydrazine, 12 N aq. HCl, EtOH, microwave, 120° C.; b) NaOMe, MeOH, 55° C.; c) DDQ, toluene, 85° C.
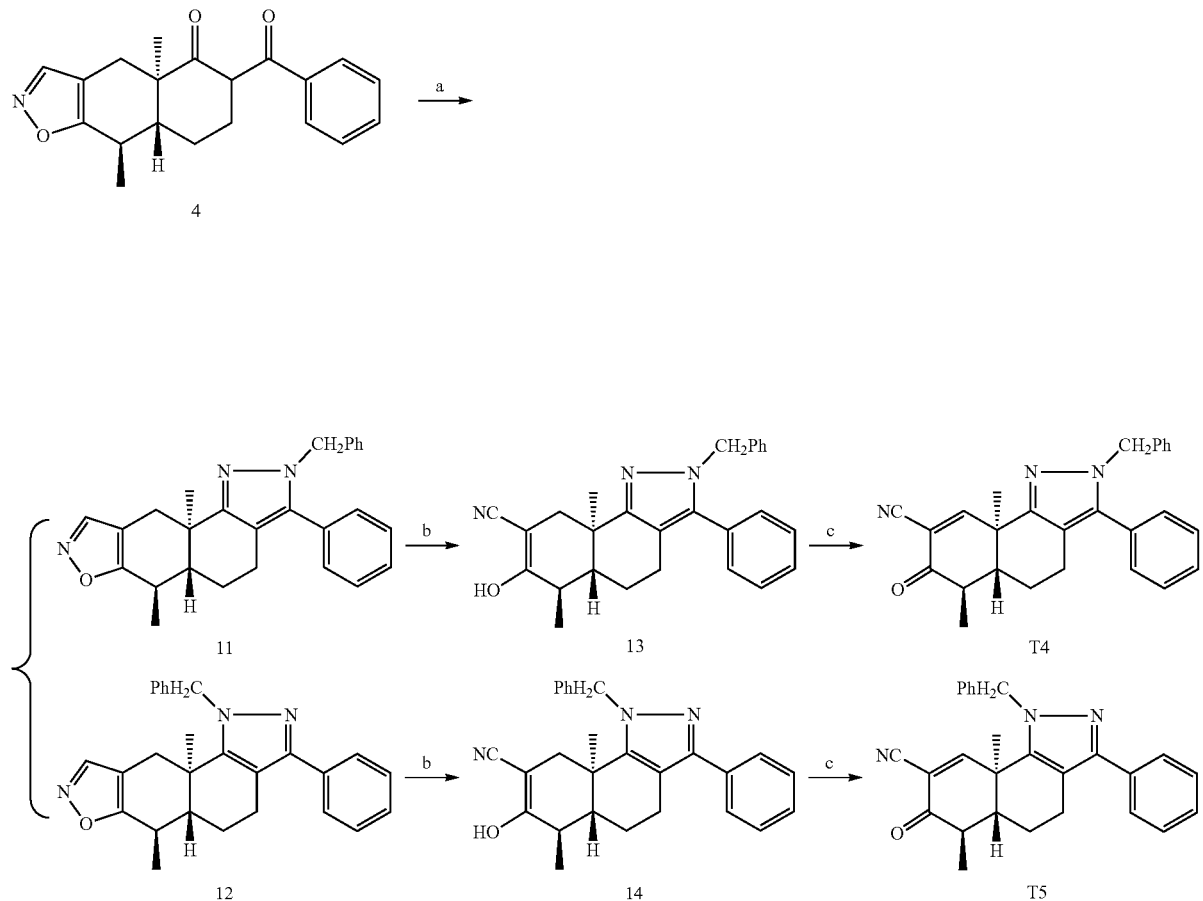
Reagents and conditions: a) benzylhydrazine dihydrochloride, EtOH, microwave, 110° C.; b) NaOMe, MeOH, 55° C.; c) DBDMH, DMF, 0° C.; pyridine, 55° C.

95
-continued
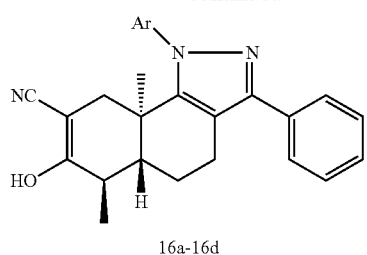
16a-16d
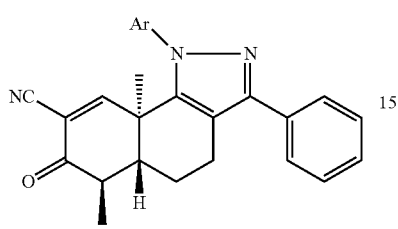
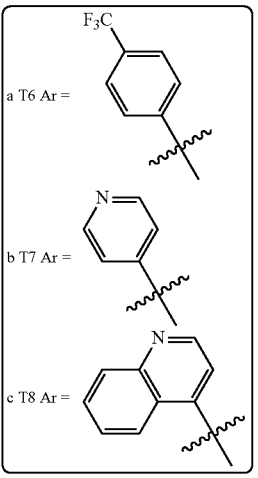
Reagents and conditions: a) ArNHNH₂ and aq. HCl (for 15a and 15c) or ArNHNH₂·HCl (for 15B), EtOH, microwave; b) NaOMe, MeOH, 55° C.; c) condition A (for T6 and T7): DBDMH, DMF, 0° C.; pyridine, 55° C.; or condition B (for T8): DDQ, benzene, reflux.
96
-continued
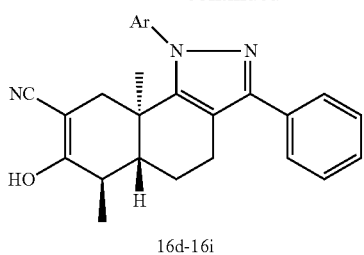
16d-16i
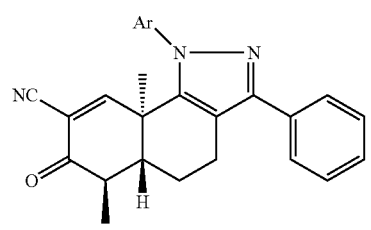
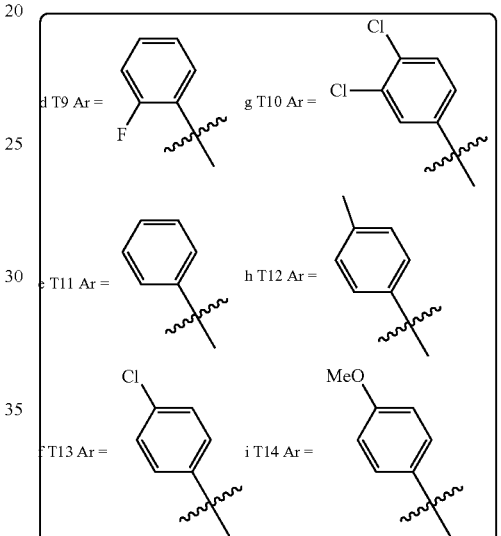
Reagents and conditions: a) ArNHNH₂·HCl, EtOH, microwave; b) K₂CO₃, MeOH, rt; c) DBDMH, DMF, 0° C.; pyridine, 60° C.
Scheme 5
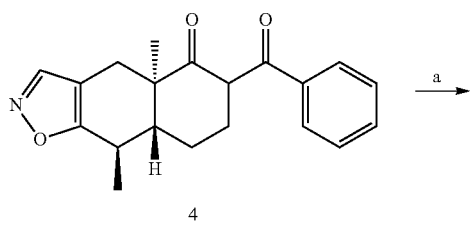
4
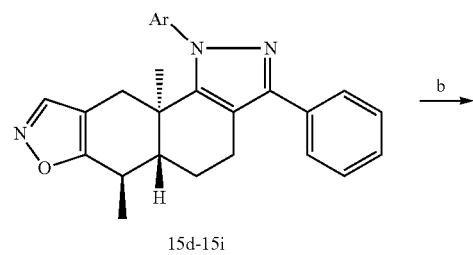
15d-15i
Scheme 6
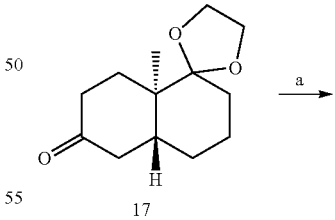
17
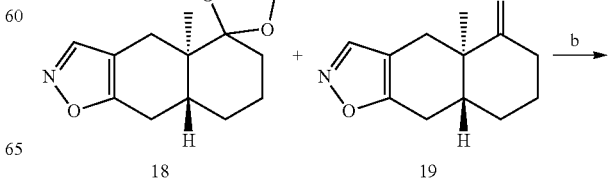
18     19

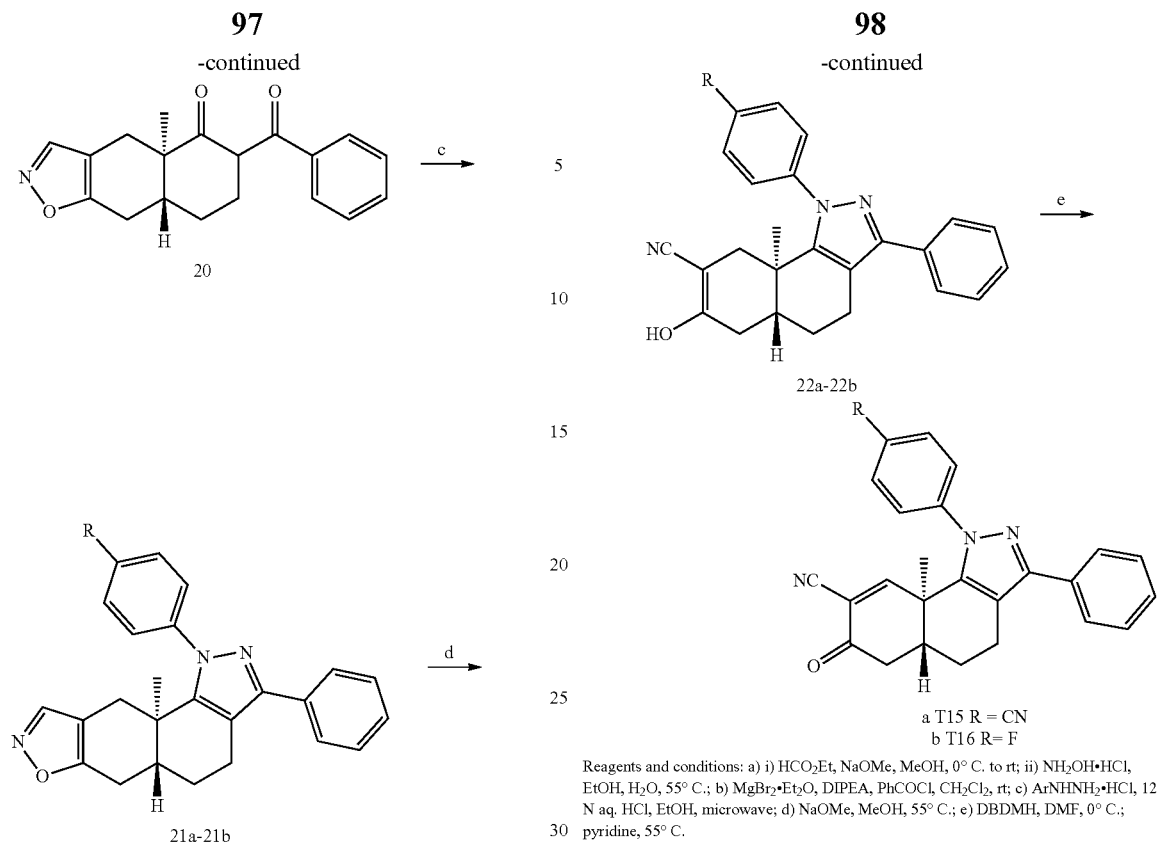
Scheme 7
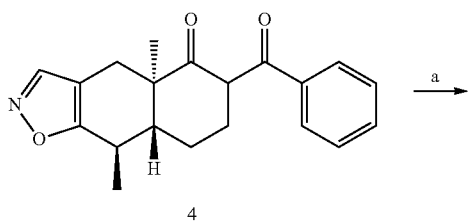
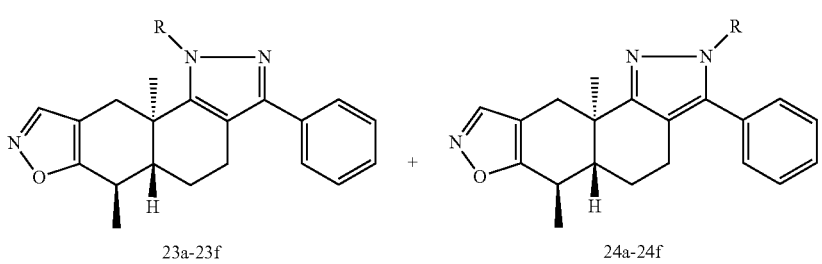

-continued
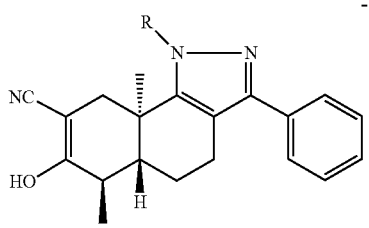
25a-25f
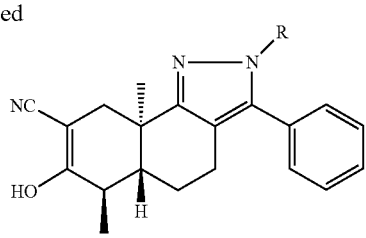
26a-26f
c ↓
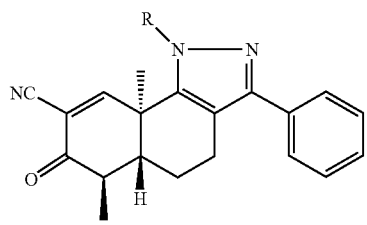
a T17
b T19
c T21
d T23
e T25
f T27
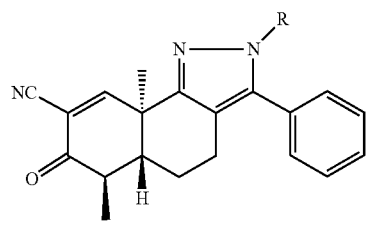
a T18
b T20
c T22
d T24
e T26
f T28
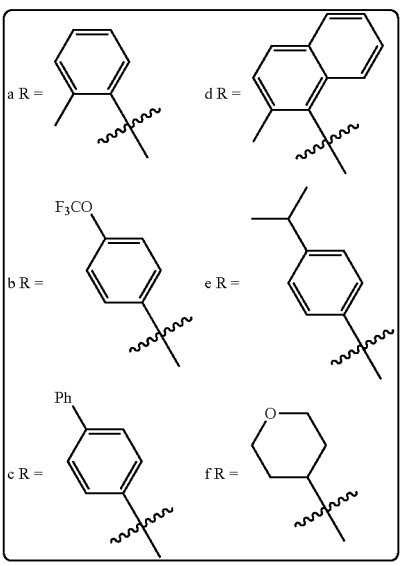
Reagents and conditions: a) ArNHNH$_2$•xHCl, EtOH, microwave; b) condition A: K$_2$CO$_3$, MeOH, rt; or condition B: NaOMe, MeOH, 55° C.; c) condition A: DBDMH, DMF, 0° C.; pyridine, 55° C.; or condition B: DDQ, toluene, 85° C.
Scheme 8
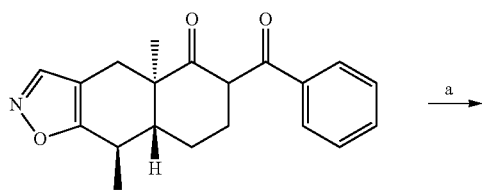
4
a →

-continued
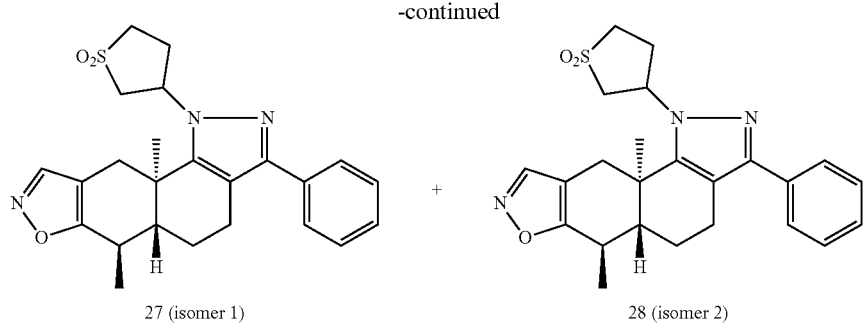
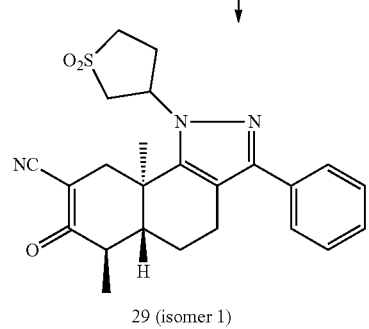
27 (isomer 1)
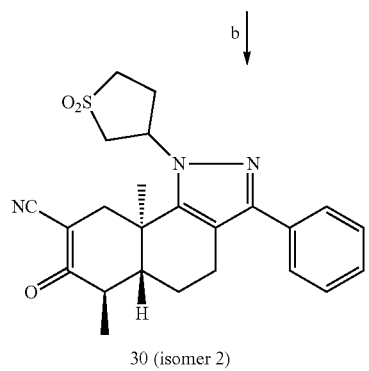
28 (isomer 2)
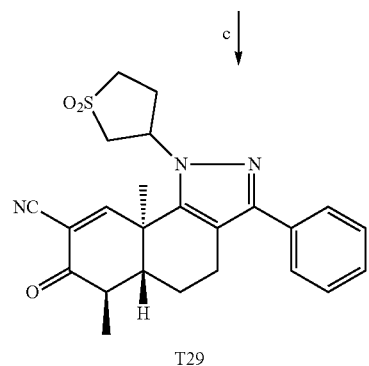
29 (isomer 1)
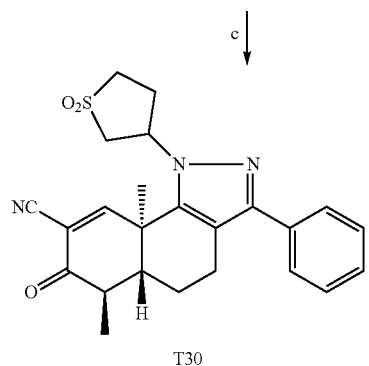
30 (isomer 2)
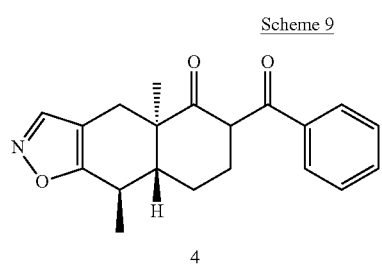
T29
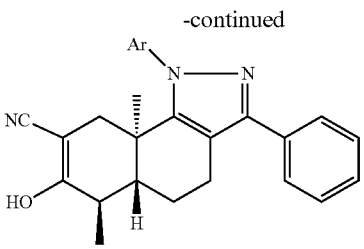
T30
Reagents and conditions: a) 3-hydrazineyltetrahydrothiophene 1,1-dioxide dihydrochloride, EtOH, microwave, 120° C.; b) $K_2CO_3$, MeOH, THF, rt; c) DBDMH, DMF, 0° C.; pyridine, 55° C.
Scheme 9
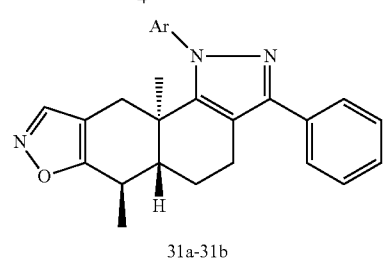
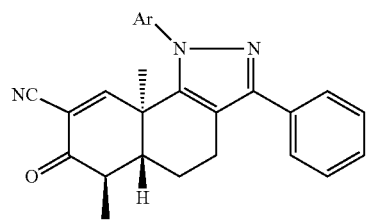

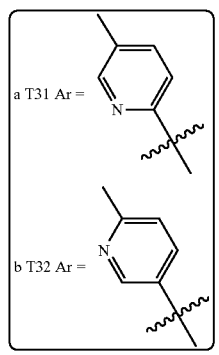

a T31 Ar =
b T32 Ar =

Reagents and conditions: a) ArNHNH₂·HCl, EtOH, microwave; b) condition A (for 32a): NaOMe, MeOH, 55° C.; or condition B (for 32b): K₂CO₃, MeOH, rt; c) DBDMH, DMF, 0° C.; pyridine, 55° C.

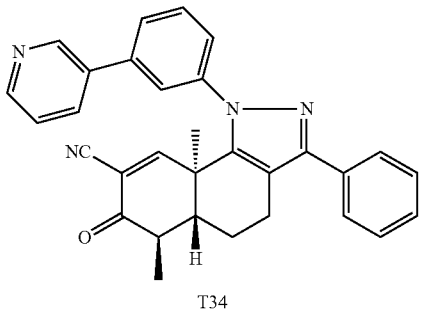

T34

Reagents and conditions: a) 3-BrPhNHNH₂·HCl, EtOH, microwave, 120° C.; b) NaOMe, MeOH, 55° C.; c) DBDMH, DMF, 0° C.; pyridine, 55° C.; d) 3-pyridinylboronic acid, K₃PO₄, Pd(PPh₃)₄, 1,4-dioxane, DMF, 90° C.

Scheme 10

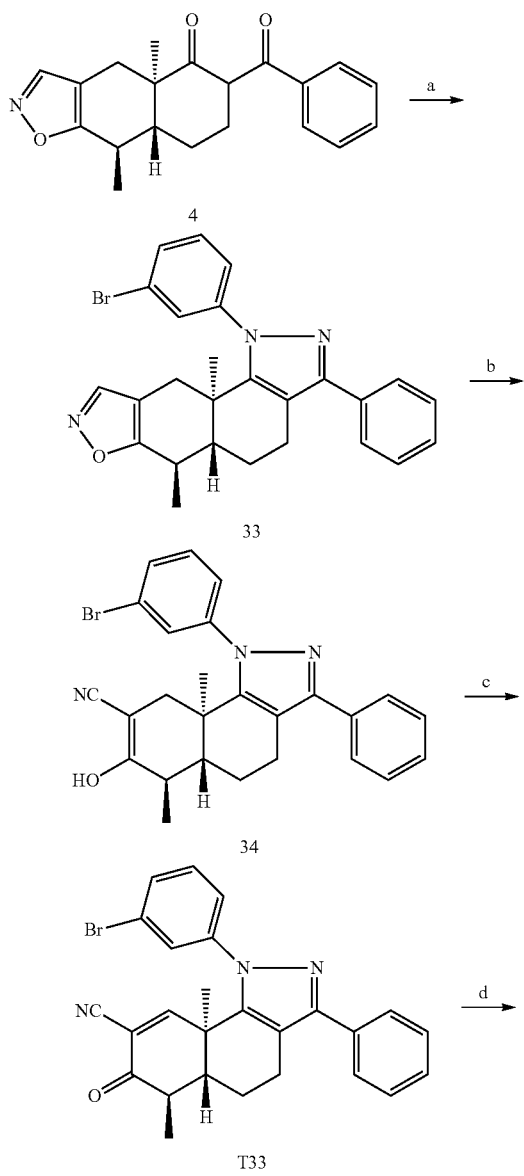

Scheme 11

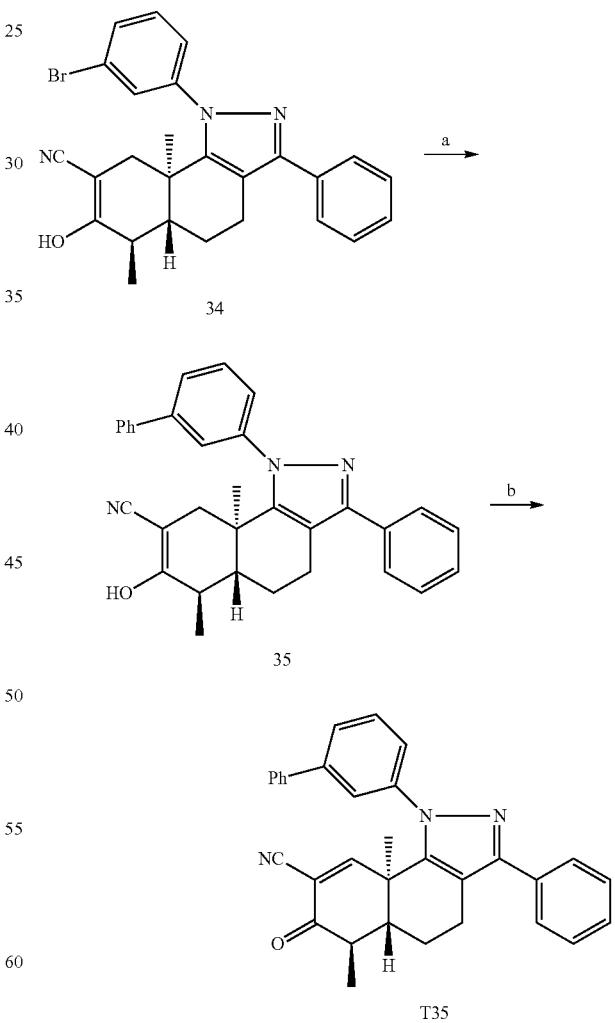

Reagents and conditions: a) PhB(OH)₂, K₃PO₄, Pd(PPh₃)₄, 1,4-dioxane, DMF, 90° C.; b) DBDMH, DMF, 0° C.; pyridine, 55° C.

Scheme 12

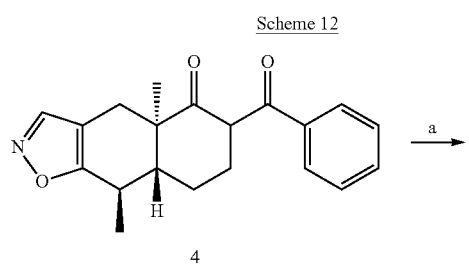
4

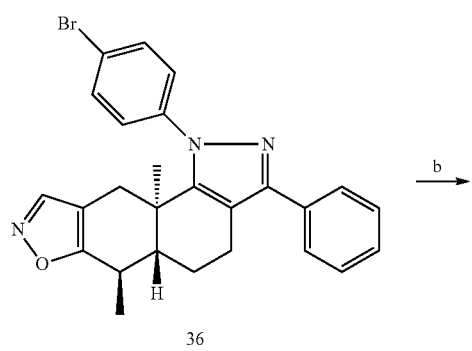
36

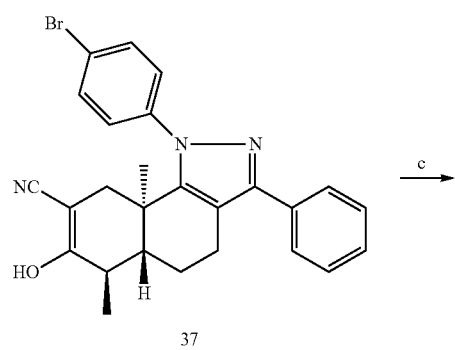
37

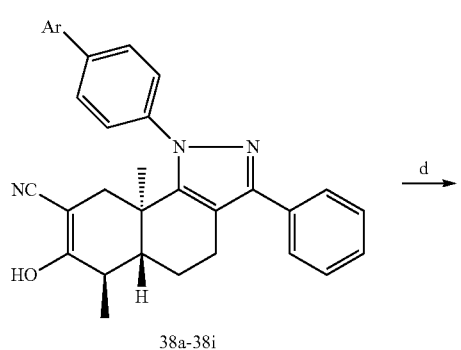
38a-38i

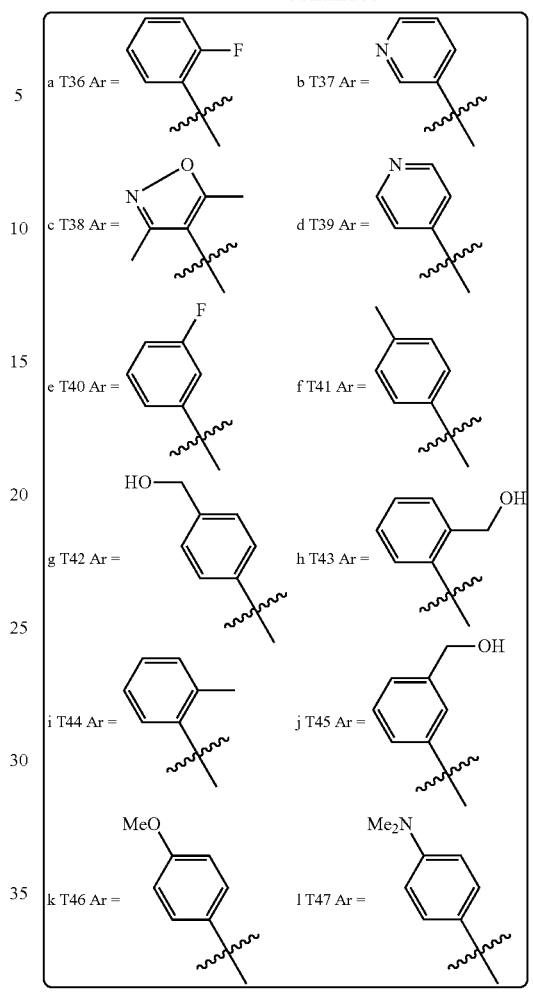

a T36 Ar = 2-fluorophenyl
b T37 Ar = pyridin-3-yl
c T38 Ar = 3,5-dimethylisoxazol-4-yl
d T39 Ar = pyridin-4-yl
e T40 Ar = 3-fluorophenyl
f T41 Ar = 4-methylphenyl
g T42 Ar = 4-(hydroxymethyl)phenyl
h T43 Ar = 2-(hydroxymethyl)phenyl
i T44 Ar = 2-methylphenyl
j T45 Ar = 3-(hydroxymethyl)phenyl
k T46 Ar = 4-methoxyphenyl
l T47 Ar = 4-(dimethylamino)phenyl Reagents and conditions: a) 4-BrPhNHNH$_2$·HCl, EtOH, microwave, 120° C.; b) NaOMe, MeOH, 55° C.; c) ArB(OH)$_2$, K$_3$PO$_4$, Pd(PPh$_3$)$_4$, 1,4-dioxane, DMF, 90° C.; d) DBDMH, DMF, 0° C.; pyridine, 55° C.

Scheme 13

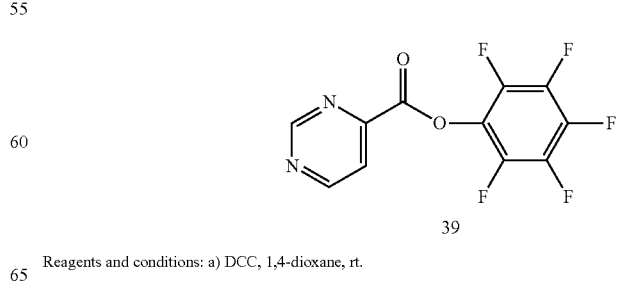
39

Reagents and conditions: a) DCC, 1,4-dioxane, rt.

Scheme 14
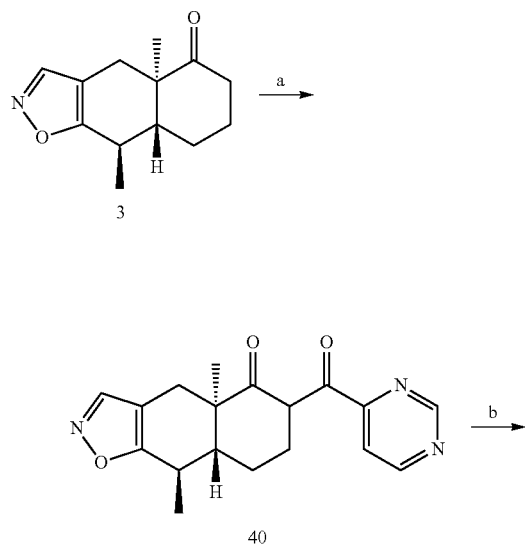
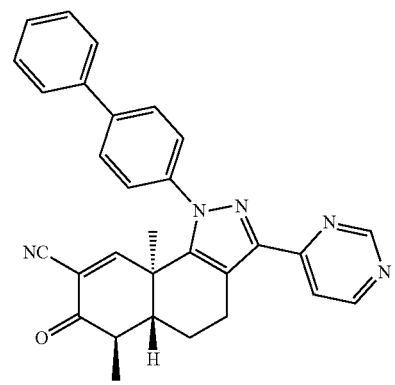
Reagents and conditions: a) 39, MgBr₂·OEt, DIPEA, CH₂Cl₂, rt; b) biphenyl-4-yl hydrazine hydrocloride, EtOH, microwave, 120° C.; c) K₂CO₃, MeOH, rt; d) DBDMH, DMF, 0° C.; pyridine, 60° C.
Scheme 15
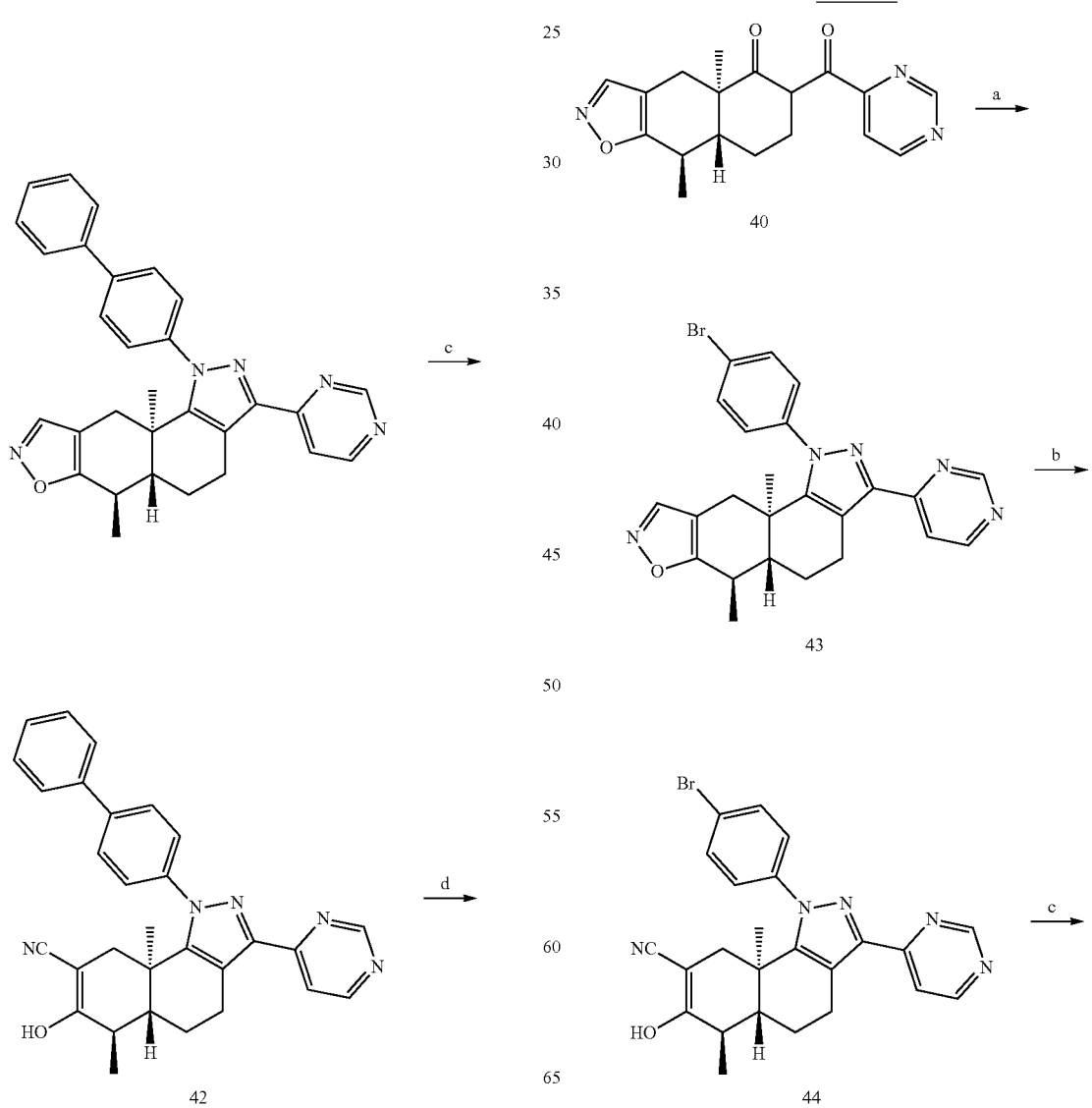

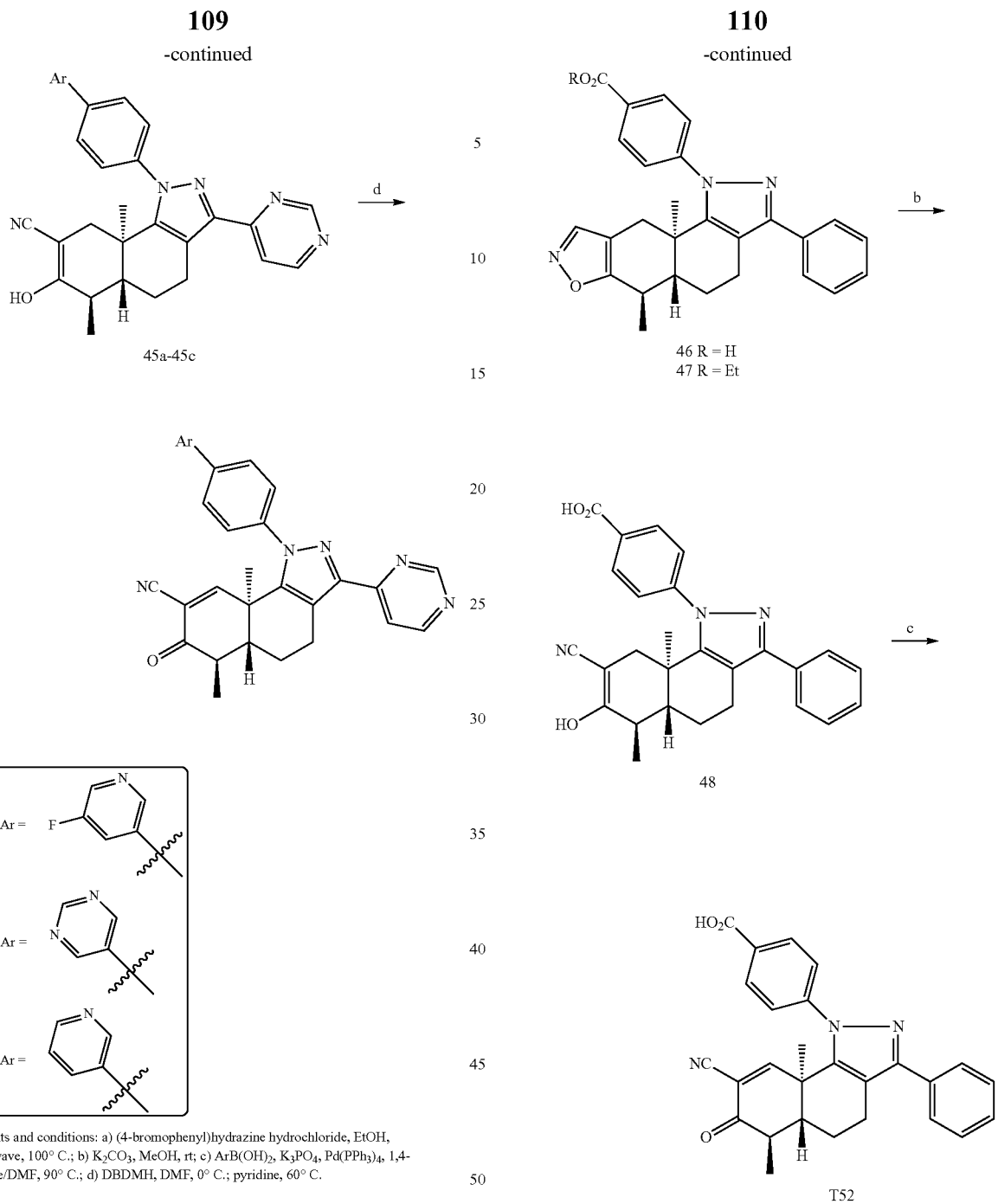
Reagents and conditions: a) (4-bromophenyl)hydrazine hydrochloride, EtOH, microwave, 100° C.; b) K2CO3, MeOH, rt; c) ArB(OH)2, K3PO4, Pd(PPh3)4, 1,4-dioxane/DMF, 90° C.; d) DBDMH, DMF, 0° C.; pyridine, 60° C.
Reagents and conditions: a) 4-hydrazineylbenzoic acid hyrochloride, EtOH, 120° C.; b) NaOMe, MeOH, 55° C.; c) DBDMH, DMF, 0° C.; pyridine, 55° C.
Scheme 16
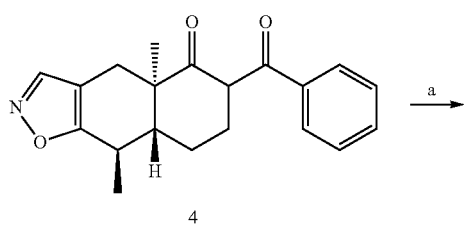
Scheme 17
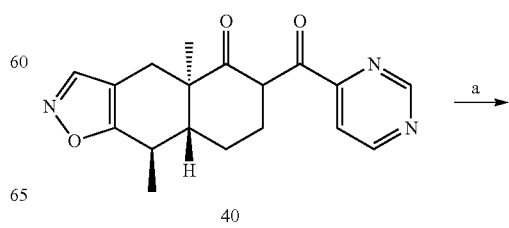

111
-continued
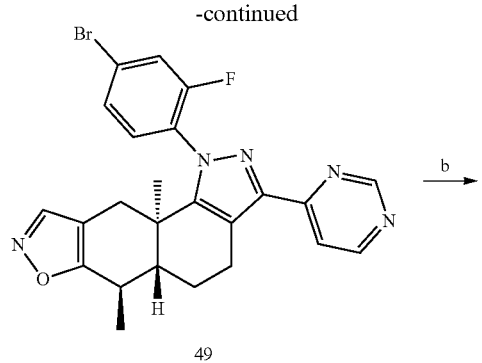
49
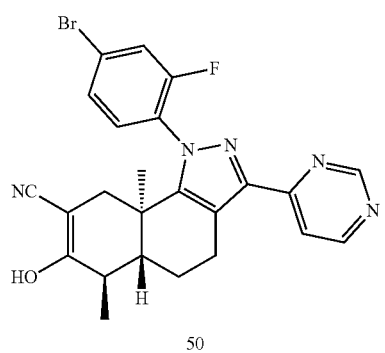
50
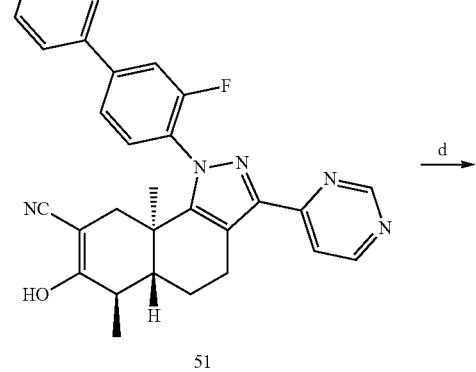
51
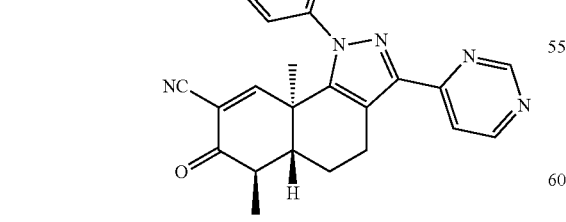
T53
Reagents and conditions: a) 4-Br-2-F-PhNHNH₂·HCl, EtOH, 100° C.; b) K₂CO₃, MeOH rt; c) pyridine-3-boronic acid, K₃PO₄, Pd(PPh₃)₄, 1,4-dioxane, DMF, microwave, 90° C.; d) DBDMH, DMF, 0° C.; pyridine, 55° C.
112
Scheme 18
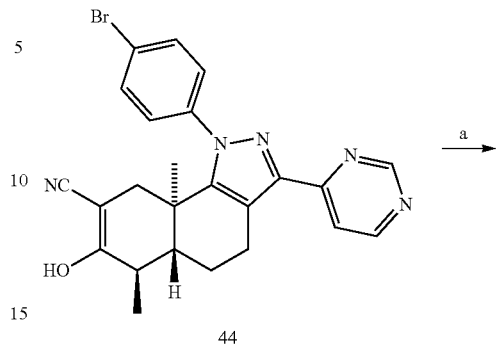
44
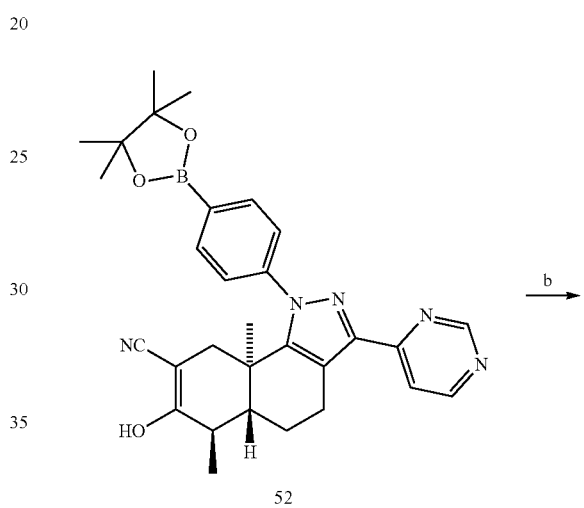
52
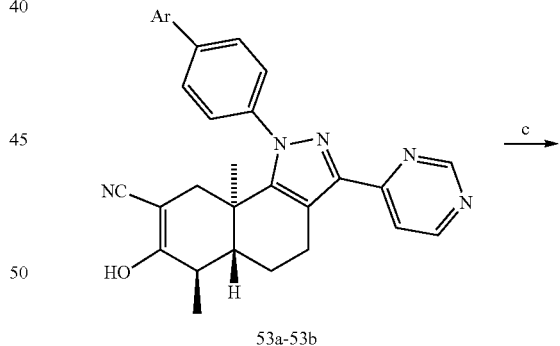
53a-53b
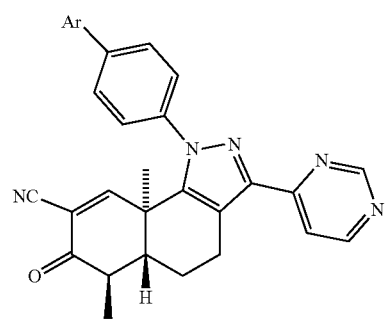

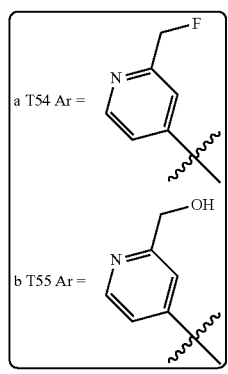
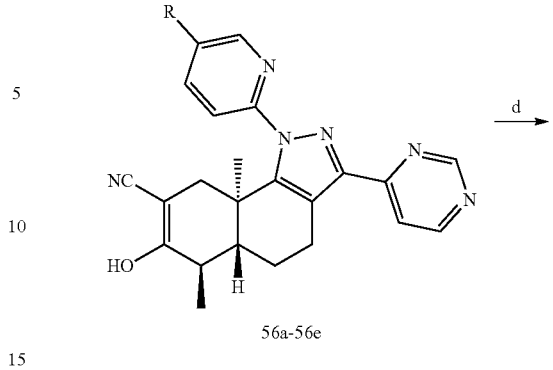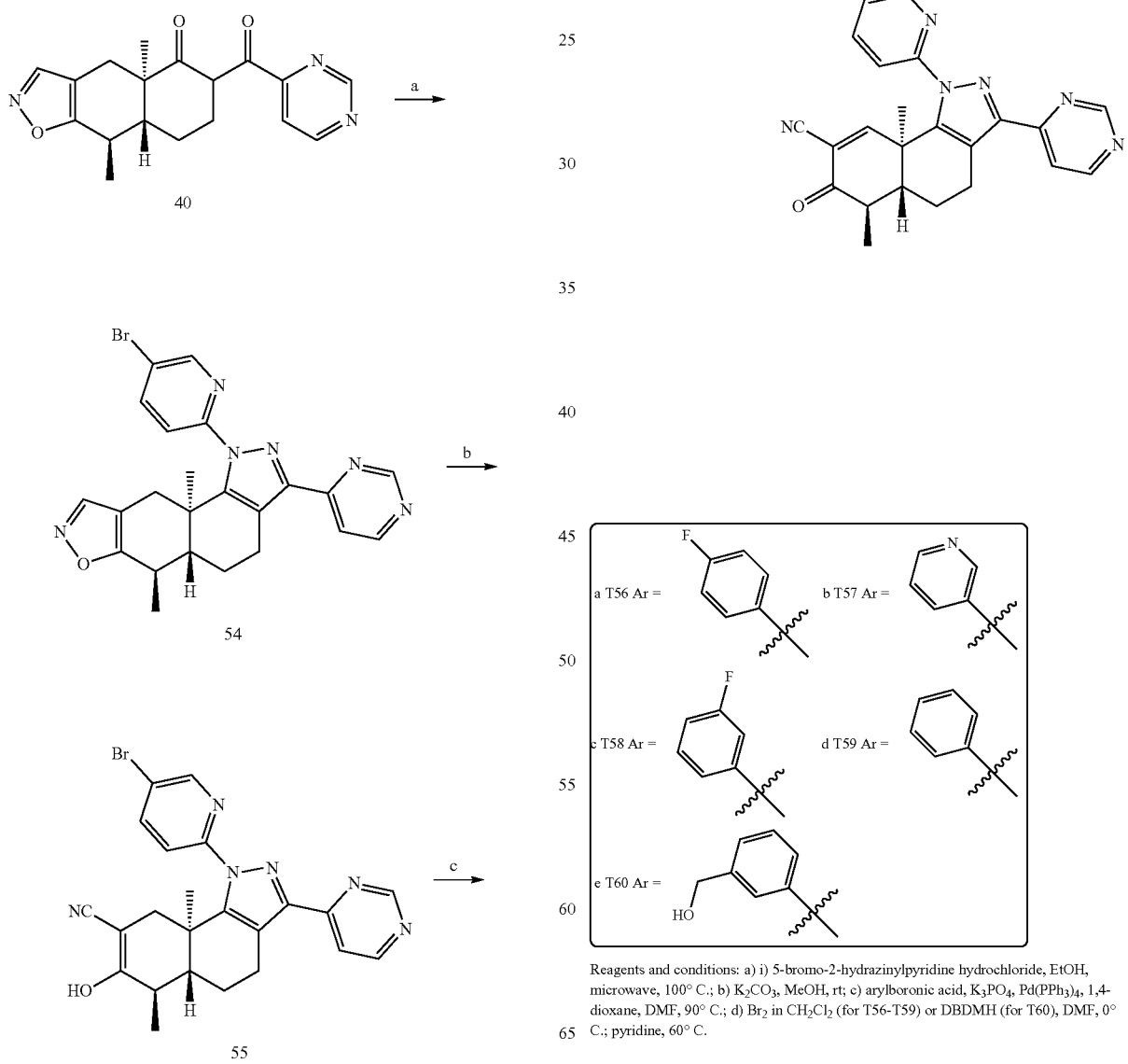
Reagents and conditions: a) bis(pinacolato)diboron, KOAc, Pd(dppf)Cl₂, 1,4-dioxane 100° C.; b) ArBr, K₃PO₄, Pd(PPh₃)₄, 1,4-dioxane, DMF, 100° C.; c) DBDMH, DMF, 0° C.; pyridine, 60° C.
Reagents and conditions: a) i) 5-bromo-2-hydrazinylpyridine hydrochloride, EtOH, microwave, 100° C.; b) K₂CO₃, MeOH, rt; c) arylboronic acid, K₃PO₄, Pd(PPh₃)₄, 1,4-dioxane, DMF, 90° C.; d) Br₂ in CH₂Cl₂ (for T56-T59) or DBDMH (for T60), DMF, 0° C.; pyridine, 60° C.

Scheme 20
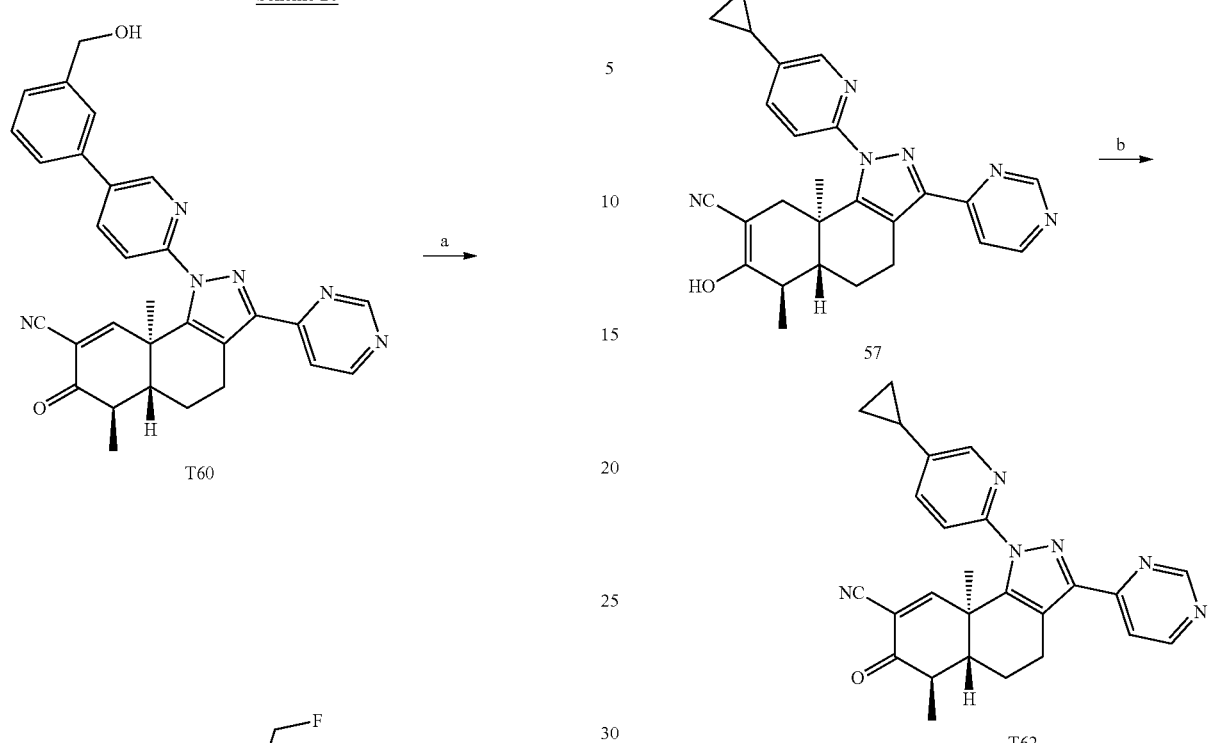
Reagents and conditions: a) potassium cyclopropyltrifluoroborate, K₃PO₄, RuPhos toluene, water, Pd(OAc)₂, 95° C.; b) DBDMH, DMF, 0° C.; pyridine, 60° C.
Reagents and conditions: a) DAST, CH₂Cl₂, -78° C.
Scheme 22
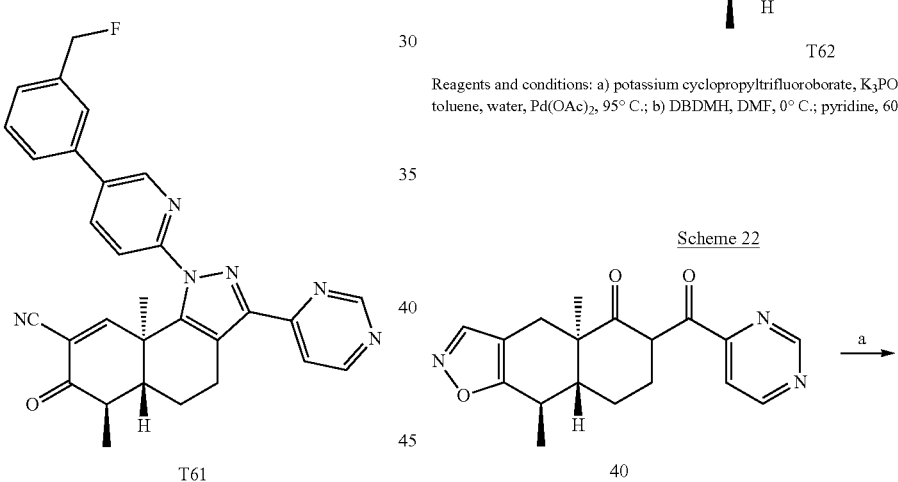
Scheme 21
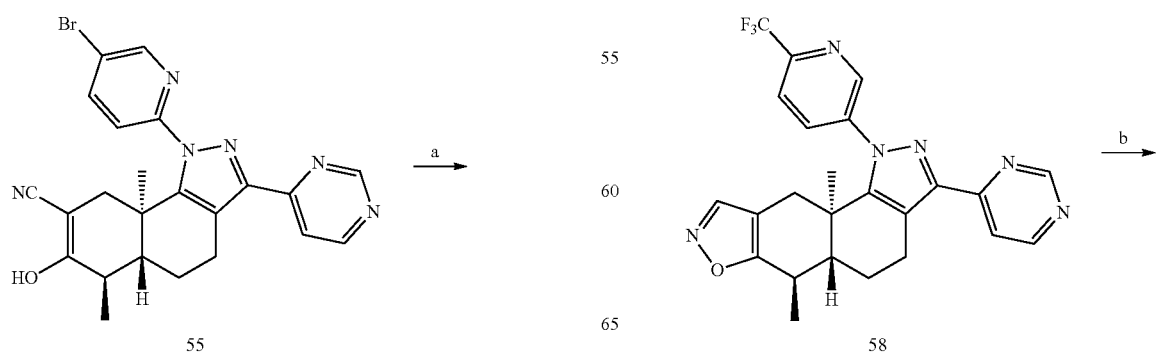

117
-continued
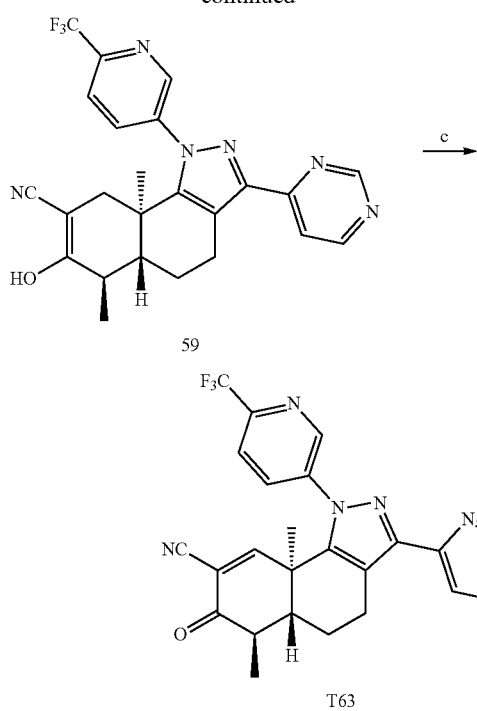
Reagents and conditions: a) 2-hydrazinyl-5-(trifluoromethyl)pyridine, 4 N HCl in 1,4-dioxane, EtOH, microwave, 100° C.; b) K$_2$CO$_3$, MeOH, rt; c) DBDMH, DMF, 0° C.; pyridine, 60° C.
Scheme 23
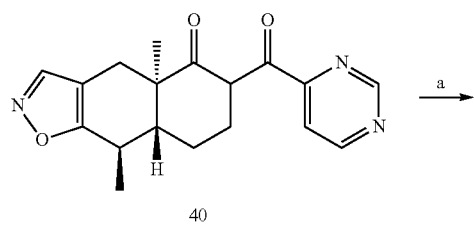
40
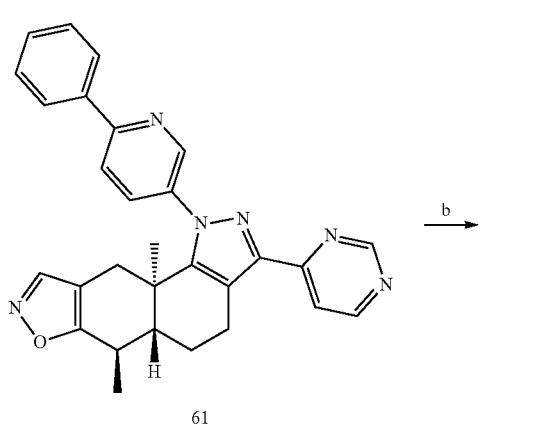
61
118
-continued
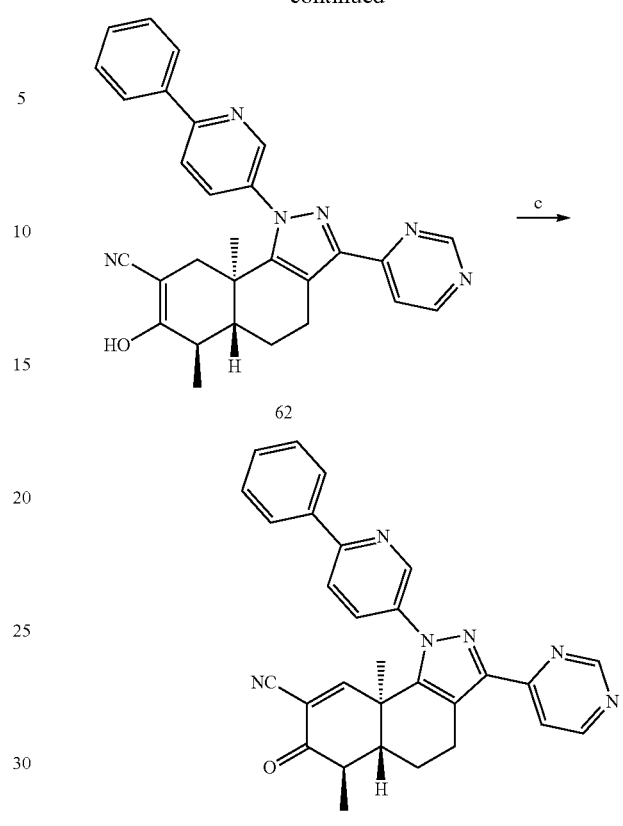
Reagents and conditions: a) 5-hydrazino-2-phenylpyridine hydrochloride, EtOH, microwave, 100° C.; b) K$_2$CO$_3$, MeOH, rt; c) DBDMH, DMF, 0° C.; pyridine, 60° C.
Scheme 24
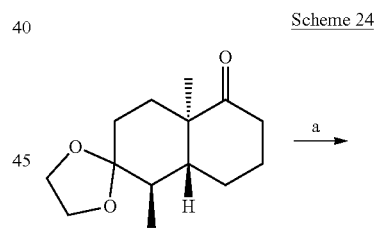
63
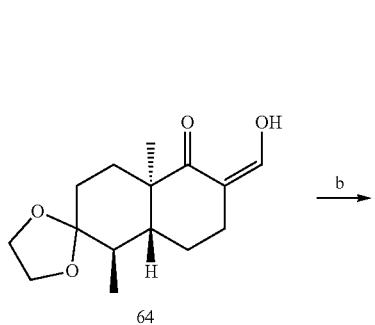
64

-continued
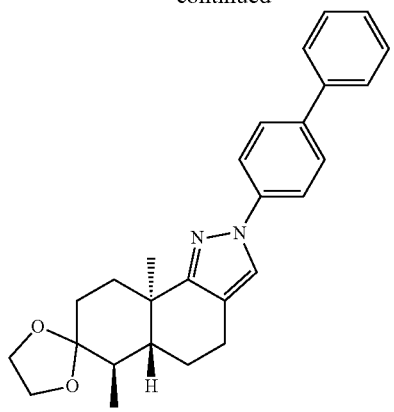
65
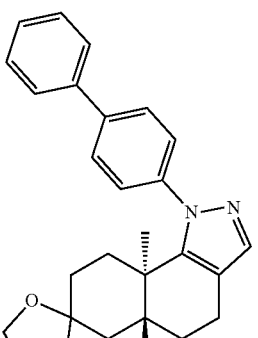
66
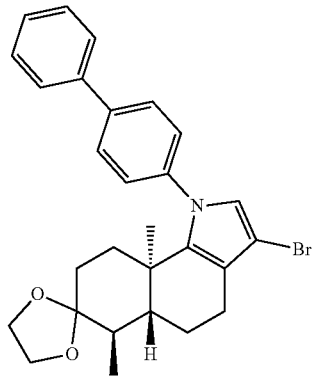
67
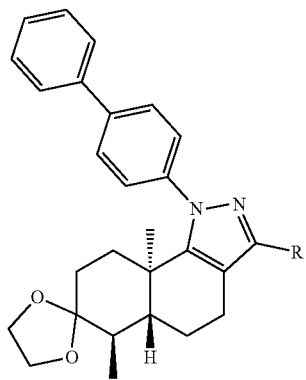
68a-68i
+
c
d
e
-continued
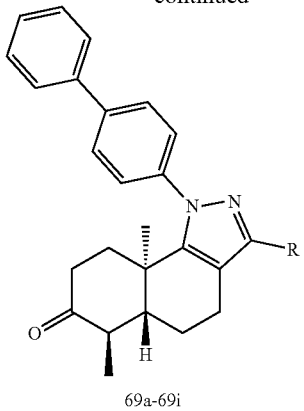
69a-69i
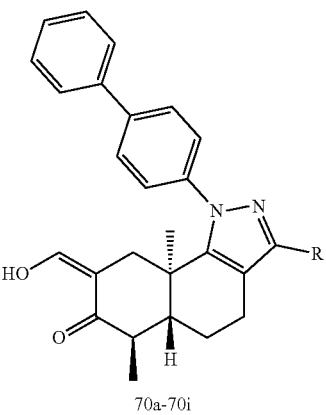
70a-70i
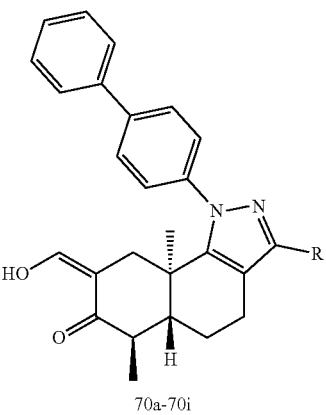
71a-71i
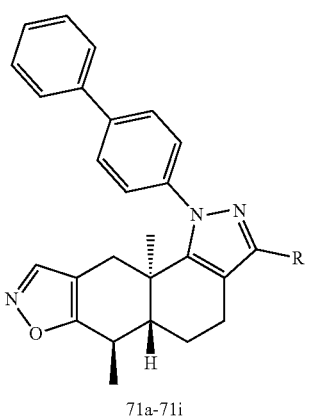
72a-72i
f
g
h
i 121
-continued
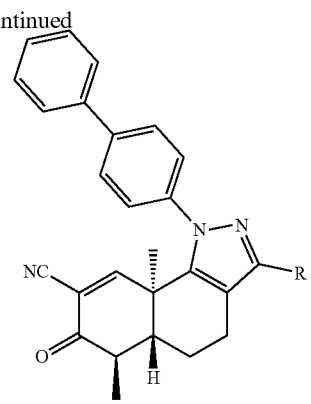
Scheme 25
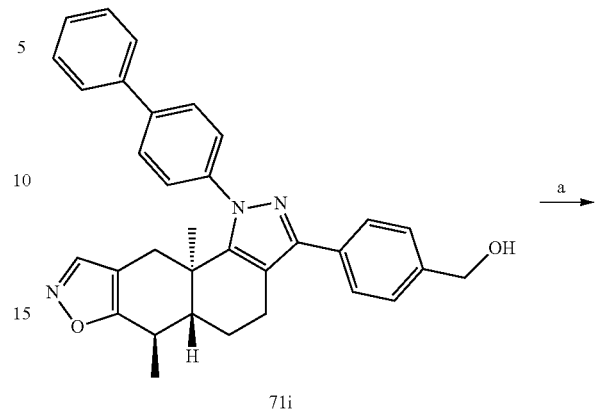
71i
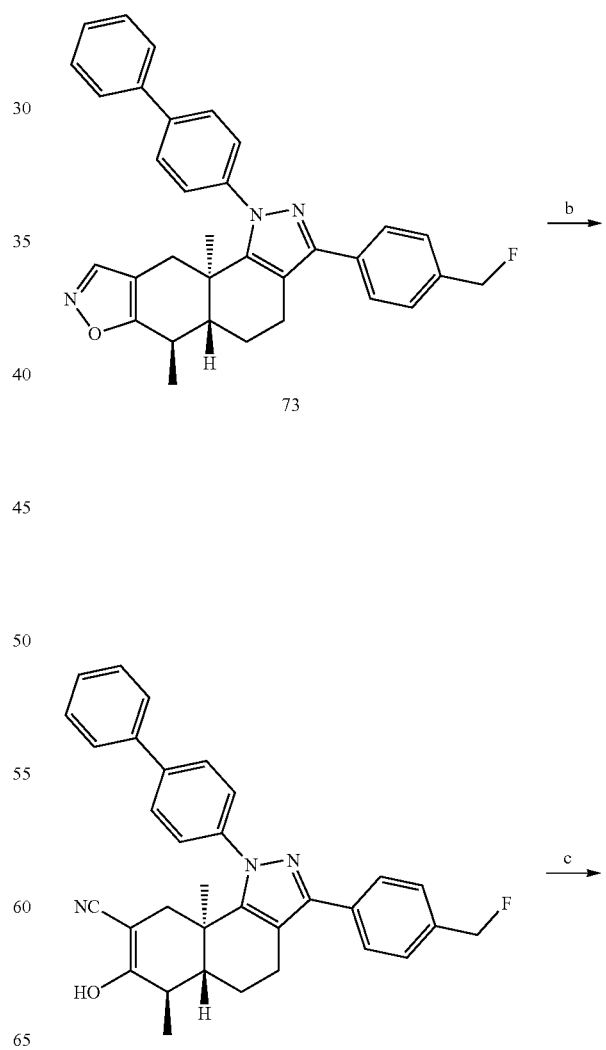
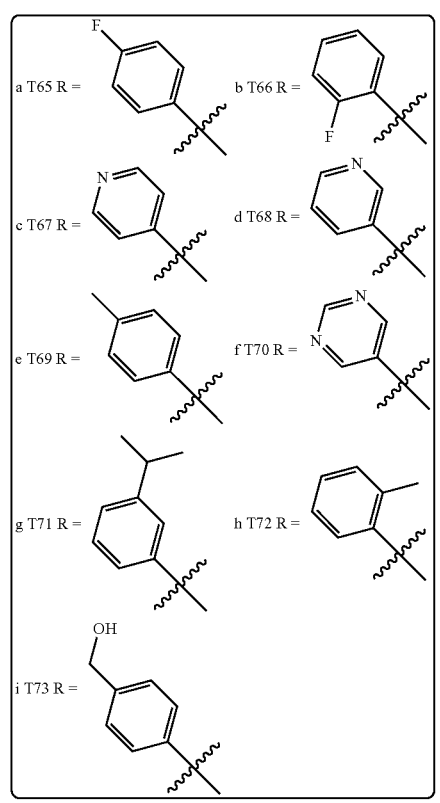
Reagents and conditions: a) HCO₂Et, NaOMe, MeOH, benzene, rt; b) biphenyl-4-ylhydrazine, AcOH, EtOH, rt; c) Br₂, Na₂CO₃, CH₂Cl₂, -10° C.; d) arylboronic acid, K₃PO₄, Pd(PPh₃)₄, 1,4-dioxane, DMF; e) 3 N aq. HCl, MeOH, rt; f) HCO₂Et, NaOMe, MeOH, rt; g) NH₂OH·HCl, AcOH, EtOH, 60° C.; h) K₂CO₃, MeOH, rt; i) DBDMH, DMF, 0° C.; pyridine, 60° C.

123
-continued
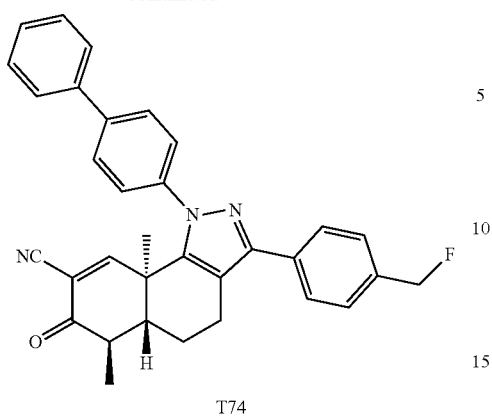
T74
Reagents and conditions: a) DAST, CH₂Cl₂, 0° C.; b) K₂CO₃, MeOH, rt; c) DBDMH, DMF, 0° C.; pyridine, 60° C.
Scheme 26
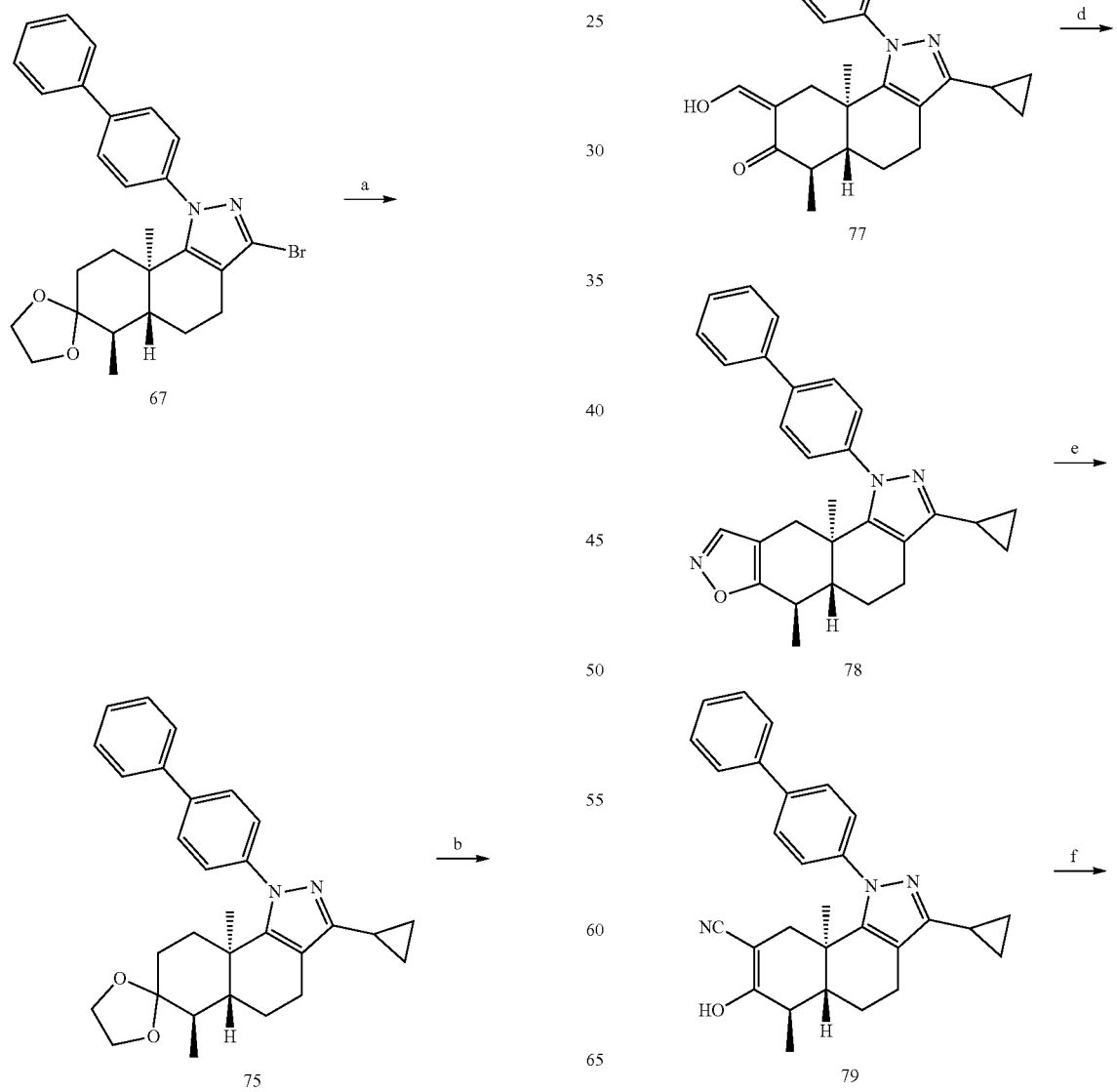

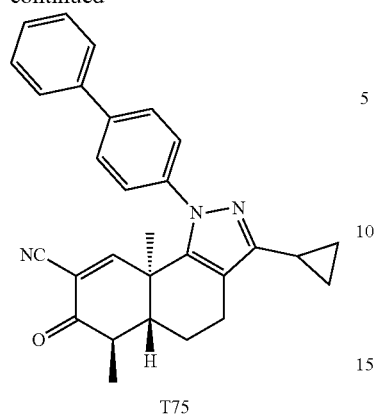
T75
Reagents and conditions: a) potassium cyclopropyltrifluoroborate, K₃PO₄, RuPhos, toluene, water, Pd(OAc)₂, 125° C.; b) 3 N aq. HCl, MeOH, rt; c) HCO₂Et, NaOMe, MeOH, rt; d) NH₂OH•HCl, AcOH, EtOH, 60° C.; e) K₂CO₃, MeOH, rt; f) DBDMH, DMF, 0° C.; pyridine, 60° C.
Scheme 27
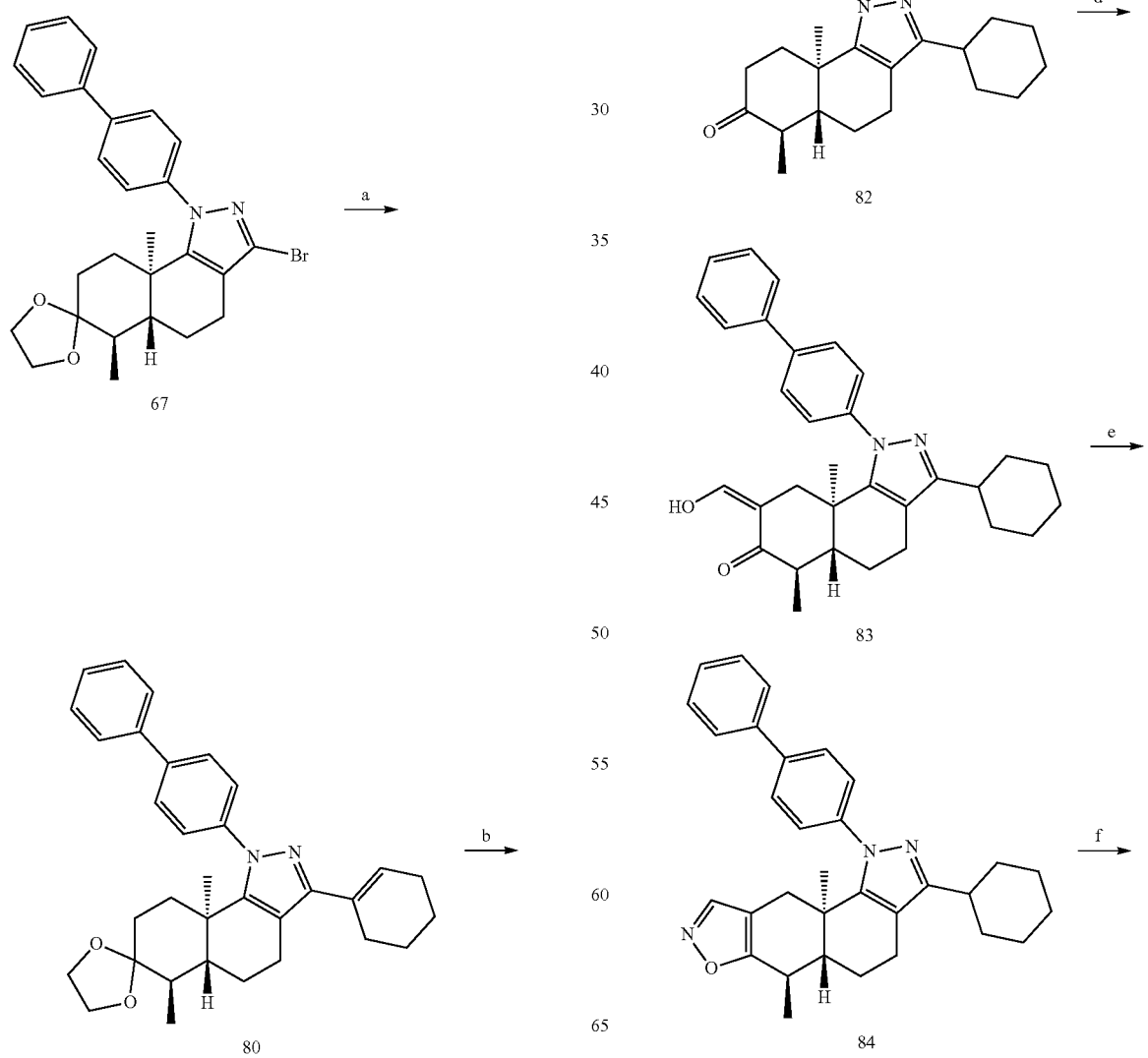

127
-continued
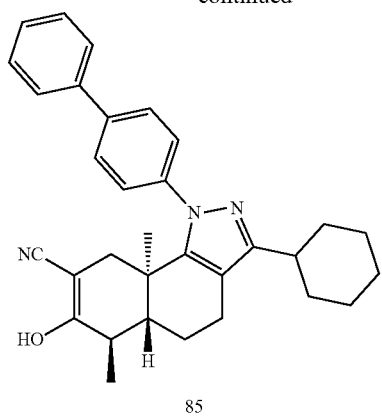
85
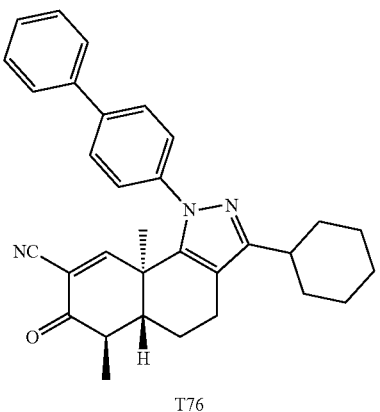
T76
Reagents and conditions: a) 1-cyclohexen-1-yl-boronic acid pinacol ester, $K_3PO_4$, Pd(PPh$_3$)$_4$, 1,4-dioxane, 100° C.; b) 3 N aq. HCl, MeOH, rt; c) H$_2$, 10% Pd/C, EtOAc, rt; d) HCO$_2$Et, NaOMe, MeOH, rt; e) NH$_2$OH·HCl, AcOH, EtOH, 60° C.; f) K$_2$CO$_3$, MeOH, rt; g) DBDMH, DMF, 0° C.; pyridine, 60° C.
Scheme 28
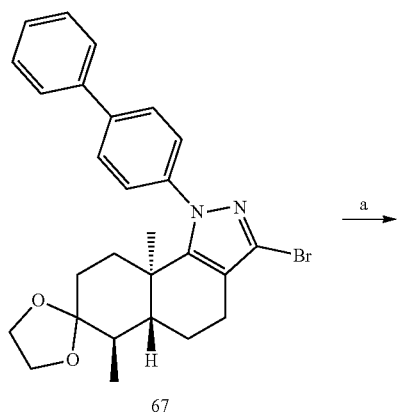
67
128
-continued
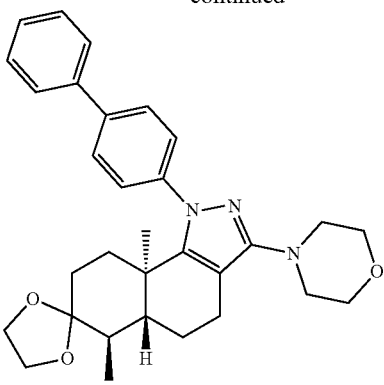
86
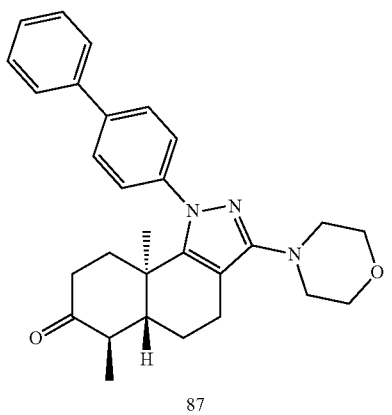
87
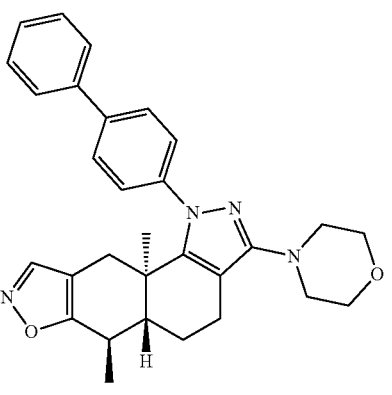
88
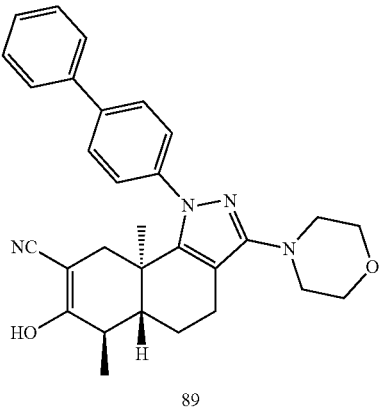
89

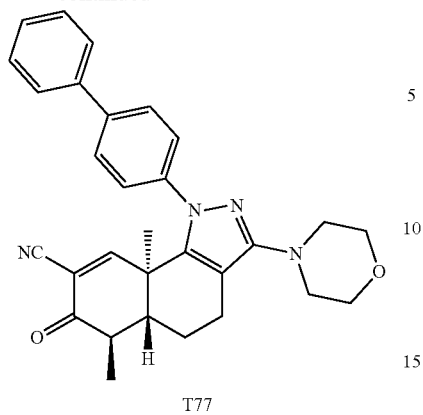
T77
Reagents and conditions: a) morpholine, t-BuXPhosPd-G3, XPhos, NaOBu$^t$, 1,4-dioxane, 120° C.; b) 3 N aq. HCl, THF, rt to 50° C.; c) HCO$_2$Et, NaOMe, MeOH, rt; 6 N aq. HCl, NH$_2$OH·HCl, EtOH, 55° C.; d) K$_2$CO$_3$, MeOH, rt; e) DBDMH, DMF, 0° C.; pyridine, 60° C.
Scheme 29
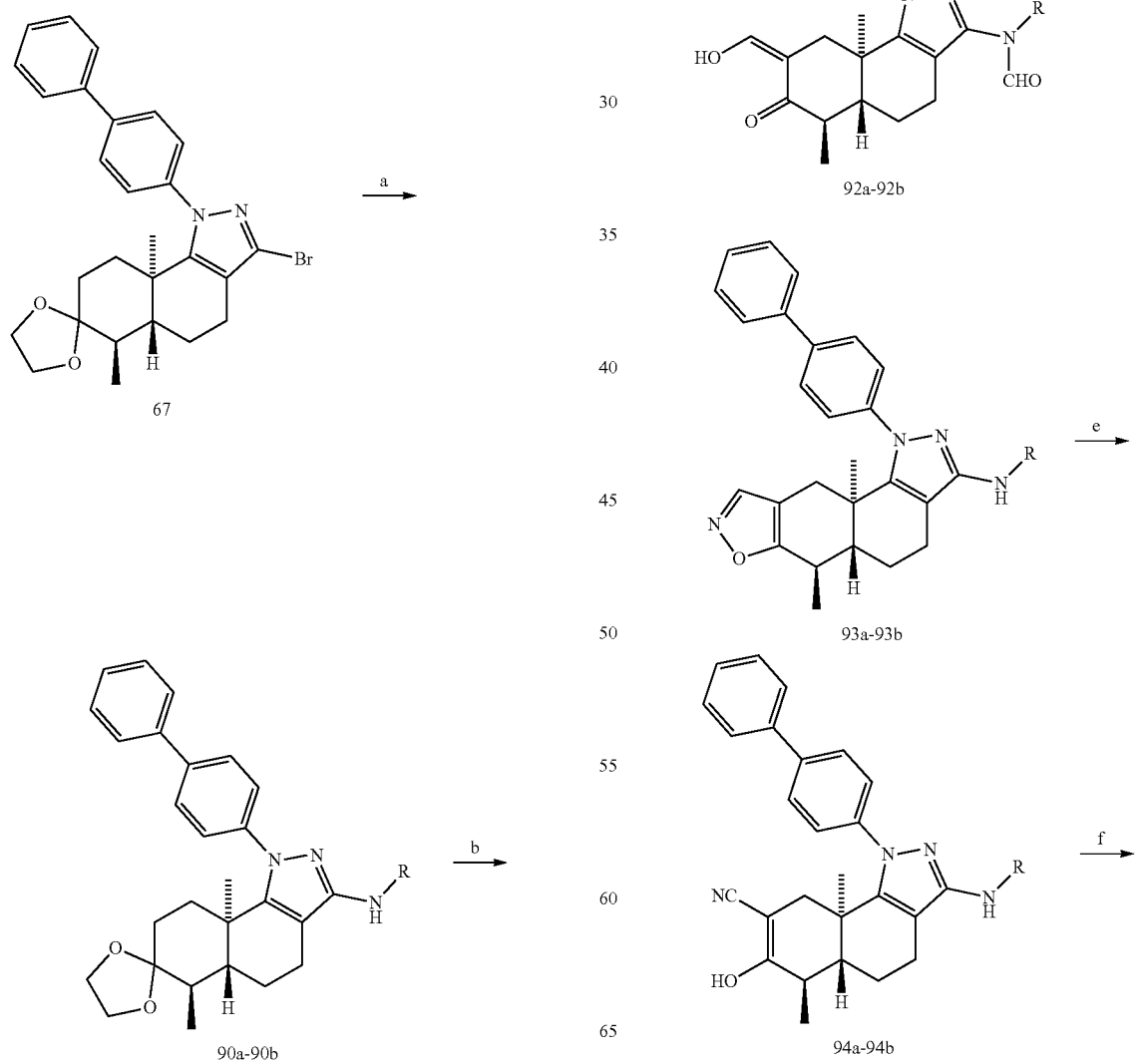

131
-continued

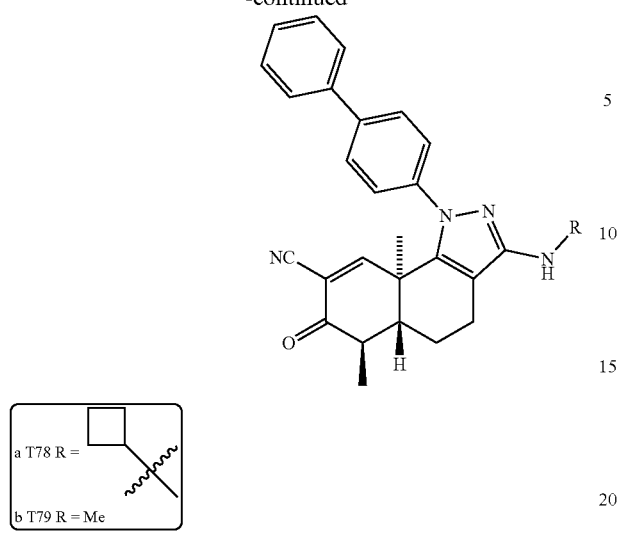

a T78 R = [cyclobutyl]
b T79 R = Me

Reagents and conditions: a) cyclobutylamine, (for 90a) or MeNH$_2$•HCl (for 90b), t-BuXPhosPd-G3, XPhos, NaOBu$^t$, 1,4-dioxane, 120° C.; b) 3 N aq. HCl, THF, rt; c) HCO$_2$Et, NaOMe, MeOH, rt; d) NH$_2$OH•HCl, EtOH, 55° C.; e) K$_2$CO$_3$, MeOH, rt; f) DBDMH, DMF, 0° C.; pyridine, 60° C.

Scheme 30

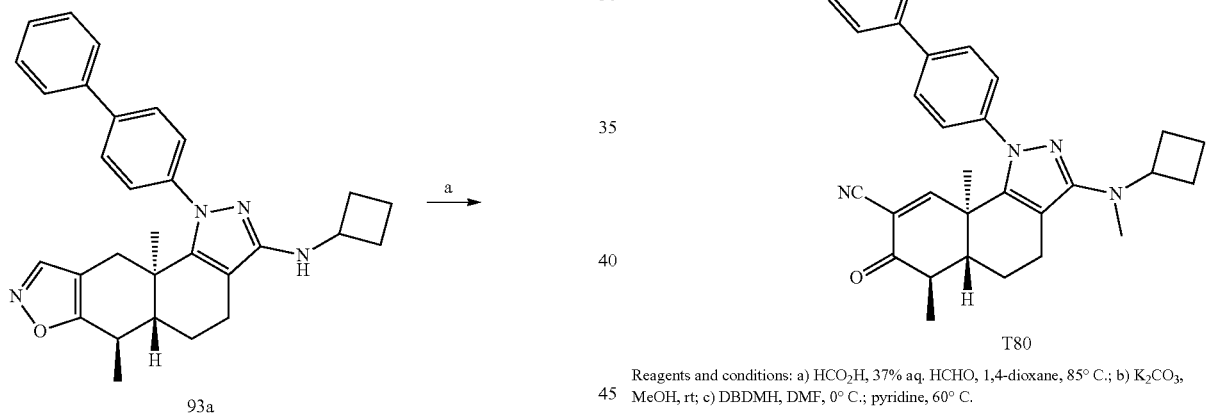

93a

95

132
-continued

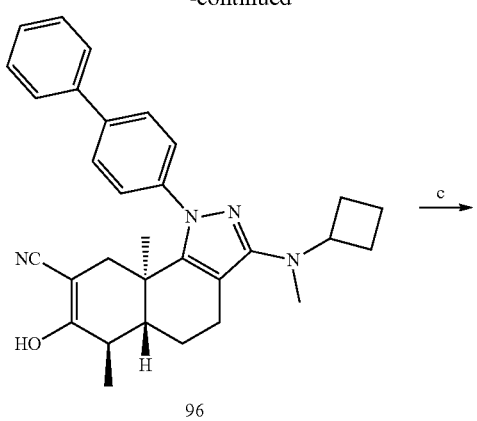

96

T80

Reagents and conditions: a) HCO$_2$H, 37% aq. HCHO, 1,4-dioxane, 85° C.; b) K$_2$CO$_3$, MeOH, rt; c) DBDMH, DMF, 0° C.; pyridine, 60° C.

Scheme 31

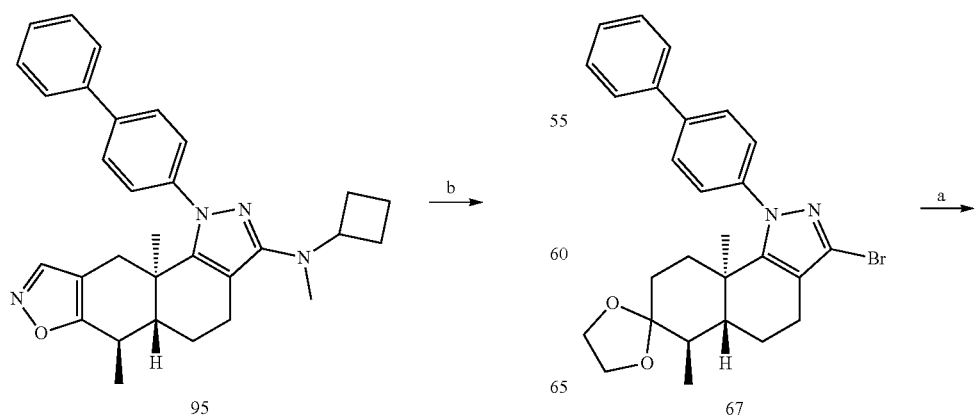

67

133
-continued
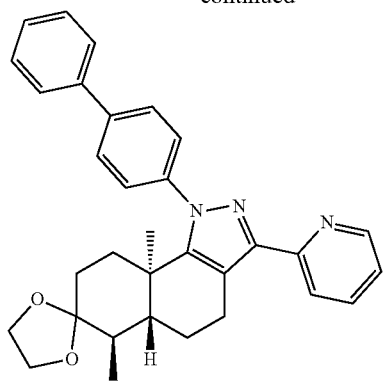
97
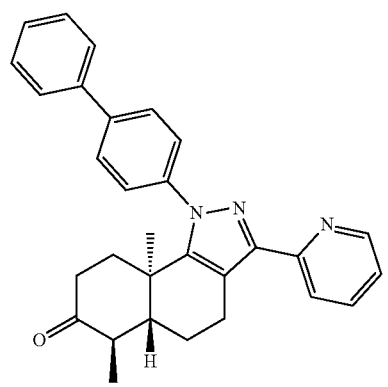
98
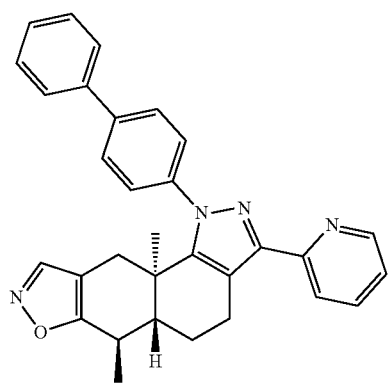
99
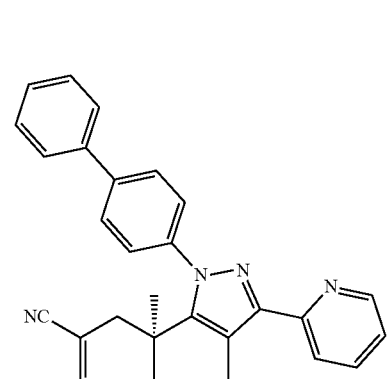
100
b →
c →
d →
e →
134
-continued
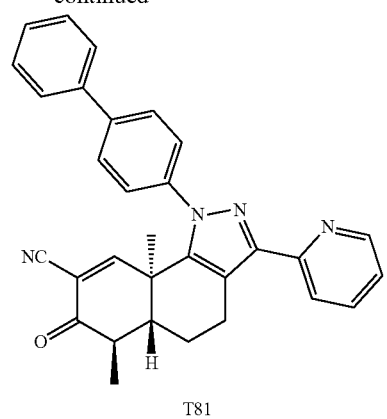
T81
Reagents and conditions: a) 2-tri-n-butylstannylpyridine, t-BuXPhosPd-G3, XPhos, NaOBu$^t$, 1,4-dioxane, 150° C.; b) 3 N aq. HCl, THF, rt; c) HCO$_2$Et, NaOMe, MeOH, rt; 6 N aq. HCl, NH$_2$OH•HCl, EtOH, 55° C.; d) K$_2$CO$_3$, MeOH, rt; e) DBDMH, DMF, 0° C.; pyridine, 60° C.
Scheme 32
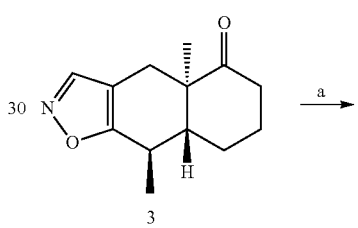
3
a →
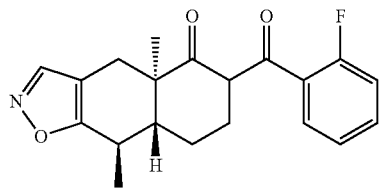
101
b →
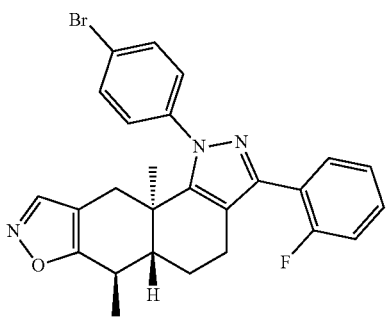
102
c →

135

-continued

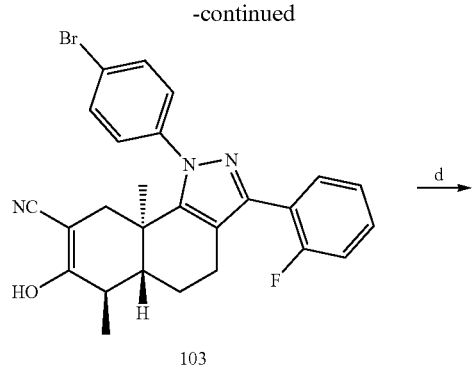

103

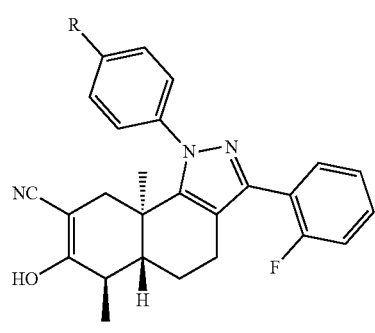

104a-104c

[structure with R group, ketone]

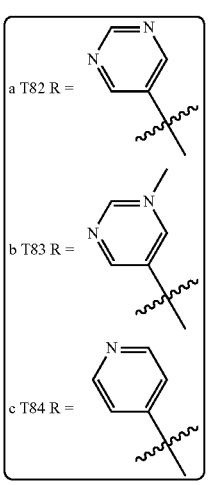

a T82 R =
b T83 R =
c T84 R =

Reagents and conditions: 2-fluorobenzoyl chloride, MgBr₂•Et₂O, DIPEA, CH₂Cl₂, rt; b) 4-bromo-phenylhydrazine hydrochloride, EtOH, microwave, 120° C.; c) K₂CO₃, MeOH, rt; d) arylboronic acid, (or arylboronic acid pinacol ester), K₃PO₄ (or K₂CO₃), palladium catalyst, 1,4-dioxane/DMF, 90° C.; e) Br₂, DMF, 0° C.; pyradine, 60° C.

136

Scheme 33

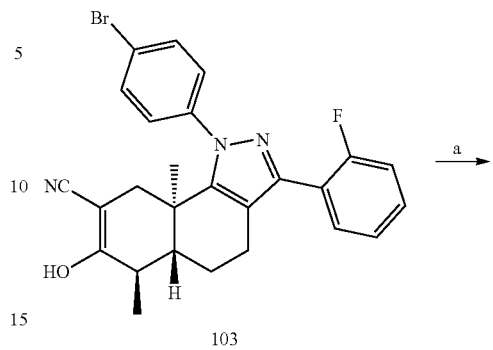

103

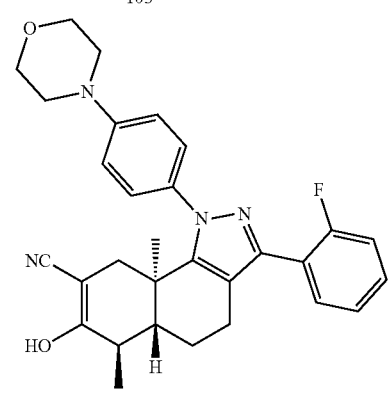

105

[structure T85]

T85

Reagents and conditions: a) morpholine, t-BuXPhosPd-G3, XPhos, NaOBuᵗ, 1,4-dioxane, 120° C.; b) DDQ, toluene, rt.

Scheme 34

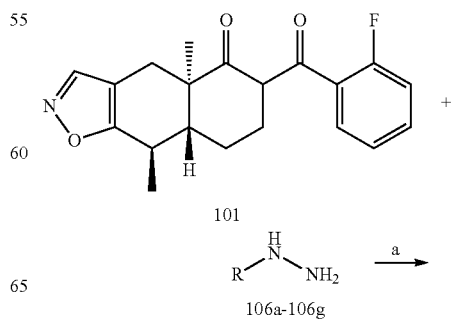

101

R-NH-NH₂

106a-106g a →

137
-continued
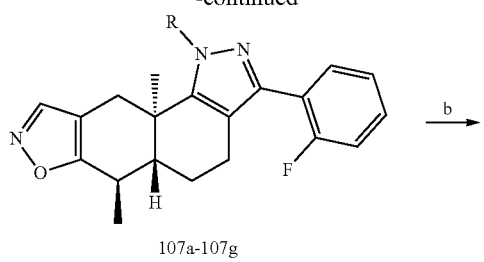
107a-107g
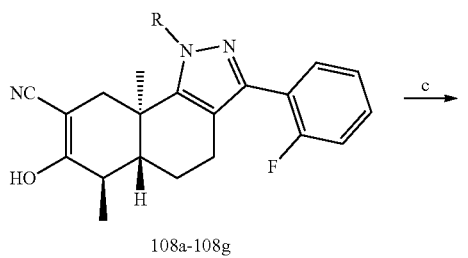
108a-108g
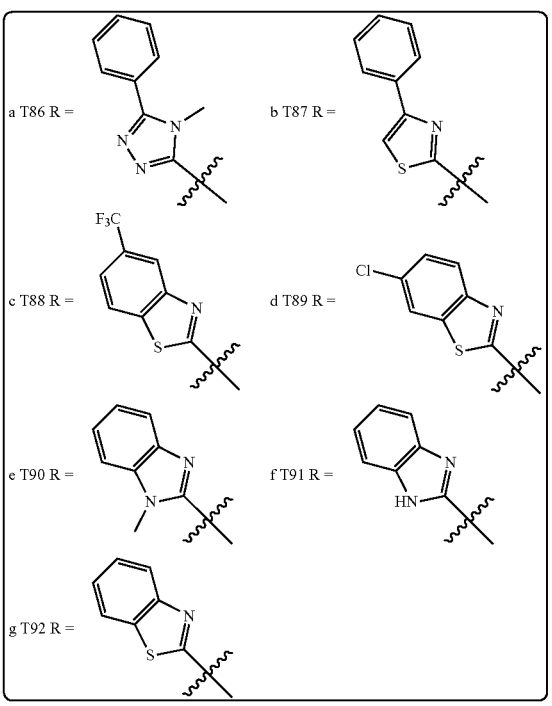
Reagents and conditions: a) 12 N aq. HCl, EtOH, microwave, 100° C.; b) K₂CO₃, MeOH, rt; c) DBDMH, DMF, 0° C.; pyridine, 55° C.
138
Scheme 35
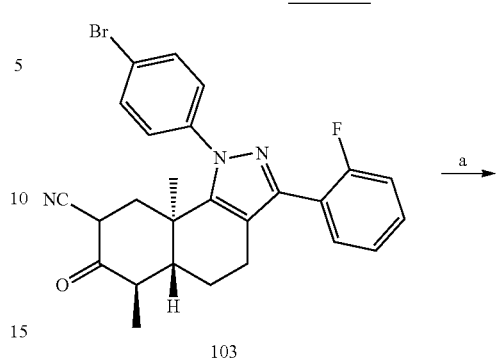
103
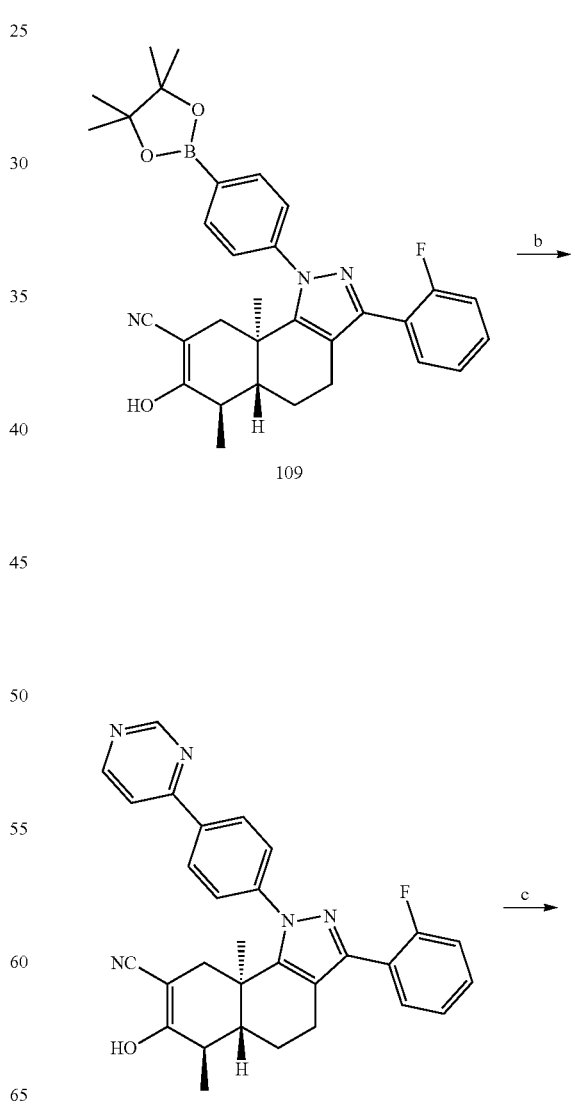
109
110

139
-continued

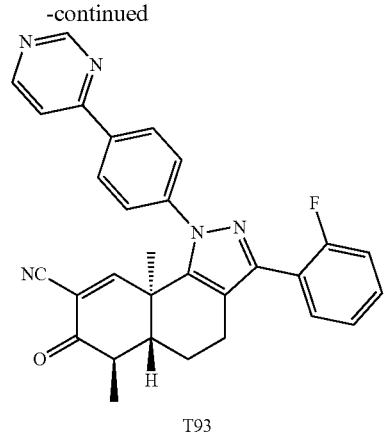

T93

Reagents and conditions: a) bis(pinacolato)diboron, KOAc, Pd(dppf)Cl₂, 1,4-dioxane, 100° C.; b) 4-chloropyrimidine, K₃PO₄, Pd(PPh₃)₄, 1,4-dioxane, DMF, 100° C.; c) DBDMH, DMF, 0° C.; pyridine, 60° C.

140
-continued

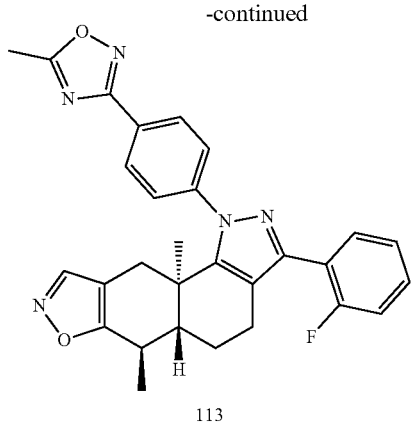

113

→ d

Scheme 36

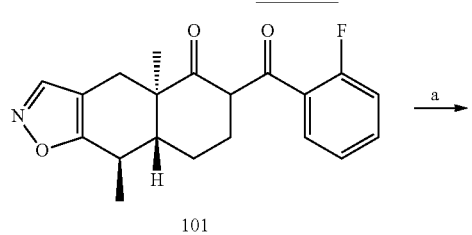

101

→ a

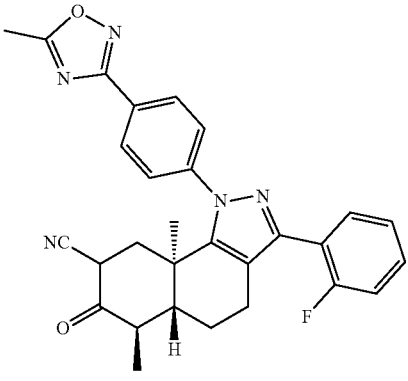

114

→ e

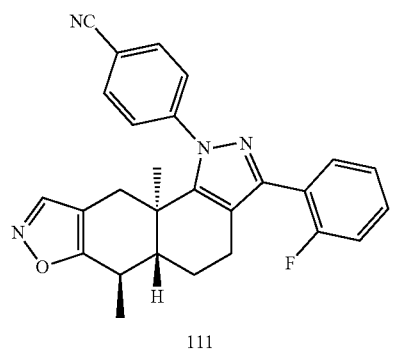

111

→ b

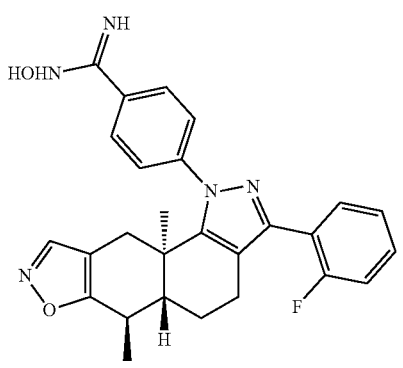

112

→ c

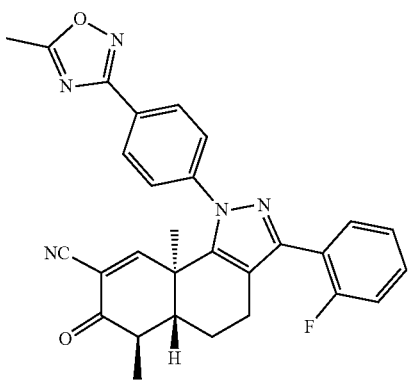

T94

Reagents and conditions: a) 4-cyanophenylhydrazine hydrochloride, EtOH, microwave, 120° C.; b) aq. NH₂OH, EtOH, 50° C.; c) dimethylacetamide dimethylacetal, 1,4-dioxane, 60° C.; d) K₂CO₃, MeOH, rt; e) Br₂, CH₂Cl₂, DMF, 0° C.; pyridine, 60° C.

Scheme 37
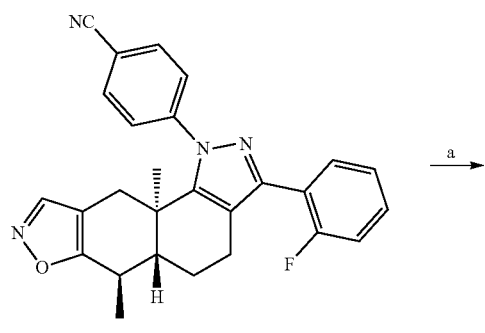
111
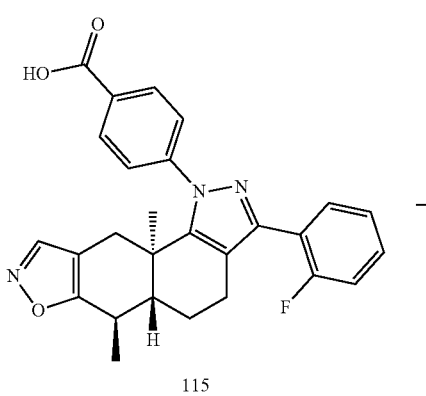
115
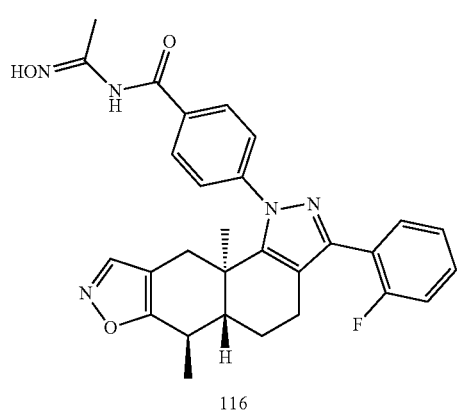
116
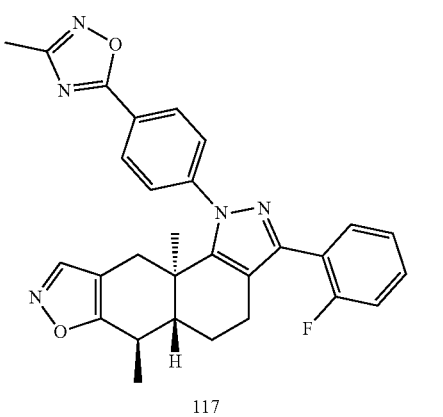
117
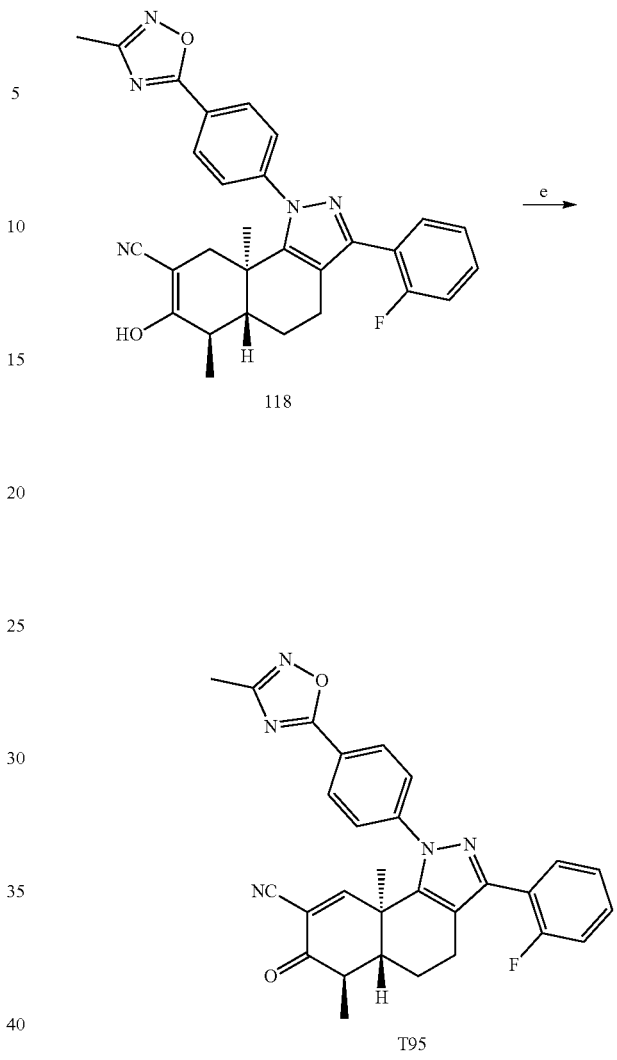
118
T95
Reagents and conditions: a) 50% aq. H$_2$SO$_4$, 130° C.; b) i) (COCl)$_2$, CH$_2$Cl$_2$, 0° C. to rt; ii) N-hydroxyacetamidine, Et$_3$N, CH$_2$Cl$_2$, 0° C. to rt; c) T$_3$P, 1,4-dioxane, 90° C.; d) K$_2$CO$_3$, MeOH, rt; e) Br$_2$, CH$_2$Cl$_2$, DMF, 0° C.; pyridine, 60° C.
Scheme 38
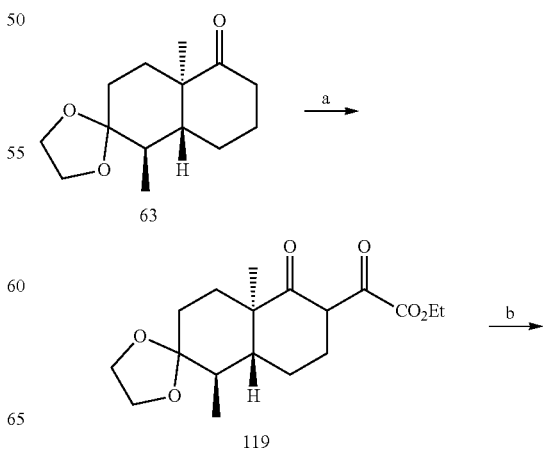
63
119

143
-continued
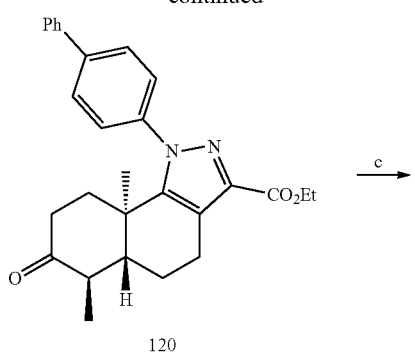
120
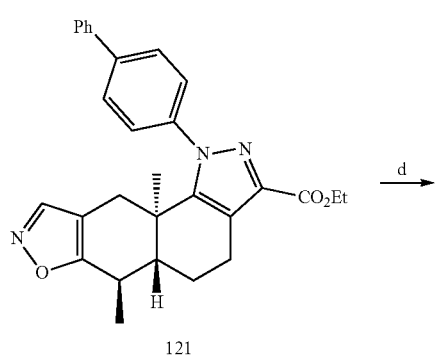
121
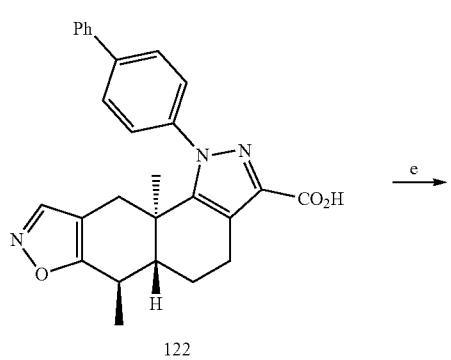
122
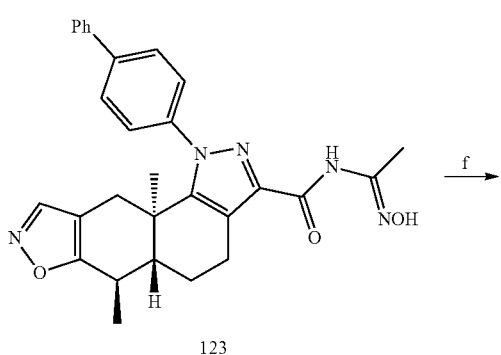
123
144
-continued
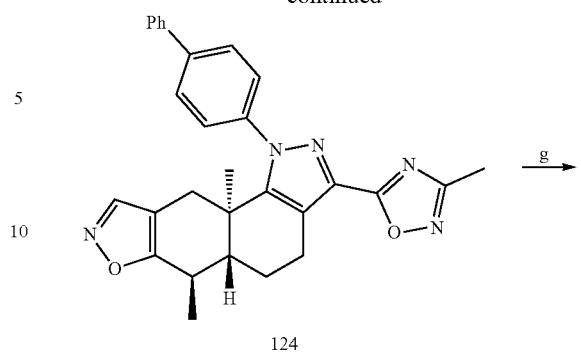
124
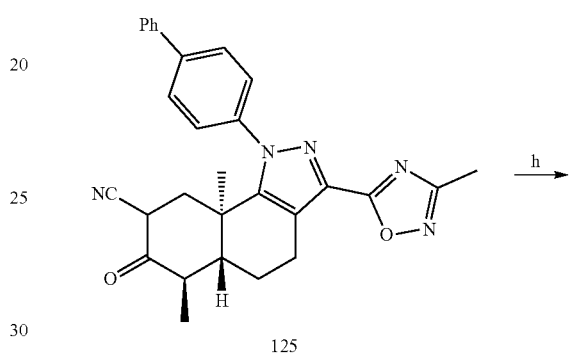
125
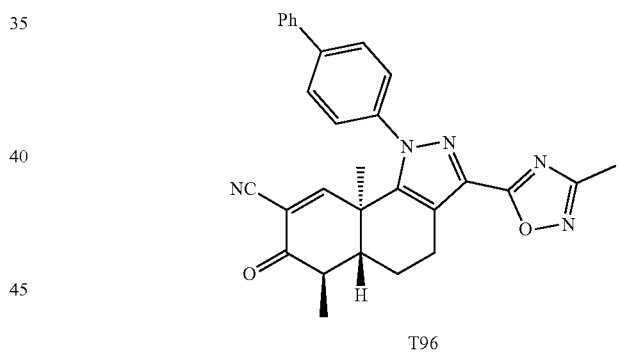
T96
Reagents and conditions: a) diethyl oxalate, NaH, THF, 80° C.; b) biphenyl-4-ylhydrazine hydrochloride, EtOH, microwave, 120° C.; ii) 3 N aq. HCl, THF; c) i) HCO₂Et, NaOMe, MeOH, rt, ii) NH₂OH•HCl, EtOH, 12 N aq. HCl, 55° C.; d) 50% aq. H₂SO₄, 130° C.; e) i) (COCl)₂, CH₂Cl₂, 0° C. to rt; ii) N-hydroxyacetamidine, Et₃N, CH₂Cl₂, 0° C. to rt; f) T₃P, 1,4-dioxane, 90° C.; g) K₂CO₃, MeOh, rt; h) DBDMH, DMF, 0° C.; pyridine, 60° C.
Scheme 39
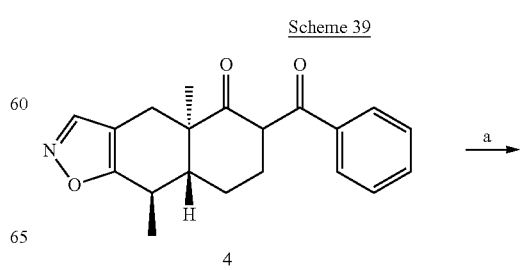
4

145
-continued
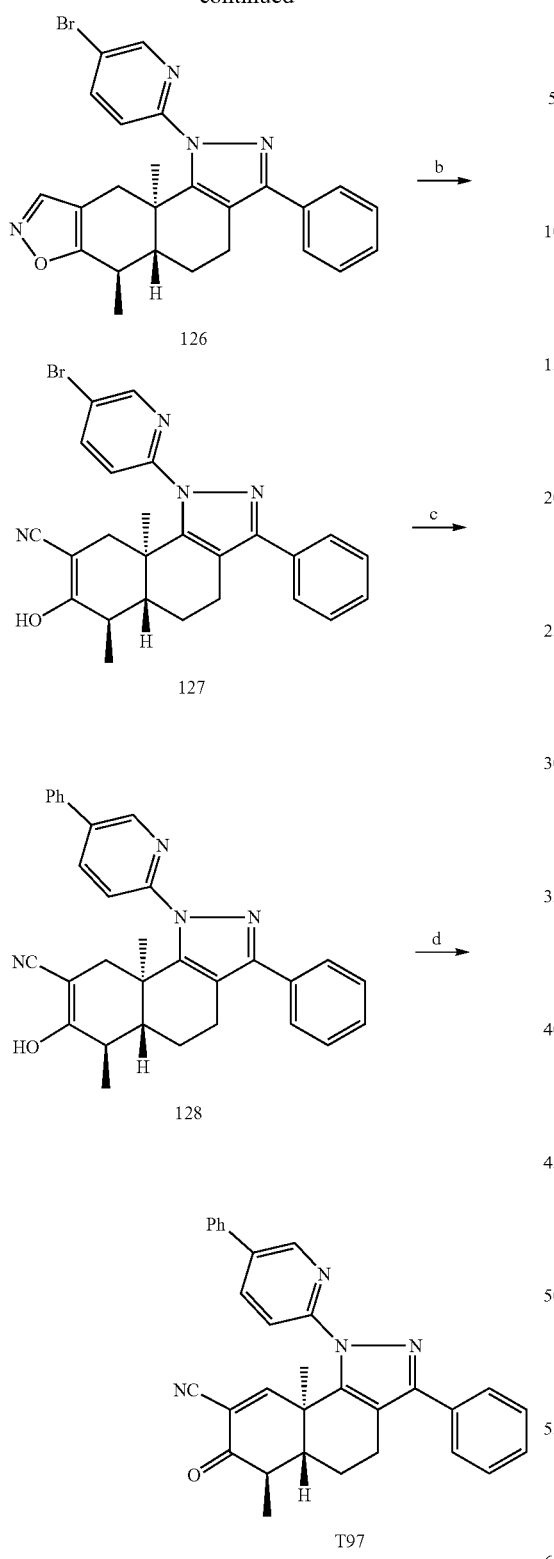
Reagents and conditions: a) 5-bromo-2-hydrazinylpyridine, 6 N aq. HCl, EtOH, microwave, 120° C.; b) NaOMe, MeOH, 55° C.; c) PhB(OH)$_2$, K$_3$PO$_4$, Pd(PPh$_3$)$_4$, 1,4-dioxane, DMF, 90° C.; d) DBDMH, DMF, 0° C.; pyridine, 55° C.
146
Scheme 40
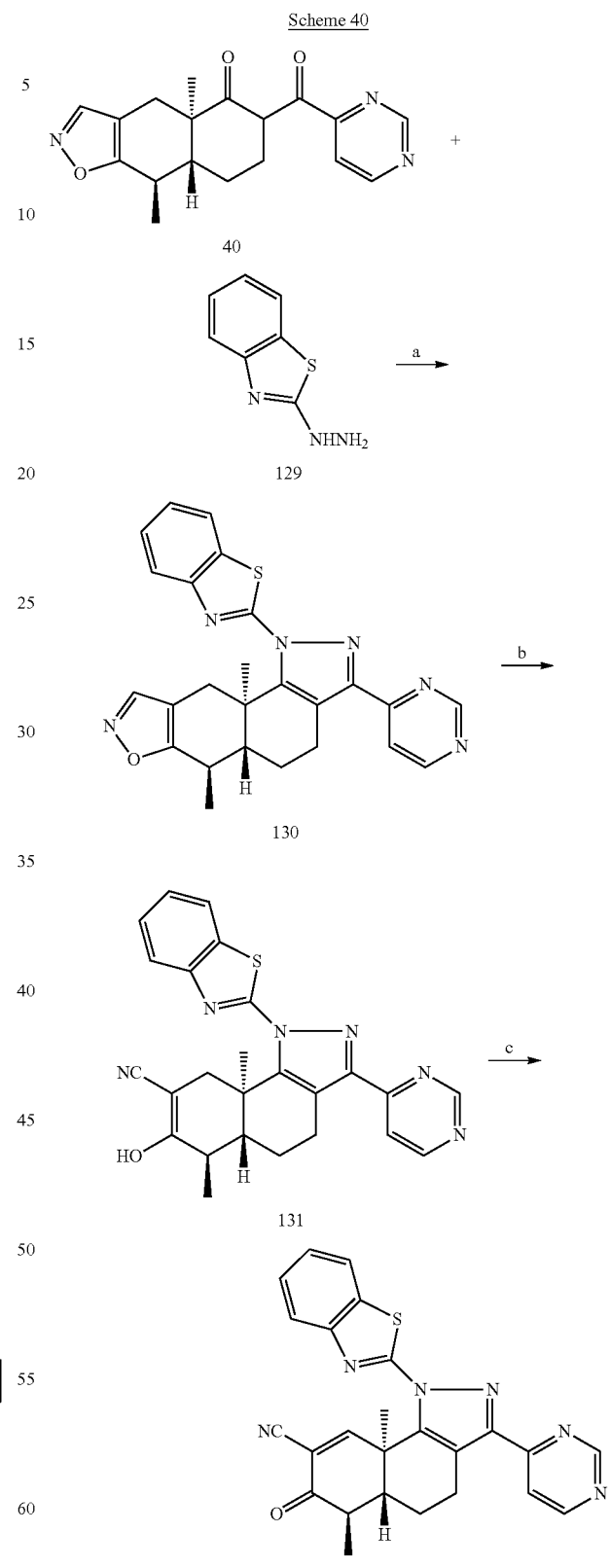
Reagents and conditions: a) 12 N aq. HCl, EtOH, microwave, 100° C.; b) K$_2$CO$_3$, MeOH, rt; c) DBDMH, DMF, 0° C.; pyridine, 55° C.

Scheme 41
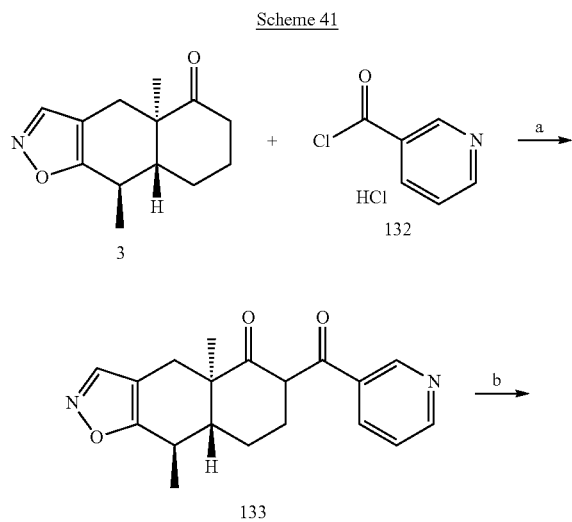
Scheme 42
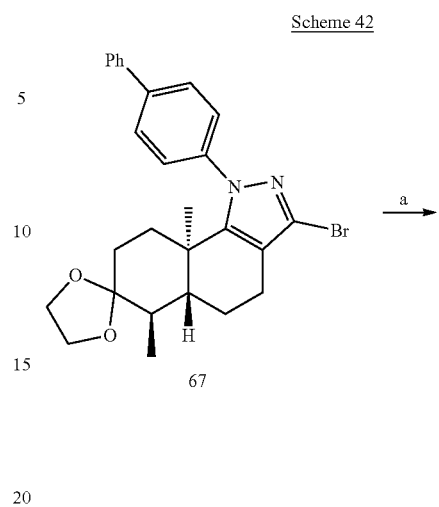
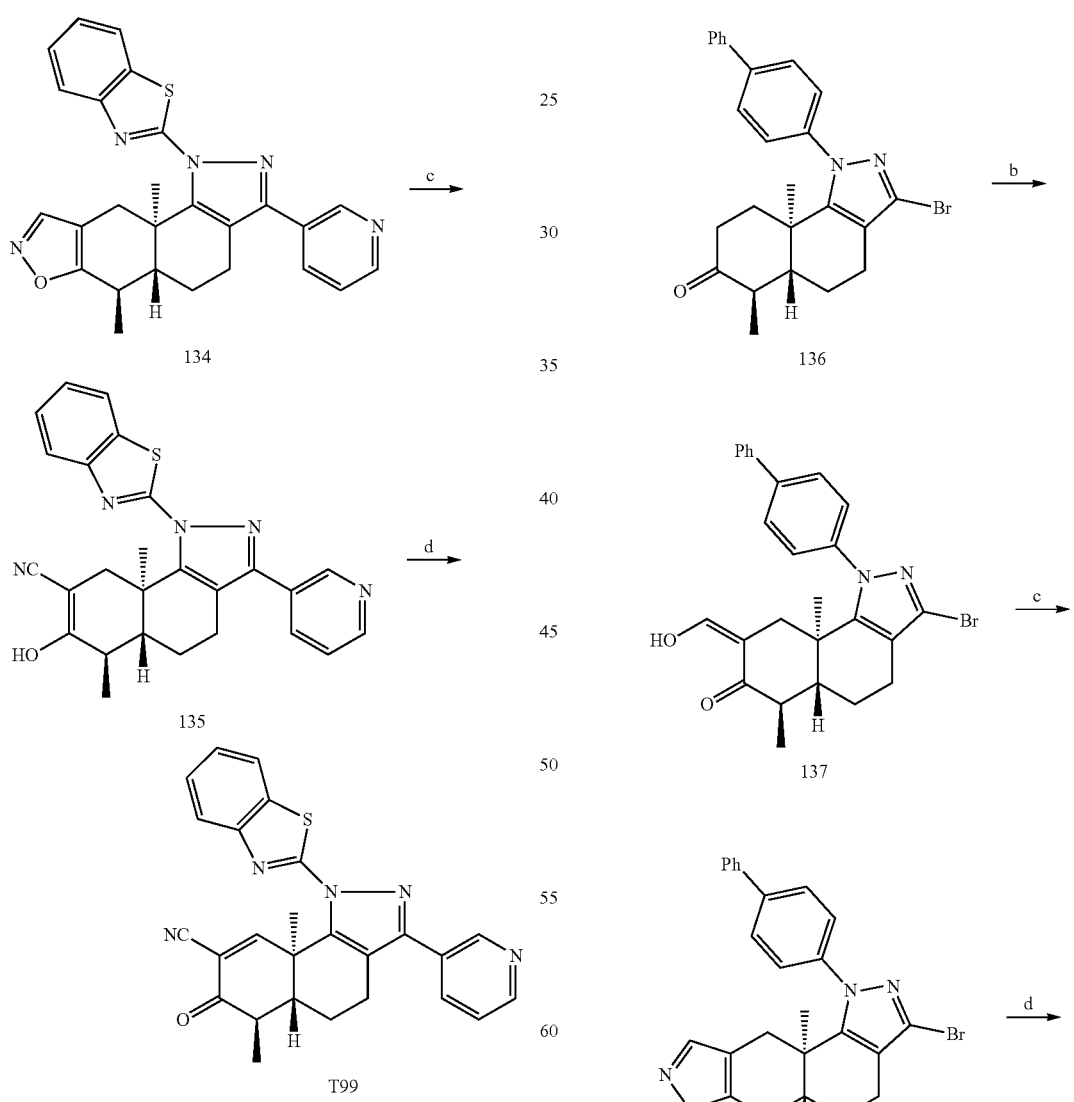
Reagents and conditions: a) MgBr₂•OEt₂, DIPEA, CH₂Cl₂, rt; b) 129, 12 N aq. HCl, EtOH, microwave, 100° C.; c) K₂CO₃, MeOH, rt; d) DBDMH, DMF, 0° C.; pyridine, 55° C.

US 11,993,574 B2

149
-continued

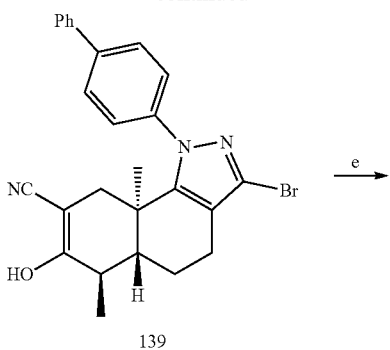
139

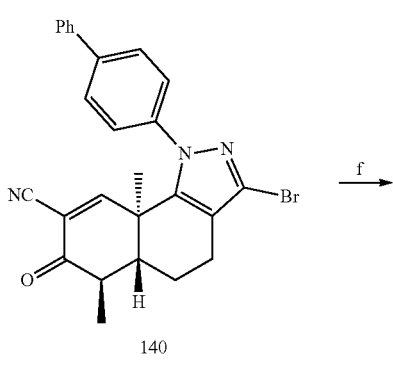
140

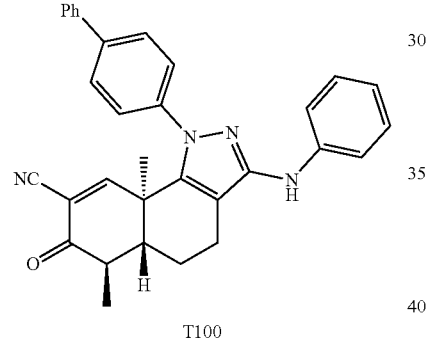
T100

Reagents and conditions: a) 6 N aq. HCl, THF, rt; b) HCO₂Et, NaOMe, MeOH, 0° C. to rt; c) H₂NOH•HCl, 6 N aq. HCl, EtOH, 60° C.; d) K₂CO₃, MeOH, rt; e) DBDMH, DMF, 0° C.; pyridine, 60° C.; f) aniline, t-BuXPhosPd-G3, NaOBu$^t$, 1,4-dioxane, 120° C.

Scheme 43

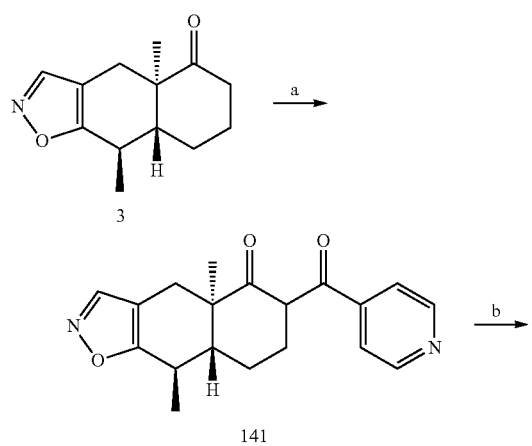

150
-continued

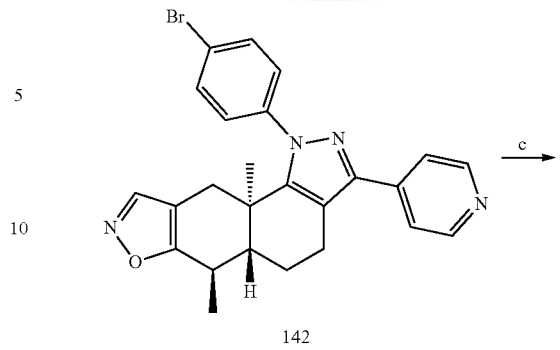
142

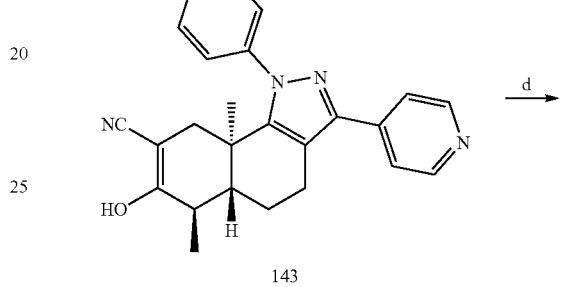
143

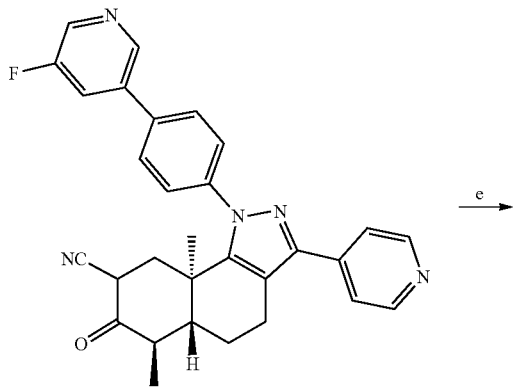
144

T101

Reagents and conditions: a) isonicotinoyl chloride hydrochloride, MgBr₂•OEt₂, DIPEA, CH₂Cl₂, rt; b) (4-bromophenyl)hydrazine hydrochloride, EtOH, microwave, 120° C.; c) K₂CO₃, MeOH, rt; d) 5-flueoropyridine-3-boronic acid, K₃PO₄, Pd(PPh₃)₄, 1,4-dioxane, DMF, 90° C.; e) DBDMH, DMF, 0° C.; pyridine, 60° C.

Scheme 44
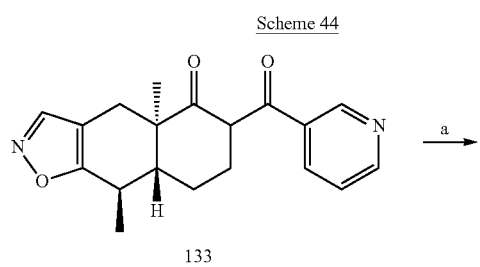
133
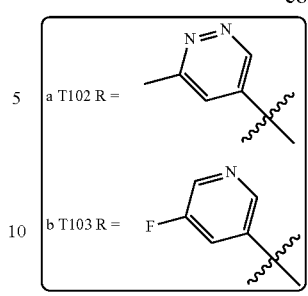
a T102 R = [3-methylpyridazin-5-yl]
b T103 R = [5-fluoropyridin-3-yl]
Reagents and conditions: a) (4-bromophenyl)hydrazine hydrochloride, EtOH, microwave, 100° C.; b) K₂CO₃, MeOH, rt; c) 3-methyl-5-(4,4,5,5-tetramethyl-1,3,2-dioxaborolan-2-yl)pyridazine, K₃PO₄, Pd(PPh₃)₄, 1,4-dioxane, H₂O, 120° C. (for 147a); 5-fluoropyridine-3-boronic acid, K₃PO₄, Ph(PPh₃)₄, 1,4-dioxane, DMF, 90° C. (for 147b); d) DBDMH, DMF, 0° C; pyridine, 60° C.
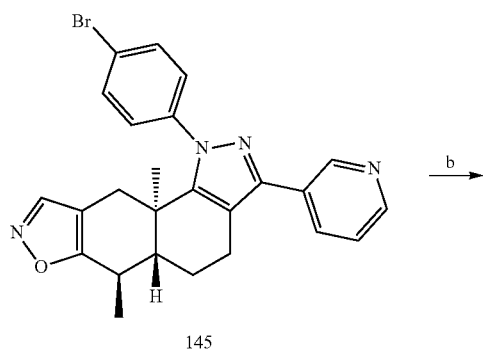
145
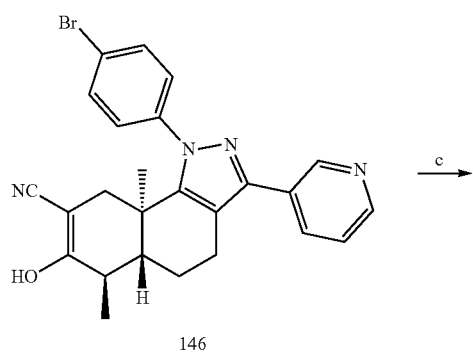
146
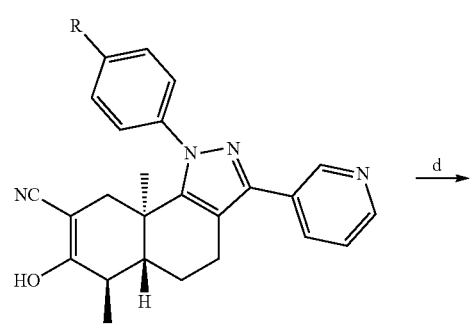
147a-147b
Scheme 45
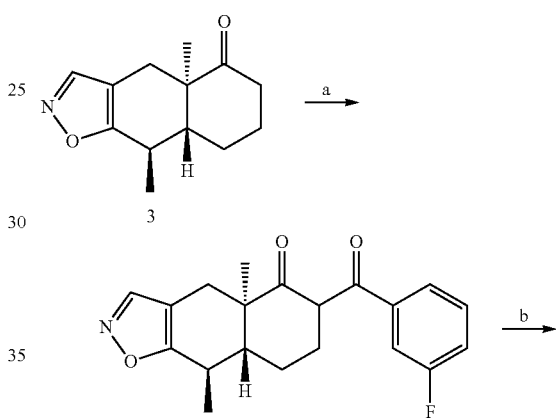
3
148
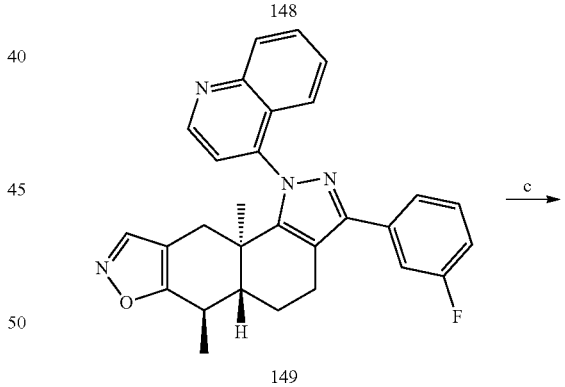
149
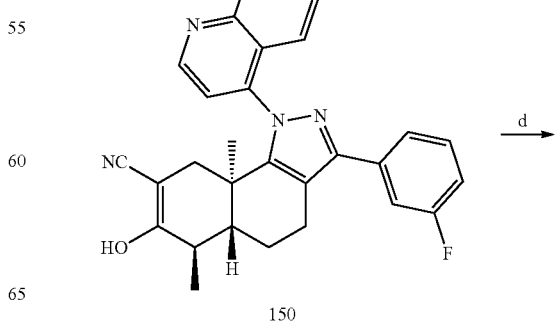
150

153
-continued

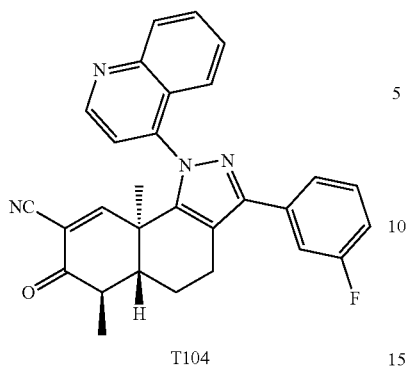

T104

Reagents and conditions: a) 3-F-PhCOCl, MgBr₂•OEt₂, DIPEA, CH₂Cl₂, rt; b) 4-hydrozinoquinoline hydrochloride, EtOH, microwave, 100° C.; c) K₂CO₃, MeOH, rt; d) DBDMH, DMF, 0° C.; pyridine, 60° C.

154
-continued

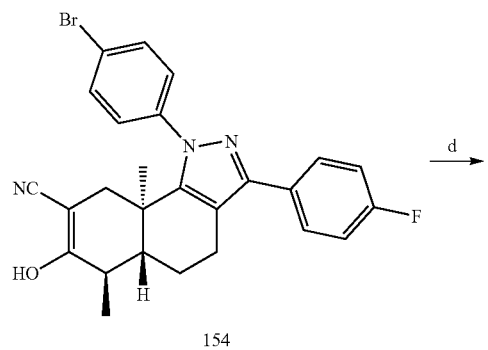

154

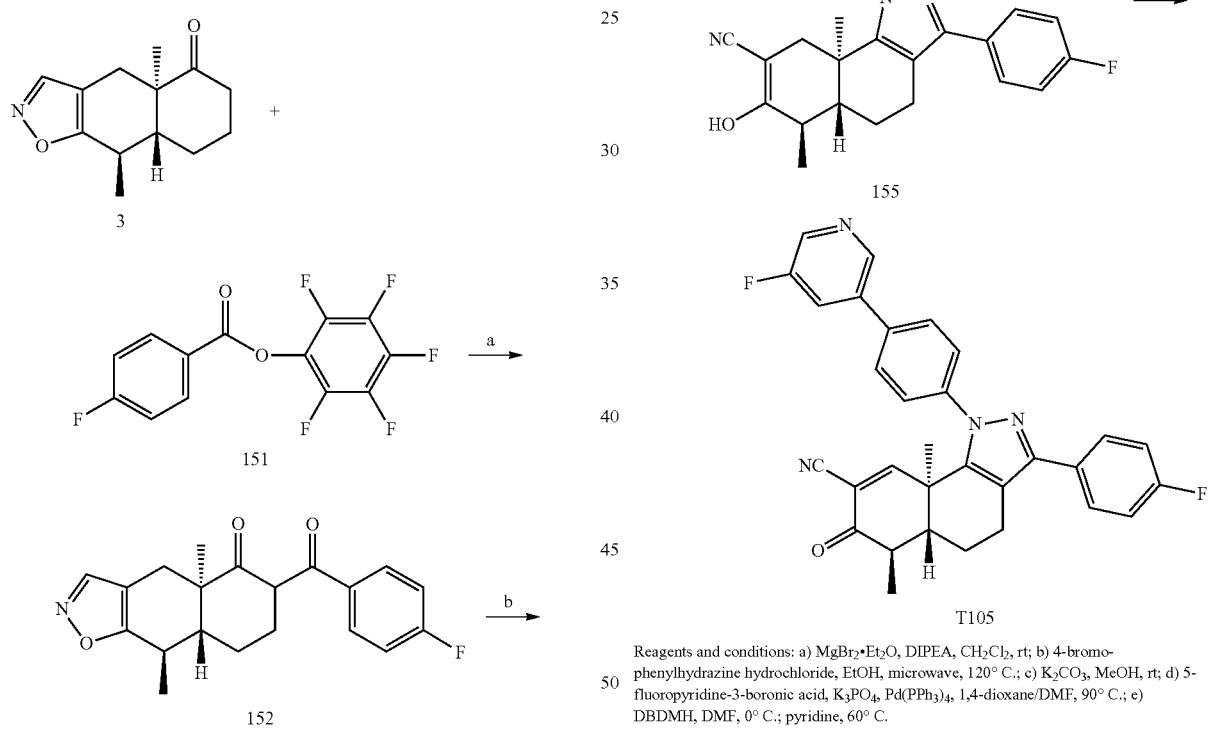

155

T105

Reagents and conditions: a) MgBr₂•Et₂O, DIPEA, CH₂Cl₂, rt; b) 4-bromo-phenylhydrazine hydrochloride, EtOH, microwave, 120° C.; c) K₂CO₃, MeOH, rt; d) 5-fluoropyridine-3-boronic acid, K₃PO₄, Pd(PPh₃)₄, 1,4-dioxane/DMF, 90° C.; e) DBDMH, DMF, 0° C.; pyridine, 60° C.

Scheme 47

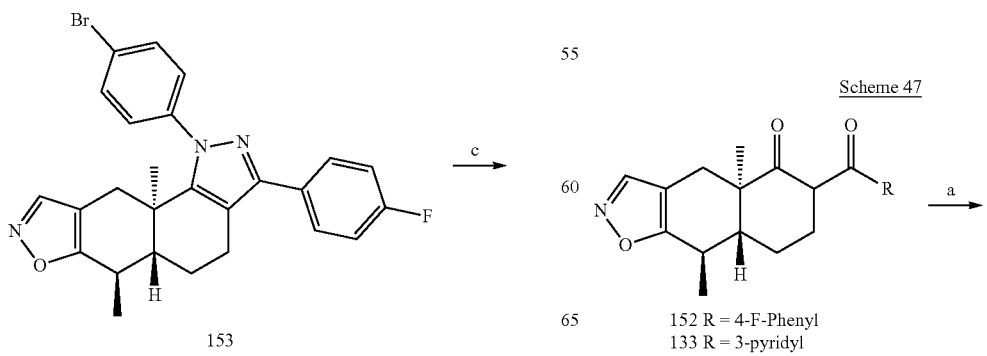

152 R = 4-F-Phenyl
133 R = 3-pyridyl

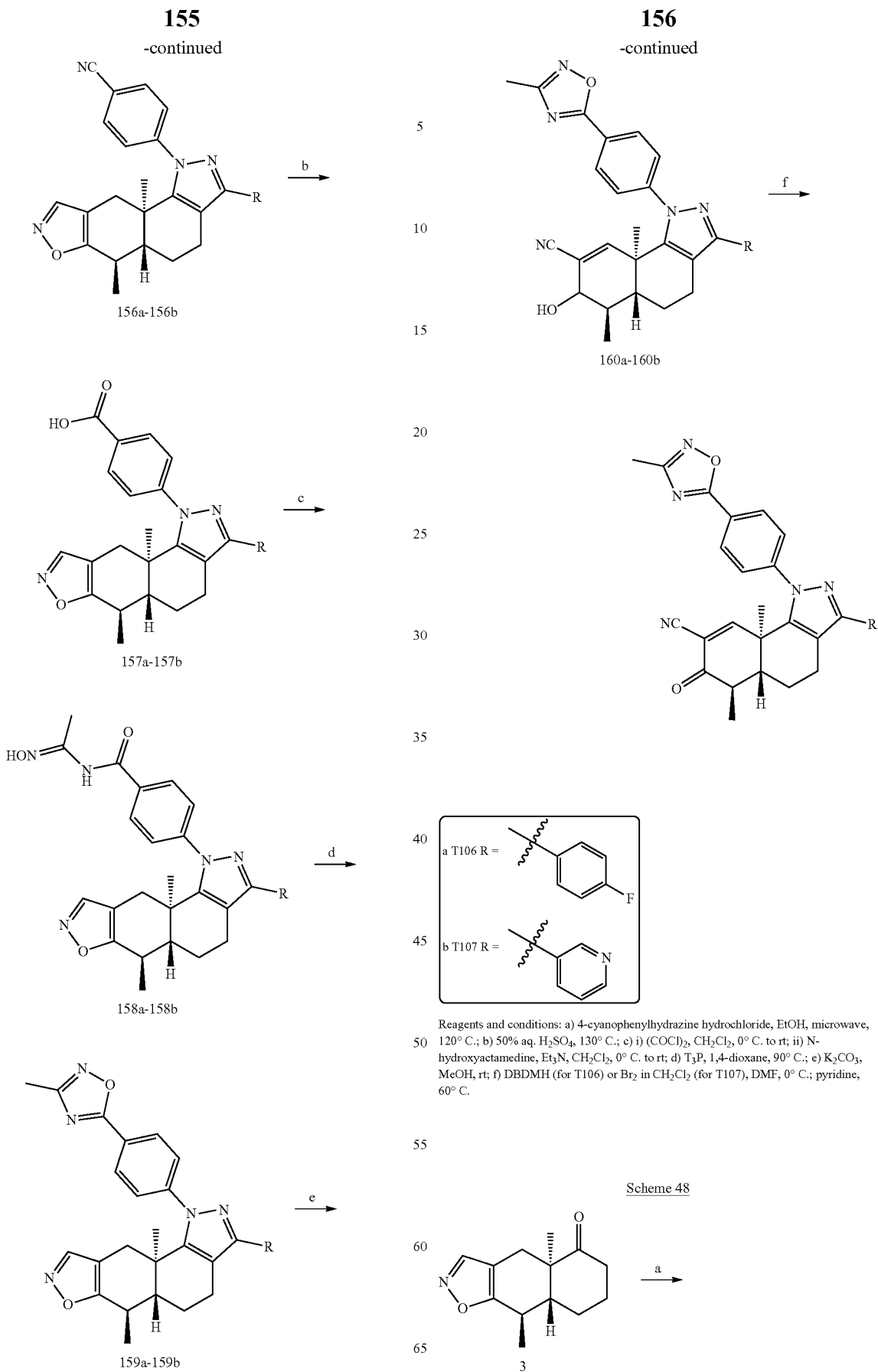

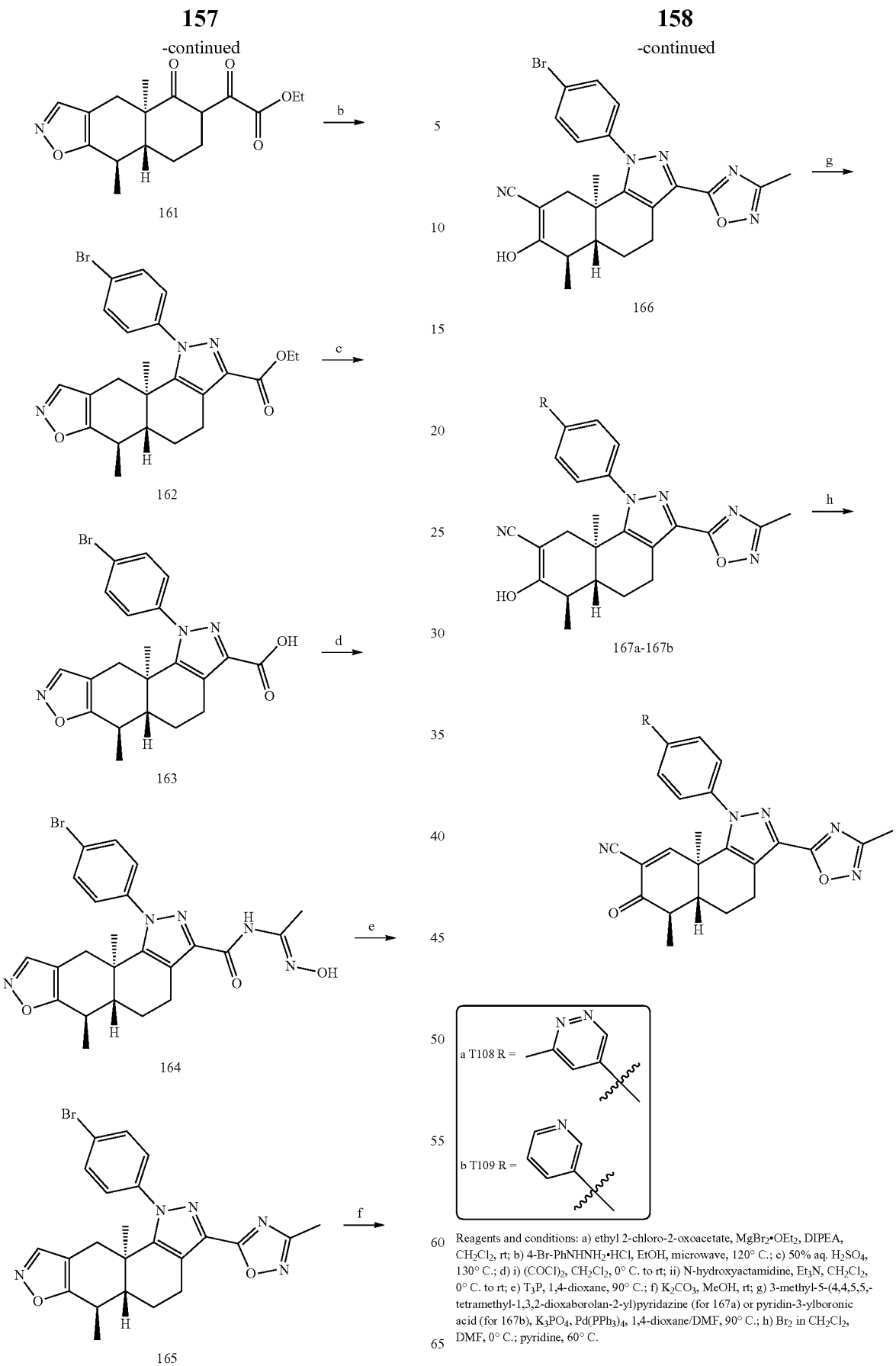

Reagents and conditions: a) ethyl 2-chloro-2-oxoacetate, MgBr$_2$•OEt$_2$, DIPEA, CH$_2$Cl$_2$, rt; b) 4-Br-PhNHNH$_2$•HCl, EtOH, microwave, 120° C.; c) 50% aq. H$_2$SO$_4$, 130° C.; d) i) (COCl)$_2$, CH$_2$Cl$_2$, 0° C. to rt; ii) N-hydroxyactamidine, Et$_3$N, CH$_2$Cl$_2$, 0° C. to rt; e) T$_3$P, 1,4-dioxane, 90° C.; f) K$_2$CO$_3$, MeOH, rt; g) 3-methyl-5-(4,4,5,5,-tetramethyl-1,3,2-dioxaborolan-2-yl)pyridazine (for 167a) or pyridin-3-ylboronic acid (for 167b), K$_3$PO$_4$, Pd(PPh$_3$)$_4$, 1,4-dioxane/DMF, 90° C.; h) Br$_2$ in CH$_2$Cl$_2$, DMF, 0° C.; pyridine, 60° C.

Scheme 49
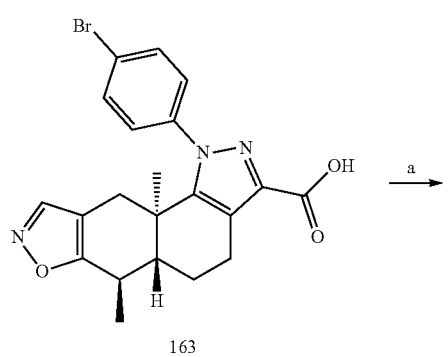
163
a →
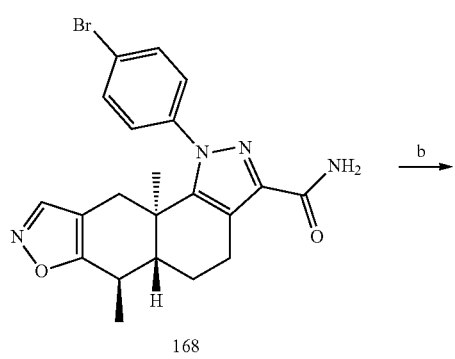
168
b →
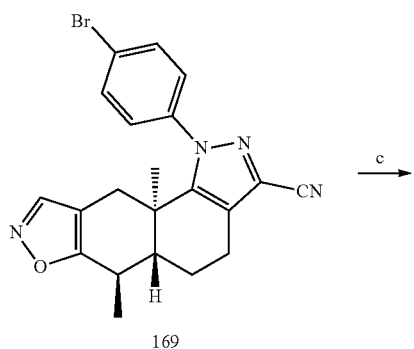
169
c →
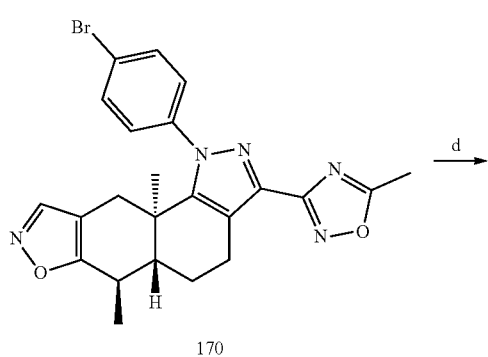
170
d →
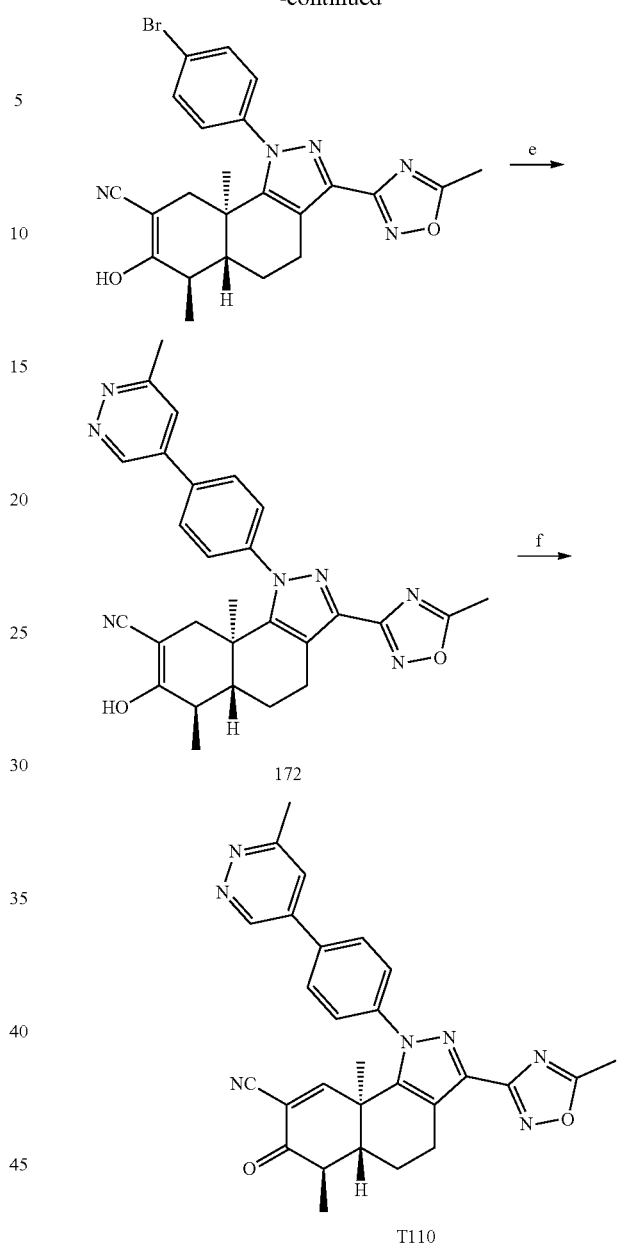
172
T110
Reagents and conditions: a) i) (COCl)₂, CH₂Cl₂, 0° C. to rt; ii) aq. ammonia, THF, 0° C. to rt; b) TFAA, Et₃N, CH₂Cl₂, rt; c) i) aq. NH₂OH, EtOH, 50° C.; ii) dimethylacetamide dimethylacetal, 1,4-dioxane, 60° C.; d) K₂CO₃, MeOH, rt; e) 3-methyl-5-(4,4,5,5,-tetramethyl-1,3,2-dioxaborolan-2-yl)pyridazine, K₃PO₄, Pd(dppf)Cl₂, 1,4-dioxane, DMF, 90° C.; f) Br₂ in CH₂Cl₂, DMF, 0° C.; pyridine, 60° C.
Scheme 50
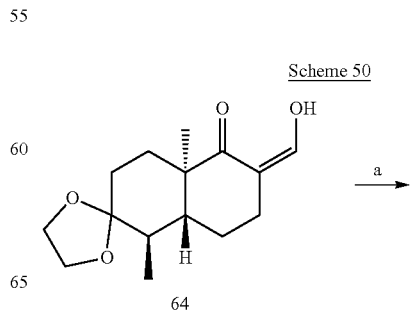
64
a →

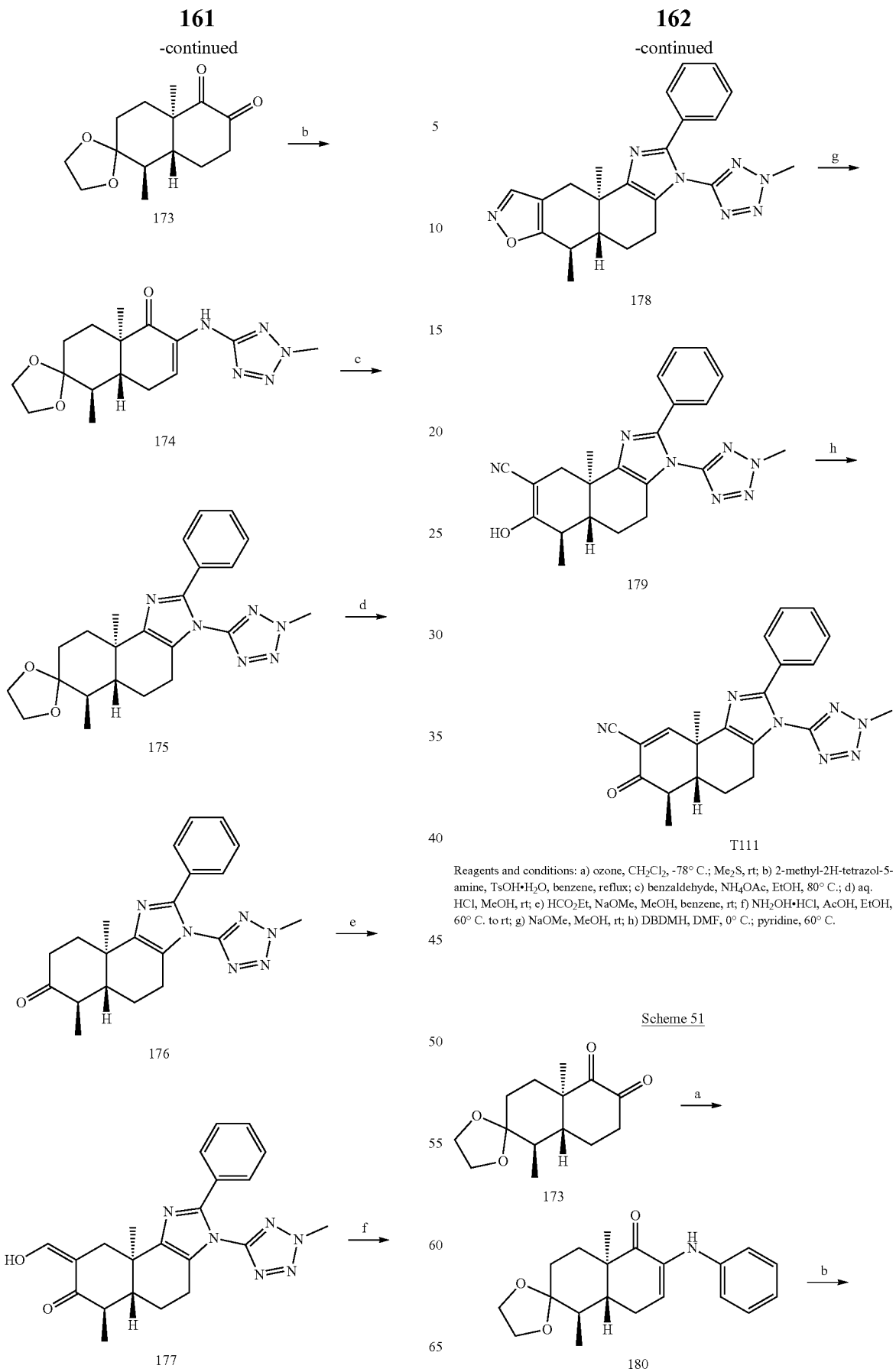

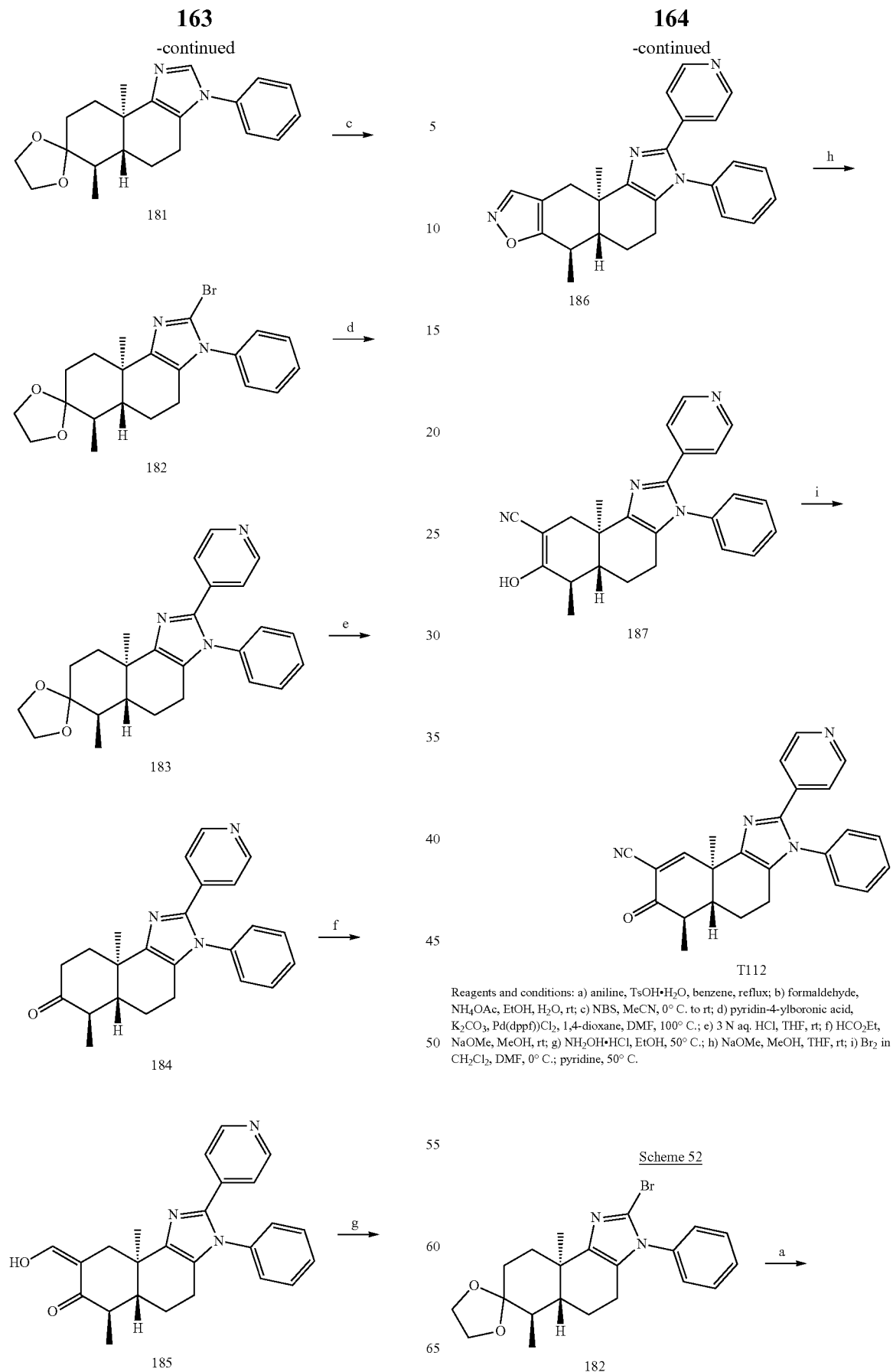

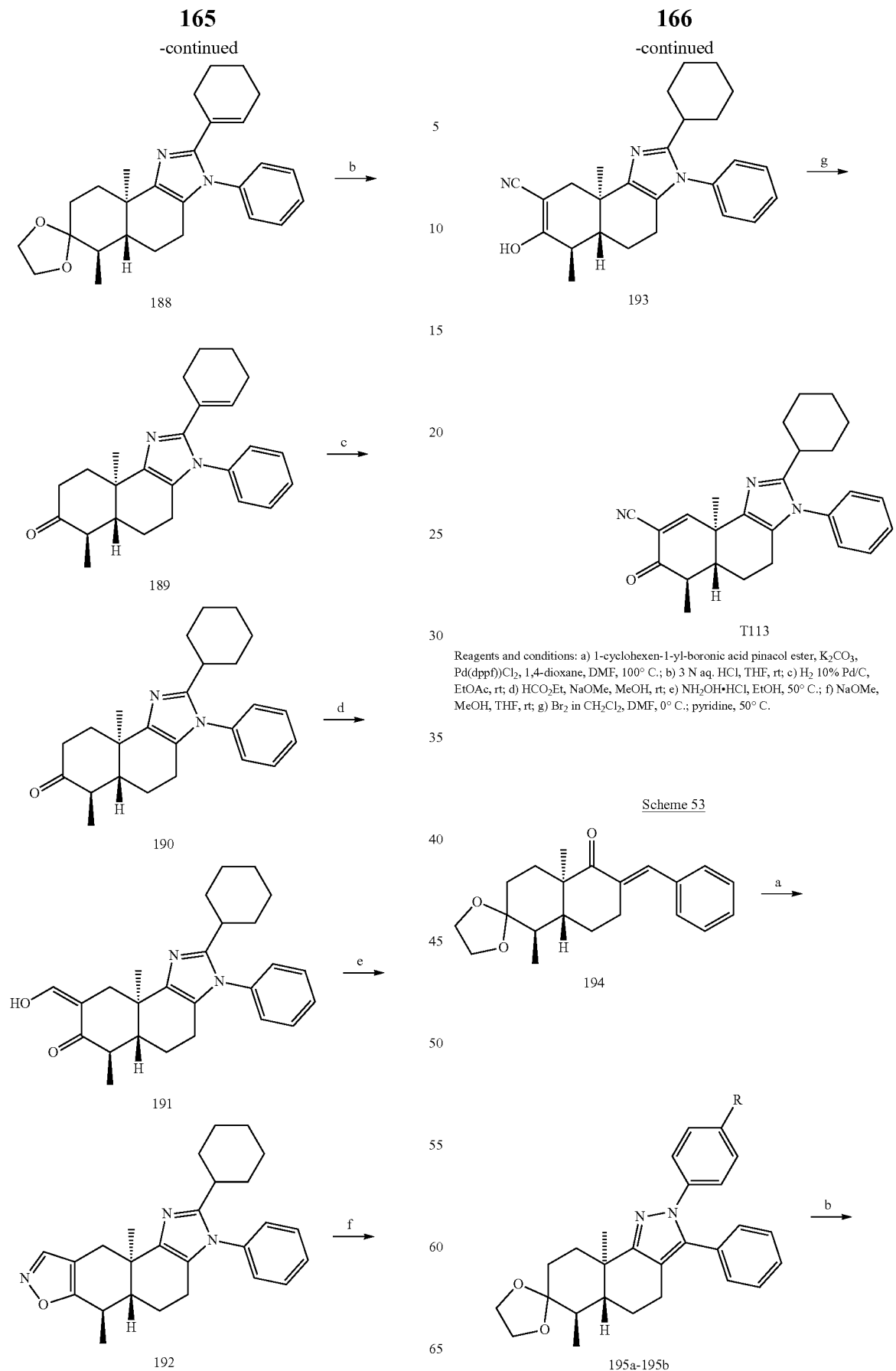

-continued

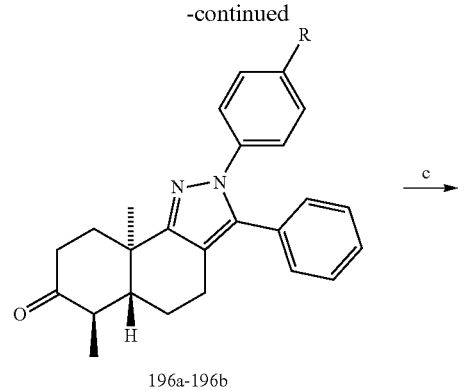
196a-196b

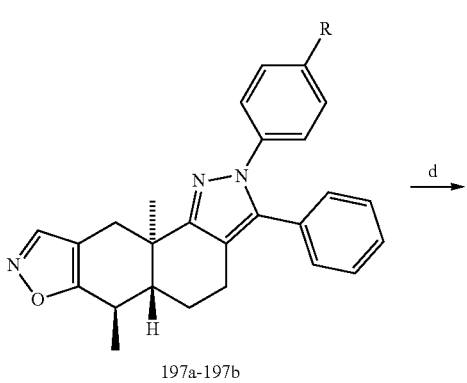
197a-197b

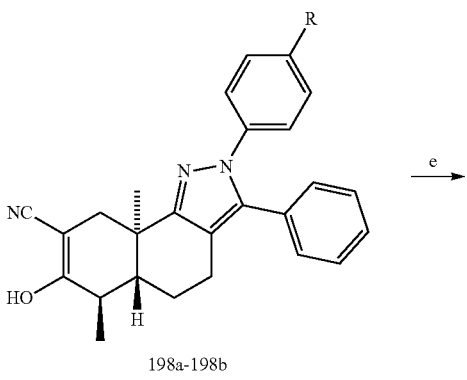
198a-198b

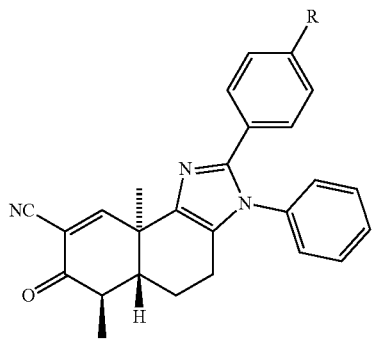
a T114 R = Cl
b T115 R = H

Reagents and conditions: a) i) aryl hydrazine, EtOH, HOAc, 80° C. (for 195a) or microwave 150° C. (for 195b); ii) MnO₂, CH₂Cl₂; b) 3 N aq. HCl, THF, rt to 50° C.; c) HCO₂Et, NaOMe, MeOH, 0° C. to rt; 6 N aq. HCl, H₂NOH·HCl, EtOH, 55° C.; d) K₂CO₃, MeOH, rt; e) DBDMH, DMF, 0° C.; pyridine, 60° C.

Scheme 54

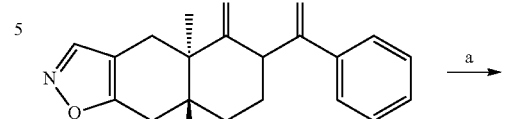
4

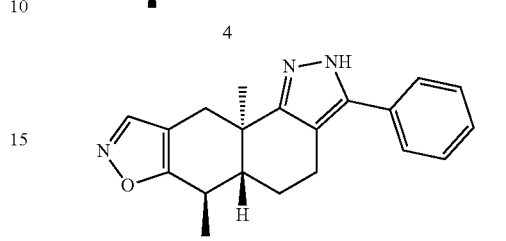
199

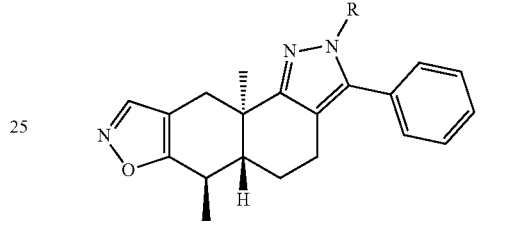
200a-200c

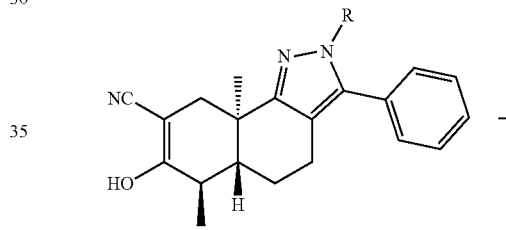
201a-201c

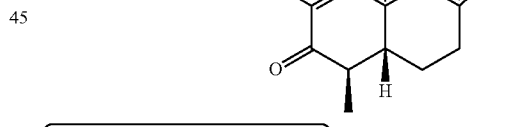

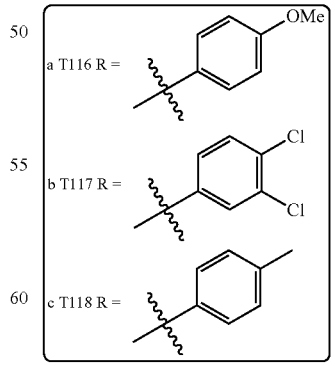
a T116 R = 4-OMe-phenyl
b T117 R = 3,4-diCl-phenyl
c T118 R = 4-Me-phenyl Reagents and conditions: a) hydrazine EtOH, 60° C.; b) arylboronic acid, 3Å molecular sieves, copper(II)acetate, pyridine, CH₂Cl₂, rt; c) K₂CO₃, MeOH, rt; d) DBDMH, DMF, 0° C.; pyridine, 60° C.

169
Scheme 55
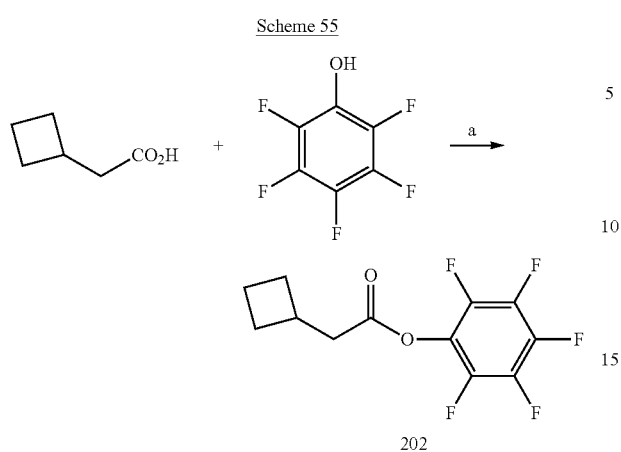
202
Reagents and conditions: a) DCC, 1,4-dioxane, rt.
Scheme 56
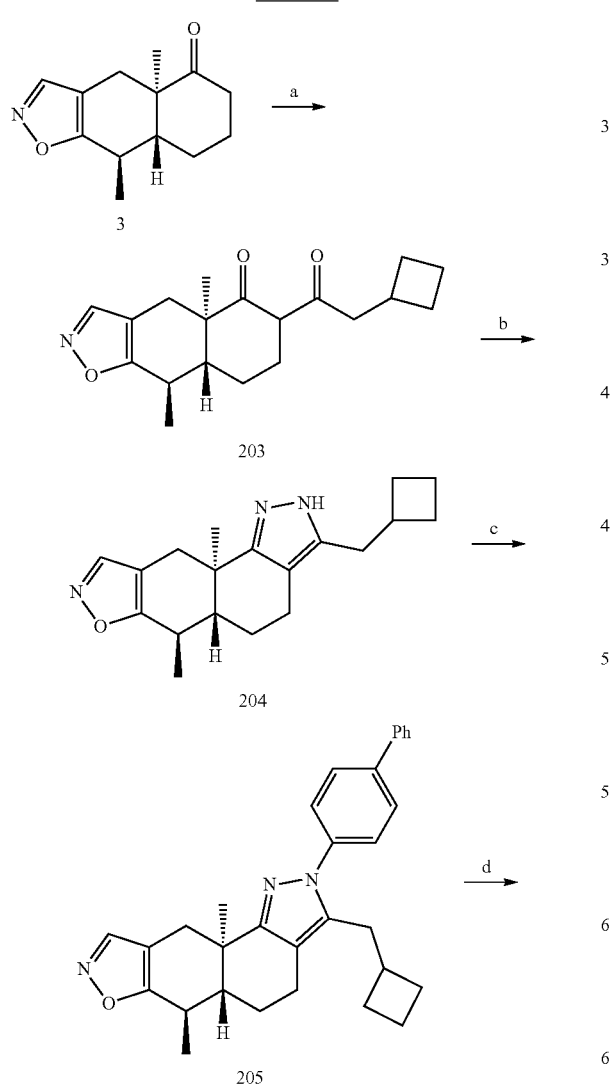
170
-continued
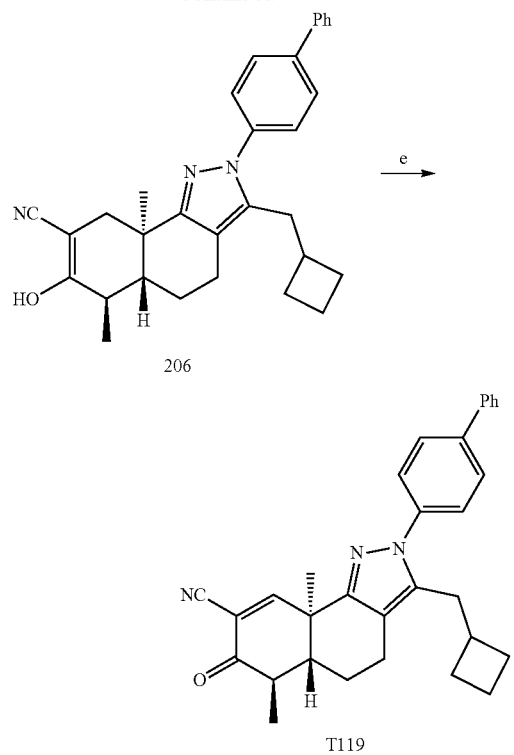
206
T119
Reagents and conditions: a) 202, MgBr₂·Et₂O, DIPEA, CH₂Cl₂, rt; b) hydrazine monohydrate, EtOH, 60° C.; c) 4-biphenylboronic acid, 3Å molecular sieves, copper(II)acetate, pyridine, CH₂Cl₂, rt; d) K₂CO₃, MeOH, rt to 50° C.; e) DBDMH, DMF, 0° C.; pyridine, 60° C.
Scheme 57
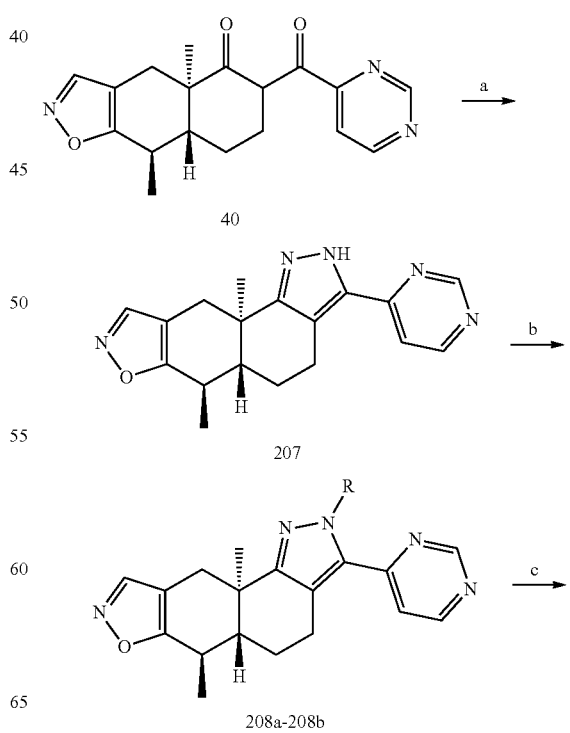
40
207
208a-208b 171
-continued

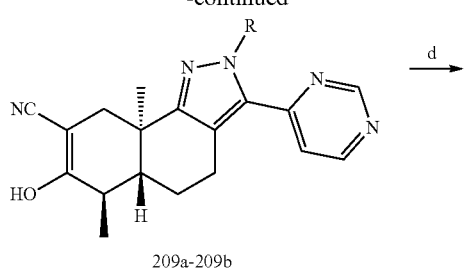
209a-209b

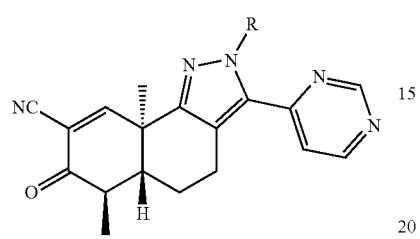

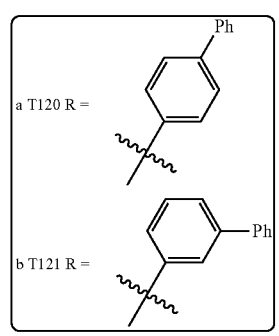

a T120 R = 4-biphenyl
b T121 R = 3-biphenyl

Reagents and conditions: a) hydrazine monohydrate, EtOH, 60° C.; b) arylboronic acid, 3Å molecular sieves, copper(II)acetate, pyridine, CH$_2$Cl$_2$, rt; c) K$_2$CO$_3$, MeOH; d) DBDMH, DMF, 0° C.; pyridine, 60° C.

Scheme 58

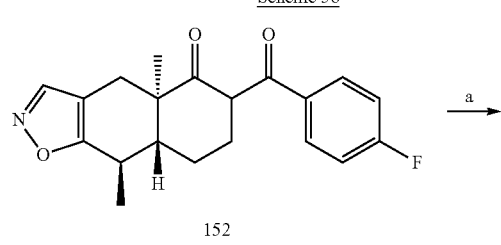
152

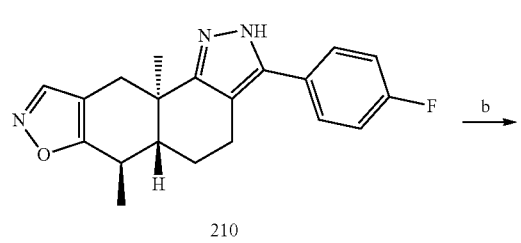
210

172
-continued

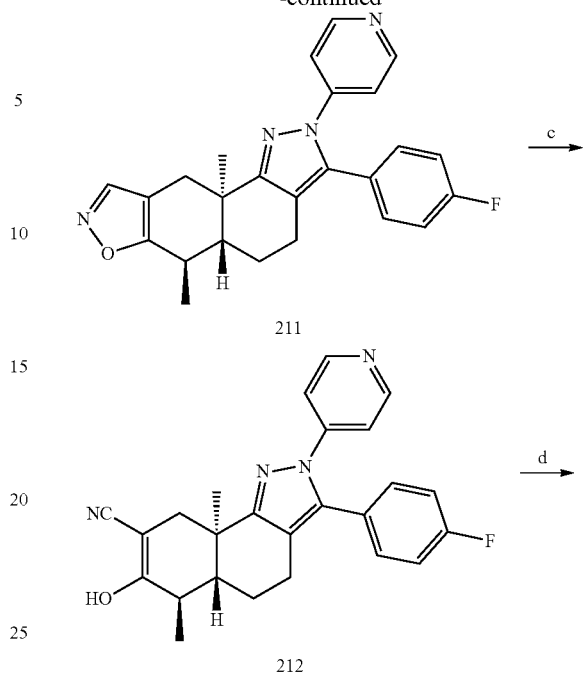
211

212

T122

Reagents and conditions: a) hydrazine monohydrate, EtOH, 60° C.; b) pyridin-4-boronic acid, 3Å molecular sieves, copper(II)acetate, pyridine, DMF, 85° C.; c) K$_2$CO$_3$, MeOH, rt; d) DBDMH, DMF, 0° C.; pyridine, 60° C.

Scheme 59

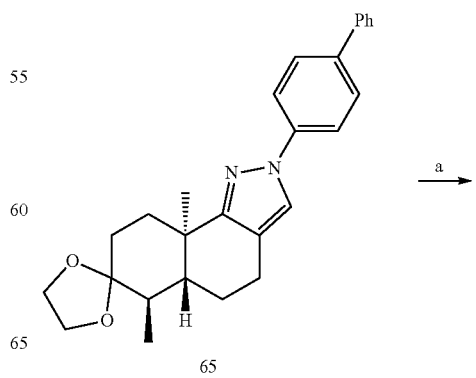
65

173
-continued
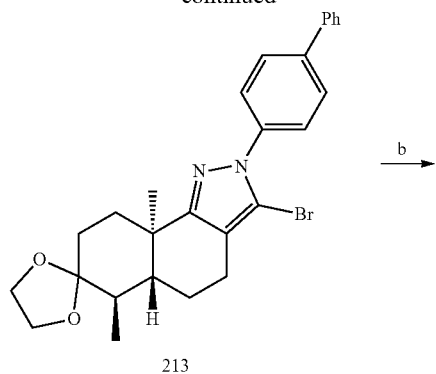
213
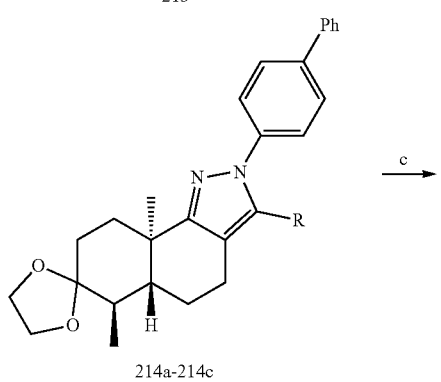
214a-214c
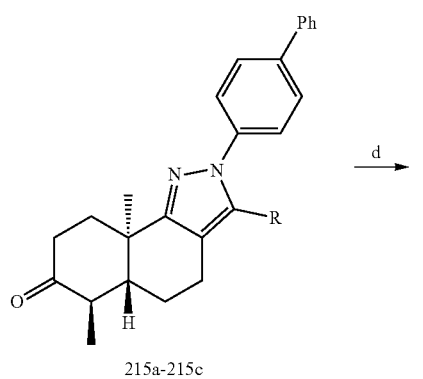
215a-215c
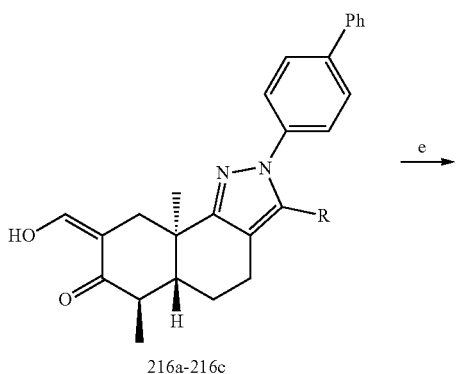
216a-216c
174
-continued
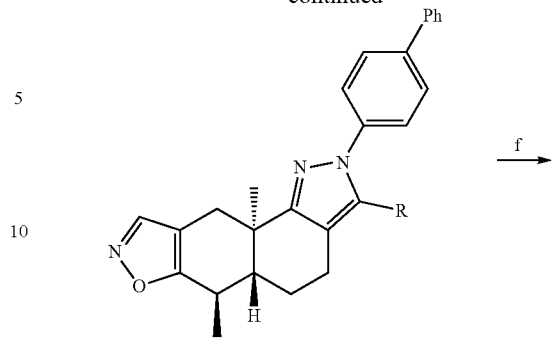
217a-217c
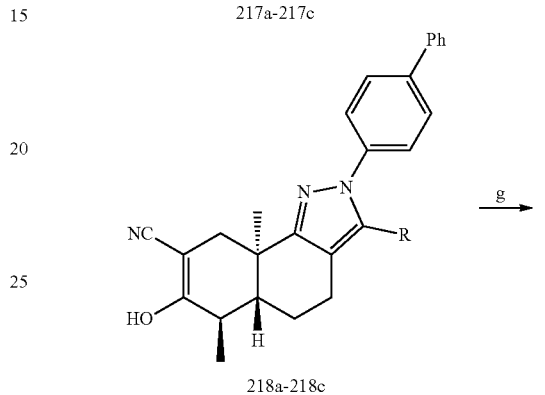
218a-218c
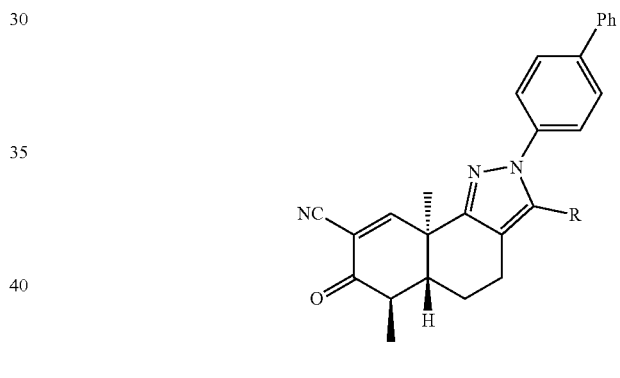
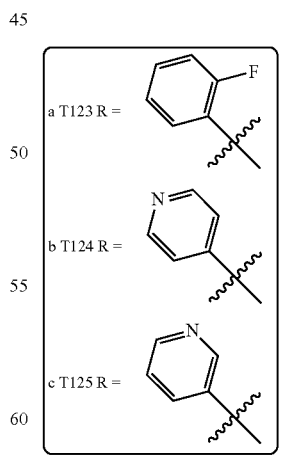
Reagents and conditions: a) Br$_2$, Na$_2$CO$_3$, CH$_2$Cl$_2$, -10° C.; b) arylboronic acid, K$_3$PO$_4$, Pd(PPh$_3$)$_4$, 1,4-dioxane, DMF, 90° C.; c) 3 N aq. HCl, MeOH, rt; d) HCO$_2$Et, NaOMe, MeOH, rt; e) NH$_2$OH·HCl, AcOH, EtOH, 60° C. to rt; f) K$_2$CO$_3$, MeOH, rt; g) DBDMH, DMF, 0° C.; pyridine, 60° C.

Scheme 60
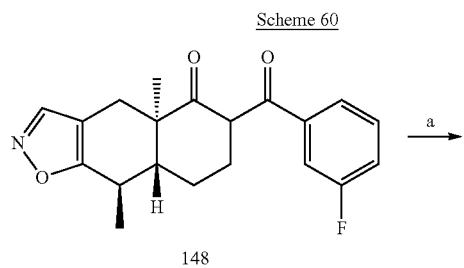
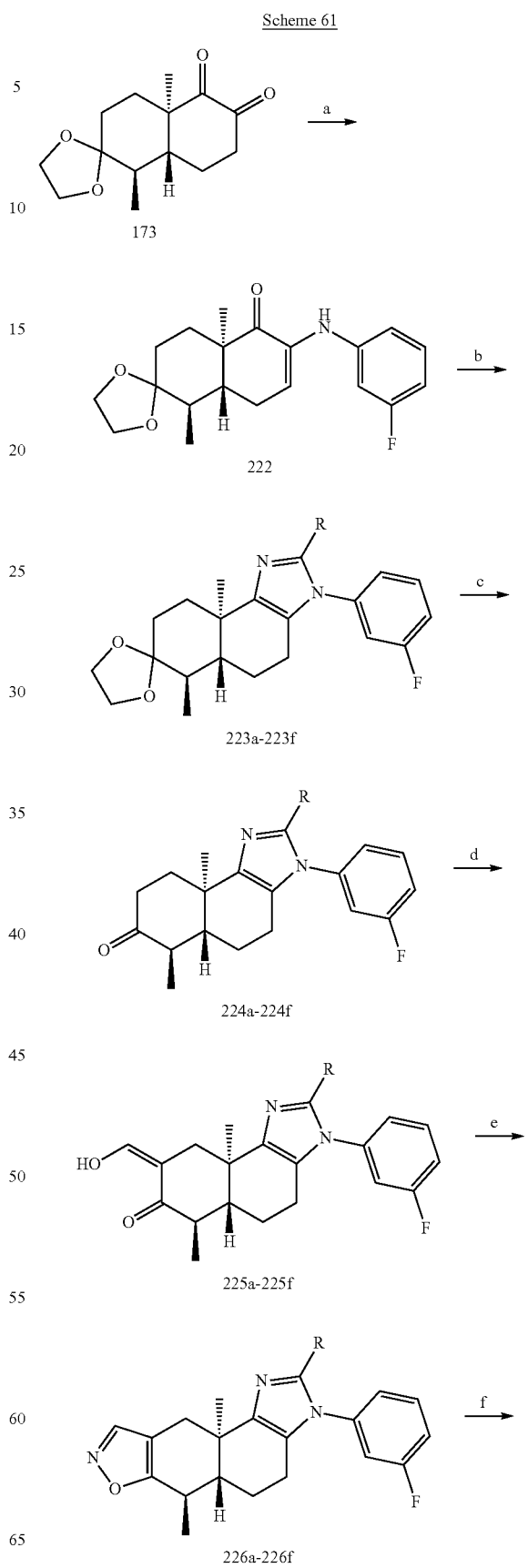
Reagents and conditions: a) hydrazine monohydrate, EtOH, 60° C.; b) 3-biphenylboronic acid, 4Å molecular sieves, copper(II)acetate, pyridine, CH₂Cl₂, rt; c) K₂CO₃, MeOH, rt; d) DBDMH, DMF, 0° C.; pyridine, 60° C.

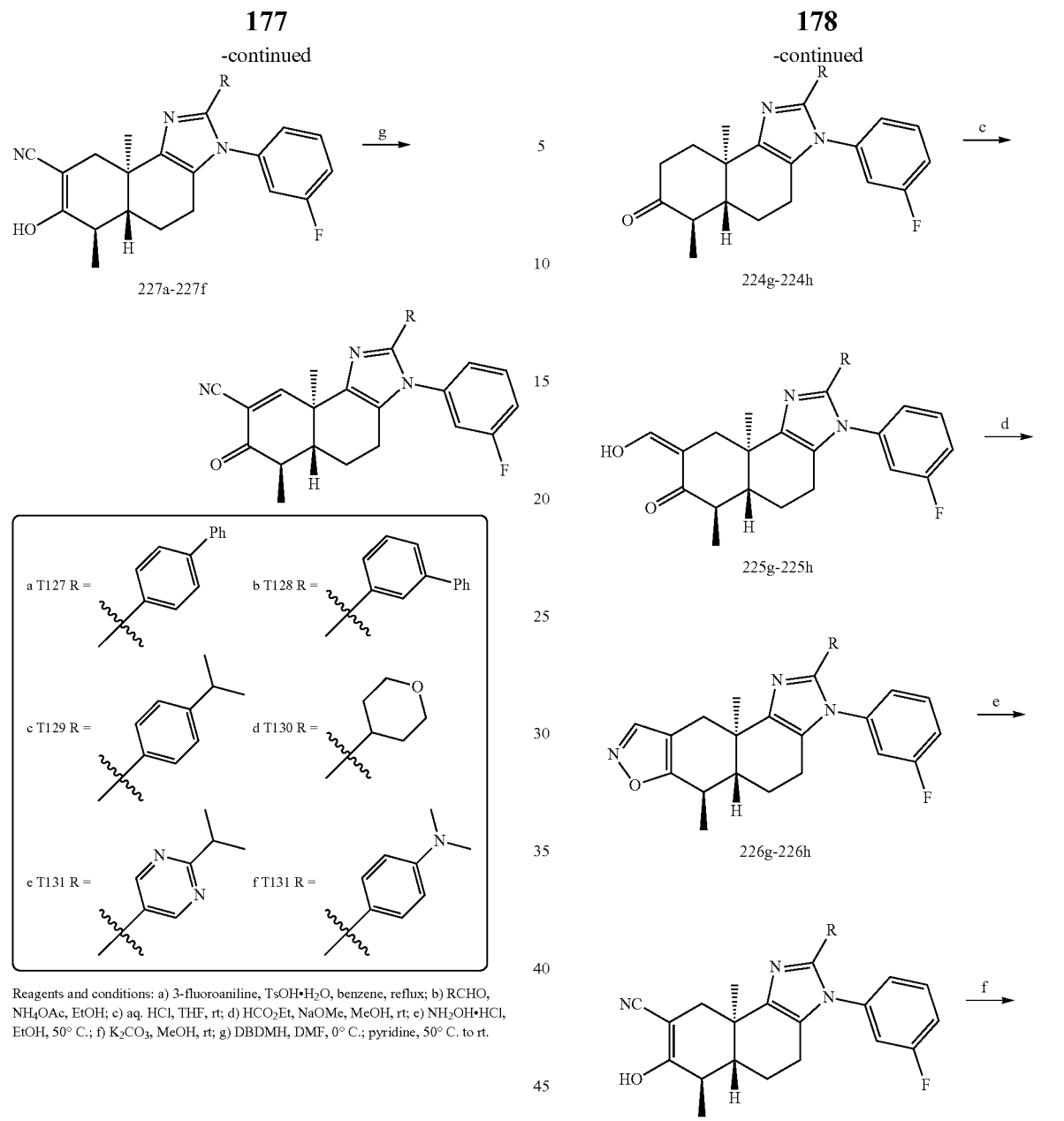
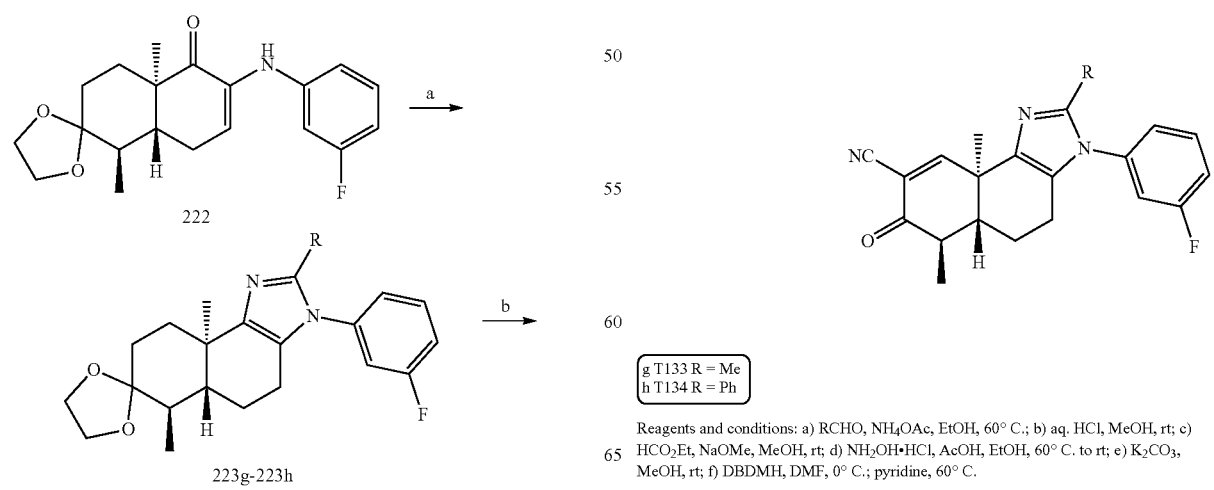
Scheme 62

Scheme 63
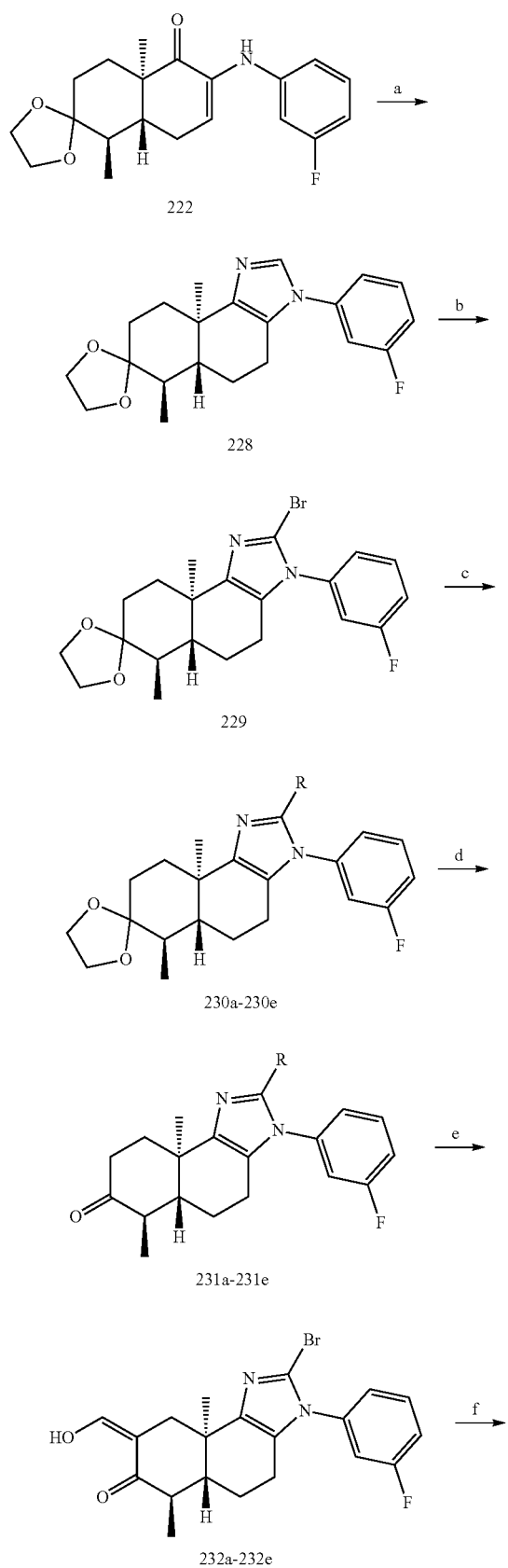
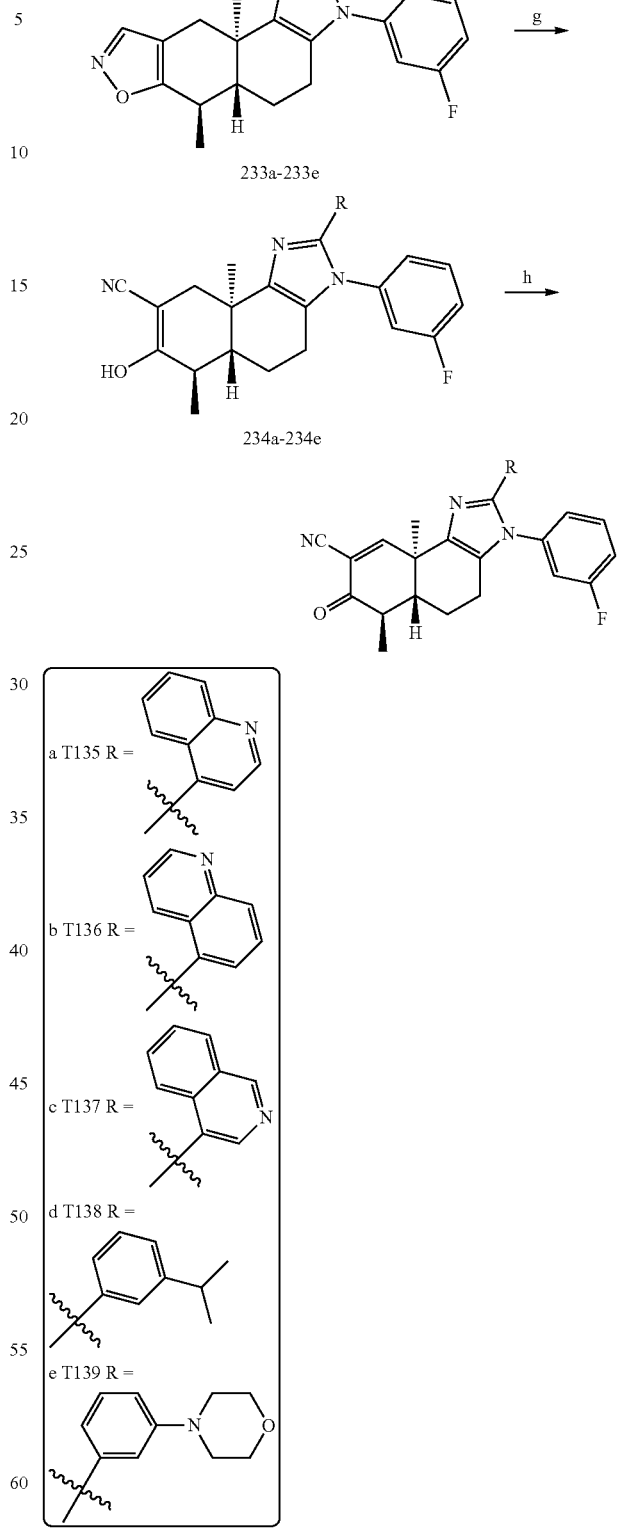
Reagents and conditions: a) 37% aq. formaldehyde, NH₄OAc, EtOH, 60° C.; b) NBS, CH₃CN, 0° C. to rt; c) arylboronic acid, K₂CO₃, Pd(PPh₃)₄, DME, H₂O, 90° C.; d) aq. HCl, THF, rt; e) HCO₂Et, NaOMe, MeOH, rt; f) NH₂OH·HCl, EtOH, 50° C.; g) K₂CO₃, MeOH, rt; h) DBDMH, DMF, 0° C.; pyridine, 50° C. to rt.

Scheme 64
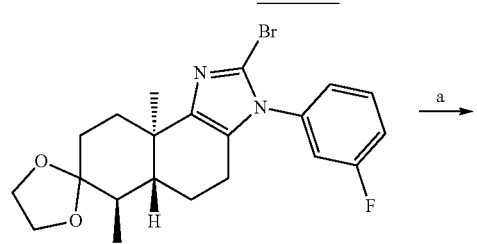
229
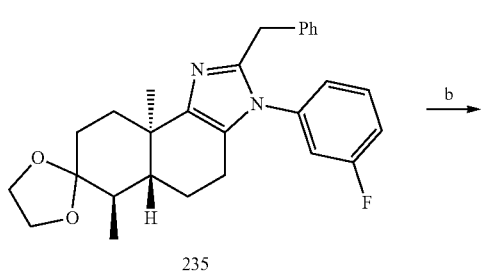
235
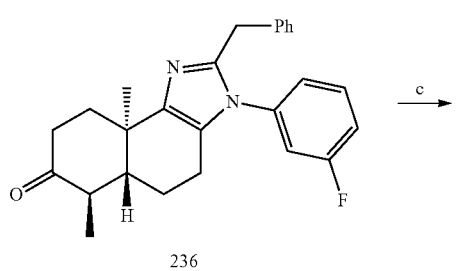
236
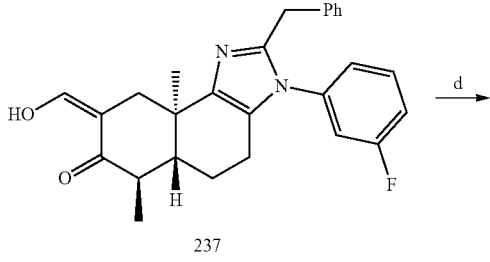
237
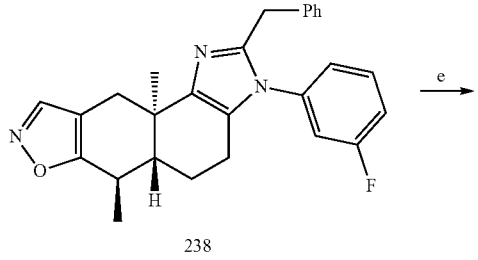
238
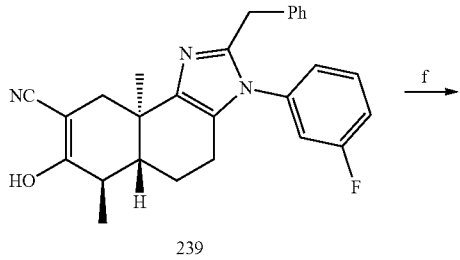
239
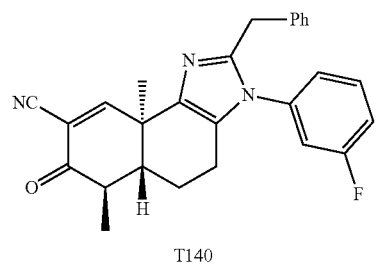
T140
Reagents and conditions: a) potassium benzyltrifluoroborate, Cs₂CO₃, Pd(dppf)Cl₂, THF, H₂O, 80° C.; b) aq. HCl, MeOH, rt; c) HCO₂Et, NaOMe, MeOH, rt; d) NH₂OH·HCl, AcOH, EtOH, 60° C. to rt; e) K₂CO₃, MeOH, rt; f) DBDMH, DMF, 0° C.; pyridine, 60° C.
Scheme 65
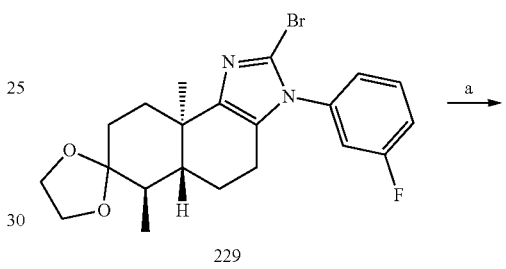
229
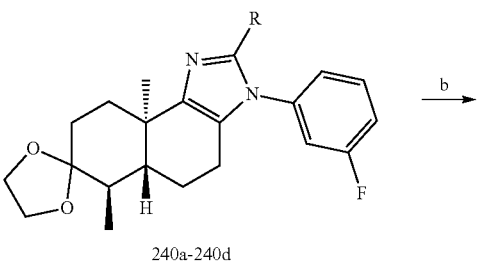
240a-240d
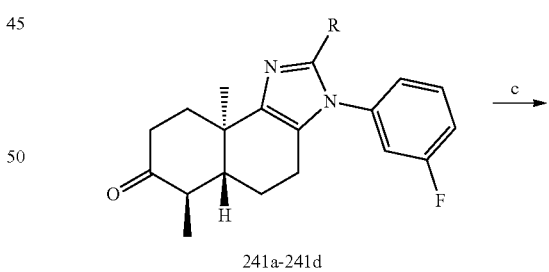
241a-241d
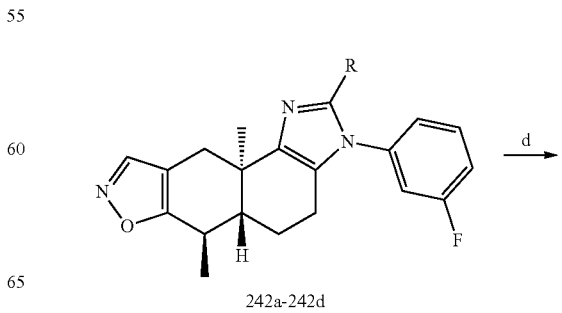
242a-242d 183
-continued

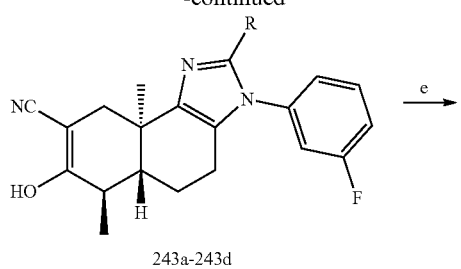

243a-243d

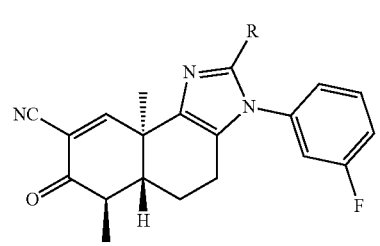

a T141 R = [4-(2-trifluoromethyl)pyridyl]   b T142 R = [5-(2-cyclopropyl)pyridyl]

c T143 R = [3-(morpholin-4-yl)phenyl]

d T144 R = [4-(2-cyclopropyl)pyridyl]

Reagents and conditions: a) arylboronic acid pinacol ester (for 240a) or arylboronic acid (for 240b-240d), K$_3$PO$_4$, Pd(PPh$_3$)$_4$, 1-4-dioxane, water, 110° C.; b) aq. HCl, THF, rt; c) i) HCO$_2$Et, NaOMe, MeOH, rt; ii) NH$_2$OH•HCl, 6 N aq. HCl, EtOH; d) K$_2$CO$_3$, MeOH; e) Method A (for T141, T142 and T144): DBDMH, DMF, 0° C.; pyridine, 60° C.; or Method B (for T143): DDQ, toluene, rt.

Scheme 66

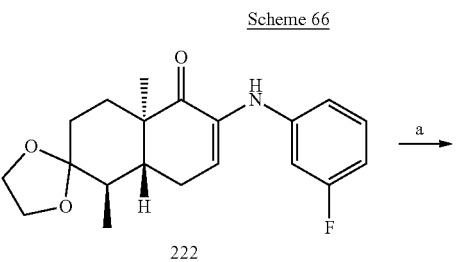

222

184
-continued

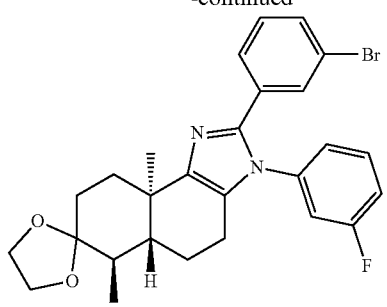

244

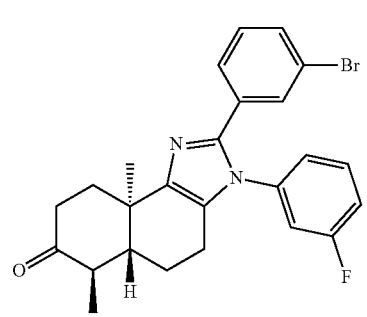

245

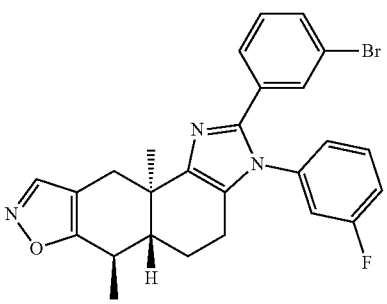

246

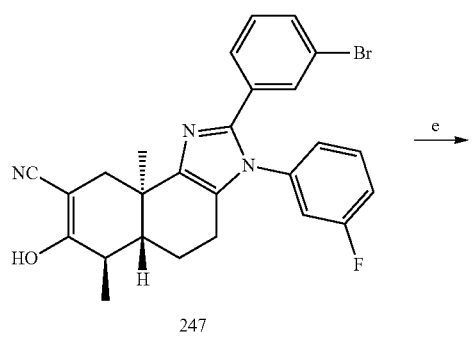

247

185
-continued
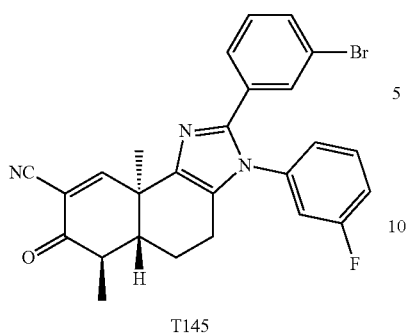
T145
Reagents and conditions: a) 3-Br-PhCHO, NH₄OAc, EtOH, rt to reflux; b) 3 N aq. HCl, THF, rt; c) HCO₂Et, NaOMe, MeOH, rt; 6 N aq. HCl, NH₂OH·HCl, EtOH, 55° C.; d) NaOMe, MeOH, 55° C.; e) DBDMH, DMF, 0° C.; pyridine, 55° C.
Scheme 67
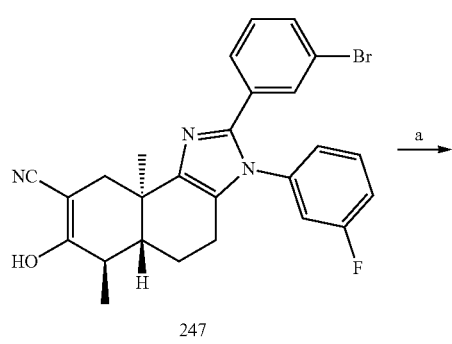
247
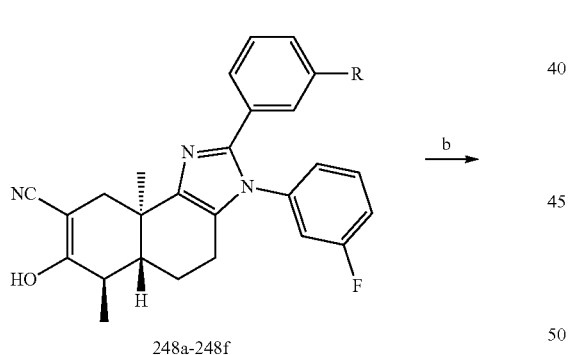
248a-248f
186
-continued
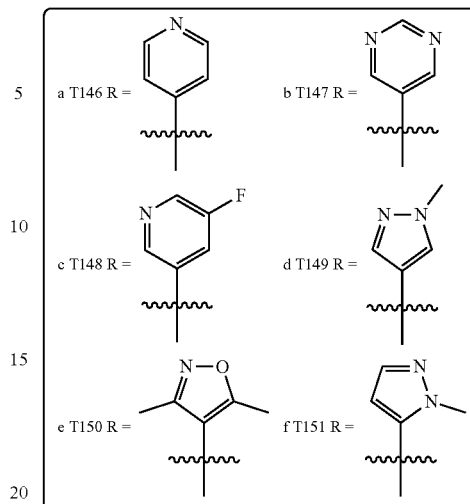
a T146 R =
b T147 R =
c T148 R =
d T149 R =
e T150 R =
f T151 R =
Reagents and conditions: a) arylboronic acid, K₃PO₄, Pd(PPh₃)₄, 1,4-dioxane, DMF, 90° C.; b) DBDMH, DMF, 0° C.; pyridine, 55° C.
Scheme 68
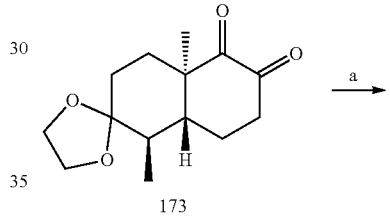
173
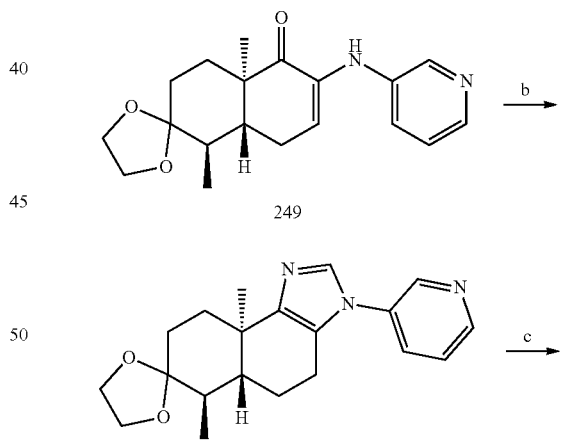
249
250
251
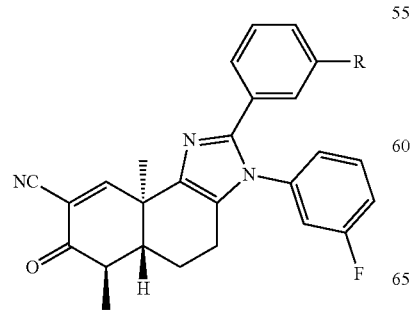

187
-continued

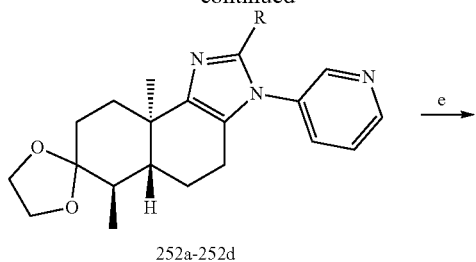
252a-252d

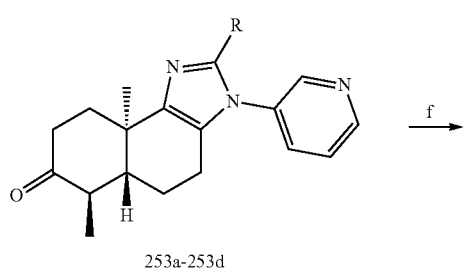
253a-253d

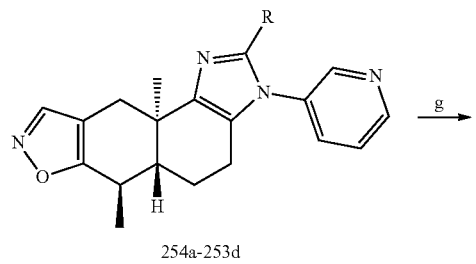
254a-253d

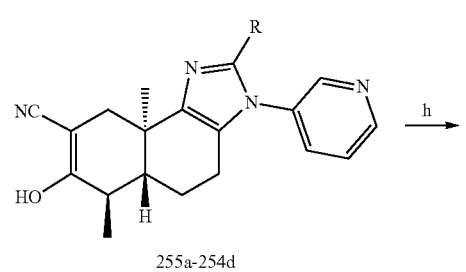
255a-254d

188
-continued

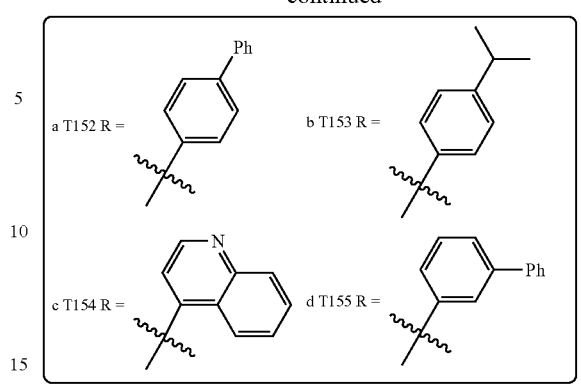

a T152 R = Ph-C6H4-
b T153 R = iPr-C6H4-
c T154 R = quinolin-4-yl
d T155 R = 3-Ph-C6H4-

Reagents and conditions: a) 3-aminopyridine, TsOH·H$_2$O, benzene, reflux; b) aq. formaldehyde, NH$_4$OAc, EtOH, 60° C.; c) NBS, MeCN, 0° C. to rt; d) arylboronic acid, K$_3$PO$_4$, Pd(PPh$_3$)$_4$, 1-4, dioxane, H$_2$O; e) 3 N aq. HCl, THF, rt; f) i) HCO$_2$Et, NaOMe, MeOH, rt; ii) NH$_2$OH·HCl, EtOH, 60° C.; g) K$_2$CO$_3$, MeOH, rt to 55° C.; h) DBDMH, DMF, 0° C.; pyridine, 60° C.

Scheme 69

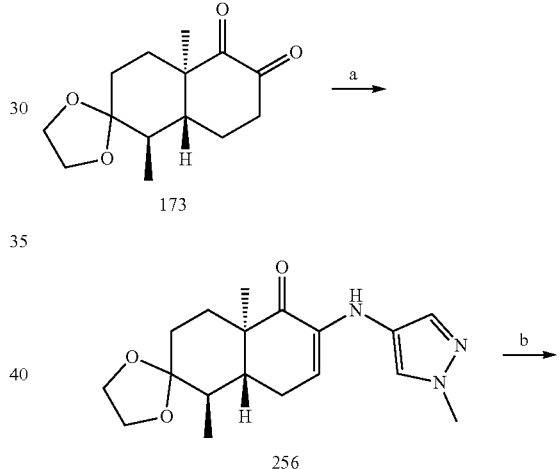

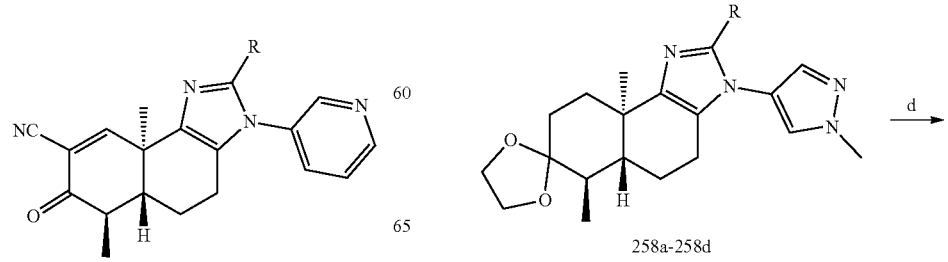

189
-continued
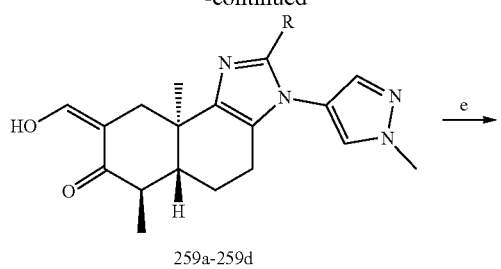
259a-259d
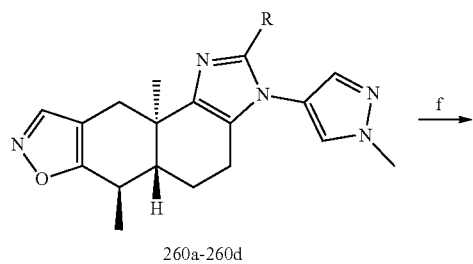
260a-260d
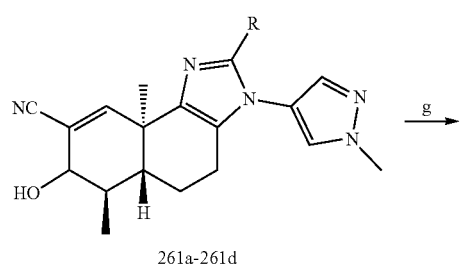
261a-261d
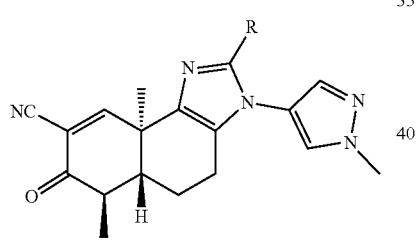
a T156 R = 4-isopropylphenyl
b T157 R = 3-chlorophenyl
c T158 R = 3,4-dichlorophenyl
d T159 R = 3-(pyridin-4-yl)phenyl
Reagents and conditions: a) 1-methyl-1H-pyrazole-4-amine, TsOH·H₂O, benzene, reflux; b) RCHO, NH₄OAc, EtOH, 60° C.; c) 3 N aq. HCl, THF, rt; d) HCO₂Et, NaOMe, MeOH, rt; e) NH₂OH·HCl, EtOH, 50° C.; f) K₂CO₃, MeOH, rt; g) DBDMH, DMF, 0° C.; pyridine, 50° C. to rt.
190
Scheme 70
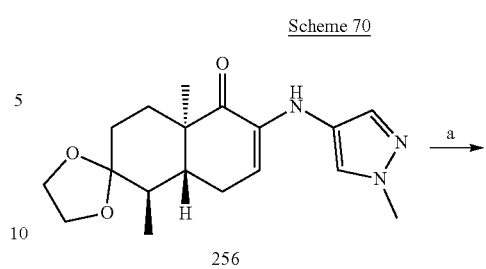
256
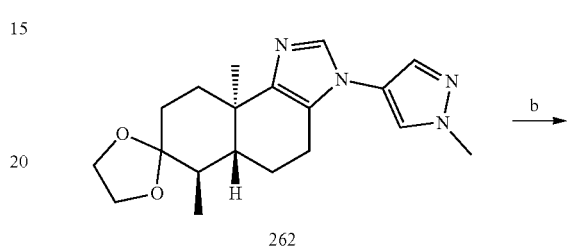
262
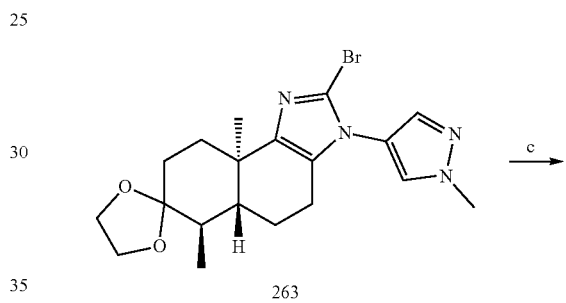
263
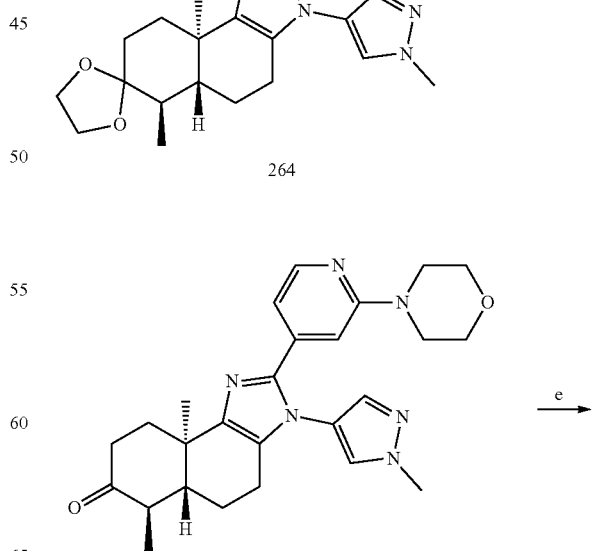
264
265

191
-continued
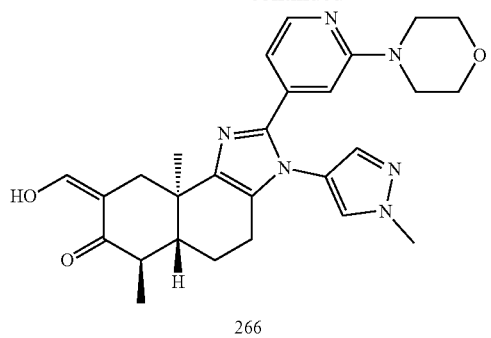
266
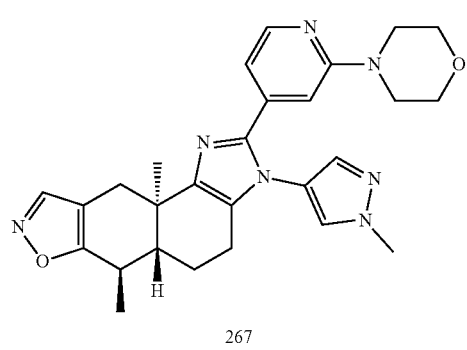
267
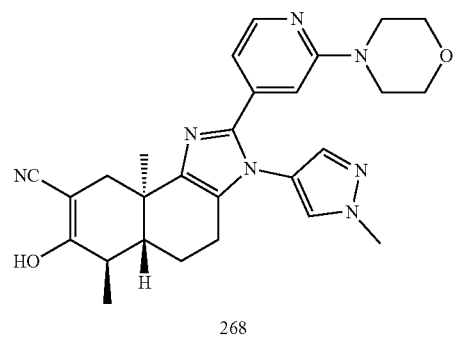
268
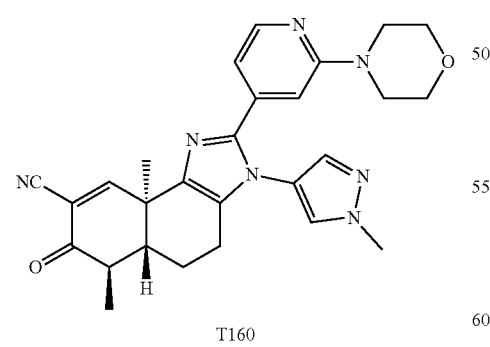
T160
Reagents and conditions: a) aq. formaldehyde, NH₄OAc, EtOH, 60° C.; b) NBS, MeCN, 0° C. to rt; c) (2-morpholinopyridin-4-yl)boronic acid, K₂CO₃, Pd(PPh₃)₄, DME, H₂O, 90° C.; d) 3 N aq. HCl, THF, rt; e) HCO₂Et, NaOMe, MeOH, rt; f) NH₂OH·HCl, EtOH, 50° C.; g) K₂CO₃, MeOH, rt; h) DBDMH, DMF, 0° C.; pyridine, 50° C. to rt.
192
Scheme 71
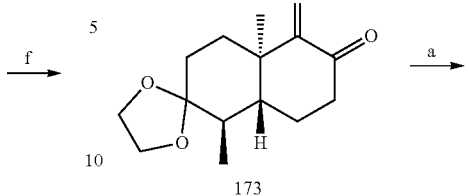
173
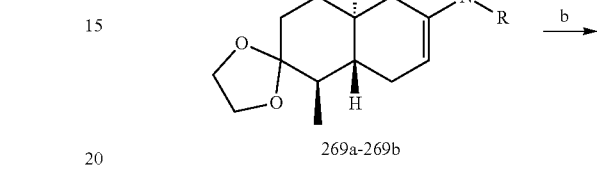
269a-269b
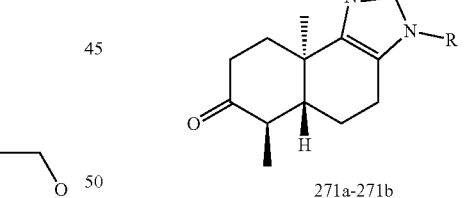
270a-270b
271a-271b
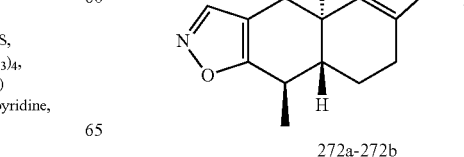
272a-272b

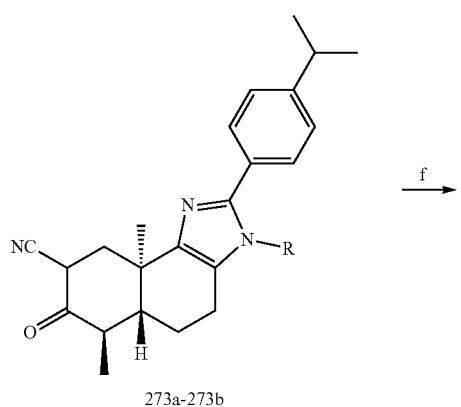
273a-273b
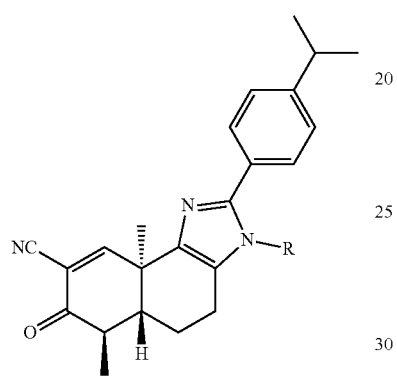
a T161 R = cyclopropyl
b T162 R = isopropyl
Reagents and conditions: a) cyclopropylamine, toluene, 45° C. (for 269a); isopropylamine, toluene, 100° C. (for 269b); b) 4-isopropylbenzaldehyde, NH₄OAc, EtOH; c) 3 N aq. HCl, THF, rt; d) i) HCO₂Et, NaOMe, MeOH, rt; ii) NH₂OH·HCl, EtOH, 60° C.; e) K₂CO₃, MeOH, rt to 50° C.; f) DBDMH, DMF, 0° C.; pyridine, 60° C.
Scheme 72
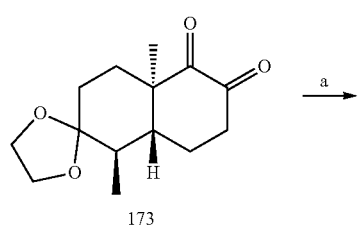
173
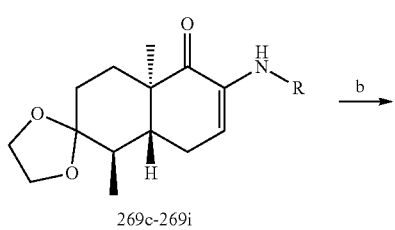
269c-269i
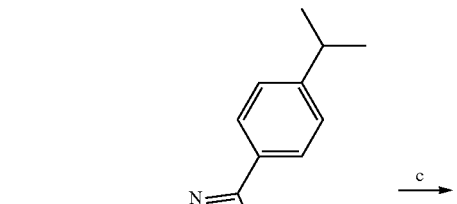
270c-270i
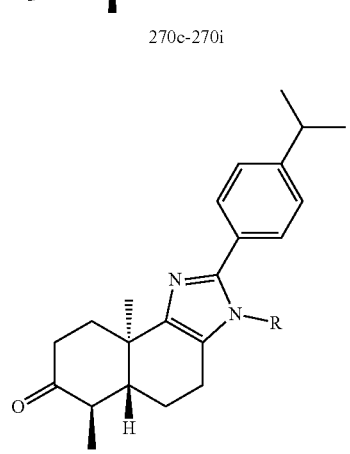
271c-271i
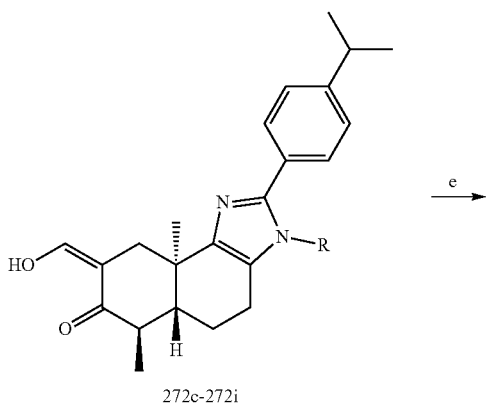
272c-272i
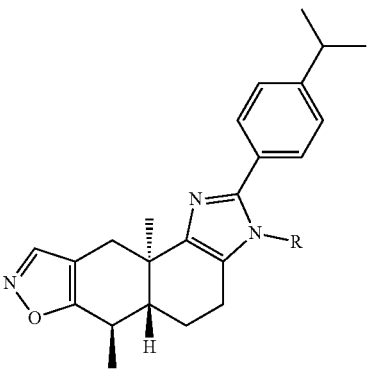
273c-273i 195
-continued
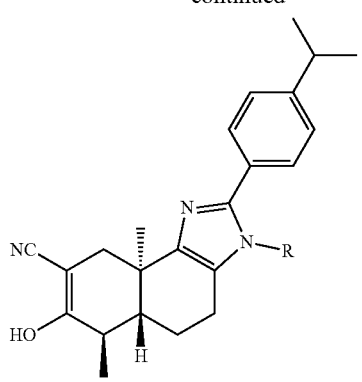
274c-274i
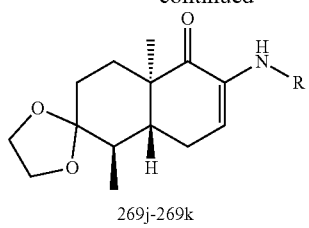
269j-269k
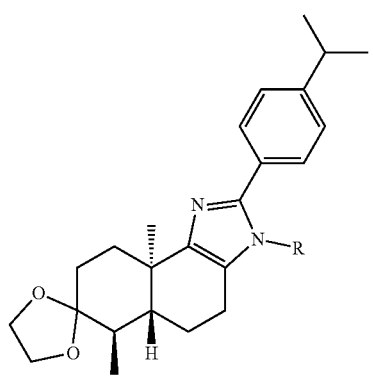
270j-270k
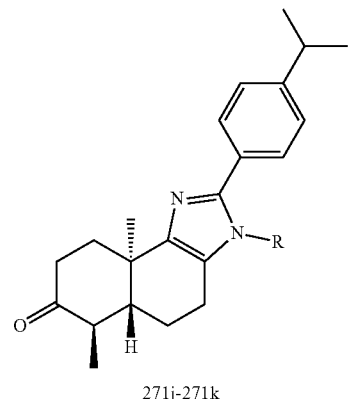
271j-271k
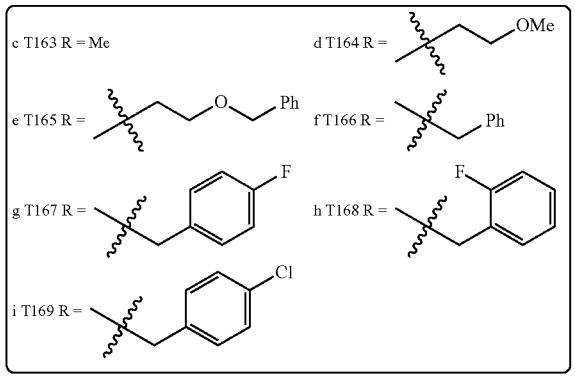
Reagents and conditions: a) RNH₂, benzene, 80° C.; b) 4-isopropylbenzaldehyde, NH₄OAc, EtOH; c) 3 N aq. HCl, MeOH, rt; d) HCO₂Et, NaOMe, MeOH, rt; e) NH₂OH·HCl, AcOH, EtOH, 60° C. to rt; f) K₂CO₃, MeOH, rt; g) DBDMH, DMF, 0° C.; pyridine, 60° C.
Scheme 73
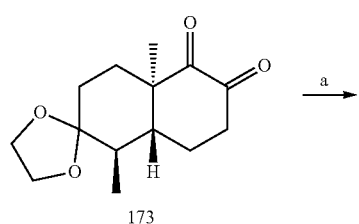
173
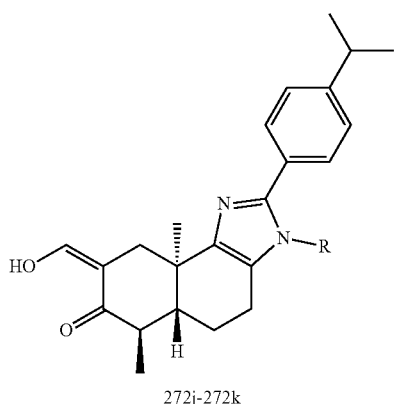
272j-272k 197　　　　　　　　　　　　　　　　　198
-continued
Scheme 74
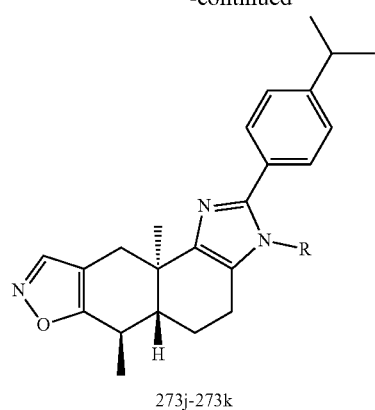
273j-273k
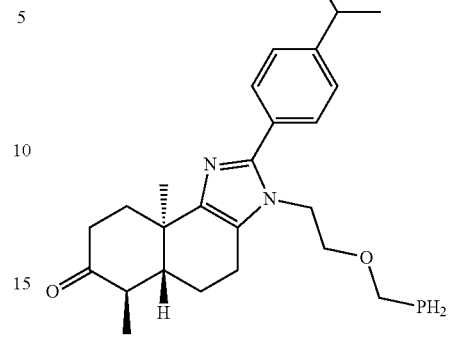
271e
f →
a →
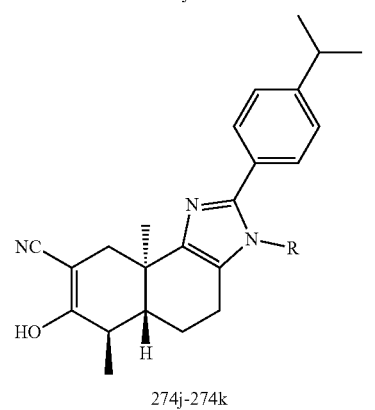
274j-274k
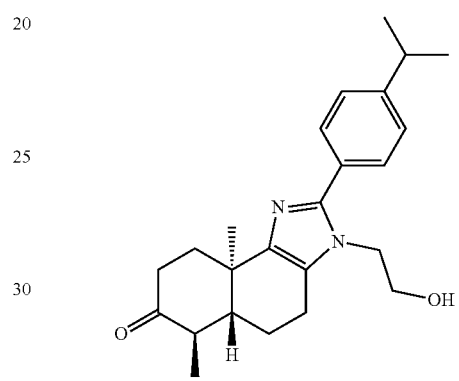
275
g →
b →
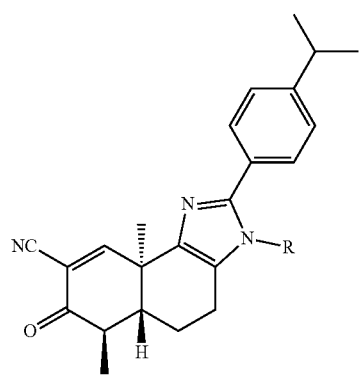
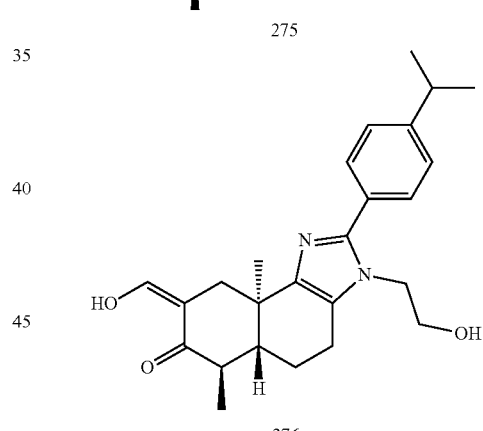
276
c →
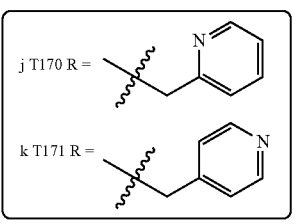
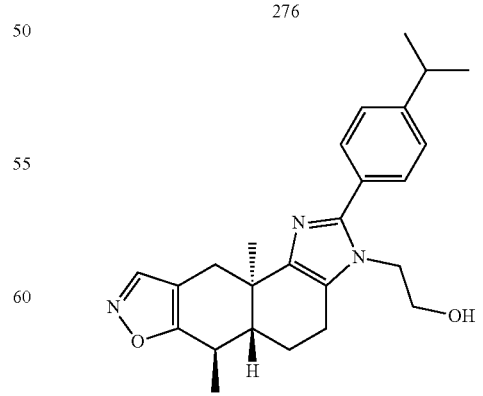
277
d →
e →
Reagents and conditions: a) RNH₂, p-TsOH·H₂O, toluene, microwave, 150° C.; b) 4-isopropylbenzaldehyde, NH₄OAc, EtOH; c) 3 N aq. HCl, THF, rt; d) HCO₂Et, NaOMe, MeOH, rt; e) NH₂OH·HCl, AcOH, EtOH, 60° C. to rt; f) K₂CO₃, MeOH, rt to 50° C.; g) DBDMH, DMF, 0° C.; pyridine, 60° C.

199
-continued
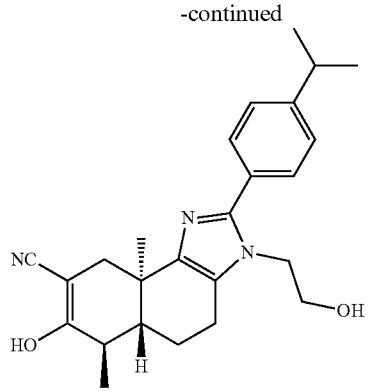
T172
Reagents and conditions: a) H₂, 10% Pd/C, EtOH, rt; b) HCO₂Et, NaOMe, MeOH, rt; c) NH₂OH•HCl, AcOH, EtOH, 60° C. to rt; d) K₂CO₃, MeOH, rt; e) DBDMH, DMF, 0° C.; pyridine, 60° C.
Scheme 75
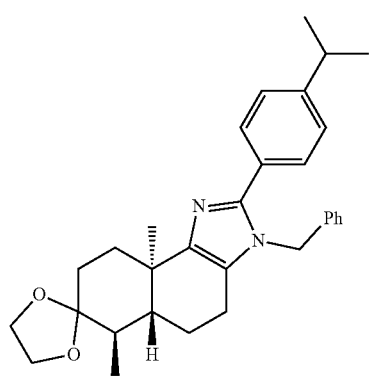
270f
200
-continued
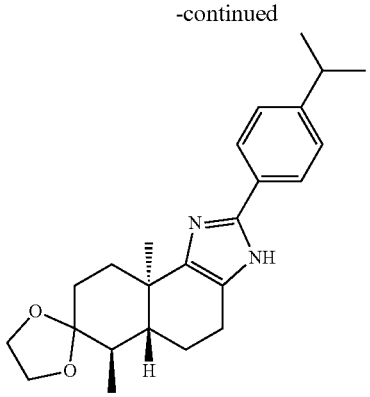
275
280
281
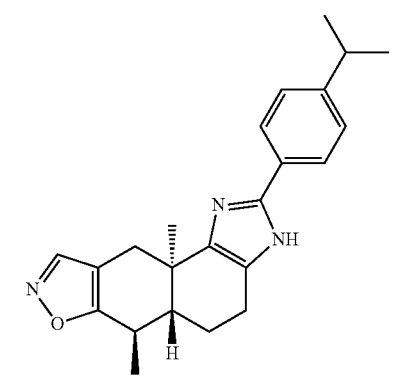
282

201
-continued
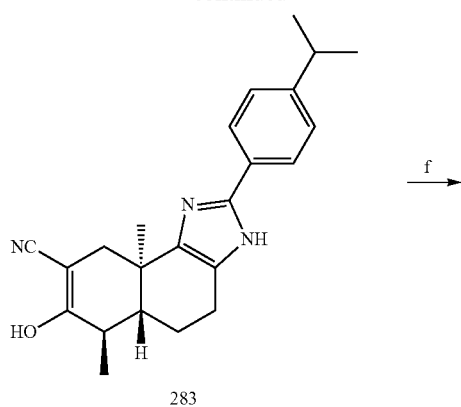
283
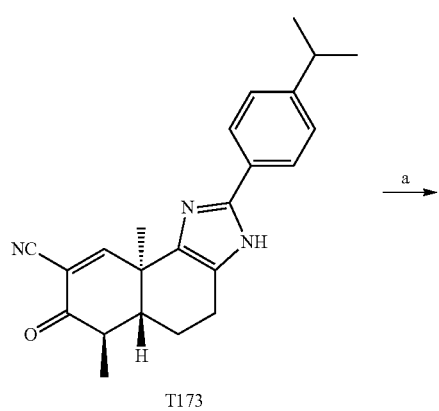
T173
Reagents and conditions: a) H₂, 10% Pd/C, EtOAc, rt; b) 3 N aq. HCl, MeOH, rt; c) HCO₂Et, NaOMe, MeOH, rt; d) NH₂OH·HCl, AcOH, EtOH, 60° C. to rt; d) K₂CO₃, MeOH, rt; e) DBDMH, DMF, 0° C.; pyridine, 60° C.
Scheme 76
202
-continued
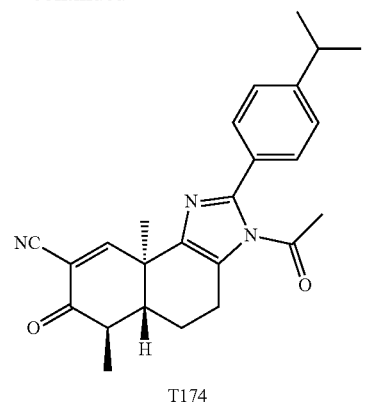
T174
Reagents and conditions: a) NaOAc, Ac₂O, 100° C.
Scheme 77
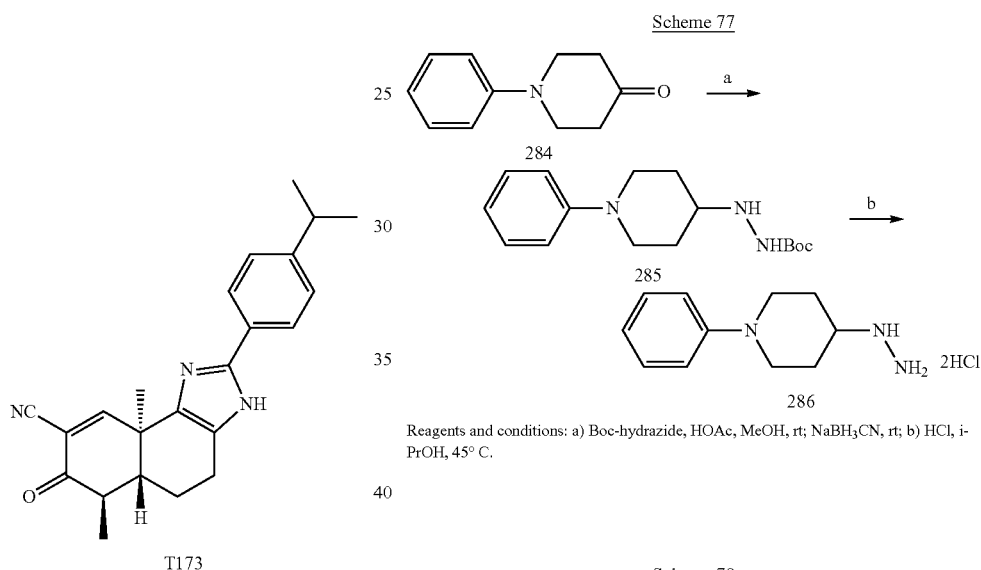
Reagents and conditions: a) Boc-hydrazide, HOAc, MeOH, rt; NaBH₃CN, rt; b) HCl, i-PrOH, 45° C.
Scheme 78
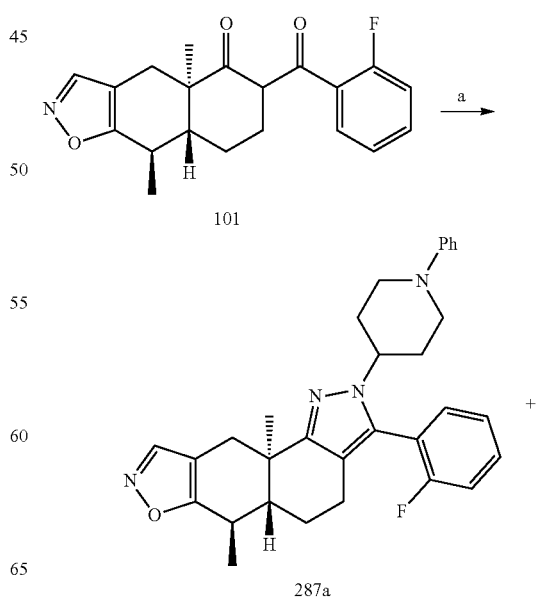

203
-continued
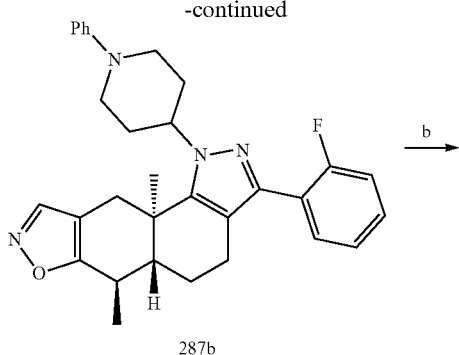
287b
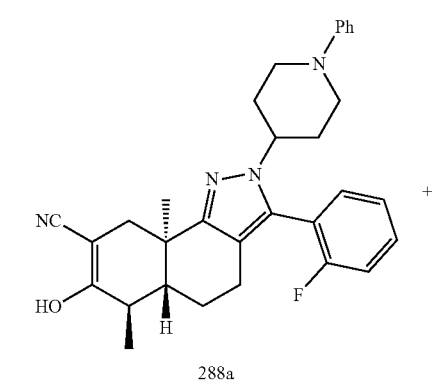
288a
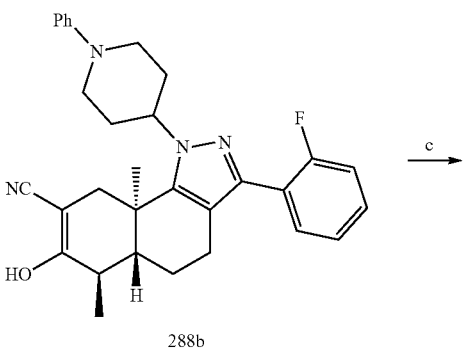
288b
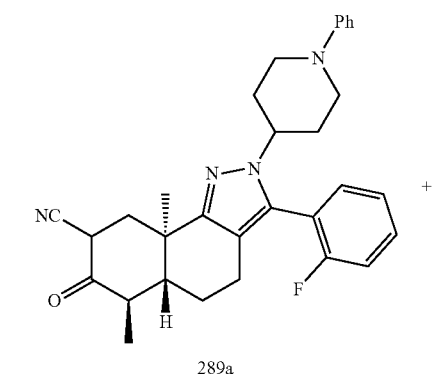
289a
204
-continued
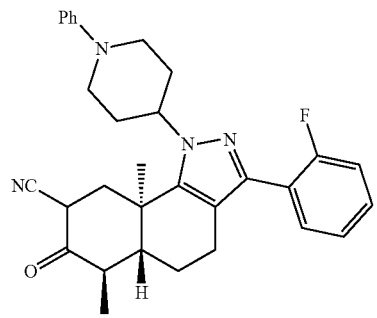
289b
Reagents and conditions: a) 286, n-BuOH, 110° C.; b) K₂CO₃, MeOH, rt to 50° C.; c) DDQ, toluene, rt.
Scheme 79
44
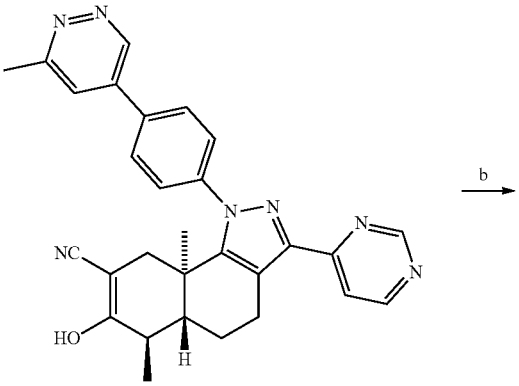
290

205
-continued
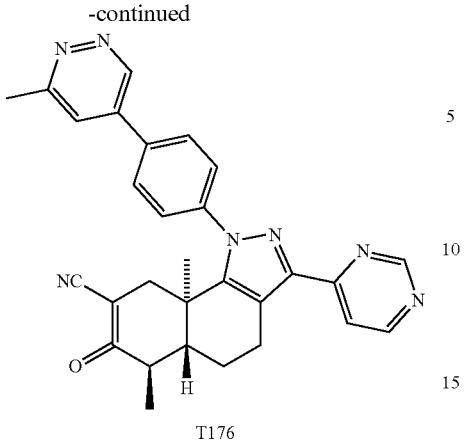
T176
Reagents and conditions: a) 3-methyl-5-(4,4,5,5-tetramethyl-1,3,2-dioxaborolan-2-yl)pyridazine, K₂CO₃, Pd(dppf)Cl₂, 1,4-dioxane, DMF, 100° C.; b) DBDMH, DMF, 0° C.; pyridine, 60° C.
206
-continued
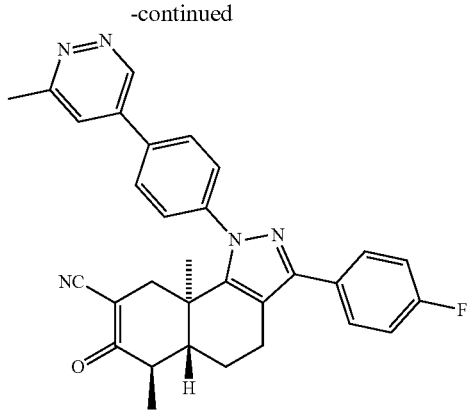
T177
Reagents and conditions: a) 3-methyl-5-(4,4,5,5-tetramethyl-1,3,2-dioxaborolan-2-yl)pyridazine, K₂CO₃, Pd(dppf)Cl₂, 1,4-dioxane, DMF, 100° C.; b) DBDMH, DMF, 0° C.; pyridine, 60° C.
Scheme 80
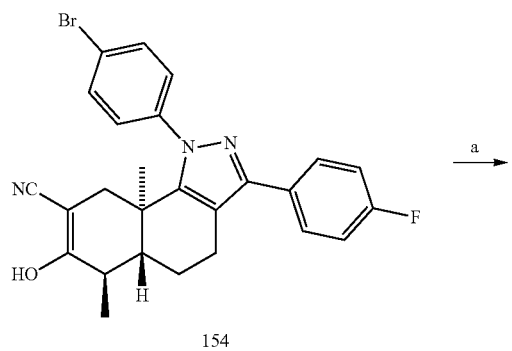
154
Scheme 81
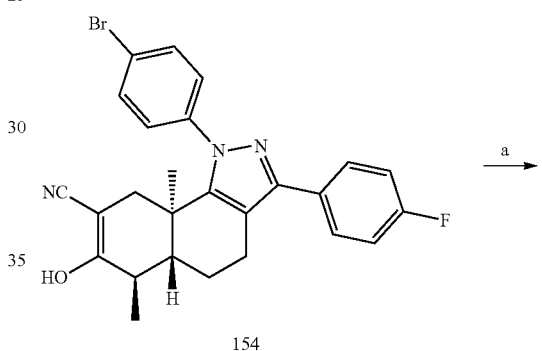
154
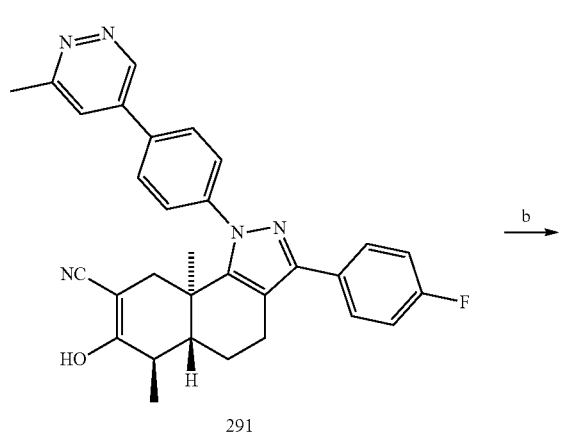
291
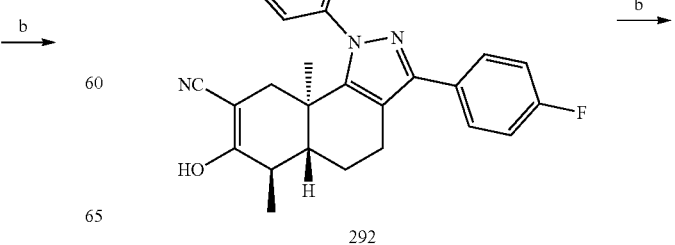
292

207
-continued

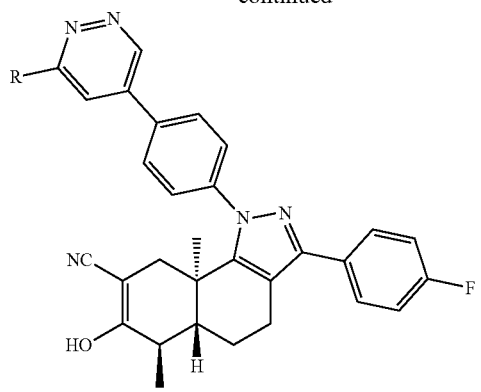

293a R = H
293b R = Me

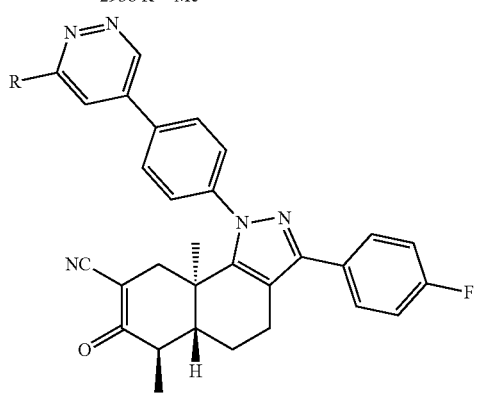

T178 R = H
T179 R = Me

Reagents and conditions: a) bis(pinacolato)diboron, KOAc, Pd(dppf)Cl₂, 1,4-dioxane, 100° C.; b) aryl halide, K₃PO₄, Pd(PPh₃)₄, 1,4-dioxane, DMF; c) DBDMH, DMF, 0° C.; pyridine, 60° C.

Scheme 82

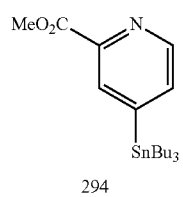
294

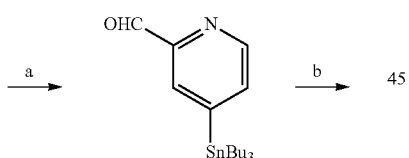
295

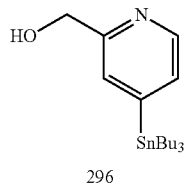
296

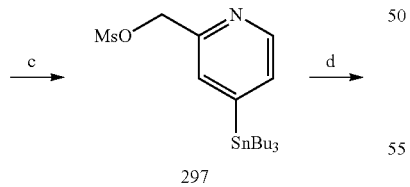
297

298

Reagents and conditions: a) DIBAL-H, toluene, CH₂Cl₂, -10° C.; b) NaBH₄, MeOH, 0° C. to rt; c) MsCl, Et₃N, CH₂Cl₂, 0° C. to rt; d) Bu₄NF, THF, CH₃CN, rt to 60° C.

208

Scheme 83

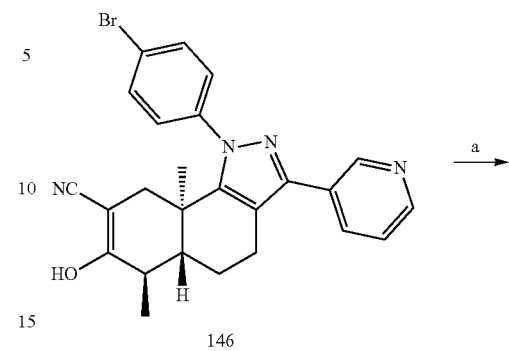

146

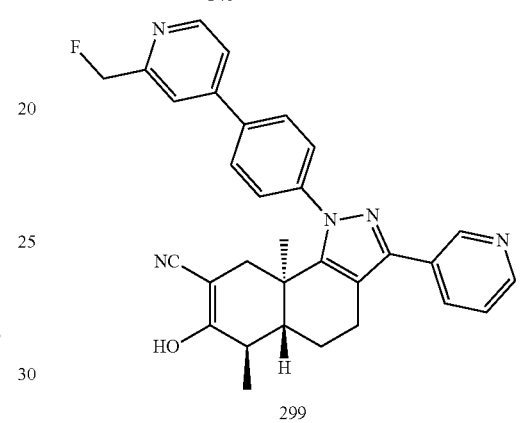

299

T180

Reagents and conditions: a) 298, Pd(PPh₃)₄, 1,4-dioxane, 120° C.; b) DBDMH, DMF, 0° C.; pyridine, 60° C.

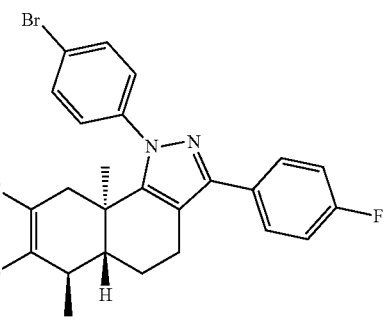

154

209
-continued
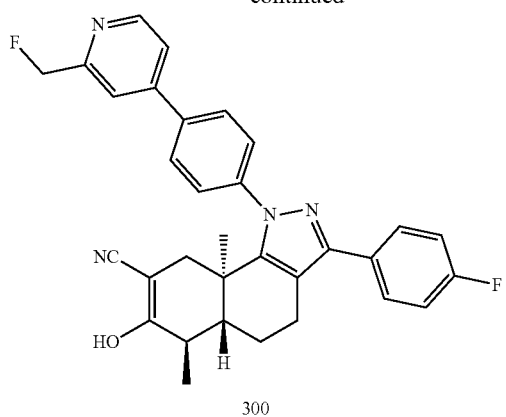
300
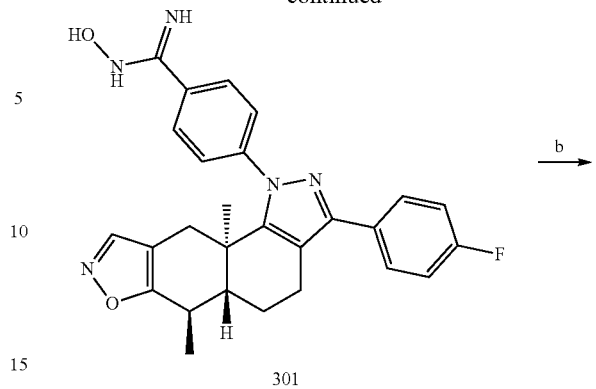
T181
Reagents and conditions: a) 298, Pd(PPh₃)₄, 1,4-dioxane, 120° C.; b) DBDMH, DMF, 0° C.; pyridine, 60° C.
Scheme 85
210
-continued
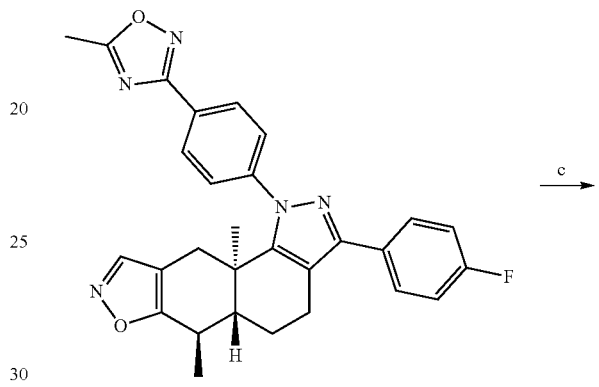
301
302
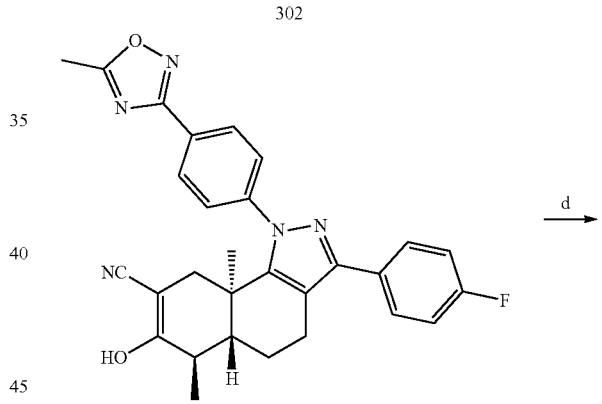
303
T182
Reagents and conditions: a) aq. NH₂OH, EtOH, 80° C.; b) dimethylacetamide dimethylacetal, 1,4-dixane, 60° C.; c) K₂CO₃, MeOH, rt; d) DBDMH, DMF, 0° C.; pyridine, 60° C.
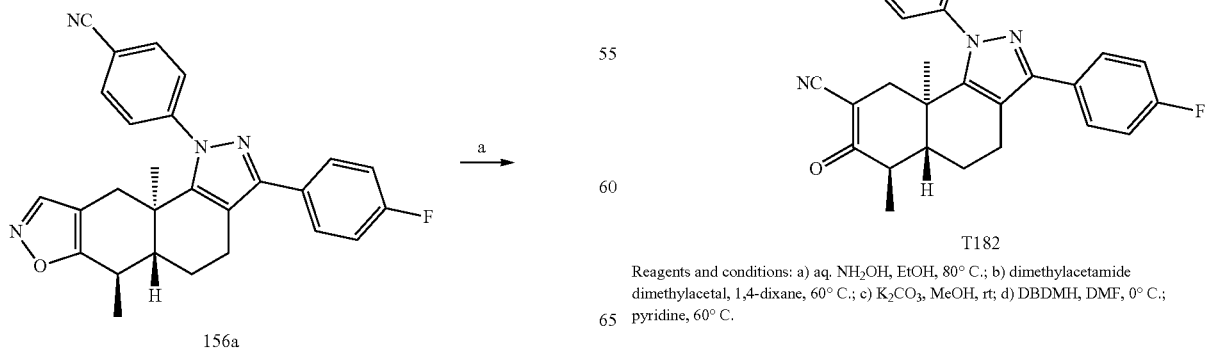
156a

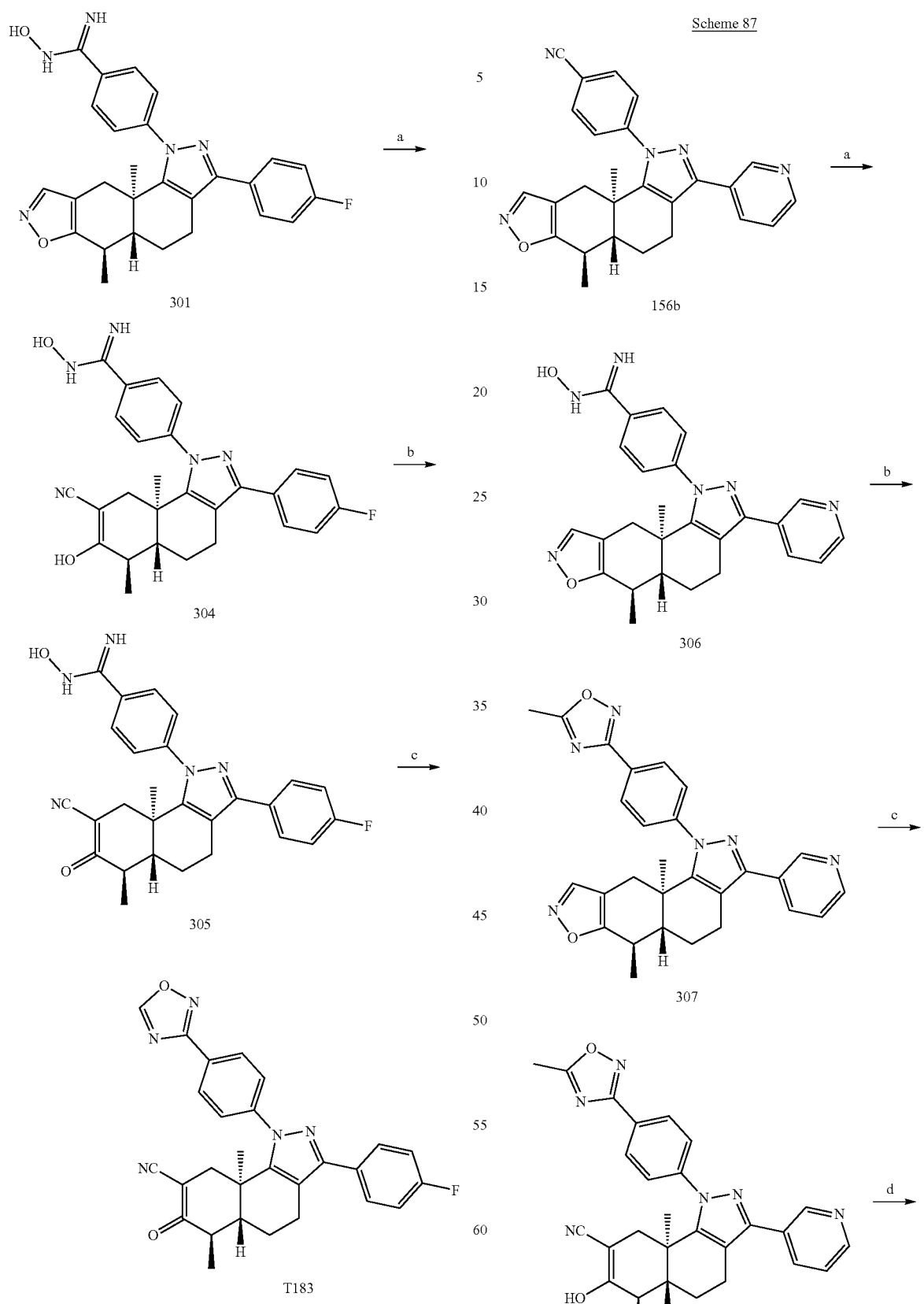
Scheme 87
Reagents and conditions: a) K$_2$CO$_3$, MeOH, rt; b) DBDMH, DMF, 0° C.; pyridine, 60° C.; c) trimethyl orthoformate, 60° C.

213
-continued
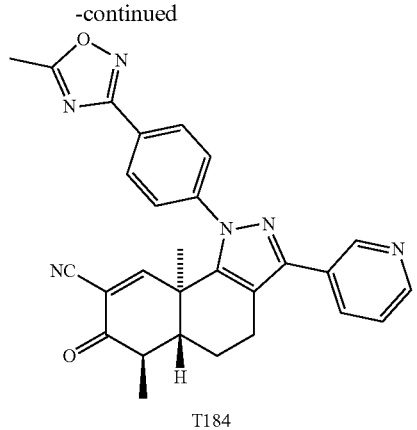
T184
Reagents and conditions: a) aq. NH₂OH, EtOH, 50° C.; b) dimethylacetamide dimethylacetal, 1,4-dioxane, 60° C.; c) K₂CO₃, MeOH, rt; d) DBDMH, DMF, 0° C.; pyridine, 60° C.
214
-continued
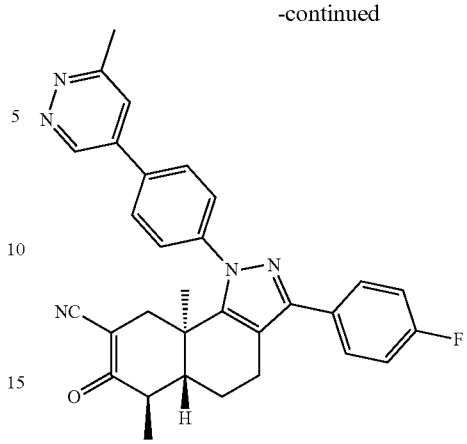
Prophetic Scheme 1
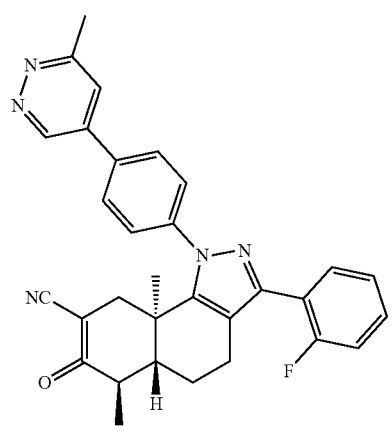
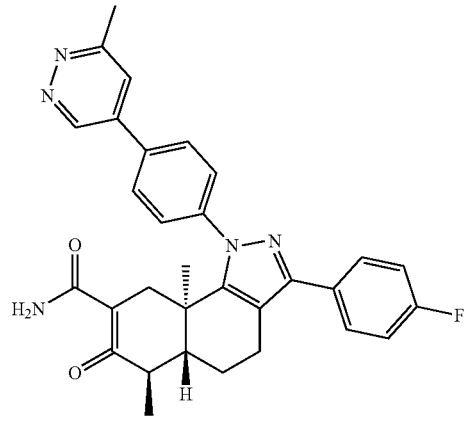
PT2
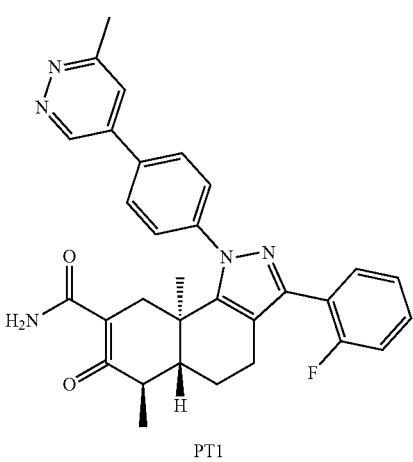
PT1

-continued
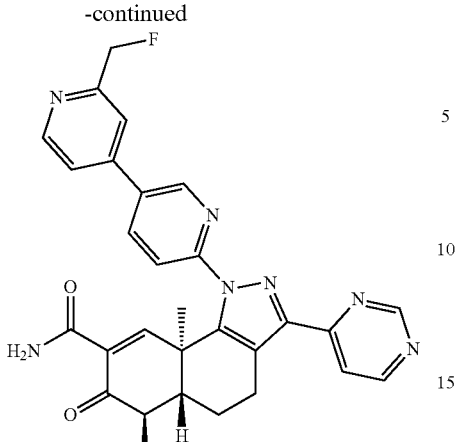
PT3
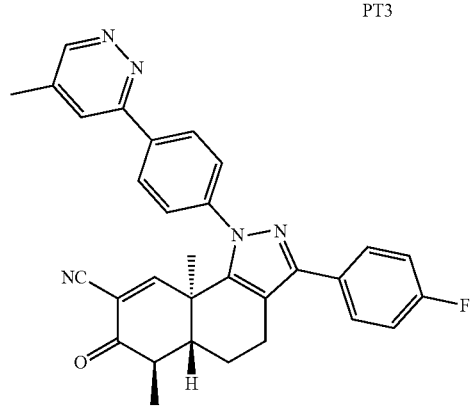
PT4
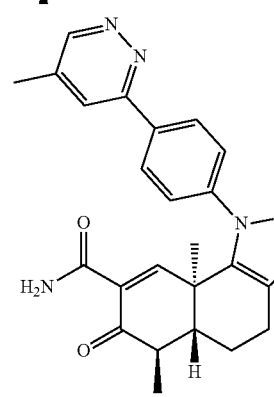
-continued
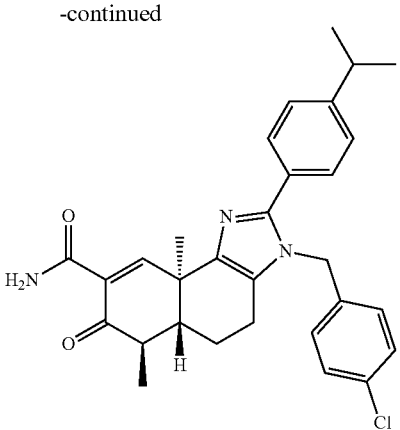
PT5
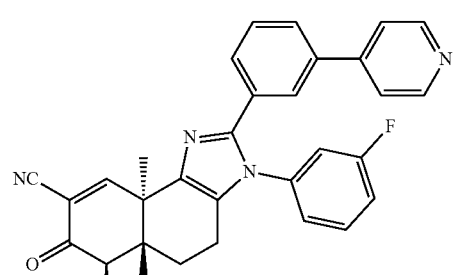
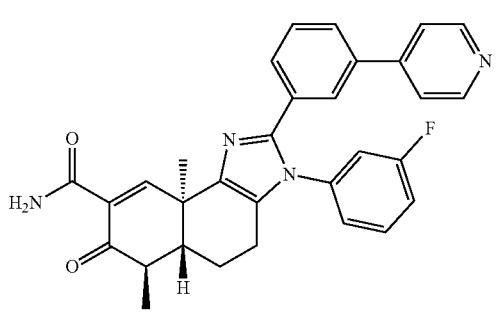
PT6
Reagents and conditions: a) hydrido(dimethylphosphinous acid-kP)[hydrogen bis(dimethylphosphinito-kP)]platinum(II), H$_2$O.
Prophetic Scheme 2
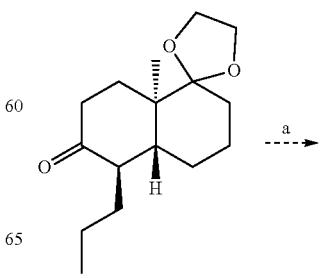

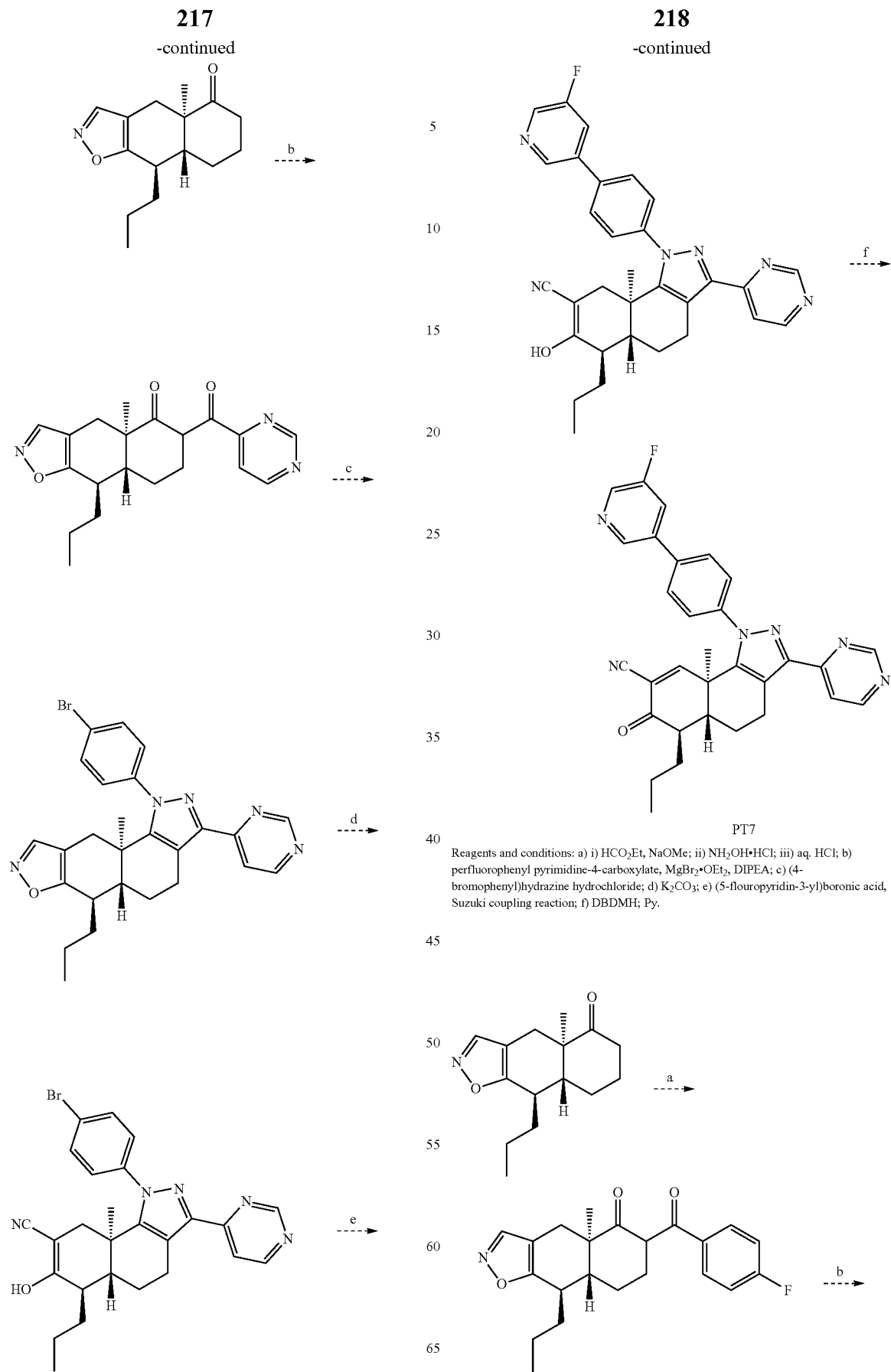
Reagents and conditions: a) i) HCO₂Et, NaOMe; ii) NH₂OH•HCl; iii) aq. HCl; b) perfluorophenyl pyrimidine-4-carboxylate, MgBr₂•OEt₂, DIPEA; c) (4-bromophenyl)hydrazine hydrochloride; d) K₂CO₃; e) (5-flouropyridin-3-yl)boronic acid, Suzuki coupling reaction; f) DBDMH; Py.

219
-continued
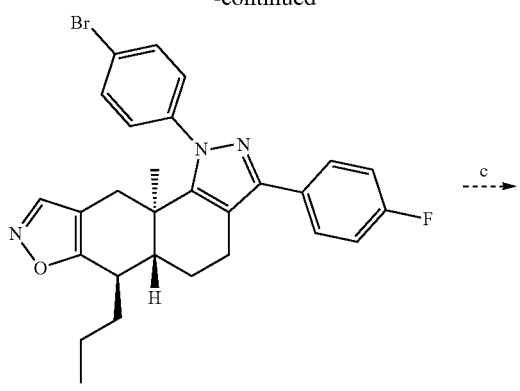
220
-continued
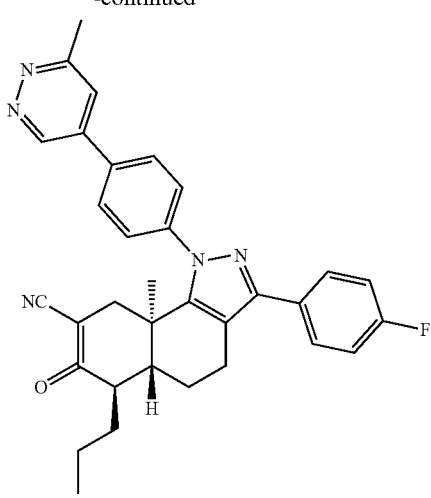
PT8
Reagents and conditions: a) perfluorophenyl 4-fluorobenzoate, MgBr$_2$•OEt$_2$, DIPEA; b) (4-bromophenyl)hydrazine hydrochloride; c) K$_2$CO$_3$; d) 6-methylpyridazin-4-ylboronic acid pinacol ester, Suzuki coupling reaction; e) DBDMH; Py.
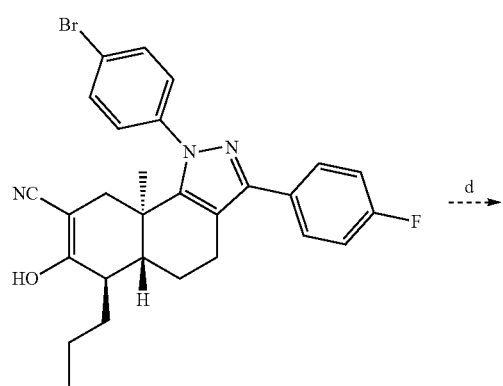
Prophetic Scheme 4
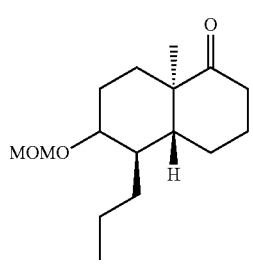
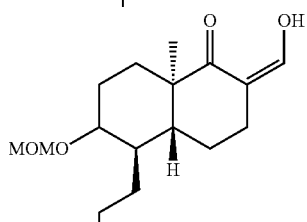
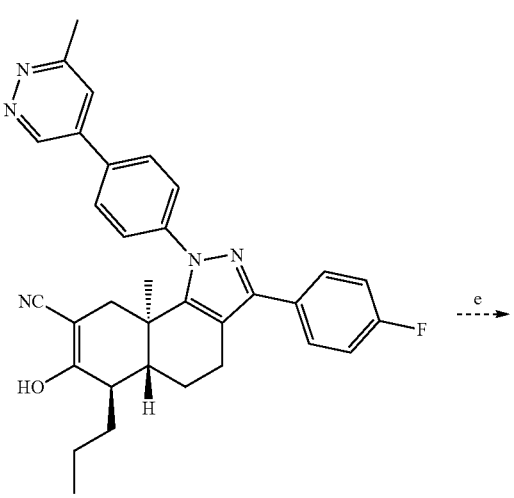
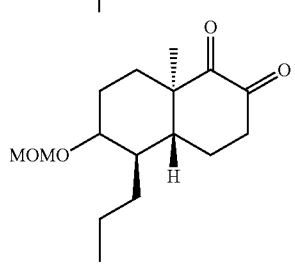

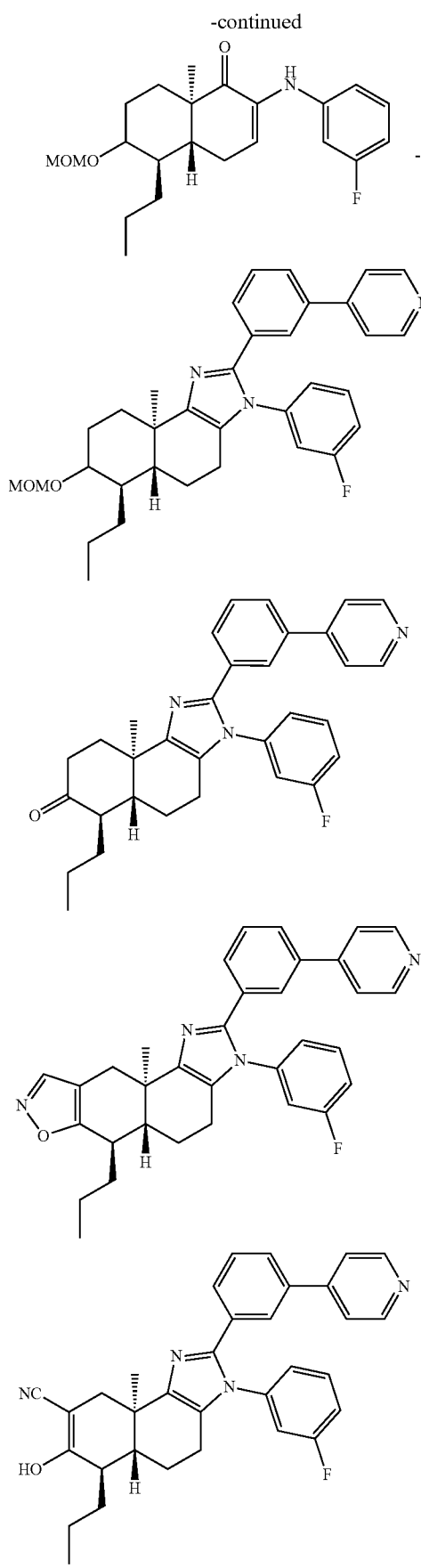

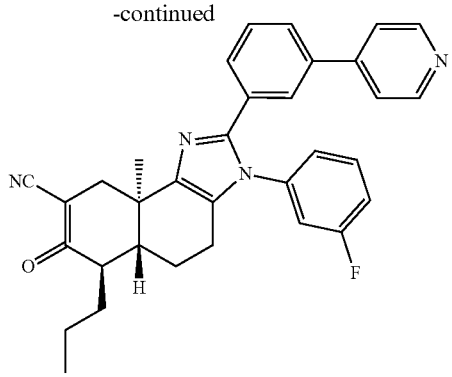

PT9

Reagents and conditions: a) MOMCl, DIPEA; b) HCO₂Et, NaOMe; c) ozone; Me₂S; d) 3-fluoroaniline; e) 3-Pyridin-4-yl-benzaldehyde, NH₄OAc; f) i) aq. HCl; ii) oxidation; g) i) HCO₂Et, NaOMe; ii) NH₂OH·HCl; h) K₂CO₃; i) DBDMH; Py.

ii. Synthetic Procedures and Characterization Data

General Information

Unless otherwise stated, commercially reagents were used as received, and all reactions were run under nitrogen atmosphere. All solvents were of HPLC or ACS grade. Nuclear magnetic resonance (NMR) spectra were recorded on a Varian Inova-400 spectrometer at operating frequencies of 400 MHz ($^1$H NMR) or 100 MHz ($^{13}$C NMR). Chemical shifts (δ) are given in ppm relative to residual solvent (usually chloroform δ 7.26 ppm for $^1$H NMR) and coupling constants (J) in Hz. Multiplicity is tabulated as s for singlet, d for doublet, t for triplet, q for quadruplet, and m for multiplet. Mass spectra were recorded on Waters Micromass ZQ or Agilent 6120 mass spectrometer.

Compound 2: To a stirring solution of compound 1 (5.0 g, 25.47 mmol) in ethyl formate (62 mL, 0.76 mol) was added sodium methoxide (25 wt. % solution in MeOH, 43.7 mL, 190.97 mmol) at 0¹° C. The reaction mixture was stirred at room temperature for 1 h and cooled to 0 TC. Aq. HCl (6 N, 31.84 mL, 191.04 mmol) was added to adjust the pH<7. The mixture was stirred at 0° C. for 20 min, and then extracted with EtOAc. The organic extract was dried over Na₂SO₄, filtered and concentrated. The residue was dissolved in EtOH (250 mL) and water (25 mL), and cooled to 0° C. Hydroxylamine hydrochloride (2.6 g, 37.42 mmol) was added. The mixture was heated 55° C. for 2 h, and then cooled to room temperature. After concentration, the residue was extracted with EtOAc. The organic extract was dried over Na₂SO₄, filtered and concentrated. The residue was purified by column chromatography (silica gel, eluting with 0% to 50% EtOAc in hexanes) to give compound 2 (4.0 mg, 71% yield) as a white solid. m/z=222 (M+1).

Compound 3: A solution of compound 2 (4.0 g, 18.08 mmol) in acetone (90 mL) was cooled to 0° C. and treated with Jones' reagent dropwise until the orange color persisted. The mixture was stirred at 0° C. for 30 min, and then i-PrOH was added until the reaction mixture turned green. The mixture was concentrated. The residue was diluted with EtOAc, and the mixture was washed with water. The organic extract was dried over Na₂SO₄, filtered and concentrated to give compound 3 (3.78 g, 95% yield) as a white solid. m/z=220 (M+1).

Compound 4: Compound 3 (246 mg, 1.12 mmol) was dissolved in CH₂Cl₂ (12 mL). Magnesium bromide ethyl etherate (738 mg, 2.86 mmol) and N,N-diisopropylethylamine (0.597 mL, 3.42 mmol) were added sequentially at room temperature. The mixture was stirred at room temperature for 5 min, and benzoyl chloride (0.173 mL, 1.49 mmol) was added. The mixture was stirred at room temperature for 2 h, and sat. aq. NaH$_2$PO$_4$ (5 mL) was added. The mixture was extracted with EtOAc. The organic extract was washed with water; dried over Na$_2$SO$_4$; filtered; and concentrated to give crude compound 4 (400 mg, quantitative yield) as a solid, which was used in the next step without further purification. m/z=324 (M+1).

Compound 5 and compound 6: Reaction A: Compound 4 (100 mg, 0.31 mmol) and cyclohexylhydrazine hydrochloride (100 mg, 0.66 mmol) in EtOH (1 mL) was heated in Biotage microwave at 110° C. for 5 h. Reaction B: Compound 4 (16 mg, 0.049 mmol) and cyclohexylhydrazine hydrochloride (15 mg, 0.10 mmol) in EtOH (0.5 mL) was heated in Biotage microwave at 110° C. for 5 h. The reaction mixture from reaction A and B were combined and concentrated. The residue was dissolved in EtOAc, and washed with 1 N aq. HCl, and sat. aq. NaHCO$_3$. The organic extract was dried over Na$_2$SO$_4$, filtered and concentrated. The residue was purified by column chromatography (silica gel, eluting with 0% to 15% EtOAc in hexanes) to give compound 5 (50 mg, 35% yield) and compound 6 (15 mg, 10% yield) as white solid. Compound 5: m/z=402 (M+1); Compound 6: m/z=402 (M+1).

Compound 7: Compound 5 (48 mg, 0.12 mmol) was dissolved in MeOH (1.2 mL). Sodium methoxide (25 wt. % in methanol, 42 µL, 0.18 mmol) was added. The reaction mixture was stirred at 55° C. for 1 h and cooled to room temperature. EtOAc was added, followed by 10% aq. NaH$_2$PO$_4$ to adjust pH<7. The organic extract was dried with Na$_2$SO$_4$, filtered and concentrated. The residue was purified by column chromatography (silica gel, eluting with 0% to 15% acetone in hexanes) to give compound 7 (38 mg, 79% yield) as a white solid. m/z=402 (M+1).

T1: Compound 7 (38 mg, 0.095 mmol) was dissolved in toluene (1 mL). DDQ (24 mg, 0.11 mmol) was added. The mixture was heated at 85° C. for 2 h and cooled to room temperature. The mixture was diluted with CH$_2$CL and sat. aq. NaHCO$_3$ and stirred for 5 min. The organic phase was separated, and the aqueous phase was extracted three times with CH$_2$Cl$_2$. The combined organic extracts were dried with Na$_2$SO$_4$, filtered and concentrated. The residue was purified by column chromatography (silica gel, eluting with 0% to 20% EtOAc in hexanes) to give partially purified product, which was purified again by column chromatography (silica gel, eluting with 0% to 15% acetone in hexanes) to give compound T1 (15 mg, 31% yield) as a yellow solid. m/z=400 (M+1); $^1$H NMR (400 MHz, CDCl$_3$) δ 8.57 (s, 1H), 7.45 (m, 3H), 7.27 (m, 2H), 3.98 (tt, J=3.9, 11.5 Hz, 1H), 2.55 (m, 3H), 2.13 (dt, J=2.3, 12.8 Hz, 1H), 1.84 (m, 9H), 1.46 (s, 3H), 1.29 (d, J=6.8 Hz, 3H), 1.26 (m, 3H).

Compound 8: Compound 8 (white solid, 10 mg, 67% yield) was synthesized from compound 6 (15 mg, 0.037 mmol) using the same procedure as described for the synthesis of compound 7. m/z=402 (M+1).

T2: Compound 8 (10 mg, 0.025 mmol) was dissolved in anhydrous DMF (0.25 mL), and the solution was cooled to 0° C. 1,3-dibromo-5,5-dimethylhydantoin (3.6 mg, 0.013 mmol) in DMF (0.1 mL) was added. The reaction was stirred at 0° C. for 1 h. Pyridine (10 µL, 0.12 mmol) was added. The reaction was heated at 55° C. for 2 h and cooled to room temperature. EtOAc was added. The mixture was washed with 1 N aq. HCl, and water. The organic extract was dried with Na$_2$SO$_4$, filtered and concentrated. The residue was purified by column chromatography (silica gel, eluting with 0% to 20% EtOAc in hexanes) to give partially purified product, which was purified again by column chromatography (silica gel, eluting with 0% to 15% acetone in hexanes) to give compound T2 (5 mg, 50% yield) as a white solid. m/z=400 (M+1); $^1$H NMR (400 MHz, CDCl$_3$) S 8.13 (s, 1H), 7.67 (m, 2H), 7.39 (m, 2H), 7.30 (m, 1H), 4.00 (tt, J=3.8, 11.4 Hz, 1H), 2.81 (ddd, J=2.0, 6.0, 16.0 Hz, 1H), 2.74 (m, 1H), 2.65 (qd, J=6.8, 13.6 Hz, 1H), 2.24 (m, 3H), 2.00 (m, 5H), 1.79 (m, 1H), 1.62 (m, 1H), 1.54 (s, 3H), 1.45 (m, 3H), 1.36 (d, J=6.8 Hz, 3H).

Compound 9: A mixture of compound 4 (100 mg, 0.25 mmol), (2,2,2-trifluoroethyl)hydrazine (70 wt. % in H$_2$O, 62 µL, 0.49 mmol) and 12 N aq. HCl (40 µL, 0.048 mmol) in EtOH (2.5 mL) was heated in Biotage microwave at 120° C. for 3 h, and cooled to room temperature. The mixture was concentrated. The residue was dissolved in EtOAc and washed with water. The organic extract was dried over Na$_2$SO$_4$, filtered and concentrated. The residue was purified by column chromatography (silica gel, eluting with 0% to 20% acetone in hexanes) to give partially purified product, which was purified again by column chromatography (silica gel, eluting with 0% to 10% EtOAc in CH$_2$Cl$_2$) to give compound 9 (48 mg, 48% yield) as a white solid. m/z=402 (M+1).

Compound 10: Compound 10 (white solid) was synthesized from compound 9 (45 mg, 0.11 mmol) using the same procedure as described for the synthesis of compound 7. m/z=402 (M+1).

T3: Compound T3 (light yellow solid, 6 mg, 13% yield from compound 9) was synthesized from compound 10 (all from the last step, ≤0.11 mmol) using the same procedure as described for the synthesis of compound T1. m/z=400 (M+1); $^1$H NMR (400 MHz, CDCl$_3$) S 8.17 (s, 1H), 7.67 (m, 2H), 7.42 (m, 2H), 7.36 (m, 1H), 4.84 (dq, J=2.2, 7.7 Hz, 2H), 2.84 (ddd, J=1.9, 6.0, 16.0 Hz, 1H), 2.77 (m, 1H), 2.64 (td, J=6.7, 13.5 Hz, 1H), 2.31 (dt, J=2.0, 12.6 Hz, 1H), 2.10 (m, 1H), 1.67 (m, 1H), 1.54 (s, 3H), 1.37 (d, J=6.8 Hz, 3H).

Compound 11 and compound 12: Reaction A: Compound 4 (108 mg, 0.33 mmol) and benzylhydrazine dihydrochloride (130 mg, 0.67 mmol) in EtOH (2.7 mL) was heated in Biotage microwave at 110° C. for 4 h. Reaction B: Compound 4 (80 mg, 0.25 mmol) and benzylhydrazine dihydrochloride (97 mg, 0.50 mmol) in EtOH (2 mL) was heated in Biotage microwave at 110° C. for 4 h. The reaction mixture from reaction A and B were combined, and concentrated. The residue was dissolved in EtOAc, and washed with 1 N aq. HCL and sat. aq. NaHCO$_3$. The organic extract was dried over Na$_2$SO$_4$, filtered and concentrated. The residue was purified by column chromatography (silica gel, eluting with 0% to 40% EtOAc in hexanes) to give compound 11 (68 mg, 29% yield) and compound 12 (65 mg, 27% yield) as white solid. Compound 11: m/z=410 (M+1); Compound 12: m/z=410 (M+1).

Compound 13: Compound 11 (68 mg, 0.17 mmol) was dissolved in MeOH (2 mL). Sodium methoxide (25 wt. % in methanol, 57 µL, 0.25 mmol) was added. The reaction mixture was stirred at 55° C. for 2 h and cooled to room temperature. The mixture was concentrated. The residue was partitioned between EtOAc and 10% aq. NaH$_2$PO$_4$. The organic extract was dried with Na$_2$SO$_4$, filtered and concentrated. The residue was purified by column chromatography (silica gel, eluting with 0% to 50% EtOAc in hexanes) to give compound 13 (65 mg, 96% yield) as a yellow solid. m/z=410 (M+1).

T4: Compound 13 (68 mg, 0.17 mmol) was dissolved in anhydrous DMF (2 mL), and the solution was cooled to 0° C. 1,3-dibromo-5,5-dimethylhydantoin (24 mg, 0.084 mmol) in DMF (1 mL) was added. The reaction was stirred at 0° C. for 1 h. Pyridine (60 µL, 0.74 mmol) was added. The reaction was heated at 55° C. for 2 h and at 40° C. overnight. The mixture was cooled to room temperature; diluted with EtOAc; and washed with water. The organic extract was dried with $Na_2SO_4$, filtered and concentrated. The residue was purified by column chromatography (silica gel, eluting with 0% to 50% EtOAc in hexanes) to give compound T4 (35 mg, 52% yield) as a light yellow solid. m/z=408 (M+1); $^1$H NMR (400 MHz, $CDCl_3$) δ 8.54 (s, 1H), 7.40 (m, 3H), 7.27 (m, 3H), 7.21 (m, 2H), 7.00 (m, 2H), 5.27 (d, J=15.6 Hz, 1H), 5.22 (d, J=16.0 Hz, 1H), 2.60 (m, 3H), 2.17 (dt, J=2.3, 12.8 Hz, 1H), 2.01 (m, 1H), 1.74 (m, 1H), 1.50 (s, 3H), 1.30 (d, J=6.7 Hz, 3H).

Compound 14: Compound 14 (65 mg, quantitative yield) was synthesized from compound 12 (65 mg, 0.16 mmol) using the same procedure as described for the synthesis of compound 13. m/z=410 (M+1).

T5: Compound T5 (31 mg, 48% yield) was synthesized from compound 14 (65 mg, 0.16 mmol) using the same procedure as described for the synthesis of compound T4. m/z=408 (M+1); 8.05 (s, 1H), 7.72 (m, 2H), 7.43 (m, 2H), 7.35 (m, 4H), 7.09 (m, 2H), 5.73 (d, J=16.8 Hz, 1H), 5.44 (d, J=16.8 Hz, 1H), 2.85 (m, 2H), 2.57 (qd, J=6.8, 13.5 Hz, 1H), 2.25 (dt, J=2.0, 12.7 Hz, 1H), 2.09 (m, 1H), 1.67 (m, 1H), 1.46 (s, 3H), 1.32 (d, J=6.8 Hz, 3H).

Compound 15a: A mixture of compound 4 (43 mg, 0.13 mmol), (4-(trifluoromethyl)phenyl)hydrazine (47 mg, 0.27 mmol) and 12 N aq. HCl (22 µL, 0.26 mmol) in EtOH (1.2 mL) was heated in Biotage microwave at 100° C. for 2 h and then cooled to room temperature. The mixture was concentrated. The residue was diluted with EtOAc and washed with 1 N aq. HCl and water. The organic extract was dried over $Na_2SO_4$, filtered and concentrated. The residue was purified by column chromatography (silica gel, 0% to 20% EtOAc in hexanes) to give compound 15a (37 mg, 60% yield) as a white solid. m/z=464 (M+1).

Compound 16a: Compound 15a (35 mg, 0.076 mmol) was dissolved in MeOH (1.5 mL). Sodium methoxide (25 wt. % in methanol, 26 µL, 0.11 mmol) was added. The reaction mixture was stirred at 55° C. for 1 h and cooled to room temperature. EtOAc was added, followed by 10% aq. $NaH_2PO_4$ to adjust pH<7. The organic extract was dried with $Na_2SO_4$, filtered and concentrated. The residue was purified by column chromatography (silica gel, eluting with 0% to 25% EtOAc in hexanes) to give compound 16a (26 mg, 74% yield) as a white solid. m/z=464 (M+1).

T6: Compound 16a (26 mg, 0.056 mmol) was dissolved in anhydrous DMF (0.36 mL), and the solution was cooled to 0° C. 1,3-dibromo-5,5-dimethylhydantoin (8 mg, 0.028 mmol) in DMF (0.2 mL) was added. The reaction was stirred at 0° C. for 1 h. Pyridine (14 µL, 0.17 mmol) was added. The reaction was heated at 55° C. for 2 h and cooled to room temperature. EtOAc was added. The mixture was washed with 1 N aq. HCl and water. The organic extract was dried with $Na_2SO_4$, filtered and concentrated. The residue was purified by column chromatography (silica gel, eluting with 0% to 30% EtOAc in hexanes) to give compound T6 (12 mg, 46% yield) as a white solid. m/z=462 (M+1); $^1$H NMR (400 MHz, $CDCl_3$) S 7.88 (d, J=8.2 Hz, 2H), 7.70 (m, 4H), 7.50 (s, 1H), 7.42 (m, 2H), 7.36 (m, 1H), 2.98 (m, 1H), 2.88 (ddd, J=6.5, 11.4, 16.3 Hz, 1H), 2.56 (qd, J=6.7, 13.4 Hz, 1H), 2.27 (dt, J=2.0, 12.7 Hz, 1H), 2.16 (dd, J=6.5, 13.8 Hz, 1H), 1.81 (m, 1H), 1.60 (s, 3H), 1.34 (d, J=6.7 Hz, 3H).

Compound 15b: Compound 4 (82 mg, 0.25 mmol) and 4-hydrazinylpyridine hydrochloride (74 mg, 0.51 mmol) in EtOH (2 mL) was heated in Biotage microwave at 100° C. for 1 h, and then cooled to room temperature. The mixture was diluted with EtOAc and washed with water. The organic extract was dried over $Na_2SO_4$, filtered and concentrated. The residue was purified by column chromatography (silica gel, 0% to 40% acetone in hexanes) to give compound 15b (51 mg, 51% yield) as a white solid. m/z=397 (M+1).

Compound 16b: Compound 15b (48 mg, 0.12 mol) was dissolved in MeOH (1.2 mL). Sodium methoxide (25 wt. % in methanol, 42 µL, 0.18 mmol) was added. The reaction mixture was stirred at 55° C. for 1 h and cooled to room temperature. EtOAc was added, followed by 10% aq. $NaH_2PO_4$ to adjust pH<7. The organic extract was dried with $Na_2SO_4$, filtered and concentrated to give crude compound 16b as a light yellow solid, which was used in the next step without purification. m/z=397 (M+1).

T7: Compound T7 was synthesized from compound 16b (56 mg, 0.14 mmol) using the same procedure as reported for the synthesis of T6. The crude product was purified by column chromatography (silica gel, eluting with 0% to 60% EtOAc in hexanes) to give partially purified product, which was purified again by column chromatography (C18, eluting with 10% to 80% acetonitrile in water) to give compound T7 (10 mg, 18% yield) as a white solid. m/z=395 (M+1); $^1$H NMR (400 MHz, $CDCl_3$) δ 8.89 (m, 2H), 7.71 (m, 2H), 7.56 (s, 1H), 7.51 (m, 2H), 7.43 (m, 2H), 7.37 (m, 1H), 2.98 (ddd, J=1.5, 6.4, 16.4 Hz, 1H), 2.88 (ddd, J=6.7, 11.5, 16.3 Hz, 1H), 2.58 (qd, J=6.8, 13.5 Hz, 1H), 2.22 (m, 2H), 1.83 (m, 1H), 1.68 (s, 3H), 1.34 (d, J=6.6 Hz, 3H).

Compound 15c: Reaction A: A mixture of compound 4 (230 mg, 0.71 mmol), 4-hydrazinylquinoline (191 mg, 1.20 mmol) and 12 N aq. HCl (0.12 mL, 0.26 mmol) in EtOH (7 mL) was heated in Biotage microwave at 110° C. for 2 h and then cooled to room temperature. Reaction B: A mixture of compound 4 (53 mg, 0.16 mmol), 4-hydrazinylquinoline (52 mg, 0.33 mmol) and 12 N aq. HCl (27 µL, 0.32 mmol) in EtOH (1.6 mL) was heated in Biotage microwave at 110° C. for 2 h and then cooled to room temperature. The two reactions were combined and concentrated. The residue was diluted with EtOAc and washed with sat. aq. $NaHCO_3$, and water. The organic extract was dried over $Na_2SO_4$, filtered and concentrated. The residue was purified by column chromatography (silica gel, eluting with 0% to 70% EtOAc in hexanes) to give compound 15c (38 mg, 101% yield) as a white solid. m/z=464 (M+1).

Compound 16c: Compound 16c was synthesized from compound 15c (65 mg, 0.16 mmol) using the same procedure as described for the synthesis of compound 16b. m/z=447 (M+1).

T8: Compound 16c (35 mg, 0.078 mmol) was dissolved in benzene (0.8 mL). DDQ (21 mg, 0.093 mmol) was added. The mixture was heated at reflux for 2 h and cooled to mom temperature. The mixture was diluted with $CH_2Cl_2$ and sat. aq. $NaHCO_3$, and stirred for 5 min. The organic phase was separated, and the aqueous phase was extracted three times with $CH_2Cl_2$. The combined organic extracts were dried with $Na_2SO_4$, filtered and concentrated. The residue was purified by column chromatography (silica gel, eluting with 0% to 20% EtOAc in hexanes) to give compound T8 (30 mg, 86% yield) as a light yellow solid. m/z=445 (M+1); $^1$H NMR (400 MHz, $CDCl_3$) δ 9.17 (br s, 1H), 8.29 (d, J=8.5 Hz, 1H), 7.85 (m, 1H), 7.74 (m, 2H), 7.61 (t, J=7.6 Hz, 2H), 7.43 (m, 2H), 7.37 (m, 1H), 7.30 (m, 1H), 6.94 (m, 1H), 3.02 (m, 2H), 2.53 (td, J=6.8, 13.1 Hz, 1H), 2.35 (dd, J=11.7, 13.7 Hz, 1H), 2.20 (dd, J=6.1, 13.7 Hz, 1H), 1.83 (m, 1H), 1.59 (s, 3H), 1.33 (d, J=6.7 Hz, 3H).

Compound 15d: Compound 4 (129 mg, 0.40 mmol) and (2-fluorophenyl)hydrazine hydrochloride (130 mg, 0.80 mmol) in EtOH (4 mL) was heated in Biotage microwave at 100° C. for 2 h and then cooled to room temperature. The mixture was concentrated, and the residue was diluted with CH$_2$Cl$_2$. The mixture was washed with 1 N aq. HCl. The organic phase was separated. The aqueous phase was extracted twice with CH$_2$Cl$_2$. The combined organic extracts were dried over Na$_2$SO$_4$, filtered and concentrated. The residue was purified by column chromatography (silica gel, eluting with 0% to 40% EtOAc in hexanes) to give compound 15d (155 mg, 94% yield) as a white solid. m/z=414 (M+1).

Compound 16d: A mixture of compound 15d (153 mg, 0.37 mmol) and K$_2$CO$_3$ (153 mg, 0.37 mmol) in MeOH (3.6 mL) was stirred at room temperature for 16 h. 10% aq. NaH$_2$PO$_4$ (20 mL) was added. The mixture was extracted with EtOAc (2×15 mL). The combined organic extracts were dried over Na$_2$SO$_4$, filtered and concentrated. The crude product was triturated with refluxing MTBE and cooled to room temperature. The precipitated solid was collected by filtration, washed with MTBE, and dried in air to give compound 16d (87 mg, 57% yield) as a white solid. m/z=414 (M+1).

T9: Compound 16d (85 mg, 0.21 mmol) was dissolved in anhydrous DMF (1.42 mL), and the solution was cooled to 0° C. 1,3-dibromo-5,5-dimethylhydantoin (29 mg, 0.10 mmol) in DMF (0.58 mL) was added. The reaction was stirred at 0° C. for 1 h. Pyridine (50 µL, 0.62 mmol) was added. The reaction was heated at 55° C. for 5.5 h and cooled to room temperature. EtOAc was added. The mixture was washed with 1 N aq. HCl and water. The organic extract was dried with Na$_2$SO$_4$, filtered and concentrated. The residue was purified by column chromatography (silica gel, eluting with 0% to 50% EtOAc in hexanes) to give compound T9 (59 mg, 70% yield) as a white solid. m/z=412 (M+1); $^1$H NMR (400 MHz, CDCl$_3$) δ 7.71 (m, 2H), 7.60 (m, 3H), 7.38 (m, 5H), 2.96 (ddd, J=1.7, 6.3, 16.1 Hz, 1H), 2.88 (m, 1H), 2.55 (qd, J=6.7, 13.4 Hz, 1H), 2.32 (br t, J=12.7 Hz, 1H), 2.15 (dd, J=6.1, 13.8 Hz, 1H), 1.79 (m, 1H), 1.47 (s, 3H), 1.33 (d, J=6.6 Hz, 3H).

Compound 15e: A mixture of compound 4 (100 mg, 0.309 mmol), phenylhydrazine (61 µL, 0.618 mmol) and 10.1 N aq. HCl (61 µL, 0.618 mmol) in EtOH (2 mL) was heated in microwave synthesizer at 100° C. for 2 h and then cooled to room temperature. The mixture was concentrated. The residue was diluted with EtOAc and washed with 1 N aq. HCl. The organic extract was dried over Na$_2$SO$_4$, filtered and concentrated to give the crude compound 15e (130 mg, quantitative yield) as a glass, which was used in the next step without further purification. m/z=396 (M+1).

Compound 16e: A mixture of compound 15e (125 mg, 0.316 mmol) and potassium carbonate (87 mg, 0.632 mmol) in MeOH (10 mL) was stirred under nitrogen at room temperature for 24 hours. The solvent was removed in vacuo and the residue was partitioned between EtOAc and sat. aq. KH$_2$PO$_4$. The organic extract was washed with brine; dried with Na$_2$SO$_4$; filtered; and concentrated. The residue was purified by column chromatography (silica gel, eluting with 40% EtOAc in hexanes) to give compound 16e (69 mg, 55% yield) as a white solid. m/z=396 (M+1); $^1$H NMR (400 MHz, CDCl$_3$) δ

T11: A solution of compound 16e (63 mg, 0.159 mmol) in anhydrous DMF (3.0 mL) was cooled to 0° C. under nitrogen. A solution of 1,3-dibromo-5,5-dimethylhydantoin (25 mg, 0.087 mmol) in anhydrous DMF (1.0 mL) was added. After the mixture was stirred at 0° C. for 1 h, anhydrous pyridine (0.128 mL, 1.59 mmol) was added. The reaction mixture was heated at 60° C. for 4 h and then cooled to room temperature. The reaction mixture was partitioned between EtOAc and sat. aq. KH$_2$PO$_4$. The organic phase was separated. The aqueous phase was extracted with EtOAc. The combined organic extracts were washed with brine; dried with Na$_2$SO$_4$; filtered; and concentrated. The residue was purified by column chromatography (silica gel, eluting with 30% EtOAc in hexanes) to give compound T11 (33 mg, 53% yield) as a white solid. m/z=394 (M+1); $^1$H NMR (400 MHz, CDCl$_3$) δ 7.73 (m, 2H), 7.59 (m, 3H), 7.51 (m, 3H), 7.41 (m, 2H), 7.34 (m, 1H), 2.98 (ddd, J=1.6, 6.3, 16.2 Hz, 1H), 2.88 (ddd, J=6.5, 11.4, 16.1 Hz, 1H), 2.54 (qd, J=6.7, 13.4 Hz, 1H), 2.27 (dt, J=2.1, 12.7 Hz, 1H), 2.14 (m, 1H), 1.80 (m, 1H), 1.57 (s, 3H), 1.33 (d, J=6.7 Hz, 3H).

Compound 15f: Compound 15f (orange glass, 133 mg, quantitative yield) was synthesized from compound 4 (100 mg, 0.309 mmol) and 4-chlorophenylhydrazine hydrochloride (111 mg, 0.618 mmol) using the same procedure as described for the synthesis of compound 15d. The reaction was heated in microwave synthesizer at 100° C. for 3 h. Compound 15f was purified by column chromatography (silica gel, eluting with 20% EtOAc in hexanes). m/z=430 & 432 (M+1).

Compound 16f: Compound 16f (orange glass, 67 mg, 52% yield) was synthesized from compound 15f (130 mg, 0.302 mmol) using the same procedure as described for the synthesis of compound 16e. The reaction was stirred at room temperature for 27 h. Compound 16f was purified by column chromatography (silica gel, eluting with 40% EtOAc in hexanes). m/z=430 & 432 (M+1).

T13: Compound T13 (yellow solid, 44 mg, 68% yield) was synthesized from compound 16f (65 mg, 0.151 mmol) using the same procedure as described for the synthesis of compound T11. T13 was purified by column chromatography (silica gel, eluting with 30% EtOAc in hexanes). m/z=428 & 430 (M+1); $^1$H NMR (400 MHz, CDCl$_3$) δ 7.70 (m, 2H), 7.57 (m, 3H), 7.44 (m, 4H), 7.35 (m, 1H), 2.96 (ddd, J=1.6, 6.3, 16.2 Hz, 1H), 2.87 (ddd, J=6.4, 11.4, 16.2 Hz, 1H), 2.55 (qd, J=6.8, 13.4 Hz, 1H), 2.27 (dt, J=2.1, 12.8 Hz, 1H), 2.14 (m, 1H), 1.79 (m, 1H), 1.56 (s, 3H), 1.33 (d, J=6.7 Hz, 3H).

Compound 15g: Compound 15g (glass, 139 mg, 80% yield) was synthesized from compound 4 (121 mg, 0.374 mmol) and 3,4-dichlorophenylhydrazine hydrochloride (159 mg, 0.748 mmol) using the same procedure as described for the synthesis of compound 15d. The reaction was heated in microwave synthesizer at 100° C. for 3 h. Compound 15g was purified by column chromatography (silica gel, eluting with 10% EtOAc in hexanes). m/z=464 & 466 (M+1).

Compound 16g: Compound 16g (glass, 105 mg, 76% yield) was synthesized from compound 15g (138 mg, 0.297 mmol) using the same procedure as described for the synthesis of compound 16e. The reaction was stirred at room temperature for 24 h. Compound 16g was purified by column chromatography (silica gel, eluting with 40% EtOAc in hexanes). m/z=464 & 466 (M+1).

T10: Compound T10 was synthesized from compound 16g (104 mg, 0.223 mmol) using the same procedure as described for the synthesis of compound T11. Crude product was purified by triturated with MeOH. The solid obtained was triturated with refluxing 50% aq. MeOH. The precipitated solid was collected by filtration and dried under vacuum to give compound T10 (37 mg, 36% yield) as a white solid. m/z=462 & 464 (M+1); $^1$H NMR (400 MHz, CDCl$_3$) δ 7.69 (m, 3H), 7.66 (m, 1H), 7.58 (s, 1H), 7.40 (m, 4H), 2.96 (ddd, J=1.5, 6.3, 16.1 Hz, 1H), 2.87 (m, 1H), 2.57

(qd, J=6.7, 13.4 Hz, 1H), 2.26 (dt, J=2.1, 12.7 Hz, 1H), 2.15 (dd, J=6.4, 13.8 Hz, 1H), 1.80 (m, 1H), 1.59 (s, 3H), 1.34 (d, J=6.7 Hz, 3H).

Compound 15h: Compound 15h (glass, 120 mg, 95% yield) was synthesized from compound 4 (100 mg, 0.309 mmol) and 4-methylphenylhydrazine hydrochloride (98 mg, 0.618 mmol) using the same procedure as described for the synthesis of compound 15d. The reaction was heated in microwave synthesizer at 100° C. for 3 h. Compound 15h was purified by column chromatography (silica gel, eluting with 20% EtOAc in hexanes). m/z=410 (M+1).

Compound 16h: Compound 16h (glass, 94 mg, 79% yield) was synthesized from compound 15h (119 mg, 0.290 mmol) using the same procedure as described for the synthesis of compound 16e. The reaction was stirred at room temperature for 24 h. Compound 16h was purified by column chromatography (silica gel, eluting with 30% EtOAc in hexanes). m/z=410 (M+1).

T12: Compound T12 (yellow solid, 24 mg, 26% yield) was synthesized from compound 16h (94 mg, 0.229 mmol) using the same procedure as described for the synthesis of compound T11. T12 was purified by column chromatography (silica gel, eluting with 30% EtOAc in hexanes). m/z=408 (M+1); $^1$H NMR (400 MHz, CDCl$_3$) δ 7.72 (m, 2H), 7.60 (s, 1H), 7.39 (m, 7H), 2.96 (m, 1H), 2.88 (m, 1H), 2.54 (qd, J=6.7, 13.4 Hz, 1H), 2.48 (s, 3H), 2.27 (td, J=2.1, 12.7 Hz, 1H), 2.14 (dd, J=6.3, 13.8 Hz, 1H), 1.79 (m, 1H), 1.56 (s, 3H), 1.33 (d, J=6.7 Hz, 3H).

Compound 15i: A mixture of compound 4 (100 mg, 0.309 mmol) and 4-methoxyphenylhydrazine hydrochloride (108 mg, 0.618 mmol) in EtOH (2.0 mL) was heated in a microwave synthesizer 100° C. for 3 h, and then at 130° C. for an additional 1 h. After cooled to room temperature, the residue was partitioned between EtOAc and 1.0 N aq. HCl. The organic phase was dried with Na$_2$SO$_4$; filtered; and concentrated. The residue was purified by column chromatography (silica gel, eluting with 30% EtOAc in hexanes) to give partially purified compound 15i (40 mg, 30% yield) as a yellow glass, which was used in the next step without further purification. m/z=426 (M+1).

Compound 16i: Compound 16i (yellow glass, 60 mg, 61% yield) was synthesized from compound 15i (98 mg, 0.230 mmol) using the same procedure as described for the synthesis of compound 16e. The reaction was stirred at room temperature for 19 h. Compound 16i was purified by column chromatography (silica gel, eluting with 40% EtOAc in hexanes). m/z=426 (M+1).

T14: Compound T14 was synthesized from compound 16i (59 mg, 0.138 mmol) using the same procedure as described for the synthesis of compound T11. The crude product was purified by column chromatography (silica gel, eluting with 30% EtOAc in hexanes), followed by trituration with MeOH to give compound T14 (14 mg, 24% yield) as a yellow solid. m/z=424 (M+1); $^1$H NMR (400 MHz, CDCl$_3$) δ 7.72 (m, 2H), 7.63 (s, 1H), 7.41 (m, 4H), 7.33 (m, 1H), 7.06 (m, 2H), 3.91 (s, 3H), 2.96 (m, 11H), 2.87 (m, 1H), 2.54 (qd, J=6.8, 13.4 Hz, 1H), 2.26 (m, 1H), 2.14 (dd, J=6.4, 13.9 Hz, 1H), 1.78 (m, 1H), 1.55 (s, 3H), 1.33 (d, J=6.7 Hz, 3H).

Compound 19: To a stirring solution of compound 17 (Coltart and Danishefsky, 2003, 2.19 g, 9.77 mmol) in ethyl formate (23 mL, 285.95 mmol) was added sodium methoxide (25 wt. % solution in MeOH, 35 mL, 152.95 mmol) at 0° C. The reaction mixture was stirred at room temperature for 2 h, and cooled to 0° C. Aq. HCl (6 N, 20 mL, 120 mmol) was added to adjust the pH<7. The mixture was extracted with EtOAc. The organic extract was dried over Na$_2$SO$_4$, filtered and concentrated. The residue was mixed with hydroxylamine hydrochloride (910 mg, 13.10 mmol). EtOH (80 mL) and water (8 mL). The mixture was heated 55° C. for 2 h and then cooled to room temperature. After concentration, the residue was extracted with EtOAc. The organic extract was dried over Na$_2$SO$_4$, filtered and concentrated. The residue was purified by column chromatography (silica gel, eluting with 0% to 30% acetone in hexanes) to give compound 18 (453 mg, 19% yield) as a white solid. m/z=250 (M+1). From the column, compound 19 (736 mg, 37% yield) was obtained as a colorless oil. m/z=206 (M+1).

Compound 20: Compound 19 (520 mg, 2.53 mmol) was dissolved in CH$_2$Cl$_2$ (25 mL). Magnesium bromide ethyl etherate (1.60 g, 6.20 mmol) and N,N-diisopropylethylamine (1.32 mL, 7.56 mmol) were added sequentially at room temperature. The mixture was stirred at room temperature for 5 min, and benzoyl chloride (0.382 mL, 3.29 mmol) was added. The mixture was stirred at room temperature for 3 h; refluxed overnight; and cooled to room temperature. Sat. aq. NaHCO$_3$ was added. The mixture was stirred at room temperature for 1 h. The organic phase was separated, dried over Na$_2$SO$_4$, filtered, and concentrated. The residue was purified by column chromatography (silica gel, eluting with 0% to 40% EtOAc in hexanes) to give compound 20 (560 mg, 71% yield) as an orange oil. m/z=310 (M+1).

Compound 21a: A mixture of compound 20 (200 mg, 0.65 mmol), (4-cyanophenyl)hydrazine hydrochloride (219 mg, 1.29 mmol) and 12 N HCl (60 μL, 0.72 mmol) in EtOH (3 mL) was heated in Biotage microwave at 100° C. for 2 h and then cooled to room temperature. The mixture was concentrated, and the residue was diluted with EtOAc, and the mixture was washed with water. The organic extract was dried over Na$_2$SO$_4$, filtered and concentrated. The residue was purified by column chromatography twice (silica gel, eluting with 0% to 50% EtOAc in hexanes) to give partially purified compound 21a (110 mg, 42% yield) as a light yellow solid. m/z=407 (M+1).

Compound 22a: Compound 21a (110 mg, 0.27 mmol) was dissolved in MeOH (4 mL). Sodium methoxide (25 wt. % in methanol, 93 μL, 0.41 mmol) was added. The reaction mixture was stirred at 55° C. for 2 h, cooled to room temperature, and concentrated. The residue was partitioned between EtOAc and 10% aq. NaH$_2$PO$_4$ to adjust pH<7. The organic extract was dried with Na$_2$SO$_4$, filtered, and concentrated. The residue was purified by column chromatography (silica gel, eluting with 65% EtOAc in hexanes) to give compound 22a (55 mg, 50% yield) as a yellow solid. m/z=407 (M+1).

T15: A solution of compound 22a (55 mg, 0.14 mmol) in anhydrous DMF (2 mL) was cooled to 0° C. under nitrogen. A solution of 1,3-dibromo-5,5-dimethylhydantoin (19.3 mg, 0.067 mmol) in anhydrous DMF (1 mL) was added. After the mixture was stirred at 0° C. for 1 h, anhydrous pyridine (60 μL, 0.74 mmol) was added. The reaction mixture was heated at 55° C. for 2 h and then cooled to room temperature. The reaction mixture was diluted with EtOAc and washed with water. The organic extract was dried with Na$_2$SO$_4$, filtered, and concentrated. The residue was purified twice by column chromatography (silica gel, eluting with 50% EtOAc in hexanes) to give compound T15 (21 mg, 38% yield) as a yellow solid. m/z=405 (M+1); $^1$H NMR (400 MHz, CDCl$_3$) δ 7.92 (m, 2H), 7.69 (m, 4H), 7.47 (s, 1H), 7.41 (m, 3H), 2.92 (m, 2H), 2.65 (m, 3H), 1.89 (m, 2H), 1.59 (s, 3H).

Compound 21b: A mixture of compound 20 (117 mg, 0.38 mmol), (4-fluorophenyl)hydrazine hydrochloride (123 mg, 0.76 mmol) and 12 N HCl (40 μL, 0.48 mmol) in EtOH (2.5 mL) was heated in Biotage microwave at 120° C. for 3 h, and then cooled to room temperature. The mixture was concentrated, and the residue was diluted with water and extracted with EtOAc. The organic extract was dried over Na$_2$SO$_4$, filtered, and concentrated. The residue was purified by column chromatography (silica gel, eluting with 0% to 40% EtOAc in hexanes) to give partially purified product, which was purified again by column chromatography (silica gel, eluting with 0% to 40% EtOAc in hexanes) to give partially purified compound 21b (35 mg, 23% yield) as a white solid. m/z=400 (M+1).

Compound 22b: Compound 21b (35 mg, 0.088 mol) was dissolved in MeOH (2 mL). Sodium methoxide (25 wt. % in methanol, 30 µL, 0.13 mmol) was added. The reaction mixture was stirred at 55° C. for 2 h and cooled to room temperature. EtOAc was added followed by 10% aq. NaH$_2$PO$_4$ to adjust pH<7. The organic extract was dried with Na$_2$SO$_4$, filtered, and concentrated. The residue was purified twice by column chromatography (silica gel, eluting with 0% to 40% EtOAc in hexanes) to give compound 22b (12 mg, 34% yield). m/z=400 (M+1).

T16: A solution of compound 22b (12 mg, 0.030 mmol) in anhydrous DMF (1 mL) was cooled to 0° C. under nitrogen. A solution of 1,3-dibromo-5,5-dimethylhydantoin (4.4 mg, 0.015 mmol) in anhydrous DMF (1 mL) was added. After the mixture was stirred at 0° C. for 1 h, anhydrous pyridine (10 µL, 0.12 mmol) was added. The reaction mixture was heated at 55° C. for 2 h and then cooled to room temperature. The reaction mixture was diluted with EtOAc and washed with water. The organic extract was dried with Na$_2$SO$_4$, filtered, and concentrated. The residue was purified by column chromatography (silica gel, eluting with 50% EtOAc in hexanes) to give compound T16 (contains 11% 1,2-epoxide, 4.9 mg, 41% yield) as a light yellow solid. m/z=398 (M+1); $^1$H NMR (400 MHz, CDCl$_3$) δ 7.71 (m, 2H), 7.55 (s, 1H), 7.52 (m, 2H), 7.36 (m, 5H), 2.91 (m, 2H), 2.64 (m, 3H), 1.82 (m, 2H), 1.53 (s, 3H).

Compound 23a and 24a: Compound 4 (180 mg, 0.56 mmol) and o-tolylhydrazine hydrochloride (180 mg, 1.13 mmol) in EtOH (4 mL) was heated in Biotage microwave at 120° C. for 1 h and then cooled to room temperature. The mixture was diluted with MTBE. The mixture was washed with 1 N aq. HCl, 1 N aq. NaOH, and water. The organic extract was dried over Na$_2$SO$_4$, filtered and concentrated. The residue was purified by column chromatography (silica gel, eluting with 0% to 30% EtOAc in hexanes) to give compound 23a (199 mg, 87% yield) as a beige solid. m/z=410 (M+1). From the column, also get compound 24a (13 mg, 6% yield), m/z=410 (M+1).

Compound 25a: A mixture of compound 23a (111 mg, 0.27 mmol) and K$_2$CO$_3$ (112 mg, 0.81 mmol) in MeOH (2.8 mL) was stirred at room temperature for 16 h. 10% aq. NaH$_2$PO$_4$ (20 mL) was added. The mixture was extracted with EtOAc (2×15 mL). The combined organic extracts were dried over Na$_2$SO$_4$, filtered, and concentrated. The crude product was triturated with refluxing MTBE, cooled to room temperature, and kept at room temperature for 2 h. The precipitated solid was collected by filtration and dried in air to give compound 25a (80 mg, 72% yield) as a white solid. m/z=410 (M+1).

T17: Compound 25a (77 mg, 0.19 mmol) was dissolved in anhydrous DMF (0.5 mL), and the solution was cooled to 0° C. 1,3-dibromo-5,5-dimethylhydantoin (27 mg, 0.094 mmol) in DMF (0.5 mL) was added. The reaction was stirred at 0° C. for 1 h. Pyridine (45 µL, 0.56 mmol) was added. The reaction was heated at 55° C. for 5.5 h and cooled to room temperature. EtOAc was added. The mixture was washed with 1 N aq. HCl and water. The organic extract was dried with Na$_2$SO$_4$, filtered, and concentrated. The residue was purified by column chromatography (silica gel, eluting with 0% to 50% EtOAc in hexanes) to give compound T17 (48 mg, 63% yield) as an off-white solid. m/z=408 (M+1); $^1$H NMR (400 MHz, CDCl$_3$) δ –3/1 mixture of atropisomers. Major isomer: 7.73 (m, 2H), 7.31-7.51 (m, 7H), 7.22 (s, 1H), 2.86-3.01 (m, 2H), 2.51 (qd, 1H, J=6.4, 13.2 Hz), 2.30 (dt, 1H, J=1.6, 12.8 Hz), 2.15 (dd, 1H, J=6.4, 14.0 Hz), 2.03 (s, 3H), 1.80 (m, 1H), 1.51 (s, 3H), 1.32 (d, 3H, J=6.8 Hz).

Compound 26a: Compound 24a (28 mg, 0.068 mmol) was dissolved in MeOH (0.7 mL). Sodium methoxide (25 wt. % in methanol, 31 µL, 0.14 mmol) was added. The reaction mixture was stirred at 55° C. for 1 h and cooled to room temperature. 10% aq. NaH$_2$PO$_4$ (10 mL) was added to adjust pH<7. The mixture was extracted with EtOAc (2×10 mL). The combined organic extracts were dried with Na$_2$SO$_4$, filtered, and concentrated. The residue was purified by column chromatography (silica gel, eluting with 0% to 30% acetone in hexanes) to give compound 26a (24 mg, 86% yield) as a white solid. m/z=410 (M+1).

T18: Compound 26a (24 mg, 0.059 mmol) was dissolved in toluene (0.6 mL). DDQ (15 mg, 0.066 mmol) was added. The mixture was heated at 85° C. for 2.5 h and cooled to room temperature. The mixture was diluted with CH$_2$Cl$_3$ (10 mL) and sat. aq. NaHCO$_3$ (10 mL) and stirred for 5 min. The organic phase was separated, and the aqueous phase was extracted three times with CH$_2$Cl$_2$ (3×10 mL). The combined organic extracts were dried with Na$_2$SO$_4$, filtered, and concentrated. The residue was purified by column chromatography (silica gel, eluting with 0% to 30% EtOAc in hexanes) to give compound T18 (10.8 mg, 45% yield) as a yellow solid. m/z=408 (M+1); $^1$H NMR (400 MHz, CDCl$_3$) δ 8.56 (s, 1H), 7.23 (m, 7H), 7.08 (m, 2H), 2.78 (m, 2H), 2.60 (m, 1H), 2.25 (m, 1H), 2.10 (dd, J=6.3, 13.2 Hz, 1H), 1.99 (s, 3H), 1.81 (qd, J=6.6, 12.6 Hz, 1H), 1.54 (s, 3H), 1.34 (dd, J=1.2, 6.8 Hz, 3H).

Compound 23b and 24b: Compound 23b and 24b (131 mg, 67% yield) was synthesized from compound 4 (129 mg, 0.40 mmol) and 4-(trifluoromethoxy)phenylhydrazine hydrochloride (100 mg, 0.44 mmol) using the same procedure as described for the synthesis of compound 23a and 24a. The crude product was purified by column chromatography (silica gel, eluting with 50% EtOAc in hexanes) to give a mixture of compound 23b and 24b. m/z=480 (M+1).

Compound 25b and 26b: A mixture of compound 23b and 24b (129 mg, 0.27 mmol) and K$_2$CO$_3$ (11 mg, 0.80 mmol) in MeOH (2.8 mL) was stirred at room temperature for 16 h. 10% aq. NaH$_2$PO$_4$ was added. The mixture was extracted with EtOAc. The organic extracts were dried over Na$_2$SO$_4$, filtered, and concentrated. The residue was purified by column chromatography (silica gel, eluting with 0% to 30% acetone in hexanes) to give compound 25b (100 mg, 78% yield) and 26b (14 mg, 11% yield). Compound 25b: white solid; m/z=480 (M+1); Compound 26b: white solid; m/z=480 (M+1).

T19: Compound T19 was synthesized from compound 25b (98 mg, 0.20 mmol) using the same procedure as described for the synthesis of compound T17. The crude product was purified twice by column chromatography (silica gel, eluting with 50% EtOAc in hexanes) to give compound T19 (78 mg, 80% yield) as a white solid. m/z=478 (M+1); $^1$H NMR (400 MHz, CDCl$_3$) δ 7.70 (m, 2H), 7.57 (m, 2H), 7.51 (s, 1H), 7.43 (m, 4H), 7.36 (m, 1H), 2.97 (ddd, J=1.6, 6.3, 16.1 Hz, 1H), 2.88 (ddd, J=6.4, 11.4, 16.2 Hz, 1H), 2.56 (qd, J=6.7, 13.4 Hz, 1H), 2.27 (dt, J=2.1, 12.7 Hz, 1H), 2.15 (m, 1H), 1.80 (tdd, J=6.3, 12.1, 18.9 Hz, 1H), 1.58 (s, 3H), 1.33 (d, J=6.7 Hz, 3H).

T20: Compound 26b (14 mg, 0.029 mmol) was dissolved in anhydrous DMF (0.1 mL), and the solution was cooled to 0° C. 1,3-dibromo-5,5-dimethylhydantoin (4.2 mg, 0.015 mmol) in DMF (0.21 mL) was added. The reaction was stirred at 0° C. for 1 h. Pyridine (10 µL, 0.12 mmol) was added. The reaction was heated at 55° C. for 3 h and cooled to room temperature. EtOAc (20 mL) was added. The mixture was washed with 1 N aq. HCl (10 mL), and water (3×10 mL). The organic extract was dried with $Na_2SO_4$, filtered, and concentrated. The residue was purified by column chromatography (silica gel, eluting with 0% to 35% EtOAc in hexanes) to give compound T20 (10.1 mg, 72% yield) as a white solid. m/z=478 (M+1); $^1$H NMR (400 MHz, $CDCl_3$) δ 8.55 (s, 1H), 7.36 (m, 3H), 7.28 (m, 2H), 7.16 (m, 4H), 2.77 (m, 1H), 2.63 (m, 2H), 2.18 (dt, J=2.3, 12.7 Hz, 1H), 2.07 (m, 1H), 1.79 (m, 1H), 1.55 (s, 3H), 1.32 (d, J=6.7 Hz, 3H).

Compound 23c and 24c: Compound 23c and 24c was synthesized from compound 4 (129 mg, 0.40 mmol) and biphenyl-4-yl-hydrazine hydrochloride (176 mg, 0.80 mmol) using the same procedure as described for the synthesis of compound 23a and 24a. The reaction was heated in microwave synthesizer at 100° C. for 2 h and then at 120° C. for 3 h. The crude product was purified by column chromatography (silica gel, eluting with 40% EtOAc in hexanes) to give a ~9/1 mixture of compound 23c and 24c (97 mg, 52% yield) as a yellow solid. Compound 23c: m/z=472 (M+1); Compound 24c: m/z=472 (M+1).

Compound 25c and 26c: A mixture of compound 23c and 24c (95 mg, 0.20 mmol) and $K_2CO_3$ (84 mg, 0.61 mmol) in MeOH (3 mL) was stirred at room temperature for 16 h. 10% aq. $NaH_2PO_4$ was added. The mixture was extracted with EtOAc. The organic extracts were dried over $Na_2SO_4$, filtered, and concentrated. The residue was purified by column chromatography (silica gel, eluting with 0% to 30% acetone in hexanes) to give compound 25c (56 mg, 59% yield) and compound 26c (10 mg, 11% yield). Compound 25c: white solid; m/z=472 (M+1); Compound 26c: white solid; m/z=472 (M+1).

T21: Compound 25c (54 mg, 0.11 mmol) was dissolved in anhydrous DMF (0.57 mL), and the solution was cooled to 0° C. 1,3-dibromo-5,5-dimethylhydantoin (16 mg, 0.056 mmol) in DMF (0.57 mL) was added. The reaction was stirred at 0° C. for 1 h. Pyridine (28 µL, 0.35 mmol) was added. The reaction was heated at 55° C. for 5.5 h and cooled to room temperature. EtOAc was added. The mixture was washed with 1 N aq. HCl and water. The organic extract was dried with $Na_2SO_4$, filtered, and concentrated. The residue was purified by column chromatography (silica gel, eluting with 0% to 50% EtOAc in hexanes). The product obtained was recrystallized from EtOAc and hexanes to give compound T21 (34 mg, 63% yield) as a white solid. m/z=470 (M+1); $^1$H NMR (400 MHz, $CDCl_3$) δ 7.80 (m, 2H), 7.74 (m, 2H), 7.67 (m, 3H), 7.58 (m, 2H), 7.50 (m, 2H), 7.42 (m, 3H), 7.35 (m, 1H), 2.99 (ddd, J=1.6, 6.3, 16.4 Hz, 1H), 2.90 (m, 1H), 2.56 (qd, J=6.7, 13.4 Hz, 1H), 2.29 (dt, J=2.0, 12.9 Hz, 1H), 2.16 (dd, J=6.4, 13.8 Hz, 1H), 1.82 (m, 1H), 1.61 (s, 3H), 1.34 (d, J=6.7 Hz, 3H).

T22: Compound 26c (10 mg, 0.021 mmol) was dissolved in anhydrous DMF (0.1 mL), and the solution was cooled to 0° C. 1,3-dibromo-5,5-dimethylhydantoin (3.0 mg, 0.010 mmol) in DMF (0.1 mL) was added. The reaction was stirred at 0° C. for 1 h. Pyridine (10 µL, 0.12 mmol) was added. The reaction was heated at 55° C. for 3 h and cooled to room temperature. EtOAc was added. The mixture was washed with 1 N aq. HCl and water. The organic extract was dried with $Na_2SO_4$, filtered, and concentrated. The residue was purified by column chromatography (silica gel, eluting with 0% to 18% EtOAc in hexanes) to give compound T22 (8.4 mg, 84% yield) as a light yellow solid. m/z=470 (M+1); $^1$H NMR (400 MHz, $CDCl_3$) δ 8.61 (s, 1H), 7.56 (m, 4H), 7.43 (m, 2H), 7.34 (m, 6H), 7.21 (m, 2H), 2.80 (m, 1H), 2.65 (m, 2H), 2.20 (dt, J=2.3, 12.8 Hz, 1H), 2.09 (dd, J=7.1, 13.7 Hz, 1H), 1.81 (m, 1H), 1.56 (s, 3H), 1.33 (d, J=6.7 Hz, 3H).

Compound 23d and 24d: Compound 4 (200 mg, 0.62 mmol) and 1-naphthylhydrazine hydrochloride (240 mg, 1.23 mmol) in EtOH (4 mL) was heated in Biotage microwave at 120° C. for 2 h and then cooled to room temperature. The mixture was concentrated. The residue was diluted with EtOAc (20 mL). The mixture was washed with 1 N aq. HCl (10 mL) and water (2×10 mL). The organic extract was dried over $Na_2SO_4$, filtered, and concentrated. The residue was purified by column chromatography (silica gel, eluting with 0% to 50% EtOAc in hexanes) to give a mixture of compound 23d and 24d (270 mg, 98% yield) as a pink solid. Compound 23d and 24d: m/z=446 (M+1).

Compound 25d and 26d: A mixture of compound 23d and 24d (270 mg, 0.61 mmol) and $K_2CO_3$ (418 mg, 3.02 mmol) in MeOH (6 mL) was stirred at room temperature for 16 h. 10% aq. $NaH_2PO_4$ (15 mL) was added. The mixture was stirred for 5 min and extracted with EtOAc (20 mL). The organic extract was dried over $Na_2SO_4$, filtered, and concentrated. The residue was purified by column chromatography (silica gel, eluting with 0% to 35% acetone in hexanes) to give compound 25d (110 mg, 41% yield) as a pink solid. The mixed fractions were combined and purified again by column chromatography (silica gel, eluting with 0% to 35% acetone in hexanes) to give compound 26d (15 mg, 6% yield) as a white solid. Compound 25d: m/z=446 (M+1); compound 26d: m/z=446 (M+1).

T23: T23 (white solid, 80 mg, 73% yield) was synthesized from compound 25d (109 mg, 0.25 mmol) using the same procedure as described for the synthesis of T21. Compound T23 was purified by column chromatography (silica gel, eluting with 0% to 35% acetone in hexanes). m/z=444 (M+1); $^1$H NMR (400 MHz, DMSO-$d_6$, 2:1 mixture of atropisomers) δ [8.28 (d, J=8.4 Hz), 8.27 (d, J=8.4 Hz); 2:1; 1H], [8.17 (d, J=8.4 Hz), 8.14 (d, J=8.4 Hz); 2:1; 1H], [8.02 (d, J=7.2 Hz), 7.92 (d, J=7.3 Hz); 1:2; 1H], 5.70 (m, 5H), 7.44 (m, 2H), 7.36 (m, 1H), [7.02 (d, J=8.5 Hz), 6.99 (d, J=8.4 Hz); 1:2; 1H], 6.66 (s, 1H), 2.94 (m, 2H), 2.67 (tt, J=6.8, 13.9 Hz, 1H), 2.39 (m, 1H), 2.06 (m, 1H), 1.81 (m, 1H), [1.56 (s), 1.10 (s); 2:1; 3H], [1.18 (d, J=7.2 Hz), 1.16 (d, J=6.8 Hz); 1:2; 3H].

T24: T24 (white solid, 9 mg, 65% yield) was synthesized from compound 26d (14 mg, 0.31 mmol) using the same procedure as described for the synthesis of T21. Compound T24 was purified by column chromatography (silica gel, eluting with 0% to 35% acetone in hexanes). m/z=444 (M+1); $^1$H NMR (400 MHz, $CDCl_3$) δ 8.58 (s, 1H), 7.89 (m, 2H), 7.62 (m, 1H), 7.52 (m, 2H), 7.38 (m, 1H), 7.24 (m, 1H), 7.15 (m, 3H), 7.04 (m, 2H), 2.84 (m, 2H), 2.64 (qd, J=6.7, 13.4 Hz, 1H), 2.31 (dt, J=2.2, 12.7 Hz, 1H), 2.15 (dd, J=6.0, 13.7 Hz, 1H), 1.87 (dq, J=6.9, 12.6 Hz, 1H), 1.62 (s, 3H), 1.36 (d, J=6.7 Hz, 3H).

Compound 23e and 24e: Compound 23e and 24e (~6/1 mixture, brown solid, 256 mg, 95% yield) was synthesized from compound 4 (200 mg, 0.62 mmol) and 4-isopropylphenylhydrazine hydrochloride (230 mg, 1.18 mmol) using the same procedure as described for the synthesis of compound 23d and 24d. Compound 23e and 24e was purified by column chromatography (silica gel, eluting with 0% to 35% EtOAc in hexanes). Compound 23e m/z=438 (M+1); compound 24e: m/z=438 (M+1).

Compound 25e and 26e: Compound 23e and 24e (256 mg, 0.59 mmol) was dissolved in MeOH (2.9 mL). Sodium methoxide (25 wt. % in methanol, 267 μL, 1.17 mmol) was added. The reaction mixture was stirred at 55° C. for 1 h and cooled to room temperature, 10% aq. $NaH_2PO_4$ was added to adjust pH<7. The mixture was extracted twice with EtOAc. The combined organic extracts were dried with $Na_2SO_4$, filtered, and concentrated. The residue was purified by column chromatography (silica gel, eluting with 0% to 40% acetone in hexanes) to give compound 25e (176 mg, 69% yield) as a white solid. The mixed fractions were combined and purified again by column chromatography (silica gel, eluting with 0% to 40% acetone in hexanes) to give compound 26e (31 mg, 12% yield) as a white solid. Compound 25e: m/z=438 (M+1); compound 26e: m/z=438 (M+1).

T25: Compound 25e (176 mg, 0.40 mmol) was dissolved in anhydrous DMF (1 mL), and the solution was cooled to 0° C. 1,3-dibromo-5,5-dimethylhydantoin (57 mg, 0.20 mmol) in DMF (1 mL) was added. The reaction was stirred at 0° C. for 1 h. Pyridine (162 μL, 2.01 mmol) was added. The reaction was heated at 55° C. for 3 h and cooled to room temperature. EtOAc was added. The mixture was washed with 1 N aq. HCl and water. The organic extract was dried with $Na_2SO_4$, filtered, and concentrated. The crude product was dissolved in $CH_2Cl_2$ (1 mL). EtOAc (3 mL) was added. The mixture was heated to reflux to let the solvent evaporate. When the volume was reduced ~1 mL, the mixture was cooled to room temperature and kept for 2 h. The precipitated solid was collected by filtration, washed with EtOAc, and dried under vacuum to give compound T25 (110 mg, 63% yield) as a light yellow solid. m/z=436 (M+1); $^1$H NMR (400 MHz, $CDCl_3$) δ 7.73 (m, 2H), 7.55 (s, 1H), 7.41 (m, 6H), 7.34 (m, 1H), 3.05 (hept, J=7.0 Hz, 1H), 2.97 (ddd, J=1.6, 6.4, 16.1 Hz, 1H), 2.88 (ddd, J=6.4, 11.4, 16.1 Hz, 1H), 2.53 (qd, J=6.7, 13.4 Hz, 1H), 2.27 (dt, J=2.1, 12.7 Hz, 1H), 2.13 (ddd, J=3.3, 5.3, 10.3 Hz, 1H), 1.79 (m, 1H), 1.57 (m, 3H), 1.32 (d, J=7.1 Hz, 6H), 1.31 (d, J=7.1 Hz, 3H).

T26: Compound 26e (31 mg, 0.071 mmol) was dissolved in anhydrous DMF (0.5 mL), and the solution was cooled to 0° C. 1,3-dibromo-5,5-dimethylhydantoin (10 mg, 0.035 mmol) in DMF (0.2 mL) was added. The reaction was stirred at 0° C. for 1 h. Pyridine (29 μL, 0.36 mmol) was added. The reaction was heated at 55° C. for 3 h and cooled to room temperature. EtOAc was added. The mixture was washed with 1 N aq. HCl and water. The organic extract was dried with $Na_2SO_4$, filtered, and concentrated. The residue was purified by column chromatography (silica gel, eluting with 0% to 35% EtOAc in hexanes) to give compound T26 (25 mg, 81% yield) as a yellow solid. m/z=436 (M+1); $^1$H NMR (400 MHz, $CDCl_3$) δ 8.60 (s, 1H), 7.32 (m, 3H), 7.17 (m, 6H), 2.89 (hept, J=6.9, 1H), 2.78 (ddd, J=1.4, 6.6, 16.4 Hz, 1H), 2.64 (m, 2H), 2.19 (dt, J=2.3, 12.8 Hz, 1H), 2.07 (m, 1H), 1.79 (m, 1H), 1.55 (s, 3H), 1.32 (d, J=6.7 Hz, 3H), 1.22 (d, J=6.9 Hz, 6H).

Compound 23f and 24f: Reaction A: Compound 4 (100 mg, 0.31 mmol) and oxan-4-ylhydrazine dihydrochloride (117 mg, 0.63 mmol) in EtOH (2 mL) was heated in Biotage microwave at 120° C. for 2.5 h and then cooled to room temperature. Reaction B: Compound 4 (100 mg, 0.31 mmol) and oxan-4-ylhydrazine dihydrochloride (117 mg, 1.13 mmol) in EtOH (2 mL) was heated in Biotage microwave at 120° C. for 5 h and then cooled to room temperature. The two reactions were combined and partitioned between $CH_2Cl_2$ (20 mL) and water (20 mL). The organic phase was separated. The aqueous phase was extracted with $CH_2Cl_2$ (2×15 mL). The combined organic extracts were dried over $Na_2SO_4$, filtered, and concentrated. The residue was purified by column chromatography (silica gel, eluting with 0% to 50% EtOAc in hexanes) to give compound 23f (78 mg, 31% yield) and compound 24f (81 mg, 32% yield). Compound 23f: white solid; m/z=404 (M+1); Compound 24f: white solid; m/z=404 (M+1).

Compound 25f: Compound 23f (76 mg, 0.19 mmol) and $K_2CO_3$ (78 mg, 0.56 mmol) in MeOH (2 mL) was stirred at room temperature for 14 h. 10% aq. $NaH_2PO_4$ (20 mL) was added. The mixture was extracted with EtOAc (2×15 mL). The combined organic extracts were dried over $Na_2SO_4$, filtered, and concentrated. The residue was triturated with EtOAc (1 mL) at reflux and then cooled to room temperature. The precipitated solid was collected by filtration, washed with EtOAc, and dried under vacuum to give compound 25f (52 mg, 68% yield) as a white solid. m/z=404 (M+1).

T27: Compound 25f (51 mg, 0.13 mmol) was dissolved in anhydrous DMF (0.6 mL), and the solution was cooled to 0° C. 1,3-dibromo-5,5-dimethylhydantoin (18 mg, 0.063 mmol) in DMF (0.6 mL) was added. The reaction was stirred at 0° C. for 1.5 h. Pyridine (51 μL, 0.62 mmol) was added. The reaction was heated at 55° C. for 3 h and cooled to room temperature. EtOAc was added. The mixture was washed with 1 N aq. HCl, and water. The organic extract was dried with $Na_2SO_4$, filtered, and concentrated. The residue was purified by column chromatography (silica gel, eluting with 0% to 50% EtOAc in hexanes) to give compound T27 (46 mg, 91% yield) as a white solid. m/z=402 (M+1); $^1$H NMR (400 MHz, $CDCl_3$) δ 8.10 (s, 1H), 7.68 (m, 2H), 7.40 (m, 2H), 7.32 (m, 1H), 4.23 (m, 3H), 3.63 (dt, J=2.2, 12.2 Hz, 1H), 3.56 (dt, J=2.2, 12.2 Hz, 1H), 2.73 (m, 5H), 2.26 (dt, J=1.9, 12.6 Hz, 1H), 2.03 (m, 2H), 1.83 (ddd, J=2.2, 4.3, 13.3 Hz, 1H), 1.63 (m, 1H), 1.56 (s, 3H), 1.37 (d, J=6.8 Hz, 3H).

Compound 26f: Compound 26f (white solid, 72 mg, 91% yield) was synthesized from compound 24f (79 mg, 0.20 mmol) using the same procedure as described for the synthesis of compound 25f. Compound 26f was purified by column chromatography (silica gel, eluting with 0% to 50% EtOAc in hexanes). m/z=404 (M+1).

T28: Compound T28 (white solid, 42 mg, 53% yield) was synthesized from compound 26f (79 mg, 0.20 mmol) using the same procedure as described for the synthesis of compound T27. Compound T28 was purified by column chromatography (silica gel, eluting with 0% to 50% EtOAc in hexanes). m/z=402 (M+1); $^1$H NMR (400 MHz, $CDCl_3$) δ 8.55 (s, 1H), 7.46 (m, 3H), 7.27 (m, 2H), 4.21 (tt, J=4.2, 11.4 Hz, 1H), 4.05 (m, 2H), 3.37 (dtd, J=2.2, 12.0, 14.1 Hz, 2H), 2.53 (m, 3H), 2.36 (pd, J=4.7, 12.0 Hz, 2H), 2.12 (dt, J=2.2, 12.8 Hz, 1H), 1.99 (dd, J=6.5, 13.6 Hz, 1H), 1.75 (m, 3H), 1.46 (s, 3H), 1.29 (d, J=6.6 Hz, 3H)

Compound 27 and 28: Reaction A: Compound 4 (100 mg, 0.31 mmol) and 3-hydrazineyltetrahydrothiophene 1,1-dioxide dihydrochloride (115 mg, 1.62 mmol) in EtOH (2 mL) was heated in Biotage microwave at 120° C. for 3 h and then cooled to room temperature. Reaction B: Compound 4 (100 mg, 0.31 mmol) and 3-hydrazineyltetrahydrothiophene 1,1-dioxide dihydrochloride (115 mg, 1.62 mmol) in EtOH (2 mL) was heated in Biotage microwave at 120° C. for 5 h and then cooled to room temperature. The two reactions were combined, and partitioned between $CH_2Cl_2$ (20 mL) and water (20 mL). The organic phase was separated. The aqueous phase was extracted with $CH_2Cl_2$ (2×15 mL). The combined organic extracts were dried over $Na_2SO_4$, filtered, and concentrated. The residue was purified by column chromatography (silica gel, eluting with 0% to 50% EtOAc in hexanes) to give compound 27 (94 mg, 35% yield) and compound 28 (89 mg, 33% yield). Compound 27: white solid; m/z=438 (M+1); Compound 28: white solid; m/z=438 (M+1).

Compound 29: A mixture of compound 27 (92 mg, 0.21 mmol) and $K_2CO_3$ (78 mg, 0.63 mmol) in MeOH (2 mL) and THF (1 mL) was stirred at room temperature for 14 h. 10% aq. $NaH_2PO_4$ (15 mL) was added. The mixture was extracted with EtOAc (20 mL). The organic extract was dried over $Na_2SO_4$, filtered, and concentrated. The residue was purified by column chromatography (silica gel, eluting with 0% to 50% EtOAc in hexanes) to give compound 29 (69 mg, 75% yield) as a white solid. m/z=438 (M+1).

T29: Compound 29 (69 mg, 0.16 mmol) was dissolved in anhydrous DMF (0.4 mL), and the solution was cooled to 0° C. 1,3-dibromo-5,5-dimethylhydantoin (23 mg, 0.080 mmol) in DMF (0.4 mL) was added. The reaction was stirred at 0° C. for 1.5 h. Pyridine (64 µL, 0.79 mmol) was added. The reaction was heated at 55° C. for 3 h and cooled to room temperature. EtOAc was added. The mixture was washed with 1 N aq. HCl and water. The organic extract was dried with $Na_2SO_4$, filtered, and concentrated. The residue was purified by column chromatography (silica gel, eluting with 0% to 60% EtOAc in hexanes) to give compound T29 (34 mg, 50% yield) as a white solid. m/z=436 (M+1); $^1$H NMR (400 MHz, CDCN) δ 8.33 (s, 1H), 7.72 (m, 2H), 7.44 (m, 2H), 7.36 (m, 1H), 5.38 (qd, J=6.6, 8.9 Hz, 1H), 3.82 (m, 1H), 3.62 (m, 2H), 3.19 (dddd, J=0.9, 7.0, 7.9, 13.0 Hz, 1H), 2.75 (m, 3H), 2.60 (m, 2H), 2.28 (dt, J=2.0, 12.6 Hz, 1H), 2.04 (m, 1H), 1.65 (m, 1H), 1.54 (s, 3H), 1.29 (d, J=6.8 Hz, 3H).

Compound 30: A mixture of compound 28 (80 mg, 0.18 mmol) and $K_2CO_3$ (80 mg, 0.58 mmol) in MeOH (2 mL) was stirred at room temperature for 18 h. 10% aq. $NaH_2PO_4$ (20 mL) was added. The mixture was extracted with EtOAc (2×15 mL). The combined organic extracts were dried over $Na_2SO_4$, filtered, and concentrated. The residue was purified by column chromatography (silica gel, eluting with 0% to 60% EtOAc in hexanes) to give compound 30 (65 mg, 81% yield) as a white solid. m/z=438 (M+1).

T30: Compound 30 (65 mg, 0.15 mmol) was dissolved in anhydrous DMF (0.75 mL), and the solution was cooled to 0° C. 1,3-dibromo-5,5-dimethylhydantoin (22 mg, 0.077 mmol) in DMF (0.75 mL) was added. The reaction was stirred at 0° C. for 1.5 h. Pyridine (60 µL, 0.74 mmol) was added. The reaction was heated at 55° C. for 3 h, and cooled to room temperature. EtOAc was added. The mixture was washed with 1 N aq. HCl and water. The organic extract was dried with $Na_2SO_4$, filtered, and concentrated. The residue was purified by column chromatography (silica gel, eluting with 0% to 60% EtOAc in hexanes) to give compound T30 (31 mg, 48% yield) as a white solid. m/z=436 (M+1); $^1$H NMR (400 MHz, CDCl$_3$) δ 8.05 (s, 1H), 7.67 (m, 2H), 7.43 (m, 2H), 7.36 (m, 1H), 5.15 (pent, J=7.3 Hz, 1H), 3.79 (dt, J=7.8, 14.0 Hz, 2H), 3.50 (dd, J=7.7, 13.5 Hz, 1H), 3.34 (m, 1H), 2.83 (m, 5H), 2.27 (dt, J=1.9, 12.6 Hz, 1H), 2.09 (m, 1H), 1.64 (m, 1H), 1.56 (s, 3H), 1.37 (d, J=6.8 Hz, 3H).

Compound 31a: Compound 4 (200 mg, 0.62 mmol) and 2-hydrazino-5-methyl-pyridine hydrochloride (198 mg, 1.24 mmol) in EtOH (4 mL) was heated in Biotage microwave at 120° C. for 2 h and then cooled to room temperature. The mixture was concentrated. The residue was diluted with EtOAc and washed with water. The organic extract was dried over $Na_2SO_4$, filtered, and concentrated. The residue was purified by column chromatography (silica gel, eluting with 0% to 50% EtOAc in hexanes) to give compound 31a (215 mg, 85% yield) as a white solid. m/z=411 (M+1).

Compound 32a: Compound 31a (215 mg, 0.52 mmol) was dissolved in MeOH (2.6 mL). Sodium methoxide (25 wt. % in methanol, 239 µL, 1.04 mmol) was added. The reaction mixture was stirred at 55° C. for 1 h and cooled to room temperature. The mixture was partitioned between 10% aq. $NaH_2PO_4$ (10 mL) and EtOAc (20 mL). The organic extract was washed with water, dried with $Na_2SO_4$, filtered, and concentrated. The residue was purified by column chromatography (silica gel, eluting with 0% to 50% EtOAc in hexanes) to give compound 32a (187 mg, 87% yield) as a white solid. m/z=411 (M+1).

T31: Compound 32a (187 mg, 0.46 mmol) was dissolved in anhydrous DMF (1 mL), and the solution was cooled to 0° C. 1,3-dibromo-5,5-dimethylhydantoin (65 mg, 0.23 mmol) in DMF (1.3 mL) was added. The reaction was stirred at 0° C. for 1 h. Pyridine (183 µL, 2.27 mmol) was added. The reaction was heated at 55° C. for 3 h and cooled to room temperature. EtOAc (20 mL) was added. The mixture was washed with water (3×15 mL). The organic extract was dried with $Na_2SO_4$, filtered, and concentrated. The residue was diluted with toluene and concentrated to remove residual pyridine. The residue was purified by column chromatography (silica gel, eluting with 0% to 50% EtOAc in hexanes) to give compound T31 (145 mg, 78% yield) as a white solid. m/z=409 (M+1); $^1$H NMR (400 MHz, CDCl$_3$) δ 8.53 (s, 1H), 8.27 (td, J=0.8, 2.5, 1H), 7.94 (d, J=8.4 Hz, 1H), 7.76 (m, 2H), 7.70 (ddd, J=0.7, 2.4, 8.4 Hz, 1H), 7.45 (m, 2H), 7.38 (m, 1H), 2.93 (ddd, J=1.7, 6.0, 16.1 Hz, 1H), 2.83 (ddd, J=6.2, 11.5, 16.2, 1H), 2.65 (td, J=6.8, 13.6 Hz, 1H), 2.42 (s, 3H), 2.21 (dt, J=2.1, 12.6 Hz, 1H), 2.10 (m, 1H), 1.94 (s, 3H), 1.80 (m, 1H), 1.35 (d, J=6.8 Hz, 3H).

Compound 31b: Compound 4 (200 mg, 0.62 mmol) and 5-hydrazinyl-2-methylpyridine hydrochloride (198 mg, 1.24 mmol) in EtOH (4 mL) was heated in Biotage microwave at 120° C. for 2 h and then cooled to room temperature. The mixture was concentrated. The residue was diluted with EtOAc (20 mL) and washed with water (3×10 mL). The organic extract was dried over $Na_2SO_4$, filtered, and concentrated. The residue was purified by column chromatography (silica gel, eluting with 0% to 35% acetone in hexanes) to give compound 31b (205 mg, 81% yield) as a white solid. m/z=411 (M+1).

Compound 32b: A mixture of compound 31b (205 mg, 0.50 mmol) and $K_2CO_3$ (345 mg, 2.50 mmol) in MeOH (5 mL) was stirred at room temperature for 15 h. 10% aq. $NaH_2PO_4$ (15 mL) was added. The mixture was stirred for 5 min and extracted with EtOAc (20 mL). The organic extract was dried over $Na_2SO_4$, filtered, and concentrated. The residue was purified by column chromatography (silica gel, eluting with 0% to 35% acetone in hexanes) to give compound 32b (185 mg, 90% yield) as a white solid. m/z=411 (M+1).

T32: Compound T32 (off-white solid, 150 mg, 82% yield) was synthesized from compound 32b (184 mg, 0.45 mmol) using the same procedure as described for the synthesis of T31. Compound T32 was purified by column chromatography (silica gel, eluting with 0% to 35% acetone in hexanes). m/z=409 (M+1); $^1$H NMR (400 MHz, CDCl$_3$, 1:1 mixture of atropisomers) δ [8.69 (s), 8.69 (s); 1:1; 1H], 7.74 (dd, J=2.6, 8.2 Hz, 1H), 7.70 (m, 2H), 7.52 (s, 1H), 7.42 (m, 3H), 7.36 (m, 1H), 2.96 (ddd, J=1.6, 6.3, 16.2 Hz, 1H), 2.87 (ddd, J=6.4, 11.4, 16.1 Hz, 1H), 2.72 (s, 3H), 2.56 (qd, J=6.7, 13.5 Hz, 1H), 2.28 (dt, J=2.1, 12.7 Hz, 1H), 2.15 (dd, J=6.0, 14.4 Hz, 1H), 1.80 (m, 1H), 1.59 (s, 314), 1.34 (d, J=6.7 Hz, 3H).

Compound 33: Compound 4 (200 mg, 0.62 mmol) and (3-bromophenyl)hydrazine hydrochloride (276 mg, 1.23 mmol) in EtOH (4 mL) was heated in Biotage microwave at 120° C. for 4 h and then cooled to room temperature. The mixture was diluted with EtOAc and washed 1N aq. HCl and water. The organic extract was dried over $Na_2SO_4$, filtered, and concentrated. The residue was purified by column chromatography (silica gel, eluting with 0% to 35% EtOAc in hexanes) to give compound 33 (250 mg, 85% yield) as a white solid. m/z=474 & 476 (M+1).

Compound 34: Compound 33 (247 mg, 0.52 mmol) was dissolved in MeOH (2.6 mL). Sodium methoxide (25 wt. % in methanol, 240 μL, 1.05 mmol) was added. The reaction mixture was stirred at 55° C. for 1 h and cooled to room temperature. The mixture was treated with 10% aq. $NaH_2PO_4$ (10 mL) to adjust pH<7 and extracted twice with EtOAc. The combined organic extracts were dried with $Na_2SO_4$, filtered, and concentrated. The residue was purified by column chromatography (silica gel, eluting with 0% to 50% EtOAc in hexanes) to give compound 34 (257 mg, quantitative yield) as a white solid. m/z=474 & 476 (M+1).

T33: Compound 34 (157 mg, 0.33 mmol) was dissolved in anhydrous DMF (0.8 mL), and the solution was cooled to 0° C. 1,3-dibromo-5,5-dimethylhydantoin (47 mg, 0.16 mmol) in DMF (0.8 mL) was added. The reaction was stirred at 0° C. for 1.5 h. Pyridine (134 μL, 1.66 mmol) was added. The reaction was heated at 55° C. for 3 h and cooled to room temperature. EtOAc (20 mL) was added. The mixture was washed with 1 N aq. HCl (10 mL) and water (3×15 mL). The organic extract was dried with $Na_2SO_4$, filtered, and concentrated. The residue was purified by column chromatography (silica gel, eluting with 0% to 50% EtOAc in hexanes) to give compound T33 (123 mg, 78% yield) as a yellow solid. m/z=472 & 474 (M+1); $^1$H NMR (400 MHz, $CDCl_3$) δ 7.72 (m, 4H), 7.53 (s, 1H), 7.48 (m, 2H), 7.42 (m, 2H), 7.36 (m, 1H), 2.96 (ddd, J=1.5, 6.3, 16.2 Hz, 1H), 2.87 (m, 1H), 2.56 (qd, J=6.7, 13.4 Hz, 1H), 2.26 (dt, J=2.1, 12.7 Hz, 1H), 2.15 (dd, J=6.5, 13.8 Hz, 1H), 1.80 (m, 11H), 1.59 (s, 3H), 1.33 (d, J=6.7 Hz, 3H).

T34: A mixture of compound T33 (73 mg, 0.15 mmol), 3-pyridinylboronic acid (29 mg, 0.24 mmol) and $K_3PO_4$ (99 mg, 0.47 mmol) in 1,4-dioxane (0.72 mL) and DMF (0.36 mL) in a vial was sparged with $N_2$ for 5 min. Tetrakis(triphenylphosphine)palladium(0) (9 mg, 0.008 mmol) was added. The vial was sealed and heated at 90° C. for 3 h. The mixture was cooled to room temperature and diluted with EtOAc (20 mL). The mixture was washed with water (4×10 mL). The organic extract was dried with $Na_2SO_4$, filtered, and concentrated. The residue was purified by column chromatography (silica gel, eluting with 0% to 50% acetone in hexanes) to give partially purified product, which was purified again by column chromatography (silica gel, eluting with 0% to 30% acetone in $CH_2Cl_2$) to give compound T34 (22 mg, 30% yield) as a white solid. m/z=471 (M+1); $^1$H NMR (400 MHz, $CDCl_3$) δ 8.90 (dd, J=0.8, 2.5 Hz, 1H), 8.66 (dd, J=1.6, 4.8 Hz, 1H), 7.93 (ddd, J=1.6, 2.4, 7.9 Hz, 1H), 7.81 (ddd, J=1.1, 1.8, 7.8 Hz, 1H), 7.73 (m, 4H), 7.62 (s, 1H), 7.57 (ddd, J=1.1, 2.1, 7.8 Hz, 1H), 7.42 (m, 3H), 7.36 (m, 1H), 2.98 (m, 1H), 2.90 (ddd, J=6.5, 11.4, 16.2 Hz, 1H), 2.55 (qd, J=6.7, 13.4 Hz, 1H), 2.29 (dt, J=2.1, 12.7 Hz, 1H), 2.17 (m, 1H), 1.82 (tdd, J=6.2, 12.2, 18.6 Hz, 1H), 1.61 (s, 3H), 1.33 (d, J=6.7 Hz, 3H).

Compound 35: A mixture of compound 34 (50 mg, 0.11 mmol), phenylboronic acid (19 mg, 0.16 mmol) and $K_3PO_4$ (67 mg, 0.32 mmol) in 1,4-dioxane (0.5 mL) and DMF (0.25 mL) in a vial was sparged with $N_2$ for 3 min. Tetrakis(triphenylphosphine)palladium(0) (6 mg, 0.005 mmol) was added. The vial was sealed and heated at 90° C. for 4.5 h. The mixture was cooled to room temperature and partitioned between EtOAc (20 mL) and 10% aq. $NaH_2PO_4$ (15 mL). The organic extract was separated and washed with water (3×15 mL). The organic extract was dried with $Na_2SO_4$, filtered, and concentrated. The residue was purified by column chromatography (silica gel, eluting with 0% to 50% EtOAc in hexanes) to give compound 35 (39 mg, 78% yield) as a white solid. m/z=472 (M+1); $^1$H NMR (400 MHz, $CDCl_3$)

T35: Compound 35 (39 mg, 0.083 mmol) was dissolved in anhydrous DMF (0.4 mL), and the solution was cooled to 0° C. 1,3-dibromo-5,5-dimethylhydantoin (12 mg, 0.041 mmol) in DMF (0.4 mL) was added. The reaction was stirred at 0° C. for 1.5 h. Pyridine (34 μL, 0.42 mmol) was added. The reaction was heated at 55° C. for 3 h and cooled to room temperature. EtOAc (20 mL) was added. The mixture was washed with 1 N aq. HCl (10 mL) and water (3×10 mL). The organic extract was dried with $Na_2SO_4$, filtered, and concentrated. The residue was purified by column chromatography (silica gel, eluting with 0% to 50% EtOAc in hexanes) to give compound T35 (28 mg, 72% yield) as a yellow solid. m/z=470 (M+1); $^1$H NMR (400 MHz, $CDCl_3$) δ 7.80 (m, 1H), 7.73 (m, 3H), 7.64 (m, 4H), 7.45 (m, 7H), 2.98 (m, 1H), 2.90 (m, 1H), 2.55 (qd, J=6.7, 13.4 Hz, 1H), 2.29 (dt, J=2.1, 12.7 Hz, 1H), 2.15 (dd, J=6.4, 13.7 Hz, $1H_1$), 1.81 (m, 1H), 1.59 (s, 3H), 1.33 (d, J=6.7 Hz, 3H).

Compound 36: Compound 4 (1.00 g, 3.09 mmol) and (4-bromophenyl)hydrazine hydrochloride (1.38 g, 6.17 mmol) in EtOH (17 mL) was heated in Biotage microwave at 120° C. for 4 h and then cooled to room temperature. The mixture was concentrated. The residue was diluted with EtOAc (80 mL) and washed 1 N aq. HCl (2×30 mL) and water (30 mL). The organic extract was dried over $Na_2SO_4$, filtered, and concentrated. The residue was purified by column chromatography (silica gel, eluting with 0% to 35% EtOAc in hexanes) to give compound 36 (1.367 g, 93% yield) as a yellow solid. Compound 36 contains 11% of the pyrazole regioisomer measured by HPLC. m/z=474/476 (M+1).

Compound 37: Compound 36 (1.365 g, 2.88 mmol) was dissolved in MeOH (14 mL). Sodium methoxide (25 wt. % in methanol, 1.32 mL, 5.77 mmol) was added. The reaction mixture was stirred at 55° C. for 1 h and cooled to room temperature. The mixture was treated with 10% aq. $NaH_2PO_4$ (50 mL) to adjust pH<7 and extracted with EtOAc (2×50 mL). The combined organic extracts were dried with $Na_2SO_4$, filtered, and concentrated. The residue was purified by column chromatography (silica gel, eluting with 0% to 35% acetone in hexanes) to give compound 37 (1.120 g, 82% yield) as a white solid. m/z=474/476 (M+1).

Compound 38a: A mixture of compound 37 (90 mg, 0.19 mmol), 2-fluorophenylboronic acid (40 mg, 0.29 mmol), $K_3PO_4$ (121 mg, 0.57 mmol) and tetrakis(triphenylphosphine)palladium(0) (11 mg, 0.010 mmol) in vial was purged with $N_2$. 1,4-dioxane (1 mL) and DMF (0.5 mL) were degassed with $N_2$ and added to the vial. The vial was filled with $N_2$ and sealed. The mixture was heated at 90° C. for 4 h and then cooled to room temperature. EtOAc (10 mL) and 10% aq. $NaH_2PO_4$ (6 mL) were added. The mixture was filtered through a pad of Celite® ® eluted with EtOAc (15 mL). The filtrate was washed with water (3×15 mL). The organic extract was dried with $Na_2SO_4$, filtered, and concentrated. The residue was purified by column chromatography (silica gel, eluting with 0% to 40% EtOAc in hexanes) to give compound 38a (78 mg, 87% yield) as a white solid. m/z=490 (M+1).

T36: Compound 38a (78 mg, 0.16 mmol) was dissolved in anhydrous DMF (0.6 mL), and the solution was cooled to 0° C. 1,3-dibromo-5,5-dimethylhydantoin (23 mg, 0.080 mmol) in DMF (0.2 mL) was added. The reaction was stirred at 0° C. for 1 h. Pyridine (64 µL, 0.79 mmol) was added. The reaction was heated at 55° C. for 3 h and cooled to room temperature. EtOAc (20 mL) was added. The mixture was washed with 1 N aq. HCl (10 mL) and water (3×10 mL). The organic extract was dried with $Na_2SO_4$, filtered, and concentrated. The residue was purified by column chromatography (silica gel, eluting with 0% to 30% EtOAc in hexanes) to give compound T36 (57 mg, 73% yield) as a light yellow solid. m/z=488 (M+1); $^1$H NMR (400 MHz, $CDCl_3$) δ 8.93 (d, J=2.4 Hz, 1H), 8.68 (dd. J=1.6, 4.8 Hz, 1H), 7.97 (td, J=2.1, 8.0 Hz, 1H), 7.81 (m, 2H), 7.74 (m, 2H), 7.65 (m, 3H), 7.43 (m, 3H), 7.36 (m, 1H), 2.98 (m, 1H), 2.90 (m, 1H), 2.57 (qd, J=6.7, 13.4 Hz, 1H), 2.30 (dt, J=2.0, 12.8 Hz, 1H), 2.16 (dd, J=6.2, 14.0 Hz, 1H), 1.82 (m, 1H), 1.62 (s, 3H), 1.34 (d, J=6.7 Hz, 3H).

Compound 38b: Compound 38b (white solid, 66 mg, 74% yield) was synthesized from compound 37 (90 mg, 0.19 mmol) and 3-pyridinylboronic acid (35 mg, 0.28 mmol) using the same procedure as described for the synthesis of compound 38a. Compound 38b was purified by column chromatography (silica gel, eluting with 0% to 40% acetone in hexanes). m/z=473 (M+1).

T37: Compound 38b (66 mg, 0.14 mmol) was dissolved in anhydrous DMF (0.5 mL), and the solution was cooled to 0° C. 1,3-dibromo-5,5-dimethylhydantoin (20 mg, 0.070 mmol) in DMF (0.2 mL) was added. The reaction was stirred at 0° C. for 1.5 h. Pyridine (56 µL, 0.69 mmol) was added. The reaction was heated at 55° C. for 3 h and cooled to room temperature. EtOAc (20 mL) was added. The mixture was washed with water (4×10 mL). The organic extract was dried with $Na_2SO_4$, filtered, and concentrated. The residue was purified by column chromatography (silica gel, eluting with 0% to 20% acetone in $CH_2Cl_2$) to give compound T37 (52 mg, 79% yield) as a yellow solid. m/z=471 (M+1); $^1$H NMR (400 MHz, $CDCl_3$) 8.93 (d, J=2.4 Hz, 1H), 8.68 (dd, J=1.6, 4.8 Hz, 1H), 7.97 (td, J=2.1, 8.0 Hz, 1H), 7.81 (m, 2H), 7.74 (m, 2H), 7.65 (m, 3H), 7.43 (m, 3H), 7.36 (m, 11H), 2.98 (m, 1H), 2.90 (m, 1H), 2.57 (qd, J=6.7, 13.4 Hz, 1H), 2.30 (dt, J=2.0, 12.8 Hz, 1H), 2.16 (dd, J=6.2, 14.0 Hz, 1H), 1.82 (m, 1H), 1.62 (s, 3H), 1.34 (d, J=6.7 Hz, 3H).

Compound 38c: Compound 38c (white solid, 58 mg, 62% yield) was synthesized from compound 37 (90 mg, 0.19 mmol) and 3,5-dimethylisoxazole-4-boronic acid (40 mg, 0.28 mmol) using the same procedure as described for the synthesis of compound 38a. Compound 38c was purified by column chromatography (silica gel, eluting with 0% to 25% EtOAc in $CH_2Cl_2$). m/z=491 (M+1).

T38: Compound T38 (white solid, 49 mg, 85% yield) was synthesized from compound 38c (58 mg, 0.12 mmol) using the same procedure as described for the synthesis of compound T36. Compound T38 was purified by column chromatography (silica gel, eluting with 0% to 50% EtOAc in hexanes). m/z=489 (M+1); $^1$H NMR (400 MHz, $CDCl_3$) δ 7.73 (m, 2H), 7.60 (m, 2H), 7.54 (s, 1H), 7.49 (m, 2H), 7.43 (m, 2H), 7.36 (m, 1H), 2.99 (m, 1H), 2.90 (m, 1H), 2.56 (qd, J=6.7, 13.4 Hz, 1H), 2.48 (s, 3H), 2.34 (s, 3H), 2.29 (dt, J=2.2, 12.8 Hz, 1H), 2.17 (dd, J=6.7, 13.7 Hz, 1H), 1.83 (m, 1H), 1.61 s, 3H), 1.34 (d, J=6.7 Hz, 3H).

Compound 38d: Compound 38d (light yellow solid, 65 mg, 72% yield) was synthesized from compound 37 (90 mg, 0.19 mmol) and 4-pyridinylboronic acid (35 mg, 0.28 mmol) using the same procedure as described for the synthesis of compound 38a. The reaction mixture was heated at 90° C. for 5 h. Compound 38d was purified by column chromatography (silica gel, eluting with 0% to 30% acetone in hexanes). m/z=473 (M+1).

T39: Compound 38d (65 mg, 0.14 mmol) was dissolved in anhydrous DMF (0.5 mL), and the solution was cooled to 0° C. 1,3-dibromo-5,5-dimethylhydantoin (20 mg, 0.070 mmol) in DMF (0.2 mL) was added. The reaction was stirred at 0° C. for 1 h. Pyridine (55 µL, 0.68 mmol) was added. The reaction was heated at 55° C. for 3 h and cooled to room temperature. EtOAc (20 mL) was added. The mixture was washed with water (4×10 mL). The organic extract was dried with $Na_2SO_4$, filtered, and concentrated. The residue was purified by column chromatography (silica gel, eluting with 0% to 55% acetone in hexanes) to give partially purified product. The product was dissolved in $CH_2Cl_2$ (1 mL) and EtOAc (2 mL). The mixture was heated to reflux to let the solvent evaporate. When the volume was reduced ~0.5 mL, the mixture was cooled to room temperature. The precipitated solid was collected by filtration, washed with EtOAc, and dried under vacuum to give compound T39 (40 mg, 62% yield) as a light yellow solid. m/z=471 (M+1): $^1$H NMR (400 MHz, $CDCl_3$) δ 8.74 (m, 2H), 7.86 (m, 2H), 7.73 (m, 2H), 7.65 (m, 3H), 7.58 (m, 2H), 7.42 (m, 2H), 7.36 (m, 1H), 2.99 (ddd, J=1.6, 6.3, 16.2 Hz, 1H), 2.90 (m, 1H), 2.57 (qd, J=6.7, 13.3 Hz, 1H), 2.29 (dt, J=2.1, 12.8 Hz, 1H), 2.17 (dd, J=6.8, 13.3 Hz, 1H), 1.82 (m, 1H), 1.62 (s, 3H), 1.34 (d, J=6.7 Hz, 3H).

Compound 38e: Compound 38e (white solid, 73 mg, 79% yield) was synthesized from compound 37 (90 mg, 0.19 mmol) and (3-fluorophenyl)boronic acid (40 mg, 0.29 mmol) using the same procedure as described for the synthesis of compound 38a. The reaction mixture was heated at 90° C. for 3.5 h. Compound 38e was purified by column chromatography (silica gel, eluting with 0% to 35% EtOAc in hexanes). m/z=490 (M+1).

Compound T40: Compound T40 (white solid, 57 mg, 79% yield) was synthesized from compound 38e (72 mg, 0.15 mmol) using the same procedure as described for the synthesis of compound T36. Compound T40 was purified by column chromatography (silica gel, eluting with 0% to 30% EtOAc in hexanes). m/z=488 (M+1); $^1$H NMR (400 MHz, $CDCl_3$) δ 7.78 (m, 2H), 7.74 (m, 2H), 7.66 (s, 1H), 7.60 (m, 2H), 7.41 (m, 6H), 7.12 (m, 1H), 2.98 (m, 1H), 2.90 (m, 1H), 2.56 (qd, J=6.7, 13.4 Hz, 1H), 2.29 (dt, J=2.0, 12.7 Hz, 1H), 2.16 (m, 1H), 1.82 (m, 1H), 1.61 (s, 3H), 1.34 (d, J=6.7 Hz, 3H).

Compound 38f: Compound 38f (white solid, 79 mg, 86% yield) was synthesized from compound 37 (90 mg, 0.19 mmol) and p-tolylboronic acid (39 mg, 0.29 mmol) using the same procedure as described for the synthesis of compound 38a. The reaction mixture was heated at 90° C. for 3.5 h. Compound 38f was purified by column chromatography (silica gel, eluting with 0% to 30% EtOAc in hexanes). m/z=486 (M+1).

Compound T41: Compound T41 (white solid, 59 mg, 76% yield) was synthesized from compound 38f (78 mg, 0.16 mmol) using the same procedure as described for the synthesis of compound T36. Compound T41 was purified by column chromatography (silica gel, eluting with 0% to 30% EtOAc in hexanes). m/z=484 (M+1); $^1$H NMR (400 MHz, $CDCl_3$) δ 7.76 (m, 4H), 7.70 (s, 1H), 7.56 (m, 4H), 7.42 (m, 2H), 7.33 (m, 3H), 2.98 (m, 1H), 2.90 (m, 1H), 2.56 (qd, J=6.7, 13.4 Hz, 1H), 2.43 (s, 3H), 2.29 (dt, J=2.0, 12.7 Hz, 1H), 2.15 (m, 1H), 1.81 (m, 1H), 1.60 (s, 3H), 1.34 (d, J=6.7 Hz, 3H).

Compound 38g: Compound 38g (white solid, 78 mg, 82% yield) was synthesized from compound 37 (90 mg, 0.19 mmol) and 4-hydroxymethylphenylboronic acid (43 mg, 0.28 mmol) using the same procedure as described for the synthesis of compound 38a. The reaction mixture was heated at 90° C. for 3.5 h. The crude product was purified by column chromatography (silica gel, eluting with 0% to 100% EtOAc in hexanes) to give partially purified compound 38g. The product was dissolved in CH$_2$Cl$_2$ (1 mL) and EtOAc (2 mL). The mixture was heated to reflux to let the solvent evaporate. When the volume was reduced ~0.5 mL, the mixture was cooled to room temperature and kept for 2 h. The precipitated solid was collected by filtration, washed with EtOAc, and dried under vacuum to give compound 38g. m/z=502 (M+1).

Compound T42: Compound T42 (yellow solid, 24 mg, 31% yield) was synthesized from compound 38g (78 mg, 0.16 mmol) using the same procedure as described for the synthesis of compound T36. Compound T42 was purified by column chromatography (silica gel, eluting with 0% to 30% acetone in CH$_2$Cl$_2$). m/z=500 (M+1): $^1$H NMR (400 MHz, CDCl$_3$) δ 7.80 (m, 2H), 7.74 (m, 2H), 7.69 (s, 1H), 7.66 (m, 2H), 7.58 (m, 2H), 7.50 (m, 2H), 7.42 (m, 2H), 7.35 (m, 1H), 4.79 (d, J=5.9 Hz, 2H), 2.99 (ddd, J=1.6, 6.5, 16.6 Hz, 1H), 2.90 (m, 1H), 2.56 (qd, J=6.7, 13.4 Hz, 1H), 2.29 (dt, J=2.0, 12.6 Hz, 1H), 2.15 (m, 1H), 1.82 (tt, J=6.3, 12.6 Hz, 1H), 1.74 (t, J=6.0 Hz, 1H), 1.61 (s, 3H), 1.34 (d, J=6.7 Hz, 3H).

Compound 38h: Compound 38h (white solid, 67 mg, 70% yield) was synthesized from compound 37 (90 mg, 0.19 mmol) and 2-(hydroxymethyl)phenylboronic acid (43 mg, 0.28 mmol) using the same procedure as described for the synthesis of compound 38a. Compound 38h was purified by column chromatography (silica gel, eluting with 0% to 90% EtOAc in hexanes). m/z=502 (M+1).

Compound T43: Compound T43 (off-white solid, 56 mg, 84% yield) was synthesized from compound 38h (67 mg, 0.13 mmol) using the same procedure as described for the synthesis of compound T36. Compound T43 was purified by column chromatography (silica gel, eluting with 0% to 50% EtOAc in hexanes). m/z=500 (M+1); $^1$H NMR (400 MHz, CDCl$_3$) δ 7.76 (m, 2H), 7.62 (m, 3H), 7.57 (m, 2H), 7.50 (s, 1H), 7.43 (m, 4H), 7.36 (m, 2H), 4.65 (d, J=4.6 Hz, 2H), 3.01 (ddd, J=1.5, 6.7, 16.5 Hz, 1H), 2.91 (m, 1H), 2.55 (qd, J=6.7, 13.4 Hz, 1H), 2.30 (dt, J=2.1, 12.7 Hz, 1H), 2.17 (dd, J=6.7, 13.8 Hz, 1H), 1.91 (t, J=4.9 Hz, 1H), 1.83 (m, 1H), 1.63 (s, 3H), 1.34 (d, J=6.7 Hz, 3H).

Compound 38i: Compound 38i (white solid, 82 mg, 89% yield) was synthesized from compound 37 (90 mg, 0.19 mmol) and o-tolylboronic acid (39 mg, 0.29 mmol) using the same procedure as described for the synthesis of compound 38a. Compound 38i was purified by column chromatography (silica gel, eluting with 0% to 25% acetone in hexanes). m/z=486 (M+1).

Compound T44: Compound T44 (off-white solid, 48 mg, 591% yield) was synthesized from compound 38i (82 mg, 0.17 mmol) using the same procedure as described for the synthesis of compound T36. Compound T44 was purified by column chromatography (silica gel, eluting with 0% to 30% EtOAc in hexanes). m/z=484 (M+1); $^1$H NMR (400 MHz, CDCl$_3$) δ 7.75 (m, 2H), 7.59 (s, 1H), 7.55 (m, 4H), 7.43 (m, 2H), 7.32 (m, 5H), 3.00 (ddd, J=1.3, 6.2, 16.1 Hz, 1H), 2.91 (m, 1H), 2.56 (qd, J=6.7, 13.4 Hz, 1H), 2.33 (s, 3H), 2.30 (dt, J=2.1, 12.7 Hz, 1H), 2.17 (dd, J=6.5, 13.9 Hz, 1H), 1.83 (m, 1H), 1.63 (s, 3H), 1.34 (d, J=6.7 Hz, 3H).

Compound 38j: Compound 38j (white solid, 62 mg, 65% yield) was synthesized from compound 37 (90 mg, 0.19 mmol) and 3-hydroxymethylphenylboronic acid (43 mg, 0.28 mmol) using the same procedure as described for the synthesis of compound 38a. Compound 38j was purified by column chromatography (silica gel, eluting with 0% to 70% EtOAc in hexanes). m/z=502 (M+1).

T45: Compound 38j (62 mg, 0.12 mmol) was dissolved in anhydrous DMF (0.6 mL), and the solution was cooled to 0° C. 1,3-dibromo-5,5-dimethylhydantoin (18 mg, 0.063 mmol) in DMF (0.6 mL) was added. The reaction was stirred at 0° C. for 1 h. Pyridine (50 μL, 0.62 mmol) was added. The reaction was heated at 55° C. for 4 h and cooled to room temperature. EtOAc (20 mL) was added. The mixture was washed with 1 N aq. HCl and water (3×10 mL). The organic extract was dried with Na$_2$SO$_4$, filtered, and concentrated. The residue was purified by column chromatography (silica gel, eluting with 0% to 35% acetone in hexanes) to give compound T45 (52 mg, 84% yield) as a white solid. m/z=500 (M+1): $^1$H NMR (400 MHz, CDCl$_3$) δ 7.81 (m, 2H), 7.74 (m, 2H), 7.68 (m, 2H), 7.58 (m, 3H), 7.50 (t, J=7.6 Hz, 1H), 7.42 (m, 3H), 7.35 (m, 1H), 4.81 (d, J=5.9 Hz, 2H), 2.99 (m, 1H), 2.90 (m, 1H), 2.56 (qd, J=6.7, 13.4 Hz, 1H), 2.29 (dt, J=2.0, 12.7 Hz, 1H), 2.16 (m, 1H), 1.83 (m, 1H), 1.79 (t, J=6.0 Hz, 1H), 1.61 (s, 3H), 1.34 (d, J=6.7 Hz, 3H).

Compound 38k: Compound 38k (white semisolid, 51 mg, 75% yield) was synthesized from compound 37 (64 mg, 0.13 mmol) and (4-methoxyphenyl)boronic acid (31 mg, 0.20 mmol) using the same procedure as described for the synthesis of compound 38a. The reaction was heated at 90° C. for 3 h. Compound 38k was purified by column chromatography (silica gel, eluting with 0% to 30% EtOAc in hexanes). m/z=502 (M+1).

T46: Compound T46 (off-white solid, 39 mg, 76% yield) was synthesized from compound 38k (51 mg, 0.10 mmol) using the same procedure as described for the synthesis of compound T45. Compound T46 was purified by column chromatography (silica gel, eluting with 0% to 35% EtOAc in hexanes). m/z=500 (M+1); $^1$H NMR (400 MHz, CDCl$_3$) δ 7.74 (m, 4H), 7.70 (s, 1H), 7.60 (m, 2H), 7.55 (m, 2H), 7.42 (m, 2H), 7.35 (m, 1H), 7.03 (m, 2H), 3.88 (s, 3H), 2.98 (m, 1H), 2.90 (m, 1H), 2.56 (qd, J=6.7, 13.4 Hz, 1H), 2.29 (dt, J=2.0, 12.7 Hz, 1H), 2.15 (dd, J=6.5, 13.9 Hz, 1H), 1.81 (m, 1H), 1.59 (s, 3H), 1.34 (d, J=6.7 Hz, 3H).

Compound 38l: Compound 38l (white solid, 27 mg, 78% yield) was synthesized from compound 37 (32 mg, 0.067 mmol) and (4-(dimethylamino)phenyl)boronic acid (17 mg, 0.10 mmol) using the same procedure as described for the synthesis of compound 38a. Compound 38l was purified by column chromatography (silica gel, eluting with 0% to 35% acetone in hexanes). m/z=515 (M+1).

T47: Compound 38l (26 mg, 0.051 mmol) was dissolved in anhydrous DMF (0.25 mL), and the solution was cooled to 0° C. 1,3-dibromo-5,5-dimethylhydantoin (7.2 mg, 0.025 mmol) in DMF (0.25 mL) was added. The reaction was stirred at 0° C. for 1 h. Pyridine (20 μL, 0.25 mmol) was added. The reaction was heated at 55° C. for 3 h and cooled to room temperature. EtOAc (20 mL) was added. The mixture was washed with 1 N aq. NaOH (10 mL), water (3×10 mL), and brine (10 mL). The organic extract was dried with Na$_2$SO$_4$, filtered, and concentrated. The residue was purified by column chromatography (silica gel, eluting with 0% to 40% EtOAc in hexanes) to give partially purified product and was purified again by column chromatography (silica gel, eluting with 0% to 30% acetone in hexanes) to give compound T47 (6 mg, 23% yield) as a yellow solid. m/z=513 (M+1); $^1$H NMR (400 MHz, CDCl$_3$) δ 7.74 (m, 5H), 7.57 (m, 2H), 7.51 (m, 2H), 7.41 (m, 2H), 7.34 (m, 1H), 6.83 (m, 2H), 3.03 (s, 6H), 2.98 (dd, J=5.6, 16.0 Hz, 1H), 2.89 (m, 1H), 2.55 (qd, J=6.7, 13.3 Hz, 1H), 2.29 (dt, J=2.0, 12.7 Hz, 1H), 2.15 (m, 1H), 1.81 (m, 1H), 1.59 (s, 3H), 1.33 (d, J=6.7 Hz, 3H).

Compound 39: A stirred solution of pyrimidine-4-carboxylic acid (500 mg, 4.02 mmol) and pentafluorophenol (815 mg, 4.43 mmol) in 1,4-dioxane (20 mL) under $N_2$ was treated with N,N'-dicyclohexylcarbodiimide (914 mg, 4.43 mmol). The reaction mixture was stirred at room temperature for 19 h. The precipitated urea was removed by filtration. The filtrate was concentrated. The residue was purified by column chromatography (silica gel, eluting with 30% EtOAc in hexanes) to give compound 39 (880 mg, 69% yield) as a yellow oil which crystallized on standing. m/z=291 (M+1).

Compound 40: To a stirring suspension of compound 3 (200 mg, 0.912 mmol) and magnesium bromide etherate (588 mg, 2.28 mmol) in $CH_2Cl_2$ (12 mL) was added N,N-diisopropylethylamine (0.45 mL, 2.58 mmol) dropwise at room temperature. The mixture was stirred at room temperature for 2 min. and a solution of 39 (396 mg, 1.36 mmol) in $CH_2Cl_2$ (6 mL) was added dropwise. The reaction mixture was stirred for 20 h at room temperature. Sat. aq. $KH_2PO_4$ (30 mL) was added. The mixture was extracted with EtOAc (100 mL). The organic extract was washed with water and brine, dried over $Na_2SO_4$, filtered, and concentrated. The residue was purified by column chromatography (silica gel, eluting with 50% EtOAc in hexanes) to give compound 40 (145 mg, 49% yield) as a yellow viscous oil. m/z=326 (M+1).

Compound 41: A mixture of compound 40 (145 mg, 0.445 mmol), biphenyl-4-yl hydrazine hydrochloride (196 mg, 0.897 mmol) and EtOH (3 mL) was heated in Biotage microwave at 120° C. for 2 h and then cooled to room temperature. The solvent was removed in vacuo and the residue was taken up in EtOAc. The mixture was washed with sat. aq. $KH_2PO_4$, and brine. The organic extract was dried with $Na_2SO_4$, filtered, and concentrated. The residue was purified by column chromatography (silica gel, eluting with 50% EtOAc in hexanes) to give compound 41 (142 mg, 67% yield) as an orange glass. m/z=474 (M+1).

Compound 42: A solution of 41 (138 mg, 0.291 mmol) in MeOH (10 mL) was treated with potassium carbonate (80 mg, 0.582 mmol). The reaction mixture was stirred at room temperature for 24 h and then concentrated. The residue was partitioned between EtOAc and sat. aq. $KH_2PO_4$. The organic extract was washed with brine, dried with $Na_2SO_4$, filtered, and concentrated. The residue was purified by column chromatography (silica gel, eluting with 50% EtOAc in hexanes) to give compound 42 (113 mg, 82% yield) as a yellow glass. m/z=474 (M+1).

T48: A solution of 42 (112 mg, 0.236 mmol) in anhydrous DMF (3 mL) was cooled to 0° C. under nitrogen. A solution of 1,3-dibromo-5,5-dimethylhydantoin (37 mg, 0.129 mmol) in anhydrous DMF (1 mL) was added. The mixture was stirred at 0° C. for 40 min, and then anhydrous pyridine (0.19 mL, 2.36 mmol) was added. The reaction mixture was heated at 60° C. for 4 h and then cooled to room temperature. The reaction mixture was partitioned between EtOAc and sat. aq. $KH_2PO_4$. The organic phase was separated. The aqueous phase was extracted with EtOAc. The combined organic extracts were washed with brine, dried over $Na_2SO_4$, filtered, and concentrated. The residue was purified by column chromatography (silica gel, eluting with 3% MeOH in $CHCl_3$) to give partially purified product and was purified again by column chromatography (silica gel, eluting with 30% EtOAc in $CH_2Cl_2$), and then purified again using a third column chromatography (silica gel, eluting with 50% EtOAc in hexanes) to give compound T48 (74 mg, 66% yield) as a white solid. m/z=472 (M+1); $^1$H NMR (400 MHz, $CDCl_3$) δ 9.23 (d, J=1.4 Hz, 1H), 8.71 (d, J=5.4 Hz, 1H), 7.95 (dd, J=1.4, 5.4 Hz, 1H), 7.83 (m, 2H), 7.67 (m, 2H), 7.62 (s, 1H), 7.58 (m, 2H), 7.52 (m, 2H), 7.45 (m, 1H), 3.42 (dd, J=5.3, 18.0 Hz, 1H), 2.99 (ddd, J=6.9, 11.8, 17.3 Hz, 1H), 2.56 (qd, J=6.7, 13.4 Hz, 1H), 2.27 (dt, J=2.1, 12.7 Hz, 1H), 2.17 (dd, J=6.8, 14.0 Hz, 1H), 1.82 (m, 1H), 1.61 (s, 3H), 1.34 (d, J=6.7 Hz, 3H).

Compound 43: A mixture of 40 (200 mg, 0.614 mmol), (4-bromophenyl)hydrazine hydrochloride (274 mg, 1.23 mmol) and EtOH (3 mL) was heated in Biotage microwave at 100° C. for 2 h and then cooled to room temperature. The solvent was removed in vacuo and the residue was taken up in EtOAc. The mixture was washed with sat. aq. $KH_2PO_4$ and brine. The organic extract was dried with $Na_2SO_4$, filtered, and concentrated. The residue was purified by column chromatography (silica gel, eluting with 40% EtOAc in hexanes) to give compound 43 (261 mg, 89% yield) as a yellow glass. m/z=476 & 478 (M+1).

Compound 44: A solution of 43 (257 mg, 0.539 mmol) in MeOH (15 mL) was treated with potassium carbonate (149 mg, 1.07 mmol). The reaction mixture was stirred at room temperature for 23 h and then concentrated. The residue was partitioned between EtOAc and sat. aq. $KH_2PO_4$. The organic extract was washed with brine, dried with $Na_2SO_4$, filtered, and concentrated. The residue was purified by column chromatography (silica gel, eluting with 50% EtOAc in hexanes) to give compound 44 (205 mg, 80% yield) as a white glass. m/z=476 & 478 (M+1).

Compound 45a (T185): A thick wall glass vessel was charged with 44 (204 mg, 0.428 mmol), potassium phosphate tribasic (272 mg, 1.28 mmol), tetrakis(triphenylphosphine)palladium (25 mg, 0.021 mmol), 5-fluoropyridine-3-boronic acid (91 mg, 0.642 mmol), anhydrous 1,4-dioxane (2 mL) and anhydrous DMF (1 mL). The mixture was sparged with $N_2$. The vessel was sealed. The reaction mixture was heated at 90° C. for 21 h and then cooled to room temperature. The mixture was diluted with EtOAc and filtered through a pad of Celite®. The filtrate was washed with sat. aq. $KH_2PO_4$ and brine, dried over $Na_2SO_4$, filtered, and concentrated. The residue was purified by column chromatography (silica gel, eluting with 20% EtOAc in hexanes) to give compound 45a (149 mg, 71% yield). Compound 45a was contaminated with triphenylphosphine oxide, which was used in the next step without further purification. m/z=493 (M+1); $^1$H NMR (400 MHz, $CDCl_3$) δ 9.22 (m, 1H), 8.75 (br s, 1H), 8.69 (m, 1H), 8.54 (m, 1H), 7.92 (dd, J=1.4, 5.4 Hz, 1H), 7.76 (m, 2H), 7.68 (m, 1H), 7.57 (m, 2H), 3.54 (dd, J=5.7, 13.5 Hz, 1H), 3.37 (m, 1H), 2.93 (ddd, J=6.7, 12.0, 17.7 Hz, 1H), 2.53 (qd, J=6.4, 12.8 Hz, 1H), 1.98 (m, 5H), 1.59 (s, 3H), 1.26 (m, 3H).

T49: A solution of 45a (148 mg, 0.300 mmol) in anhydrous DMF (3 mL) was cooled to 0° C. under nitrogen. A solution of 1,3-dibromo-5,5-dimethylhydantoin (47 mg, 0.165 mmol) in anhydrous DMF (1 mL) was added. The mixture was stirred at 0° C. for 60 min, and then anhydrous pyridine (0.24 mL, 2.97 mmol) was added. The reaction mixture was heated at 60° C. for 4 h and then cooled to room temperature. The reaction mixture was partitioned between EtOAc and sat. aq. $KH_2PO_4$. The organic phase was separated. The aqueous phase was extracted with EtOAc. The combined organic extracts were washed with brine, dried over $Na_2SO_4$, filtered, and concentrated. The residue was purified by column chromatography (silica gel, eluting with 50% EtOAc in hexanes) to give partially purified product, was dissolved in a minimal amount of 1,4-dioxane, and kept at 5° C. for 1 h. The precipitated solid was collected by filtration and dried in vacuum to give compound T49 (38 mg, 26% yield) as a yellow solid. m/z=491 (M+1): $^1$H NMR (400 MHz, $CDCl_3$) δ 9.23 (d, J=1.4 Hz, 1H), 8.77 (t, J=1.7 Hz, 1H), 8.71 (d, J=5.3 Hz, 1H), 8.56 (d, J=2.7 Hz, 1H), 7.93

(dd, J=1.5, 5.4 Hz, 1H), 7.84 (m, 2H), 7.67 (m, 3H), 7.57 (s, 1H), 3.42 (m, 1H), 2.99 (ddd, J=6.9, 11.8, 18.1 Hz, 1H), 2.57 (m, 1H), 2.27 (dt, J=2.1, 12.7 Hz, 1H), 2.18 (m, 1H), 1.83 (tdd, J=6.2, 12.6, 18.7 Hz, 1H), 1.63 (s, 3H), 1.34 (d, J=6.7 Hz, 3H).

Compound 45b: Compound 44 (200 mg, 0.42 mmol) was taken up in 1,4-dioxane (2 mL) and DMF (1 mL). $K_3PO_4$ (270 mg, 1.27 mmol), $Pd(PPh_3)_4$ (25 mg, 0.021 mmol) and pyrimidin-5-ylboronic acid (80 mg, 0.65 mmol) were added. The mixture was sparged with $N_2$ for 10 min and then stirred at 90° C. for 4 h. After cooled to room temperature, the reaction mixture was filtered. The filtrate was concentrated. The residue was purified by column chromatography (silica gel, eluting with 0% to 100% EtOAc in hexanes) to give compound 45b (150 mg, 75% yield) as a solid. m/z=476 (M+1).

T50: A solution of compound 45b (150 mg, 0.32 mmol) was in dry DMF (2 mL) was cooled to 0° C. A solution of 1,3-dibromo-5,5-dimethylhydantoin (47 mg, 0.16 mmol) in DMF (1 mL) was added. The reaction mixture stirred at 0° C. for 2 h. Pyridine (2 mL, 24.73 mmol) was added. The reaction was heated at 60° C. for 4 h and then concentrated. The residue was diluted with EtOAc and was washed with water, and brine. The organic extract was dried with $MgSO_4$, filtered, and concentrated. The residue was purified by column chromatography (silica gel, eluting with 0% to 100% EtOAc in hexanes) to give T50 (90 mg, 60% yield) as a light yellow solid. m/z=474 (M+1); $^1H$ NMR (400 MHz, $CDCl_3$) δ 9.31 (d, J=0.7 Hz, 1H), 9.23 (d, J=1.2 Hz, 1H), 9.07 (m, 2H), 8.71 (dd, J=0.7, 5.3 Hz, 1H), 7.93 (td, J=1.1, 5.4 Hz, 1H), 7.86 (m, 2H), 7.69 (m, 2H), 7.57 (s, 1H), 3.42 (m, 1H), 2.99 (ddd, J=6.9, 11.8, 18.0 Hz, 1H), 2.57 (qd, J=6.7, 13.4 Hz, 1H), 2.27 (dt, J=2.1, 12.8 Hz, 1H), 2.18 (dd, J=6.9, 13.9 Hz, 1H), 1.84 (m, 1H), 1.63 (s, 3H), 1.34 (d, J=6.7 Hz, 3H).

Compound 45c: Compound 45c (solid, 110 mg, 55% yield) was synthesized from compound 44 (200 mg, 0.42 mmol) and pyridin-3-ylboronic acid (80 mg, 0.65 mmol) using the same procedure as described for the synthesis of compound 45b. The reaction was heated at 90° C. for 5 h. Compound 45c was purified by column chromatography (silica gel, eluting with 0% to 100% EtOAc in hexanes). m/z=475 (M+1).

T51: A solution of compound 45c (110 mg, 0.23 mmol) in dry DMF (2 mL) was cooled to 0° C. A solution of 1,3-dibromo-5,5-dimethylhydantoin (35 mg, 0.12 mmol) in DMF (1 mL) was added. The reaction stirred at 0° C. for 2 h. Pyridine (2 mL, 24.73 mmol) was added. The reaction was stirred at 60° C. for 4 h and then concentrated. The residue was diluted with EtOAc and was washed with water and brine. The organic extract was dried with $MgSO_4$, filtered, and concentrated. The residue was purified by column chromatography (silica gel, eluting with 0% to 100% EtOAc in hexanes) to give T51 (75 mg, 68% yield) as an off-white solid. m/z=473 (M+1); $^1H$ NMR (400 MHz, $CDCl_3$) δ 9.23 (d, J=1.4 Hz, 1H), 8.94 (dd, J=0.8, 2.5 Hz, 1H), 8.71 (d, J=5.5 Hz, 1H), 8.69 (m, 1H), 7.98 (ddd, J=1.7, 2.4, 7.9 Hz, 1H), 7.94 (dd, J=1.5, 5.4 Hz, 1H), 7.84 (m, 2H), 7.63 (m, 2H), 7.59 (s, 1H), 7.45 (ddd, J=0.8, 4.8, 7.9 Hz, 1H), 3.42 (dd, J=5.9, 17.6 Hz, 1H), 2.99 (ddd, J=6.9, 11.8, 18.0 Hz, 1H), 2.56 (qd, J=6.7, 13.4 Hz, 1H), 2.27 (dt, J=2.1, 12.8 Hz, 1H), 2.18 (dd, J=6.9, 14.0 Hz, 1H), 1.83 (tt, J=6.4, 12.7 Hz, 1H), 1.62 (s, 3H), 1.34 (d, J=6.7 Hz, 3H).

Compound 46: Compound 4 (82 mg, 0.62 mmol) and 4-hydrazineylbenzoic acid hydrochloride (232 mg, 1.23 mmol) in EtOH (4 mL) was heated in Biotage microwave at 120° C. for 4 h and then cooled to room temperature. The mixture was concentrated. The residue was diluted with EtOAc (20 mL) and washed with water (2×15 mL). The organic extract was dried over $Na_2SO_4$, filtered, and concentrated. The residue was purified by column chromatography (silica gel, 0% to 100% acetone in hexanes) to give compound 46 (82 mg, 30% yield) and compound 47 (192 mg, 66% yield). Compound 46: light yellow solid; m/z=440 (M+1); Compound 47: light yellow solid; m/z=468 (M+1).

Compound 48: Compound 47 (80 mg, 0.18 mol) was dissolved in MeOH (1.8 mL). Sodium methoxide (25 wt. % in methanol, 104 μL, 0.45 mmol) was added. The reaction mixture was stirred at 55° C. for 2 h and cooled to room temperature. 10% aq. $NaH_2PO_4$ (15 mL) was added. The mixture was extracted with EtOAc (2×20 mL). The organic extract was dried with $Na_2SO_4$, filtered, and concentrated. The residue was purified by column chromatography (silica gel, 0% to 100% acetone in hexanes) to give compound 48 (49 mg, 61% yield) as a light yellow solid. m/z=440 (M+1).

T52: Compound T52 (brown solid, 41 mg, 85% yield) was synthesized from compound 48 (48 mg, 0.11 mmol) using the same procedure as described for the synthesis of compound T45. Compound T52 was purified by column chromatography (silica gel, eluting with 0% to 50% acetone in hexanes). m/z=438 (M+1); $^1H$ NMR (400 MHz, $CDCl_3$) δ 8.34 (m, 2H), 7.72 (m, 2H), 7.66 (m, 2H), 7.52 (s, 1H), 7.43 (m, 2H), 7.36 (m, 1H), 2.99 (dd, J=5.6, 16.6 Hz, 1H), 2.89 (m, 1H), 2.57 (qd, J=6.6, 13.4 Hz, 1H), 2.27 (dt, J=2.0, 12.7 Hz, 1H), 2.16 (m, 1H), 1.82 (m, 1H), 1.62 (s, 3H), 1.34 (d, J=6.7 Hz, 3H).

Compound 49: A thick wall glass vessel was charged with compound 40 (100 mg, 0.307 mmol), 4-bromo-2-fluorophenylhydrazine hydrochloride (148 mg, 0.614 mmol) and EtOH (3 mL). The vessel was sealed, and the reaction mixture was heated at 100° C. for 21 h. The solvent was removed in vacuo and the residue was partitioned between EtOAc and sat. aq. $KH_2PO_4$. The organic extract was washed with brine, dried with $Na_2SO_4$, filtered, and concentrated. The residue was purified by column chromatography (silica gel, 40% EtOAc in hexanes) to give compound 49 (161 mg, quantitative yield) as a yellow glass. m/z=494/496 (M+1).

Compound 50: A mixture of 49 (155 mg, 0.313 mmol) and potassium carbonate (87 mg, 0.626 mmol) in MeOH (10 mL) was stirred at room temperature for 21 h. The reaction mixture was concentrated, and the residue was partitioned between EtOAc and sat. aq. $KH_2PO_4$. The organic extract was washed with brine, dried with $Na_2SO_4$, filtered, and concentrated. The residue was purified by column chromatography (silica gel, 40% EtOAc in hexanes) to give compound 50 (103 mg, 66% yield) as a white glass. m/z=494/496 (M+1).

Compound 51: A mixture of compound 50 (102 mg, 0.206 mmol), potassium phosphate tribasic (131 mg, 0.618 mmol), tetrakis(triphenylphosphine)palladium (12 mg, 0.0103 mmol) and pyridine-3-boronic acid (38 mg, 0.309 mmol) in anhydrous 1,4-dioxane (2 mL) and anhydrous DMF (1 mL) was purged with $N_2$. The reaction vessel was sealed, and the mixture was irradiated in a Biotage microwave at 90° C. for 4 h and then cooled to room temperature. The reaction mixture was diluted with EtOAc and filtered through a pad of Celite®. The filtrate was washed with sat. aq. $KH_2PO_4$ and brine. The organic extract was washed with brine, dried with $Na_2SO_4$, filtered, and concentrated. The residue was purified by column chromatography (silica gel, 60% to 100% EtOAc in hexanes) to give compound 51 (69.5 mg, 68% yield) as a white glass. m/z=493 (M+1).

T53: A solution of 51 (69 mg, 0.140 mmol) in anhydrous DMF (3 mL) was cooled to 0° C. under nitrogen. 1,3-dibromo-5,5-dimethylhydantoin (22 mg, 0.077 mmol) in anhydrous DMF (1 mL) was added. The mixture was stirred at 0° C. for 1 h, and then anhydrous pyridine (0.11 mL, 1.36 mmol) was added. The mixture was heated at 60° C. for 4 h and then cooled to room temperature. The mixture was partitioned between EtOAc and sat. aq. $KH_2PO_4$. The organic phase was separated. The aqueous phase was extracted with EtOAc. The combined organic extracts were washed with brine dried with $Na_2SO_4$, filtered, and concentrated. The residue was purified by column chromatography (silica gel, 40% EtOAc in hexanes) to give compound T53 (52 mg, 76% yield) as a yellow solid. m/z=491 (M+1); $^1$H NMR (400 MHz, $CDCl_3$) δ 9.23 (d, J=1.5 Hz, 1H), 8.94 (d, J=2.4 Hz, 1H), 8.72 (m, 2H), 7.97 (td, J=2.0, 8.0 Hz, 1H), 7.92 (dd, J=1.4, 5.3 Hz, 1H), 7.63 (m, 4H), 7.47 (dd, J=4.8, 7.9 Hz, 1H), 3.43 (dd, J=5.8, 17.5 Hz, 1H), 2.98 (ddd, =6.8, 11.8, 18.0 Hz, 1H), 2.57 (qd, J=6.7, 13.4 Hz, 1H), 2.32 (t, J=12.7 Hz, 1H), 2.18 (dd, J=6.8, 13.8 Hz, 1H), 1.81 (qd, J=6.0, 12.5 Hz, 1H), 1.52 (s, 3H), 1.35 (d, J=6.7 Hz, 3H).

Compound 52: In a sealable vial, a mixture of compound 44 (0.51 g, 1.07 mmol), bis(pinacolato)diboron (0.41 g, 1.61 mmol) and potassium acetate (0.32 g, 3.26 mmol) in 1,4-dioxane (11 mL) was degassed and treated with [1,1'-bis(diphenylphosphino)ferrocene]-dichloropalladium(II) (78 mg, 0.11 mmol). The mixture was degassed, sealed, and heated at 100° C. for 16 h. The mixture was cooled to room temperature, diluted with EtOAc (50 mL), and washed with sat. aq. $KH_2PO_4$. The organic extract was washed with brine (50 mL), dried with $MgSO_4$, filtered, and concentrated. The residue was purified by column chromatography (silica gel, 50% EtOAc in hexanes) to give compound 52 (0.41 g, 73% yield) as light yellow solid. m/z=524 (M+1).

Compound 53a: In a sealable vial, a mixture of compound 52 (0.30 g, 0.57 mmol), 4-bromo-2-(fluoromethyl)pyridine (0.11 g, 0.58 mmol) and $K_3PO_4$ (0.36 g, 1.70 mmol) in 1,4-dioxane (4.8 mL) and DMF (1.2 mL) was degassed. Tetrakis(triphenylphosphine)palladium (0) (66 mg, 0.057 mmol) was added. The mixture was degassed again. The vial was sealed. The mixture was heated at 100° C. for 16 h. cooled to room temperature, diluted with EtOAc (50 mL), and washed with sat. aq. $KH_2PO_4$ (50 mL). The organic extract was washed with brine (50 mL); dried with $MgSO_4$, filtered, and concentrated. The residue was purified by column chromatography (silica gel, eluting with 5% MeOH in $CHCl_3$) to give compound 53a (0.17 g, 59% yield) as a light yellow solid. m/z=507 (M+1).

T54: To a stirring solution of compound 53a (0.17 g, 0.34 mmol) in degassed DMF (4 mL) at 0° C. under $N_2$ was added dropwise a solution of 1,3-dibromo-5,5-dimethylhydantoin (47 mg, 0.16 mmol) in degassed DMF (1 mL). The mixture was stirred at 0° C. for 30 min. and then pyridine (0.27 mL, 3.34 mmol) was added. The mixture was heated at 60° C. for 4 h and then concentrated. The residue was partitioned between sat. aq. $KH_2PO_4$ (25 mL) and EtOAc (25 mL). The organic extract was washed with brine (25 mL), dried with $MgSO_4$, filtered, and concentrated. The residue was purified by column chromatography (silica gel, eluting with 5% MeOH in $CHCl_3$) to give compound T54 (90 mg, 53% yield) as a light yellow solid. m/z=505 (M+1); $^1$H NMR (400 MHz, $CDCl_3$) δ 9.23 (d, J=1.4 Hz, 1H), 8.71 (m, 2H), 7.93 (m, 3H), 7.77 (m, 1H), 7.66 (m, 2H), 7.57 (s, 1H), 7.55 (dd. J=1.8, 5.1 Hz, 1H), 5.60 (d, J=46.8 Hz, 2H), 3.42 (dd, J=5.9, 17.6 Hz, 1H), 3.00 (ddd, J=6.9, 11.8, 18.1 Hz, 1H), 2.57 (qd, J=6.7, 13.4 Hz, 1H), 2.27 (dt, J=2.1, 12.7 Hz, 1H), 2.18 (dd, J=7.2, 14.2 Hz, 1H), 1.83 (tdd, J=6.4, 13.2, 19.3 Hz, 1H), 1.63 (s, 3H), 1.34 (d, J=6.7 Hz, 3H).

Compound 53b: In a sealable vial, a mixture of compound 52 (0.22 g, 0.42 mmol), (4-bromopyridin-2-yl)methanol (59 mg, 0.31 mmol) and $K_3PO_4$ (0.20 g, 0.94 mmol) in 1,4-dioxane (4 mL) and DMF (1 mL) was degassed. Tetrakis(triphenylphosphine)palladium(0) (36 mg, 0.031 mmol) was added. The mixture was degassed again. The vial was sealed. The mixture was heated at 100° C. for 16 h and then cooled to room temperature. The mixture was diluted with 10% MeOH in $CHCl_3$ (25 mL) and washed with sat. aq. $KH_2PO_4$ (25 mL). The organic extract was washed with brine (25 mL), dried with $MgSO_4$, filtered, and concentrated. The residue was purified by column chromatography (silica gel, eluting with 5% MeOH in $CHCl_3$) to give compound 53b (0.10 g, 63% yield) as a light yellow solid. m/z=505 (M+1).

T55: To a stirring solution of compound 53b (0.10 g, 0.20 mmol) in degassed DMF (3 mL) at 0° C. under $N_2$ was added dropwise a solution of 1,3-dibromo-5,5-dimethylhydantoin (31 mg, 0.11 mmol) in degassed DMF (1 mL). The mixture was stirred at 0° C. for 30 min, and then pyridine (0.16 mL, 1.98 mmol) was added. The mixture was heated at 60° C. for 4 h and then concentrated. The residue was partitioned between sat. aq. $KH_2PO_4$ (25 mL) and 10% MeOH in $CHCl_3$ (25 mL). The organic extract was washed with brine (25 mL), dried with $MgSO_4$, filtered, and concentrated. The residue was purified by column chromatography (silica gel, eluting with 5% MeOH in $CHCl_3$) to give compound T55 (26 mg, 26% yield) as a light yellow solid. m/z=503 (M+1); $^1$H NMR (400 MHz, $CDCl_3$) δ 9.23 (d, J=1.4 Hz, 1H), 8.71 (m, 2H), 7.93 (dd, J=1.5, 5.3 Hz, 1H), 7.89 (m, 2H), 7.65 (m, 2H), 7.56 (m, 2H), 7.51 (dd, J=1.7, 5.2 Hz, 1H), 4.89 (br s, 2H), 3.64 (br s, 1H), 3.42 (dd, J=5.7, 17.7 Hz, 1H), 2.99 (ddd, J=6.9, 11.8, 18.1 Hz, 1H), 2.57 (qd, J=6.7, 13.4 Hz, 1H), 2.27 (dt, J=2.0, 12.7 Hz, 1H), 2.18 (dd, J=6.9, 13.8 Hz, 1H), 1.84 (ddd, J=6.4, 12.6, 19.8 Hz, 1H), 1.62 (s, 3H), 1.34 (d, J=6.7 Hz, 3H).

Compound 54: Compound 40 (1.31 g, 4.05 mmol) and 5-bromo-2-hydrazinylpyridine hydrochloride (1.52 g, 6.77 mmol) in EtOH (10 mL) was heated at 100° C. in a Biotage microwave synthesizer for 2 h. The reaction mixture was concentrated. The residue was diluted with sat. aq. $NaHCO_3$ and extracted with EtOAc. The organic extract was dried with $MgSO_4$, filtered, and concentrated. The residue was purified by column chromatography (silica gel, eluting with 0% to 50% EtOAc in hexanes) to give compound 54 (1.4 g, 73% yield) as a solid. m/z=477/479 (M+1).

Compound 55: Compound 54 (1.4 g, 2.93 mmol) was taken up in MeOH (30 mL), and $K_2CO_3$ (2.05 g, 14.8 mmol) was added. The reaction mixture was stirred at room temperature overnight and then concentrated. The residue was neutralized by addition of sat. aq. $KH_2PO_4$ and was extracted with EtOAc. The organic extract was washed with brine, dried with $MgSO_4$, filtered, and concentrated. The residue was purified by column chromatography (silica gel, eluting with 0% to 50% EtOAc in hexanes) to give compound 55 (1.29 g, 92% yield) as a solid. m/z=477/479 (M+1).

Compound 56a: Compound 55 (260 mg, 0.55 mmol) was dissolved in 1,4-dioxane (2 mL) and DMF (1 mL). $K_3PO_4$ (350 mg, 1.65 mmol), tetrakis(triphenylphosphine)palladium(0) (50 mg, 0.043 mmol) and 4-fluorophenylboronic acid (115 mg, 0.82 mmol) were added. The mixture was sparged with $N_2$ for 10 min and then stirred at 90° C. for 16 h. After cooled to room temperature, the reaction mixture was filtered. The filtrate was concentrated. The residue was purified by column chromatography (silica gel, eluting with 0% to 50% EtOAc in hexanes) to give compound 56a (265 mg, 98% yield) as a solid. m/z=493 (M+1).

T56: Compound 56a (265 mg, 0.54 mmol) was dissolved in dry DMF (3 mL) and cooled 30 to 0° C. Bromine (95 mg, 0.59 mmol) in $CH_2Cl_2$ (1 mL) was added. The reaction was stirred at 0° C. for 2 h. Pyridine (2 mL, 24.73 mmol) was added. The mixture was heated at 60° C. for 4 h and then concentrated. The residue was diluted with water and extracted with EtOAc. The organic extract was washed with brine, dried with $MgSO_4$, filtered, and concentrated. The residue was purified by column chromatography (silica gel, eluting with 0% to 50% EtOAc in hexanes) to give compound T56 (30 mg, 11% yield) as a light orange solid. m/z=491 (M+1); $^1H$ NMR (400 MHz, $CDCl_3$) δ 9.25 (d, J=1.4 Hz, 1H), 8.77 (d, J=5.3 Hz, 1H), 8.67 (dd, J=0.8, 2.4 Hz, 1H), 8.49 (s, 1H), 8.15 (dd, J=0.8, 8.6 Hz, 1H), 8.10 (dd, J=2.4, 8.6 Hz, 1H), 8.06 (dd, J=1.4, 5.3 Hz, 1H), 7.63 (m, 2H), 7.23 (m, 2H), 3.41 (dd. J=5.6, 17.6 Hz, 1H), 2.96 (ddd, J=6.6, 11.9, 17.9 Hz, 1H), 2.68 (td, J=6.7, 13.5 Hz, 1H), 2.20 (m, 2H), 2.00 (s, 3H), 1.84 (m, 1H), 1.37 (d, J=6.8 Hz, 3H).

Compound 56b: Compound 55 (250 mg, 0.52 mmol) was dissolved in 1,4-dioxane (2 mL) and DMF (1 mL). $K_3PO_4$ (350 mg, 1.65 mmol), tetrakis(triphenylphosphine)palladium (0) (50 mg, 0.043 mmol) and pyridin-3-ylboronic acid (115 mg, 0.94 mmol) were added. The mixture was sparged with $N_2$ for 10 min and the stirred at 90° C. for 16 h. After cooled to room temperature, the reaction mixture was filtered. The filtrate was concentrated. The residue was purified by column chromatography (silica gel, eluting with 0% to 50% EtOAc in hexanes) to give compound 56b (170 mg, 68% yield) as a solid. m/z=476 (M+1).

T57: Compound 56b (170 mg, 0.36 mmol) was dissolved in dry DMF (3 mL) and cooled to 0° C. Bromine (60 mg, 0.38 mmol) in $CH_2Cl_2$ (1 mL) was added. The reaction was stirred at 0° C. for 2 h. Pyridine (2 mL, 24.73 mmol) was added. The reaction mixture was heated at 60° C. for 4 h and then concentrated. The residue was diluted with water and extracted with EtOAc. The organic extract was washed with brine, dried with $MgSO_4$, filtered, and concentrated. The residue was purified by column chromatography (silica gel, eluting with 0% to 100% EtOAc in hexanes) to give compound T57 (60 mg, 35% yield) as a white solid. m/z=474 (M+1): $^1H$ NMR (400 MHz, $CDCl_3$) δ 9.25 (d, J=1.4 Hz, 1H), 8.94 (dd, J=0.8, 2.5 Hz, 1H), 8.78 (d, J=5.3 Hz, 1H), 8.72 (m, 2H), 8.51 (s, 1H), 8.23 (dd, J=0.8, 8.5 Hz, 1H), 8.16 (dd. J=2.4, 8.6 Hz, 1H), 8.07 (dd, J=1.4, 5.3 Hz, 1H), 7.99 (ddd, J=1.6, 2.4, 7.9 Hz, 1H), 7.48 (ddd, J=0.9, 4.8, 7.8 Hz, 1H), 3.42 (m, 1H), 2.97 (ddd, J=6.6, 11.9, 17.3 Hz, 1H), 2.70 (qd, J=6.8, 13.6 Hz, 1H), 2.22 (dt, J=2.1, 12.6 Hz, 1H), 2.15 (dd, J=6.6, 13.7 Hz, 1H), 2.01 (s, 3H), 1.85 (qt, J=5.8, 12.7 Hz, 1H), 1.38 (d, J=6.8 Hz, 3H).

Compound 56c: Compound 55 (250 mg, 0.52 mmol) was dissolved in 1,4-dioxane (2 mL) and DMF (1 mL). $K_3PO_4$ (350 mg, 1.65 mmol), tetrakis(triphenylphosphine)palladium(0) (50 mg, 0.043 mmol) and 3-fluorophenylboronic acid (115 mg, 0.82 mmol) were added. The mixture was sparged with $N_2$ for 10 min and then stirred at 90° C. for 16 h. After cooled to room temperature, the reaction mixture was filtered. The filtrate was concentrated. The residue was purified by column chromatography (silica gel, eluting with 0% to 50% EtOAc in hexanes) to give compound 56c (126 mg, 49% yield) as a solid. m/z=493 (M+1).

T58: Compound 56c (125 mg, 0.25 mmol) was dissolved in dry DMF (3 mL) and cooled to 0° C. Bromine (41 mg, 0.26 mmol) in $CH_2Cl_2$ (1 mL) was added. The reaction was stirred at 0° C. for 2 h. Pyridine (2 mL, 24.73 mmol) was added. The reaction mixture was stirred at 60° C. for 4 h and then concentrated. The residue was diluted with water and extracted with EtOAc. The organic extract was washed with brine, dried with $MgSO_4$, filtered, and concentrated. The residue was purified by column chromatography (silica gel, eluting with 0% to 50% EtOAc in hexanes) to give compound T58 (80 mg, 64% yield) as an off-white solid. m/z=491 (M+1); $^1H$ NMR (400 MHz, $CDCl_3$) δ 9.25 (d, J=1.4 Hz, 1H), 8.78 (d, J=5.3 Hz, 1H), 8.71 (dd, J=0.8, 2.4 Hz, 1H), 8.51 (s, 1H), 8.18 (dd, J=0.8, 8.6 Hz, 1H), 8.12 (dd, J=2.4, 8.6 Hz, 1H), 8.06 (dd, J=1.5, 5.3 Hz, 1H), 7.48 (m, 2H), 7.37 (td, J=2.1, 9.6 Hz, 1H), 7.16 (ddt, J=1.1, 2.6, 8.2 Hz, 1H), 3.42 (dd, J=5.5, 17.6 Hz, 1H), 2.96 (ddd, J=6.6, 11.9, 17.9 Hz, 1H), 2.68 (td, J=6.7, 13.5 Hz, 1H), 2.22 (td, J=2.0, 12.6 Hz, 1H), 2.14 (m, 1H), 2.00 (s, 3H), 1.84 (qd, J=5.9, 13.0 Hz, 1H), 1.37 (d, J=6.8 Hz, 3H).

Compound 56d: Compound 55 (260 mg, 0.55 mmol) was dissolved in 1,4-dioxane (2 mL) and DMF (1 mL). $K_3PO_4$ (350 mg, 1.65 mmol), tetrakis(triphenylphosphine)palladium(0) (50 mg, 0.043 mmol) and phenylboronic acid (100 mg, 0.82 mmol) were added. The mixture was sparged with $N_2$ for 10 min and then stirred at 90° C. for 16 h. After cooled to room temperature, the reaction mixture was filtered. The filtrate was concentrated. The residue was purified by column chromatography (silica gel, eluting with 0% to 50% EtOAc in hexanes) to give compound 56d (250 mg, 97% yield) as a solid. m/z=475 (M+1).

T59: Compound 56d (250 mg, 0.53 mmol) was dissolved in dry DMF (3 mL) and cooled to 0° C. Bromine (90 mg, 0.56 mmol) in $CH_2Cl_2$ (1 mL) was added. The reaction was stirred at 0° C. for 2 h. Pyridine (2 mL, 24.73 mmol) was added. The reaction mixture was stirred at 60° C. for 4 h and then concentrated. The residue was diluted with water and extracted with EtOAc. The organic extract was washed with brine, dried with $MgSO_4$, filtered, and concentrated. The residue was purified by column chromatography (silica gel, eluting with 0% to 50% EtOAc in hexanes) to give compound T59 (27 mg, 11% yield) as an off-white solid. m/z=473 (M+1); $^1H$ NMR (400 MHz, $CDCl_3$) δ 9.25 (d, J=1.4 Hz, 1H), 8.77 (d, J=5.3 Hz, 1H), 8.72 (t, J=1.6 Hz, 1H), 8.51 (s, 1H), 8.15 (d, J=1.6 Hz, 2H), 8.07 (dd, J=1.5, 5.3 Hz, 1H), 7.66 (m, 2H), 7.53 (m, 2H), 7.47 (m, 1H), 3.42 (dd, J=5.5, 17.5 Hz, 1H), 2.96 (ddd, J=6.6, 12.0, 18.0 Hz, 1H), 2.69 (qd, J=6.8, 13.5 Hz, 1H), 2.22 (m, 1H), 2.14 (m, 1H), 2.01 (s, 3H), 1.85 (m, 1H), 1.37 (d, J=6.8 Hz, 3H).

Compound 56e: In a sealable vial, a mixture of compound 55 (0.20 g, 0.42 mmol), 3-(hydroxymethyl)phenylboronic acid (0.13 g, 0.86 mmol) and $K_3PO_4$ (0.27 g, 1.27 mmol) in 1,4-dioxane (4 mL) and DMF (1 mL) was degassed. Tetrakis(triphenylphosphine)palladium(0) (48 mg, 0.042 mmol) was added. The mixture was degassed again. The vial was sealed. The mixture was heated at 90° C. for 6 h and then at room temperature overnight. The mixture was diluted with EtOAc (50 mL) and washed with aq. $KH_2PO_4$ (50 mL). The organic extract was washed with brine (50 mL), dried with $MgSO_4$, filtered, and concentrated. The residue was purified by column chromatography (silica gel, eluting with 5% MeOH in $CHCl_3$) to give compound 56e (0.14 g, 66%) as a light yellow solid. m/z=505 (M+1).

T60: To a stirring solution of compound 56e (0.14 g, 0.28 mmol) in degassed DMF (4 mL) at 0° C. under $N_2$ was added a solution of 1,3-dibromo-5,5-dimethylhydantoin (44 mg, 0.15 mmol) in degassed DMF (1 mL) dropwise. The mixture was stirred at 0° C. for 30 min, and then pyridine (0.23 mL, 2.84 mmol) was added. The mixture was heated at 60° C. for 4 h and then concentrated. The residue was partitioned between sat. aq. $KH_2PO_4$ (25 mL) and 5% MeOH in $CHCl_3$ (25 mL). The organic extract was washed with brine (25 mL), dried with MgSO$_4$, filtered, and concentrated. The residue was purified by column chromatography (silica gel, eluting with 5% MeOH in CHCl$_3$). The product obtained was triturated with Et$_2$O. The solid was collected by filtration and dried under vacuum to give compound T60 (34 mg, 24% yield) as a light yellow solid. m/z=503 (M+1); $^1$H NMR (400 MHz, DMSO-d$_6$) δ 9.26 (d, J=1.4 Hz, 1H), 8.93 (d, J=2.4 Hz, 1H), 8.87 (d, J=5.3 Hz, 1H), 8.45 (dd, J=2.5, 8.6 Hz, 1H), 8.37 (s, 1H), 8.11 (m, 2H), 7.80 (s, 1H), 7.74 (td, J=1.5, 7.9 Hz, 1H), 7.51 (t, J=7.6 Hz, 1H), 7.43 (d, J=7.6 Hz, 1H), 5.31 (t, J=5.7 Hz, 1H), 4.62 (t, J=5.7 Hz, 2H), 3.28 (m, 1H), 2.85 (m, 2H), 2.29 (m, 1H), 2.04 (dd, J=6.5, 13.3 Hz, 1H), 1.96 (s, 3H), 1.80 (dq, J=5.7, 12.7 Hz, 1H), 1.23 (d, J=6.7 Hz, 3H).

T61: To a stirring solution of compound T60 (30 mg, 0.059 mmol) in CH$_2$Cl$_2$ (2 mL) at −78° C. under N$_2$ was added dropwise a solution of diethylaminosulfur trifluoride (14 mg, 0.087 mmol) in CH$_2$C$_2$ (1 mL). After stirring for 2 h, the cold solution was poured into cold sat. aq. NaHCO$_3$ (25 mL). The mixture was allowed to warm to room temperature and extracted with CH$_2$Cl$_2$ (25 mL). The organic extract was washed with brine (25 mL), dried with MgSO$_4$, filtered, and concentrated. The residue was purified by column chromatography (silica gel, eluting with 50% EtOAc in hexanes) to give compound T61 (12 mg, 40% yield) as an off-white solid. m/z=505 (M+1); $^1$H NMR (400 MHz, CDCl$_3$) δ 9.25 (d, J=1.4 Hz, 1H), 8.78 (d, J=5.3 Hz, 1H), 8.73 (dd, J=1.3, 2.0 Hz, 1H), 8.52 (s, 1H), 8.16 (m, 2H), 8.07 (dd. J=1.4, 5.3 Hz, 1H), 7.67 (m, 2H), 7.57 (t, J=7.6 Hz, 1H), 7.47 (dd, J=1.6, 7.7 Hz, 1H), 5.50 (d, J=47.6 Hz, 2H), 3.42 (dd, J=5.5, 17.5 Hz, 1H), 2.96 (ddd, J=6.6, 11.9, 18.0 Hz, 1H), 2.68 (m, 1H), 2.22 (dt, J=2.1, 12.6 Hz, 1H), 2.14 (dd, J=6.5, 13.6 Hz, 1H), 2.01 (s, 3H), 1.84 (m, 1H), 1.37 (d, J=6.8 Hz, 3H).

Compound 57: In a sealable vial, a mixture of compound 55 (0.25 g, 0.52 mmol), potassium cyclopropyltrifluoroborate (0.23 g, 1.55 mmol), K$_3$PO$_4$ (0.33 g, 1.55 mmol) and RuPhos (24 mg, 0.051 mmol) in toluene (3.2 mL) and water (0.8 mL) was degassed. Palladium(II) acetate (6 mg, 0.027 mmol) was added. The mixture was degassed again. The vial was sealed. The mixture was heated 95° C. for 16 h and then cooled to room temperature. The mixture was concentrated. The residue was partitioned between 5% MeOH in CHCl$_3$ (25 mL) and sat. aq. KH$_2$PO$_4$ (25 mL). The organic extract was washed with brine (25 mL), dried with MgSO$_4$, filtered, and concentrated. The residue was purified by column chromatography (silica gel, eluting with 70% EtOAc in hexanes) to give compound 57 (82 mg, 36% yield) as a light blue solid. m/z=439 (M+1).

T62: To a stirring solution of compound 57 (82 mg, 0.19 mmol) in degassed DMF (4 mL) at 0° C. under N$_2$ was added dropwise a solution of 1,3-dibromo-5,5-dimethylhydantoin (30 mg, 0.10 mmol) in degassed DMF (1 mL). The mixture was stirred at 0° C. for 30 min, and then pyridine (0.15 mL, 1.85 mmol) was added. The mixture was heated at 60° C. for 4 h and then concentrated. The residue was partitioned between sat. aq. KH$_2$PO$_4$ (25 mL) and EtOAc (25 mL). The organic extract was washed with brine (25 mL), dried with MgSO$_4$, filtered, and concentrated. The residue was purified by column chromatography (silica gel, eluting with 70% EtOAc in hexanes) to give compound T62 (52 mg, 63% yield) as a tan solid. m/z=437 (M+1); $^1$H NMR (400 MHz, CDCl$_3$) δ 9.22 (d, J=1.4 Hz, 1H), 8.74 (d, J=5.3 Hz, 1H), 8.33 (s, 1H), 8.30 (d, J=2.4 Hz, 1H), 8.02 (dd, J=1.4, 5.3 Hz, 1H), 7.88 (d, J=8.4 Hz, 1H), 7.53 (dd, J=2.5, 8.5 Hz, 1H), 3.39 (dd, J=5.8, 17.6 Hz, 1H), 2.94 (ddd, J=6.6, 12.0, 18.0 Hz, 1H), 2.65 (m, 1H), 2.17 (m, 2H), 2.00 (m, 1H), 1.95 (s, 3H), 1.84 (m, 1H), 1.35 (d, J=6.8 Hz, 3H), 1.14 (m, 2H), 0.83 (m, 2H).

Compound 58: Compound 40 (0.25 g, 0.77 mmol) and 2-hydrazinyl-5-(trifluoromethyl)pyridine (275 mg, 1.55 mmol) and 4 N HCl in 1,4-dioxane (0.4 mL) in EtOH (2 mL) were heated at 100° C. in a Biotage microwave synthesizer for 2 h. The reaction mixture was concentrated. The residue was treated with aq. NaHCO$_3$ and extracted with EtOAc. The organic extract was dried with MgSO$_4$, filtered, and concentrated. The residue was purified by column chromatography (silica gel, eluting with 0% to 35% EtOAc in hexanes) to give compound 58 (350 mg, 97% yield) as a solid. m/z=467 (M+1).

Compound 59: Compound 58 (0.34 g, 0.73 mmol) was in MeOH (10 mL) was treated with K$_2$CO$_3$ (0.5 g, 3.62 mmol). The reaction mixture was stirred at room temperature overnight and then concentrated. The residue was neutralized by addition of sat. aq. KH$_2$PO$_4$ and extracted with EtOAc. The organic extract was washed with brine, dried with MgSO$_4$, filtered, and concentrated. The residue was purified by column chromatography (silica gel, eluting with 0% to 35% EtOAc in hexanes) to give compound 59 (175 mg, 51% yield) as a solid. m/z=467 (M+1).

T63: Compound 59 (175 mg, 0.37 mmol) was dissolved in dry DMF (2 mL) and cooled to 0° C. 1,3-dibromo-5,5-dimethylhydantoin (58 mg, 0.20 mmol) in DMF (1 mL) was added. The reaction was stirred at 0° C. for 2 h, and then pyridine (2 mL, 24.73 mmol) was added. The mixture was stirred at 60° C. for 4 h and then concentrated. The residue was diluted with water and extracted with EtOAc. The organic extract was washed with brine, dried with MgSO$_4$, filtered, and concentrated. The residue was purified by column chromatography (silica gel, eluting with 0% to 35% EtOAc in hexanes) to give compound T63 (150 mg, 86% yield) as a white solid. m/z=465 (M+1); $^1$H NMR (400 MHz, CDCl$_3$) δ 9.26 (d, J=1.4 Hz, 1H), 8.80 (d, J=5.3 Hz, 1H), 8.77 (m, 1H), 8.50 (s, 1H), 8.33 (d, J=8.7 Hz, 1H), 8.16 (dd, J=2.4, 8.8 Hz, 1H), 8.06 (dd, J=1.5, 5.3 Hz, 1H), 3.41 (m, 1H), 2.95 (ddd, J=6.6, 12.0, 18.1 Hz, 1H), 2.69 (m, 1H), 2.21 (dt, J=2.1, 12.5 Hz, 1H), 2.13 (m, 1H), 1.95 (s, 3H), 1.82 (m, 1H), 1.37 (d, J=6.8 Hz, 3H).

Compound 61: A mixture of compound 40 (55 mg, 0.169 mmol) and 5-hydrazino-2-phenylpyridine hydrochloride (75 mg, 0.338 mmol) in EtOH (3 mL) was heated in Biotage microwave synthesizer at 100° C. for 5 h. The mixture was cooled to room temperature and concentrated. The residue was partitioned between EtOAc and sat. aq. KH$_2$PO$_4$. The organic extract was washed with brine, dried with Na$_2$SO$_4$, filtered, and concentrated. The residue was purified by column chromatography (silica gel, eluting with 50% EtOAc in hexanes) to give compound 61 (64 mg, 80% yield) as a yellow glass. m/z=475 (M+1).

Compound 62: A mixture of 61 (63 mg, 0.132 mmol) and potassium carbonate (36 mg, 0.265 mmol) in MeOH (7 mL) was stirred at room temperature for 20 h. The reaction mixture was concentrated, and the residue was partitioned between EtOAc and sat. aq. KH$_2$PO$_4$. The organic extract was washed with brine, dried with Na$_2$SO$_4$, filtered, and concentrated. The residue was triturated with MeOH to give compound 62 (35 mg, 56% yield) as an orange solid. m/z=475 (M+1).

T64: A solution of 62 (35 mg, 0.074 mmol) in anhydrous DMF (3 mL) was cooled to 0° C. under nitrogen. A solution of 1,3-dibromo-5,5-dimethylhydantoin (11.5 mg, 0.040 mmol) in anhydrous DMF (1 mL) was added. The mixture was stirred at 0° C. for 1 h. Anhydrous pyridine (0.06 mL, 0.742 mmol) was added. The reaction mixture was heated at 60° C. for 4 h and then cooled to room temperature. The mixture was partitioned between EtOAc and sat. aq. $KH_2PO_4$. The organic phase was separated. The aqueous phase was extracted with EtOAc. The combined organic extracts were washed with brine, dried with $Na_2SO_4$, filtered, and concentrated. The residue was triturated with MeOH to give compound T64 (21 mg, 60% yield) as an off-white solid. m/z=473 (M+1); $^1$H NMR (400 MHz, $CDCl_3$) δ 9.24 (s, 1H), 8.86 (d, J=2.6 Hz, 1H), 8.73 (d, J=5.3 Hz, 1H), 8.11 (d, J=7.2 Hz, 2H), 8.02 (d, J=8.4 Hz, 1H), 7.92 (m, 2H), 7.54 (m, 4H), 3.42 (dd, J=5.9, 17.6 Hz, 1H), 2.99 (ddd, J=6.8, 11.6, 17.9 Hz, 1H), 2.57 (m, 1H), 2.27 (t, J=12.8 Hz, 1H), 2.18 (dd, J=6.8, 14.1 Hz, 1H), 1.84 (m, 1H), 1.64 (s, 3H), 1.34 (d, J=6.7 Hz, 3H).

Compound 64: A solution of compound 63 (4.31 g, 18.08 mmol) in ethyl formate (50 mL, 0.61 mol) and benzene (50 mL) was treated with sodium methoxide (30 wt. % MeOH, 17 mL, 91 mmol) dropwise at room temperature under $N_2$. The mixture was stirred at room temperature for 16 h and then concentrated. The residue was partitioned between sat. aq. $KH_2PO_4$ (100 mL) and $Et_2O$ (100 mL). The organic extract was washed with brine (100 mL), dried with $MgSO_4$, filtered, and concentrated to give compound 64 (4.69 g, 97% yield) as light pink solid. m/z=267 (M+1, 100%).

Compounds 65 and 66: A solution of compound 64 (0.66 g, 2.48 mmol) and acetic acid (1.4 mL, 24.4 mmol) in EtOH (25 mL) was degassed, and cooled to 0° C. Biphenyl-4-ylhydrazine (0.55 g, 2.99 mmol) was added. The mixture was allowed to warm to room temperature under $N_2$ overnight and then concentrated. The residue was partitioned between sat. aq. $NaHCO_3$ (50 mL) and EtOAc (50 mL). The organic extract was washed with brine (50 mL), dried with $MgSO_4$, filtered, and concentrated. The residue was purified by column chromatography (silica gel, eluting with 25% EtOAc in hexanes) to give compound 65 (0.49 g, 47% yield) and compound 66 (0.46 g, 45% yield). Compound 65: orange-yellow solid; m/z=415 (M+1). Compound 66: yellow solid; m/z=415 (M+1).

Compound 67: To a stirring suspension of compound 66 (1.31 g, 3.16 mmol) and sodium carbonate (1.67 g, 15.76 mmol) in $CH_2Cl_2$ (30 mL) was added dropwise a solution of bromine (1.5 g, 9.4 mmol) in $CH_2Cl_2$ (10 mL) at −10° C. under $N_2$. After stirring for 4 h, the cold reaction mixture was quenched with dropwise addition of sat. aq. sodium thiosulfate (50 mL). The ice bath was removed. The mixture was stirred at room temperature for 1 h and then concentrated. The residue was extracted with EtOAc (50 mL). The organic extract was washed with brine (50 mL), dried with $MgSO_4$, filtered, and concentrated. The residue was purified by column chromatography (silica gel, eluting with 25% EtOAc in hexanes) to give compound 67 (1.32 g, 85% yield) as a light orange solid. m/z=493 & 495 (M+1).

Compound 68a: In a sealable vial, a mixture of compound 67 (0.25 g, 0.51 mmol), 4-fluorophenylboronic acid (0.14 g, 1.00 mmol) and potassium phosphate (0.32 g, 1.51 mmol) in 1,4-dioxane (4 mL) and DMF (1 mL) was degassed and treated with tetrakis(triphenylphosphine)palladium(0) (58 mg, 0.050 mmol). The mixture was degassed again. The vial was sealed, and the mixture was heated at 100° C. for 16 h. After cooled to room temperature, the mixture was diluted with EtOAc (50 mL) and washed with 1 N aq. NaOH (50 mL). The organic extract was washed with brine (50 mL), dried with $MgSO_4$, filtered, and concentrated. The residue was purified by column chromatography (silica gel, eluting with 1/5/5 EtOAc/$CH_2Cl_2$/hexanes) to give compound 68a (0.22 g, 85% yield) as a yellow oil. m/z=509 (M+1).

Compound 69a: A solution of compound 68a (0.22 g, 0.43 mmol) and 3 N aq. HCl (1.4 mL, 4.2 mmol) in MeOH (10 mL) was stirred at room temperature under $N_2$ overnight. The mixture was concentrated. The residue was cooled and basified with 10% aq. $NH_4OH$ to pH 9-10. The mixture was extracted with $CHCl_3$ (25 mL). The organic extract was washed with brine (25 mL), dried with $MgSO_4$, filtered, and concentrated to give compound 69a (0.22 g, quantitative yield) as a yellow oil. m/z=465 (M+1).

Compound 70a: A solution of compound 69a (0.22 g, ≤0.43 mmol) in ethyl formate (10 mL, 0.12 mol) was treated with sodium methoxide (30 wt. % in MeOH, 0.40 mL, 2.13 mmol). The mixture was stirred at room temperature under $N_2$ overnight and then concentrated. The residue was partitioned between EtOAc (50 mL) and sat. aq. $KH_2PO_4$ (50 mL). The organic extract was washed with brine (50 mL), dried with $MgSO_4$, filtered, and concentrated to give compound 70a (0.17 g, 80% yield) as an orange solid. m/z=493 (M+1).

Compound 71a: A solution of compound 70a (0.17 g, 0.34 mmol), acetic acid (0.20 mL, 3.50 mmol) and hydroxylamine hydrochloride (35 mg, 0.50 mmol) in EtOH (10 mL) was stirred at 60° C. for 2 h and then at room temperature overnight. The mixture was concentrated. The residue was partitioned between sat. aq. $NaHCO_3$ (25 mL) and EtOAc (25 mL). The organic extract was washed with brine (25 mL), dried with $MgSO_4$, filtered, and concentrated to give compound 71a (0.17 g, quantitative yield) as a tan solid. m/z=490 (M+1).

Compound 72a: A mixture of compound 71a (0.17 g, ≤0.34 mmol) and potassium carbonate (0.24 g, 1.74 mmol) in MeOH (10 mL) was stirred at room temperature under $N_2$ overnight. The mixture was concentrated, and the residue was partitioned between sat. aq. $KH_2PO_4$ (25 mL) and EtOAc (25 mL). The organic extract was washed with brine (25 mL), dried with $MgSO_4$, filtered, and concentrated. The residue was purified by column chromatography (silica gel, eluting with 50% EtOAc in hexanes) to give compound 72a (0.10 g, 60% yield) as a yellow solid. m/z=490 (M+1).

T65: To a stirring solution of compound 72a (93 mg, 0.19 mmol) in degassed DMF (4 mL) at 0° C. under $N_2$ was added a solution of 1,3-dibromo-5,5-dimethylhydantoin (30 mg, 0.10 mmol) in degassed DMF (1 mL) dropwise. The mixture was stirred at 0° C. for 30 min, and then pyridine (0.15 mL, 1.86 mmol) was added. The mixture was heated at 60° C. for 4 h and then concentrated. The residue was partitioned between sat. aq. $KH_2PO_4$ (25 mL) and EtOAc (25 mL). The organic extract was washed with brine, dried with $MgSO_4$, filtered, and concentrated. The residue was purified by column chromatography (silica gel, eluting with 25% EtOAc in hexanes) to give compound T65 (48 mg, 52% yield) as a light yellow solid. m/z=488 (M+1); $^1$H NMR (400 MHz, $CDCl_3$) δ 7.80 (m, 2H), 7.72 (m, 2H), 7.66 (m, 3H), 7.57 (m, 2H), 7.50 (m, 2H), 7.43 (m, 1H), 7.11 (m, 2H), 2.94 (m, 1H), 2.87 (m, 1H), 2.56 (qd, J=6.7, 13.4 Hz, 1H), 2.28 (dt, J=2.0, 12.7 Hz, 1H), 2.16 (dd, J=6.3, 13.9 Hz, 1H), 1.82 (m, 1H), 1.61 (s, 3H), 1.34 (d, J=6.7 Hz, 3H).

Compound 68b: Compound 68b (yellow gummy solid, 0.20 g, 78% yield) was synthesized from compound 67 (0.25 g, 0.51 mmol) and 2-fluorophenylboronic acid (0.14 g, 1.00 mmol) using the same procedure as compound 68a. Compound 68b was purified by column chromatography (silica gel, eluting with 25% EtOAc in hexanes). m/z=509 (M+1).

Compound 69b: A solution of compound 69b (0.20 g, 0.39 mmol) and 3 N aq. HCl (1.4 mL, 4.2 mmol) in MeOH (10 mL) was stirred at room temperature under $N_2$ overnight. The mixture was concentrated. The residue was cooled and basified with 10% aq. NH$_4$OH to pH 9-10. The mixture was extracted with CHCl$_3$ (25 mL). The organic extract was washed with brine (25 mL), dried with MgSO$_4$, filtered, and concentrated to give compound 69b (0.17 g, 94% yield) as light yellow solid. m/z=465 (M+1).

Compound 70b: A solution of compound 69b (0.17 g, 0.37 mmol) in ethyl formate (10 mL, 0.12 mol) was treated with sodium methoxide (30 wt. % in MeOH, 0.34 mL, 1.81 mmol). The mixture was stirred at room temperature under N$_2$ overnight and then concentrated. The residue was partitioned between EtOAc (50 mL) and sat. aq. KH$_2$PO$_4$ (50 mL). The organic extract was washed with brine (50 mL), dried with MgSO$_4$, filtered, and concentrated to give compound 70b (0.17 g, 94% yield) as dark yellow solid. m/z=493 (M+1).

Compound 71b: A solution of compound 70b (0.17 g, 0.34 mmol), acetic acid (0.20 mL, 3.50 mmol) and hydroxylamine hydrochloride (35 mg, 0.50 mmol) in EtOH (10 mL) was stirred at 60° C. for 2 h and then at room temperature overnight. The mixture was concentrated. The residue was partitioned between sat. aq. NaHCO$_3$ (25 mL) and EtOAc (25 mL). The organic extract was washed with brine (25 mL), dried with MgSO$_4$, filtered, and concentrated to give compound 71b (0.16 g, 94% yield) as a dark yellow solid. m/z=490 (M+1).

Compound 72b: A mixture of compound 71b (0.16 g, 0.33 mmol) and potassium carbonate (0.23 g, 1.66 mmol) in MeOH (10 mL) was stirred at room temperature under N$_2$ overnight. The mixture was concentrated, and the residue was partitioned between sat. aq. KH$_2$PO$_4$ (25 mL) and EtOAc (25 mL). The organic extract was washed with brine (25 mL), dried with MgSO$_4$, filtered, and concentrated to give compound 72b (0.15 g, 94% yield) as a tan foamy solid. m/z=490 (M+1).

T66: To a stirring solution of compound 72b (0.15 g, 0.31 mmol) in degassed DMF (4 mL) at 0° C. under N$_2$ was added a solution of 1,3-dibromo-5,5-dimethylhydantoin (44 mg, 0.15 mmol) in degassed DMF (1 mL) dropwise. The mixture was stirred at 0° C. for 30 min, and then pyridine (0.25 mL, 3.10 mmol) was added. The mixture was heated at 60° C. for 4 h and then concentrated. The residue was partitioned between sat aq. KH$_2$PO$_4$ (25 mL) and EtOAc (25 mL). The organic extract was washed with brine, dried with MgSO$_4$, filtered, and concentrated. The residue was purified by column chromatography (silica gel, eluting with 25% EtOAc in hexanes) to give compound T66 (87 mg, 58% yield) as a light yellow solid. m/z=488 (M+1); $^1$H NMR (400 MHz, CDCl$_3$) δ 7.80 (m, 2H), 7.70 (s, 1H), 7.66 (m, 2H), 7.59 (m, 3H), 7.50 (m, 2H), 7.38 (m, 2H), 7.18 (m, 2H), 2.74 (m, 2H), 2.56 (qd, J=6.7, 13.4 Hz, 1H), 2.31 (dt, J=2.1, 12.7 Hz, 1H), 2.09 (m, 1H), 1.79 (m, 1H), 1.62 (s, 3H), 1.33 (d, J=6.7 Hz, 3H).

Compound 68c: Compound 68c (yellow solid, 0.18 g, 72% yield) was synthesized from compound 67 (0.25 g, 0.51 mmol) and pyridine-4-boronic acid (0.12 g, 0.98 mmol) using the same procedure as compound 68a. The reaction was heated at 110° C. for 16 h. Compound 68c was purified by column chromatography (silica gel, eluting with 100% EtOAc). m/z=492 (M+1).

Compound 69c: A solution of compound 68c (0.18 g, 0.37 mmol) and 3 N aq. HCl (1.3 mL, 3.9 mmol) in MeOH (10 mL) was stirred at room temperature under N$_2$ overnight. The mixture was concentrated. The residue was cooled and basified with 10% aq. NH$_4$OH to pH 9-10. The mixture was extracted with CHCl$_3$ (25 mL). The organic extract was washed with brine (25 mL), dried with MgSO$_4$, filtered, and concentrated to give compound 69c (0.19 g, quantitative yield) as yellow oil. m/z=448 (M+1).

Compound 70c: A solution of compound 69c (0.19 g, ≤0.37 mmol) in ethyl formate (10 mL, 0.12 mol) was treated with sodium methoxide (30 wt. % MeOH, 0.35 mL, 1.86 mmol). The mixture was stirred at room temperature under N$_2$ overnight and then concentrated. The residue was partitioned between EtOAc (50 mL) and sat. aq. KH$_2$PO$_4$ (50 mL). The organic extract was washed with brine (50 mL), dried with MgSO$_4$, filtered, and concentrated to give compound 70c (0.16 g, 91% yield) as a dark yellow solid. m/z=476 (M+1).

Compound 71c: A solution of compound 70c (0.16 g, 0.34 mmol), acetic acid (0.20 mL, 3.50 mmol) and hydroxylamine hydrochloride (35 mg, 0.50 mmol) in EtOH (10 mL) was stirred at 60° C. for 2 h, and then at room temperature overnight. The mixture was concentrated. The residue was partitioned between sat. aq. NaHCO$_3$ (25 mL) and EtOAc (25 mL). The organic extract was washed with brine (25 mL), dried with MgSO$_4$, filtered, and concentrated. The residue was purified by column chromatography (silica gel, eluting with 75% EtOAc in hexanes) to give compound 71c (90 mg, 56% yield) as a light yellow foamy solid. m/z=473 (M+1).

Compound 72c: A mixture of compound 71c (90 mg, 0.19 mmol) and potassium carbonate (0.13 g, 0.94 mmol) in MeOH (10 mL) was stirred at room temperature under N$_2$ overnight. The mixture was concentrated, and the residue was partitioned between sat. aq. KH$_2$PO$_4$ (25 mL) and EtOAc (25 mL). The organic extract was washed with brine (25 mL), dried with MgSO$_4$, filtered, and concentrated to give compound 72c (70 mg, 78% yield) as off-white solid. m/z=473 (M+1).

T67: To a stirring solution of compound 72c (70 mg, 0.15 mmol) in degassed DMF (4 mL) at 0° C. under N$_2$ was added a solution of 1,3-dibromo-5,5-dimethylhydantoin (23 mg, 0.080 mmol) in degassed DMF (1 mL) dropwise. The mixture was stirred at 0° C. for 30 min, and then pyridine (0.12 mL, 1.48 mmol) was added. The mixture was heated at 60° C. for 4 h and then concentrated. The residue was partitioned between sat. aq. KH$_2$PO$_4$ (25 mL) and CHCl$_3$ (25 mL). The organic extract was washed with brine, dried with MgSO$_4$, filtered, and concentrated. The residue was purified by column chromatography (silica gel, eluting with 100% EtOAc in hexanes) to give compound T67 (40 mg, 57% yield) as a light yellow solid. m/z=471 (M+1); $^1$H NMR (400 MHz, CDCl$_3$) δ 8.66 (br s, 2H), 7.83 (m, 2H), 7.67 (m, 5H), 7.57 (m, 2H), 7.51 (m, 2H), 7.44 (m, 1H), 3.04 (m, 1H), 2.93 (m, 1H), 2.57 (qd, J=6.7, 13.3 Hz, 1H), 2.29 (dt, J=2.1, 12.7 Hz, 1H), 2.20 (dd, J=6.5, 13.7 Hz, 1H), 1.84 (m, 1H), 1.61 (s, 3H), 1.35 (d, J=6.7 Hz, 3H).

Compound 68d: Compound 68d (light yellow solid, 0.19 g, 76% yield) was synthesized from compound 67 (0.25 g, 0.51 mmol) and pyridine-3-boronic acid (0.13 g, 1.06 mmol) using the same procedure as compound 68a. The reaction was heated at 110° C. for 16 h. Compound 68d was purified by column chromatography (silica gel, eluting with 75% EtOAc in hexanes). m/z=492 (M+1).

Compound 69d: A solution of compound 68d (0.19 g, 0.39 mmol) and 3 N aq. HCl (1.3 mL, 3.9 mmol) in MeOH (10 mL) was stirred at room temperature under N$_2$ overnight. The mixture was concentrated. The residue was cooled and basified with 10% aq. NH$_4$OH to pH 9-10. The mixture was extracted with CHCl$_3$ (25 mL). The organic extract was washed with brine (25 mL), dried with MgSO$_4$, filtered, and concentrated to give compound 69d (0.23 g, quantitative yield) as a yellow oil. m/z=448 (M+1).

Compound 70d: A solution of compound 69d (0.23 g, ≤0.39 mmol) in ethyl formate (10 mL, 0.12 mol) was treated with sodium methoxide (30 wt. % in MeOH, 0.37 mL, 1.97 mmol). The mixture was stirred at room temperature under $N_2$ overnight and then concentrated. The residue was partitioned between EtOAc (50 mL) and sat. aq. $KH_2PO_4$ (50 mL). The organic extract was washed with brine (50 mL), dried with $MgSO_4$, filtered, and concentrated to give compound 70d (0.17 g, 92% yield) as a tan foamy solid. m/z=476 (M+1).

Compound 71d: A solution of compound 70d (0.17 g, 0.36 mmol), acetic acid (0.21 mL, 3.67 mmol) and hydroxylamine hydrochloride (38 mg, 0.55 mmol) in EtOH (10 mL) was stirred at 60° C. for 2 h and then at room temperature overnight. The mixture was concentrated. The residue was partitioned between sat. aq. $NaHCO_3$ (25 mL) and EtOAc (25 mL). The organic extract was washed with brine (25 mL), dried with $MgSO_4$, filtered, and concentrated to give compound 71d (0.15 g, 88% yield) as a tan foamy solid. m/z=473 (M+1).

Compound 72d: A mixture of compound 71d (0.15 g, 0.32 mmol) and potassium carbonate (0.22 g, 1.59 mmol) in MeOH (10 mL) was stirred at room temperature under $N_2$ overnight. The mixture was concentrated, and the residue was partitioned between sat. aq. $KH_2PO_4$ (25 mL) and EtOAc (25 mL). The organic extract was washed with brine (25 mL), dried with $MgSO_4$, filtered, and concentrated. The residue was purified by column chromatography (silica gel, eluting with 75% EtOAc in hexanes) to give compound 72d (99 mg, 66% yield) as a light yellow solid. m/z=473 (M+1).

T68: To a stirring solution of compound 72d (99 mg, 0.21 mmol) in degassed DMF (4 mL) at 0° C. under $N_2$ was added a solution of 1,3-dibromo-5,5-dimethylhydantoin (33 mg, 0.12 mmol) in degassed DMF (1 mL) dropwise. The mixture was stirred at 0° C. for 30 min, and then pyridine (0.17 mL, 2.11 mmol) was added. The mixture was heated at 60° C. for 4 h and then concentrated. The residue was partitioned between sat. aq. $KH_2PO_4$ (25 mL) and $CHCl_3$ (25 mL). The organic extract was washed with brine, dried with $MgSO_4$, filtered, and concentrated. The residue was purified by column chromatography (silica gel, eluting with 5% MeOH in $CHCl_3$) to give compound T68 (57 mg, 58% yield) as a light yellow solid. m/z=471 (M+1); $^1H$ NMR (400 MHz, $CDCl_3$) δ 8.98 (d, J=2.0 Hz, 1H), 8.59 (d, J=4.0 Hz, 1H), 8.08 (td, J=1.9, 8.0 Hz, 1H), 7.82 (m, 2H), 7.67 (m, 3H), 7.58 (m, 2H), 7.51 (m, 2H), 7.44 (m, 1H), 7.35 (dd, J=4.5, 7.8 Hz, 1H), 2.99 (m, 1H), 2.91 (m, 1H), 2.57 (qd, J=6.7, 13.3 Hz, 1H), 2.30 (dt, J=2.0, 12.7 Hz, 1H), 2.19 (dd, J=6.4, 13.8 Hz, 1H), 1.84 (m, 1H), 1.62 (s, 3H), 1.34 (d, J=6.7 Hz, 3H).

Compound 68e: In a sealable vial, a mixture of compound 67 (0.21 g, 0.42 mmol), 4-methylphenylboronic acid (0.11 g, 0.81 mmol) and potassium phosphate (0.27 g, 1.27 mmol) in 1,4-dioxane (2.6 mL) and DMF (1.3 mL) was degassed and treated with tetrakis(triphenylphosphine)palladium(0) (59 mg, 0.051 mmol). The mixture was degassed again. The vial was sealed, and the mixture was heated at 100° C. for 48 h. After cooled to room temperature, the mixture was diluted with EtOAc (50 mL) and washed with 1 N aq. NaOH (50 mL). The organic extract was washed with brine (50 mL), dried with $MgSO_4$, filtered, and concentrated. The residue was purified by column chromatography (silica gel, eluting with 1/10/10 EtOAc/$CH_2Cl_2$/hexanes) to give compound 68e (0.13 g, 61% yield) as a tan solid. m/z=505 (M+1).

Compound 69e: A solution of compound 68e (0.13 g, 0.26 mmol) and 3 N aq. HCl (1.0 mL, 3.0 mmol) in MeOH (10 mL) was stirred at room temperature under $N_2$ overnight. The mixture was concentrated. The residue was cooled and basified with 10% aq. $NH_4OH$ to pH 9-10. The mixture was extracted with $CHCl_3$ (25 mL). The organic extract was washed with brine (25 mL), dried with $MgSO_4$, filtered, and concentrated to give compound 69e (0.11 g, 93%) as an off-white solid. m/z=461 (M+1).

Compound 70e: A solution of compound 69e (0.11 g, 0.24 mmol) in ethyl formate (10 mL, 0.12 mol) was treated with sodium methoxide (30 wt. % in MeOH, 0.22 mL, 1.17 mmol). The mixture was stirred at room temperature under $N_2$ overnight and then concentrated. The residue was partitioned between EtOAc (50 mL) and sat. aq. $KH_2PO_4$ (50 mL). The organic extract was washed with brine (50 mL), dried with $MgSO_4$, filtered, and concentrated to give compound 70e (0.15 g, quantitative yield) as a tan solid. m/z=489 (M+1).

Compound 71e: A solution of compound 70e (0.15 g, ≤0.24 mmol), acetic acid (0.14 mL, 2.44 mmol) and hydroxylamine hydrochloride (25 mg, 0.36 mmol) in EtOH (10 mL) was stirred at 60° C. for 2 h and then at room temperature overnight. The mixture was concentrated. The residue was partitioned between sat. aq. $NaHCO_3$ (25 mL) and EtOAc (25 mL). The organic extract was washed with brine (25 mL), dried with $MgSO_4$, filtered, and concentrated to give compound 71e (0.12 g, quantitative yield) as a light yellow solid. m/z=486 (M+1).

Compound 72e: A mixture of compound 71e (0.12 g, ≤0.24 mmol) and potassium carbonate (0.17 g, 1.23 mmol) in MeOH (10 mL) was stirred at room temperature under $N_2$ overnight. The mixture was concentrated, and the residue was partitioned between sat. aq. $KH_2PO_4$ (25 mL) and EtOAc (25 mL). The organic extract was washed with brine (25 mL), dried with $MgSO_4$, filtered, and concentrated to give compound 72e (0.11 g, 94% yield) as a tan solid. m/z=486 (M+1).

T69: To a stirring solution of compound 72e (0.11 g, 0.23 mmol) in degassed DMF (4 mL) at 0° C. under $N_2$ was added a solution of 1,3-dibromo-5,5-dimethylhydantoin (32 mg, 0.11 mmol) in degassed DMF (1 mL) dropwise. The mixture was stirred at 0° C. for 30 min, and then pyridine (0.19 mL, 2.35 mmol) was added. The mixture was heated at 60° C. for 4 h and then concentrated. The residue was partitioned between sat. aq. $KH_2PO_4$ (25 mL) and EtOAc (25 mL). The organic extract was washed with brine, dried with $MgSO_4$, filtered, and concentrated. The residue was purified by column chromatography (silica gel, eluting with 25% EtOAc in hexanes) to give compound T69 (40 mg, 37% yield) as a light yellow solid. m/z=484 (M+1); $^1H$ NMR (400 MHz, $CDCl_3$) δ 7.79 (m, 2H), 7.69 (s, 1H), 7.65 (m, 4H), 7.58 (m, 2H), 7.50 (m, 2H), 7.43 (m, 1H), 7.23 (d, J=7.9 Hz, 2H), 2.96 (m, 1H), 2.88 (m, 1H), 2.56 (qd, J=6.7, 13.4 Hz, 1H), 2.38 (s, 3H), 2.28 (dt, J=2.0, 12.7 Hz, 1H), 2.15 (dd, J=6.4, 13.8 Hz, 1H), 1.81 (m, 1H), 1.60 (s, 3H), 1.33 (d, J=6.7 Hz, 3H).

Compound 68f: In a sealable vial, a mixture of compound 67 (0.30 g, 0.61 mmol), pyrimidine-5-boronic acid (0.15 g, 1.21 mmol) and potassium phosphate (0.39 g, 1.84 mmol) in 1,4-dioxane (4 mL) and DMF (2 mL) was degassed and treated with tetrakis(triphenylphosphine)palladium(0) (70 mg, 0.060 mmol). The mixture was degassed again. The vial was sealed, and the mixture was heated at 100° C. for 48 h. After cooled to room temperature, the mixture was diluted with EtOAc (50 mL) and washed with 1 N aq. NaOH (50 mL). The organic extract was washed with brine (50 mL), dried with $MgSO_4$, filtered, and concentrated. The residue was purified by column chromatography (silica gel, eluting with 50% EtOAc in hexanes) to give compound 68f (0.11 g, 37% yield) as a tan solid. m/z=493 (M+1).

Compound 69f: A solution of compound 68f (0.11 g, 0.22 mmol) and 3 N aq. HCl (0.75 mL, 2.25 mmol) in MeOH (10 mL) was stirred at room temperature under $N_2$ overnight. The mixture was concentrated. The residue was cooled and basified with 10% aq. $NH_4OH$ to pH 9-10. The mixture was extracted with $CHCl_3$ (25 mL). The organic extract was washed with brine (25 mL), dried with $MgSO_4$, filtered, and concentrated to give compound 69f (94 mg, 94% yield) as tan solid. m/z=449 (M+1).

Compound 70f: A solution of compound 69f (94 mg, 0.21 mmol) in ethyl formate (10 mL, 0.12 mol) was treated with sodium methoxide (30 wt. % in MeOH, 0.20 mL, 1.07 mmol). The mixture was stirred at room temperature under $N_2$ overnight and then concentrated. The residue was partitioned between EtOAc (50 mL) and sat. aq. $KH_2PO_4$ (50 mL). The organic extract was washed with brine (50 mL), dried with $MgSO_4$, filtered, and concentrated to give compound 70f (% mg, 96% yield) as a tan solid. m/z=477 (M+1).

Compound 71f: A solution of compound 70f (96 mg, 0.20 mmol), acetic acid (0.15 mL, 2.62 mmol) and hydroxylamine hydrochloride (21 mg, 0.30 mmol) in EtOH (10 mL) was stirred at 60° C. for 2 h and then at room temperature overnight. The mixture was concentrated. The residue was partitioned between sat. aq. $NaHCO_3$ (25 mL) and EtOAc (25 mL). The organic extract was washed with brine (25 mL), dried with $MgSO_4$, filtered, and concentrated to give compound 71f (86 mg, 90% yield) as a dark yellow solid. m/z=474 (M+1).

Compound 72f: A mixture of compound 71f (86 mg, 0.18 mmol) and potassium carbonate (0.13 g, 0.94 mmol) in MeOH (10 mL) was stirred at room temperature under $N_2$ overnight. The mixture was concentrated, and the residue was partitioned between sat. aq. $KH_2PO_4$ (25 mL) and EtOAc (25 mL). The organic extract was washed with brine (25 mL), dried with $MgSO_4$, filtered, and concentrated to give compound 72f (77 mg, 90% yield) as a tan solid. m/z=474 (M+1).

T70: To a stirring solution of compound 72f (77 mg, 0.16 mmol) in degassed DMF (4 mL) at 0° C. under $N_2$ was added a solution of 1,3-dibromo-5,5-dimethylhydantoin (23 mg, 0.080 mmol) in degassed DMF (1 mL) dropwise. The mixture was stirred at 0° C. for 30 min, and then pyridine (0.13 mL, 1.61 mmol) was added. The mixture was heated at 60° C. for 4 h and then concentrated. The residue was partitioned between sat. aq. $KH_2PO_4$ (25 mL) and $CHCl_3$ (25 mL).

The organic extract was washed with brine, dried with $MgSO_4$, filtered, and concentrated. The residue was purified by column chromatography (silica gel, eluting with 5% MeOH in $CHCl_3$) to give partially purified product and was purified again by column chromatography (silica gel, eluting with 75% EtOAc in hexanes) to give compound T70 (35 mg, 46% yield) as an off-white solid. m/z=472 (M+1); $^1H$ NMR (400 MHz, $CDCl_3$) δ 9.19 (s, 1H), 9.12 (s, 2H), 7.83 (m, 2H), 7.67 (m, 2H), 7.64 (s, 1H), 7.57 (m, 2H), 7.51 (m, 2H), 7.44 (m, 1H), 2.98 (m, 1H), 2.91 (m, 1H), 2.57 (qd, J=6.7, 13.3 Hz, 1H), 2.29 (dt, J=2.1, 12.7 Hz, 1H), 2.21 (dd, J=6.3, 14.0 Hz, 1H), 1.86 (m, 1H), 1.62 (s, 3H), 1.35 (d, J=6.7 Hz, 3H).

Compound 68g: In a sealable vial, a mixture of compound 67 (0.25 g, 0.51 mmol), 3-isopropylphenylboronic acid (0.17 g, 1.04 mmol) and potassium phosphate (0.32 g, 1.51 mmol) in 1,4-dioxane (4 mL) and DMF (2 mL) was degassed and treated with tetrakis(triphenylphosphine)palladium(0) (59 mg, 0.051 mmol). The mixture was degassed again. The vial was sealed, and the mixture was heated at 100° C. for 48 h. After cooled to room temperature, the mixture was diluted with EtOAc (50 mL) and washed with 1 N aq. NaOH (50 mL). The organic extract was washed with brine (50 mL), dried with $MgSO_4$, filtered, and concentrated. The residue was purified by column chromatography (silica gel, eluting with 1/20/20 EtOAc/$CH_2Cl_2$/hexanes) to give compound 68g (0.10 g, 37% yield) as an off-white solid. m/z=533 (M+1).

Compound 69g: A solution of compound 68g (0.10 g, 0.19 mmol) and 3 N aq. HCl (0.60 mL, 1.80 mmol) in MeOH (10 mL) was stirred at room temperature under $N_2$ for 48 h. The mixture was concentrated. The residue was cooled and basified with 10% aq. $NH_4OH$ to pH 9-10. The mixture was extracted with $CHCl_3$ (25 mL). The organic extract was washed with brine (25 mL), dried with $MgSO_4$, filtered, and concentrated to give compound 69g (90 mg, 98% yield) as an off-white solid. m/z=489 (M+1).

Compound 70g: A solution of compound 69g (90 mg, 0.18 mmol) in ethyl formate (10 mL, 0.12 mol) was treated with sodium methoxide (30 wt. % MeOH, 0.17 mL, 0.91 mmol). The mixture was stirred at room temperature under $N_2$ overnight and then concentrated. The residue was partitioned between EtOAc (50 mL) and sat. aq. $KH_2PO_4$ (50 mL). The organic extract was washed with brine (50 mL), dried with $MgSO_4$, filtered, and concentrated to give compound 70g (90 mg, 95% yield) as a tan foamy solid. m/z=517 (M+1).

Compound 71g: A solution of compound 70g (90 mg, 0.17 mmol), acetic acid (0.10 mL, 1.75 mmol) and hydroxylamine hydrochloride (18 mg, 0.26 mmol) in EtOH (10 mL) was stirred at 60° C. for 2 h, and then at room temperature overnight. The mixture was concentrated. The residue was partitioned between sat. aq. $NaHCO_3$ (25 mL) and EtOAc (25 mL). The organic extract was washed with brine (25 mL), dried with $MgSO_4$, filtered, and concentrated to give compound 71g (89 mg, quantitative yield) as a light yellow solid. m/z=514 (M+1).

Compound 72g: A mixture of compound 71g (89 mg, 0.17 mmol) and potassium carbonate (0.12 g, 0.87 mmol) in MeOH (10 mL) was stirred at room temperature under $N_2$ overnight. The mixture was concentrated, and the residue was partitioned between sat. aq. $KH_2PO_4$ (25 mL) and EtOAc (25 mL). The organic extract was washed with brine (25 mL), dried with $MgSO_4$, filtered, and concentrated to give compound 72g (91 mg, quantitative yield) as a light yellow solid. m/z=514 (M+1).

T71: To a stirring solution of compound 72g (91 mg, ≤0.17 mmol) in degassed DMF (4 mL) at 0° C. under $N_2$ was added a solution of 1,3-dibromo-5,5-dimethylhydantoin (24 mg, 0.084 mmol) in degassed DMF (1 mL) dropwise. The mixture was stirred at 0° C. for 30 min, and then pyridine (0.14 mL, 1.73 mmol) was added. The mixture was heated at 60° C. for 4 h and then concentrated. The residue was partitioned between sat. aq. $KH_2PO_4$ (25 mL) and EtOAc (25 mL). The organic extract was washed with brine, dried with $MgSO_4$, filtered, and concentrated. The residue was purified by column chromatography (silica gel, eluting with 25% EtOAc in hexanes) to give compound T71 (54 mg, 62% yield) as a light yellow solid. m/z=512 (M+1); $^1H$ NMR (400 MHz, $CDCl_3$) δ 7.80 (m, 2H), 7.67 (m, 3H), 7.60 (m, 3H), 7.51 (m, 3H), 7.43 (m, 1H), 7.35 (t, J=7.7 Hz, 1H), 7.23 (m, 1H), 2.95 (m, 3H), 2.56 (qd, J=6.7, 13.4 Hz, 1H), 2.29 (dt, J=2.0, 12.7 Hz, 1H), 2.16 (dd, J=6.2, 13.8 Hz, 1H), 1.81 (m, 1H), 1.60 (s, 3H), 1.34 (d, J=6.7 Hz, 3H), 1.28 (d, J=6.9 Hz 6H).

Compound 68h: Compound 68h (light yellow solid, 0.15 g, 67% yield) was synthesized from compound 67 (0.22 g, 0.44 mmol), 2-methylphenylboronic acid (0.12 g, 0.88 mmol) using the same procedure as compound 68g. Compound 68h was purified by column chromatography (silica gel, eluting with 1/20/20 EtOAc/$CH_2Cl_2$/hexanes). m/z=505 (M+1).

Compound 69h: A solution of compound 68h (0.15 g, 0.30 mmol) and 3 N aq. HCl (1.0 mL, 3.0 mmol) in MeOH (10 mL) was stirred at room temperature under $N_2$ overnight. The mixture was concentrated. The residue was cooled and basified with 10% aq. $NH_4OH$ to pH 9-10. The mixture was extracted with $CHCl_3$ (25 mL). The organic extract was washed with brine (25 mL), dried with $MgSO_4$, filtered, and concentrated to give compound 69h (0.15 g, quantitative yield) as dark yellow oil. m/z=461 (M+1).

Compound 70h: A solution of compound 69h (0.15 g, ≤0.30 mmol) in ethyl formate (10 mL, 0.12 mol) was treated with sodium methoxide (30 wt. % in MeOH, 0.28 mL, 1.49 mmol). The mixture was stirred at room temperature under $N_2$ overnight, and then concentrated. The residue was partitioned between EtOAc (50 mL) and sat. aq. $KH_2PO_4$ (50 mL). The organic extract was washed with brine (50 mL), dried with $MgSO_4$, filtered, and concentrated to give compound 70h (0.15 g, quantitative yield) as a light yellow solid. m/z=489 (M+1).

Compound 71h: A solution of compound 70h (0.15 g, ≤0.30 mmol), acetic acid (0.17 mL, 2.97 mmol) and hydroxylamine hydrochloride (31 mg, 0.45 mmol) in EtOH (10 mL) was stirred at 60° C. for 2 h and then at room temperature overnight. The mixture was concentrated. The residue was partitioned between sat. aq. $NaHCO_3$ (25 mL) and EtOAc (25 mL). The organic extract was washed with brine (25 mL), dried with $MgSO_4$, filtered, and concentrated to give compound 71h (0.15 g, quantitative yield) as a light yellow foamy solid. m/z=486 (M+1).

Compound 72h: A mixture of compound 11h (0.15 g, ≤0.30 mmol) and potassium carbonate (0.21 g, 1.52 mmol) in MeOH (10 mL) was stirred at room temperature under $N_2$ overnight. The mixture was concentrated, and the residue was partitioned between sat. aq. $KH_2PO_4$ (25 mL) and EtOAc (25 mL). The organic extract was washed with brine (25 mL), dried with $MgSO_4$, filtered, and concentrated to give compound 72h (0.14 g, 96% yield) as a tan solid. m/z=486 (M+1).

T72: To a stirring solution of compound 72h (0.14 g, 0.29 mmol) in degassed DMF (4 mL) at 0° C. under $N_2$ was added a solution of 1,3-dibromo-5,5-dimethylhydantoin (43 mg, 0.15 mmol) in degassed DMF (1 mL) dropwise. The mixture was stirred at 0° C. for 30 min, and then pyridine (0.25 mL, 3.09 mmol) was added. The mixture was heated at 60° C. for 4 h and then concentrated. The residue was partitioned between sat. aq. $KH_2PO_4$ (25 mL) and EtOAc (25 mL). The organic extract was washed with brine, dried with $MgSO_4$, filtered, and concentrated. The residue was purified by column chromatography (silica gel, eluting with 25% EtOAc in hexanes) to give compound T72 (91 mg, 65% yield) as a light yellow solid. m/z=484 (M+1); $^1$H NMR (400 MHz, $CDCl_3$) δ 7.78 (m, 2H), 7.73 (s, 1H), 7.66 (m, 2H), 7.58 (m, 2H), 7.50 (m, 2H), 7.42 (m, 1H), 7.32 (m, 1H), 7.28 (m, 2H), 7.22 (m, 1H), 2.59 (m, 3H), 2.36 (s, 3H), 2.29 (dt, J=2.1, 12.7 Hz, 1H), 2.07 (m, 1H), 1.80 (m, 1H), 1.63 (s, 3H), 1.32 (d, J=6.7 Hz, 3H).

Compound 68i: Compound 68i (light yellow solid, 0.28 g, 78% yield) was synthesized from compound 67 (0.34 g, 0.69 mmol), 4-(hydroxymethyl)phenylboronic acid (0.21 g, 1.38 mmol) using the same procedure as compound 68g. Compound 68i was purified by column chromatography (silica gel, eluting with 50% EtOAc in hexanes). m/z=521 (M+1).

Compound 69i: A solution of compound 68i (0.28 g, 0.54 mmol) and 3 N aq. HCl (1.8 mL, 5.4 mmol) in MeOH (10 mL) was stirred at room temperature under $N_2$ overnight. The mixture was concentrated. The residue was cooled and basified with 10% aq. $NH_4OH$ to pH 9-10. The mixture was extracted with $CHCl_3$ (25 mL). The organic extract was washed with brine (25 mL), dried with $MgSO_4$, filtered, and concentrated to give compound 69i (0.27 g, quantitative yield) as a light yellow solid. m/z=477 (M+1).

Compound 70i: A solution of compound 69i (0.27 g, ≤0.54 mmol) in ethyl formate (10 mL, 0.12 mol) was treated with sodium methoxide (30 wt. % in MeOH, 0.53 mL, 2.82 mmol). The mixture was stirred at room temperature under $N_2$ overnight and then concentrated. The residue was partitioned between EtOAc (50 mL) and sat. aq. $KH_2PO_4$ (50 mL). The organic extract was washed with brine (50 mL), dried with $MgSO_4$, filtered, and concentrated to give compound 70i (0.28 g, quantitative yield) as a tan-orange solid. m/z=505 (M+1).

Compound 71i: A solution of compound 70i (0.28 g, ≤0.54 mmol), acetic acid (0.33 mL, 5.76 mmol) and hydroxylamine hydrochloride (0.10 g, 1.44 mmol) in EtOH (10 mL) was stirred at 60° C. for 2 h and then at room temperature overnight. The mixture was concentrated. The residue was partitioned between sat. aq. $NaHCO_3$ (25 mL) and EtOAc (25 mL). The organic extract was washed with brine (25 mL), dried with $MgSO_4$, filtered, and concentrated to give compound 71i (0.29 g, quantitative yield) as a tan foamy solid. m/z=502 (M+1).

Compound 72i: A mixture of compound 71i (70 mg, 0.14 mmol) and potassium carbonate (0.10 g, 0.72 mmol) in MeOH (10 mL) was stirred at room temperature under $N_2$ overnight. The mixture was concentrated, and the residue was partitioned between sat. aq. $KH_2PO_4$ (25 mL) and EtOAc (25 mL). The organic extract was washed with brine (25 mL), dried with $MgSO_4$, filtered, and concentrated to give compound 72i (59 mg, 84% yield) as a yellow solid. m/z=502 (M+1).

T73: To a stirring solution of compound 72i (59 mg, 0.12 mmol) in degassed DMF (4 mL) at 0° C. under $N_2$ was added a solution of 1,3-dibromo-5,5-dimethylhydantoin (21 mg, 0.073 mmol) in degassed DMF (1 mL) dropwise. The mixture was stirred at 0° C. for 30 min, and then pyridine (0.10 mL, 1.24 mmol) was added. The mixture was heated at 60° C. for 4 h and then concentrated. The residue was partitioned between sat. aq. $KH_2PO_4$ (25 mL) and EtOAc (25 mL). The organic extract was washed with brine, dried with $MgSO_4$, filtered, and concentrated. The residue was purified by column chromatography (silica gel, eluting with 50% EtOAc in hexanes) to give compound T73 (25 mg, 43% yield) as a light yellow solid. m/z=500 (M+1); $^1$H NMR (400 MHz, $CDCl_3$) δ 7.80 (d, J=8.3 Hz, 2H), 7.75 (d, J=8.0 Hz, 2H), 7.67 (m, 3H), 7.58 (d, J=8.3 Hz, 2H), 7.50 (t, J=7.5 Hz, 2H), 7.43 (m, 3H), 4.74 (s, 2H), 2.98 (dd, J=5.9, 16.4 Hz, 1H), 2.90 (m, 1H), 2.56 (qd, J=6.7, 13.4 Hz, 1H), 2.29 (m, 1H), 2.16 (dd, J=6.1, 13.7 Hz, 1H), 1.83 (tt, J=6.2, 12.6 Hz, 1H), 1.69 (br s, 1H), 1.61 (s, 3H), 1.34 (d, J=6.7 Hz, 3H).

Compound 73: To a stirring solution of compound 71i (0.28 g, 0.56 mmol) in $CH_2Cl_2$ (6 mL) at 0° C. under $N_2$ was added a solution of diethylaminosulfur trifluoride (0.11 g, 0.68 mmol) in $CH_2Cl$ (2 mL) dropwise. After 30 min, the cold reaction mixture was poured into cold sat. aq. $NaHCO_3$ (25 mL). The mixture was allowed to warm to room temperature. The organic layer was separated, washed with brine (25 mL), dried with $MgSO_4$, filtered, and concentrated.

The residue was purified by column chromatography (silica gel, eluting with 25% EtOAc in hexanes) to give compound 73 (0.13 g, 46% yield) as light yellow-white solid. m/z=504 (M+1, 100%).

Compound 74: A mixture of compound 73 (0.16 g, 0.32 mmol) and potassium carbonate (0.22 g, 1.59 mmol) in MeOH (10 mL) was stirred at room temperature under $N_2$ overnight. The mixture was concentrated, and the residue was partitioned between sat. aq. $KH_2PO_4$ (25 mL) and EtOAc (25 mL). The organic extract was washed with brine, dried $MgSO_4$, filtered, and concentrated. The residue was purified by column chromatography (silica gel, eluting with 25% EtOAc in hexanes) to give compound 74 (82 mg, 51% yield) as a tan solid. m/z=504 (M+1).

T74: To a stirring solution of compound 74 (79 mg, 0.16 mmol) in degassed DMF (4 mL) at 0° C. under $N_2$ was added a solution of 1,3-dibromo-5,5-dimethylhydantoin (25 mg, 0.087 mmol) in degassed DMF (1 mL) dropwise. The mixture was stirred at 0° C. for 30 min, and then pyridine (0.13 mL, 1.61 mmol) was added. The mixture was heated at 60° C. for 4 h and then concentrated. The residue was partitioned between sat. aq. $KH_2PO_4$ (25 mL) and EtOAc (25 mL). The organic extract was washed with brine, dried with $MgSO_4$, filtered, and concentrated. The residue was purified by column chromatography (silica gel, eluting with 25% EtOAc in hexanes) to give compound T74 (37 mg, 47% yield) as a light yellow solid. m/z=502 (M+1): $^1$H NMR (400 MHz, $CDCl_3$) δ 7.79 (m, 4H), 7.67 (m, 3H), 7.58 (m, 2H), 7.50 (m, 2H), 7.44 (m, 3H), 5.41 (d, $J_{F-H}$=47.8 Hz, 2H), 2.94 (m, 2H), 2.56 (qd, J=6.7, 13.4 Hz, 1H), 2.29 (dt, J=2.1, 12.8 Hz, 1H), 2.17 (dd, J=6.3, 13.8 Hz, 1H), 1.82 (m, 1H), 1.61 (s, 3H), 1.34 (d, J=6.7 Hz, 3H).

Compound 75: In a sealable vial, a mixture of compound 67 (0.50 g, 1.01 mmol), potassium cyclopropyltrifluoroborate (0.45 g, 3.04 mmol), potassium phosphate (0.64 g, 3.01 mmol) and RuPhos (47 mg, 0.10 mmol) in toluene:water (10:1, 10 mL) was degassed. Palladium(II) acetate (11 mg, 0.049 mmol) was added. The mixture was degassed again. The vial was sealed. The mixture was heated at 125° C. for 48 h. After cooled to room temperature, the mixture was diluted with EtOAc (50 mL) and washed with 1 N aq. NaOH (50 mL). The organic extract was washed with brine (50 mL), dried with $MgSO_4$, filtered, and concentrated. The residue was purified by column chromatography (silica gel, eluting with 1/10/10 EtOAc/$CH_2Cl_2$/hexanes) to give compound 75 (0.16 g, 35% yield) as tan solid. m/z=455 (M+1).

Compound 76: A solution of compound 75 (0.14 g, 0.31 mmol) and 3 N aq. HCl (1.0 mL, 3.0 mmol) in MeOH (10 mL) was stirred at room temperature under $N_2$ overnight. The mixture was concentrated. The residue was cooled and basified with 10% aq. $NH_4OH$ solution to pH 9-10. The mixture was extracted with $CHCl_3$ (25 mL). The organic extract was washed with brine (25 mL), dried with $MgSO_4$, filtered, and concentrated to give compound 76 (0.16 g, quantitative yield) as yellow oil. m/z=411 (M+1).

Compound 77: A solution of compound 76 (0.16 g, ≤0.31 mmol) in ethyl formate (10 mL, 0.12 mol) was treated with and sodium methoxide (30 wt. % in MeOH, 0.30 mL, 1.60 mmol). The mixture was stirred at room temperature under $N_2$ overnight and then concentrated. The residue was partitioned between EtOAc (50 mL) and sat. aq. $KH_2PO_4$ (50 mL). The organic extract was washed with brine (50 mL), dried with $MgSO_4$, filtered, and concentrated to give compound 77 (0.14 g, quantitative yield) as a yellow solid. m/z=439 (M+1).

Compound 78: A solution of compound 78 (0.14 g, ≤0.31 mmol), acetic acid (0.20 mL, 3.50 mmol) and hydroxylamine hydrochloride (43 mg, 0.62 mmol) in EtOH (10 mL) was stirred at 60° C. for 2 h, and then at room temperature overnight. The mixture was concentrated, and the residue was partitioned between sat. aq. $NaHCO_3$ (25 mL) and EtOAc (25 mL). The organic extract was washed with brine (25 mL), dried with $MgSO_4$, filtered, and concentrated to give compound 78 (0.13 g, 96% yield) as a tan solid. m/z=436 (M+1).

Compound 79: A mixture of compound 78 (0.13 g, 0.30 mmol) and potassium carbonate (0.22 g, 1.59 mmol) in MeOH (10 mL) was stirred at room temperature under $N_2$ overnight. The mixture was concentrated, and the residue was partitioned between sat. aq. $KH_2PO_4$ (25 mL) and EtOAc (25 mL). The organic extract was washed with brine (25 mL), dried with $MgSO_4$, filtered, and concentrated to give compound 79 (0.13 g, quantitative yield) as a tan solid. m/z=436 (M+1).

T75: To a stirring solution of compound 79 (0.13 g, 0.30 mmol) in degassed DMF (4 mL) at 0° C. under $N_2$ was added a solution of 1,3-dibromo-5,5-dimethylhydantoin (44 mg, 0.15 mmol) in degassed DMF (1 mL) dropwise. The mixture was stirred at 0° C. for 30 min, and then pyridine (0.25 mL, 3.09 mmol) was added. The mixture was heated at 60° C. for 4 h and then concentrated. The residue was partitioned between sat. aq. $KH_2PO_4$ (25 mL) and EtOAc (25 mL). The organic extract was washed with brine, dried with $MgSO_4$, filtered, and concentrated. The residue was purified by column chromatography (silica gel, eluting with 50% EtOAc in hexanes) to give compound T75 (57 mg, 44% yield) as a yellow solid. m/z=434 (M+1); $^1$H NMR (400 MHz, $CDCl_3$) δ 7.74 (m, 2H), 7.63 (m, 2H), 7.61 (s, 1H), 7.48 (m, 4H), 7.41 (m, 1H), 2.80 (ddd, J=1.3, 6.3, 16.1 Hz, 1H), 2.62 (ddd, J=6.7, 11.7, 16.1 Hz, 1H), 2.52 (qd, J=6.8, 13.4 Hz, 1H), 2.18 (dt, J=2.1, 12.7 Hz, 1H), 2.10 (dd, J=6.8, 13.8 Hz, 1H), 1.76 (m, 2H), 1.55 (s, 3H), 1.31 (d, J=6.8 Hz, 3H), 0.90 (m, 4H).

Compound 80: In a sealable vial, a mixture of compound 67 (0.46 g, 0.93 mmol), 1-cyclohex-1-yl-boronic acid pinacol ester (0.39 g, 1.87 mmol) and potassium phosphate (0.59 g, 2.78 mmol) in 1,4-dioxane (9 mL) was degassed and treated with tetrakis(triphenylphosphine)palladium(0) (0.11 g, 0.095 mmol). The mixture was degassed again. The vial was sealed, and the mixture was heated at 100° C. for 48 h. After cooled to room temperature, the mixture was diluted with EtOAc (50 mL) and washed with 1 N aq. NaOH (50 mL). The organic extract was washed with brine (50 mL), dried with $MgSO_4$, filtered, and concentrated. The residue was purified by column chromatography (silica gel, eluting with 10% EtOAc in hexanes) to give compound 80 (0.16 g, 35% yield) as an off-white solid. m/z=495 (M+1).

Compound 81: A solution of compound 80 (0.16 g, 0.32 mmol) and 3 N aq. HCl (1.1 mL, 3.3 mmol) in MeOH (10 mL) was stirred at room temperature under $N_2$ overnight. The mixture was concentrated. The residue was cooled and basified with 10% aq. $NH_4OH$ solution to pH 9-10. The mixture was extracted with $CHCl_3$ (25 mL). The organic extract was washed with brine (25 mL), dried with $MgSO_4$, filtered, and concentrated to give compound 81 (0.14 g, 96% yield) as a tan solid. m/z=451 (M+1).

Compound 82: A mixture of compound 81 (0.14 g, 0.31 mmol) and 10% palladium on carbon (50 mg) in EtOAc (20 mL) was hydrogenated (balloon pressure) at room temperature overnight. The catalyst was removed by filtration. The filtrate was concentrated to give compound 82 (0.16 g, quantitative yield) as light yellow oil. m/z=453 (M+1).

Compound 83: A solution of compound 82 (0.16 g, S 0.31 mmol) in ethyl formate (10 mL, 0.12 mol) was treated with sodium methoxide (30 wt. % in MeOH, 0.29 mL, 1.54 mmol). The mixture was stirred at room temperature under N₂ overnight, and then concentrated. The residue was partitioned between EtOAc (50 mL) and sat. aq. KH₂PO₄ (50 mL). The organic extract was washed with brine (50 mL), dried with MgSO₄, filtered, and concentrated to give compound 83 (0.15 g, quantitative yield) as yellow oil. m/z=481 (M+1).

Compound 84: A solution of compound 83 (0.15 g, ≤0.31 mmol), acetic acid (0.18 mL, 3.14 mmol) and hydroxylamine hydrochloride (33 mg, 0.47 mmol) in EtOH (10 mL) was stirred at 60° C. for 2 h and then at room temperature overnight. The mixture was concentrated, and the residue was partitioned between sat. aq. NaHCO₃ (25 mL) and EtOAc (25 mL). The organic extract was washed with brine (25 mL), dried with MgSO₄, filtered, and concentrated to give compound 84 (0.13 g, 88% yield) as a tan foamy solid. m/z=478 (M+1).

Compound 85: A mixture of compound 84 (0.13 g, 0.27 mmol) and potassium carbonate (0.19 g, 1.37 mmol) in MeOH (10 mL) was stirred at room temperature under N₂ overnight. The mixture was concentrated, and the residue was partitioned between sat. aq. KH₂PO₄ (25 mL) and EtOAc (25 mL). The organic extract was washed with brine (25 mL), dried with MgSO₄, filtered, and concentrated to give compound 85 (0.12 g, 92% yield) as a tan foamy solid. m/z=478 (M+1).

T76: To a stirring solution of compound 85 (0.12 g, 0.25 mmol) in degassed DMF (4 mL) at 0° C. under N₂ was added a solution of 1,3-dibromo-5,5-dimethylhydantoin (36 mg, 0.13 mmol) in degassed DMF (1 mL) dropwise. The mixture was stirred at 0° C. for 30 min, and then pyridine (0.20 mL, 2.47 mmol) was added. The mixture was heated at 60° C. for 4 h and then concentrated. The residue was partitioned between sat. aq. KH₂PO₄ (25 mL) and EtOAc (25 mL). The organic extract was washed with brine, dried with MgSO₄, filtered, and concentrated. The residue was purified by column chromatography (silica gel, eluting with 25% EtOAc in hexanes) to give compound T76 (73 mg, 61% yield) as a light yellow solid. m/z=476 (M+1); $^1$H NMR (400 MHz, CDCl₃) δ 7.75 (m, 2H), 7.64 (m, 3H), 7.49 (m, 4H), 7.41 (m, 1H), 2.75 (m, 1H), 2.58 (m, 2H), 2.19 (dt, J=2.1, 12.7 Hz, 1H), 2.08 (dd, J=6.5, 13.7 Hz, 1H), 1.65 (m, 10H), 1.57 (s, 3H), 1.35 (m, 2H), 1.30 (d, J=6.7 Hz, 3H).

Compound 86: A thick wall glass vessel was charged with compound 67 (130 mg, 0.263 mmol), t-BuXPhosPd-G3 (20.8 mg, 0.0263 mmol), XPhos (25 mg, 0.052 mmol), morpholine (0.034 mL, 0.390 mmol), sodium-t-butoxide (75.8 mg, 0.789 mmol) and 1,4-dioxane (3 mL). The vessel was sealed. The reaction mixture was heated at 120° C. with stirring for 22 h and then cooled to room temperature. The reaction mixture was filtered through a plug of Celite®, and the filtrate was concentrated. The residue was purified by column chromatography (silica gel, eluting with 50% EtOAc in hexanes) to give compound 86 (75 mg, 57% yield) as an off-white amorphous solid. m/z=500 (M+1).

Compound 87: A solution of compound 86 (147 mg, 0.294 mmol) in THF (10 mL) was treated with 3.0 N aq. HCl (0.98 mL, 2.94 mmol). The reaction mixture was stirred at room temperature for 23 h. Additional amount of 3.0 N aq. HCl (0.49 mL, 1.47 mmol) was added. The reaction mixture was heated at 50° C. for 1.5 h. The solvent was removed in vacuo and the residue was neutralized with sat. aq. NaHCO₃. The mixture was extracted with EtOAc. The organic extract was washed with water and brine, dried with Na₂SO₄, filtered, and concentrated to give compound 87 (147 mg, quantitative yield) as a glass. m/z=456 (M+1).

Compound 88: A mixture of compound 87 (134 mg, 0.294 mmol) in ethyl formate (10 mL, 0.12 mol) was treated dropwise with sodium methoxide (5.4 M in MeOH, 0.54 mL, 2.92 mmol) at 0° C. The mixture was stirred at room temperature for 2 h, and then cooled to 0° C. 6.0N aq. HCl (0.55 mL, 3.30 mmol) was added to adjust the pH to ~2. EtOH (25 mL) and hydroxylamine hydrochloride (30.6 mg, 0.441 mmol) were added. The reaction mixture was heated at 55° C. for 15 h. The solvent was removed in vacuo and the residue was partitioned between EtOAc and sat. aq. NaHCO₃. The organic phase was separated. The aqueous phase was extracted with EtOAc. The combined organic extracts were dried with Na₂SO₄, filtered, and concentrated. The residue was purified by column chromatography (silica gel, eluting with 50% EtOAc in hexanes) to give compound 88 (42 mg, 30% yield) as a yellow glass. m/z=481 (M+1).

Compound 89: A mixture of compound 88 (42 mg, 0.0873 mmol) and potassium carbonate (24 mg, 0.174 mmol) in MeOH (10 mL) was stirred at room temperature for 20 h. The reaction mixture was concentrated. The residue was partitioned between EtOAc and sat. aq. KH₂PO₄. The organic extract was washed with brine, dried with Na₂SO₄, filtered, and concentrated. The residue was purified by column chromatography (silica gel, eluting with 50% EtOAc in hexanes) to give compound 89 (15 mg, 36% yield) as a white glass. m/z=481 (M+1).

T77: A solution of compound 89 (14 mg, 0.029 mmol) in anhydrous DMF (2 mL) was cooled to 0° C. under nitrogen. 1,3-dibromo-5,5-dimethylhydantoin (4.5 mg, 0.016 mmol) in anhydrous DMF (0.5 mL) was added. The mixture was stirred at 0° C. for 1 h, and then anhydrous pyridine (0.024 mL, 0.30 mmol) was added. The reaction mixture was heated at 60° C. for 4 h and then cooled to room temperature. The reaction mixture was partitioned between EtOAc and sat. aq. KH₂PO₄. The organic phase was separated. The aqueous phase was extracted with EtOAc. The combined organic extracts were washed with brine, dried with Na₂SO₄, filtered, and concentrated. The residue was purified by column chromatography (silica gel, eluting with 50% EtOAc in hexanes) to give compound T77 (6 mg, 43% yield) as a yellow solid. m/z=479 (M+1); $^1$H NMR (400 MHz, CDCl₃) δ 7.75 (m, 2H), 7.67 (s, 1H), 7.63 (m, 2H), 7.48 (m, 4H), 7.41 (m, 1H), 3.83 (m, 4H), 3.23 (m, 2H), 3.16 (m, 2H), 2.72 (dd, J=4.8, 12.6 Hz, 1H), 2.54 (m, 2H), 2.20 (t, J=10.1 Hz, 1H), 2.08 (dd, J=5.3, 11.0 Hz, 1H), 1.76 (qd, J=5.0, 10.0 Hz, 1H), 1.53 (s, 3H), 1.30 (d, J=6.6 Hz, 3H).

Compound 90a: A thick wall glass vessel was charged with compound 67 (200 mg, 0.405 mmol), t-BuXPhosPd-G3 (32 mg, 0.040 mmol), XPhos (38 mg, 0.080 mmol), cyclobutylamine (0.052 mL, 0.609 mmol), sodium t-butoxide (116 mg, 1.21 mmol) and 1,4-dioxane (3 mL). The vessel was sealed. The reaction mixture was heated at 120° C. with stirring for 23 h and then cooled to room temperature. The reaction mixture was filtered through a plug of Celite®, and the filtrate was concentrated. The residue was purified by column chromatography (silica gel, eluting with 25% EtOAc in hexanes) to give compound 90a (207 mg, quantitative yield) as an orange glass. m/z=484 (M+1).

Compound 91a: A solution of 90a (207 mg, ≤0.427 mmol) in THF (30 mL) was treated with 3.0 N aq. HCl (1.43 mL, 4.27 mmol). The reaction mixture was stirred at room temperature for 20 h. The solvent was removed in vacuo and the residue was neutralized with sat. aq. NaHCO₃. The mixture was extracted with EtOAc. The organic extract was washed with water and brine; dried with Na₂SO₄; filtered; and concentrated to give compound 91a (151 mg, 80% yield) as a glass. m/z=440 (M+1).

Compound 92a: A mixture of compound 91a (150 mg, 0.341 mmol) in ethyl formate (15 mL, 0.18 mmol) was treated dropwise with sodium methoxide (5.4 M in MeOH, 0.32 mL, 1.73 mmol). After addition was complete, the reaction mixture was stirred at room temperature for 20 h. The solvent was removed in vacuo and the residue was partitioned between EtOAc and sat. aq. $KH_2PO_4$. The combined organic extract was washed with brine, dried with $Na_2SO_4$, filtered, and concentrated. The residue was purified by column chromatography (silica gel, eluting with 50% EtOAc in hexanes) to give compound 92a (113 mg, 67% yield) as a clear glass. m/z=496 (M+1).

Compound 93a: A solution of compound 92a (112 mg, 0.226 mmol) in EtOH (5 mL) was treated with 6.0 N aq. HCl (0.38 mL, 2.28 mmol) and hydroxylamine hydrochloride (23 mg, 0.331 mmol). The reaction mixture was heated at 55° C. for 16 h and then concentrated. The residue was partitioned between EtOAc and sat. aq. $NaHCO_3$. The organic layer was separated, washed with brine, dried with $Na_2SO_4$, filtered, and concentrated to give compound 93a (83 mg, 79% yield) as a yellow viscous oil. m/z=465 (M+1).

Compound 94a: A mixture of compound 93a (82 mg, 0.176 mmol) and potassium carbonate (49 mg, 0.355 mmol) in MeOH (10 mL) was stirred at room temperature for 17 h. The reaction mixture was concentrated. The residue was partitioned between EtOAc and sat. aq. $KH_2PO_4$. The organic extract was washed with brine, dried with $Na_2SO_4$, filtered, and concentrated. The residue was purified by column chromatography (silica gel, eluting with 40% EtOAc in hexanes) to give compound 94a (61 mg, 75% yield) as a glass. m/z=465 (M+1).

T78: A solution of compound 94a (60 mg, 0.129 mmol) in anhydrous DMF (3 mL) was cooled to 0° C. under nitrogen. 1,3-dibromo-5,5-dimethylhydantoin (20 mg, 0.070 mmol) in anhydrous DMF (1 mL) was added. The mixture was stirred at 0° C. for 1 h, and then anhydrous pyridine (0.104 mL, 1.29 mmol) was added. The reaction mixture was heated at 60° C. for 4 h and then cooled to room temperature. The reaction mixture was partitioned between EtOAc and sat. aq. $KH_2PO_4$. The organic phase was separated. The aqueous phase was extracted with EtOAc. The combined organic extracts were washed with brine, dried with $Na_2SO_4$, filtered, and concentrated. The residue was purified by column chromatography (silica gel, eluting with 60% EtOAc in hexanes) to give partially purified product and was purified again by column chromatography (silica gel, eluting with 80% MTBE in hexanes) to give compound T78 (28 mg, 47% yield) as a yellow glass. m/z=463 (M+1); $^1$H NMR (400 MHz, $CDCl_3$) δ 7.72 (m, 2H), 7.63 (m, 3H), 7.48 (m, 4H), 7.40 (m, 1H), 4.18 (pent, J=7.8 Hz, 1H), 2.47 (m, 4H), 2.12 (m, 2H), 1.69 (m, 6H), 1.54 (s, 3H), 1.30 (d, J=6.8 Hz, 3H).

Compound 90b: A thick wall glass vessel was charged with compound 67 (200 mg, 0.405 mmol), t-BuXPhosPd-G3 (32 mg, 0.040 mmol), XPhos (38 mg, 0.080 mmol), methylamine hydrochloride (41 mg, 0.608 mmol), sodium t-butoxide (183 mg, 1.90 mmol) and 1,4-dioxane (3 mL). The vessel was sealed. The reaction mixture was heated at 120° C. with stirring for 21 h and then cooled to room temperature. The reaction mixture was filtered through a plug of Celite®, and the filtrate was concentrated. The residue was purified by column chromatography (silica gel, eluting with 40% EtOAc in hexanes) to give compound 90b (119 mg, 66% yield) as a white solid. m/z=444 (M+1).

Compound 91b: A solution of compound 90b (140 mg, 0.315 mmol) in THF (10 mL) was treated with 3.0 N aq. HCl (1.05 mL, 3.15 mmol). The reaction mixture was stirred at room temperature for 19 h. The solvent was removed in vacuo and the residue was neutralized with sat. aq. $NaHCO_3$. The mixture was extracted with EtOAc. The organic extract was washed with water and brine, dried with $Na_2SO_4$, filtered, and concentrated to give compound 91b (126 mg, quantitative yield) as yellow viscous oil. m/z=400 (M+1).

Compound 92b: A mixture of compound 91b (125 mg, 0.312 mmol) in ethyl formate (15 mL, 0.18 mmol) was treated dropwise with sodium methoxide (5.4 M in MeOH, 0.29 mL, 1.56 mmol). After addition was complete, the reaction mixture was stirred at room temperature for 18 h. The solvent was removed in vacuo and the residue was partitioned between EtOAc and sat. aq. $KH_2PO_4$. The combined organic extract was washed with brine, dried with $Na_2SO_4$, filtered, and concentrated to give compound 92b (126 mg, 86% yield) as a yellow glass. m/z=456 (M+1).

Compound 93b: A solution of compound 92b (125 mg, 0.274 mmol) in EtOH (6 mL) was treated with 6.0 N aq. HCl (0.45 mL, 2.70 mmol) and hydroxylamine hydrochloride (28 mg, 0.403 mmol). The reaction mixture was heated at 55° C. for 17 h and then concentrated. The residue was partitioned between EtOAc and sat. aq. $NaHCO_3$. The organic layer was separated, washed with brine, dried with $Na_2SO_4$, filtered, and concentrated to give compound 93b (109 mg, 94% yield) as a yellow glass. m/z=425 (M+1).

Compound 94b: A mixture of 93b (108 mg, 0.254 mmol) and potassium carbonate (70 mg, 0.508 mmol) in methanol (10 mL) was stirred at room temperature for 22 h. The reaction mixture was concentrated. The residue was partitioned between EtOAc and sat. aq. $KH_2PO_4$. The organic extract was washed with brine, dried with $Na_2SO_4$, filtered, and concentrated. The residue was purified by column chromatography (silica gel, eluting with 50% to 60% EtOAc in hexanes) to give compound 94b (74 mg, 69% yield) as a white glass. m/z=425 (M+1).

T79: A solution of compound 94b (73 mg, 0.172 mmol) in anhydrous DMF (3 mL) was cooled to 0° C. under nitrogen. 1,3-dibromo-5,5-dimethylhydantoin (27 mg, 0.098 mmol) in anhydrous DMF (1 mL) was added. The mixture was stirred at 0° C. for 1 h, and then anhydrous pyridine (0.139 mL, 1.72 mmol) was added. The reaction mixture was heated at 60° C. for 4 h and then cooled to room temperature. The reaction mixture was partitioned between EtOAc and sat. aq. $KH_2PO_4$. The organic phase was separated. The aqueous phase was extracted with EtOAc. The combined organic extracts were washed with brine, dried with $Na_2SO_4$, filtered, and concentrated. The residue was purified by column chromatography (silica gel, eluting with MTBE) to give compound T79 (41 mg, 56% yield) as a yellow glass. m/z=423 (M+1); $^1$H NMR (400 MHz, $CDCl_3$) δ 7.73 (m, 2H), 7.63 (m, 3H), 7.49 (m, 4H), 7.40 (m, 1H), 3.33 (br s, 1H), 2.94 (s, 3H), 2.47 (m, 3H), 2.16 (dt, J=2.1, 12.6 Hz, 1H), 2.09 (m, 1H), 1.76 (m, 1H), 1.55 (s, 3H), 1.30 (d, J=6.7 Hz, 3H).

Compound 95: A solution of compound 93a (77 mg, 0.17 mmol) in 1,4-dioxane (5 mL) was treated with 37% aq. formalin solution (0.067 mL, 0.90 mmol) and formic acid (88%, 0.021 mL, 0.49 mmol). The reaction mixture was stirred at 85° C. for 1 h and then cooled to room temperature. The mixture was partitioned between EtOAc and sat. aq. $KH_2PO_4$. The organic extract was washed with brine, dried with $Na_2SO_4$, filtered, and concentrated. The residue was purified by column chromatography (silica gel, eluting with 30% EtOAc in hexanes) to give compound 95 (31 mg, 39% yield) as an orange glass. m/z=479 (M+1).

Compound 96: A mixture of 95 (30 mg, 0.063 mmol) and potassium carbonate (17 mg, 0.12 mmol) in MeOH (7 mL) was stirred at mom temperature for 20 h. The reaction mixture was concentrated, and the residue was partitioned between EtOAc and sat. aq. $KH_2PO_4$. The organic extract was washed with brine, dried with $Na_2SO_4$, filtered, and concentrated. The residue was purified by column chromatography (silica gel, eluting with 40% EtOAc in hexanes) to give compound 96 (18 mg, 60% yield) as a glass. m/z=479 (M+1).

T80: A solution of 96 (18 mg, 0.038 mmol) in anhydrous DMF (3 mL) was cooled to 0° C. under nitrogen. 1,3-dibromo-5,5-dimethylhydantoin (5.9 mg, 0.021 mmol) in anhydrous DMF (0.5 mL) was added. The mixture was stirred at 0° C. for 1 h, and then anhydrous pyridine (0.030 mL, 0.37 mmol) was added. The reaction mixture was heated at 60° C. for 4 h and then cooled to room temperature. The reaction mixture was partitioned between EtOAc and sat. aq. $KH_2PO_4$. The organic extract was washed with brine, dried with $Na_2SO_4$, filtered, and concentrated. The residue was purified by column chromatography (silica gel, eluting with MTBE) to give compound T80 (11 mg, 61% yield) as a yellow glass. m/z=477 (M+1); $^1H$ NMR (400 MHz, $CDCl_3$) δ 7.72 (m, 3H), 7.63 (m, 2H), 7.48 (m, 4H), 7.41 (m, 1H), 3.98 (m, 11H), 2.75 (s, 3H), 2.74 (m, 1H), 2.60 (m, 1H), 2.51 (qd, J=6.8, 13.4 Hz, 1H), 2.13 (m, 5H), 1.68 (m, 2H), 1.52 (s, 3H), 1.31 (d, J=6.8 Hz, 3H), 1.28 (m, 2H).

Compound 97: A thick wall glass vessel was charged with compound 67 (500 mg, 1.01 mmol), 2-tri-n-butylstannylpyridine (559 mg, 1.52 mmol), t-BuXPhosPd-G3 (80 mg, 0.10 mmol), XPhos (96 mg, 0.20 mmol), sodium-t-butoxide (291 mg, 3.02 mmol) and 1,4-dioxane (10 mL). The vessel was sealed, and the reaction mixture was heated at 150° C. for 23 h. After cooled to room temperature, the reaction mixture was diluted with EtOAc and filtered through a plug of Celite®. The filtrate was concentrated. The residue was purified by column chromatography (silica gel, eluting with 25% EtOAc in hexanes) to give partially purified compound 97 (184 mg, 37% yield) which was used in the next step without further purification. m/z=492 (M+1).

Compound 98: A solution of compound 97 (199 mg, 0.41 mol) in THF (20 mL) was treated with 3.0 N aq. HCl (3 mL, 9 mmol). The reaction mixture was stirred at room temperature for 24 h. The solvent was removed in vacuo, and the residue was partitioned between EtOAc and sat. aq. $NaHCO_3$. The organic extract was washed with brine, dried with $Na_2SO_4$, filtered, and concentrated. The residue was mixed with small amount of EtOAc. The insoluble solid was removed by filtration. The filtrate was concentrated to give partially purified compound 98 (64 mg, 35% yield) and was used without further purification. m/z=448 (M+1).

Compound 99: A mixture of compound 98 (63 mg, 0.14 mmol) in ethyl formate (5 mL, 61 mmol) was treated with sodium methoxide (5.4 M in MeOH, 0.26 mL, 1.40 mmol) dropwise. The mixture was stirred at room temperature for 2 h and then cooled to 0° C. 6.0 N aq. HCl (0.26 mL, 1.56 mmol) was added to adjust the pH to 2. EtOH (15 mL) and hydroxylamine hydrochloride (15 mg, 0.22 mmol) were added. The reaction mixture was heated at 55° C. for 2.5 h and concentrated. The residue was partitioned between EtOAc and sat. aq. $NaHCO_3$. The organic phase was separated. The aqueous phase was extracted with EtOAc. The combined organic extracts were dried with $Na_2SO_4$, filtered, and concentrated. The residue was purified by column chromatography (silica gel, eluting with 50% EtOAc in hexanes) to give partially purified compound 99 (67 mg, quantitative yield), which was used without further purification. m/z=473 (M+1).

Compound 100: A solution of compound 99 (67 mg, ≤0.14 mmol) and potassium carbonate (39 mg, 0.28 mmol) in MeOH (10 mL) was stirred at room temperature for 28 h. The solvent was removed in vacuo and the residue was partitioned between EtOAc and sat. aq. $KH_2PO_4$. The organic extract was washed with brine; dried with $Na_2SO_4$; filtered and concentrated. The residue was purified by column chromatography (silica gel, eluting with 30% EtOAc in hexanes) to give compound 100 (17 mg, 25% yield) as a white glass. m/z=473 (M+1).

T81: A solution of compound 100 (16 mg, 0.034 mmol) in anhydrous DMF (2 mL) was cooled to 0° C. under nitrogen. 1,3-dibromo-5,5-dimethylhydantoin (5.3 mg, 0.019 mmol) in anhydrous DMF (0.5 mL) was added. The mixture was stirred at 0° C. for 1 h, and then anhydrous pyridine (0.027 mL, 0.34 mmol) was added. The reaction mixture was heated at 60° C. for 4 h and then cooled to room temperature. The reaction mixture was partitioned between EtOAc and sat. aq. $KH_2PO_4$. The organic phase was separated. The aqueous phase was extracted with EtOAc. The combined organic extracts were washed with brine, dried with $Na_2SO_4$, filtered, and concentrated. The residue was purified by column chromatography (silica gel, eluting with 30% EtOAc in hexanes) to give compound T81 (11 mg, 69% yield) as a yellow solid. m/z=471 (M+1); $^1H$ NMR (400 MHz, $CDCl_3$) δ 8.64 (td, J=1.4, 4.9 Hz, 1H), 7.96 (td, J=1.1, 8.0 Hz, 1H), 7.81 (m, 2H), 7.68 (m, 4H), 7.59 (m, 2H), 7.50 (m, 2H), 7.43 (m, 1H), 7.21 (ddd, J=1.2, 4.9, 7.5 Hz 1H), 3.36 (dd, J=5.9, 17.2 Hz, 1H), 2.97 (ddd, J=6.8, 11.8, 17.8 Hz, 1H), 2.55 (qd, J=6.7, 13.4 Hz, 1H), 2.27 (dt, J=2.1, 12.7 Hz, 1H), 2.15 (dd, J=6.7, 13.8 Hz, 1H), 1.82 (m, 1H), 1.61 (s, 3H), 1.33 (d, J=6.7 Hz, 3H).

Compound 101: To a solution of compound 3 (1 g, 4.56 mmol) in $CH_2Cl_2$ (15 mL) was added magnesium bromide ethyl etherate (2.96 g, 11.46 mmol) and N,N-diisopropylethylamine (1.8 g, 13.93 mmol) sequentially at room temperature. The mixture was stirred at room temperature for 10 min and treated with 2-fluorobenzoyl chloride (0.9 g, 5.68 mmol). The mixture was stirred at room temperature for 16 h. Sat. aq. $KH_2PO_4$ was added. The mixture was extracted with EtOAc. The organic extract was washed with brine, dried with $MgSO_4$, filtered, and concentrated. The residue was purified by column chromatography (silica gel, eluting with 0% to 35% EtOAc in hexanes) to give compound 101 (675 mg, 43% yield) as a solid. m/z=342 (M+1).

Compound 102: Compound 101 (0.78 g, 2.28 mmol) and 4-bromo-phenylhydrazine HCl salt (1.2 g, 5.37 mmol) in EtOH (10 mL) was heated at 120° C. in a Biotage microwave synthesizer for 10 h. The reaction mixture was concentrated. The residue was partitioned between aq. $NaHCO_3$ and EtOAc. The organic extract was washed with brine, dried with $MgSO_4$, filtered, and concentrated. The residue was purified by column chromatography (silica gel, eluting with 0% to 35% EtOAc in hexanes) to give compound 102 (845 mg, 75% yield) as a solid. m/z=492/494 (M+1).

Compound 103: Compound 102 (0.25 g, 0.51 mmol) was taken up in MeOH (10 mL). $K_2CO_3$ (0.35 g, 2.54 mmol) was added. The reaction mixture was stirred at room temperature overnight, and then concentrated. The residue was neutralized by addition of sat. aq. $KH_2PO_4$. The mixture was extracted with EtOAc. The organic extract was washed with brine, dried with $MgSO_4$, filtered, and concentrated. The residue was purified by column chromatography (silica gel, eluting with 0% to 35% EtOAc in hexanes) to give compound 103 (225 mg, 90% yield) as a solid. m/z=492/494 (M+1).

Compound 104a: Compound 103 (240 mg, 0.49 mmol) was taken up in 1,4-dioxane (2 mL) and DMF (1 mL). $K_3PO_4$ (320 mg, 1.51 mmol), tetrakis(triphenylphosphine)

palladium(0) (50 mg, 0.043 mmol) and pyrimidin-5-ylboronic acid (95 mg, 0.77 mmol) were added. The mixture was sparged with $N_2$ for 10 min and then stirred at 90° C. for 16 h. After cooled to room temperature, the reaction mixture was filtered. The filtrate was concentrated. The residue was purified by column chromatography (silica gel, eluting with 0% to 70% EtOAc in hexanes) to give compound 104a (110 mg, 46% yield) as a solid. m/z=492 (M+1).

T82: Compound 104a (110 mg, 0.22 mmol) was dissolved in dry DMF (2 mL) and cooled to 0° C. Bromine (37 mg, 0.23 mmol) in $CH_2Cl_2$ (1 mL) was added. The reaction stirred at 0° C. for 2 h, and then pyridine (2 mL, 24.7 mmol) was added. The reaction was heated at 60° C. for 4 h and then concentrated. The residue was diluted with water and extracted with EtOAc. The organic extract was washed with brine, dried with $MgSO_4$, filtered, and concentrated. The residue was purified by column chromatography (silica gel, eluting with 0% to 70% EtOAc in hexanes) to give compound T82 (30 mg, 27% yield) as a light yellow solid. m/z=490 (M+1); $^1$H NMR (400 MHz, $CDCl_3$) δ 9.29 (s, 1H), 9.05 (s, 2H), 7.82 (m, 2H), 7.71 (m, 2H), 7.65 (s, 1H), 7.58 (dt, J=1.9, 7.5 Hz, 1H), 7.38 (m, 1H), 7.18 (m, 2H), 2.74 (m, 2H), 2.58 (qd, J=6.7, 13.4 Hz, 1H), 2.31 (dt, J=2.0, 12.6 Hz, 1H), 2.11 (m, 1H), 1.79 (m, 1H), 1.64 (s, 3H), 1.34 (d, J=6.7 Hz, 3H).

Compound 104b (T186): Compound 103 (200 mg, 0.41 mmol) was taken up in 1,4-dioxane (2 mL) and DMF (1 mL). $K_2CO_3$ (170 mg, 1.23 mmol), Pd(dppf)$Cl_2$ (30 mg, 0.041 mmol) and 6-methylpyridazin-4-ylboronic acid pinacol ester (125 mg, 0.57 mmol) were added. The mixture was sparged with $N_2$ for 10 min and then stirred at 90° C. for 16 h. After cooled to room temperature, the reaction mixture was filtered. The filtrate was concentrated. The residue was purified by column chromatography (silica gel, eluting with 0% to 100% EtOAc in hexanes) to give compound 104b (150 mg, 73% yield) as a solid. m/z=506 (M+1).

T83: Compound 104b (150 mg, 0.30 mmol) was dissolved in dry DMF (3 mL) and cooled to 0° C. Bromine (47 mg, 0.29 mmol) in $CH_2Cl_2$ (1 mL) was added. The reaction stirred at 0° C. for 2 h, and then pyridine (2 mL, 24.7 mmol) was added. The reaction was heated at 60° C. for 4 h and then concentrated. The residue was diluted with water and extracted with EtOAc. The organic extract was washed with brine, dried with $MgSO_4$, filtered, and concentrated. The residue was purified by column chromatography (silica gel, eluting with 0% to 100% EtOAc in hexanes) to give compound T83 (68 mg, 46% yield) as a light yellow solid. m/z=504 (M+1); $^1$H NMR (400 MHz, $CDCl_3$) δ 9.37 (d, J=2.2 Hz, 1H), 7.89 (m, 2H), 7.72 (m, 2H), 7.62 (s, 1H), 7.58 (m, 2H), 7.38 (m, 1H), 7.19 (m, 2H), 2.84 (s, 3H), 2.74 (m, 2H), 2.57 (qd, J=6.7, 13.4 Hz, 1H), 2.31 (dt, J=2.0, 12.7 Hz, 1H), 2.12 (m, 1H), 1.81 (m, 1H), 1.64 (s, 3H), 1.33 (d, J=6.7 Hz, 3H).

Compound 104c: Compound 103 (250 mg, 0.51 mmol) was taken up in 1,4-dioxane (2 mL) and DMF (1 mL). $K_2CO_3$ (205 mg, 1.49 mmol), Pd(dppf)$Cl_2$ (50 mg, 0.068 mmol) and pyridin-4-ylboronic acid (95 mg, 0.77 mmol) were added. The mixture was sparged with $N_2$ for min and then stirred at 90° C. for 16 h. After cooled to room temperature, the reaction mixture was filtered. The filtrate was concentrated. The residue was purified by column chromatography (silica gel, eluting with 0% to 70% EtOAc in hexanes) to give compound 104c (105 mg, 42% yield) as a solid. m/z=491 (M+1).

T84: Compound 104c (105 mg, 0.21 mmol) was dissolved in dry DMF (3 mL) and cooled to 0° C. Bromine (35 mg, 0.22 mmol) in $CH_2Cl_2$ (1 mL) was added. The reaction stirred at 0° C. for 2 h, and then pyridine (2 mL, 24.7 mmol) was added. The reaction was heated at 60° C. for 4 h and then concentrated. The residue was diluted with water and extracted with EtOAc. The organic extract was washed with brine, dried with $MgSO_4$, filtered, and concentrated. The residue was purified by column chromatography (silica gel, eluting with 0% to 100% EtOAc in hexanes) to give compound T84 (44 mg, 42% yield) as an off-white solid. m/z=489 (M+1); $^1$H NMR (400 MHz, $CDCl_3$) δ 8.74 (m, 2H), 7.85 (m, 2H), 7.66 (m, 3H), 7.58 (m, 3H), 7.37 (dddd, J=1.9, 5.2, 7.2, 8.2 Hz, 1H), 7.20 (dt, J=1.1, 7.5 Hz, 1H), 7.15 (m, 1H), 2.74 (m, 2H), 2.57 (qd, J=6.7, 13.4 Hz, 1H), 2.31 (dt, J=2.1, 12.7 Hz, 1H), 2.11 (m, 1H), 1.80 (m, 1H), 1.63 (s, 3H), 1.33 (d, J=6.7 Hz, 3H).

Compound 105: A thick wall glass vessel was charged with compound 103 (225 mg, 0.456 mmol), t-BuXPhosPd-G3 (36 mg, 0.045 mmol), XPhos (43 mg, 0.090 mmol), morpholine (0.059 mL, 0.67 mmol), sodium t-butoxide (131 mg, 1.36 mmol) and 1,4-dioxane (4 mL). The vessel was sealed and the reaction mixture was heated at 120° C. with stirring for 16 h. After cooled to room temperature, the reaction mixture was diluted with EtOAc and filtered through a plug of Celite®. The filtrate was concentrated. The residue was purified by column chromatography (silica gel, eluting with 50% EtOAc in hexanes) to give compound 105 (139 mg, 61% yield) as a white glass. m/z=499 (M+1).

T85: A solution of 105 (138 mg, 0.277 mmol) in anhydrous toluene (15 mL) under nitrogen was treated with DDQ (81 mg, 0.358 mmol). The reaction mixture was stirred at room temperature for 4.5 h. The solvent was removed in vacuo and the residue was purified by column chromatography (silica gel, eluting with 50% EtOAc in hexanes) to give compound T85 (30 mg, 22% yield) as a brownish-white solid. m/z=497 (M+1); $^1$H NMR (400 MHz, $CDCl_3$) δ 7.70 (s, 1H), 7.59 (dt, J=1.8, 7.5 Hz, 1H), 7.37 (m, 3H), 7.15 (m, 2H), 7.00 (m, 2H), 3.90 (m, 4H), 3.27 (m, 4H), 2.70 (m, 2H), 2.54 (qd, J=6.7, 13.4 Hz, 1H), 2.28 (dt, J=2.0, 12.7 Hz, 1H), 2.05 (m, 1H), 1.75 (m, 1H), 1.55 (s, 3H), 1.32 (d, J=6.7 Hz, 3H).

Compound 107a: A mixture of compound 101 (150 mg, 0.44 mmol), compound 106a (166 mg, 0.88 mmol) and 12 N aq. HCl (73 µL, 0.88 mmol) in EtOH (4 mL) was heated in Biotage microwave at 100° C. for 2 h. After cooled to room temperature, the mixture was concentrated. The residue was diluted with EtOAc and washed with 1 N aq. HCl. The organic extract was dried with $Na_2SO_4$, filtered, and concentrated. The residue was purified by column chromatography (silica gel, eluting with 0% to 40% EtOAc in hexanes) to give compound 107a (64 mg, 29% yield) as a yellow solid. m/z=495 (M+1).

Compound 108a: A mixture of compound 107a (60 mg, 0.12 mmol) in MeOH (1.2 mL) was treated with potassium carbonate (25 mg, 0.18 mmol). The mixture was stirred at room temperature overnight. The solvent was removed in vacuo and the residue was diluted with EtOAc. The mixture was washed with 1 N aq. HCl. The organic extract was dried with $Na_2SO_4$, filtered, and concentrated to give compound 108a (59 mg, 98% yield) as an off-white solid. m/z=495 (M+1).

T86: A solution of compound 108a (59 mg, 0.12 mmol) in anhydrous DMF (0.8 mL) was cooled to 0° C. under nitrogen. 1,3-dibromo-5,5-dimethylhydantoin (17 mg, 0.059 mmol) in anhydrous DMF (0.4 mL) was added. The mixture was stirred at 0° C. for 2 h, and then anhydrous pyridine (29 µL, 0.36 mmol) was added. The reaction mixture was heated at 55° C. overnight and then cooled to room temperature. The reaction mixture was diluted with EtOAc and washed with 1 N aq. HCl and water. The organic extract was dried with Na$_2$SO$_4$, filtered, and concentrated. The residue was purified by column chromatography (silica gel, eluting with 0% to 15% EtOAc in hexanes) to give compound T86 (40 mg, 68% yield) as a white solid. m/z=493 (M+1): $^1$H NMR (400 MHz, CDCl$_3$) δ 8.03 (s, 1H), 7.77 (m, 2H), 7.57 (m, 4H), 7.44 (dddd, J=1.8, 5.2, 7.2, 8.2 Hz, 1H), 7.25 (dt, J=1.2, 7.6 Hz, 1H), 7.20 (ddd, J=1.1, 8.3, 10.5 Hz, 1H), 3.74 (s, 3H), 2.68 (m, 3H), 2.30 (dt, J=2.1, 12.7 Hz, 1H), 2.11 (m, 1H), 1.90 (s, 3H), 1.81 (m, 1H), 1.34 (d, J=6.7 Hz, 3H).

Compound 107b: Compound 107a (orange solid, 65 mg, 30% yield) was synthesized from compound 101 (150 mg, 0.44 mmol) and compound 106b (168 mg, 0.88 mmol) using the same procedure as described for the synthesis of compound 107a. Compound 107b was purified by column chromatography (silica gel, eluting with 0% to 10% EtOAc in hexanes). m/z=497 (M+1).

Compound 108b: Compound 108b (orange solid, 59 mg, 98% yield) was synthesized from compound 107b (60 mg, 0.12 mmol) using the same procedure as described for the synthesis of compound 108a. After workup, the crude product was used in the next step without further purification. m/z=497 (M+1).

T87: Compound T87 (white solid, 25 mg, 42% yield) was synthesized from compound 108b (59 mg, 0.12 mmol) and 1,3-dibromo-5,5-dimethylhydantoin (17 mg, 0.059 mmol) using the same procedure as described for the synthesis of compound T86. Compound T87 was purified by column chromatography (silica gel, eluting with 0% to 40% EtOAc in hexanes). m/z=495 (M+1); $^1$H NMR (400 MHz, CDCl$_3$) δ 9.54 (s, 1H), 7.81 (m, 2H), 7.64 (dt, J=1.8, 7.5 Hz, 1H), 7.37 (m, 6H), 7.19 (m, 1H), 2.67 (m, 3H), 2.34 (dt, J=2.0, 12.5 Hz, 1H), 2.07 (m, 1H), 1.87 (s, 3H), 1.71 (dq, J=5.4, 12.6 Hz, 1H), 1.39 (d, J=6.8 Hz, 3H).

Compound 107c: A mixture of compound 101 (150 mg, 0.44 mmol), compound 106c (154 mg, 0.66 mmol) and 12 N aq. HCl (73 µL, 0.88 mmol) in EtOH (4 mL) was heated in Biotage microwave at 100° C. for 3 h. After cooled to room temperature, the mixture was concentrated. The residue was diluted with EtOAc and washed with 1 N aq. HCl and water. The organic extract was dried with Na$_2$SO$_4$, filtered, and concentrated. The residue was purified by column chromatography (silica gel, eluting with 0% to 100% EtOAc in hexanes) to give compound 107c (94 mg, 40% yield) as a yellow solid. m/z=539 (M+1).

Compound 108c: Compound 108c (pale yellow solid, 85 mg, 94% yield) was synthesized from compound 107c (90 mg, 0.17 mmol) using the same procedure as described for the synthesis of compound 108a. After workup, the crude product was used in the next step without further purification. m/z=539 (M+1).

T88: Compound T88 (pale yellow solid, 60 mg, 71% yield) was synthesized from compound 108c (85 mg, 0.16 mmol) and 1,3-dibromo-5,5-dimethylhydantoin (23 mg, 0.080 mmol) using the same procedure as described for the synthesis of compound T86. Compound T88 was purified by column chromatography (silica gel, eluting with 0% to 40% EtOAc in hexanes). m/z=537 (M+1); $^1$H NMR (400 MHz, CDCl$_3$) δ 9.29 (s, 1H), 8.16 (m, 1H), 7.94 (d, J=8.3 Hz, 1H), 7.63 (m, 2H), 7.47 (dddd, J=1.8, 5.2, 7.2, 8.3 Hz, 1H), 7.29 (dt, J=1.1, 7.5 Hz, 1H), 7.20 (ddd, J=1.1, 8.3, 10.5 Hz, 1H), 2.68 (m, 3H), 2.30 (dt, J=1.9, 12.6 Hz, 1H), 2.09 (m, 1H), 1.88 (s, 3H), 1.72 (dq, J=5.3, 12.2 Hz, 1H), 1.38 (d, J=6.8 Hz, 3H).

Compound 107d: A mixture of compound 101 (55 mg, 0.16 mmol), compound 106d (48 mg, 0.24 mmol) and 12 N aq. HCl (20 µL, 0.24 mmol) in EtOH (2 mL) was heated in Biotage microwave at 100° C. for 4 h. After cooled to room temperature, the mixture was concentrated. The residue was diluted with EtOAc and washed with 1 N aq. HCl and water. The organic extract was dried with Na$_2$SO$_4$, filtered, and concentrated. The residue was purified by column chromatography (silica gel) to give compound 107d (40 mg, 49% yield) as a yellow solid. m/z=505 (M+1).

Compound 108d: A mixture of compound 107d (40 mg, 0.079 mmol) in MeOH (1 mL) was treated with potassium carbonate (16 mg, 0.12 mmol). The mixture was stirred at room temperature overnight. The solvent was removed in vacuo and the residue was diluted with EtOAc. The mixture was washed with 1 N aq. HCl. The organic extract was dried with Na$_2$SO$_4$, filtered, and concentrated to give compound 108d (31 mg, 78% yield) as an orange solid. m/z=505 (M+1).

T89: A solution of compound 108d (30 mg, 0.059 mmol) in anhydrous DMF (0.6 mL) was cooled to 0° C. under nitrogen. 1,3-dibromo-5,5-dimethylhydantoin (8.5 mg, 0.030 mmol) in anhydrous DMF (0.4 mL) was added. The mixture was stirred at 0° C. for 2 h, and then anhydrous pyridine (14 µL, 0.17 mmol) was added. The reaction mixture was heated at 55° C. overnight and then cooled to room temperature. The reaction mixture was diluted with EtOAc and washed with 1 N aq. HCl and water. The organic extract was dried with Na$_2$SO$_4$, filtered, and concentrated. The residue was purified by column chromatography (silica gel, eluting with 0% to 100% EtOAc in hexanes) to give compound T89 (17 mg, 57% yield) as a pale yellow solid. m/z=503 (M+1); $^1$H NMR (400 MHz, CDCl$_3$) δ9.35 (s, 1H), 7.81 (m, 2H), 7.63 (dt, J=1.7, 7.4 Hz, 1H), 7.45 (m, 2H), 7.29 (m, 1H), 7.19 (m, 1H), 2.67 (m, 3H), 2.30 (dt, J=1.9, 12.6 Hz, 1H), 2.08 (m, 1H), 1.85 (s, 3H), 1.70 (dq, J=5.5, 12.5 Hz, 1H), 1.38 (d, J=6.7 Hz, 3H).

Compound 107e: A mixture of compound 101 (100 mg, 0.29 mmol), compound 106e (71 mg, 0.44 mmol) and 12 N aq. HCl (50 µL, 0.60 mmol) in EtOH (3 mL) was heated in Biotage microwave at 100° C. for 3 h. After cooled to room temperature, the mixture was concentrated. The residue was diluted with EtOAc and washed with 1 N aq. HCl. The organic extract was dried with Na$_2$SO$_4$, filtered, and concentrated. The residue was purified by column chromatography (silica gel, eluting with 0% to 70% EtOAc in hexanes) to give compound 107e (45 mg, 33% yield) as an off-white solid. m/z=468 (M+1).

Compound 108e: A mixture of compound 107e (40 mg, 0.096 mmol) in MeOH (1 mL) was treated with potassium carbonate (20 mg, 0.14 mmol). The mixture was stirred at room temperature for 4 h. The solvent was removed in vacuo and the residue was diluted with EtOAc. The mixture was washed with 1 N aq. HCl. The organic extract was dried with Na$_2$SO$_4$, filtered, and concentrated to give compound 108e (42 mg, quantitative yield) as a white solid. m/z=468 (M+1).

T90: A solution of compound 108e (42 mg, 0.090 mmol) in anhydrous DMF (0.5 mL) was cooled to 0° C. under nitrogen. 1,3-dibromo-5,5-dimethylhydantoin (12.8 mg, 0.045 mmol) in anhydrous DMF (0.5 mL) was added. The mixture was stirred at 0° C. for 2 h, and then anhydrous pyridine (22 µL, 0.27 mmol) was added. The reaction mixture was heated at 55° C. overnight and then cooled to room temperature. The reaction mixture was diluted with EtOAc and washed with 1 N aq. HCl and water. The organic extract was dried with Na$_2$SO$_4$, filtered, and concentrated. The residue was purified by column chromatography (silica gel, eluting with 0% to 40% EtOAc in hexanes) to give partially purified product and was purified again by column chromatography (silica gel, eluting with 0% to 20% EtOAc in CH$_2$Cl$_2$) to give compound T90 (10 mg, 24% yield) as an off-white solid. m/z=466 (M+1); $^1$H NMR (400 MHz, CDCl$_3$) δ 8.27 (s, 1H), 7.81 (m, 1H), 7.57 (dt, J=1.8, 7.5 Hz, 1H), 7.41 (m, 4H), 7.21 (m, 2H), 3.86 (s, 3H), 2.72 (m, 2H), 2.63 (qd, J=6.8, 13.4 Hz, 1H), 2.31 (dt, J=2.0, 12.7 Hz, 1H), 2.10 (m, 1H), 1.85 (s, 3H), 1.79 (m, 1H), 1.34 (d, J=6.8 Hz, 3H).

Compound 107f: Compound 107f (white solid, 100 mg, 75% yield) was synthesized from compound 101 (100 mg, 0.29 mmol), compound 106f (65 mg, 0.44 mmol) using the same procedure as described for the synthesis of compound 107e. The reaction was heated at 100° C. for 4 h. Compound 107f was purified by column chromatography (silica gel, eluting with 0% to 30% EtOAc in hexanes). m/z=454 (M+1).

Compound 108f: A mixture of compound 107f (100 mg, 0.22 mmol) in MeOH (2.2 mL) was treated with potassium carbonate (45 mg, 0.33 mmol). The mixture was stirred at room temperature overnight. The solvent was removed in vacuo and the residue was diluted with EtOAc. The mixture was washed with 1 N aq. HCl. The organic extract was dried with Na$_2$SO$_4$, filtered, and concentrated to give compound 108f (100 mg, quantitative yield) as a white solid. m/z=454 (M+1).

T91: A solution of compound 108f (100 mg, 0.22 mmol) in anhydrous DMF (1.2 mL) was cooled to 0° C. under nitrogen. 1,3-dibromo-5,5-dimethylhydantoin (31 mg, 0.11 mmol) in anhydrous DMF (1 mL) was added. The mixture was stirred at 0° C. for 2 h, and then anhydrous pyridine (54 μL, 0.67 mmol) was added. The reaction mixture was heated at 55° C. overnight and then cooled to room temperature. The reaction mixture was diluted with EtOAc and washed with 1 N aq. HCl and water. The organic extract was dried with Na$_2$SO$_4$, filtered, and concentrated. The residue was purified by column chromatography (silica gel, eluting with 0% to 30% EtOAc in hexanes) to give partially purified product, which was purified again by column chromatography (silica gel, eluting with 0% to 10% EtOAc in CH$_2$Cl$_2$) to give compound T91 (30 mg, 30% yield) as white solid. m/z=452 (M+1) $^1$H NMR (400 MHz, CDCl$_3$) δ 9.96 (br s, 1H), 9.64 (s, 1H), 7.74 (m, 1H), 7.61 (dt, J=1.8, 7.5 Hz, 1H), 7.45 (m, 2H), 7.29 (m, 3H), 7.21 (ddd, J=1.1, 8.3, 10.5 Hz, 1H), 2.69 (m, 3H), 2.30 (dt, J=1.9, 12.6 Hz, 1H), 2.08 (dd, J=5.6, 13.5 Hz, 1H), 1.93 (s, 3H), 1.73 (dq, J=5.7, 12.4 Hz, 1H), 1.38 (d, J=6.8 Hz, 3H).

Compound 107g: Compound 107g (yellow solid, 93 mg, 67% yield) was synthesized from compound 101 (100 mg, 0.29 mmol), compound 106g (72 mg, 0.44 mmol) using the same procedure as described for the synthesis of compound 107e. Compound 107g was purified by column chromatography (silica gel, eluting with 0% to 15% EtOAc in hexanes). m/z=471 (M+1).

Compound 108g: A mixture of compound 107g (60 mg, 0.13 mmol) in MeOH (2 mL) was treated with potassium carbonate (35 mg, 0.25 mmol). The mixture was stirred at room temperature for 14 h. The solvent was removed in vacuo and the residue was diluted with EtOAc. The mixture was washed with 1 N aq. HCL. The organic extract was dried with Na$_2$SO$_4$, filtered, and concentrated to give compound 108g (55 mg, 92% yield) as a white solid. m/z=471 (M+1).

T92: A solution of compound 108g (55 mg, 0.12 mmol) in anhydrous DMF (0.6 mL) was cooled to 0° C. under nitrogen. 1,3-dibromo-5,5-dimethylhydantoin (17 mg, 0.059 mmol) in anhydrous DMF (0.5 mL) was added. The mixture was stirred at 0° C. for 12 h, and then anhydrous pyridine (28 μL, 0.35 mmol) was added. The reaction mixture was heated at 55° C. overnight and then cooled to room temperature. The reaction mixture was diluted with EtOAc and washed with 1 N aq. HCl and water. The organic extract was dried with Na$_2$SO$_4$, filtered, and concentrated. The residue was purified by column chromatography (silica gel, eluting with 0% to 10% EtOAc in CH$_2$Cl$_2$) to give partially purified product, which was purified again by column chromatography (silica gel, eluting with 0% to 20% EtOAc in hexanes) to give compound T92 (30 mg, 55% yield) as white solid. m/z=469 (M+1); $^1$H NMR (400 MHz, CDCl$_3$) δ 9.41 (s, 1H), 7.90 (ddd, J=0.6, 1.2, 8.2 Hz, 1H), 7.84 (ddd, J=0.6, 1.3, 7.9 Hz, 1H), 7.65 (dt, J=1.8, 7.5 Hz, 1H), 7.44 (m, 3H), 7.29 (dd, J=1.2, 7.6 Hz, 1H), 7.19 (ddd, J=1.0, 8.3, 10.5 Hz, 1H), 2.68 (m, 3H), 2.32 (dt, J=1.9, 12.5 Hz, 1H), 2.07 (m, 1H), 1.89 (s, 3H), 1.71 (dq, J=5.5, 12.4 Hz, 1H), 1.38 (d, J=6.8 Hz, 3H).

Compound 109: In a sealable vial, a mixture of compound 103 (0.52 g, 1.06 mmol), bis(pinacolato)diboron (0.40 g, 1.58 mmol) and potassium acetate (0.32 g, 3.26 mmol) in 1,4-dioxane (11 mL) was degassed. 1,1'-bis(diphenylphosphino)ferrocene-palladium (II) chloride (78 mg, 0.11 mmol) was added. The mixture was degassed again. The vial was sealed. The mixture was heated at 100° C. for 16 h. After cooled to room temperature, the mixture was diluted with EtOAc (50 mL) and filtered through a pad of Celite®. The filtrate was washed with sat. aq. KH$_2$PO$_4$ (50 mL) and sat. aq. NaCl (50 mL). The organic extract was dried with MgSO$_4$, filtered, and concentrated. The residue was purified by column chromatography (silica gel, eluting with 0% to 50% EtOAc in hexanes) to give compound 109 (0.29 g, 51% yield) as an off-white solid. m/z=540 (M+1).

Compound 110: In a sealable vial, a mixture of compound 109 (0.29 g, 0.54 mmol), 4-chloropyrimidine (77 mg, 0.67 mmol) and potassium phosphate (0.34 g, 1.60 mmol) in 1,4-dioxane (4.8 mL) and DMF (1.2 mL) was degassed. Tetrakis(triphenylphosphine)palladium(0) (62 mg, 0.054 mmol) was added. The mixture was degassed again. The vial was sealed. The mixture was heated at 100° C. for 16 h. The mixture was cooled to room temperature, diluted with EtOAc (50 mL), and washed with sat. aq. KH$_2$PO$_4$ (50 mL). The organic extract was washed with sat. aq. NaCl solution (50 mL), dried with MgSO$_4$, filtered, and concentrated. The residue was purified by column chromatography (silica gel, eluting with 50% to 100% EtOAc in hexanes) to give compound 110 (0.16 g, 61% yield) as alight yellow solid. m/z=492 (M+1).

T93: To a stirring solution of compound 110 (0.16 g, 0.33 mmol) in degassed DMF (4 mL) at 0° C. under N$_2$ was added dropwise a solution of 1,3-dibromo-5,5-dimethylhydantoin (46 mg, 0.16 mmol) in degassed DMF (1 mL). The mixture was stirred at 0° C. for 30 min, and then pyridine (0.26 mL, 3.22 mmol) was added. The mixture was heated at 60° C. for 4 h and then concentrated. The residue was partitioned between sat. aq. KH$_2$PO$_4$ (25 mL) and EtOAc (25 mL). The organic extract was washed with sat. aq. NaCl solution (25 mL), dried with MgSO$_4$, filtered, and concentrated. The residue was purified by column chromatography (silica gel, eluting with 5% MeOH in CHCl$_3$). The impure product obtained was triturated with EtOAc. The solid was collected by filtration and dried under vacuum to give T93 (29 mg, 18% yield) as an off-white solid. m/z=490 (M+1); $^1$H NMR (400 MHz, CDCl$_3$) δ 9.34 (d, J=1.4 Hz, 1H), 8.87 (d, J=5.3 Hz, 1H), 8.35 (m, 2H), 7.83 (dd, J=1.5, 5.4 Hz, 1H), 7.70 (m, 2H), 7.59 (m, 2H), 7.38 (dddd, J=1.9, 5.2, 7.1, 8.3 Hz, 1H), 7.18 (m, 2H), 2.74 (m, 2H), 2.56 (qd, J=6.7, 13.4 Hz, 1H), 2.30 (dt, J=2.0, 12.7 Hz, 1H), 2.11 (m, 1H), 1.80 (m, 1H), 1.63 (s, 3H), 1.33 (d, J=6.7 Hz, 3H).

Compound 111: Compound 101 (0.18 g, 0.53 mmol) and 4-cyanophenylhydrazine hydrochloride (220 mg, 1.30 mmol) in EtOH (2 mL) was heated at 120° C. in a Biotage microwave synthesizer for 10 h. The reaction mixture was concentrated. The residue was partitioned between aq. NaHCO$_3$ and EtOAc. The organic extract was dried with MgSO$_4$, filtered, and concentrated. The residue was purified by column chromatography (silica gel, eluting with 0% to 30% EtOAc in hexanes) to give compound 111 (180 mg, 78% yield) as a solid. m/z=439 (M+1).

Compound 112: Compound 111 (172 mg, 0.39 mmol) was taken up in EtOH (5 mL). Hydroxylamine (50% in water, 85 mg, 1.29 mmol) was added. The reaction mixture was stirred at 50° C. overnight and then concentrated to give compound 112 (180 mg, 97% yield) as a solid. m/z=472 (M+1).

Compound 113: Compound 112 (0.18 g, 0.38 mmol) was taken up in 1,4-dioxane (10 mL). Dimethylacetamide dimethylacetal (0.2 g, 1.50 mmol) was added. The reaction mixture was heated at 60° C. for 2 h and then concentrated. The residue was purified by column chromatography (silica gel, eluting with 0% to 35% EtOAc in hexanes) to give compound 113 (120 mg, 63% yield) as a solid. m/z=496 (M+1).

Compound 114: Compound 113 (0.12 g, 0.24 mmol) was taken up in MeOH (10 mL) and K$_2$CO$_3$ (0.17 g, 1.23 mmol) was added. The reaction mixture was stirred at room temperature overnight and then concentrated. The residue was neutralized by addition of sat. aq. KH$_2$PO$_4$. The mixture was extracted with EtOAc. The organic extract was washed with brine, dried with MgSO$_4$, filtered, and concentrated. The residue was purified by column chromatography (silica gel, eluting with 0% to 35% EtOAc in hexanes) to give compound 114 (85 mg, 71% yield) as a solid. m/z=496 (M+1).

T94: Compound 114 (85 mg, 0.17 mmol) was dissolved in dry DMF (2 mL) and cooled 20 to 0° C. Bromine (30 mg, 0.19 mmol) in CH$_2$Cl$_2$ (1 mL) was added, and the reaction was stirred at 0° C. for 2 h. Pyridine (2 mL, 24.7 mmol) was added. The reaction mixture was stirred at 60° C. for 4 h and then concentrated. The residue was diluted with water and extracted with EtOAc. The organic extract was washed with brine, dried with MgSO$_4$, filtered, and concentrated. The residue was purified by column chromatography (silica gel, eluting with 0% to 35% EtOAc in hexanes) to give compound T94 (50 mg, 59% yield) as an off-white solid. m/z=494 (M+1); $^1$H NMR (400 MHz, CDCl$_3$) δ 8.31 (m, 2H), 7.66 (m, 2H), 7.58 (m, 2H), 7.37 (m, 1H), 7.18 (m, 2H), 2.73 (m, 2H), 2.70 (s, 3H), 2.56 (qd, J=6.7, 13.4 Hz, 1H), 2.29 (dt, J=2.0, 12.7 Hz, 1H), 2.10 (m, 1H), 1.78 (m, 1H), 1.62 (s, 3H), 1.32 (d, J=6.7 Hz, 3H).

Compound 115: Compound 111 (0.56 g, 1.28 mmol) was mixed in 50% aq. H$_2$SO$_4$ (10 mL) and heated at 130° C. for 2 h. The mixture was cooled to 0° C. diluted with water (20 mL), and neutralized with NaHCO$_3$ (solid) to pH 5. The precipitated solid was collected by filtration and dried in vacuo to give compound 115 (0.57 g, 98% yield). m/z=458 (M+1).

Compound 116: Compound 115 (0.56 g, 1.22 mmol) in CH$_2$Cl$_2$ (15 mL) was cooled to 0° C. Oxalyl chloride (0.8 g, 6.30 mmol) and 1 drop of DMF was added. The solution was stirred at room temperature for 2 h and concentrated to give the acid chloride. The acid chloride was dissolved in CH$_2$Cl$_2$ (5 mL). The solution was added to a solution of N-hydroxyacetamidine (145 mg, 1.96 mmol) and Et$_3$N (1 g, 9.90 mmol) in CH$_2$Cl$_2$ (10 mL) at 0° C. The reaction mixture was stirred at rt for 16 h and then concentrated. The residue was diluted with sat. aq. NaHCO$_3$ and extracted with EtOAc. The organic extract was dried with MgSO$_4$, filtered, and concentrated. The residue was purified by column chromatography (silica gel, eluting with 0% to 100% EtOAc in hexanes) to give compound 116 (0.4 g, 64% yield) as a solid. m/z=514 (M+1).

Compound 117: Compound 116 (0.4 g, 0.78 mmol) in 1,4-dioxane (10 mL) was treated with propylphosphonic anhydride (50 wt. % in EtOAc, 1.5 g, 2.36 mmol). The mixture was heated at 90° C. for 16 h and then cooled and concentrated. The residue was diluted with aq. NaHCO$_3$ and extracted with EtOAc. The organic extract was dried with MgSO$_4$, filtered, and concentrated. The residue was purified by column chromatography (silica gel, eluting with 0% to 35% EtOAc in hexanes) to give compound 117 (0.26 g, 67% yield) as a solid. m/z=496 (M+1).

Compound 118: Compound 117 (0.26 g, 0.53 mmol) in MeOH (10 mL) was treated with K$_2$CO$_3$ (365 mg, 2.64 mmol). The reaction mixture was stirred at room temperature overnight and then concentrated. The residue was neutralized by addition of sat. aq. KH$_2$PO$_4$ and extracted with EtOAc. The organic extract was washed with brine, dried with MgSO$_4$, filtered, and concentrated. The residue was purified by column chromatography (silica gel, eluting with 0% to 35% EtOAc in hexanes) to give compound 118 (0.25 g, 96% yield) as a solid. m-Z=496 (M+1).

T95: Compound 118 (0.25 g, 0.50 mmol) was taken up in dry DMF (3 mL), and was cooled to 0° C. Bromine (81 mg, 0.51 mmol) was added. The reaction was stirred at 0° C. for 2 h, and then pyridine (2 mL, 24.7 mmol) was added. The mixture was heated at 60° C. for 4 h and then concentrated. The residue was diluted with water and extracted with EtOAc. The organic extract was washed with brine, dried with MgSO$_4$, filtered, and concentrated. The residue was purified by column chromatography (silica gel, eluting with 0% to 35% EtOAc in hexanes) to give compound T95 (0.17 g, 68% yield) as a white solid. m/z=494 (M+1); $^1$H NMR (400 MHz, CDCl$_3$) δ 8.36 (m, 2H), 7.72 (m, 2H), 7.57 (dt, J=1.8, 7.5 Hz, 1H), 7.54 (s, 1H), 7.38 (dddd, J=1.8, 5.2, 7.2, 8.3 Hz, 1H), 7.21 (d, J=1.2, 7.6 Hz, 1H), 7.15 (m, 111), 2.74 (m, 2H), 2.56 (m, 1H), 2.52 (s, 3H), 2.29 (dt, J=2.1, 12.7 Hz, 1H), 2.11 (m, 1H), 1.79 (m, 1H), 1.64 (s, 3H), 1.33 (d, J=6.7 Hz, 3H).

Compound 119: A mixture of compound 63 (0.8 g, 3.36 mmol), diethyl oxalate (5 g, 34.21 mmol) and sodium hydride (60% in mineral oil, 0.55 g, 13.75 mmol) in THF (25 mL) was heated at 80° C. overnight. The reaction mixture was cooled to room temperature and quenched by aq. KH$_2$PO$_4$. The mixture was extracted with EtOAc. The organic extract was washed with brine, dried with MgSO$_4$, filtered, and concentrated. The residue was purified by column chromatography (silica gel, eluting with 0% to 35% EtOAc in hexanes) to give compound 119 (0.78 g, 69% yield) as an oil. m/z=339 (M+1).

Compound 120: Compound 119 (365 mg, 1.08 mmol) and biphenyl-4-ylhydrazine hydrochloride (0.3 g, 1.36 mmol) in EtOH (10 mL) was heated at 120° C. in Biotage microwave synthesizer for 75 min. The reaction mixture was concentrated. The residue was treated with aq. NaHCO$_3$ and extracted with EtOAc. The organic extract was concentrated. The residue was mixed with THF (5 mL) and 3 N aq. HCl (3 mL, 9 mmol). The mixture was stirred at room temperature overnight and then concentrated. The residue was neutralized with sat. aq. NaHCO$_3$ and extracted with EtOAc. The organic extract was dried with MgSO$_4$, filtered, and concentrated. The residue was purified by column chromatography (silica gel, eluting with 0% to 35% EtOAc in hexanes) to give compound 120 (0.32 g, 67% yield) as an oil. m/z=443 (M+1).

Compound 121: Compound 120 (0.31 g, 0.70 mmol) was taken up in ethyl formate (10 mL, 0.12 mol). Sodium methoxide (30 wt. % in MeOH, 1.27 g, 7.05 mmol) was added. After stirring at room temperature for 4 h, the reaction mixture was neutralized with aq. $KH_2PO_4$ and extracted with EtOAc. The organic extract was dried with $MgSO_4$, filtered, and concentrated. The crude product was dissolved in EtOH (15 mL). Hydroxylamine hydrochloride (70 mg, 1.01 mmol) and 12 N aq. HCl (3 drops) were added. The reaction mixture was stirred at 55° C. overnight, cooled to room temperature, and concentrated. The residue was diluted with EtOAc and washed with aq. $NaHCO_3$. The organic extract was dried with $MgSO_4$, filtered, and concentrated. The residue was purified by column chromatography (silica gel, eluting with 0% to 30% EtOAc in hexanes) to give compound 121 (125 mg, 38% yield) as a solid. m/z=468 (M+1).

Compound 122: A mixture of compound 121 (125 mg, 0.27 mmol) and 50% aq. $H_2SO_4$ (3 mL) was heated at 130° C. for 2 h. The mixture was cooled to 0° C., diluted with water (10 mL), and neutralized with $NaHCO_3$ (solid) to pH 5. The precipitated solid was collected by filtration and dried in vacuo to give compound 122 (0.12 g, quantitative yield) as an off-white solid. m/z=440 (M+1).

Compound 123: Compound 122 (0.12 g, 0.27 mmol) in $CH_2Cl_2$ (5 mL) was cooled to 0° C. Oxalyl chloride (175 mg, 1.38 mmol) and 1 drop of DMF were added. The solution was stirred at room temperature for 3 h and concentrated to give the acid chloride. The acid chloride was dissolved in $CH_2Cl_2$ (5 mL). The solution was added to a solution of N-hydroxyacetamidine (30 mg, 0.40 mmol) and $Et_3N$ (250 mg, 2.47 mmol) in $CH_2Cl_2$ (5 mL) at 0° C. The reaction mixture was stirred at room temperature for 16 h and then concentrated. The residue was diluted with sat. aq. $NaHCO_3$ and extracted with EtOAc. The organic extract was dried with $MgSO_4$, filtered, and concentrated. The residue was purified by column chromatography (silica gel, eluting with 0% to 100% EtOAc in hexanes) to give compound 123 (75 mg, 55% yield) as a solid. m/z=496 (M+1).

Compound 124: Compound 123 (72 mg, 0.15 mmol) in 1,4-dioxane (5 mL) was treated with propylphosphonic anhydride (50 wt. % in EtOAc, 0.25 g, 0.39 mmol). The mixture was heated at 90° C. for 16 h and then cooled and concentrated. The residue was diluted with aq. $NaHCO_3$ and extracted with EtOAc. The organic extract was dried with $MgSO_4$, filtered, and concentrated. The residue was purified by column chromatography (silica gel, eluting with 0% to 35% EtOAc in hexanes) to give compound 124 (40 mg, 56% yield) as a solid. m/z=478 (M+1).

Compound 125: A mixture of compound 124 (80 mg, 0.17 mmol) in MeOH (10 mL) was treated with $K_2CO_3$ (115 mg, 0.83 mmol). The reaction mixture was stirred at room temperature overnight and then concentrated. The residue was neutralized by addition of sat. aq. $KH_2PO_4$ and extracted with EtOAc. The organic extract was washed with brine, dried with $MgSO_4$, filtered, and concentrated. The residue was purified by column chromatography (silica gel, eluting with 0% to 30% EtOAc in hexanes) to give compound 125 (80 mg, quantitative yield) as a solid. m/z=478 (M+1).

T96: A solution of compound 125 (80 mg, 0.17 mmol) in dry DMF (3 mL) was treated with 1,3-dibromo-5,5-dimethylhydantoin (26 mg, 0.091 mmol) at 0° C. The reaction was stirred at 0° C. for 2 h, and then pyridine (2 mL, 24.73 mmol) was added. The reaction mixture was heated at 60° C. for 4 h and then concentrated. The residue was diluted with water and extracted with EtOAc. The organic extract was washed with brine, dried with $MgSO_4$, filtered, and concentrated. The residue was purified by column chromatography (silica gel, eluting with 0% to 30% EtOAc in hexanes) to give T96 (45 mg, 56% yield) as an off-white solid. m/z=476 (M+1); $^1$H NMR (400 MHz, $CDCl_3$) δ 7.82 (m, 2H), 7.66 (m, 2H), 7.60 (s, 1H), 7.56 (m, 2H), 7.51 (m, 2H), 7.44 (m, 1H), 3.24 (dd, J=6.0, 18.0 Hz, 1H), 2.90 (ddd, J=6.9, 11.8, 17.9 Hz, 1H), 2.56 (qd, J=6.7, 13.4 Hz, 1H), 2.48 (s, 3H), 2.27 (dt, J=2.1, 12.7 Hz, 1H), 2.20 (dd, J=7.0, 14.1 Hz, 1H), 1.84 (m, 1H), 1.61 (s, 3H), 1.34 (d, J=6.7 Hz, 3H).

Compound 126: A mixture of compound 4 (200 mg, 0.62 mmol), 5-bromo-2-hydrazinylpyridine (232 mg, 1.23 mmol) and 6 N aq. HCl (0.21 mL, 1.26 mmol) in EtOH (4 mL) was heated in Biotage microwave at 120° C. for 4 h and then cooled to room temperature. The mixture was concentrated. The residue was diluted with EtOAc (20 mL) and washed water (2×15 mL). The organic extract was dried over $Na_2SO_4$, filtered, and concentrated. The residue was purified by column chromatography (silica gel, eluting with 0% to 40% EtOAc in hexanes) to give compound 126 (264 mg, 90% yield) as a light yellow solid. m/z=475/477 (M+1).

Compound 127: Compound 126 (164 mg, 0.35 mmol) was dissolved in MeOH (3.4 mL). Sodium methoxide (25 wt. % in methanol, 0.15 mL, 0.66 mmol) was added. The reaction mixture was stirred at 55° C. for 2 h and cooled to room temperature. The mixture was treated with 10% aq. $NaH_2PO_4$ (15 mL) and extracted with EtOAc (2×15 mL). The combined organic extracts were dried with $Na_2SO_4$, filtered, and concentrated. The residue was purified by column chromatography (silica gel, eluting with 0% to 40% EtOAc in hexanes) to give compound 127 (159 mg, 97% yield) as a white solid. m/z=475/477 (M+1).

Compound 128: A mixture of compound 127 (47 mg, 0.099 mmol), phenylboronic acid (18 mg, 0.15 mmol), $K_3PO_4$ (63 mg, 0.30 mmol) and tetrakis(triphenylphosphine)palladium(0) (6 mg, 0.0052 mmol) in vial was purged with $N_2$. 1,4-dioxane (0.5 mL) and DMF (0.25 mL) were degassed with $N_2$ and added to the vial. The vial filled with $N_2$ and sealed. The mixture was heated at 90° C. for 4 h and then cooled to room temperature. EtOAc (20 mL) was added. The mixture was washed with water (3×15 mL). The organic extract was dried with $Na_2SO_4$, filtered, and concentrated. The residue was purified by column chromatography (silica gel, eluting with 0% to 40% EtOAc in hexanes) to give compound 128 (34 mg, 73% yield) as a light yellow solid. m/z=473 (M+1).

T97: Compound 128 (33 mg, 0.070 mmol) was dissolved in anhydrous DMF (0.6 mL), and the solution was cooled to 0° C. 1,3-dibromo-5,5-dimethylhydantoin (10 mg, 0.035 mmol) in DMF (0.1 mL) was added. The reaction was stirred at 0° C. for 1 h. Pyridine (28 µL, 0.35 mmol) was added. The reaction was heated at 55° C. for 3 h and cooled to room temperature. EtOAc (20 mL) was added. The mixture was washed with water (3×10 mL). The organic extract was dried with $Na_2SO_4$, filtered, and concentrated. Toluene (10 mL) was added, and the mixture was concentrated to remove residual pyridine. The residue was purified by column chromatography (silica gel, eluting with 0% to 30% EtOAc in hexanes) to give compound T97 (20 mg, 61% yield) as a white solid. m/z=471 (M+1); $^1$H NMR (400 MHz, $CDCl_3$) δ 8.73 (s, 1H), 8.68 (d, J=2.4 Hz, 1H), 8.19 (m, 1H), 8.10 (dd, J=2.5, 8.6 Hz, 1H), 7.79 (m, 2H), 7.66 (m, 2H), 7.47 (m, 6H), 2.94 (dd, J=5.8, 16.0 Hz, 1H), 2.86 (m, 1H), 2.69 (qd, J=6.8, 13.6 Hz, 1H), 2.25 (dt, J=2.0, 12.5 Hz, 1H), 2.12 (dd, J=6.1, 13.7 Hz, 1H), 1.98 (s, 3H), 1.82 (tdd, J=6.0, 12.6, 18.7 Hz, 1H), 1.37 (d, J=6.8 Hz, 3H).

Compound 130: A mixture of compound 40 (120 mg, 0.37 mmol), compound 129 (91 mg, 0.55 mmol) and 12 N aq. HCl (0.05 mL, 0.60 mmol) in EtOH (3 mL) was heated in Biotage microwave at 100° C. for 4 h and then cooled to room temperature. The mixture was diluted with EtOAc and washed water. The organic extract was dried over $Na_2SO_4$, filtered, and concentrated. The residue was purified by column chromatography (silica gel, eluting with 0% to 50% EtOAc in hexanes) to give compound 130 (70 mg, 42% yield) as a light yellow solid. m/z=455 (M+1).

Compound 131: A mixture of compound 130 (70 mg, 0.15 mmol) in MeOH (2 mL) was treated with $K_2CO_3$ (43 mg, 0.31 mmol). The mixture was stirred at room temperature overnight and then concentrated. The residue was diluted with EtOAc and washed with 1 N aq. HCl and water. The combined organic extracts were dried with $Na_2SO_4$, filtered, and concentrated to give compound 131 (63 mg, 90% yield) as an off-white solid. m/z=455 (M+1).

T98: Compound 131 (63 mg, 0.14 mmol) was dissolved in anhydrous DMF (1 mL), and the solution was cooled to 0° C. 1,3-dibromo-5,5-dimethylhydantoin (20 mg, 0.069 mmol) in DMF (0.4 mL) was added. The reaction was stirred at 0° C. for 2 h. Pyridine (34 µL, 0.42 mmol) was added. The reaction was heated at 55° C. overnight and then cooled to room temperature. The mixture was diluted with EtOAc and washed with 1 N aq. HCl and water. The organic extract was dried with $Na_2SO_4$, filtered, and concentrated. The residue was purified by column chromatography (silica gel, eluting with 0% to 50% EtOAc in $CH_2Cl_2$) to give compound T98 (26 mg, 41% yield) as an off-white solid. m/z=453 (M+1); $^1$H NMR (400 MHz, $CDCl_3$) δ 9.30 (s, 1H), 9.27 (d, J=1.4 Hz, 1H), 8.83 (d, J=5.3 Hz, 1H), 8.09 (dd, J=1.5, 5.3 Hz, 1H), 7.93 (d, J=8.2 Hz, 1H), 7.88 (d, J=7.6 Hz, 1H), 7.52 (ddd, J=1.3, 7.2, 8.3 Hz, 1H), 7.44 (dt, J=1.2, 7.7 Hz, 1H), 3.42 (dd, J=5.2, 17.6 Hz, 1H), 2.92 (ddd, J=6.3, 12.0, 17.9 Hz, 1H), 2.72 (qd, J=6.8, 13.5 Hz, 1H), 2.27 (dt, J=1.7, 12.5 Hz, 1H), 2.15 (dd, J=6.1, 13.9 Hz, 1H), 1.91 (s, 3H), 1.77 (dq, J=5.6, 12.8 Hz, 1H), 1.40 (d, J=6.8 Hz, 3H).

Compound 133: To a stirring suspension of compound 3 (2.45 g, 11.17 mmol) in $CH_2Cl_2$ (100 mL) was added and magnesium bromide etherate (7.21 g, 27.92 mmol) and N,N-diisopropylethylamine (8.12 mL, 46.42 mmol) at room temperature. The mixture was stirred at room temperature for 5 min, nicotinoyl chloride hydrochloride 132 (2.58 g, 14.52 mmol) was added portionwise over 30 min. The reaction mixture was stirred for 21 h at room temperature and then washed with sat. aq. $KH_2PO_4$. The organic extract was dried over $Na_2SO_4$: filtered; and concentrated. The residue was purified by column chromatography (silica gel, eluting with EtOAc) to give compound 133 (2.10 g, 58% yield). m/z=325 (M+1).

Compound 134: A mixture of compound 133 (100 mg, 0.31 mmol), compound 129 (76 mg, 0.46 mmol) and 12 N aq. HCl (0.051 mL, 0.62 mmol) in EtOH (3 mL) was heated in Biotage microwave at 100° C. for 4 h and then cooled to room temperature. The mixture was diluted with EtOAc and washed with water. The organic extract was dried over $Na_2SO_4$, filtered, and concentrated. The residue was purified by column chromatography (silica gel, eluting with 0% to 50% EtOAc in hexanes) to give compound 134 (90 mg, 64% yield) as an orange solid. m/z=454 (M+1).

Compound 135: A mixture of compound 134 (90 mg, 0.20 mmol) in MeOH (2 mL) was treated with $K_2CO_3$ (55 mg, 0.40 mmol). The mixture was stirred at room temperature overnight and then concentrated. The residue was diluted with EtOAc and washed with 1 N aq. HCl and water. The organic extract was dried with $Na_2SO_4$, filtered, and concentrated to give compound 135 (57 mg, 63% yield) as an off-white solid. m/z=454 (M+1).

T99: Compound 135 (57 mg, 0.13 mmol) was dissolved in anhydrous DMF (1 mL), and the solution was cooled to 0° C. 1,3-dibromo-5,5-dimethylhydantoin (18 mg, 0.063 mmol) in DMF (0.4 mL) was added. The reaction was stirred at 0° C. for 2 h. Pyridine (34 µL, 0.42 mmol) was added. The reaction was heated at 55° C. overnight, and then cooled to room temperature. The mixture was diluted with EtOAc and washed with 1 N aq. HCl and water. The organic extract was dried with $Na_2SO_4$, filtered, and concentrated. The residue was purified by column chromatography (silica gel, eluting with 0% to 50% acetone in hexanes) to give compound T99 (19 mg, 33% yield) as a pale pink solid. m/z=452 (M+1); $^1$H NMR (400 MHz, $CDCl_3$) δ 9.37 (s, 1H), 9.02 (d, J=1.5 Hz, 1H), 8.67 (dd, J=1.7, 4.9 Hz, 1H), 8.13 (td, J=2.0, 8.0 Hz, 1H), 7.91 (d, J=8.1 Hz, 1H), 7.86 (d, J=7.9 Hz, 1H), 7.51 (ddd, J=1.3, 7.3, 8.2 Hz, 1H), 7.43 (m, 2H), 2.90 (m, 2H), 2.72 (td, J=6.7, 13.5 Hz, 1H), 2.31 (dt, J=1.7, 12.4 Hz, 1H), 2.17 (m, 1H), 1.90 (s, 3H), 1.78 (tdd, J=6.4, 13.2, 19.5 Hz, 1H), 1.40 (d, J=6.8 Hz, 3H).

Compound 136: A solution of compound 67 (847 mg, 1.72 mmol) in THF (50 mL) was treated with 6.0 N aq. HCl (2.86 mL, 17.16 mmol). The reaction mixture was stirred at ambient temperature for 16 h. The solvent was removed in vacuo and the residue was partitioned between EtOAc and sat. aq. $NaHCO_3$. The organic extract was washed with brine, dried with $Na_2SO_4$, filtered, and concentrated to give compound 136 (862 mg, quantitative yield) as a viscous oil and was used without further purification. m/z=449/451 (M+1).

Compound 137: A solution of compound 136 (862 mg, ≤1.72 mmol) in ethyl formate (120 mL, 1.49 mol) was treated with sodium methoxide (5.4 M in MeOH, 3.53 mL, 19.06 mmol) dropwise at 0° C. The mixture was stirred at ambient temperature for 2 h and then concentrated. The residue was partitioned between EtOAc and sat. aq. $NaHCO_3$. The organic phase was separated. The aqueous layer was extracted with EtOAc. The combined organic extracts were dried with $Na_2SO_4$, filtered, and concentrated. The residue was purified by column chromatography (silica gel, eluting with 30% EtOAc in hexanes) to give compound 137 (753 mg, 92% yield). m/z=477/479 (M+1).

Compound 138: A solution of compound 137 (753 mg, 1.58 mmol) in EtOH (15 mL) was treated with 6.0 N aq. HCl (2.61 mL, 15.66 mmol) and hydroxylamine hydrochloride (164 mg, 2.36 mmol). The reaction mixture was heated at 60° C. under nitrogen for 22 h. The solvent was removed in vacuo and the residue was partitioned between EtOAc and sat. aq. $NaHCO_3$. The organic extract was washed with brine, dried with $Na_2SO_4$, filtered, and concentrated to give compound 138 (706 mg, 94% yield) as a light brown viscous oil which gradually solidified upon standing. Compound 138 was used without further purification. m/z=474/476 (M+1).

Compound 139: A solution of compound 138 (706 mg, 1.49 mmol) in MeOH (20 mL) was treated with potassium carbonate (411 mg, 2.97 mmol). The reaction mixture was stirred at ambient temperature for 6 h. The solvent was removed in vacuo and the residue was partitioned between EtOAc and sat. aq. $KH_2PO_4$. The organic extract was washed with brine, dried with $Na_2SO_4$, filtered, and concentrated. The residue was purified by column chromatography (silica gel, eluting with 0% to 40% EtOAc in hexanes) to give compound 139 (380 mg, 54% yield) as a white solid. m/z=474/476 (M+1).

Compound 140: A solution of compound 139 (150 mg, 0.316 mmol) in anhydrous DMF (3 mL) was cooled to 0° C.

under nitrogen. 1,3-dibromo-5,5-dimethylhydantoin (49.6 mg, 0.173 mmol) in anhydrous DMF (1 mL) was added. The mixture was stirred 0° C. for 1 h, and then anhydrous pyridine (0.25 mL, 3.10 mmol) was added. The reaction mixture was heated at 60° C. for 4 h and then cooled to room temperature. The mixture was partitioned between EtOAc and sat. aq. $KH_2PO_4$. The organic phase was separated. The aqueous layer was extracted with EtOAc. The combined organic extracts were washed with brine, dried with $Na_2SO_4$, filtered, and concentrated. The residue was purified by column chromatography (silica gel, eluting with 0% to 40% EtOAc in hexanes) to give compound 140 (133 mg, 89% yield) as a yellow solid. m/z=472/474 (M+1).

T100: A thick wall glass vessel was charged with compound 140 (133 mg, 0.281 mmol), aniline (0.038 mL, 0.421 mmol), t-BuXPhosPd-G3 (22.3 mg, 0.028 mmol), XPhos (26.7 mg, 0.056 mmol), sodium t-butoxide (81 mg, 0.843 mmol) and 1,4-dioxane (4 mL). The vessel was sealed, and the reaction mixture was heated at 120° C. with stirring for 22 h. After cooled to room temperature, the mixture was diluted with EtOAc and filtered through a plug of Celite®. The filtrate was concentrated. The residue was purified by column chromatography (silica gel, eluting with 0% to 40% EtOAc in hexanes) to give partially purified product, which was purified again by column chromatography (silica gel, eluting with 2% EtOAc in $CH_2Cl_2$) to give compound T100 as an orange glass (33 mg, 24% yield). m/z=485 (M+1); $^1H$ NMR (400 MHz, $CDCl_3$) δ 7.77 (m, 2H), 7.66 (m, 3H), 7.55 (m, 2H), 7.49 (m, 2H), 7.42 (m, 1H), 7.25 (d, J=0.7 Hz, 2H), 7.24 (s, 2H), 6.87 (m, 1H), 5.66 (br s, 1H), 2.54 (m, 3H), 2.22 (dt, J=2.1, 12.7 Hz, 1H), 2.11 (dd, J=6.5, 13.9 Hz, 1H), 1.79 (m, 1H), 1.60 (s, 3H), 1.32 (d, J=6.7 Hz, 3H).

Compound 141: To a solution of compound 3 (600 mg, 2.74 mmol) in $CH_2Cl_2$ (30 mL) was added magnesium bromide etherate (1.77 g, 6.85 mmol) and N,N-diisopropylethylamine (1.99 mL, 11.42 mmol) sequentially at room temperature. The mixture was stirred for 5 min, and isonicotinoyl chloride hydrochloride (633 mg, 3.56 mmol) was added portionwise. After stirring at room temperature for 22 h, the reaction mixture was washed with sat. aq. $KH_2PO_4$, water, and brine. The organic extract was dried with $Na_2SO_4$, filtered, and concentrated. The residue was purified by column chromatography (silica gel, eluting with EtOAc) to give compound 141 (428 mg, 48% yield). m/z=325 (M+1).

Compound 142: A mixture of compound 141 (428 mg, 1.32 mmol), (4-bromophenyl)hydrazine hydrochloride (590 mg, 2.64 mmol) in EtOH (10 mL) was heated in Biotage microwave synthesizer at 120° C. for 3 h. The mixture was cooled to room temperature and concentrated. The residue was partitioned between EtOAc and sat. aq. $KH_2PO_4$. The organic extract was washed with brine, dried with $Na_2SO_4$, filtered, and concentrated. The residue was purified by column chromatography (silica gel, eluting with EtOAc) to give compound 142 (465 mg, 74% yield) as an orange glass. m/z=475/477 (M+1).

Compound 143: A solution of compound 142 (459 mg, 0.965 mmol) in MeOH (15 mL) was treated with potassium carbonate (267 mg, 1.93 mmol). The reaction mixture was stirred at ambient temperature for 24 h and then concentrated. The residue was partitioned between EtOAc and sat. aq. $KH_2PO_4$. The insoluble solid was collected by filtration and dried to give compound 143 (290 mg, 63% yield) as an orange solid. The filtrate was washed with sat. aq. $KH_2PO_4$ and brine. The organic extract was dried with $Na_2SO_4$, filtered, and concentrated. The residue was purified by column chromatography (silica gel, eluting with 2% MeOH in EtOAc) to give a second crop of compound 143 (56 mg, 12% yield) as an orange glass. m/z=475/477 (M+1).

Compound 144: A thick wall glass vessel was charged with compound 143 (345 mg, 0.725 mmol), 5-fluoropyridine-3-boronic acid (153 mg, 1.09 mmol), potassium phosphate tribasic (462 mg, 2.17 mmol), tetrakis(triphenylphosphine)palladium(0) (42 mg, 0.036 mmol), 1,4-dioxane (4 mL) and DMF (2 mL). The vessel was purged with $N_2$ and sealed. The reaction mixture was heated at 90° C. for 22 h. The mixture was cooled to room temperature, diluted with EtOAc, and filtered through a plug of Celite®. The filtrate was washed with sat. aq. $KH_2PO_4$ and brine. The organic extract was dried with $Na_2SO_4$, filtered, and concentrated. The residue was purified by column chromatography (silica gel, eluting with 5% MeOH in EtOAc) to give compound 144 (175 mg, 49% yield) as a white solid. m/z=492 (M+1).

T101: A solution of compound 144 (137 mg, 0.278 mmol) in anhydrous DMF (3 mL) was cooled to 0° C. under nitrogen. 1,3-dibromo-5,5-dimethylhydantoin (44 mg, 0.153 mmol) in anhydrous DMF (1 mL) was added. The mixture was stirred 0° C. for 1 h, and then anhydrous pyridine (0.22 mL, 2.73 mmol) was added. The reaction mixture was heated at 60° C. for 4 h and then cooled to room temperature. The mixture was partitioned between EtOAc and sat. aq. $KH_2PO_4$. The organic phase was separated. The aqueous layer was extracted with EtOAc. The combined organic extracts were washed with brine, dried with $Na_2SO_4$, filtered, and concentrated. The residue was purified by column chromatography (silica gel, eluting with 5% MeOH in EtOAc) to give compound T101 (115 mg, 84% yield) as a yellow glass. m/z=490 (M+1); $^1H$ NMR (400 MHz, $CDCl_3$) δ 8.77 (t, J=1.7 Hz, 1H), 8.66 (br d, J=5.2 Hz, 2H), 8.56 (d, J=2.7 Hz, 1H), 7.83 (m, 2H), 7.70 (ddd, J=1.9, 2.7, 9.2 Hz, 1H), 7.65 (m, 4H), 7.60 (s, 1H), 3.04 (m, 1H), 2.94 (m, 1H), 2.57 (td, J=6.7, 13.4 Hz, 1H), 2.29 (dt, J=2.1, 12.8 Hz, 1H), 2.21 (dd, J=6.5, 13.9 Hz, 1H), 1.85 (tdd, J=6.4, 12.8, 19.1 Hz, 1H), 1.63 (s, 3H), 1.35 (d, J=6.7 Hz, 3H).

Compound 145: A mixture of compound 133 (284 mg, 0.875 mmol), (4-bromophenyl)hydrazine hydrochloride (391 mg, 1.75 mmol) in EtOH (10 mL) was heated in Biotage microwave synthesizer at 100° C. for 4 h. The mixture was cooled to room temperature and concentrated. The residue was partitioned between EtOAc and sat. aq. $KH_2PO_4$. The organic extract was washed with brine, dried with $Na_2SO_4$, filtered, and concentrated. The residue was purified by column chromatography (silica gel, eluting with EtOAc) to give compound 145 (349 mg, 84% yield) as an orange glass. m/z=475/477 (M+1).

Compound 146: A solution of 145 (448 mg, 0.942 mmol) in MeOH (15 mL) was treated with potassium carbonate (260 mg, 1.88 mmol). The reaction mixture was stirred at room temperature for 24 h. The solvent was removed in vacuo and the residue was partitioned between EtOAc and sat. aq. $KH_2PO_4$. The organic extract was washed with brine, dried with $Na_2SO_4$, filtered, and concentrated. The residue was purified by column chromatography (silica gel, eluting with EtOAc). The product obtained was triturated with hexanes. The precipitated solid was collected by filtration and dried under vacuum to give compound 146 (350 mg, 78% yield) as an off-white solid. m/z=475/477 (M+1).

Compound 147a: A microwave vessel was charged with compound 146 (150 mg, 0.315 mmol), 3-methyl-5-(4,4,5,5-tetramethyl-1,3,2-dioxaborolan-2-yl)pyridazine (104 mg, 0.473 mmol), potassium phosphate tribasic (200 mg, 0.945 mmol), tetrakis(triphenylphosphine)palladium(0) (18 mg, 0.016 mmol), 1,4-dioxane (2 mL) and water (1 mL). The vessel was sealed and the reaction mixture was heated in Biotage microwave synthesizer at 120° C. for 3 h. The mixture was cooled to room temperature and concentrated. The residue was partitioned between EtOAc and sat. aq. $KH_2PO_4$. The organic extract was washed with brine, dried with $Na_2SO_4$, filtered, and concentrated. The residue was purified by column chromatography (silica gel, eluting with 10% MeOH in EtOAc) to give compound 147a (34 mg, 22% yield) as a white solid. m/z=489 (M+1).

T102: A solution of compound 147a (34 mg, 0.070 mmol) in anhydrous DMF (3 mL) was cooled to 0° C. under nitrogen. A solution of 1,3-dibromo-5,5-dimethylhydantoin (10.9 mg, 0.038 mmol) in anhydrous DMF (1 mL) was added. The mixture was stirred 0° C. for 1 h, and then anhydrous pyridine (0.056 mL, 0.695 mmol) was added. The reaction mixture was heated at 60° C. for 4 h and then cooled to room temperature. The mixture was partitioned between EtOAc and sat. aq. $KH_2PO_4$. The organic phase was separated. The aqueous layer was extracted with EtOAc. The combined organic extracts were washed with brine, dried with $Na_2SO_4$, filtered, and concentrated. The residue was purified by column chromatography (silica gel, eluting with 10% MeOH in EtOAc) to give compound T102 (29 mg, 85% yield) as a yellow solid. m/z=487 (M+1); $^1$H NMR (400 MHz, $CDCl_3$) δ 9.38 (d, J=2.0 Hz, 1H), 8.97 (m, 1H), 8.60 (dd, J=1.7, 4.9 Hz, 1H), 8.06 (ddd, J=1.7, 2.3, 8.0 Hz, 1H), 7.91 (m, 2H), 7.70 (m, 2H), 7.60 (d, J=2.3 Hz, 1H), 7.59 (s, 1H), 7.36 (ddd, J=0.9, 4.8, 8.0 Hz, 1H), 3.00 (ddd, J=1.3, 6.3, 15.9 Hz, 1H), 2.91 (m, 1H), 2.85 (s, 3H), 2.58 (qd, J=6.7, 13.4 Hz, 1H), 2.30 (dt, =2.0, 12.7 Hz, 1H), 2.20 (dd, J=6.4, 13.8 Hz, 1H), 1.85 (tdd, J=6.3, 12.6 Hz, 1H), 1.64 (s, 3H), 1.35 (d, J=6.7 Hz, 3H).

Compound 147b: A thick wall glass vessel was charged with compound 146 (150 mg, 0.315 mmol), 5-fluoropyridine-3-boronic acid (67 mg, 0.48 mmol), potassium phosphate tribasic (200 mg, 0.945 mmol), tetrakis(triphenylphosphine)palladium(0) (18 mg, 0.0157 mmol), 1,4-dioxane (2 mL), and DMF (1 mL). The vessel was sealed and the reaction mixture was heated at 90° C. for 22 h. The mixture was cooled to room temperature, diluted with EtOAc, and filtered through a plug of Celite®. The filtrate was washed with sat. aq. $KH_2PO_4$ and brine. The organic extract was dried with $Na_2SO_4$, filtered, and concentrated. The residue was purified by column chromatography (silica gel, eluting with 3% MeOH in EtOAc) to give compound 147b (86 mg, 56% yield) as a glass. m/z=492 (M+1).

T103: A solution of compound 147b (86 mg, 0.174 mmol) in anhydrous DMF (3 mL) was cooled to 0° C. under nitrogen. A solution of 1,3-dibromo-5,5-dimethylhydantoin (27.3 mg, 0.095 mmol) in anhydrous DMF (1 mL) was added. The mixture was stirred 0° C. for 1 h, and then anhydrous pyridine (0.14 mL, 1.74 mmol) was added. The reaction mixture was heated at 60° C. for 4 h and then cooled to room temperature. The mixture was partitioned between EtOAc and sat. aq. $KH_2PO_4$. The organic phase was separated. The aqueous layer was extracted with EtOAc. The combined organic extracts were washed with brine, dried with $Na_2SO_4$, filtered, and concentrated. The residue was purified by column chromatography (silica gel, eluting with EtOAc) to give compound T103 (82 mg, 96% yield) as a yellow solid. m/z=490 (M+1); $^1$H NMR (400 MHz, $CDCl_3$) δ 8.97 (d, J=1.5 Hz, 1H), 8.77 (m, 1H), 8.60 (dd, J=1.7, 4.8 Hz, 1H), 8.56 (dd, J=0.4, 2.7 Hz, 1H), 8.07 (ddd, J=1.7, 2.3, 8.0 Hz, 1H), 7.83 (m, 2H), 7.70 (m, 1H), 7.66 (m, 2H), 7.62 (s, 1H), 7.36 (ddd, J=0.9, 4.8, 7.9 Hz, 1H), 3.00 (ddd, J=1.3, 6.2, 16.0 Hz, 1H), 2.91 (m, 1H), 2.57 (m, 1H), 2.30 (dt, J=2.1, 12.6 Hz, 1H), 2.20 (dd, J=6.3, 13.8 Hz, 1H), 1.84 (m, 1H), 1.64 (s, 3H), 1.35 (d, J=6.7 Hz, 3H).

Compound 148: To a solution of compound 3 (1.0 g, 4.56 mmol) in $CH_2Cl_2$ (100 mL) was added magnesium bromide etherate (2.94 g, 11.39 mmol) and N,N-diisopropylethylamine (2.34 mL, 13.40 mmol) sequentially at room temperature. The mixture was stirred at room temperature for 5 min, and then 3-fluorobenzoyl chloride (0.72 mL, 5.93 mmol) was added dropwise. The mixture was stirred at room temperature for 22 h and then washed with sat. aq. $KH_2PO_4$, water, and brine. The organic extract was dried over $Na_2SO_4$, filtered, and concentrated to give compound 148 (1.96 g, quantitative yield) as dark red oil, which was used without further purification. m/z=342 (M+1).

Compound 149: A mixture of compound 148 (716 mg, 2.11 mmol), 4-hydrazinoquinoline hydrochloride (871 mg, 4.47 mmol) in EtOH (10 mL) was heated in Biotage microwave at 100° C. for 2 h and then cooled to room temperature. The mixture was concentrated. The residue was partitioned between EtOAc and sat. aq. $NaH_2PO_4$. The organic extract was washed with brine, dried over $Na_2SO_4$, filtered, and concentrated. The residue was purified by column chromatography (silica gel, eluting with EtOAc) to give compound 149 (540 mg, 55%) as a yellow glass. m/z=465 (M+1).

Compound 150: A solution of 145 (534 mg, 1.15 mmol) in MeOH (20 mL) was treated with potassium carbonate (318 mg, 2.30 mmol). The reaction mixture was stirred at room temperature for 24 h. The solvent was removed in vacuo and the residue was partitioned between EtOAc and sat. aq. $KH_2PO_4$ The organic extract was washed with brine, dried with $Na_2SO_4$, filtered, and concentrated. The residue was purified by column chromatography (silica gel, eluting with EtOAc) to give compound 150 (488 mg, 91% yield) as a yellow glass. m/z=465 (M+1).

T104: A solution of compound 150 (487 mg, 1.04 mmol) in anhydrous DMF (6 mL) was cooled to 0° C. under nitrogen. A solution of 1,3-dibromo-5,5-dimethylhydantoin (164 mg, 0.572 mmol) in anhydrous DMF (2 mL) was added. The mixture was stirred 0° C. for 1 h, and then anhydrous pyridine (0.84 mL, 10.39 mmol) was added. The reaction mixture was heated at 60° C. for 4 h and then cooled to room temperature. The mixture was diluted with EtOAc and washed with sat. aq. $KH_2PO_4$, water, and brine. The organic extract was dried with $Na_2SO_4$, filtered, and concentrated. The residue was purified by column chromatography (silica gel, eluting with EtOAc) to give compound T104 (326 mg, 68% yield) as a yellow solid. m/z=463 (M+1); $^1$H NMR (400 MHz, $CDCl_3$) δ 9.17 (br s, 1H), 8.30 (td, J=0.9, 8.4 Hz, 1H), 7.86 (m, 1H), 7.62 (m, 2H), 7.53 (td, J=1.3, 7.8 Hz, 1H), 7.46 (ddd, J=1.7, 2.7, 10.2 Hz, 1H), 7.39 (dt, J=5.9, 8.0 Hz, 1H), 7.27 (m, 1H), 7.06 (ddt, J=1.0, 2.6, 8.4 Hz, 1H), 6.93 (m, 1H), 2.99 (m, 2H), 2.52 (m, 1H), 2.34 (t, J=12.7 Hz, 1H), 2.21 (dd, J=6.1, 14.1 Hz, 1H), 1.85 (m, 1H), 1.58 (s, 3H), 1.33 (d, J=6.7 Hz, 3H).

Compound 152: To a stirring mixture of compound 3 (500 mg, 2.28 mmol) and magnesium bromide etherate (1.47 g, 5.70 mmol) in $CH_2Cl_2$ (20 mL) at room temperature was added dropwise N,N-diisopropylethylamine (1.13 mL, 6.49 mmol). The mixture was stirred at room temperature for 5 min, and then a solution of compound 151 (1.05 g, 3.42 mmol) in $CH_2Cl_2$ (20 mL) was added dropwise. After stirring at room temperature for 23 h, the reaction mixture was washed with sat. aq. $KH_2PO_4$. The organic layer was separated. The aqueous layer was extracted with $CH_2Cl_2$. The combined organic extracts were dried with $Na_2SO_4$, filtered, and concentrated. The residue was purified by column chromatography (silica gel, eluting with 18% EtOAc in hexanes) to give partially purified compound 152

(412 mg, 53% yield), which was used in the next step without further purification. m/z=342 (M+1).

Compound 153: In a sealable microwave vial, a mixture of compound 152 (1.29 g, 3.78 mmol) and (4-bromophenyl) hydrazine hydrochloride (1.69 g, 7.56 mmol) in EtOH (15 mL) was flushed with $N_2$. The vial was sealed and heated in a Biotage microwave synthesizer at 120° C. for 10 h. After cooled to room temperature, the mixture was concentrated. The residue was partitioned between sat. aq. $NaHCO_3$ (50 mL) and EtOAc (50 mL). The organic extract was washed with brine (50 mL), dried with $MgSO_4$, filtered, and concentrated. The residue was purified by column chromatography (silica gel, eluting with 25% EtOAc in hexanes) to give partially purified product and was purified again by column chromatography (silica gel, eluting with 1/20/20 EtOAc/$CH_2Cl_2$/hexanes) to give compound 153 (0.62 g, 33% yield) as a tan solid. m/z=492 & 494 (M+1).

Compound 154: A mixture of compound 153 (0.62 g, 1.26 mmol) and $K_2CO_3$ (0.87 g, 6.29 mmol) in MeOH (20 mL) was stirred at room temperature under $N_2$ for 16 h and then concentrated. The residue was partitioned between sat. aq. $KH_2PO_4$ (50 mL) and EtOAc (50 mL). The organic extract was washed with brine (50 mL), dried with $MgSO_4$, filtered, and concentrated. The product was triturated with $Et_2O$, filtered, and dried under vacuum to give compound 154 (0.35 g, 56% yield) as an off-white solid. m/z=492 & 494 (M+1).

Compound 155: A thick wall glass vessel was charged with compound 154 (200 mg, 0.406 mmol), potassium phosphate tribasic (258 mg, 1.21 mmol), tetrakis(triphenylphosphine)palladium(0) (23 mg, 0.020 mmol), 5-fluoropyridine-3-boronic acid (85 mg, 0.60 mmol), 1,4-dioxane (2 mL), and DMF (1 mL). The vessel was sealed and the reaction mixture was heated at 90° C. for 23 h. The reaction mixture was cooled to room temperature, diluted with EtOAc, and filtered through a plug of Celite®. The filtrate was washed with sat. aq. $KH_2PO_4$ and brine. The organic extract was dried with $Na_2SO_4$, filtered, and concentrated. The residue was purified by column chromatography (silica gel, eluting with 60% EtOAc in hexanes) to give compound 155 (77 mg, 37% yield) as a yellow glass. m/z=509 (M+1).

T105: A solution of compound 155 (77 mg, 0.15 mmol) in anhydrous DMF (3 mL) was cooled to 0° C. under nitrogen. A solution of 1,3-dibromo-5,5-dimethylhydantoin (23.7 mg, 0.083 mmol) in anhydrous DMF (1 mL) was added. The mixture was stirred 0° C. for 1 h, and then anhydrous pyridine (0.12 mL, 1.48 mmol) was added. The reaction mixture was heated at 60° C. for 4 h and then cooled to room temperature. The mixture was partitioned between EtOAc and sat. aq. $KH_2PO_4$. The organic phase was separated. The aqueous layer was extracted with EtOAc. The combined organic extracts were washed with brine, dried with $Na_2SO_4$, filtered, and concentrated. The residue was purified by column chromatography (silica gel, eluting with 50% EtOAc in hexanes) to give partially purified product and was purified again by column chromatography (silica gel, eluting with 20% EtOAc in $CH_2Cl_2$) to give compound T105 (39 mg, 51% yield) as an orange solid. m/z=507 (M+1); $^1H$ NMR (400 MHz, $CDCl_3$) δ 8.76 (t, J=1.7 Hz, 1H), 8.55 (d, J=2.7 Hz, 1H), 7.81 (m, 2H), 7.67 (m, 6H), 7.11 (m, 2H), 2.96 (m, 1H), 2.87 (m, 1H), 2.57 (qd, J=6.7, 13.4 Hz, 1H), 2.28 (dt, J=2.0, 12.7 Hz, 1H), 2.17 (dd, J=6.3, 13.9 Hz, 1H), 1.83 (tdd, J=6.3, 12.7, 19.1 Hz, 1H), 1.62 (s, 3H), 1.34 (d, J=6.7 Hz, 3H).

Compound 156a: In a sealable microwave vial, a mixture of compound 152 (1.32 g, 3.87 mmol) and (4-cyanophenyl) hydrazine hydrochloride (1.34 g, 7.90 mmol) in EtOH (15 mL) was flushed with $N_2$. The vial was sealed and heated in Biotage microwave synthesizer at 120° C. for 10 h. The mixture was cooled to room temperature and concentrated. The residue was partitioned between sat. aq. $NaHCO_3$ (50 mL) and EtOAc (50 mL). The organic extract was washed with sat. aq. NaCl (50 mL), dried with $MgSO_4$, filtered, and concentrated. The residue was purified by column chromatography (silica gel, eluting with 25% EtOAc in hexanes) to give compound 156a (0.98 g, 58% yield) as a light yellow solid. m/z=439 (M+1).

Compound 157a: Compound 156a (0.58 g, 1.32 mmol) was mixed in 50% aq. $H_2SO_4$ (10 mL) and heated at 130° C. for 2 h. The mixture was cooled to 0° C., diluted with water (20 mL), and neutralized with $NaHCO_3$ (solid) to pH 5. The precipitated solid was collected by filtration and dried under vacuum to give compound 157a (0.59 g, 98% yield). m/z=458 (M+1).

Compound 158a: Compound 157a (0.25 g, 0.55 mmol) in $CH_2Cl_2$ (10 mL) was cooled to 0° C. Oxalyl chloride (0.35 g, 2.76 mmol) and 1 drop of DMF was added. The solution was stirred at room temperature for 2 h and concentrated to give the acid chloride. The acid chloride was dissolved in $CHCl_2$ (5 mL). The solution was added to a solution of N-hydroxyacetamidine (65 mg, 0.88 mmol) and $Et_3N$ (0.7 g, 6.93 mmol) in $CH_2Cl_2$ (10 mL) at 0° C. The reaction mixture was stirred at room temperature for 16 h and then concentrated. The residue was diluted with sat. aq. $NaHCO_3$ and extracted with EtOAc. The organic extract was dried with $MgSO_4$, filtered, and concentrated. The residue was purified by column chromatography (silica gel, eluting with 0% to 100% EtOAc in hexanes) to give compound 158a (0.19 g, 68% yield) as a solid. m/z=514 (M+1).

Compound 159a: Compound 158a (0.19 g, 0.37 mmol) in 1,4-dioxane (5 mL) was treated with propylphosphonic anhydride (50 wt. % in EtOAc, 0.5 g, 0.78 mmol). The mixture was heated at 90° C. for 16 h and then cooled and concentrated. The residue was diluted with aq. $NaHCO_3$ and extracted with EtOAc. The organic extract was dried with $MgSO_4$, filtered, and concentrated. The residue was purified by column chromatography (silica gel, eluting with 0% to 35% EtOAc in hexanes) to give compound 159a (0.17 g, 92% yield) as a solid. m/z=496 (M+1).

Compound 160a: Compound 159a (0.17 g, 0.34 mmol) in MeOH (10 mL) was treated with $K_2CO_3$ (240 mg, 1.74 mmol). The reaction mixture was stirred at room temperature overnight and then concentrated. The residue was neutralized by addition of sat. aq. $KH_2PO_4$ and extracted with EtOAc. The organic extract was washed with brine, dried with $MgSO_4$, filtered, and concentrated. The residue was purified by column chromatography (silica gel, eluting with 0% to 35% EtOAc in hexanes) to give compound 160a (90 mg, 53% yield) as a solid. m/z=496 (M+1).

T106: Compound 160a (90 mg, 0.18 mmol) was taken up in dry DMF (2 mL), and was cooled to 0° C. A solution of 1,3-dibromo-5,5-dimethylhydantoin (30 mg, 0.10 mmol) in DMF (1 mL) was added. The reaction was stirred at 0° C. for 2 h, and then pyridine (2 mL, 24.7 mmol) was added. The mixture was heated at 60° C. for 4 h and then concentrated. The residue was diluted with water and extracted with EtOAc. The organic extract was washed with brine, dried with $MgSO_4$, filtered, and concentrated. The residue was purified by column chromatography (silica gel, eluting with 0% to 35% EtOAc in hexanes) to give compound T106 (28 mg, 31% yield) as an off-white solid. m/z=494 (M+1); $^1H$ NMR (400 MHz, $CDCl_3$) δ 8.36 (m, 2H), 7.70 (m, 4H), 7.51 (s, 1H), 7.12 (m, 2H), 2.95 (dd, J=6.1, 16.3 Hz, 1H), 2.86 (m, 1H), 2.56 (m, 1H), 2.52 (s, 3H), 2.26 (dt, J=2.0, 12.7 Hz, 1H), 2.17 (dd, J=6.6, 14.0 Hz, 1H), 1.83 (tdd, J=6.5, 12.8, 19.2 Hz, 1H), 1.63 (s, 3H), 1.34 (d, J=6.7 Hz, 3H).

Compound 156b: In a sealable microwave vial, a mixture of compound 133 (1.17 g, 3.61 mmol) and (4-cyanophenyl) hydrazine hydrochloride (1.22 g, 7.19 mmol) in EtOH (10 mL) was flushed with $N_2$. The vial was sealed and heated in Biotage microwave synthesizer at 120° C. for 10 h. The mixture was cooled to room temperature and concentrated. The residue was partitioned between sat. aq. $NaHCO_3$ (50 mL) and EtOAc (50 mL). The organic extract was washed with sat. aq. NaCl (50 mL), dried with $MgSO_4$, filtered, and concentrated. The residue was purified by column chromatography (silica gel, eluting with 2% MeOH in $CHCl_3$) to give compound 156b (1.24 g, 82% yield) as a yellow solid. m/z=422 (M+1).

Compound 157b: Compound 156b (0.56 g, 1.33 mmol) was mixed in 50% aq. $H_2SO_4$ (10 mL) and heated at 130° C. for 2 h. The mixture was cooled to 0° C., diluted with water (20 mL), and neutralized with $NaHCO_3$ (solid) to pH 5. The precipitated solid was collected by filtration and dried in vacuo to give compound 157b (0.57 g, 97% yield). m/z=441 (M+1).

Compound 158b: Compound 157a (0.31 g, 0.70 mmol) in $CH_2Cl_2$ (15 mL) was cooled to 0° C. Oxalyl chloride (0.45 g, 3.54 mmol) and 1 drop of DMF was added. The solution was stirred at room temperature for 2 h and concentrated to give the acid chloride. The acid chloride was dissolved in $CH_2Cl_2$ (5 mL). The solution was added to a solution of N-hydroxyacetamidine (80 mg, 1.08 mmol) and $Et_3N$ (0.85 g, 8.42 mmol) in $CH_2Cl_2$ (10 mL) at 0° C. The reaction mixture was stirred at rt for 16 h and then concentrated. The residue was diluted with sat. aq. $NaHCO_3$ and extracted with EtOAc. The organic extract was dried with $MgSO_4$, filtered, and concentrated. The residue was purified by column chromatography (silica gel, eluting with 0% to 100% EtOAc in hexanes) to give compound 158b (0.2 g, 57% yield) as a solid. m/z=497 (M+1).

Compound 159b: Compound 158b (0.2 g, 0.40 mmol) in 1,4-dioxane (5 mL) was treated with propylphosphonic anhydride (50 wt. % in EtOAc, 515 mg, 0.81 mmol). The mixture was heated at 90° C. for 16 h and then cooled and concentrated. The residue was diluted with aq. $NaHCO_3$ and extracted with EtOAc. The organic extract was dried with $MgSO_4$, filtered, and concentrated. The residue was purified by column chromatography (silica gel, eluting with 0% to 100% EtOAc in hexanes) to give compound 159b (0.1 g, 52% yield) as a solid. m/z=479 (M+1).

Compound 160b: Compound 159b (0.1 g, 0.21 mmol) in MeOH (10 mL) was treated with $K_2CO_3$ (145 mg, 1.05 mmol). The reaction mixture was stirred at room temperature overnight and then concentrated. The residue was neutralized by addition of sat. aq. $KH_2PO_4$ and extracted with EtOAc. The organic extract was washed with brine, dried with $MgSO_4$, filtered, and concentrated. The residue was purified by column chromatography (silica gel, eluting with 0% to 100% EtOAc in hexanes) to give compound 160b (95 mg, 95% yield) as a solid. m/z=479 (M+1).

T107: Compound 160b (95 mg, 0.20 mmol) was taken up in dry DMF (2 mL) and was cooled to 0° C. A solution of bromine (35 mg, 0.22 mmol) in $CH_2Cl_2$ (1 mL) was added. The reaction was stirred at 0° C. for 2 h, and then pyridine (2 mL, 24.7 mmol) was added. The mixture was heated at 60° C. for 4 h and then concentrated. The residue was diluted with water and extracted with EtOAc. The organic extract was washed with brine, dried with $MgSO_4$, filtered, and concentrated. The residue was purified by column chromatography (silica gel, eluting with 0% to 100% EtOAc in hexanes) to give compound T107 (68 mg, 72% yield) as a white solid. m/z=477 (M+1); $^1H$ NMR (400 MHz, $CDCl_3$) δ 8.96 (m, 1H), 8.60 (dd, J=1.7, 4.9 Hz, 1H), 8.38 (m, 2H), 8.06 (td, J=2.0, 7.9 Hz, 1H), 7.70 (m, 2H), 7.51 (s, 1H), 7.36 (ddd, J=0.9, 4.8, 8.0 Hz, 1H), 3.00 (ddd, J=1.2, 6.2, 16.1 Hz, 1H), 2.91 (m, 1H), 2.57 (m, 1H), 2.53 (s, 3H), 2.28 (dt, J=2.1, 12.7 Hz, 1H), 2.19 (dd, J=6.5, 13.9 Hz, 1H), 1.84 (m, 1H), 1.64 (s, 3H), 1.34 (d, J=6.7 Hz, 3H).

Compound 161: Compound 3 (1 g, 4.56 mmol) was dissolved in $CH_2Cl_2$ (75 mL). Magnesium bromide etherate (3 g, 11.62 mmol) and N,N-diisopropylethylamine (2.5 mL, 14.35 mmol) were added at room temperature. The mixture was stirred for 5 min, and then ethyl 2-chloro-2-oxoacetate (0.8 g, 5.86 mmol) was added. The reaction mixture was stirred at room temperature for 2 days and then quenched with sat. aq. $KH_2PO_4$ (75 mL). The organic phase was separated. The aqueous phase was extracted with EtOAc. The organic extracts were washed with water and brine, dried over $Mg_2SO_4$, filtered, and concentrated. The residue was purified by column chromatography (silica gel, eluting with 0% to 100% EtOAc in hexanes) to give compound 161 (1.12 g, 77% yield) as an oil. m/z=320 (M+1).

Compound 162: Compound 161 (1.12 g, 3.53 mmol) and 4-bromophenylhydrazine hydrochloride (1.1 g, 4.96 mmol) in EtOH (20 mL) was heated at 120° C. in a Biotage microwave synthesizer for 90 min. The reaction mixture was concentrated. The residue was partitioned between aq. $NaHCO_3$ and EtOAc. The organic extract was dried with $MgSO_4$, filtered, and concentrated. The residue was purified by column chromatography (silica gel, eluting with 0% to 35% EtOAc in hexanes) to give compound 162 (0.85 g, 52% yield) as an oil. m/z=470 & 472 (M+1).

Compound 163: Compound 162 (1.2 g, 2.55 mmol) was mixed in 50% aq. $H_2SO_4$ (10 mL) and heated at 130° C. for 2 h. The mixture was cooled to 0° C. diluted with water (10 mL), and neutralized with $NaHCO_3$ (solid) to pH 5. The precipitated solid was collected by filtration and dried under vacuum to give compound 163 (0.92 g, 82% yield). m/z=442 & 444 (M+1).

Compound 164: Compound 163 (0.92 g, 2.08 mmol) in $CH_2Cl_2$ (15 mL) was cooled to 0° C. Oxalyl chloride (1.3 g, 10.23 mmol) and 3 drops of DMF were added. The solution was stirred at room temperature for 3 h and concentrated to give the acid chloride. The acid chloride was dissolved in $CH_2Cl_2$ (5 mL). The solution was added to a solution of N-hydroxyacetamidine (230 mg, 3.1 mmol) and $Et_3N$ (1.5 g, 14.85 mmol) in $CH_2Cl_2$ (15 mL) at 0° C. The reaction mixture was stirred at rt for 16 h and then concentrated. The residue was diluted with sat. aq. $NaHCO_3$ and extracted with EtOAc. The organic extract was dried with $MgSO_4$, filtered, and concentrated. The residue was purified by column chromatography (silica gel, eluting with 0% to 100% EtOAc in hexanes) to give compound 164 (0.67 g, 64% yield) as a solid. m/z=498/500 (M+1).

Compound 165: Compound 164 (0.67 g, 1.34 mmol) in 1,4-dioxane (10 mL) was treated with propylphosphonic anhydride (50 wt. % in EtOAc, 1.8 g, 2.82 mmol). The mixture was heated at 90° C. for 16 h and then cooled and concentrated. The residue was diluted with aq. $NaHCO_3$ and extracted with EtOAc. The organic extract was dried with $MgSO_4$, filtered, and concentrated. The residue was purified by column chromatography (silica gel, eluting with 0% to 35% EtOAc in hexanes) to give compound 165 (0.52 g, 80% yield) as a solid. m/z=480/482 (M+1).

Compound 166: Compound 165 (0.52 g, 1.08 mmol) in MeOH (15 mL) was treated with $K_2CO_3$ (0.75 g, 5.43 mmol). The reaction mixture was stirred at room temperature overnight, and then concentrated. The residue was neutralized by addition of sat. aq. KH$_2$PO$_4$ and extracted with EtOAc. The organic extract was washed with brine, dried with MgSO$_4$, filtered, and concentrated. The residue was purified by column chromatography (silica gel, eluting with 0% to 35% EtOAc in hexanes) to give compound 166 (0.5 g, 96% yield) as a solid. m/z=480/482 (M+1).

Compound 167a: Compound 166 (250 mg, 0.52 mmol) was dissolved in 1,4-dioxane (3 mL) and DMF (1 mL). K$_3$PO$_4$ (350 mg, 1.65 mmol), tetrakis(triphenylphosphine)palladium(0) (50 mg, 0.043 mmol), and 3-methyl-5-(4,4,5,5-tetramethyl-1,3,2-dioxaborolan-2-yl)pyridazine (175 mg, 0.79 mmol) were added. The mixture was sparged with N$_2$ for 10 min and then heated at 90° C. for 16 h. After cooled to room temperature, the reaction mixture was filtered, and the filtrate was concentrated. The residue was purified by column chromatography (silica gel, eluting with 0% to 5% MeOH in CHCl$_3$) to give compound 167a (40 mg, 16% yield) as a solid. m/z=494 (M+1).

T108: Compound 167a (40 mg, 0.081 mmol) was taken up in dry DMF (2 mL) and was cooled to 0° C. A solution of bromine (15 mg, 0.094 mmol) in CH$_2$Cl$_2$ (1 mL) was added. The reaction was stirred at 0° C. for 2 h, and then pyridine (2 mL, 24.7 mmol) was added. The mixture was heated at 60° C. for 4 h and then concentrated. The residue was diluted with water and extracted with EtOAc. The organic extract was washed with brine, dried with MgSO$_4$, filtered, and concentrated. The residue was purified by column chromatography (silica gel, eluting with 0% to 5% MeOH in CHCl$_3$) to give compound T108 (18 mg, 45% yield) as an off-white solid. m/z=492 (M+1); $^1$H NMR (400 MHz, CDCl$_3$) δ 9.38 (d, J=2.3 Hz, 1H), 7.91 (m, 2H), 7.69 (m, 2H), 7.60 (d, J=2.3 Hz, 1H), 7.52 (s, 1H), 3.25 (dd, J=5.9, 17.4 Hz, 1H), 2.91 (ddd, J=6.9, 11.8, 17.9 Hz, 1H), 2.85 (s, 3H), 2.58 (m, 1H), 2.49 (s, 3H), 2.26 (m, 2H), 1.86 (tdd, J=6.3, 12.9, 18.9 Hz, 1H), 1.63 (s, 3H), 1.35 (d, J=6.7 Hz, 3H).

Compound 167b: Compound 166 (250 mg, 0.52 mmol) was dissolved in 1,4-dioxane (2.7 mL) and DMF (1.3 mL). K$_3$PO$_4$ (350 mg, 1.65 mmol), tetrakis(triphenylphosphine)palladium(0) (50 mg, 0.043 mmol), and pyridin-3-ylboronic acid (115 mg, 0.93 mmol) were added. The mixture was sparged with N$_2$ for 10 min and then heated at 90° C. for 16 h. After cooled to room temperature, the reaction mixture was filtered, and the filtrate was concentrated. The residue was purified by column chromatography (silica gel, eluting with 0% to 100% EtOAc in hexanes) to give compound 167b (105 mg, 42% yield) as a solid. m/z=479 (M+1)

T109: Compound 167b (105 mg, 0.22 mmol) was taken up in dry DMF (2 mL) and was cooled to 0° C. A solution of bromine (38 mg, 0.24 mmol) in CH$_2$Cl$_2$ (1 mL) was added. The reaction was stirred at 0° C. for 2 h, and then pyridine (2 mL, 24.7 mmol) was added. The mixture was heated at 60° C. for 4 h and then concentrated. The residue was diluted with water and extracted with EtOAc. The organic extract was washed with brine, dried with MgSO$_4$, filtered, and concentrated. The residue was purified by column chromatography (silica gel, eluting with 0% to 100% EtOAc in hexanes) to give compound T109 (35 mg, 33% yield) as an off-white solid. m/z=477 (M+1); $^1$H NMR (400 MHz, CDCl$_3$) δ 8.94 (dd, J=0.9, 2.4 Hz, 1H), 8.69 (dd, J=1.6, 4.8 Hz, 1H), 7.97 (dd, J=1.6, 2.4, 7.9 Hz, 1H), 7.83 (m, 2H), 7.62 (m, 2H), 7.57 (s, 1H), 7.45 (ddd, J=0.9, 4.8, 7.9 Hz, 1H), 3.24 (m, 1H), 2.91 (ddd, J=6.9, 11.8, 17.9 Hz, 1H), 2.57 (qd, J=6.7, 13.4 Hz, 1H), 2.48 (s, 3H), 2.28 (dt, J=2.1, 12.7 Hz, 1H), 2.20 (dd, J=7.2, 13.9 Hz, 1H), 1.85 (tdd, J=6.2, 12.7, 18.8 Hz, 1H), 1.62 (s, 3H), 1.35 (d, J=6.7 Hz, 3H).

Compound 168: Compound 163 (0.46 g, 1.04 mmol) was dissolved in CH$_2$Cl$_2$ (15 mL), and cooled to 0° C. Oxalyl chloride (0.66 g, 5.20 mmol) and 3 drop of DMF were added. The solution was stirred at room temperature for 3 h and then concentrated to give the crude acid chloride. The crude acid chloride was dissolved in CH$_2$Cl$_2$ (5 mL) and added to a solution of ammonia (30% in water, 625 mg, 11.03 mmol) in THF (25 mL) at 0° C. The reaction mixture was stirred at room temperature for 16 h and then concentrated. The residue was diluted with sat. aq. NaHCO$_3$ and extracted with EtOAc. The organic extract was dried with MgSO$_4$, filtered, and concentrated to give compound 168 (0.46 g, quantitative yield) as a solid. m/z=441 & 443 (M+1).

Compound 169: Compound 168 (0.21 g, 0.48 mmol) was dissolved in CH$_2$C$_2$ (5 mL). Et$_3$N (250 mg, 2.48 mmol) and trifluoroacetic anhydride (350 mg, 1.67 mmol) were added at room temperature. The mixture was stirred at room temperature for 16 h and then concentrated. The residue was diluted with aq. NaHCO$_3$ and extracted with EtOAc. The organic extract was dried with MgSO$_4$, filtered, and concentrated. The residue was purified by column chromatography (silica gel, eluting with 0% to 35% EtOAc in hexanes) to give compound 169 (0.1 g, 50% yield) as a solid. m/z=423 & 425 (M+1).

Compound 170: Compound 169 (0.82 g, 1.94 mmol) was taken up in EtOH (15 mL). Hydroxylamine (50% in water, 0.4 g, 6.06 mmol) was added. The reaction mixture was stirred at 50° C. overnight and then concentrated. The crude product was dissolved in 1,4-dioxane (25 mL). Dimethylacetamide dimethylacetal (1.2 g, 9.01 mmol) was added. The reaction mixture was heated at 60° C. for 16 h and then concentrated. The residue was purified by column chromatography (silica gel, eluting with 0% to 50% EtOAc in hexanes) to give compound 170 (450 mg, 48% yield) as a solid. m/z=480/482 (M+1).

Compound 171: Compound 170 (0.45 g, 0.93 mmol) in MeOH (10 mL) was treated with K$_2$CO$_3$ (0.65 g, 4.71 mmol). The reaction mixture was stirred at room temperature overnight and then concentrated. The residue was neutralized by addition of sat. aq. KH$_2$PO$_4$ and extracted with EtOAc. The organic extract was washed with brine, dried with MgSO$_4$, filtered, and concentrated. The residue was purified by column chromatography (silica gel, eluting with 0% to 50% EtOAc in hexanes) to give compound 171 (330 mg, 73% yield) as a solid. m/z=480/482 (M+1).

Compound 172: Compound 171 (330 mg, 0.68 mmol) was dissolved in 1,4-dioxane (3.3 mL) and DMF (1.7 mL). K$_3$PO$_4$ (350 mg, 1.65 mmol), Pd(dppf)Cl$_2$ (50 mg, 0.068 mmol), and 3-methyl-5-(4,4,5,5-tetramethyl-1,3,2-dioxaborolan-2-yl)pyridazine (230 mg, 1.04 mmol) were added. The mixture was sparged with N$_2$ for 10 min and then heated at 90° C. for 16 h. After cooled to room temperature, the reaction mixture was filtered. The filtrate was concentrated. The residue was purified by column chromatography (silica gel, eluting with 0% to 5% MeOH in CHCl$_3$) to give compound 172 (135 mg, 40% yield) as a foam. m/z=494 (M+1).

T110: Compound 172 (135 mg, 0.27 mmol) was taken up in dry DMF (2 mL) and was cooled to 0° C. A solution of bromine (45 mg, 0.28 mmol) in CH$_2$Cl$_2$ (1 mL) was added. The reaction was stirred at 0° C. for 2 h, and then pyridine (2 mL, 24.7 mmol) was added. The mixture was heated at 60° C. for 4 h and then concentrated. The residue was diluted with water and extracted with EtOAc. The organic extract was washed with brine, dried with MgSO$_4$, filtered, and concentrated. The residue was purified by column chromatography (silica gel, eluting with 0% to 5% MeOH in CHCl$_3$) to give compound T110 (45 mg, 33% yield) as a tan solid. m/z=492 (M+1); $^1$H NMR (400 MHz, CDCl$_3$) δ 9.38 (d, J=2.3 Hz, 1H), 7.88 (m, 2H), 7.69 (m, 2H), 7.60 (d, J=2.3 Hz, 1H), 7.55 (s, 1H), 3.17 (dd, J=6.0, 17.3 Hz, 1H), 2.86 (m, 1H), 2.85 (s, 3H), 2.66 (s, 3H), 2.57 (qd, J=6.7, 13.2 Hz, 1H), 2.27 (m, 1H), 2.19 (dd, J=6.9, 13.8 Hz, 1H), 1.86 (tdd, J=6.0, 12.8, 19.6 Hz, 1H), 1.63 (s, 3H), 1.34 (d, J=6.7 Hz, 3H).

Compound 173: Compound 64 (2.841 g, 10.67 mmol) dissolved in CH$_2$Cl$_2$ (140 mL) and cooled to −78° C. Ozone was bubbled through the reaction mixture until compound 64 was completely consumed. Oxygen was bubbled through the reaction for 10 min, and then dimethyl sulfide (3.92 mL, 53.33 mmol) was added. The cold bath was removed, and the mixture was stirred at ambient temperature for 15 h. The mixture was concentrated. The residue was purified by column chromatography (silica gel, eluting with 0% to 40% EtOAc in hexanes) to give 173 (2.32 g, 86% yield) as a white solid. m/z=253 (M+1).

Compound 174: A solution of compound 173 (1.52 g, 6.03 mmol), 5-amino-2-methyl-2H-tetrazole (0.76 g, 7.67 mmol), and p-toluenesulfonic acid monohydrate (0.11 g, 0.58 mmol) in benzene (50 mL) was refluxed with Dean-Stark apparatus under N$_2$ overnight. After cooled to room temperature, the mixture was diluted with EtOAc and washed with sat. aq. NaHCO$_3$, sat. aq. KH$_2$PO$_4$, and brine sequentially. The organic extract was dried with MgSO$_4$, filtered, and concentrated. The residue was purified by column chromatography (silica gel, eluting with 30% EtOAc in hexanes) to give compound 174 (1.15 g, 57% yield) as an off-white solid. m/z=334 (M+1).

Compound 175: Compound 174 (1.54 g, 4.62 mmol) was dissolved in EtOH (50 mL). Ammonium acetate (2.7 g, 35.03 mmol) and benzaldehyde (0.70 mL, 6.89 mmol) were added. The reaction mixture was heated at 80° C. under N$_2$ for 24 h. Additional amount of benzaldehyde (0.70 mL, 6.89 mmol) was added. The mixture was heated at 80° C. for another 48 h. After cooled to room temperature, the reaction mixture was concentrated. The residue was partitioned between 10% aq. NH$_4$OH solution (100 mL) and CHCl$_3$ (100 mL). The organic extract was washed with brine, dried with MgSO$_4$, filtered, and concentrated. The residue was purified by column chromatography (silica gel, eluting with 50% EtOAc in hexanes) to give compound 175 (1.40 g, 72% yield) as a light yellow solid. m/z=421 (M+1).

Compound 176: A solution of compound 175 (1.40 g, 3.34 mmol) and 3 N aq. HCl (12 mL, 36 mmol) in MeOH (25 mL) was stirred at room temperature under N$_2$ overnight. The mixture was concentrated. The residue was cooled and basified with 10% aq. NH$_4$OH to pH 9-10. The mixture was extracted with CHCl$_3$ (2×50 mL). The combined organic extracts were washed with brine, dried with MgSO$_4$, filtered, and concentrated to give compound 176 (1.38 g, quantitative yield) as alight yellow solid and was used in the next step without purification. m/z=377 (M+1).

Compound 177: To a stirring solution of compound 176 (1.38 g, ≤3.34 mmol) and ethyl formate (26 mL, 319 mmol) in benzene (25 mL) sodium methoxide (30 wt. % in MeOH, 3.1 mL, 16.5 mmol) was added at room temperature under N$_2$. The mixture was stirred at room temperature for 16 h and then concentrated. The residue was partitioned between sat. aq. KH$_2$PO$_4$ (100 mL) and EtOAc (100 mL). The organic extract was washed with brine, dried with MgSO$_4$, filtered, and concentrated to give compound 177 (1.51 g, quantitative yield) as yellow oil and was used in the next reaction without purification. m/z=405 (M+1).

Compound 178: A stirring solution of compound 177 (1.51 g, ≤3.34 mmol), acetic acid (1.9 mL, 33.2 mmol) and hydroxylamine hydrochloride (0.35 g, 5.04 mmol) in EtOH (50 mL) was stirred at 60° C. under N$_2$ for 4 h and then at room temperature overnight. The mixture was concentrated. The residue was cooled and basified with sat. aq. NaHCO$_3$ (100 mL). The mixture was extracted with CHCl$_3$ (100 mL). The organic extract was washed with brine, dried with MgSO$_4$, filtered, and concentrated to give compound 178 (1.46 g, quantitative yield) as a yellow solid and was used in the next reaction without purification. m/z=402 (M+1).

Compound 179: To a stirring solution of compound 178 (1.46 g, ≤3.34 mmol) in MeOH (50 mL) sodium methoxide (30 wt. % in MeOH, 3.1 mL, 16.5 mmol) was added at mom temperature under N$_2$. The mixture was stirred at room temperature overnight and then concentrated. The residue was partitioned between sat. aq. KH$_2$PO$_4$ (100 mL) and CHCl$_3$ (100 mL). The organic extract was washed with brine, dried with MgSO$_4$, filtered, and concentrated. The residue was purified by column chromatography (silica gel, eluting with 100% EtOAc) to give compound 179 (1.08 g, 81% yield) as a light yellow solid. m/z=402 (M+1).

T111: To a stirring solution of compound 179 (1.08 g, 2.69 mmol) in DMF (10 mL) was added dropwise a solution of 1,3-dibromo-5,5-dimethylhydantoin (0.38 g, 1.33 mmol) in DMF (5 mL) at 0° C. under N$_2$. The mixture was stirred at 0° C. for 30 min. and then pyridine (2.2 mL, 27.2 mmol) was added. The mixture was heated at 60° C. for 4 h and then concentrated. The residue was partitioned between sat. aq. NaHCO$_3$ (50 mL) and CHCl$_3$ (50 mL). The organic extract was washed with brine, dried with MgSO$_4$, filtered, and concentrated. The residue was purified by column chromatography (silica gel, eluting with 50% EtOAc in hexanes) to give compound T111 (0.45 g, 42% yield) as a light yellow solid. m/z=400 (M+1); $^1$H NMR (400 MHz, CDCl$_3$) δ 8.63 (s, 1H), 7.40 (m, 2H), 7.34 (m, 3H), 4.36 (s, 3H), 2.62 (m, 3H), 2.15 (m, 2H), 1.85 (m, 1H), 1.51 (s, 3H), 1.31 (d, J=6.8 Hz, 3H).

Compound 180: A mixture of compound 173 (2.4 g, 9.51 mmol) was dissolved in benzene (125 mL). Aniline (1.1 g, 11.81 mmol) and p-toluenesulfonic acid monohydrate (300 mg, 1.58 mmol) were added. The reaction mixture was refluxed for 2 days and then cooled to room temperature. The reaction mixture was filtered, and the filtrate was concentrated. The residue was purified by column chromatography (silica gel, eluting with 0% to 35% EtOAc in hexanes) to give compound 180 (2.35 g, 75% yield) as an oil. m/z=328 (M+1).

Compound 181: Compound 180 (2.35 g, 7.18 mmol) was dissolved in EtOH (15 mL). Formaldehyde (37 wt. % in water, 3 g, 36.99 mmol) and ammonium acetate (5.5 g, 71.38 mmol) were added. The reaction mixture was stirred for 2 days at room temperature and then concentrated. The residue was diluted with EtOAc and washed with aq. NaHCO$_3$. The organic extract was dried with MgSO$_4$, filtered, and concentrated. The residue was purified by column chromatography (silica gel, eluting with 0% to 10% MeOH in EtOAc) to give compound 181 (2.3 g, 95% yield) as an oil. m/z=339 (M+1).

Compound 182: Compound 181 (1.94 g, 5.75 mmol) was dissolved in dry MeCN (10 mL), and the solution was cooled to 0° C. N-Bromosuccinimide (1.2 g, 6.74 mmol) was added. The reaction mixture was stirred at 0° C. for 1 h and at room temperature for 16 h. The reaction mixture was concentrated, and the residue was purified by column chromatography (silica gel, eluting with 0% to 35% EtOAc in hexane) to give compound 182 (1.7 g, 71% yield) as an off-white solid. m/z=417/419 (M+1).

Compound 183: A mixture of compound 182 (730 mg, 1.75 mmol), pyridin-4-ylboronic acid (430 mg, 3.50 mmol), $K_2CO_3$ (730 mg, 5.29 mmol), and Pd(dppf)$Cl_2$ (130 mg, 0.18 mmol) in 1,4-dioxane (8 mL) and DMF (2 mL) was sparged with $N_2$ for 10 min. The reaction mixture was stirred at 100° C. for 16 h and then cooled to room temperature. The reaction mixture was filtered, and the filtrate was concentrated. The residue was purified by column chromatography (silica gel, eluting 0% to 10% MeOH in EtOAc) to give compound 183 (560 mg, 77% yield) as a solid. m/z=416 (M+1).

Compound 184: Compound 183 (560 mg, 1.35 mmol) was dissolved in THF (10 mL), and 3 N aq. HCl (5 mL, 15 mmol) was added. The mixture was stirred overnight at room temperature and then concentrated. The residue was neutralized with sat. aq. $NaHCO_3$, and the mixture was extracted with EtOAc. The organic extract was washed with water, dried with $MgSO_4$, filtered, and concentrated to give compound 184 (500 mg, quantitative yield) as a solid. m/z=372 (M+1).

Compound 185: A mixture of compound 184 (500 mg, 1.35 mmol) in ethyl formate (15 mL, 186.5 mmol) was treated with sodium methoxide (30 wt. % in MeOH, 950 mg, 5.28 mmol). The mixture was stirred at room temperature overnight and then neutralized with aq. $KH_2PO_4$. The mixture was extracted with EtOAc. The organic extract was dried with $MgSO_4$, filtered, and concentrated to give compound 185 (525 mg, 98% yield) as a solid. m/z=400 (M+1).

Compound 186: Compound 185 (525 mg, 1.32 mmol) was dissolved in EtOH (10 mL). Hydroxylamine hydrochloride (190 mg, 2.73 mmol) was added. The reaction mixture was stirred at 50° C. overnight, cooled to room temperature, and concentrated. The residue was diluted with EtOAc and washed with aq. $NaHCO_3$. The organic extract was dried with $MgSO_4$, filtered, and concentrated to give compound 186 (485 mg, 93% yield). m/z=397 (M+1).

Compound 187: Compound 186 (485 mg, 1.22 mmol) was dissolved in THF (5 mL) and treated with sodium methoxide (30 wt. % in MeOH, 1 g, 5.55 mmol). The reaction mixture was stirred at room temperature overnight and then neutralized by addition of sat. aq. $KH_2PO_4$. The mixture was extracted with EtOAc. The organic extract was washed with brine, dried with $MgSO_4$, filtered, and concentrated to give compound 187 (400 mg, 82% yield) as an oil. m/z=397 (M+1).

T112: Compound 187 (400 mg, 1.01 mmol) was taken up in dry DMF (4 mL), and was cooled to 0° C. A solution of bromine (180 mg, 1.13 mmol) in $CH_2Cl_2$ (1 mL) was added. The reaction was stirred at 0° C. for 2 h, and then pyridine (2 mL, 24.7 mmol) was added. The mixture was heated at 50° C. for 16 h and then concentrated. The residue was purified by column chromatography (silica gel, eluting with 0% to 5% MeOH in EtOAc) to give compound T112 (95 mg, 24% yield) as a light yellow solid. m/z=395 (M+1); $^1$H NMR (400 MHz, $CDCl_3$) δ 8.64 (s, 1H), 8.46 (m, 2H), 7.51 (m, 3H), 7.22 (m, 4H), 2.59 (td, J=6.7, 13.4 Hz, 1H), 2.50 (m, 2H), 2.13 (m, 2H), 1.82 (m, 1H), 1.52 (s, 3H), 1.30 (d, J=6.8 Hz, 3H).

Compound 188: A mixture of compound 182 (530 mg, 1.27 mmol), 1-cyclohexen-1-yl-boronic acid pinacol ester (400 mg, 1.92 mmol), $K_2CO_3$ (525 mg, 3.80 mmol), and Pd(dppf)$Cl_2$ (95 mg, 0.13 mmol) in 1,4-dioxane (8 mL) and DMF (2 mL) was sparged with $N_2$ for 10 min. The reaction mixture was stirred at 100° C. for 16 h and then cooled to room temperature. The reaction mixture was filtered, and the filtrate was concentrated. The residue was purified by column chromatography (silica gel, eluting 0% to 30% EtOAc in hexanes) to give compound 188 (300 mg, 57% yield) as an oil. m/z=419 (M+1).

Compound 189: Compound 188 (300 mg, 0.72 mmol) was dissolved in THF (4 mL), and 3 N aq. HCl (2 mL, 6 mmol) was added. The mixture was stirred overnight at room temperature and then concentrated. The residue was neutralized with sat. aq. $NaHCO_3$, and the mixture was extracted with EtOAc. The organic extract was washed with water, dried with $MgSO_4$, filtered, and concentrated to give compound 189 (260 mg, 97% yield) as a solid. m/z=375 (M+1).

Compound 190: A mixture of compound 189 (260 mg, 0.69 mmol) and 10% Pd/C (35 mg) in EtOAc (15 mL) was hydrogenated under a hydrogen balloon at room temperature for 16 h. The reaction mixture was filtered through a plug of Celite®. The filtrate was concentrated to give compound 190 (230 mg, 88% yield). m/z=377 (M+1).

Compound 191: A mixture of compound 190 (230 mg, 0.61 mmol) in ethyl formate (15 mL, 186.5 mmol) was treated with sodium methoxide (30 wt. % in MeOH, 500 mg, 2.78 mmol). The mixture was stirred at room temperature overnight and then neutralized with aq. $KH_2PO_4$. The mixture was extracted with EtOAc. The organic extract was dried with $MgSO_4$, filtered, and concentrated to give compound 191 (220 mg, 89% yield) as a solid. m/z=405 (M+1).

Compound 192: Compound 191 (220 mg, 0.54 mmol) was dissolved in EtOH (10 mL). Hydroxylamine hydrochloride (80 mg, 1.15 mmol) was added. The reaction mixture was stirred at 50° C. overnight, cooled to room temperature, and concentrated. The residue was diluted with EtOAc and washed with aq. $NaHCO_3$. The organic extract was dried with $MgSO_4$, filtered, and concentrated to give compound 192 (200 mg, 92% yield) as a solid. m/z=402 (M+1).

Compound 193: Compound 192 (200 mg, 0.50 mmol) was dissolved in THF (5 mL) and treated with sodium methoxide (30 wt. % in MeOH, 360 mg, 2.00 mmol). The reaction mixture was stirred at room temperature overnight and then neutralized by addition of sat. aq. $KH_2PO_4$. The mixture was extracted with EtOAc. The organic extract was washed with brine, dried with $MgSO_4$, filtered, and concentrated to give compound 193 (195 mg, 97% yield) as a solid. m/z=402 (M+1).

T113: Compound 193 (195 mg, 0.48 mmol) was taken up in dry DMF (2 mL) and was cooled to 0° C. A solution of bromine (86 mg, 0.54 mmol) in $CH_2Cl_2$ (1 mL) was added. The reaction was stirred at 0° C. for 2 h, and then pyridine (2 mL, 24.7 mmol) was added. The mixture was heated at 50° C. for 16 h and then concentrated. The residue was purified by column chromatography (silica gel, eluting with 0% to 30% EtOAc in hexanes) to give compound T113 (40 mg, 21% yield) as a solid. m/z=400 (M+1); $^1$H NMR (400 MHz, $CDCl_3$) δ 8.63 (s, 1H), 7.49 (m, 3H), 7.20 (m, 2H), 2.54 (qd, J=6.8, 13.5 Hz, 1H), 2.44 (tt, J=3.6, 11.5 Hz, 1H), 2.36 (dd, J=6.4, 11.0 Hz, 11H), 2.29 (ddd, J=1.5, 6.4, 16.4 Hz, 1H), 2.09 (dt, J=2.2, 12.8 Hz, 1H), 1.98 (m, 1H), 1.69 (m, 7H), 1.45 (s, 3H), 1.27 (d, J=6.8 Hz, 3H), 1.25 (m, 4H).

Compound 195a: A solution of compound 194 (400 mg, 1.23 mmol), 4-chlorophenylhydrazine (347 mg, 2.43 mmol) and glacial acetic acid (2 drops) in EtOH (20 mL) was heated at 80° C. for 43 h. The reaction mixture was concentrated and the residue was partitioned between EtOAc and sat. aq. $NaHCO_3$. The organic extract was washed with brine, dried with $Na_2SO_4$, filtered, and concentrated. The residue was purified by column chromatography (silica gel, eluting with 3% EtOAc in CH$_2$CL). The product obtained was dissolved in CH$_2$Cl$_2$ (10 mL), and treated with manganese(IV)oxide (88%, 940 mg, 9.52 mmol). The reaction mixture was stirred under nitrogen at room temperature for 15 h and filtered through a plug of Celite®. The filtrate was concentrated to give compound 195a (108 mg, 20% yield) as a brown glass and was used without further purification. m/z=449 (M+1).

Compound 196a: A solution of compound 195a (107 mg, 0.238 mmol) in THF (10 mL) was treated with 3.0 N aq. HCl (0.79 mL, 2.37 mmol). The reaction mixture was stirred at room temperature for 17 h and then heated at 50° C. for 5 h. After cooled to room temperature, the mixture was concentrated. The residue was neutralized with sat. aq. NaHCO$_3$ and extracted with EtOAc. The organic extract was washed with brine, dried with Na$_2$SO$_4$, filtered, and concentrated to give compound 196a (94 mg, 98% yield) as an orange glass and was used without further purification. m/z=405 (M+1).

Compound 197a: A mixture of compound 196a (93 mg, 0.230 mmol) in ethyl formate (5 mL, 62 mmol) was cooled 0° C. and treated with sodium methoxide (5.4 M in MeOH, 0.42 mL, 2.27 mmol) dropwise. The reaction mixture was stirred at room temperature for 2 h and then cooled to 0° C. The mixture was treated with 6.0 N aq. HCl (0.43 mL, 2.58 mmol) to adjust pH to ~2. EtOH (15 mL) and hydroxylamine hydrochloride (24 mg, 0.345 mmol) were added. The reaction mixture was heated at 55° C. for 5.5 h and then concentrated. The residue was partitioned between EtOAc and sat. aq. NaHCO$_3$. The organic layer was separated. The aqueous layer was extracted with EtOAc. The combined organic extracts were dried with Na$_2$SO$_4$, filtered, and concentrated to give compound 197a (129 mg, quantitative yield) as an orange glass and was used without further purification. m/z=430 (M+1).

Compound 198a: A mixture of compound 197a (98 mg, 0.228 mmol) and potassium carbonate (83 mg, 0.60 mmol) in MeOH (10 mL) was stirred at room temperature for 24 h. The reaction mixture was concentrated, and the residue was partitioned between EtOAc and sat. aq. KH$_2$PO$_4$. The organic extract was washed with brine, dried with Na$_2$SO$_4$, filtered, and concentrated. The residue was purified by column chromatography (silica gel, eluting with 30% EtOAc in hexanes) to give compound 198a (29 mg, 30% yield) as a yellow glass. m/z=430 (M+1).

T114: A solution of compound 198a (29 mg, 0.067 mmol) in anhydrous DMF (2 mL) was cooled to 0° C. under nitrogen. A solution of 1,3-dibromo-5,5-dimethylhydantoin (10.6 mg, 0.037 mmol) in anhydrous DMF (1 mL) was added. The mixture was stirred at 0° C. for 50 min, and then anhydrous pyridine (0.054 mL, 0.67 mmol) was added. The mixture was heated at 60° C. for 4 h and then cooled to room temperature. The mixture was partitioned between EtOAc and sat. aq. KH$_2$PO$_4$. The organic layer was separated. The aqueous layer was extracted with EtOAc. The combined organic extracts were washed with brine, dried with Na$_2$SO$_4$, filtered, and concentrated. The residue was purified by column chromatography (silica gel, eluting with 20% EtOAc in hexanes) to give compound T114 (25 mg, 86% yield) as a yellow solid. m/z=428 (M+1); $^1$H NMR (400 MHz, CDCl$_3$) δ 8.56 (s, 1H), 7.35 (m, 3H), 7.28 (m, 2H), 7.17 (m, 4H), 2.77 (ddd, J=1.3, 6.5, 16.4 Hz, 1H), 2.62 (m, 2H), 2.18 (m, 1H), 2.07 (dd, J=7.0, 13.9 Hz, 1H), 1.79 (m, 1H), 1.54 (s, 3H), 1.32 (d, J=6.7 Hz, 3H).

Compound 195b: A solution of compound 194 (200 mg, 0.612 mmol), phenylhydrazine (0.12 mL, 1.22 mmol), and glacial acetic acid (2 drops) in EtOH (3 mL) was heated in a Biotage microwave synthesizer at 150° C. for 2 h. The reaction mixture was concentrated, and the residue was purified by column chromatography (silica gel, eluting with 10% EtOAc in hexanes). The product obtained was dissolved in CH$_2$Cl$_2$ (10 mL) and treated with manganese(IV) oxide (88%, 471 mg, 4.77 mmol). The reaction mixture was stirred under nitrogen at room temperature for 40 h and then filtered through a plug of Celite®. The filtrate was concentrated, and the residue was purified by column chromatography (silica gel, eluting with 30% EtOAc in hexanes) to give compound 195b (85 mg, 34% yield) as an off-white solid. m/z=415 (M+1).

Compound 196b: A solution of compound 195b (85 mg, 0.205 mmol) in THF (10 mL) was treated with 3.0 N aq. HCl (0.68 mL, 2.05 mmol). The reaction mixture was stirred at room temperature for 20 h and then heated at 50° C. for 5 h. After cooled to room temperature, the mixture was concentrated. The residue was neutralized with sat. aq. NaHCO$_3$ and extracted with EtOAc. The organic extract was washed with brine, dried with Na$_2$SO$_4$, filtered, and concentrated to give compound 196b (76 mg, quantitative yield) as a yellow glass and was used without further purification. m/z=371 (M+1).

Compound 197b: A mixture of compound 196b (76 mg, 0.205 mmol) in ethyl formate (10 mL, 124 mmol) was cooled 0° C. and treated with sodium methoxide (5.4 M in MeOH, 0.38 mL, 2.05 mmol) dropwise. The reaction mixture was stirred at room temperature for 2 h and then cooled to 0° C. The mixture was treated with 6.0 N aq. HCl (0.38 mL, 2.28 mmol) to adjust pH 25 to 2. EtOH (13 mL) and hydroxylamine hydrochloride (21 mg, 0.302 mmol) were added. The reaction mixture was heated at 55° C. for 4 h and then concentrated. The residue was partitioned between EtOAc and sat. aq. NaHCO$_3$. The organic layer was separated. The aqueous layer was extracted with EtOAc. The combined organic extracts were dried with Na$_2$SO$_4$, filtered, and concentrated to give compound 197b (81 mg, quantitative yield) as a yellow glass, which was used without further purification. m/z=396 (M+1).

Compound 198b: A mixture of compound 197b (81 mg, 0.205 mmol) and potassium carbonate (57 mg, 0.41 mmol) in MeOH (10 mL) was stirred at room temperature for 40 h. The reaction mixture was concentrated and the residue was partitioned between EtOAc and sat. aq. KH$_2$PO$_4$. The organic extract was washed with brine, dried with Na$_2$SO$_4$, filtered, and concentrated. The residue was purified by column chromatography (silica gel, eluting with 30% EtOAc in hexanes) to give compound 198b (58 mg, 72% yield) as a yellow glass. m/z=396 (M+1).

T115: A solution of compound 198b (58 mg, 0.146 mmol) in anhydrous DMF (2 mL) was cooled to 0° C. under nitrogen. A solution of 1,3-dibromo-5,5-dimethylhydantoin (23 mg, 0.080 mmol) in anhydrous DMF (1 mL) was added. The mixture was stirred at 0° C. for 45 min, and then anhydrous pyridine (0.12 mL, 1.48 mmol) was added. The mixture was heated at 60° C. for 4 h and then cooled to room temperature. The mixture was partitioned between EtOAc and sat. aq. KH$_2$PO$_4$. The organic layer was separated. The aqueous layer was extracted with EtOAc. The combined organic extracts were washed with brine, dried with Na$_2$SO$_4$, filtered, and concentrated. The residue was purified by column chromatography (silica gel, eluting with 20% EtOAc in hexanes) to give compound T115 (44 mg, 76% yield) as a yellow solid. m/z=394 (M+1); $^1$H NMR (400 MHz, CDCl$_3$) δ 8.60 (s, 1H), 7.29 (m, 8H), 7.16 (m, 2H), 2.78 (ddd, J=1.5, 6.6, 16.5 Hz, 1H), 2.64 (m, 2H), 2.20 (dt, J=2.3, 12.8 Hz, 1H), 2.08 (dd, J=6.3, 13.1 Hz, 1H), 1.80 (m, 1H), 1.55 (s, 3H), 1.33 (d, J=6.7 Hz, 3H).

Compound 199: A solution of compound 4 (100 mg, 0.309 mmol) in EtOH (10 mL) was treated with anhydrous hydrazine (0.065 mL, 2.07 mmol). The reaction mixture was heated at 60° C. for 35 min and then concentrated. The residue was purified by column chromatography (silica gel, eluting with EtOAc) to give compound 199 in quantitative yield as a clear glass. m/z=320 (M+1).

Compound 200a: To a solution of compound 199 (58 mg, 0.181 mmol) in CH$_2$Cl$_2$ (10 mL) was added 3 Å molecular sieves (250 mg), 4-methoxyphenylboronic acid (55 mg, 0.362 mmol), copper(II) acetate (49 mg, 0.271 mmol), and anhydrous pyridine (0.022 mL, 0.271 mmol). The reaction mixture was stirred at room temperature for 3 h and then concentrated. The residue was diluted with EtOAc and washed with 10% aq. ammonium hydroxide solution and brine. The organic extract was dried with Na$_2$SO$_4$, filtered, and concentrated. The residue was purified by column chromatography (silica gel, eluting with 40% EtOAc in hexanes) to give compound 200a (66 mg, 86% yield) as a clear glass. m/z=426 (M+1).

Compound 201a: A mixture of compound 200a (63 mg, 0.148 mmol) and potassium carbonate (41 mg, 0.296 mmol) in MeOH (4 mL) and acetone (1 mL) was stirred at room temperature for 24 h. The reaction mixture was concentrated and the residue was partitioned between EtOAc and sat. aq. KH$_2$PO$_4$. The organic extract was washed with brine, dried with Na$_2$SO$_4$, filtered, and concentrated. The residue was purified by column chromatography (silica gel, eluting with 40% EtOAc in hexanes) to give compound 201a (49 mg, 78% yield) as a yellow glass. m/z=426 (M+1).

T116: A solution of compound 201a (48 mg, 0.112 mmol) in anhydrous DMF (2 mL) was cooled to 0° C. under nitrogen. A solution of 1,3-dibromo-5,5-dimethylhydantoin (17.6 mg, 0.061 mmol) in anhydrous DMF (1 mL) was added. The mixture was stirred at 0° C. for 2 h, and then anhydrous pyridine (0.09 mL, 1.11 mmol) was added. The mixture was heated at 60° C. for 4 h and then cooled to room temperature. The mixture was partitioned between EtOAc and sat. aq. KH$_2$PO$_4$. The organic layer was separated. The aqueous layer was extracted with EtOAc. The combined organic extracts were dried with Na$_2$SO$_4$, filtered, and concentrated. The residue was purified by column chromatography (silica gel, eluting with 30% EtOAc in hexanes) to give compound T116 (30 mg, 63% yield) as a yellow solid. m/z=424 (M+1): $^1$H NMR (400 MHz, CDCl$_3$) δ 8.59 (s, 1H), 7.31 (m, 3H), 7.15 (m, 4H), 6.83 (m, 2H), 3.80 (s, 3H), 2.77 (m, 1H), 2.63 (m, 2H), 2.19 (dt, J=2.3, 12.8 Hz, 1H), 2.06 (m, 1H), 1.79 (m, 1H), 1.54 (s, 3H), 1.32 (d, J=6.7 Hz, 3H).

Compound 200b: To a solution of compound 199 (100 mg, 0.313 mmol) in CH$_2$Cl$_2$ (15 mL) was added 3 Å molecular sieves (500 mg), 3,4-dichlorophenylboronic acid (119 mg, 0.623 mmol), copper(II)acetate (85 mg, 0.47 mmol), and anhydrous pyridine (0.037 mL, 0.46 mmol). The reaction mixture was stirred at room temperature for 21 h and then concentrated. The residue was diluted with EtOAc and washed with 10% aq. ammonium hydroxide solution and brine. The organic extract was dried with Na$_2$SO$_4$, filtered, and concentrated. The residue was purified by column chromatography (silica gel, eluting with 20% EtOAc in hexanes) to give compound 200b (116 mg, 80% yield) as a clear glass. m/z=464 (M+1).

Compound 201b: A mixture of compound 200b (110 mg, 0.236 mmol) and potassium carbonate (65 mg, 0.47 mmol) in MeOH (10 mL) was stirred at room temperature for 41 h. The reaction mixture was concentrated and the residue was partitioned between EtOAc and sat. aq. KH$_2$PO$_4$. The organic extract was washed with brine, dried with Na$_2$SO$_4$, filtered, and concentrated. The residue was purified by column chromatography (silica gel, eluting with 30% EtOAc in hexanes) to give compound 201b (93 mg, 85% yield) as a clear glass. m/z=464 (M+1).

T117: A solution of compound 201b (91 mg, 0.195 mmol) in anhydrous DMF (3 mL) was cooled to 0° C. under nitrogen. A solution of 1,3-dibromo-5,5-dimethylhydantoin (30.6 mg, 0.107 mmol) in anhydrous DMF (1 mL) was added. The mixture was stirred at 0° C. for 1 h, and then anhydrous pyridine (0.16 mL, 1.98 mmol) was added. The mixture was heated at 60° C. for 4 h and then cooled to room temperature. The mixture was partitioned between EtOAc and sat. aq. KH$_2$PO$_4$. The organic layer was separated. The aqueous layer was extracted with EtOAc. The combined organic extracts were dried with Na$_2$SO$_4$, filtered, and concentrated. The residue was purified by column chromatography (silica gel, eluting with 20% EtOAc in hexanes) to give compound T117 (71 mg, 78% yield) as a white solid. m/z=462 (M+1); $^1$H NMR (400 MHz, CDCl$_3$) δ 8.54 (s, 1H), 7.49 (d, J=2.4 Hz, 1H), 7.38 (m, 3H), 7.32 (d, J=8.7 Hz, 1H), 7.17 (m, 2H), 6.97 (dd, J=2.5, 8.7 Hz, 1H), 2.76 (ddd, J=1.4, 6.7, 16.6 Hz, 1H), 2.62 (m, 2H), 2.17 (dt, J=2.3, 12.8 Hz, 1H), 2.07 (m, 1H), 1.79 (m, 1H), 1.54 (s, 3H), 1.32 (d, J=6.7 Hz, 3H).

Compound 200c: To a solution of compound 199 (117 mg, 0.366 mmol) in CH$_2$Cl$_2$ (15 mL) was added 3 Å molecular sieves (500 mg), 4-methylphenylboronic acid (99 mg, 0.732 mmol), copper(II)acetate (100 mg, 0.549 mmol), and anhydrous pyridine (0.044 mL, 0.544 mmol). The reaction mixture was stirred at room temperature for 21 h and then concentrated. The residue was diluted with EtOAc and washed with 10% aq. ammonium hydroxide solution and brine. The organic extract was dried with Na$_2$SO$_4$, filtered, and concentrated. The residue was purified by column chromatography (silica gel, eluting with 20% EtOAc in hexanes) to give compound 200c (112 mg, 75% yield) as a clear glass. m/z=410 (M+1).

Compound 201c: A mixture of compound 200c (108 mg, 0.263 mmol) and potassium carbonate (72 mg, 0.52 mmol) in MeOH (10 mL) was stirred at room temperature for 41 h. The reaction mixture was concentrated and the residue was partitioned between EtOAc and sat. aq. KH$_2$PO$_4$. The organic extract was washed with brine, dried with Na$_2$SO$_4$, filtered, and concentrated. The residue was purified by column chromatography (silica gel, eluting with 30% EtOAc in hexanes) to give compound 201c (87 mg, 81% yield) as a clear glass. m/z=410 (M+1).

T118: A solution of compound 201c (85 mg, 0.207 mmol) in anhydrous DMF (3 mL) was cooled to 0° C. under nitrogen. A solution of 1,3-dibromo-5,5-dimethylhydantoin (32.5 mg, 0.113 mmol) in anhydrous DMF (1 mL) was added. The mixture was stirred at 0° C. for 1 h, and then anhydrous pyridine (0.17 mL, 2.10 mmol) was added. The mixture was heated at 60° C. for 4 h and then cooled to room temperature. The mixture was partitioned between EtOAc and sat. aq. KH$_2$PO$_4$. The organic layer was separated. The aqueous layer was extracted with EtOAc. The combined organic extracts were dried with Na$_2$SO$_4$, filtered, and concentrated. The residue was purified by column chromatography (silica gel, eluting with 20% EtOAc in hexanes) to give compound T118 (66 mg, 78% yield) as a white solid. m/z=408 (M+1); $^1$H NMR (400 MHz, CDCl$_3$) δ 8.60 (s, 1H), 7.32 (m, 4H), 7.13 (m, 5H), 2.77 (ddd, J=1.5, 6.6, 16.5

Hz, 1H), 2.63 (m, 2H), 2.34 (s, 3H), 2.19 (dt, J=2.3, 12.8 Hz, 1H), 2.07 (m, 1H), 1.79 (m, 1H), 1.55 (s, 3H), 1.32 (d, J=6.7 Hz, 3H).

Compound 202: 2-Cyclobutylacetic acid (367 mg, 3.22 mmol) and pentafluorophenol (652 mg, 3.54 mmol) was dissolved in 1,4-dioxane (15 mL) under nitrogen. N,N'-dicyclohexylcarbodiimide (730 mg, 3.54 mmol) was added. The reaction mixture was stirred at room temperature for 14 h. The precipitated urea was removed by filtration. The filtrate was concentrated. The residue was purified by column chromatography (silica gel, eluting with 20% EtOAc in hexanes) to give compound 202 (948 mg, quantitative yield) as a clear oil. $^1$H NMR (400 MHz, CDCl$_3$) δ 2.74-2.87 (m, 3H), 2.20 (m, 2H), 1.70-2.00 (m, 4H).

Compound 203: To a stirring mixture of compound 3 (226 mg, 1.03 mmol) and magnesium bromide etherate (665 mg, 2.57 mmol) in CH$_2$Cl$_2$ (20 mL) at room temperature was added dropwise N,N-diisopropylethylamine (0.51 mL, 2.93 mmol). The mixture was stirred at room temperature for 2 min, and then a solution of compound 202 (433 mg, 1.54 mmol) in CH$_2$Cl$_2$ (5 mL) was added dropwise. After stirring at room temperature for 26 h, the reaction mixture was washed with sat. aq. KH$_2$PO$_4$. The organic layer was separated. The aqueous layer was extracted with EtOAc. The combined organic extracts were dried with Na$_2$SO$_4$, filtered, and concentrated. The residue was purified by column chromatography (silica gel, eluting with 10% EtOAc in hexanes) to give partially purified compound 203 (99 mg, 30% yield) as a clear glass. m/z=316 (M+1).

Compound 204: A solution of compound 203 (98 mg, 0.31 mmol) in EtOH (5 mL) was treated with hydrazine monohydrate (0.038 mL, 0.78 mmol). The reaction mixture was heated at 60° C. for 21 h and then cooled to room temperature. The solvent was removed in vacuo and the residue was purified by column chromatography (silica gel, eluting with 30% EtOAc in hexanes, and then 5% MeOH in EtOAc) to give compound 204 (47 mg, 49% yield) as a clear glass. m/z=312 (M+1).

Compound 205: To a solution of compound 204 (44 mg, 0.14 mmol) in CH$_2$Cl$_2$ (10 mL) was added 3 Å molecular sieves (190 mg), 4-biphenylboronic acid (56 mg, 0.28 mmol), copper(II)acetate (38 mg, 0.21 mmol), and pyridine (0.017 mL, 0.21 mmol). The reaction mixture was stirred at room temperature for 32 h. The mixture was washed with sat. aq. KH$_2$PO$_4$. The organic extract was dried with Na$_2$SO$_4$, filtered, and concentrated. The residue was purified by column chromatography (silica gel, eluting with 30% EtOAc in hexanes) to give compound 205 (42 mg, 64% yield) as a clear glass. m/z=464 (M+1).

Compound 206: A mixture of compound 205 (39 mg, 0.084 mmol) and potassium carbonate (23 mg, 0.17 mmol) in MeOH (5 mL) was stirred at room temperature for 17 h, heated at 50° C. for 8 h, and stirred at room temperature for an additional 23 h. The reaction mixture was concentrated and the residue was partitioned between EtOAc and sat. aq. KH$_2$PO$_4$. The organic extract was washed with brine, dried with Na$_2$SO$_4$, filtered, and concentrated to give compound 206 (35 mg, 90% yield) as a clear glass. m/z=464 (M+1).

T119: A solution of compound 206 (34 mg, 0.073 mmol) in anhydrous DMF (3 mL) was cooled to 0° C. under nitrogen. A solution of 1,3-dibromo-5,5-dimethylhydantoin (11.5 mg, 0.0402 mmol) in anhydrous DMF (1 mL) was added. The mixture was stirred at 0° C. for 1 h, and then anhydrous pyridine (0.059 mL, 0.73 mmol) was added. The mixture was heated at 60° C. for 4 h and then cooled to room temperature. The mixture was partitioned between EtOAc and sat. aq. KH$_2$PO$_4$. The organic layer was separated. The aqueous layer was extracted with EtOAc. The combined organic extracts were dried with Na$_2$SO$_4$, filtered, and concentrated. The residue was purified by column chromatography (silica gel, eluting with 30% EtOAc in hexanes) to give compound T119 (29 mg, 86% yield) as a yellow solid. m/z=462 (M+1): $^1$H NMR (400 MHz, CDCl$_3$) δ 8.54 (s, 1H), 7.70 (m, 2H), 7.63 (m, 2H), 7.47 (m, 4H), 7.40 (m, 1H), 2.75 (m, 3H), 2.58 (tt, J=6.6, 13.3 Hz, 1H), 2.44 (pent, J=7.9 Hz, 1H), 2.11 (m, 2H), 1.93 (m, 2H), 1.75 (m, 3H), 1.55 (m, 3H), 1.48 (s, 3H), 1.32 (d, J=6.8 Hz, 3H).

Compound 207: A solution of compound 40 (120 mg, 0.368 mmol) in EtOH (5 mL) was treated with hydrazine monohydrate (0.045 mL, 0.93 mmol). The reaction mixture was heated at 60° C. for 15 h and then cooled to room temperature. The solvent was removed in vacuo and the residue was purified by column chromatography (silica gel, eluting with EtOAc) to give compound 207 (127 mg, quantitative yield) as a white solid. m/z=322 (M+1).

Compound 208a: To a solution of compound 207 (125 mg, 0.388 mmol) in CH$_2$Cl$_2$ (15 mL) was added 3 Å molecular sieves (500 mg), 4-biphenylboronic acid (153 mg, 0.773 mmol), copper(II)acetate (106 mg, 0.584 mmol), and pyridine (0.047 mL, 0.58 mmol). The reaction mixture was stirred at room temperature for 23 h and then concentrated. The residue was partitioned between EtOAc and 10% aq. NH$_4$OH. The organic extract was washed with brine, dried with Na$_2$SO$_4$, filtered, and concentrated. The residue was purified by column chromatography (silica gel, eluting with 30% EtOAc in hexanes) to give compound 208a (88 mg, 48% yield) as a white glass. m/z=474 (M+1).

Compound 209a: A mixture of compound 208a (85 mg, 0.179 mmol) and potassium carbonate (49 mg, 0.36 mmol) in MeOH (10 mL) was stirred at mom temperature for 23 h. The reaction mixture was concentrated and the residue was partitioned between EtOAc and sat. aq. KH$_2$PO$_4$. The organic extract was washed with brine, dried with Na$_2$SO$_4$, filtered, and concentrated. The residue was purified by column chromatography (silica gel, eluting with 40% EtOAc in hexanes) to give compound 209a (77 mg, 91% yield) as a white solid. m/z=474 (M+1).

T120: A solution of compound 209a (76 mg, 0.16 mmol) in anhydrous DMF (3 mL) was cooled to 0° C. under nitrogen. A solution of 1,3-dibromo-5,5-dimethylhydantoin (25 mg, 0.087 mmol) in anhydrous DMF (1 mL) was added. The mixture was stirred at 0° C. for 1 h, and then anhydrous pyridine (0.13 mL, 1.61 mmol) was added. The mixture was heated at 60° C. for 4 h, and then cooled to room temperature. The mixture was partitioned between EtOAc and sat. aq. KH$_2$PO$_4$. The organic layer was separated. The aqueous layer was extracted with EtOAc. The combined organic extracts were washed with brine, dried with Na$_2$SO$_4$, filtered, and concentrated. The residue was purified by column chromatography (silica gel, eluting with 50% EtOAc in hexanes) to give compound T120 (59 mg, 78% yield) as an off-white solid. m/z=472 (M+1); $^1$H NMR (400 MHz, CDCl$_3$) δ 9.24 (d, J=1.4 Hz, 1H), 8.63 (d, J=5.3 Hz, 1H), 8.57 (s, 1H), 7.63 (m, 4H), 7.47 (m, 2H), 7.38 (m, 3H), 7.00 (dd, J=1.4, 5.3 Hz, 1H), 3.11 (m, 1H), 2.83 (ddd, J=7.1, 11.6, 17.9 Hz, 1H), 2.61 (qd, J=6.7, 13.4 Hz, 1H), 2.18 (m, 2H), 1.84 (m, 1H), 1.55 (s, 3H), 1.34 (d, J=6.8 Hz, 3H).

Compound 208b: To a solution of compound 207 (400 mg, 1.24 mmol) in CH$_2$Cl$_2$ (40 mL) was added 3 Å molecular sieves (1.72 g), 3-biphenylboronic acid (493 mg, 2.49 mmol), copper(II)acetate (338 mg, 1.86 mmol), and pyridine (0.15 mL, 1.86 mmol). The reaction mixture was stirred open to air at room temperature for 23 h and then concentrated. The residue was partitioned between EtOAc and sat.

aq. KH$_2$PO$_4$. The organic extract was washed with brine, dried with Na$_2$SO$_4$, filtered, and concentrated. The residue was purified by column chromatography (silica gel, eluting with EtOAc) to give compound 208b (165 mg, 28% yield) as a white glass. m/z=474 (M+1).

Compound 209b: A mixture of compound 208b (162 mg, 0.342 mmol) in MeOH (10 mL) was treated with potassium carbonate (95 mg, 0.688 mmol). The reaction mixture was stirred at room temperature for 19 h and then heated at 50° C. for 1.5 h. The reaction mixture was concentrated, and the residue was partitioned between EtOAc and sat. aq. KH$_2$PO$_4$. The organic extract was washed with brine, dried with Na$_2$SO$_4$, filtered, and concentrated. The residue was purified by column chromatography (silica gel, eluting with 60% EtOAc in hexanes) to give compound 209b (119 mg, 73% yield) as a white solid. m/z=474 (M+1).

T121: A solution of compound 209b (118 mg, 0.249 mmol) in anhydrous DMF (3 mL) was cooled to 0° C. under nitrogen. A solution of 1,3-dibromo-5,5-dimethylhydantoin (39 mg, 0.136 mmol) in anhydrous DMF (1 mL) was added. The mixture was stirred at 0° C. for 1 h, and then anhydrous pyridine (0.20 mL, 2.47 mmol) was added. The mixture was heated at 60° C. for 4 h and then cooled to room temperature. The mixture was partitioned between EtOAc and sat. aq. KH$_2$PO$_4$. The organic layer was separated. The aqueous layer was extracted with EtOAc. The combined organic extracts were washed with brine, dried with Na$_2$SO$_4$, filtered, and concentrated. The residue was purified by column chromatography (silica gel, eluting with MTBE) to give compound T121 (66 mg, 56% yield) as a yellow solid. m/z=472 (M+1); $^1$H NMR (400 MHz, CDCl$_3$) δ 9.23 (d, J=1.5 Hz, 1H), 8.61 (d, J=5.3 Hz, 1H), 8.58 (s, 1H), 7.63 (ddd, J=1.1, 1.8, 7.8 Hz, 1H), 7.48 (m, 7H), 7.22 (ddd, J=1.1, 2.2, 7.9 Hz, 1H), 6.97 (dd, J=1.5, 5.4 Hz, 1H), 3.13 (dd, J=6.3, 17.4 Hz, 1H), 2.83 (ddd, J=7.2, 11.6, 17.9 Hz, 1H), 2.61 (qd, J=6.7, 13.4 Hz, 1H), 2.18 (m, 2H), 1.85 (m, 1H), 1.55 (s, 3H), 1.34 (d, J=6.7 Hz, 3H).

Compound 210: A solution of compound 152 (412 mg, 1.21 mmol) in EtOH (20 mL) was treated with hydrazine monohydrate (0.15 mL, 3.09 mmol). The reaction mixture was heated at 60° C. for 6 h and then cooled to room temperature. The solvent was removed in vacuo and the residue was purified by column chromatography (silica gel, eluting with 60% EtOAc in hexanes) to give compound 210 (211 mg, 52% yield) as a clear glass. m/z=338 (M+1).

Compound 211: To a solution of compound 210 (210 mg, 0.622 mmol) in DMF (7 mL) was added 3 Å molecular sieves (1.5 g), pyridine-4-boronic acid (382 mg, 3.11 mmol), copper(II) acetate (565 mg, 3.11 mmol) and pyridine (0.25 mL, 3.09 mmol). The reaction mixture was heated in open air at 85° C. for 21 h. After cooled to room temperature, the mixture was diluted with EtOAc and filtered through a plug of Celite®. The filtrate was washed with 10% aq. NH$_4$OH and brine. The organic extract was dried with Na$_2$SO$_4$, filtered, and concentrated. The residue was purified by column chromatography (silica gel, eluting with 90% EtOAc in hexanes) to give compound 211 (49 mg, 19% yield) as a glass. m/z=415 (M+1).

Compound 212: A mixture of compound 211 (48 mg, 0.12 mmol) in MeOH (10 mL) was treated with potassium carbonate (32 mg, 0.23 mmol). The mixture stirred at room temperature for 23 h and then concentrated. The residue was partitioned between EtOAc and sat. aq. KH$_2$PO$_4$. The organic extract was washed with brine, dried with Na$_2$SO$_4$, filtered, and concentrated. The residue was purified by column chromatography (silica gel, eluting with 80% EtOAc in hexanes) to give compound 212 (30 mg, 63% yield) as a solid. m/z=415 (M+1).

T122: A solution of compound 212 (29 mg, 0.070 mmol) in anhydrous DMF (2 mL) was cooled to 0° C. under nitrogen. A solution of 1,3-dibromo-5,5-dimethylhydantoin (11 mg, 0.038 mmol) in anhydrous DMF (0.5 mL) was added. The mixture was stirred at 0° C. for 1 h, and then anhydrous pyridine (0.056 mL, 0.69 mmol) was added. The mixture was heated at 60° C. for 4 h and then cooled to room temperature. The mixture was partitioned between EtOAc and sat. aq. KH$_2$PO$_4$. The organic layer was separated. The aqueous layer was extracted with EtOAc. The combined organic extracts were washed with brine, dried with Na$_2$SO$_4$, filtered, and concentrated. The residue was purified by column chromatography (silica gel, eluting with 60% EtOAc in hexanes) to give compound T122 (24 mg, 83% yield) as an off-white solid. m/z=413 (M+1); $^1$H NMR (400 MHz, CDCl$_3$) δ 8.53 (m, 3H), 7.16 (m, 6H), 2.72 (ddd, J=1.4, 6.6, 16.7 Hz, 1H), 2.58 (m, 2H), 2.16 (dt, J=2.3, 12.7 Hz, 1H), 2.08 (dd, J=7.1, 14.5 Hz, 1H), 1.79 (tdd, J=6.6, 12.6, 19.1 Hz, 1H), 1.54 (s, 3H), 1.32 (d, J=6.7 Hz, 3H).

Compound 213: To a stirring suspension of compound 65 (0.58 g, 1.40 mmol) and sodium carbonate (0.74 g, 6.98 mmol) in CH$_2$Cl$_2$ (14 mL) at −10° C. under N$_2$ was added a solution of bromine (0.67 g, 4.19 mmol) in CH$_2$Cl$_2$ (5 mL) dropwise. After stirring for 30 min, the cold reaction mixture was treated with sat. aq. sodium thiosulfate (50 mL). The cold bath was removed, and the mixture stirred at room temperature for 1 h. The mixture was concentrated, and the residue was extracted with EtOAc (50 mL). The organic extract was washed with brine (50 mL), dried with MgSO$_4$, filtered, and concentrated to give compound 213 (0.62 g, 90% yield) as a yellow solid. m/z=493/495 (M+1).

Compound 214a: In a sealable vial, a mixture of compound 213 (0.29 g, 0.59 mmol), 2-fluorophenylboronic acid (0.16 g, 1.14 mmol), and potassium phosphate (0.38 g, 1.79 mmol) in 1,4-dioxane (4.8 mL) and DMF (1.2 mL) was degassed. Tetrakis(triphenylphosphine)-palladium(0) (69 mg, 0.060 mmol) was added. The mixture was degassed again. The vial was sealed, and heated at 90° C. for 16 h. The mixture was cooled to room temperature, diluted with EtOAc (50 mL), and washed with 1 N aq. NaOH (50 mL). The organic extract was washed with brine (50 mL), dried with MgSO$_4$, filtered, and concentrated. The residue was purified by column chromatography (silica gel, eluting with 1/10/10 EtOAc/CH$_2$Cl$_2$/hexanes) to give compound 214a (92 mg, 31% yield) as a yellow solid. m/z=509 (M+1).

Compound 215a: A solution of compound 214a (92 mg, 0.18 mmol) and 3 N aq. HCl (0.6 mL, 1.8 mmol) in MeOH (10 mL) was stirred at room temperature under N$_2$ overnight. The mixture was concentrated. The residue was cooled and basified with 10% aq. NH$_4$OH (25 mL) to pH 9-10. The mixture was extracted with CHCl$_3$ (25 mL). The organic extract was washed with brine (25 mL), dried with MgSO$_4$, filtered, and concentrated to give compound 215a (83 mg, 99% yield) as a light yellow solid. m/z=465 (M+1).

Compound 216a: A solution of compound 215a (83 mg, 0.18 mmol) in ethyl formate (10 mL, 124 mmol) was treated with sodium methoxide (30 wt. % in MeOH, 0.17 mL, 0.91 mmol). The mixture was stirred at room temperature under N$_2$ overnight and then concentrated. The residue was partitioned between EtOAc (50 mL) and sat. aq. KH$_2$PO$_4$ (50 mL). The organic extract was washed with brine (50 mL), dried with MgSO$_4$, filtered, and concentrated to give compound 216a (97 mg, quantitative yield) as a yellow solid. m/z=493 (M+1).

Compound 217a: A solution of compound 216a (97 mg, ≤0.18 mmol), acetic acid (0.10 mL, 1.75 mmol) and hydroxylamine hydrochloride (19 mg, 0.27 mmol) in EtOH (10 mL) was stirred at 60° C. for 2 h and then at room temperature overnight. The mixture was concentrated. The residue was partitioned between sat. aq. NaHCO$_3$ (25 mL) and EtOAc (25 mL). The organic extract was washed with brine (25 mL), dried with MgSO$_4$, filtered, and concentrated to give compound 217a (84 mg, 95% yield) as a tan solid. m/z=490 (M+1).

Compound 218a: A mixture of compound 217a (84 mg, 0.17 mmol) and potassium carbonate (0.12 g, 0.87 mmol) in MeOH (10 mL) was stirred at room temperature under N$_2$ overnight. The mixture was concentrated. The residue was partitioned between sat. aq. KH$_2$PO$_4$ (25 mL) and EtOAc (25 mL). The organic extract was washed with brine (25 mL), dried with MgSO$_4$, filtered, and concentrated to give compound 218a (82 mg, 98% yield) as a dark yellow solid. m/z=490 (M+1).

T123: To a stirring solution of compound 218a (82 mg, 0.17 mmol) in degassed DMF (4 mL) at 0° C. under N$_2$ was added dropwise a solution of 1,3-dibromo-5,5-dimethylhydantoin (24 mg, 0.084 mmol) in degassed DMF (1 mL). The mixture was stirred at 0° C. for 30 min. and then pyridine (0.13 mL, 1.61 mmol) was added. The mixture was heated at 60° C. for 4 h and then concentrated. The residue was partitioned between sat. aq. KH$_2$PO$_4$ (25 mL) and EtOAc (25 mL). The organic extract was washed with brine (25 mL), dried with MgSO$_4$, filtered, and concentrated. The residue was purified by column chromatography (silica gel, eluting with 25% EtOAc in hexanes) to give compound T123 (31 mg, 38% yield) as a light yellow solid. m/z=488 (M+1); $^1$H NMR (400 MHz, CDCl$_3$) δ 8.61 (s, 1H), 7.55 (m, 4H), 7.37 (m, 6H), 7.14 (m, 3H), 2.64 (m, 3H), 2.22 (dt, J=2.3, 12.9 Hz, 1H), 2.05 (m, 1H), 1.81 (m, 1H), 1.57 (s, 3H), 1.33 (d, J=6.7 Hz, 3H).

Compound 214b: In a sealable vial, a mixture of compound 213 (0.30 g, 0.61 mmol), pyridine-4-boronic acid (0.15 g, 1.22 mmol) and potassium phosphate (0.39 g, 1.84 mmol) in 1,4-dioxane (4.8 mL) and DMF (1.2 mL) was degassed. Tetrakis(triphenylphosphine)palladium(0) (70 mg, 0.060 mmol) was added. The mixture was degassed again. The vial was sealed and heated at 90° C. for 16 h. The mixture was cooled to room temperature, diluted with EtOAc (50 mL), and washed with 1 N aq. NaOH (50 mL). The organic extract was washed with brine (50 mL), dried with MgSO$_4$, filtered, and concentrated. The residue was purified by column chromatography (silica gel, eluting with EtOAc) to give compound 214b (0.19 g, 63% yield) as an off-white solid. m/z=492 (M+1).

Compound 215b: A solution of compound 214b (0.19 g, 0.39 mmol) and 3 N aq. HCl (1.3 mL, 3.9 mmol) in MeOH (10 mL) was stirred at room temperature under N$_2$ overnight. The mixture was concentrated. The residue was cooled and basified with 10% aq. NH$_4$OH (25 mL) to pH 9-10. The mixture was extracted with CHCl$_3$ (25 mL). The organic extract was washed with brine (25 mL), dried with MgSO$_4$, filtered, and concentrated to give compound 215b (0.23 g, quantitative yield) as light yellow oil. m/z=448 (M+1).

Compound 216b: A solution of compound 215b (0.23 g, ≤0.39 mmol) in ethyl formate (10 mL, 124 mmol) was treated with sodium methoxide (30 wt. % in MeOH, 0.40 mL, 2.13 mmol). The mixture was stirred at room temperature under N$_2$ overnight and then concentrated. The residue was partitioned between EtOAc (50 mL) and sat. aq. KH$_2$PO$_4$ (50 mL). The organic extract was washed with brine (50 mL), dried with MgSO$_4$, filtered, and concentrated to give compound 216b (0.20 g, quantitative yield) as a dark yellow solid. m/z=476 (M+1).

Compound 217b: A solution of compound 216b (0.20 g, ≤0.39 mmol), acetic acid (0.23 mL, 4.02 mmol) and hydroxylamine hydrochloride (41 mg, 0.59 mmol) in EtOH (10 mL) was stirred at 60° C. for 2 h and then at room temperature overnight. The mixture was concentrated. The residue was partitioned between sat. aq. NaHCO$_3$ (25 mL) and EtOAc (25 mL). The organic extract was washed with brine (25 mL), dried with MgSO$_4$, filtered, and concentrated to give compound 217b (0.20 g, quantitative yield) as a dark yellow solid. m/z=473 (M+1).

Compound 218b: A mixture of compound 217b (0.20 g, ≤0.39 mmol) and potassium carbonate (0.27 g, 1.95 mmol) in MeOH (10 mL) was stirred at room temperature under N$_2$ overnight. The mixture was concentrated. The residue was partitioned between sat. aq. KH$_2$PO$_4$ (25 mL) and EtOAc (25 mL). The organic extract was washed with brine (25 mL), dried with MgSO$_4$, filtered, and concentrated. The residue was purified by column chromatography (silica gel, eluting with 2% MeOH in CHCl$_3$) to give compound 218b (0.13 g, 71% yield) as a light yellow solid. m/z=473 (M+1).

T124: To a stirring solution of compound 218b (0.13 g, 0.28 mmol) in degassed DMF (4 mL) at 0° C. under N$_2$ was added dropwise a solution of 1,3-dibromo-5,5-dimethylhydantoin (39 mg, 0.14 mmol) in degassed DMF (1 mL). The mixture was stirred at 0° C. for 30 min. and then pyridine (0.22 mL, 2.72 mmol) was added. The mixture was heated at 60° C. for 4 h and then concentrated. The residue was partitioned between sat. aq. KH$_2$PO$_4$ (25 mL) and EtOAc (25 mL). The organic extract was washed with brine (25 mL), dried with MgSO$_4$, filtered, and concentrated. The residue was purified by column chromatography (silica gel, eluting with 2% MeOH in CHCl$_3$) to give compound T124 (90 mg, 69% yield) as a yellow solid. m/z=471 (M+1); $^1$H NMR (400 MHz, CDCl$_3$) δ 8.61 (d, J=6.1 Hz, 2H), 8.58 (s, 1H), 7.59 (m, 4H), 7.46 (m, 2H), 7.38 (m, 1H), 7.32 (m, 2H), 7.12 (m, 2H), 2.84 (m, 1H), 2.73 (ddd, J=6.8, 11.3, 16.7 Hz, 1H), 2.62 (qd, J=6.7, 3.4 Hz, 1H), 2.20 (dt, J=2.3, 12.8 Hz, 1H), 2.13 (dd, J=7.0, 14.0 Hz, 1H), 1.83 (tdd, J=6.6, 12.6, 19.3 Hz, 1H), 1.58 (s, 3H), 1.34 (d, J=6.7 Hz, 3H).

Compound 214c: In a sealable vial, a mixture of compound 213 (0.32 g, 0.65 mmol), pyridine-3-boronic acid (0.16 g, 1.30 mmol) and potassium phosphate (0.41 g, 1.93 mmol) in 1,4-dioxane (4.8 mL) and DMF (1.2 mL) was degassed. Tetrakis(triphenylphosphine)palladium(0) (76 mg, 0.066 mmol) was added. The mixture was degassed again. The vial was sealed and heated at 90° C. for 16 h. The mixture was cooled to room temperature, diluted with EtOAc (50 mL), and washed with 1 N aq. NaOH (50 mL). The organic extract was washed with brine (50 mL), dried with MgSO$_4$, filtered, and concentrated. The residue was purified by column chromatography (silica gel, eluting with 50% EtOAc in hexanes) to give compound 214c (0.20 g, 62% yield) as a light yellow solid. m/z=492 (M+1).

Compound 215c: A solution of compound 214c (0.20 g, 0.41 mmol) and 3 N aq. HCl (1.4 mL, 4.2 mmol) in MeOH (10 mL) was stirred at room temperature under N$_2$ overnight. The mixture was concentrated. The residue was cooled and basified with 10% aq. NH$_4$OH (25 mL) to pH 9-10. The mixture was extracted with CHCl$_3$ (25 mL). The organic extract was washed with brine (25 mL), dried with MgSO$_4$, filtered, and concentrated to give compound 215c (0.18 g, 99% yield) as light yellow solid. m/z=448 (M+1).

Compound 216c: A solution of compound 215c (0.18 g, 0.40 mmol) in ethyl formate (10 mL, 124 mmol) was treated with sodium methoxide (30 wt. % in MeOH, 0.40 mL, 2.13 mmol). The mixture was stirred at room temperature under N₂ overnight and then concentrated. The residue was partitioned between EtOAc (50 mL) and sat. aq. KH₂PO₄ (50 mL). The organic extract was washed with brine (50 mL), dried with MgSO₄, filtered, and concentrated to give compound 216c (0.19 g, 99% yield) as a yellow solid. m/z=476 (M+1).

Compound 217c: A solution of compound 216c (0.19 g, 0.40 mmol), acetic acid (0.25 mL, 4.37 mmol), and hydroxylamine hydrochloride (43 mg, 0.62 mmol) in EtOH (10 mL) was stirred at 60° C. for 2 h and then at room temperature overnight. The mixture was concentrated. The residue was partitioned between sat. aq. NaHCO₃ (25 mL) and EtOAc (25 mL). The organic extract was washed with brine (25 mL), dried with MgSO₄, filtered, and concentrated to give compound 217c (0.29 g, quantitative yield) as a yellow oil. m/z=473 (M+1).

Compound 218c: A mixture of compound 217c (0.29 g, ≤0.40 mmol) and potassium carbonate (0.28 g, 2.03 mmol) in MeOH (10 mL) was stirred at room temperature under N₂ overnight. The mixture was concentrated. The residue was partitioned between sat. aq. KH₂PO₄ (25 mL) and EtOAc (25 mL). The organic extract was washed with brine (25 mL), dried with MgSO₄, filtered, and concentrated. The residue was purified by column chromatography (silica gel, eluting with 50% EtOAc in hexanes) to give compound 218c (0.14 g, 74% yield) as a light yellow solid. m/z=473 (M+1).

T125: To a stirring solution of compound 218c (0.14 g, 0.30 mmol) in degassed DMF (4 mL) at 0° C. under N₂ was added dropwise a solution of 1,3-dibromo-5,5-dimethylhydantoin (42 mg, 0.15 mmol) in degassed DMF (1 mL). The mixture was stirred at 0° C. for 30 min, and then pyridine (0.25 mL, 3.09 mmol) was added. The mixture was heated at 60° C. for 4 h and then concentrated. The residue was partitioned between sat aq. KH₂PO₄ (25 mL) and EtOAc (25 mL). The organic extract was washed with brine (25 mL), dried with MgSO₄, filtered, and concentrated. The residue was purified by column chromatography (silica gel, eluting with 2% MeOH in CHCl₃) to give compound T125 (95 mg, 68% yield) as a light yellow solid. m/z=471 (M+1): ¹H NMR (400 MHz, CDCl₃) δ 8.58 (m, 2H), 8.55 (dd, J=0.8, 2.3 Hz, 1H), 7.57 (m, 4H), 7.46 (m, 3H), 7.37 (m, 1H), 7.30 (m, 3H), 2.82 (ddd, J=1.4, 6.6, 16.4 Hz, 1H), 2.71 (m, 1H), 2.62 (qd, J=6.8, 13.4 Hz, 1H), 2.21 (dt, J=2.3, 12.8 Hz, 1H), 2.11 (m, 1H), 1.83 (tdd, J=6.6, 12.7, 19.4 Hz, 1H), 1.54 (s, 3H), 1.34 (d, J=6.8 Hz, 3H).

Compound 219: A solution of compound 148 (1.95 g, 5.71 mmol) in EtOH (25 mL) was treated with hydrazine monohydrate (0.69 mL, 14.22 mmol). The reaction mixture was heated at 60° C. for 22 h and then cooled to room temperature. The solvent was removed in vacuo and the residue was purified by column chromatography (silica gel, eluting with EtOAc) give compound 219 (1.34 g, 70% yield) as a glass. m/z=338 (M+1).

Compound 220: To a solution of compound 219 (500 mg, 1.48 mmol) in CH₂Cl₂ (50 mL) was added 4 Å molecular sieves (2.15 g), 3-biphenylboronic acid (586 mg, 2.96 mmol), copper(II)acetate (403 mg, 2.22 mmol), and pyridine (0.18 mL, 2.23 mmol). The reaction mixture was stirred at room temperature for 13 h and then concentrated. The residue was partitioned between EtOAc and sat. aq. KH₂PO₄. The organic extract was washed with brine, dried with Na₂SO₄: filtered and concentrated. The residue was purified by column chromatography (silica gel, eluting with 20% EtOAc in hexanes) to give compound 220 (503 mg, 69% yield) as a white glass. m/z=490 (M+1).

Compound 221: A mixture of compound 220 (500 mg, 1.02 mmol) in MeOH (15 mL) was treated with potassium carbonate (282 mg, 2.04 mmol). The mixture stirred at room temperature for 24 h and then concentrated. The residue was partitioned between EtOAc and sat. aq. KH₂PO₄. The organic extract was washed with brine, dried with Na₂SO₄, filtered, and concentrated. The residue was purified by column chromatography (silica gel, eluting with 40% EtOAc in hexanes) to give compound 221 (481 mg, 96% yield) as a clear glass. m/z=490 (M+1).

T126: A solution of compound 221 (480 mg, 0.980 mmol) in anhydrous DMF (6 mL) was cooled to 0° C. under nitrogen. A solution of 1,3-dibromo-5,5-dimethylhydantoin (154 mg, 0.539 mmol) in anhydrous DMF (3 mL) was added. The mixture was stirred at 0° C. for 1 h, and then anhydrous pyridine (0.79 mL, 9.77 mmol) was added. The mixture was heated at 60° C. for 4 h and then cooled to room temperature. The mixture was partitioned between EtOAc and sat. aq. KH₂PO₄. The organic layer was separated. The aqueous layer was extracted with EtOAc. The combined organic extracts were washed with brine, dried with Na₂SO₄, filtered, and concentrated. The residue was purified by column chromatography (silica gel, eluting with 30% EtOAc in hexanes) to give compound T126 (420 mg, 88% yield) as a light yellow solid. m/z=488 (M+1); ¹H NMR (400 MHz, CDCl₃) δ 8.60 (s, 1H), 7.42 (m, 9H), 7.20 (ddd, J=1.1, 2.2, 7.9 Hz, 1H), 7.05 (ddt, J=1.0, 2.6, 8.4 Hz, 1H), 6.96 (m, 2H), 2.80 (m, 1H), 2.65 (m, 2H), 2.20 (dt, J=2.3, 12.8 Hz, 1H), 2.10 (dd, J=7.0, 13.9 Hz, 1H), 1.82 (tdd, J=6.6, 12.8, 19.2 Hz, 1H), 1.56 (s, 3H), 1.33 (d, J=6.7 Hz 3H).

Compound 222: Compound 173 (1.73 g, 6.86 mmol) was taken up in benzene (50 mL). 3-Fluoroaniline (0.94 g, 8.46 mmol) and p-toluenesulfonic acid monohydrate (0.13 g, 0.68 mmol) were added. The mixture was refluxed for 4 days with Dean Stark trap for removal of water. After cooled to room temperature, the mixture was concentrated. The residue was purified by column chromatography (silica gel, eluting with 10% EtOAc in hexanes) to give compound 222 (1.53 g, 65% yield) as a brown oil. m/z=346 (M+1).

Compound 223a: Compound 222 (0.23 g, 0.67 mmol) was taken up in absolute EtOH (4 mL), and treated with 4-phenylbenzaldehyde (0.25 g, 1.37 mmol) and ammonium acetate (0.53 g, 6.87 mmol) sequentially. The mixture was stirred at 60° C. overnight, cooled to room temperature, and concentrated. The residue was triturated with EtOAc and filtered. The filter cake was washed with EtOAc. The combined filtrate and wash were concentrated. The residue was purified by column chromatography (silica gel, eluting with 40% EtOAc in hexanes) to give compound 223a (205 mg, 61% yield) as a yellow solid. m/z=509 (M+1).

Compound 224a: Compound 223a (0.205 g, 0.403 mmol) was taken up in THF (8 mL). 3 N aq. HCl (5 mL, 15 mmol) was added. The mixture was stirred at room temperature overnight, and then concentrated. The residue was neutralized by addition of sat. aq. NaHCO₃ to pH 7. The mixture was extracted with EtOAc. The organic extract was dried with MgSO₄, filtered, and concentrated to give compound 224a (0.195 g, quantitative yield) as a yellow solid. m/z=465 (M+1).

Compound 225a: Compound 224a (0.195 g, ≤0.403 mmol) was mixed with ethyl formate (12 mL, 149 mmol), and treated with sodium methoxide (30 wt. % in MeOH, 0.25 g, 1.39 mmol). The reaction mixture was stirred at room temperature overnight, and then treated with sat. aq. KH₂PO₄ to adjust pH to 5. The mixture was extracted with EtOAc. The organic extract was dried with MgSO₄, filtered, and concentrated to give compound 225a (0.14 g, 71% yield) as a beige solid. m/z=493 (M+1).

Compound 226a: A mixture of compound 225a (0.14 g, 0.28 mmol) in EtOH (10 mL) was treated with hydroxylamine hydrochloride (0.038 g, 0.55 mmol). The mixture was heated at 50° C. overnight, cooled to room temperature; and concentrated. The residue was diluted with EtOAc, and washed with sat. aq. NaHCO$_3$. The organic extract was dried with MgSO$_4$; filtered and concentrated. The residue was purified by column chromatography (silica gel, eluting with 40% EtOAc in hexanes) to give compound 226a (0.104 g, 75% yield) as a yellow viscous oil. m/z=490 (M+1).

Compound 227a: A mixture of compound 226a (0.104 g, 0.21 mmol) in MeOH (4 mL) was treated with potassium carbonate (0.117 g, 0.85 mmol). The mixture stirred at room temperature overnight and then concentrated. The residue was partitioned between EtOAc and sat. aq. KH$_2$PO$_4$. The organic extract was dried with MgSO$_4$, filtered, and concentrated to give compound 227a (0.091 g, 88% yield) as a yellow solid. m/z=490 (M+1).

T127: A solution of compound 227a (88 mg, 0.18 mmol) in anhydrous DMF (3 mL) was cooled to 0° C. under nitrogen. A solution of 1,3-dibromo-5,5-dimethylhydantoin (26 mg, 0.091 mmol) in anhydrous DMF (1 mL) was added. The mixture was stirred at 0° C. for 30 min, and then anhydrous pyridine (0.15 mL, 1.86 mmol) was added. The mixture was stirred at 50° C. for 4 h and at room temperature overnight. The mixture was concentrated. The residue was partitioned between EtOAc and sat. aq. KH$_2$PO$_4$. The organic extract was washed with water, dried with MgSO$_4$, filtered, and concentrated. The residue was purified by column chromatography (silica gel, eluting with 20% EtOAc in CH$_2$Cl$_2$) to give compound T127 (44 mg, 50% yield) as a yellow solid. m/z=488 (M+1); $^1$H NMR (400 MHz, CDCl$_3$) δ 8.69 (s, 1H), 7.56 (m, 2H), 7.50 (m, 2H), 7.42 (m, 5H), 7.35 (m, 1H), 7.17 (ddt, J=0.9, 2.6, 8.4 Hz, 1H), 7.01 (m, 2H), 2.57 (m, 3H), 2.15 (m, 2H), 1.83 (tt, J=9.1, 13.1 Hz, 1H), 1.53 (s, 3H), 1.31 (d, J=6.8 Hz, 3H).

Compound 223b: Compound 222 (0.278 g, 0.80 mmol) was taken up in absolute EtOH (4 mL), and treated with 3-phenylbenzaldehyde (0.29 g, 1.59 mmol) and ammonium acetate (0.61 g, 7.91 mmol) sequentially. The mixture was stirred at 50° C. overnight, cooled to room temperature, and concentrated. The residue was triturated with EtOAc and filtered. The filter cake was washed with EtOAc. The combined filtrate and wash were concentrated. The residue was purified by column chromatography (silica gel, eluting with 40% EtOAc in hexanes) to give compound 223b (283 mg, 69% yield) as a yellow solid. m/z=509 (M+1).

Compound 224b: Compound 223b (0.280 g, 0.55 mmol) was taken up in THF (10 mL). 3 N aq. HCl (6 mL, 18 mmol) was added. The mixture was stirred at room temperature overnight and then concentrated. The residue was neutralized by addition of sat. aq. NaHCO$_3$ to pH 7. The mixture was extracted with EtOAc. The organic extract was dried with MgSO$_4$, filtered, and concentrated to give compound 224b (0.262 g, quantitative yield) as a yellow solid. m/z=465 (M+1).

Compound 225b: Compound 224b (0.26 g, ≤0.55 mmol) was mixed with ethyl formate (15 mL, 186 mmol), and treated with sodium methoxide (30 wt. % in MeOH, 0.43 g, 2.39 mmol). The reaction mixture was stirred at room temperature overnight and then treated with sat. aq. KH$_2$PO$_4$ to adjust pH to 5. The mixture was extracted with EtOAc. The organic extract was dried with MgSO$_4$, filtered, and concentrated to give compound 225b (0.27 g. quantitative yield) as a beige solid. m/z=493 (M+1).

Compound 226b: A mixture of compound 225b (0.27 g, 0.55 mmol) in EtOH (20 mL) was treated with hydroxylamine hydrochloride (75 mg, 1.08 mmol). The mixture was heated at 50° C. overnight, cooled to room temperature, and concentrated. The residue was diluted with EtOAc and washed with sat. aq. NaHCO$_3$. The organic extract was dried with MgSO$_4$, filtered, and concentrated. The residue was purified by column chromatography (silica gel, eluting with 40% EtOAc in hexanes) to give compound 226b (0.151 g, 56% yield) as a yellow viscous oil. m/z=490 (M+1).

Compound 227b: A mixture of compound 226b (0.15 g, 0.31 mmol) in MeOH (10 mL) was treated with potassium carbonate (0.17 g, 1.23 mmol). The mixture stirred at room temperature overnight and then concentrated. The residue was partitioned between EtOAc and sat. aq. KH$_2$PO$_4$. The organic extract was dried with MgSO$_4$, filtered, and concentrated to give compound 227b (0.130 g, 87% yield) as a yellow solid. m/z=490 (M+1).

T128: A solution of compound 227b (0.13 g, 0.27 mmol) in anhydrous DMF (3 mL) was cooled to 0° C. under nitrogen. A solution of 1,3-dibromo-5,5-dimethylhydantoin (37 mg, 0.13 mmol) in anhydrous DMF (1 mL) was added. The mixture was stirred at 0° C. for 30 min, and then anhydrous pyridine (0.21 mL, 2.60 mmol) was added. The mixture was stirred at 50° C. for 4 h and at room temperature overnight. The mixture was concentrated. The residue was partitioned between EtOAc and sat. aq. KH$_2$PO$_4$. The organic extract was washed with water, dried with Na$_2$SO$_4$, filtered, and concentrated. The residue was purified by column chromatography (silica gel, eluting with 20% EtOAc in CH$_2$Cl$_2$) to give compound T128 (0.11 g, 85% yield) as a yellow solid. m/z=488 (M+1); $^1$H NMR (400 MHz, CDCl$_3$) δ 8.69 (s, 1H), 7.61 (m, 1H), 7.51 (td, J=1.9, 7.0, 1H), 7.44 (dt, J=6.1, 8.2 Hz, 1H), 7.40 (m, 4H), 7.32 (m, 3H), 7.19 (ddt, J=0.9, 2.5, 8.4 Hz, 1H), 7.03 (ddd, J=0.9, 2.1, 7.9 Hz, 1H), 6.99 (td, J=2.2, 9.1 Hz, 1H), 2.57 (m, 3H), 2.15 (m, 2H), 1.85 (m, 1H), 1.53 (s, 3H), 1.31 (d, J=6.8 Hz, 3H).

Compound 223c: Compound 223c (white solid, 263 mg, 69% yield) was synthesized from compound 222 (0.278 g, 0.80 mmol), 4-isopropylbenzaldehyde (0.24 g, 1.62 mmol), and ammonium acetate (0.61 g, 7.91 mmol) using the same procedure as described for the synthesis of compound 223b. The reaction was heated at 60° C. overnight. Compound 223c was purified by column chromatography (silica gel, eluting with 40% EtOAc in hexanes). m/z=475 (M+1)

Compound 224c: Compound 224c (yellow solid, 0.211 g, 89% yield) was synthesized from compound 223c (0.262 g, 0.55 mmol) and 3 N aq. HCl (6 mL, 18 mmol) using the same procedure as described for the synthesis of compound 224b. m/z=431 (M+1).

Compound 225c: Compound 225c (beige solid, 0.21 g, 94% yield) was synthesized from compound 224c (0.211 g, 0.49 mmol), ethyl formate (14 mL, 174 mmol), and sodium methoxide (30 wt. % in MeOH, 0.35 g, 1.94 mmol) using the same procedure as described for the synthesis of compound 225b. m/z=459 (M+1).

Compound 226c: Compound 226c (yellow viscous oil, 0.134 g, 64% yield) was synthesized from compound 225c (0.21 g, 0.46 mmol) and hydroxylamine hydrochloride (64 mg, 0.92 mmol) in EtOH (15 mL) using the same procedure as described for the synthesis of compound 226b. Compound 226c was purified by column chromatography (silica gel, eluting with 40% EtOAc in hexanes). m/z=456 (M+1).

Compound 227c: Compound 227c (yellow solid, 0.145 g, quantitative yield) was synthesized from compound 226c (0.134 g, 0.29 mmol) and potassium carbonate (0.162 g, 1.17 mmol) in MeOH (10 mL) using the same procedure as described for the synthesis of compound 227b. m/z=456 (M+1).

T129: A solution of compound 227c (0.14 g, 0.31 mmol) in anhydrous DMF (3 mL) was cooled to 0° C. under nitrogen. A solution of 1,3-dibromo-5,5-dimethylhydantoin (44 mg, 0.15 mmol) in anhydrous DMF (1 mL) was added. The mixture was stirred at 0° C. for 30 min, and then anhydrous pyridine (0.25 mL, 3.09 mmol) was added. The mixture was stirred at 50° C. for 4 h and at room temperature overnight. The mixture was concentrated. The residue was partitioned between EtOAc and sat. aq. $KH_2PO_4$. The organic extract was washed with water, dried with $Na_2SO_4$, filtered, and concentrated. The residue was purified by column chromatography (silica gel, eluting with 5% EtOAc in $CH_2Cl_2$) to give compound T129 (82 mg, 59% yield) as a white solid. m/z=454 (M+1); $^1$H NMR (400 MHz, $CDCl_3$) δ 8.67 (s, 1H), 7.41 (dt, J=6.1, 8.2 Hz, 1H), 7.25 (m, 2H), 7.15 (ddd, J=0.9, 2.6, 8.3 Hz, 1H), 7.11 (m, 2H), 6.99 (ddd, J=1.0, 2.1, 7.9 Hz, 1H), 6.94 (td, J=2.2, 9.0 Hz, 1H), 2.85 (hept, J=6.9 Hz, 1H), 2.59 (qd, J=6.8, 13.5 Hz, 1H), 2.51 (m, 2H), 2.15 (dt, J=2.3, 12.9 Hz, 1H), 2.08 (m, 1H), 1.82 (m, 1H), 1.51 (s, 3H), 1.30 (d, J=6.8 Hz, 3H), 1.20 (d, J=6.9 Hz, 6H).

Compound 223d: Compound 223d (colorless oil, 217 mg, 55% yield) was synthesized from compound 222 (0.31 g, 0.90 mmol), tetrahydro-2H-pyran-4-carbaldehyde (0.20 g, 1.75 mmol) and ammonium acetate (0.69 g, 8.95 mmol) in absolute EtOH (6 mL) using the same procedure as described for the synthesis of compound 223b. The reaction was heated at 60° C. overnight. Compound 223d was purified by column chromatography (silica gel, eluting with 5% MeOH in EtOAc). m/z=441 (M+1)

Compound 224d: Compound 224d (viscous oil, 0.167 g, 86% yield) was synthesized from compound 223d (0.215 g, 0.49 mmol) and 3 N aq. HCl (5 mL, 15 mmol) in THF (8 mL) using the same procedure as described for the synthesis of compound 224b. m/z=397 (M+1).

Compound 225d: Compound 225d (beige solid, 0.156 g, 88% yield) was synthesized from compound 224d (0.165 g, 0.42 mmol), ethyl formate (12 mL, 149 mmol), and sodium methoxide (30 wt. % in MeOH, 0.30 g, 1.67 mmol) using the same procedure as described for the synthesis of compound 225b. m/z=425 (M+1).

Compound 226d: Compound 226d (brown viscous oil, 0.168 g, quantitative yield) was synthesized from compound 225d (0.156 g, 0.37 mmol) and hydroxylamine hydrochloride (51 mg, 0.73 mmol) in EtOH (15 mL) using the same procedure as described for the synthesis of compound 226b. Compound 226d was purified by column chromatography (silica gel, eluting with 40% EtOAc in hexanes). m/z=422 (M+1).

Compound 227d: Compound 227d (brown solid, 0.151 g, 97% yield) was synthesized from compound 226d (0.165 g, <0.37 mmol) and potassium carbonate (0.20 g, 1.45 mmol) in MeOH (10 mL) using the same procedure as described for the synthesis of compound 227b. m/z=422 (M+1).

T130: A solution of compound 227d (0.148 g, 0.35 mmol) in anhydrous DMF (3 mL) was cooled to 0° C. under nitrogen. A solution of 1,3-dibromo-5,5-dimethylhydantoin (50 mg, 0.17 mmol) in anhydrous DMF (1 mL) was added. The mixture was stirred at 0° C. for 30 min, and then anhydrous pyridine (0.30 mL, 3.71 mmol) was added. The mixture was stirred at 50° C. for 4 h and at room temperature overnight. The mixture was concentrated. The residue was partitioned between EtOAc and sat. aq. $KH_2PO_4$. The organic extract was washed with water, dried with $Na_2SO_4$, filtered, and concentrated. The residue was purified by column chromatography (silica gel, eluting with 20% EtOAc in $CH_2Cl_2$) to give compound T130 (68 mg, 46% yield) as a beige solid. m/z=420 (M+1); $^1$H NMR (400 MHz, $CDCl_3$) δ 8.59 (s, 1H), 7.50 (dt, J=6.1, 8.2 Hz, 1H), 7.22 (ddt, J=0.9, 2.5, 8.4 Hz, 1H), 7.03 (dd, J=1.5, 7.8 Hz, 1H), 6.97 (td, J=2.4, 9.3 Hz, 1H), 3.98 (ddt, J=2.2, 4.4, 11.2 Hz, 2H), 3.32 (m, 2H), 2.73 (t, J=3.9, 11.5 Hz, 1H), 2.55 (qd, J=6.8, 13.5 Hz, 1H), 2.41 (ddd, J=6.3, 11.0, 17.1 Hz, 1H), 2.33 (ddd, J=1.4, 6.4, 16.3 Hz, 1H), 2.00 (m, 4H), 1.75 (m, 1H), 1.61 (m, 2H), 1.44 (s, 3H), 1.27 (d, J=6.8 Hz, 3H).

Compound 223e: Compound 223e (colorless oil, 105 mg, 23% yield) was synthesized from compound 222 (0.33 g, 0.96 mmol), 2-isopropylpyrimidine-5-carbaldehyde (0.25 g, 1.66 mmol), and ammonium acetate (0.73 g, 9.47 mmol) in absolute EtOH (10 mL) using the same procedure as described for the synthesis of compound 223b. The reaction was heated at 60° C. overnight. Compound 223e was purified by column chromatography (silica gel, eluting with EtOAc). m/z=477 (M+1)

Compound 224e: Compound 224e (yellow solid, 93 mg, 98% yield) was synthesized from compound 223e (0.105 g, 0.22 mmol) and 3 N aq. HCl (2.5 mL, 7.5 mmol) in THF (4 mL) using the same procedure as described for the synthesis of compound 224b. m/z=433 (M+1).

Compound 225e: Compound 225e (beige oil, 0.117 g, quantitative yield) was synthesized from compound 224e (93 mg, 0.22 mmol), ethyl formate (7 mL, 87 mmol), and sodium methoxide (30 wt. % in MeOH, 0.16 g, 0.89 mmol) using the same procedure as described for the synthesis of compound 225b. m/z=461 (M+1).

Compound 226e: Compound 226e (yellow solid, 64 mg, 64% yield) was synthesized from compound 225e (0.117 g, ≤0.22 mmol) and hydroxylamine hydrochloride (35 mg, 0.50 mmol) in EtOH (5 mL) using the same procedure as described for the synthesis of compound 226b. Compound 226e was purified by column chromatography (silica gel, eluting with EtOAc). m/z=458 (M+1).

Compound 227e: Compound 227e (yellow solid, 63 mg, quantitative yield) was synthesized from compound 226e (63 mg, 0.14 mmol) and potassium carbonate (76 mg, 0.55 mmol) in MeOH (4 mL) using the same procedure as described for the synthesis of compound 227b. m/z=458 (M+1).

T131: A solution of compound 227e (63 mg, 0.14 mmol) in anhydrous DMF (3 mL) was cooled to 0° C. under nitrogen. A solution of 1,3-dibromo-5,5-dimethylhydantoin (20 mg, 0.070 mmol) in anhydrous DMF (1 mL) was added. The mixture was stirred at 0° C. for 30 min, and then anhydrous pyridine (0.30 mL, 3.71 mmol) was added. The mixture was stirred at 50° C. for 4 h and at room temperature overnight. The mixture was concentrated. The residue was partitioned between EtOAc and sat. aq. $KH_2PO_4$. The organic extract was washed with water, dried with $Na_2SO_4$, filtered, and concentrated. The residue was purified by column chromatography (silica gel, eluting with 20% EtOAc in $CH_2Cl_2$) to give compound T131 (30 mg, 48% yield) as a beige solid. m/z=456 (M+1); $^1$H NMR (400 MHz, $CDCl_3$) δ 8.64 (s, 2H), 8.60 (s, 1H), 7.49 (dt, J=6.0, 8.2 Hz, 1H), 7.22 (ddt, J=1.0, 2.5, 8.3 Hz, 1H), 7.03 (ddd, J=0.9, 2.1, 7.8 Hz, 1H), 6.98 (td, J=2.2, 8.7 Hz, 1H), 3.19 (hept, J=6.9 Hz, 1H), 2.60 (qd, J=6.7, 13.5 Hz, 1H), 2.52 (m, 2H), 2.14 (m, 2H), 1.83 (m, 1H), 1.51 (s, 3H), 1.31 (d, J=6.9 Hz, 6H), 1.30 (d, J=6.8 Hz, 3H).

Compound 223f: Compound 223f (tan solid, 173 mg, 43% yield) was synthesized from compound 222 (0.289 g, 0.84 mmol), 4-dimethylaminobenzaldehyde (0.25 g, 1.68 mmol), and ammonium acetate (0.65 g, 8.43 mmol) in absolute EtOH (8 mL) using the same procedure as described for the synthesis of compound 223b. The reaction was heated at 60° C. overnight.

Compound 223f was purified by column chromatography (silica gel, eluting with EtOAc). m/z=476 (M+1)

Compound 224f: Compound 224f (tan solid, 0.165 g, quantitative yield) was synthesized from compound 223f (0.173 g, 0.36 mmol) and 3 N aq. HCl (5 mL, 15 mmol) in THF (8 mL) using the same procedure as described for the synthesis of compound 224b. m/z=432 (M+1).

Compound 225f: Compound 225f (beige solid, 0.177 g. quantitative yield) was synthesized from compound 224f (0.165 g, ≤0.36 mmol), ethyl formate (10 mL, 124 mmol), and sodium methoxide (30 wt. % in MeOH, 0.29 g, 1.61 mmol) using the same procedure as described for the synthesis of compound 225b. m/z=460 (M+1).

Compound 226f: Compound 226f (beige solid, 0.104 g, 63% yield) was synthesized from compound 225f (0.177 g, ≤0.36 mmol) and hydroxylamine hydrochloride (54 mg, 0.78 mmol) in EtOH (10 mL) using the same procedure as described for the synthesis of compound 226b.

Compound 226f was purified by column chromatography (silica gel, eluting with 50% EtOAc in $CH_2Cl_2$). m/z=457 (M+1).

Compound 227f: Compound 227f (beige solid, 96 mg, 92% yield) was synthesized from compound 226f (0.104 g, 0.23 mmol) and potassium carbonate (0.133 g, 0.96 mmol) in MeOH (10 mL) using the same procedure as described for the synthesis of compound 227b. m/z=457 (M+1).

T132: A solution of compound 227f (92 mg, 0.20 mmol) in anhydrous DMF (3 mL) was cooled to 0° C. under nitrogen. A solution of 1,3-dibromo-5,5-dimethylhydantoin (29 mg, 0.10 mmol) in anhydrous DMF (1 mL) was added. The mixture was stirred at 0° C. for 30 min, and then anhydrous pyridine (0.30 mL, 3.71 mmol) was added. The mixture was stirred at 50° C. for 4 h and at room temperature overnight. The mixture was concentrated. The residue was partitioned between EtOAc and sat. aq. $KH_2PO_4$. The organic extract was washed with water, dried with $Na_2SO_4$, filtered, and concentrated. The residue was purified by column chromatography (silica gel, eluting with 5% MeOH in EtOAc) to give compound T132 (16 mg, 17% yield) as a white solid. m/z=455 (M+1); $^1$H NMR (400 MHz, $CDCl_3$) δ 8.69 (s, 1H), 7.39 (dt, J=6.1, 8.2 Hz, 1H), 7.20 (m, 2H), 7.12 (ddt, J=0.9, 2.5, 8.4 Hz, 1H), 6.98 (ddd, J=0.9, 2.0, 7.9 Hz, 1H), 6.94 (td, J=2.3, 9.1 Hz, 1H), 6.56 (m, 2H), 2.94 (s, 6H), 2.57 (td, J=6.7, 13.4 Hz, 1H), 2.49 (m, 2H), 2.14 (dt, J=2.2, 12.8 Hz, 1H), 2.07 (m, 1H), 1.80 (m, 1H), 1.51 (s, 3H), 1.30 (d, J=6.8 Hz, 3H).

Compound 223g: A sealable vial was charged with compound 222 (0.40 g, 1.16 mmol) acetaldehyde (0.52 g, 11.80 mmol) and EtOH (5 mL). Ammonium acetate (1.79 g, 23.22 mmol) was added. The mixture was flushed with $N_2$. The vial was sealed and heated at 60° C. for 4 days and then concentrated. The residue was diluted with EtOAc (50 mL) and stirred at room temperature under $N_2$ for 1 h. The mixture was filtered through a pad of Celite®. The filtrate was concentrated. The residue was purified by column chromatography (silica gel, eluting with 10% MeOH in EtOAc) to give compound 223g (0.15 g, 35% yield) as a tan foamy solid. m/z=371 (M+1).

Compound 224g: A solution of compound 223g (0.15 g, 0.40 mmol) and 3 N aq. HCl (1.35 mL, 4.05 mmol) in MeOH (25 mL) was stirred at room temperature under $N_2$ overnight. The mixture was concentrated, and the residue was partitioned between 10% aq. $NH_4OH$ (25 mL) and $CHCl_3$ (25 mL). The organic extract was washed with brine (25 mL), dried with $MgSO_4$, filtered, and concentrated to give compound 224g (0.12 g, 91% yield) as a tan solid. m/z=327 (M+1).

Compound 225g: A solution of compound 224g (0.12 g, 0.37 mmol) in ethyl formate (10 mL, 124 mmol) was treated with sodium methoxide (30 wt. % in MeOH, 0.35 mL, 1.86 mmol). The mixture was stirred at room temperature overnight and then concentrated. The residue was partitioned between sat. aq. $KH_2PO_4$ (25 mL) and EtOAc (25 mL). The organic extract was washed with brine (25 mL), dried with $MgSO_4$, filtered, and concentrated to give compound 225g (0.12 g, 92% yield) as a dark yellow solid. m/z=355 (M+1).

Compound 226g: A solution of compound 225g (0.12 g, 0.34 mmol) and acetic acid (0.20 mL, 3.49 mmol) in EtOH (5 mL) was treated with hydroxylamine hydrochloride (35 mg, 0.50 mmol). The mixture was stirred at 60° C. under $N_2$ for 2 h then at room temperature overnight. The mixture was concentrated, and the residue was partitioned between sat. aq. $NaHCO_3$ (25 mL) and $CHCl_3$ (25 mL). The organic extract was washed with brine (25 mL), dried with $MgSO_4$, filtered, and concentrated to give compound 226g (0.10 g, 84% yield) as a yellow-orange solid. m/z=352 (M+1).

Compound 227g: A solution of compound 226g (0.10 g, 0.28 mmol) in MeOH (10 mL) was treated with potassium carbonate (0.20 g, 1.45 mmol). The mixture was stirred at room temperature under $N_2$ for 16 h and then concentrated. The residue was partitioned between sat. aq. $KH_2PO_4$ (25 mL) and $CHCl_3$ (25 mL). The organic extract was washed with brine (25 mL), dried with $MgSO_4$, filtered, and concentrated. The residue was purified by column chromatography (silica gel, eluting with 5% MeOH in $CHCl_3$) to give compound 227g (51 mg, 51% yield) as a light yellow solid. m/z=352 (M+1).

T133: Compound 227g (51 mg, 0.15 mmol) in degassed DMF (4 mL) was cooled to 0° C. under $N_2$. A solution of 1,3-dibromo-5,5-dimethylhydantoin (20 mg, 0.070 mmol) in degassed DMF (1 mL) was added. The mixture was stirred at 0° C. for 30 min, and then pyridine (0.12 mL, 1.48 mmol) was added. The mixture was heated at 60° C. for 4 h and then concentrated. The residue was partitioned between sat. aq. $KH_2PO_4$ (25 mL) and $CHCl_3$ (25 mL). The organic extract was washed with brine (25 mL), dried with $MgSO_4$, filtered, and concentrated. The residue was purified by column chromatography (silica gel, eluting with 75% EtOAc in hexanes) to give compound T133 (14 mg, 28% yield) as a light yellow solid. m/z=350 (M+1); $^1$H NMR (400 MHz, $CDCl_3$) δ 8.53 (s, 1H), 7.49 (dt, J=6.1, 8.2 Hz, 1H), 7.19 (ddt, J=0.9, 2.5, 8.4 Hz, 1H), 7.02 (ddd, J=0.9, 2.1, 7.9 Hz, 1H), 6.96 (td, J=22, 9.0 Hz, 1H), 2.46 (m, 3H), 2.28 (s, 3H), 2.07 (m, 2H), 1.76 (m, 1H), 1.44 (s, 3H), 1.28 (d, J=6.8 Hz, 3H).

Compound 223h: A sealable vial was charged with compound 222 (0.44 g, 1.27 mmol) benzaldehyde (0.27 g, 2.54 mmol) and EtOH (5 mL). Ammonium acetate (1.0 g, 13.0 mmol) was added. The mixture was flushed with $N_2$. The vial was sealed and heated at 60° C. for 48 h and then concentrated. The residue was diluted with EtOAc (50 mL) and stirred at room temperature under $N_2$ for 1 h. The mixture was filtered through a pad of Celite®. The filtrate was concentrated. The residue was purified by column chromatography (silica gel, eluting with 50% EtOAc in hexanes) to give compound 223h (0.44 g, 80% yield) as light yellow solid. m/z=433 (M+1).

Compound 224h: A solution of compound 223h (0.44 g, 1.02 mmol) and 3 N aq. HCl (3.4 mL, 10.2 mmol) in MeOH (25 mL) was stirred at room temperature under $N_2$ overnight.

The mixture was concentrated, and the residue was partitioned between 10% aq. NH$_4$OH (25 mL) and CHCl$_3$ (25 mL). The organic extract was washed with brine (25 mL), dried with MgSO$_4$, filtered, and concentrated to give compound 224h (0.46 g, quantitative yield) as a light yellow solid. m/z=389 (M+1).

Compound 225h: A solution of compound 224h (0.46 g, 1.02 mmol) in ethyl formate (10 mL, 124 mmol) was treated with sodium methoxide (30 wt. % in MeOH, 1.0 mL, 5.3 mmol, mmol). The mixture was stirred at room temperature overnight and then concentrated. The residue was partitioned between sat. aq. KH$_2$PO$_4$ (25 mL) and EtOAc (25 mL). The organic extract was washed with brine (25 mL), dried with MgSO$_4$, filtered, and concentrated to give compound 225h (0.42 g, 99% yield) as a yellow-orange solid. m/z=417 (M+1).

Compound 226h: A solution of compound 225h (0.41 g, 0.98 mmol) and acetic acid (0.60 mL, 10.48 mmol) in EtOH (5 mL) was treated with hydroxylamine hydrochloride (0.10 g, 1.44 mmol). The mixture was stirred at 60° C. under N$_2$ for 2 h then at room temperature overnight. The mixture was concentrated, and the residue was partitioned between sat. aq. NaHCO$_3$ (25 mL) and CHCl$_3$ (25 mL). The organic extract was washed with brine (25 mL), dried with MgSO$_4$, filtered, and concentrated to give compound 226h (0.42 g, quantitative yield) as a tan solid. m/z=414 (M+1).

Compound 227h: A solution of compound 226h (0.42 g, ≤0.98 mmol) in MeOH (20 mL) was treated with potassium carbonate (0.68 g, 4.93 mmol). The mixture was stirred at room temperature under N$_2$ for 16 h and then concentrated. The residue was partitioned between sat. aq. KH$_2$PO$_4$ (50 mL) and CHCl$_3$ (50 mL). The organic extract was washed with brine (50 mL), dried with MgSO$_4$, filtered, and concentrated. The residue was purified by column chromatography (silica gel, eluting with 50% EtOAc in hexanes) to give compound 227h (0.26 g, 64% yield) as a light yellow solid. m/z=414 (M+1).

T134: Compound 227h (0.26 g, 0.63 mmol) in degassed DMF (4 mL) was cooled to 0° C. under N$_2$. A solution of 1,3-dibromo-5,5-dimethylhydantoin (90 mg, 0.31 mmol) in degassed DMF (1 mL) was added. The mixture was stirred at 0° C. for 30 min, and then pyridine (0.51 mL, 6.31 mmol) was added. The mixture was heated at 60° C. for 4 h and then concentrated. The residue was partitioned between sat. aq. KH$_2$PO$_4$ (25 mL) and CHCl$_3$ (25 mL). The organic extract was washed with brine (25 mL), dried with MgSO$_4$, filtered, and concentrated. The residue was purified by column chromatography (silica gel, eluting with 50% EtOAc in hexanes) to give compound T134 (0.19 g, 73% yield) as a light yellow solid. m/z=412 (M+1); $^1$H NMR (400 MHz, CDCl$_3$) δ 8.67 (s, 1H), 7.40 (dt, J=6.1, 8.1 Hz, 1H), 7.34 (m, 2H), 7.27 (m, 3H), 7.14 (ddt, J=0.9, 2.5, 8.4 Hz, 1H), 6.97 (ddd, J=0.9, 2.0, 7.9 Hz, 1H), 6.93 (td, J=2.3, 9.0 Hz, 1H), 2.55 (m, 3H), 2.13 (m, 2H), 1.83 (m, 1H), 1.52 (s, 3H), 1.30 (d, J=6.8 Hz, 3H).

Compound 228: A mixture of compound 222 (0.66 g, 1.91 mmol) in absolute EtOH (10 mL) was treated with formaldehyde (37 wt. % in water, 0.32 g, 3.94 mmol) and ammonium acetate (1.47 g, 19.07 mmol) sequentially. The solution was stirred at 60° C. for overnight, cooled to room temperature, and concentrated. The residue was triturated with EtOAc and filtered. The filter cake was washed with EtOAc. The combined filtrate and wash were concentrated. The residue was purified by column chromatography (silica gel, eluting with 5% MeOH in EtOAc) to give compound 228 (546 mg, 80% yield) as a viscous oil. m/z=357 (M+1).

Compound 229: Compound 228 (545 mg, 1.53 mmol) was dissolved in acetonitrile (20 mL) and cooled to 0° C. A solution of N-bromosuccinimide (0.38 g, 2.14 mmol) in acetonitrile (5 mL) was added. The reaction mixture was gradually warmed to room temperature and stirred overnight. The mixture was concentrated, and the residue was partitioned between EtOAc and sat. aq. NaHCO$_3$. The organic extract was washed with brine, dried over Na$_2$SO$_4$, filtered, and concentrated. The residue was purified by column chromatography (silica gel, eluting with 40% EtOAc in hexanes) to give compound 229 (0.45 g, 68% yield) as a white solid. m/z=435/437 (M+1).

Compound 230a: A reaction vessel was charged with compound 229 (0.31 g, 0.71 mmol), 4-quinoline boronic acid (0.23 g, 1.33 mmol), potassium carbonate (0.29 g, 2.10 mmol), tetrakis(triphenylphosphine)palladium(0) (0.17 g, 0.15 mmol), dimethoxyethane (20 mL), and water (5 mL). The reaction mixture was purged with nitrogen for 10 min. The reaction vessel was sealed and heated at 90° C. overnight. After cooled to room temperature, the mixture was concentrated. The residue was partitioned between EtOAc and brine. The organic extract was dried with MgSO$_4$, filtered, and concentrated. The residue was purified by column chromatography (silica gel, eluting with 5% EtOH in CH$_2$Cl$_2$) to give compound 230a (0.32 g, 93% yield) as an off white solid. m/z=484 (M+1).

Compound 231a: Compound 230a (0.325 g, 0.67 mmol) was taken up in THF (15 mL). 3 N aq. HCl (9 mL, 27 mmol) was added. The mixture was stirred at room temperature overnight and then concentrated. The residue was neutralized by addition of sat. aq. NaHCO$_3$ to pH 7. The mixture was extracted with EtOAc. The organic extract was dried with MgSO$_4$, filtered, and concentrated to give compound 231a (0.283 g, 96% yield) as a yellow solid. m/z=440 (M+1).

Compound 232a: Compound 231a (0.28 g, 0.64 mmol) was mixed with ethyl formate (15 mL, 186 mmol) and treated with sodium methoxide (30 wt. % in MeOH, 0.46 g, 2.55 mmol). The reaction mixture was stirred at room temperature overnight and then treated with sat. aq. KH$_2$PO$_4$ to adjust pH to 5. The mixture was extracted with EtOAc. The organic extract was dried with MgSO$_4$, filtered, and concentrated to give compound 232a (0.277 g, 93% yield) as a beige solid. m/z=468 (M+1).

Compound 233a: A mixture of compound 232a (0.277 g, 0.59 mmol) in EtOH (20 mL) was treated with hydroxylamine hydrochloride (82 mg, 1.18 mmol). The mixture was heated at 50° C. overnight, cooled to room temperature, and concentrated. The residue was diluted with EtOAc and washed with sat. aq. NaHCO$_3$. The organic extract was dried with MgSO$_4$, filtered, and concentrated to give compound 233a (0.17 g, 62% yield) as a yellow solid. m/z=465 (M+1).

Compound 234a: A mixture of compound 233a (0.168 g, 0.36 mmol) in MeOH (10 mL) was treated with potassium carbonate (0.20 g, 1.45 mmol). The mixture stirred at room temperature overnight and then concentrated. The residue was partitioned between EtOAc and sat. aq. KH$_2$PO$_4$. The organic extract was dried with MgSO$_4$, filtered, and concentrated to give compound 234a (0.173 g, quantitative yield) as a brown solid. m/z=465 (M+1).

T135: A solution of compound 234a (0.17 g, 0.36 mmol) in anhydrous DMF (3 mL) was cooled to 0° C. under nitrogen. A solution of 1,3-dibromo-5,5-dimethylhydantoin (52 mg, 0.18 mmol) in anhydrous DMF (1 mL) was added. The mixture was stirred at 0° C. for 30 min, and then anhydrous pyridine (0.30 mL, 3.71 mmol) was added. The mixture was stirred at 50° C. for 4 h and at room temperature overnight. The mixture was concentrated. The residue was partitioned between EtOAc and sat. aq. $KH_2PO_4$. The organic extract was washed with water, dried with $Na_2SO_4$, filtered, and concentrated. The residue was purified by column chromatography (silica gel, eluting with 20% EtOAc in $CH_2Cl_2$) to give compound T135 (84 mg, 51% yield) as a light yellow solid. m/z=463 (M+1); $^1H$ NMR (400 MHz, $CDCl_3$) δ 8.74 (d, J=4.5 Hz, 1H), 8.64 (s, 1H), 8.31 (m, 1H), 8.13 (m, 1H), 7.77 (ddd, J=1.5, 6.9, 8.5 Hz, 1H), 7.63 (ddd, J=1.3, 6.9, 8.3 Hz, 1H), 7.28 (dt, J=5.9, 8.1 Hz, 1H), 7.06 (ddt, J=0.9, 2.5, 8.3 Hz, 1H), 7.00 (d, J=4.5 Hz, 1H), 6.85 (m, 2H), 2.65 (m, 3H), 2.25 (dt, J=2.2, 12.8 Hz, 1H), 2.17 (dtd, J=2.4, 5.1, 9.7 Hz, 1H), 1.89 (m, 1H), 1.59 (s, 3H), 1.34 (d, J=6.7 Hz, 3H).

Compound 230b: Compound 230b (off white solid, 0.217 g, 63% yield) was synthesized from compound 229 (0.31 g, 0.71 mmol), 5-quinoline boronic acid (0.23 g, 1.33 mmol), potassium carbonate (0.29 g, 2.10 mmol), tetrakis(triphenylphosphine)palladium(0) (0.17 g, 0.15 mmol) in dimethoxyethane (20 mL), and water (5 mL) using the same procedure as described for the synthesis of compound 230a. Compound 230b was purified by column chromatography (silica gel, eluting with 5% EtOH in $CH_2Cl_2$). m/z=484 (M+1).

Compound 231b: Compound 231b (white solid, 0.177 g, 91% yield) was synthesized from compound 230b (0.215 g, 0.44 mmol) and 3 N aq. HCl (5 mL, 15 mmol) in THF (8 mL) using the same procedure as described for the synthesis of compound 231a. m/z=440 (M+1).

Compound 232b: Compound 232b (beige solid, 0.186 g, quantitative yield) was synthesized from compound 231b (0.175 g, 0.40 mmol), ethyl formate (12 mL, 149 mmol), and sodium methoxide (30 wt. % in MeOH, 0.29 g, 1.61 mmol) using the same procedure as described for the synthesis of compound 232a. m/z=468 (M+1).

Compound 233b: Compound 233b (yellow solid, 0.17 g, 92% yield) was synthesized from compound 232b (0.186 g, 0.40 mmol) and hydroxylamine hydrochloride (55 mg, 0.79 mmol) in EtOH (15 mL) using the same procedure as described for the synthesis of compound 233a. m/z=465 (M+1).

Compound 234b: Compound 234b (brown solid, 0.120 g, 69% yield) was synthesized from compound 233b (0.173 g, 0.37 mmol) and potassium carbonate (0.20 g, 1.45 mmol) in MeOH (12 mL) using the same procedure as described for the synthesis of compound 234a. m/z=465 (M+1).

T136: A solution of compound 234b (0.12 g, 0.26 mmol) in anhydrous DMF (3 mL) was cooled to 0° C. under nitrogen. A solution of 1,3-dibromo-5,5-dimethylhydantoin (37 mg, 0.13 mmol) in anhydrous DMF (1 mL) was added. The mixture was stirred at 0° C. for 30 min, and then anhydrous pyridine (0.30 mL, 3.71 mmol) was added. The mixture was stirred at 50° C. for 4 h, and at room temperature overnight. The mixture was concentrated. The residue was partitioned between EtOAc and sat. aq. $KH_2PO_4$. The organic extract was washed with water; dried with $Na_2SO_4$, filtered, and concentrated. The residue was purified by column chromatography (silica gel, eluting with 20% EtOAc in $CH_2Cl_2$) to give compound T136 (65 mg, 54% yield) as a white solid. m/z=463 (M+1); $^1H$ NMR (400 MHz, $CDCl_3$) δ 8.95 (dd, J=1.7, 4.2 Hz, 1H), 8.64 (s, 1H), 8.58 (ddd, J=0.9, 1.8, 8.6 Hz, 1H), 8.09 (d, J=8.5 Hz, 1H), 7.53 (dd, J=7.2, 8.5 Hz, 1H), 7.48 (dd, J=4.2, 8.6 Hz, 1H), 7.24 (m, 2H), 7.02 (ddt, J=0.9, 2.5, 8.3 Hz, 1H), 6.81 (m, 2H), 2.64 (m, 3H), 2.25 (dt, J=2.2, 12.8 Hz, 1H), 2.17 (m, 1H), 1.89 (ddt, J=7.1, 10.3, 13.2 Hz, 1H), 1.58 (s, 3H), 1.34 (d, J=6.7 Hz, 3H).

Compound 230c: Compound 230c (white solid, 0.32 g, 93% yield) was synthesized from compound 229 (0.31 g, 0.71 mmol), 3-quinoline boronic acid (0.23 g, 1.33 mmol), potassium carbonate (0.29 g, 2.10 mmol), tetrakis(triphenylphosphine)palladium(0) (0.17 g, 0.15 mmol) in dimethoxyethane (20 mL), and water (5 mL) using the same procedure as described for the synthesis of compound 230a. Compound 230c was purified by column chromatography (silica gel, eluting with 5% EtOH in $CH_2Cl_3$). m/z=484 (M+1).

Compound 231c: Compound 231c (white solid, 0.278 g, 97% yield) was synthesized from compound 230c (0.316 g, 0.65 mmol) and 3 N aq. HCl (9 mL, 27 mmol) in THF (15 mL) using the same procedure as described for the synthesis of compound 231a. m/z=440 (M+1).

Compound 232c: Compound 232c (beige solid, 0.219 g, quantitative yield) was synthesized from compound 231c (0.19 g, 0.44 mmol), ethyl formate (13 mL, 161 mmol), and sodium methoxide (30 wt. % in MeOH, 0.32 g, 1.78 mmol) using the same procedure as described for the synthesis of compound 232a. m/z=468 (M+1).

Compound 233c: Compound 233c (white solid, 0.14 g, 69% yield) was synthesized from compound 232c (0.219 g, ≤0.44 mmol) and hydroxylamine hydrochloride (64 mg, 0.92 mmol) in EtOH (15 mL) using the same procedure as described for the synthesis of compound 233a. Compound 233c was purified by column chromatography (silica gel, eluting with 50% to 100% EtOAc in hexanes). m/z=465 (M+1).

Compound 234c: Compound 234c (yellow solid, 0.15 g, quantitative yield) was synthesized from compound 233c (0.14 g, 0.30 mmol) and potassium carbonate (0.17 g, 1.23 mmol) in MeOH (12 mL) using the same procedure as described for the synthesis of compound 234a. m/z=465 (M+1).

T137: A solution of compound 234c (0.15 g, ≤0.30 mmol) in anhydrous DMF (3 mL) was cooled to 0° C. under nitrogen. A solution of 1,3-dibromo-5,5-dimethylhydantoin (46 mg, 0.16 mmol) in anhydrous DMF (1 mL) was added. The mixture was stirred at 0° C. for 30 min, and then anhydrous pyridine (0.30 mL, 3.71 mmol) was added. The mixture was stirred at 50° C. for 4 h and at room temperature overnight. The mixture was concentrated. The residue was partitioned between EtOAc and sat. aq. $KH_2PO_4$. The organic extract was washed with water, dried with $Na_2SO_4$, filtered, and concentrated. The residue was purified by column chromatography (silica gel, eluting with 50% EtOAc in $CH_2Cl_2$) to give compound T137 (84 mg, 60% yield) as an off-white solid. m/z=463 (M+1), $^1H$ NMR (400 MHz, $CDCl_3$) δ 8.80 (d, J=2.2 Hz, 1H), 8.68 (s, 1H), 8.23 (dd, J=0.8, 2.3 Hz, 1H), 8.04 (dd, J=1.0, 8.3 Hz, 1H), 7.72 (m, 2H), 7.55 (ddd, J=1.2, 6.9, 8.2 Hz, 1H), 7.44 (dt, J=6.2, 8.3 Hz, 1H), 7.20 (ddt, J=1.0, 2.5, 8.3 Hz, 1H), 7.03 (m, 2H), 2.60 (m, 3H), 2.18 (m, 2H), 1.86 (tt, J=8.9, 13.3 Hz, 1H), 1.55 (s, 3H), 1.32 (d, J=6.8 Hz, 3H).

Compound 230d: Compound 230d (off white solid, 0.14 g, 64% yield) was synthesized from compound 229 (0.20 g, 0.46 mmol), 3-isopropylphenylboronic acid (98 mg, 0.60 mmol), potassium carbonate (0.20 g, 1.45 mmol), tetrakis (triphenylphosphine)palladium(0) (0.12 g, 0.10 mmol) in dimethoxyethane (20 mL), and water (5 mL) using the same procedure as described for the synthesis of compound 230a. Compound 230d was purified by column chromatography (silica gel, eluting with 40% EtOAc in hexanes). m/z=475 (M+1).

Compound 231d: Compound 231d (white solid, 0.126 g, quantitative yield) was synthesized from compound 230d (0.132 g, 0.28 mmol) and 3 N aq. HCl (3 mL, 9 mmol) in THF (5 mL) using the same procedure as described for the synthesis of compound 231a. m/z=431 (M+1).

Compound 232d: Compound 232d (yellow solid, 0.135 g, quantitative yield) was synthesized from compound 231d (0.126 g, ≤0.28 mmol), ethyl formate (8 mL, 99 mmol), and sodium methoxide (30 wt. % in MeOH, 0.21 g, 1.17 mmol) using the same procedure as described for the synthesis of compound 232a. m/z=459 (M+1).

Compound 233d: Compound 233d (white solid, 86 mg, 68% yield) was synthesized from compound 232d (0.135 g, ≤0.28 mmol) and hydroxylamine hydrochloride (41 mg, 0.59 mmol) in EtOH (5 mL) using the same procedure as described for the synthesis of compound 233a. Compound 233d was purified by column chromatography (silica gel, eluting with 20% EtOAc in $CH_2Cl_2$). m/z=456 (M+1).

Compound 234d: Compound 234d (white solid, 90 mg, quantitative yield) was synthesized from compound 233d (85 mg, 0.19 mmol) and potassium carbonate (0.103 g, 0.75 mmol) in MeOH (5 mL) using the same procedure as described for the synthesis of compound 234a. m/z=456 (M+1).

T138: A solution of compound 234d (89 mg, 0.20 mmol) in anhydrous DMF (3 mL) was cooled to 0° C. under nitrogen. A solution of 1,3-dibromo-5,5-dimethylhydantoin (28 mg, 0.098 mmol) in anhydrous DMF (1 mL) was added. The mixture was stirred at 0° C. for 30 min, and then anhydrous pyridine (0.25 mL, 3.09 mmol) was added. The mixture was stirred at 50° C. for 4 h and at room temperature overnight. The mixture was concentrated. The residue was partitioned between EtOAc and sat. aq. $KH_2PO_4$. The organic extract was washed with water, dried with $Na_2SO_4$, filtered, and concentrated. The residue was purified by column chromatography (silica gel, eluting with 5% EtOAc in $CH_2Cl_2$) to give compound T138 (48 mg, 54% yield) as an off-white solid. m/z=454 (M+1): $^1$H NMR (400 MHz, $CDCl_3$) δ 8.69 (s, 1H), 7.40 (dt, J=6.1, 8.2 Hz, 1H), 7.16 (m, 5H), 6.98 (ddd, J=1.0, 2.0, 7.9 Hz, 1H), 6.93 (td, J=2.3, 9.0 Hz, 1H), 2.78 (hept, J=6.9 Hz, 1H), 2.56 (m, 3H), 2.13 (m, 2H), 1.82 (m, 1H), 1.52 (s, 3H), 1.31 (d, J=6.8 Hz, 3H), 1.08 (d, J=6.9 Hz, 6H).

Compound 230e: Compound 230e (beige solid, 0.25 g, 68% yield) was synthesized from compound 229 (0.31 g, 0.71 mmol), 2-morpholinopyridine 4-boronic acid (0.19 g, 0.91 mmol), potassium carbonate (0.29 g, 2.10 mmol), tetrakis(triphenylphosphine)palladium(0) (0.17 g, 0.15 mmol) in dimethoxyethane (20 mL), and water (5 mL) using the same procedure as described for the synthesis of compound 230a. Compound 230e was purified by column chromatography (silica gel, eluting with 5% EtOH in $CH_2Cl_2$). m/z=519 (M+1).

Compound 231e: Compound 231e (yellow solid, 0.245 g, quantitative yield) was synthesized from compound 230e (0.25 g, 0.48 mmol) and 3 N aq. HCl (5 mL, 15 mmol) in THF (8 mL) using the same procedure as described for the synthesis of compound 231a. m/z=475 (M+1).

Compound 232e: Compound 232e (yellow solid, 0.25 g, quantitative yield) was synthesized from compound 231e (0.242 g, 0.48 mmol), ethyl formate (15 mL, 186 mmol), and sodium methoxide (30 wt. % in MeOH, 0.40 g, 2.22 mmol) using the same procedure as described for the synthesis of compound 232a. m/z=503 (M+1).

Compound 233e: Compound 233e (white solid, 0.167 g, 69% yield) was synthesized from compound 232e (0.25 g, ≤50.48 mmol) and hydroxylamine hydrochloride (69 mg, 0.99 mmol) in EtOH (15 mL) using the same procedure as described for the synthesis of compound 233a. Compound 233e was purified by column chromatography (silica gel, eluting with EtOAc). m/z=500 (M+1).

Compound 234e: Compound 234e (white solid, 0.164 g, 98% yield) was synthesized from compound 233e (0.167 g, 0.33 mmol) and potassium carbonate (0.184 g, 1.33 mmol) in MeOH (15 mL) using the same procedure as described for the synthesis of compound 234a. m/z=500 (M+1).

T139: A solution of compound 234e (0.162 g, 0.32 mmol) in anhydrous DMF (3 mL) was cooled to 0° C. under nitrogen. A solution of 1,3-dibromo-5,5-dimethylhydantoin (46 mg, 0.16 mmol) in anhydrous DMF (1 mL) was added. The mixture was stirred at 0° C. for 30 min, and then anhydrous pyridine (0.25 mL, 3.09 mmol) was added. The mixture was stirred at 50° C. for 4 h and at room temperature overnight. The mixture was concentrated. The residue was partitioned between EtOAc and sat. aq. $KH_2PO_4$. The organic extract was washed with water, dried with $Na_2SO_4$, filtered, and concentrated. The residue was purified by column chromatography (silica gel, eluting with 50% EtOAc in $CH_2Cl_2$) to give compound T139 (80 mg, 50% yield) as a white solid. m/z=498 (M+1): $^1$H NMR (400 MHz, $CDCl_3$) δ 8.65 (s, 1H), 8.01 (dd, J=0.6, 5.2 Hz, 1H), 7.46 (dt, J=6.1, 8.2 Hz, 1H), 7.20 (ddt, J=0.9, 2.5, 8.4 Hz, 1H), 7.01 (m, 1H), 6.97 (td, J=2.2, 8.8 Hz, 1H), 6.80 (s, 1H), 6.36 (dd, J=1.3, 5.3 Hz, 1H), 3.79 (m, 4H), 3.45 (m, 4H), 2.54 (m, 3H), 2.12 (m, 2H), 1.83 (m, 1H), 1.51 (s, 3H), 1.30 (d, J=6.8 Hz, 3H).

Compound 235: A sealable vial was charged with compound 229 (0.41 g, 0.94 mmol), potassium benzyltrifluoroborate (0.28 g, 1.41 mmol), cesium carbonate (0.92 g, 2.83 mmol), THF (9 mL) and water (1 mL). The mixture was degassed. [1,1'-bis(diphenylphosphino)-ferrocene]dichloropalladium(II) (69 mg, 0.094 mmol) was added. The mixture was degassed again. The vial was sealed and heated at 80° C. overnight. After cooled to room temperature, the mixture was diluted with EtOAc (50 mL) and stirred for 30 min. The mixture was filtered through a pad of Celite®. The filtrate was washed with sat. aq. $KH_2PO_4$ and brine. The organic extract was dried with $MgSO_4$, filtered, and concentrated. The residue was purified by column chromatography (silica gel, eluting with 75% EtOAc in hexanes) to give compound 235 (83 mg, 20% yield) as a yellow solid. m/z=447 (M+1).

Compound 236: A solution of compound 235 (83 mg, 0.19 mmol) and 3 N aq. HCl (0.62 mL, 1.86 mmol) in MeOH (10 mL) was stirred at room temperature under $N_2$ overnight. The mixture was concentrated, and the residue was partitioned between 10% aq. $NH_4OH$ (25 mL) and $CHCl_3$ (25 mL). The organic extract was washed with brine (25 mL), dried with $MgSO_4$, filtered, and concentrated to give compound 236 (94 mg, quantitative yield) as a yellow solid. m/z=403 (M+1).

Compound 237: A solution of compound 236 (94 mg, ≤0.19 mmol) in ethyl formate (10 mL, 124 mmol) was treated with sodium methoxide (30 wt. % in MeOH, 0.17 mL, 0.91 mmol). The mixture was stirred at room temperature overnight and then concentrated. The residue was partitioned between sat. aq. $KH_2PO_4$ (25 mL) and EtOAc (25 mL). The organic extract was washed with brine (25 mL), dried with $MgSO_4$, filtered, and concentrated to give compound 237 (95 mg, quantitative yield) as a yellow solid. m/z=431 (M+1).

Compound 238: A solution of compound 237 (95 mg, ≤0.19 mmol) and acetic acid (0.11 mL, 1.92 mmol) in EtOH (5 mL) was treated with hydroxylamine hydrochloride (19 mg, 0.27 mmol). The mixture was stirred at 60° C. under $N_2$ for 2 h then at room temperature overnight. The mixture was concentrated, and the residue was partitioned between sat. aq. NaHCO$_3$ (25 mL) and CHCl$_3$ (25 mL). The organic extract was washed with brine (25 mL), dried with MgSO$_4$, filtered, and concentrated to give compound 238 (85 mg, quantitative yield) as yellow solid. m/z=428 (M+1).

Compound 239: A solution of compound 238 (85 mg, ≤0.19 mmol) in MeOH (10 mL) was treated with potassium carbonate (0.14 g, 1.01 mmol). The mixture was stirred at room temperature under N$_2$ for 16 h and then concentrated. The residue was partitioned between sat. aq. KH$_2$PO$_4$ (25 mL) and CHCl$_3$ (25 mL). The organic extract was washed with brine (25 mL), dried with MgSO$_4$, filtered, and concentrated to give compound 239 (70 mg, 88% yield) as a dark yellow solid. m/z=428 (M+1).

T140: Compound 239 (70 mg, 0.16 mmol) in degassed DMF (4 mL) was cooled to 0° C. under N$_2$. A solution of 1,3-dibromo-5,5-dimethylhydantoin (23 mg, 0.080 mmol) in degassed DMF (1 mL) was added. The mixture was stirred at 0° C. for 30 min, and then pyridine (0.13 mL, 1.61 mmol) was added. The mixture was heated at 60° C. for 4 h and then concentrated. The residue was partitioned between sat. aq. KH$_2$PO$_4$ (25 mL) and CHCl$_3$ (25 mL). The organic extract was washed with brine (25 mL), dried with MgSO$_4$, filtered, and concentrated. The residue was purified by column chromatography (silica gel, eluting with 50% EtOAc in hexanes) to give compound T140 (21 mg, 30% yield) as a light yellow solid. m/z=426 (M+1); $^1$H NMR (400 MHz, CDCl$_3$) δ 8.60 (s, 1H), 7.36 (dt, J=6.1, 8.2 Hz, 1H), 7.16 (m, 4H), 6.94 (m, 2H), 6.81 (m, 1H), 6.72 (td, J=2.3, 9.0 Hz, 1H), 3.96 (s, 2H), 2.56 (qd, J=6.8, 13.5 Hz, 1H), 2.41 (ddd, J=6.4, 11.0, 17.2 Hz, 1H), 2.34 (m, 1H), 2.12 (dt, J=2.2, 12.8 Hz, 1H), 2.02 (m, 1H), 1.74 (tdd, J=6.5, 13.0, 19.1 Hz, 1H), 1.48 (s, 3H), 1.28 (d, J=6.8 Hz, 3H).

Compound 240a: A thick wall glass vessel was charged with compound 229 (200 mg, 0.459 mmol), 4-(4,4,5,5-tetramethyl-1,3,2-dioxaborolan-2-yl)-2-(trifluoromethyl)pyridine (188 mg, 0.688 mmol), tetrakis (triphenylphosphine)palladium(0) (53 mg, 0.046 mmol), potassium phosphate tribasic (292 mg, 1.38 mmol), 1,4-dioxane (6 mL), and water (2 mL). The mixture was purged with N$_2$. The reaction vessel was sealed and heated at 110° C. for 22 h. After cooled to room temperature, the mixture was diluted with EtOAc, and filtered through a plug of Celite®. The filtrate was washed with sat. aq. KH$_2$PO$_4$ and brine. The organic extract was dried with Na$_2$SO$_4$, filtered, and concentrated. The residue was purified by column chromatography (silica gel, eluting with 40% EtOAc in hexanes) to give compound 240a (211 mg, 92% yield) as a white glass. m/z=502 (M+1).

Compound 241a: A solution of compound 240a (210 mg, 0.418 mmol) in THF (25 mL) was treated with 3.0 N aq. HCl (1.39 mL, 4.17 mmol). The reaction mixture was stirred at room temperature for 23 h and then concentrated. The residue was partitioned between EtOAc and sat. aq. NaHCO$_3$. The organic extract was washed with brine, dried with Na$_2$SO$_4$, filtered, and concentrated to give compound 241a (187 mg, 98% yield) as a white glass and was used in the next step without further purification. m/z=458 (M+1).

Compound 242a: Compound 241a (185 mg, 0.404 mmol) in ethyl formate (25 mL, 311 mmol) was cooled to 0° C. Sodium methoxide (5.4 M in MeOH, 0.75 mL, 4.05 mmol) was added. The mixture was stirred at room temperature for 2.5 h and then concentrated. The residue was partitioned between EtOAc and sat. aq. KH$_2$PO$_4$. The organic extract was washed with brine, dried with Na$_2$SO$_4$, filtered, and concentrated. The product obtained was dissolved in EtOH (16 mL). 6.0 N aq. HCl (0.67 mL, 4.02 mmol) and hydroxylamine hydrochloride (42 mg, 0.604 mmol) were added. The reaction mixture was heated at 55° C. for 19 h and then concentrated. The residue was partitioned between EtOAc and sat. aq. NaHCO$_3$. The organic extract was washed with brine, dried with Na$_2$SO$_4$, filtered, and concentrated to give compound 242a (184 mg, 94% yield) as a yellow glass, which was used in the next step without further purification. m/z=483 (M+1).

Compound 243a: A solution of compound 242a (183 mg, 0.379 mmol) in MeOH (10 mL) was treated with potassium carbonate (105 mg, 0.758 mmol). The reaction mixture was stirred at room temperature for 17 h and then heated at 55° C. for 2 h. The solvent was removed in vacuo and the residue was partitioned between EtOAc and sat. aq. KH$_2$PO$_4$. The organic extract was washed with brine, dried with Na$_2$SO$_4$, filtered, and concentrated. The residue was purified by column chromatography (silica gel, eluting with 60% EtOAc in hexanes) to give compound 243a (136 mg, 74% yield) as a yellow glass. m/z=483 (M+1).

T141: Compound 243a (135 mg, 0.279 mmol) in anhydrous DMF (4 mL) was cooled to 0° C. under N$_2$. A solution of 1,3-dibromo-5,5-dimethylhydantoin (44 mg, 0.15 mmol) in anhydrous DMF (1 mL) was added. The mixture was stirred at 0° C. for 1 h, and then pyridine (0.23 mL, 2.84 mmol) was added. The mixture was heated at 60° C. for 4 h. After cooled to room temperature, the mixture was diluted with EtOAc and washed with sat. aq. KH$_2$PO$_4$. The organic layer was separated. The aqueous layer was extracted with EtOAc. The combined organic extracts were washed with water and brine, dried with Na$_2$SO$_4$, filtered, and concentrated. The residue was purified by column chromatography (silica gel, eluting with 50% EtOAc in hexanes) to give compound T141 (94 mg, 70% yield) as a yellow solid. m/z=481 (M+1): $^1$H NMR (400 MHz, CDCl$_3$) δ 8.60 (s, 1H), 8.57 (d, J=5.1 Hz, 1H), 7.74 (m, 1H), 7.53 (dt, J=6.0, 8.2 Hz, 1H), 7.30 (m, 2H), 7.02 (m, 2H), 2.60 (qd, J=6.8, 13.6 Hz, 1H), 2.53 (dd. J=3.9, 8.7 Hz, 2H), 2.14 (m, 2H), 1.83 (tt, J=9.1, 13.5 Hz, 1H), 1.51 (s, 3H), 1.31 (d, J=6.8 Hz, 3H).

Compound 240b: A thick wall glass vessel was charged with compound 229 (200 mg, 0.459 mmol), (6-cyclopropylpyridin-3-yl)boronic acid (112 mg, 0.687 mmol), tetrakis (triphenylphosphine)palladium(0)(53 mg, 0.046 mmol), potassium phosphate tribasic (292 mg, 1.38 mmol), 1,4-dioxane (6 mL), and water (2 mL). The mixture was purged with N$_2$. The reaction vessel was sealed and heated at 110° C. for 23 h. After cooled to room temperature, the mixture was diluted with EtOAc and washed with sat. aq. KH$_2$PO$_4$ and brine. The organic extract was dried with Na$_2$SO$_4$, filtered, and concentrated. The residue was purified by column chromatography (silica gel, eluting with EtOAc) to give compound 240b (93 mg, 43% yield) as a yellow solid. m/z=474 (M+1).

Compound 241b: A solution of compound 240b (93 mg, 0.196 mmol) in THF (10 mL) was treated with 3.0 N aq. HCl (0.65 mL, 1.95 mmol). The reaction mixture was stirred at room temperature for 18 h and then concentrated. The residue was partitioned between EtOAc and sat. aq. NaHCO$_3$. The organic extract was washed with brine, dried with Na$_2$SO$_4$, filtered, and concentrated to give compound 241b (88 mg, quantitative yield) as a yellow glass, which was used in the next step without further purification. m/z=430 (M+1).

Compound 242b: Compound 241b (88 mg, ≤0.196 mmol) in ethyl formate (10 mL, 124 mmol) was cooled to 0° C. Sodium methoxide (5.4 M in MeOH, 0.38 mL, 2.05 mmol) was added. The mixture was stirred at room temperature for 2.5 h and then concentrated. The residue was partitioned between EtOAc and sat. aq. KH$_2$PO$_4$. The organic extract was washed with brine, dried with Na$_2$SO$_4$, filtered, and concentrated. The product obtained was dissolved in EtOH (10 mL). 6.0 N aq. HCl (0.34 mL, 2.04 mmol) and hydroxylamine hydrochloride (21 mg, 0.302 mmol) were added. The reaction mixture was heated at 60° C. for 21 h and then concentrated. The residue was partitioned between EtOAc and sat. aq. NaHCO$_3$. The organic extract was washed with brine, dried with Na$_2$SO$_4$, filtered, and concentrated to give compound 242b (90 mg, quantitative yield) as a yellow glass and was used in the next step without further purification. m/z=455 (M+1).

Compound 243b: A solution of compound 242b (90 mg, ≤0.196 mmol) in MeOH (10 mL) was treated with potassium carbonate (55 mg, 0.40 mmol). The reaction mixture was stirred at room temperature for 16 h and then heated at 50° C. for 4.5 h. The solvent was removed in vacuo and the residue was partitioned between EtOAc and sat. aq. KH$_2$PO$_4$. The organic extract was washed with brine, dried with Na$_2$SO$_4$, filtered, and concentrated. The residue was purified by column chromatography (silica gel, eluting with 60% EtOAc in hexanes) to give compound 243b (58 mg, 65% yield) as a yellow glass. m/z=455 (M+1).

T142: Compound 243b (57 mg, 0.125 mmol) in anhydrous DMF (3 mL) was cooled to 0° C. under N$_2$. A solution of 1,3-dibromo-5,5-dimethylhydantoin (19.6 mg, 0.069 mmol) in anhydrous DMF (1 mL) was added. The mixture was stirred at 0° C. for 1 h, and then pyridine (0.10 mL, 1.24 mmol) was added. The mixture was heated at 60° C. for 4 h. After cooled to room temperature, the mixture was diluted with EtOAc and washed with sat. aq. KH$_2$PO$_4$. The organic layer was separated. The aqueous layer was extracted with EtOAc. The combined organic extracts were washed with water and brine, dried with Na$_2$SO$_4$, filtered, and concentrated. The residue was purified by column chromatography (silica gel, eluting with EtOAc) to give compound T142 (45 mg, 79% yield) as a yellow solid. m/z=453 (M+1); $^1$H NMR (400 MHz, CDCl$_3$) δ 8.62 (s, 1H), 8.27 (dd, J=0.8, 2.3 Hz, 1H), 7.64 (ddd, J=0.7, 2.3, 8.2 Hz, 1H), 7.43 (dt, J=6.0, 8.1 Hz, 1H), 7.17 (ddt, J=0.9, 2.5, 8.4 Hz, 1H), 7.07 (td, J=0.7, 8.1 Hz, 1H), 6.98 (ddd, J=0.9, 2.1, 7.9 Hz, 1H), 6.94 (td, J=2.2, 8.9 Hz, 1H), 2.59 (qd, J=6.8, 13.5 Hz, 1H), 2.51 (m, 2H), 2.13 (m, 2H), 1.99 (m, 1H), 1.81 (m, 1H), 1.51 (s, 3H), 1.30 (d, J=6.8 Hz, 3H), 0.99 (m, 4H).

Compound 240c: A thick wall glass vessel was charged with compound 229 (183 mg, 0.420 mmol), (3-morpholinophenyl)boronic acid (131 mg, 0.633 mmol), potassium phosphate tribasic (268 mg, 1.26 mmol), tetrakis(triphenylphosphine)palladium(0) (48.5 mg, 0.042 mmol), 1,4-dioxane (3 mL), and water (1 mL). The mixture was purged with N$_2$. The reaction vessel was sealed and heated at 110° C. for 17 h. After cooled to room temperature, the mixture was diluted with EtOAc, and the product precipitated. The mixture was filtered through a plug of Celite® and washed with EtOAc. The filtrate and EtOAc wash were discarded. The filter cake was washed thoroughly with CH$_2$Cl$_2$. The CH$_2$Cl$_2$ filtrate was dried with Na$_2$SO$_4$, filtered, and concentrated to give compound 240c (151 mg, 69% yield) as a white solid and was used in the next step without further purification. m/z=518 (M+1).

Compound 241c: A solution of compound 240c (151 mg, 0.292 mmol) in THF (20 mL) was treated with 3.0 N aq. HCl (0.97 mL, 2.91 mmol). The reaction mixture was stirred at room temperature for 24 h and then concentrated. The residue was partitioned between CH$_2$Cl$_2$ and sat. aq. NaHCO$_3$. The organic extract was washed with brine, dried with Na$_2$SO$_4$, filtered, and concentrated to give compound 241c (121 mg, 87% yield) as an off-white solid and was used in the next step without further purification. m/z=474 (M+1).

Compound 242c: Compound 241c (120 mg, 0.253 mmol) in ethyl formate (15 mL, 186 mmol) was cooled to ° C. Sodium methoxide (5.4 M in MeOH, 0.47 mL, 2.54 mmol) was added. The mixture was stirred at room temperature for 2 h and then concentrated. The residue was partitioned between EtOAc and sat. aq. KH$_2$PO$_4$. The organic extract was washed with brine, dried with Na$_2$SO$_4$, filtered, and concentrated. The product obtained was dissolved in EtOH (15 mL). 6.0 N aq. HCl (0.42 mL, 2.52 mmol) and hydroxylamine hydrochloride (26 mg, 0.37 mmol) were added. The reaction mixture was heated at 60° C. for 3 h and then concentrated. The residue was partitioned between EtOAc and sat. aq. NaHCO$_3$. The organic extract was washed with brine, dried with Na$_2$SO$_4$, filtered, and concentrated to give compound 242c (126 mg, quantitative yield) as a glass, which was used in the next step without further purification. m/z=499 (M+1).

Compound 243c: A solution of compound 242c (125 mg, 0.251 mmol) in MeOH (15 mL) was treated with potassium carbonate (69 mg, 0.50 mmol). The reaction mixture was heated at 50° C. for 5 h. The solvent was removed in vacuo and the residue was partitioned between EtOAc and sat. aq. KH$_2$PO$_4$. The organic extract was washed with brine, dried with Na$_2$SO$_4$, filtered, and concentrated. The residue was purified by column chromatography (silica gel, eluting with EtOAc) to give compound 243c (84 mg, 67% yield) as an off-white solid. m/z=499 (M+1).

T143: A solution of compound 243c (83 mg, 0.17 mmol) in anhydrous toluene (15 mL) under nitrogen was treated with DDQ (49 mg, 0.22 mmol). The reaction mixture was stirred at room temperature for 2 h and then concentrated. The residue was purified by column chromatography (silica gel, eluting with EtOAc). The product obtained was dissolved in EtOAc and washed with sat. aq. NaHCO$_3$. The organic extract was dried with Na$_2$SO$_4$, filtered, and concentrated to give compound T143 (30 mg, 36% yield) as an orange solid. m/z=497 (M+1); $^1$H NMR (400 MHz, CDCl$_3$) δ 8.68 (s, 1H), 7.40 (dt, J=6.1, 8.2 Hz, 1H), 7.13 (m, 2H), 6.98 (m, 2H), 6.94 (td, J=2.2, 9.0 Hz, 1H), 6.82 (dd, J=2.6, 8.4 Hz, 1H), 6.73 (td, J=1.2, 7.7 Hz, 1H), 3.82 (m, 4H), 3.05 (m, 4H), 2.55 (m, 3H), 2.14 (m, 2H), 1.82 (tt, J=8.3, 13.2 Hz, 1H), 1.52 (s, 3H), 1.30 (d, J=6.8 Hz, 3H).

Compound 240d: A thick wall glass vessel was charged with compound 229 (170 mg, 0.390 mmol), 2-(cyclopropylpyridin-4-yl)boronic acid (95 mg, 0.58 mmol) tetrakis(triphenylphosphine)palladium(0)(45 mg, 0.039 mmol), potassium phosphate tribasic (248 mg, 1.17 mmol), 1,4-dioxane (3 mL), and water (1 mL). The mixture was purged with N$_2$. The reaction vessel was sealed and heated at 110° C. for 19 h. After cooled to room temperature, the mixture was diluted with EtOAc and washed with brine. The organic extract was dried with Na$_2$SO$_4$, filtered, and concentrated. The residue was purified by column chromatography (silica gel, eluting with EtOAc) to give compound 240d (79 mg, 43% yield) as an off-white solid. m/z=474 (M+1).

Compound 241d: A solution of compound 240d (114 mg, 0.241 mmol) in THF (20 mL) was treated with 3.0 N aq. HCl (0.80 mL, 2.40 mmol). The reaction mixture was stirred at room temperature for 23 h and then concentrated. The residue was partitioned between EtOAc and sat. aq. NaHCO$_3$. The organic extract was washed with brine, dried with Na$_2$SO$_4$, filtered, and concentrated to give compound 241d (121 mg, quantitative yield) as a yellow glass and was used in the next step without further purification. m/z=430 (M+1).

Compound 242d: Compound 241d (120 mg, ≤0.241 mmol) in ethyl formate (15 mL, 186 mmol) was cooled to 0° C. Sodium methoxide (5.4 M in MeOH, 0.52 mL, 2.81 mmol) was added. The mixture was stirred at room temperature for 26 h and then concentrated. The residue was partitioned between EtOAc and sat. aq. $KH_2PO_4$. The organic extract was washed with brine, dried with $Na_2SO_4$, filtered, and concentrated. The product obtained was dissolved in EtOH (15 mL). 6.0 N aq. HCl (0.47 mL, 2.82 mmol) and hydroxylamine hydrochloride (29 mg, 0.42 mmol) were added. The reaction mixture was heated at 60° C. for 16 h and then concentrated. The residue was partitioned between EtOAc and sat. aq. $NaHCO_3$. The organic extract was washed with brine, dried with $Na_2SO_4$, filtered, and concentrated to give compound 242d (152 mg, quantitative yield) as a brown viscous oil, which was used in the next step without further purification. m/z=455 (M+1).

Compound 243d: A solution of compound 242d (150 mg, <0.241 mmol) in MeOH (20 mL) was treated with potassium carbonate (91 mg, 0.66 mmol). The reaction mixture was stirred at room temperature for 14 h and then heated at 50° C. for 5.5 h. The solvent was removed in vacuo and the residue was partitioned between EtOAc and sat. aq. $KH_2PO_4$. The organic extract was washed with brine, dried with $Na_2SO_4$, filtered, and concentrated. The residue was purified by column chromatography (silica gel, eluting with EtOAc) to give compound 243d (50 mg, 46% yield) as a yellow glass. m/z=455 (M+1).

T144: Compound 243d (50 mg, 0.11 mmol) in anhydrous DMF (3 mL) was cooled to 0° C. under $N_2$. A solution of 1,3-dibromo-5,5-dimethylhydantoin (17 mg, 0.059 mmol) in anhydrous DMF (1 mL) was added. The mixture was stirred at 0° C. for 1 h, and then pyridine (0.09 mL, 1.11 mmol) was added. The mixture was heated at 60° C. for 4 h. After cooled to room temperature, the mixture was diluted with EtOAc and washed with sat. aq. $KH_2PO_4$. The organic layer was separated. The aqueous layer was extracted with EtOAc. The combined organic extracts were washed with water and brine, dried with $Na_2SO_4$, filtered, and concentrated. The residue was purified by column chromatography (silica gel, eluting with EtOAc) to give compound T144 (34 mg, 68% yield) as a yellow solid. m/z=453 (M+1); $^1$H NMR (400 MHz, $CDCl_3$) δ 8.64 (s, 1H), 8.27 (d, J=5.2 Hz, 1H), 7.47 (dt, J=6.0, 8.1 Hz, 1H), 7.24 (m, 1H), 7.20 (m, 1H), 6.98 (m, 2H), 6.81 (dd, J=1.7, 5.2 Hz, 1H), 2.59 (qd, J=6.8, 13.5 Hz, 1H), 2.52 (m, 2H), 2.13 (m, 2H), 1.96 (m, 1H), 1.82 (tt, J=8.8, 13.3 Hz, 1H), 1.51 (s, 3H), 1.31 (d, J=6.8 Hz, 3H), 0.93 (m, 4H).

Compound 244: To a mixture of compound 222 (1.665 g, 4.82 mmol) in EtOH (33 mL) was added ammonium acetate (3.716 g, 48.20 mmol) and 3-bromobenzaldehyde (1.784 g, 9.64 mmol) at room temperature. The mixture was stirred under $N_2$ at room temperature for 60 h and then at refluxed for 24 h. After cooled to room temperature, the mixture was concentrated. The residue was diluted with EtOAc (60 mL) and washed with sat. aq. $NaHCO_3$ (2×30 mL) and water (30 mL). The organic extract was dried with $Na_2SO_4$, filtered, and concentrated. The residue was purified by column chromatography (silica gel, eluting with 0% to 40% EtOAc in hexanes) to give compound 244 (1.815 g, 74% yield) as a yellow solid. m/z=511/513 (M+1).

Compound 245: A solution of compound 244 (1.815 g, 3.55 mmol) in THF (90 mL) was treated with 3 N aq. HCl (11.5 mL, 34.5 mmol). The mixture was stirred at room temperature under $N_2$ for 20 h and then concentrated. The residue was cooled to 0° C. 1 N aq. NaOH (35 mL, 35 mmol) and sat. aq. $NaHCO_3$ (30 mL) were added sequentially. The organic layer was separated. The aqueous layer was extracted with $CH_2C_2$ (2×30 mL). The combined organic extracts were dried with $Na_2SO_4$, filtered, and concentrated. The residue was purified by column chromatography (silica gel, eluting with 0% to 40% EtOAc in hexanes) to give compound 245 (1.538 g, 93% yield) as red solid. m/z=467/469 (M+1).

Compound 246: A solution of compound 245 (300 mg, 0.64 mmol) in ethyl formate (1.6 mL, 19.89 mmol) was treated with sodium methoxide (25 wt. % in MeOH, 1.47 mL, 6.42 mmol). The mixture was stirred at room temperature for 1 h, and then cooled to 0° C. 6 N aq. HCl (1.07 mL, 6.42 mmol), EtOH (6.5 mL) and hydroxylamine hydrochloride (67 mg, 0.96 mmol) were added sequentially. The mixture was stirred at 55° C. for 16 h and then concentrated. The residue was diluted with EtOAc (50 mL) and sashed with water (2×20 mL). The organic extract was dried with $Na_2SO_4$, filtered, and concentrated. The residue was purified by column chromatography (silica gel, eluting with 0% to 40% EtOAc in hexanes) to give compound 246 (170 mg, 54% yield) as a light brown solid. m/z=492/494 (M+1).

Compound 247: To a solution of compound 246 (170 mg, 0.35 mmol) in MeOH (3.5 mL) was added sodium methoxide (25 wt. % in MeOH, 0.158 mL, 0.69 mmol). The mixture was heated under $N_2$ at 55° C. for 3 h and then cooled to room temperature. 10% aq. $NaH_2PO_4$ (10 mL) was added. The mixture was extracted with EtOAc (2×20 mL). The combined organic extracts were dried with $Na_2SO_4$, filtered, and concentrated. The residue was purified by column chromatography (silica gel, eluting with 0% to 50% EtOAc in hexanes) to give compound 247 (158 mg, 93% yield) as a white solid. m/z=492/494 (M+1).

T145: Compound 247 (80 mg, 0.16 mmol) and 1,3-dibromo-5,5-dimethylhydantoin (23 mg, 0.081 mmol) were weighed in a flask and cooled to 0° C. under $N_2$. DMF (1.6 mL) was added. The mixture was stirred at 0° C. for 1 h. Pyridine (39 μL, 0.49 mmol) was added. The mixture was heated at 55° C. for 4 h and then cooled to room temperature. The mixture was diluted with EtOAc (20 mL) and washed with water (3×15 mL). The organic extract was dried with $Na_2SO_4$, filtered, and concentrated. The residue was purified by column chromatography (silica gel, eluting with 0% to 80% EtOAc in hexanes) to give compound T145 (19 mg, 24% yield) as a light yellow solid. m/z=490/492 (M+1); $^1$H NMR (400 MHz, $CDCl_3$) δ 8.63 (s, 1H), 7.63 (t, J=1.8 Hz, 1H), 7.42 (m, 2H), 7.18 (ddt, J=0.9, 2.6, 8.4 Hz, 1H), 7.14 (td, J=1.4, 7.8 Hz, 1H), 7.08 (t, J=7.8 Hz, 1H), 6.97 (ddd, J=0.9, 2.0, 7.9 Hz, 1H), 6.94 (td, J=2.2, 8.8 Hz, 1H), 2.55 (m, 3H), 2.13 (m, 2H), 1.82 (tt, J=9.2, 13.1 Hz, 1H), 1.51 (s, 3H), 1.30 (d, J=6.8 Hz, 3H).

Compound 248a: Compound 247 (74.6 mg, 0.152 mmol), pyridin-4-ylboronic acid (27.9 mg, 0.227 mmol), $K_3PO_4$ (96.5 mg, 0.455 mmol), and tetrakis(triphenylphosphine)palladium(0) (8.8 mg, 0.0076 mmol) were weighed in a microwave vial. A mixture of 1,4-dioxane (1 mL) and DMF (0.5 mL) were sparged with $N_2$ for 5 min and added. The mixture was sparged with $N_2$ for another 5 min and then heated in a Biotage microwave synthesizer at 90° C. for 4 h. After cooled to room temperature, the mixture was partitioned between EtOAc (20 mL) and 10% $NaH_2PO_4$ (10 mL). The organic layer was separated. The aqueous layer was extracted with EtOAc (2×10 mL). The combined organic extracts were dried with $Na_2SO_4$, filtered, and concentrated. The residue was purified by column chromatography (silica gel, eluting with 0% to 100% acetone in hexanes) to give compound 248a (59 mg, 79% yield) as an off-white solid. m/z=491 (M+1).

T146: Compound 248a (56 mg, 0.11 mmol) and 1,3-dibromo-5,5-dimethylhydantoin (16 mg, 0.056 mmol) were weighed in a flask and cooled to 0° C. under $N_2$. DMF (1.1 mL) was added. The mixture was stirred at 0° C. for 1 h. Pyridine (28 µL, 0.35 mmol) was added. The mixture was heated at 55° C. for 4 h and then cooled to room temperature. The mixture was diluted with EtOAc (20 mL) and washed with water (3×15 mL). The organic extract was dried with $Na_2SO_4$; filtered and concentrated. The residue was purified by column chromatography (silica gel, eluting with 0% to 80% acetone in hexanes) to give compound T146 (43 mg, 77% yield) as a light yellow solid. m/z=489 (M+1); $^1$H NMR (400 MHz, $CDCl_3$) δ 8.67 (s, 1H), 8.64 (m, 2H), 7.69 (m, 1H), 7.55 (m, 1H), 7.47 (dt, J=6.1, 8.2 Hz, 1H), 7.37 (m, 2H), 7.34 (m, 2H), 7.21 (ddt, J=0.9, 2.5, 8.3 Hz, 1H), 7.04 (m, 1H), 6.99 (td, J=2.2, 8.9 Hz, 1H), 2.58 (m, 3H), 2.16 (m, 2H), 1.84 (tt. J=9.0, 13.2 Hz, 1H), 1.53 (s, 3H), 1.31 (d, J=6.8 Hz, 3H).

Compound 248b: Compound 247 (85 mg, 0.17 mmol), pyrimidin-5-ylboronic acid (32 mg, 0.26 mmol), $K_3PO_4$ (110 mg, 0.52 mmol), and tetrakis(triphenylphosphine)palladium(0) (10 mg, 0.0086 mmol) were weighed in a microwave vial. A mixture of 1,4-dioxane (1 mL) and DMF (0.5 mL) were sparged with $N_2$ for 5 min and added. The mixture was sparged with $N_2$ for another 5 min and then heated in a Biotage microwave synthesizer at 90° C. for 3 h. After cooled to room temperature, the mixture was partitioned between EtOAc (20 mL) and 10% $NaH_2PO_4$ (10 mL). The organic layer was separated. The aqueous layer was extracted with EtOAc (2×10 mL). The combined organic extracts were dried with $Na_2SO_4$, filtered, and concentrated. The residue was purified by column chromatography (silica gel, eluting with 0% to 100% acetone in hexanes) to give compound 248b (73 mg, 86% yield) as an off-white solid. m/z=492 (M+1).

T147: A solution of compound 248b (70 mg, 0.14 mmol) in DMF (2 mL) was cooled to 0° C. A solution of 1,3-dibromo-5,5-dimethylhydantoin (20 mg, 0.071 mmol) in DMF (1 mL) was added. The mixture was stirred at 0° C. for 2 h. Pyridine (34 µL, 0.43 mmol) was added. The mixture was heated at 55° C. overnight and then cooled to room temperature. The mixture was diluted with EtOAc and washed with water. The organic extract was dried with $Na_2SO_4$, filtered, and concentrated. The residue was purified by column chromatography (silica gel, eluting with 0% to 50% EtOAc in hexanes) to give partially purified product and was purified again by column chromatography (silica gel, eluting with 0% to 30% acetone in $CH_2Cl_2$) to give compound T147 (25 mg, 36% yield) as a pale pink solid. m/z=490 (M+1); $^1$H NMR (400 MHz, $CDCl_3$) δ 9.20 (s, 1H), 8.76 (s, 2H), 8.65 (s, 1H), 7.57 (m, 1H), 7.46 (m, 4H), 7.22 (m, 1H), 7.05 (m, 1H), 6.98 (td, J=2.3, 9.0 Hz, 1H), 2.57 (m, 3H), 2.15 (m, 2H), 1.85 (m, 1H), 1.53 (s, 3H), 1.31 (d, J=6.7 Hz, 3H).

Compound 248c: Compound 248c (off-white solid, 75 mg, 85% yield) was synthesized from compound 247 (85 mg, 0.17 mmol), (5-fluoropyridin-3-yl)boronic acid (36 mg, 0.26 mmol), $K_3PO_4$ (110 mg, 0.52 mmol), and tetrakis(triphenylphosphine)palladium(0) (10 mg, 0.0086 mmol) using the same procedure as described for the synthesis of compound 248b. Compound 248c was purified by column chromatography (silica gel, eluting with 0% to 100% acetone in hexanes). m/z=509 (M+1).

T148: A solution of compound 248c (75 mg, 0.15 mmol) in DMF (2 mL) was cooled to 0° C. A solution of 1,3-dibromo-5,5-dimethylhydantoin (21 mg, 0.074 mmol) in DMF (1 mL) was added. The mixture was stirred at 0° C. for 2 h. Pyridine (35 µL, 0.44 mmol) was added. The mixture was heated at 55° C. overnight and then cooled to room temperature. The mixture was diluted with EtOAc and washed with water. The organic extract was dried with $Na_2SO_4$, filtered, and concentrated. The residue was purified by column chromatography (silica gel, eluting with 0% to 50% acetone in $CH_2Cl_2$) to give compound T148 (30 mg, 40% yield) as a pale pink solid. m/z=507 (M+1). $^1$H NMR (400 MHz, $CDCl_3$) δ 8.66 (s, 1H), 8.44 (m, 2H), 7.57 (m, 1H), 7.44 (m, 5H), 7.22 (ddt, J=0.9, 2.5, 8.4 Hz, 1H), 7.05 (ddd, J=0.9, 2.0, 7.9 Hz, 1H), 6.98 (td, J=2.3, 8.8 Hz, 1H), 2.58 (m, 3H), 2.15 (m, 2H), 1.84 (m, 1H), 1.53 (s, 3H), 1.31 (d, J=6.7 Hz, 3H).

Compound 248d: Compound 248d (off-white solid, 46 mg, 54% yield) was synthesized from compound 247 (85 mg, 0.17 mmol), (1-methyl-1H-pyrazol-4-yl)boronic acid (33 mg, 0.26 mmol). $K_3PO_4$ (110 mg, 0.52 mmol), and tetrakis(triphenylphosphine)palladium(0) (10 mg, 0.0086 mmol) using the same procedure as described for the synthesis of compound 248b. Compound 248d was purified by column chromatography (silica gel, eluting with 0% to 50% acetone in $CH_2Cl_2$). m/z=494 (M+1).

T149: A solution of compound 248d (46 mg, 0.093 mmol) in DMF (2 mL) was cooled to 0° C. A solution of 1,3-dibromo-5,5-dimethylhydantoin (13 mg, 0.047 mmol) in DMF (1 mL) was added. The mixture was stirred at 0° C. for 2 h. Pyridine (22 mg, 0.28 mmol) was added. The mixture was heated at 55° C. overnight and then cooled to room temperature. The mixture was diluted with EtOAc and washed with water. The organic extract was dried with $Na_2SO_4$, filtered, and concentrated. The residue was purified by column chromatography (silica gel, eluting with 0% to 50% acetone in $CH_2Cl_2$) to give compound T149 (18 mg, 39% yield) as an off-white solid. m/z=492 (M+1); $^1$H NMR (400 MHz, $CDCl_3$) δ 8.70 (s, 1H), 7.54 (m, 3H), 7.40 (m, 2H), 7.22 (t, J=7.8 Hz, 1H), 7.17 (ddt, J=0.9, 2.6, 8.3 Hz, 1H), 7.11 (m, 1H), 7.01 (ddd, J=1.0, 2.0, 7.9 Hz, 1H), 6.97 (td, J=2.3, 8.9 Hz, 1H), 3.93 (s, 3H), 2.56 (m, 3H), 2.14 (m, 2H), 1.83 (m, 1H), 1.53 (s, 3H), 1.31 (d, J=6.8 Hz, 3H).

Compound 248e: Compound 248e (off-white solid, 60 mg, 77% yield) was synthesized from compound 247 (75 mg, 0.15 mmol), (3,5-dimethylisoxazol-4-yl)boronic acid (32 mg, 0.23 mmol), $K_3PO_4$ (97 mg, 0.46 mmol), and tetrakis(triphenylphosphine)palladium(0) (8.8 mg, 0.0076 mmol) using the same procedure as described for the synthesis of compound 248a. The reaction mixture was heated in Biotage microwave synthesizer at 90° C. for 3 h. Compound 248e was purified by column chromatography (silica gel, eluting with 0% to 50% acetone in $CH_2Cl_2$). m/z=509 (M+1).

T150: A solution of compound 248e (60 mg, 0.12 mmol) in DMF (2 mL) was cooled to 0° C. A solution of 1,3-dibromo-5,5-dimethylhydantoin (17 mg, 0.059 mmol) in DMF (1 mL) was added. The mixture was stirred at 0° C. for 2 h. Pyridine (28 mg, 0.35 mmol) was added. The mixture was heated at 55° C. overnight and then cooled to room temperature. The mixture was diluted with EtOAc and washed with water. The organic extract was dried with $Na_2SO_4$, filtered, and concentrated. The residue was purified by column chromatography (silica gel, eluting with 0% to 50% acetone in $CH_2Cl_2$) to give compound T150 (27 mg, 45% yield) as an off-white solid. m/z=507 (M+1); $^1$H NMR (400 MHz, $CDCl_3$) δ 8.64 (s, 1H), 7.53 (ddd, J=1.2, 1.8, 7.9

Hz, 1H), 7.42 (m, 2H), 7.17 (m, 2H), 7.10 (t, J=0.6, 1.8 Hz, 1H), 7.04 (ddd, J=0.9.2.0, 7.9 Hz, 1H), 6.96 (td, J=2.3, 8.9 Hz, 1H), 2.55 (m, 3H), 2.20 (s, 3H), 2.12 (m, 2H), 2.04 (s, 3H), 1.83 (m, 1H), 1.52 (s, 3H), 1.31 (d, J=6.8 Hz, 3H).

Compound 248f: Compound 248f (off-white solid, 51 mg, 60% yield) was synthesized from compound 247 (85 mg, 0.17 mmol), (1-methyl-1H-pyrazol-5-yl)boronic acid (33 mg, 0.26 mmol), $K_3PO_4$ (110 mg, 0.52 mmol), and tetrakis (triphenylphosphine)palladium(0) (10 mg, 0.0086 mmol) using the same procedure as described for the synthesis of compound 248b. Compound 248f was purified by column chromatography (silica gel, eluting with 0% to 50% acetone in $CH_2Cl_2$). m/z=494 (M+1).

T151: A solution of compound 248f (51 mg, 0.10 mmol) in DMF (2 mL) was cooled to 0° C. A solution of 1,3-dibromo-5,5-dimethylhydantoin (15 mg, 0.052 mmol) in DMF (1 mL) was added. The mixture was stirred at 0° C. for 2 h. Pyridine (25 mg, 0.31 mmol) was added. The mixture was heated at 55° C. overnight and then cooled to room temperature. The mixture was diluted with EtOAc and washed with water. The organic extract was dried with $Na_2SO_4$, filtered, and concentrated. The residue was purified by column chromatography (silica gel, eluting with 0% to 50% acetone in $CH_2Cl_2$) to give compound T151 (34 mg, 67% yield) as an off-white solid. m/z=492 (M+1); $^1H$ NMR (400 MHz, $CDCl_3$) δ 8.64 (s, 1H), 7.47 (m, 3H), 7.39 (dd, J=7.7, 8.2 Hz, 1H), 7.33 (m, 2H), 7.18 (ddt, J=0.9, 2.5, 8.4 Hz, 1H), 7.03 (ddd, J=0.9, 2.1, 7.9 Hz, 1H), 6.97 (td, J=2.3, 8.8 Hz, 1H), 6.14 (d, J=1.9 Hz, 1H), 3.68 (s, 3H), 2.56 (m, 3H), 2.11 (m, 2H), 1.84 (m, 1H), 1.52 (s, 3H), 1.31 (d, J=6.8 Hz, 3H).

Compound 249: A mixture of compound 173 (0.33 g, 1.31 mmol), 3-aminopyridine (0.18 g, 1.91 mmol) and a catalytic amount of p-toluenesulfonic acid monohydrate in benzene was refluxed overnight with Dean Stark trap for removal of water. The mixture was cooled to room temperature and partitioned between EtOAc (50 mL) and sat. aq. $KH_2PO_4$ (50 mL). The organic extract was washed with sat. aq. $NaHCO_3$ (50 mL) and sat. aq. NaCl (50 mL), dried with $MgSO_4$, filtered, and concentrated. The residue was purified by column chromatography (silica gel, eluting with 50% to 100% EtOAc in hexanes) to give compound 249 (0.14 g, 33% yield) as a yellow solid. m/z=329 (M+1).

Compound 250: A thick wall glass vessel was charged with compound 249 (600 mg, 1.82 mmol) and EtOH (22 mL). Ammonium acetate (1.44 g, 18.68 mmol) and 37% aq. formalin solution (0.74 mL, 9.10 mmol) were added. The vessel was sealed, and the reaction mixture was heated at 60° C. for 17 h. After cooled to room temperature, the mixture was concentrated. The residue was diluted with EtOAc and washed with sat. aq. $NaHCO_3$. The organic extract was dried with $Na_2SO_4$, filtered, and concentrated. The residue was purified by column chromatography (silica gel, eluting with 8% MeOH in EtOAc) to give compound 250 (529 mg, 86% yield) as an off-white solid. m/z 340 (M+1).

Compound 251: To a solution of compound 250 (528 mg, 1.56 mmol) in anhydrous acetonitrile (25 mL) at 0° C. under nitrogen was added N-bromosuccinimide (333 mg, 1.87 mmol). The reaction mixture was kept at 0° C. for 1 h and then allowed to warm up to room temperature. After 2.5 h, the reaction mixture was concentrated. The residue was purified by column chromatography (silica gel, eluting with EtOAc) to give compound 251 (669 mg, quantitative yield) as a tan solid. m/z=418/420 (M+1).

Compound 252a: A thick wall glass vessel was charged with compound 251 (250 mg, 0.597 mmol), 4-biphenylboronic acid (177 mg, 0.894 mmol), tetrakis(triphenylphosphine)-palladium(0) (69 mg, 0.060 mmol), potassium phosphate tribasic (380 mg, 1.79 mmol), 1,4-dioxane (6 mL), and water (2 mL). The vessel was purged with $N_2$ and then sealed. The reaction mixture was heated at 110° C. for 21 h. After cooled to room temperature, the reaction mixture was diluted with EtOAc and filtered through a plug of Celite®. The filtrate was washed with sat. aq. $KH_2PO_4$ and brine. The organic extract was dried with $Na_2SO_4$, filtered, and concentrated. The residue was purified by column chromatography (silica gel, eluting with 60% EtOAc in hexanes) to give compound 252a (208 mg, 71% yield) as a white solid. m/z=492 (M+1).

Compound 253a: A solution of compound 252a (205 mg, 0.416 mmol) in THF (15 mL) was treated with 3.0 N aq. HCl (1.38 mL, 4.14 mmol). The reaction mixture was stirred at room temperature for 26 h and then concentrated. The residue was partitioned between EtOAc and sat. aq. $NaHCO_3$. The organic extract was washed with brine, dried with $Na_2SO_4$, filtered, and concentrated to give compound 253a (178 mg, 96% yield) as a white solid and was used in the next step without further purification. m/z=448 (M+1).

Compound 254a: Compound 253a (178 mg, 0.398 mmol) in ethyl formate (24 mL, 298 mmol) was cooled to 0° C. Sodium methoxide (5.4 M in MeOH, 0.74 mL, 4.00 mmol) was added. The mixture was stirred at room temperature for 3 h and then concentrated. The residue was partitioned between EtOAc and sat. aq. $KH_2PO_4$. The organic extract was washed with brine, dried with $Na_2SO_4$, filtered, and concentrated. The product obtained was dissolved in EtOH (15 mL). 6.0 N aq. HCl (0.66 mL, 3.96 mmol) and hydroxylamine hydrochloride (41 mg, 0.59 mmol) were added. The reaction mixture was heated at 60° C. for 20 h and then concentrated. The residue was partitioned between EtOAc and sat. aq. $NaHCO_3$. The organic extract was washed with brine, dried with $Na_2SO_4$, filtered, and concentrated to give compound 254a (191 mg, quantitative) as a glass and was used in the next step without further purification. m/z=473 (M+1).

Compound 255a: A solution of 254a (190 mg, <0.398 mmol) in MeOH (10 mL) was treated with potassium carbonate (111 mg, 0.804 mmol). The reaction mixture was stirred at room temperature for 16 h and then heated at 55° C. for 2 h. The solvent was removed in vacuo and the residue was partitioned between EtOAc and sat. aq. $KH_2PO_4$. The organic extract was washed with brine, dried with $Na_2SO_4$, filtered, and concentrated. The residue was purified by column chromatography (silica gel, eluting with EtOAc) to give compound 255a (157 mg, 83% yield) as a glass. m/z=473 (M+1).

T152: A solution of compound 255a (155 mg, 0.328 mmol) in anhydrous DMF (3 mL) was cooled to 0° C. under nitrogen. A solution of 1,3-dibromo-5,5-dimethylhydantoin (52 mg, 0.182 mmol) in anhydrous DMF (1 mL) was added. The mixture was stirred at 0° C. for 1 h, and then anhydrous pyridine (0.27 mL, 3.34 mmol) was added. The mixture was heated at 60° C. for 4 h. After cooled to room temperature, the reaction mixture was diluted with EtOAc and washed with sat. aq. $KH_2PO_4$. The organic layer was separated. The aqueous layer was extracted with EtOAc. The combined organic extracts were washed with water and brine, dried with $Na_2SO_4$, filtered, and concentrated. The residue was purified by column chromatography (silica gel, eluting with EtOAc) to give compound T152 (117 mg, 76% yield) as an orange solid. m/z=471 (M+1); $^1H$ NMR (400 MHz, $CDCl_3$) δ 8.70 (dd, J=1.6, 4.8 Hz, 1H), 8.68 (s, 1H), 8.57 (dd, J=0.8, 2.5 Hz, 1H), 7.54 (m, 3H), 7.50 (m, 2H), 7.40 (m, 6H), 2.57 (m, 3H), 2.17 (m, 2H), 1.86 (m, 1H), 1.54 (s, 3H), 1.32 (d, J=6.8 Hz, 3H).

Compound 252b: Compound 252b (white solid, 187 mg, 68% yield) was synthesized from compound 251 (250 mg, 0.597 mmol), 4-isopropylphenylboronic acid (147 mg, 0.896 mmol), tetrakis(triphenylphosphine)palladium(0) (69 mg, 0.060 mmol), potassium phosphate tribasic (380 mg, 1.79 mmol) in 1,4-dioxane (6 mL), and water (2 mL) using the same procedure as described for the synthesis of compound 252a. The reaction mixture was heated at 110° C. for 23 h. Compound 252b was purified by column chromatography (silica gel, eluting with 60% EtOAc in hexanes). m/z=458 (M+1).

Compound 253b: A solution of compound 252b (184 mg, 0.402 mmol) in THF (15 mL) was treated with 3.0 N aq. HCl (1.34 mL, 4.02 mmol). The reaction mixture was stirred at room temperature for 27 h and then concentrated. The residue was partitioned between EtOAc and sat. aq. NaHCO$_3$. The organic extract was washed with brine, dried with Na$_2$SO$_4$, filtered, and concentrated to give compound 253b (160 mg, 96% yield) as a clear glass and was used in the next step without further purification. m/z=414 (M+1).

Compound 254b: Compound 253b (160 mg, 0.386 mmol) in ethyl formate (22 mL, 273 mmol) was cooled to 0° C. Sodium methoxide (5.4 M in MeOH, 0.71 mL, 3.83 mmol) was added. The mixture was stirred at room temperature for 3 h and then concentrated. The residue was partitioned between EtOAc and sat. aq. KH$_2$PO$_4$. The organic extract was washed with brine, dried with Na$_2$SO$_4$, filtered, and concentrated. The product obtained was dissolved in EtOH (15 mL). 6.0 N aq. HCl (0.64 mL, 3.84 mmol) and hydroxylamine hydrochloride (40 mg, 0.58 mmol) were added. The reaction mixture was heated at 60° C. for 18 h and then concentrated. The residue was partitioned between EtOAc and sat. aq. NaHCO$_3$. The organic extract was washed with brine, dried with Na$_2$SO$_4$, filtered, and concentrated to give compound 254b (175 mg, quantitative) as a glass, which was used in the next step without further purification. m/z=439 (M+1).

Compound 255b: A solution of 254b (174 mg, ≤0.386 mmol) in MeOH (10 mL) was treated with potassium carbonate (109 mg, 0.790 mmol). The reaction mixture was stirred at room temperature for 16 h and then heated at 55° C. for 2 h. The solvent was removed in vacuo and the residue was partitioned between EtOAc and sat. aq. KH$_2$PO$_4$. The organic extract was washed with brine, dried with Na$_2$SO$_4$, filtered, and concentrated. The residue was purified by column chromatography (silica gel, eluting with EtOAc) to give compound 255b (147 mg, 87% yield) as a glass. m/z=439 (M+1).

T153: A solution of compound 255b (145 mg, 0.331 mmol) in anhydrous DMF (3 mL) was cooled to 0° C. under nitrogen. A solution of 1,3-dibromo-5,5-dimethylhydantoin (52 mg, 0.182 mmol) in anhydrous DMF (1 mL) was added. The mixture was stirred at 0° C. for 1 h, and then anhydrous pyridine (0.27 mL, 3.34 mmol) was added. The mixture was heated at 60° C. for 4 h. After cooled to room temperature, the reaction mixture was diluted with EtOAc and washed with sat. aq. KH$_2$PO$_4$. The organic layer was separated. The aqueous layer was extracted with EtOAc. The combined organic extracts were washed with water and brine, dried with Na$_2$SO$_4$, filtered, and concentrated. The residue was purified by column chromatography (silica gel, eluting with EtOAc) to give compound T153 (110 mg, 76% yield) as an orange solid. m/z=437 (M+1); $^1$H NMR (400 MHz, CDCl$_3$) δ 8.67 (m, 2H), 8.51 (dd, J=0.7, 2.6 Hz, 1H), 7.51 (ddd, J=1.6, 2.5, 8.1 Hz, 1H), 7.40 (ddd, J=0.8, 4.8, 8.1 Hz, 1H), 7.21 (m, 2H), 7.11 (m, 2H), 2.85 (hept, J=7.0 Hz, 1H), 2.56 (m, 3H), 2.14 (m, 2H), 1.84 (m, 1H), 1.52 (s, 3H), 1.31 (d, J=6.8 Hz, 3H), 1.20 (d, J=6.9 Hz, 6H).

Compound 252c: Compound 252c (white solid, 246 mg, 74% yield) was synthesized from compound 251 (300 mg, 0.717 mmol), quinoline-4-boronic acid (186 mg, 1.075 mmol), tetrakis(triphenyl-phosphine)palladium(0) (83 mg, 0.072 mmol), potassium phosphate tribasic (456 mg, 2.15 mmol) in 1,4-dioxane (6 mL), and water (2 mL) using the same procedure as described for the synthesis of compound 252a. The reaction mixture was heated at 90° C. for 14 h. Compound 252c was purified by column chromatography (silica gel, eluting with 10% MeOH in EtOAc). m/z=467 (M+1).

Compound 253c: A solution of compound 252c (245 mg, 0.525 mmol) in THF (25 mL) was treated with 3.0 N aq. HCl (1.75 mL, 5.25 mmol). The reaction mixture was stirred at room temperature for 24 h and then concentrated. The residue was partitioned between EtOAc and sat. aq. NaHCO$_3$. The organic extract was washed with brine, dried with Na$_2$SO$_4$, filtered, and concentrated to give compound 253c (210 mg, 95% yield) as a glass, which was used in the next step without further purification. m/z=423 (M+1).

Compound 254c: Compound 253c (210 mg, 0.497 mmol) in ethyl formate (28 mL, 348 mmol) was cooled to 0° C. Sodium methoxide (5.4 M in MeOH, 0.92 mL, 4.97 mmol) was added. The mixture was stirred at room temperature for 3 h and then concentrated. The residue was partitioned between EtOAc and sat. aq. KH$_2$PO$_4$. The organic extract was washed with brine, dried with Na$_2$SO$_4$, filtered, and concentrated. The product obtained was dissolved in EtOH (18 mL). 6.0 N aq. HCl (0.83 mL, 4.98 mmol) and hydroxylamine hydrochloride (52 mg, 0.75 mmol) were added. The reaction mixture was heated at 60° C. for 20 h and then concentrated. The residue was partitioned between EtOAc and sat. aq. NaHCO$_3$. The organic extract was washed with brine, dried with Na$_2$SO$_4$, filtered, and concentrated to give compound 254c (213 mg, 96% yield) as a yellow glass and was used in the next step without further purification. m/z=448 (M+1).

Compound 255c: A solution of 254c (212 mg, 0.474 mmol) in MeOH (10 mL) was treated with potassium carbonate (131 mg, 0.949 mmol). The reaction mixture was stirred at room temperature for 16 h and then heated at 55° C. for 4 h. The solvent was removed in vacuo and the residue was partitioned between EtOAc and sat. aq. KH$_2$PO$_4$. The organic extract was washed with brine, dried with Na$_2$SO$_4$, filtered, and concentrated. The residue was purified by column chromatography (silica gel, eluting with 11% MeOH in EtOAc) to give compound 255c (182 mg, 86% yield) as a yellow glass. m/z=448 (M+1).

T154: A solution of compound 255c (180 mg, 0.402 mmol) in anhydrous DMF (3 mL) was cooled to 0° C. under nitrogen. A solution of 1,3-dibromo-5,5-dimethylhydantoin (63 mg, 0.220 mmol) in anhydrous DMF (1 mL) was added. The mixture was stirred at 0° C. for 1 h, and then anhydrous pyridine (0.33 mL, 4.08 mmol) was added. The mixture was heated at 60° C. for 4 h. After cooled to room temperature, the reaction mixture was diluted with EtOAc and washed with sat. aq. KH$_2$PO$_4$. The organic layer was separated. The aqueous layer was extracted with EtOAc. The combined organic extracts were washed with water and brine, dried with Na$_2$SO$_4$, filtered, and concentrated. The residue was purified by column chromatography (silica gel, eluting with 10% MeOH in EtOAc) to give compound T154 (104 mg, 58% yield) as a yellow solid. m/z=446 (M+1); $^1$H NMR (400 MHz, CDCl$_3$) δ 8.75 (d, J=4.4 Hz, 1H), 8.63 (s, 1H), 8.57 (dd, J=1.5, 4.8 Hz, 1H), 8.47 (dd, J=0.8, 2.6 Hz, 1H), 8.23 (ddd, J=0.7, 1.5, 8.4 Hz, 1H), 8.13 (ddd, J=0.6, 1.3, 8.4 Hz, 1H), 7.76 (ddd, J=1.5, 6.9, 8.4 Hz, 1H), 7.62 (ddd, J=1.3, 6.9, 8.3 Hz, 1H), 7.36 (ddd, J=1.6, 2.6, 8.1 Hz, 1H), 7.25 (m, 1H), 7.00 (d, J=4.4 Hz, 1H), 2.65 (m, 3H), 2.27 (dt, J=2.2, 12.9 Hz, 1H), 2.19 (m, 1H), 1.91 (ddt, J=6.8, 10.6, 13.2 Hz, 1H), 1.60 (s, 3H), 1.35 (d, J=6.7 Hz, 3H).

Compound 252d: Compound 252d (white solid, 253 mg, 67% yield) was synthesized from compound 251 (320 mg, 0.764 mmol), 3-biphenylboronic acid (227 mg, 1.14 mmol), tetrakis(triphenylphosphine)palladium(0)(88 mg, 0.076 mmol), potassium phosphate tribasic (486 mg, 2.29 mmol) in 1,4-dioxane (6 mL), and water (2 mL) using the same procedure as described for the synthesis of compound 252a. The reaction mixture was heated at 110° C. for 16 h. Compound 252d was purified by column chromatography (silica gel, eluting with 60% EtOAc in hexanes). m/z=492 (M+1).

Compound 253d: A solution of compound 252d (253 mg, 0.514 mmol) in THF (25 mL) was treated with 3.0 N aq. HCl (1.71 mL, 5.13 mmol). The reaction mixture was stirred at room temperature for 21 h and then concentrated. The residue was partitioned between EtOAc and sat. aq. NaHCO$_3$. The organic extract was washed with brine, dried with Na$_2$SO$_4$, filtered, and concentrated to give compound 253d (230 mg, quantitative yield) as a glass and was used in the next step without further purification. m/z=448 (M+1).

Compound 254d: Compound 253d (230 mg, 0.514 mmol) in ethyl formate (32 mL, 398 mmol) was cooled to 0° C. Sodium methoxide (5.4 M in MeOH, 0.95 mL, 5.13 mmol) was added. The mixture was stirred at mom temperature for 4 h and then concentrated. The residue was partitioned between EtOAc and sat. aq. KH$_2$PO$_4$. The organic extract was washed with brine; dried with Na$_2$SO$_4$, filtered, and concentrated. The product obtained was dissolved in EtOH (32 mL). 6.0 N aq. HCl (0.86 mL, 5.16 mmol) and hydroxylamine hydrochloride (54 mg, 0.78 mmol) were added. The reaction mixture was heated at 60° C. for 17 h and then concentrated. The residue was partitioned between EtOAc and sat. aq. NaHCO$_3$. The organic extract was washed with brine, dried with Na$_2$SO$_4$, filtered, and concentrated to give compound 254d (254 mg, quantitative yield) as a yellow glass and was used in the next step without further purification. m/z=473 (M+1).

Compound 255d: A solution of 254d (252 mg, <0.514 mmol) in MeOH (20 mL) was treated with potassium carbonate (147 mg, 1.06 mmol). The reaction mixture was heated at 55° C. for 4 h. The solvent was removed in vacuo and the residue was partitioned between EtOAc and sat. aq. KH$_2$PO$_4$. The organic extract was washed with brine, dried with Na$_2$SO$_4$, filtered, and concentrated. The residue was purified by column chromatography (silica gel, eluting with EtOAc) to give compound 255d (185 mg, 76% yield) as a glass. m/z=473 (M+1).

T155: A solution of compound 255d (147 mg, 0.311 mmol) in anhydrous DMF (3 mL) was cooled to 0° C. under nitrogen. A solution of 1,3-dibromo-5,5-dimethylhydantoin (49 mg, 0.171 mmol) in anhydrous DMF (1 mL) was added. The mixture was stirred at 0° C. for 1 h, and then anhydrous pyridine (0.25 mL, 3.09 mmol) was added. The mixture was heated at 60° C. for 4 h. After cooled to room temperature, the reaction mixture was diluted with EtOAc and washed with sat. aq. KH$_2$PO$_4$. The organic layer was separated. The aqueous layer was extracted with EtOAc. The combined organic extracts were washed with water and brine, dried with Na$_2$SO$_4$, filtered, and concentrated. The residue was purified by column chromatography (silica gel, eluting with 80% EtOAc in hexanes) to give compound T155 (117 mg, 80% yield) as a yellow solid. m/z=471 (M+1); $^1$H NMR (400 MHz, CDCl$_3$) δ 8.70 (dd, J=1.5, 4.8 Hz, 1H), 8.69 (s, 1H), 8.57 (dd, J=0.8, 2.6 Hz, 1H), 7.58 (dt, J=0.5, 1.8 Hz, 1H), 7.53 (m, 2H), 7.40 (m, 5H), 7.33 (m, 2H), 7.23 (ddd, J=1.2, 1.8, 7.8 Hz, 1H), 2.58 (m, 3H), 2.17 (m, 2H), 1.86 (m, 1H), 1.54 (s, 3H), 1.32 (d, J=6.8 Hz, 3H).

Compound 256: To a solution of compound 173 (1.5 g, 5.94 mmol) in benzene (50 mL) were added 1-methyl-1H-pyrazole-4-amine (0.72 g, 7.41 mmol) and p-toluenesulfonic acid monohydrate (0.11 g, 0.59 mmol). The mixture was refluxed for 4 days with Dean Stark trap for removal of water, cooled to room temperature, and concentrated. The residue was purified by column chromatography (silica gel, eluting with 20% EtOAc in CH$_2$Cl$_2$) to give compound 256 (1.0 g, 51% yield) as a brown solid. m/z=332 (M+1).

Compound 257a: A mixture of compound 256 (0.23 g, 0.69 mmol) in absolute EtOH (5 mL) was treated with 4-isopropylbenzaldehyde (0.21 g, 1.42 mmol) and ammonium acetate (0.54 g, 7.01 mmol) sequentially. The solution was stirred at 60° C. for overnight, cooled to room temperature, and concentrated. The residue was triturated with EtOAc and filtered. The filter cake was washed with EtOAc. The combined filtrate and wash were concentrated. The residue was purified by column chromatography (silica gel, eluting with 50% EtOAc in hexanes) to give compound 257a (283 mg, 88% yield) as a yellow solid. m/z=461 (M+1).

Compound 258a: Compound 257a (0.278 g, 0.60 mmol) was taken up in THF (15 mL), 3 N aq. HCl (9 mL, 27 mmol) was added. The mixture was stirred at room temperature overnight and then concentrated. The residue was neutralized by addition of sat. aq. NaHCO$_3$ to pH 7. The mixture was extracted with EtOAc. The organic extract was dried with MgSO$_4$, filtered, and concentrated to give compound 258a (0.27 g, quantitative yield) as a yellow solid. m/z=417 (M+1).

Compound 259a: Compound 258a (0.269 g, 50.60 mmol) was mixed with ethyl formate (15 mL, 186 mmol) and treated with sodium methoxide (30 wt. % in MeOH, 0.46 g, 2.55 mmol). The reaction mixture was stirred at room temperature overnight and then treated with sat. aq. KH$_2$PO$_4$ to adjust pH to 5. The mixture was extracted with EtOAc. The organic extract was dried with MgSO$_4$, filtered, and concentrated to give compound 259a (0.295 g, quantitative yield) as an orange solid. m/z=445 (M+1).

Compound 260a: A mixture of compound 259a (0.295 g, ≤0.60 mmol) in EtOH (15 mL) was treated with hydroxylamine hydrochloride (91 mg, 1.31 mmol). The mixture was heated at 50° C. overnight, cooled to room temperature, and concentrated. The residue was diluted with EtOAc and washed with sat. aq. NaHCO$_3$. The organic extract was dried with MgSO$_4$, filtered, and concentrated. The residue was purified by column chromatography (silica gel, eluting with 20% EtOAc in CH$_2$Cl$_2$) to give compound 260a (0.223 g, 84% yield) as a yellow solid. m/z=442 (M+1).

Compound 261a: A mixture of compound 260a (0.223 g, 0.50 mmol) in MeOH (10 mL) was treated with potassium carbonate (0.279 g, 2.02 mmol). The mixture stirred at room temperature overnight and then concentrated. The residue was partitioned between EtOAc and sat. aq. KH$_2$PO$_4$. The organic extract was dried with MgSO$_4$, filtered, and concentrated. The residue was purified by column chromatography (silica gel, eluting with EtOAc) to give compound 261a (0.168 g, 75%) as a yellow solid. m/z=442 (M+1).

T156: A solution of compound 261a (0.166 g, 0.38 mmol) in anhydrous DMF (3 mL) was cooled to 0° C. under nitrogen. A solution of 1,3-dibromo-5,5-dimethylhydantoin (54 mg, 0.19 mmol) in anhydrous DMF (1 mL) was added. The mixture was stirred at 0° C. for 30 min, and then anhydrous pyridine (0.30 mL, 3.71 mmol) was added. The mixture was stirred at 50° C. for 4 h and at room temperature overnight. The mixture was concentrated. The residue was partitioned between EtOAc and sat. aq. $KH_2PO_4$. The organic extract was washed with water, dried with $Na_2SO_4$, filtered, and concentrated. The residue was purified by column chromatography (silica gel, eluting with 20% EtOAc in $CH_2Cl_2$) to give compound T156 (85 mg, 51% yield) as an orange solid. m/z=440 (M+1); $^1$H NMR (400 MHz, $CDCl_3$) δ 8.65 (s, 1H), 7.44 (d, J=0.7 Hz, 1H), 7.37 (m, 2H), 7.31 (m, 1H), 7.15 (m, 2H), 3.92 (s, 3H), 2.88 (hept, J=6.9 Hz, 1H), 2.53 (m, 3H), 2.12 (m, 2H), 1.80 (ddt, J=7.4, 10.2, 13.3 Hz, 1H), 1.49 (s, 3H), 1.30 (d, J=6.8 Hz, 3H), 1.22 (d, J=6.9 Hz, 6H).

Compound 257b: A mixture of compound 256 (0.25 g, 0.75 mmol) in absolute EtOH (10 mL) was treated with 3-chlorobenzaldehyde (0.21 g, 1.49 mmol) and ammonium acetate (0.58 g, 7.52 mmol) sequentially. The solution was stirred at 60° C. for overnight; cooled to room temperature; and concentrated. The residue was triturated with EtOAc and filtered. The filter cake was washed with EtOAc. The combined filtrate and wash were concentrated. The residue was purified by column chromatography (silica gel, eluting with 20% EtOAc in $CH_2Cl_2$) to give compound 257b (330 mg, 97% yield) as a yellow solid. m/z=453 (M+1).

Compound 258b: Compound 257b (0.33 g, 0.73 mmol) was taken up in THF (15 mL). 3 N aq. HCl (9 mL, 27 mmol) was added. The mixture was stirred at room temperature overnight, and then concentrated. The residue was neutralized by addition of sat. aq. $NaHCO_3$ to pH 7. The mixture was extracted with EtOAc. The organic extract was dried with $MgSO_4$, filtered and concentrated to give compound 258b (0.29 g, 97% yield) as a yellow solid. m/z=409 (M+1).

Compound 259b: Compound 258b (0.291 g, 0.71 mmol) was mixed with ethyl formate (15 mL, 186 mmol), and treated with sodium methoxide (30 wt. % in MeOH, 0.51 g, 2.83 mmol). The reaction mixture was stirred at room temperature overnight, and then treated with sat. aq. $KH_2PO_4$ to adjust pH to 5. The mixture was extracted with EtOAc. The organic extract was dried with $MgSO_4$; filtered and concentrated to give compound 259b (0.291 g, 94% yield) as an orange solid. m/z=437 (M+1).

Compound 260b: A mixture of compound 259b (0.291 g, 0.67 mmol) in EtOH (15 mL) was treated with hydroxylamine hydrochloride (0.102 g, 1.47 mmol). The mixture was heated at 50° C. overnight, cooled to room temperature, and concentrated. The residue was diluted with EtOAc and washed with sat. aq. $NaHCO_3$. The organic extract was dried with $MgSO_4$, filtered, and concentrated. The residue was purified by column chromatography (silica gel, eluting with 20% EtOAc in $CH_2Cl_2$) to give compound 260b (0.171 g, 59% yield) as a white solid. m/z=434 (M+1).

Compound 261b: Compound 260b (0.171 g, 0.39 mmol) in MeOH (10 mL) was treated with potassium carbonate (0.22 g, 1.59 mmol). The mixture stirred at room temperature overnight and then concentrated. The residue was partitioned between EtOAc and sat. aq. $KH_2PO_4$. The organic extract was dried with $MgSO_4$, filtered, and concentrated to give compound 261b (0.183 g, quantitative yield) as a yellow solid. m/z=434 (M+1).

T157: A solution of compound 261b (0.182 g, 0.42 mmol) in anhydrous DMF (4 mL) was cooled to 0° C. under nitrogen. A solution of 1,3-dibromo-5,5-dimethylhydantoin (60 mg, 0.21 mmol) in anhydrous DMF (1 mL) was added. The mixture was stirred at 0° C. for 30 min, and then anhydrous pyridine (0.40 mL, 4.95 mmol) was added. The mixture was stirred at 50° C. for 4 h and at room temperature overnight. The mixture was concentrated. The residue was partitioned between EtOAc and sat. aq. $KH_2PO_4$. The organic extract was washed with water, dried with $Na_2SO_4$, filtered, and concentrated. The residue was purified by column chromatography (silica gel, eluting with 20% EtOAc in $CH_2Cl_2$) to give compound T157 (120 mg, 66% yield) as a beige solid. m/z=432 (M+1); $^1$H NMR (400 MHz, $CDCl_3$) δ 8.61 (s, 1H), 7.56 (m, 1H), 7.45 (d, J=0.8 Hz, 1H), 7.31 (s, 1H), 7.28 (m, 2H), 7.22 (m, 1H), 3.94 (s, 3H), 2.53 (m, 3H), 2.12 (m, 2H), 1.81 (m, 1H), 1.49 (s, 3H), 1.30 (d, J=6.8 Hz, 3H).

Compound 257c: A mixture of compound 256 (0.25 g, 0.75 mmol) in absolute EtOH (10 mL) was treated with 3,4-dichlorobenzaldehyde (0.26 g, 1.49 mmol) and ammonium acetate (0.58 g, 7.52 mmol) sequentially. The solution was stirred at 60° C. for overnight, cooled to room temperature, and concentrated. The residue was triturated with EtOAc and filtered. The filter cake was washed with EtOAc. The combined filtrate and wash were concentrated. The residue was purified by column chromatography (silica gel, eluting with 20% EtOAc in $CH_2Cl_2$) to give compound 257c (283 mg, 77% yield) as a white solid. m/z=487 (M+1).

Compound 258c: Compound 257c (0.282 g, 0.58 mmol) was taken up in THF (10 mL). 3 N aq. HCl (6 mL, 18 mmol) was added. The mixture was stirred at room temperature overnight and then concentrated. The residue was neutralized by addition of sat. aq. $NaHCO_3$ to pH 7. The mixture was extracted with EtOAc. The organic extract was dried with $MgSO_4$, filtered, and concentrated to give compound 258c (0.25 g, 97% yield) as a white solid. m/z=443 (M+1).

Compound 259c: Compound 258 (0.22 g, 0.50 mmol) was mixed with ethyl formate (15 mL, 186 mmol), and treated with sodium methoxide (30 wt. % in MeOH, 0.35 g, 1.94 mmol). The reaction mixture was stirred at room temperature overnight and then treated with sat. aq. $KH_2PO_4$ to adjust pH to 5. The mixture was extracted with EtOAc. The organic extract was dried with $MgSO_4$, filtered, and concentrated to give compound 259c (0.229 g, 98% yield) as a beige solid. m/z=471 (M+1).

Compound 260c: A mixture of compound 259c (0.229 g, 0.49 mmol) in EtOH (15 mL) was treated with hydroxylamine hydrochloride (75 mg, 1.08 mmol). The mixture was heated at 50° C. overnight, cooled to mom temperature and concentrated. The residue was diluted with EtOAc and washed with sat. aq. $NaHCO_3$. The organic extract was dried with $MgSO_4$, filtered, and concentrated. The residue was purified by column chromatography (silica gel, eluting with 50% EtOAc in $CH_2Cl_2$) to give compound 260c (0.192 g, 84% yield) as a white solid. m/z=468 (M+1).

Compound 261c: A mixture of compound 260c (0.192 g, 0.41 mmol) in MeOH (10 mL) was treated with potassium carbonate (0.23 g, 1.67 mmol). The mixture stirred at room temperature overnight and then concentrated. The residue was partitioned between EtOAc and sat. aq. $KH_2PO_4$. The organic extract was dried with $MgSO_4$, filtered, and concentrated. The residue was purified by column chromatography (silica gel, eluting with 20% EtOAc in $CH_2Cl_2$) to give compound 261c (0.182 g, 95% yield) as a yellow solid. m/z=468 (M+1).

T158: A solution of compound 261c (0.182 g, 0.39 mmol) in anhydrous DMF (4 mL) was cooled to 0° C. under nitrogen. A solution of 1,3-dibromo-5,5-dimethylhydantoin (60 mg, 0.21 mmol) in anhydrous DMF (1 mL) was added. The mixture was stirred at 0° C. for 30 min, and then anhydrous pyridine (0.40 mL, 4.95 mmol) was added. The mixture was stirred at 50° C. for 4 h and at room temperature overnight. The mixture was concentrated. The residue was partitioned between EtOAc and sat. aq. $KH_2PO_4$. The organic extract was washed with water, dried with $Na_2SO_4$, filtered, and concentrated. The residue was purified by column chromatography (silica gel, eluting with 20% EtOAc in $CH_2Cl_2$) to give compound T158 (0.118 g, 65% yield) as a beige solid. m/z=466 (M+1); $^1$H NMR (400 MHz, $CDCl_3$) δ 8.59 (s, 1H), 7.67 (d, J=2.0 Hz, 1H), 7.47 (s, 1H), 7.34 (m, 2H), 7.21 (dd, J=2.0, 8.4 Hz, 1H), 3.95 (s, 3H), 2.53 (m, 3H), 2.10 (m, 2H), 1.80 (ddt, J=7.3, 10.2, 13.4 Hz, 1H), 1.48 (s, 3H), 1.30 (d, J=6.7 Hz, 3H).

Compound 257d: A mixture of compound 256 (0.225 g, 0.68 mmol) in absolute EtOH (10 mL) was treated with 3-(pyridin-4-yl)benzaldehyde (0.25 g, 1.36 mmol) and ammonium acetate (0.52 g, 6.75 mmol) sequentially. The solution was stirred at 60° C. for overnight, cooled to room temperature, and concentrated. The residue was triturated with EtOAc and filtered. The filter cake was washed with EtOAc. The combined filtrate and wash were concentrated. The residue was purified by column chromatography (silica gel, eluting with 20% EtOAc in $CH_2Cl_2$) to give compound 257d (300 mg, 89% yield) as a white solid. m/z=496 (M+1).

Compound 258d: Compound 257d (0.30 g, 0.61 mmol) was taken up in THF (15 mL). 3 N aq. HCl (9 mL, 27 mmol) was added. The mixture was stirred at room temperature overnight and then concentrated. The residue was neutralized by addition of sat. aq. $NaHCO_3$ to pH 7. The mixture was extracted with EtOAc. The organic extract was dried with $MgSO_4$, filtered, and concentrated to give compound 258d (0.30 g, quantitative yield) as a white solid. m/z=452 (M+1).

Compound 259d: Compound 258d (0.30 g, ≤0.61 mmol) was mixed with ethyl formate (15 mL, 186 mmol), and treated with sodium methoxide (30 wt. % in MeOH, 0.55 g, 3.05 mmol). The reaction mixture was stirred at room temperature overnight and then treated with sat. aq. $KH_2PO_4$ to adjust pH to 5. The mixture was extracted with EtOAc. The organic extract was dried with $MgSO_4$, filtered, and concentrated to give compound 259d (0.32 g, quantitative yield) as a yellow solid. m/z=480 (M+1).

Compound 260d: A mixture of compound 259d (0.32 g, ≤0.61 mmol) in EtOH (15 mL) was treated with hydroxylamine hydrochloride (0.12 g, 1.72 mmol). The mixture was heated at 50° C. overnight, cooled to mom temperature, and concentrated. The residue was diluted with EtOAc and washed with sat. aq. $NaHCO_3$. The organic extract was dried with $MgSO_4$, filtered, and concentrated. The residue was purified by column chromatography (silica gel, eluting with 5% MeOH in EtOAc) to give compound 260d (0.148 g, 51% yield) as a yellow solid. m/z=477 (M+1).

Compound 261d: A mixture of compound 260d (0.148 g, 0.31 mmol) in MeOH (10 mL) was treated with potassium carbonate (0.17 g, 1.23 mmol). The mixture stirred at room temperature overnight and then concentrated. The residue was partitioned between EtOAc and sat. aq. $KH_2PO_4$. The organic extract was dried with $MgSO_4$, filtered, and concentrated. The residue was purified by column chromatography (silica gel, eluting with 20% EtOAc in $CH_2Cl_2$) to give compound 261d (0.148 g, 100% yield) as a yellow solid. m/z=477 (M+1).

T159: A solution of compound 261d (0.148 g, 0.31 mmol) in anhydrous DMF (3 mL) was cooled to 0° C. under nitrogen. A solution of 1,3-dibromo-5,5-dimethylhydantoin (44 mg, 0.15 mmol) in anhydrous DMF (1 mL) was added. The mixture was stirred at 0° C. for 30 min, and then anhydrous pyridine (0.40 mL, 4.95 mmol) was added. The mixture was stirred at 50° C. for 4 h and at room temperature overnight. The mixture was concentrated. The residue was partitioned between EtOAc and sat. aq. $KH_2PO_4$. The organic extract was washed with water, dried with $Na_2SO_4$, filtered, and concentrated. The residue was purified by column chromatography (silica gel, eluting with 10% MeOH in EtOAc) to give compound T159 (48 mg, 33% yield) as an orange solid. m/z=475 (M+1): $^1$H NMR (400 MHz, $CDCl_3$) δ 8.66 (m, 3H), 7.81 (m, 1H), 7.48 (m, 6H), 7.35 (s, 1H), 3.94 (s, 3H), 2.55 (m, 3H), 2.11 (m, 2H), 1.84 (m, 1H), 1.51 (s, 3H), 1.31 (d, J=6.7 Hz, 3H).

Compound 262: A mixture of compound 256 (0.25 g, 0.75 mmol) in absolute EtOH (5 mL) was treated with formaldehyde (37 wt. % in water, 0.122 g, 1.50 mmol) and ammonium acetate (0.58 g, 7.52 mmol) sequentially. The solution was stirred at 60° C. for overnight, cooled to room temperature, and concentrated. The residue was triturated with EtOAc and filtered. The filter cake was washed with EtOAc. The combined filtrate and wash were concentrated. The residue was purified by column chromatography (silica gel, eluting with 10% MeOH in EtOAc) to give compound 262 (200 mg, 78% yield) as a viscous oil. m/z=343 (M+1).

Compound 263: Compound 262 (200 mg, 0.58 mmol) was dissolved in acetonitrile (18 mL) and cooled to 0° C. A solution of N-bromosuccinimide (0.108 g, 0.61 mmol) in acetonitrile (5 mL) was added. The reaction mixture was gradually warmed to room temperature and stirred overnight. The mixture was concentrated, and the residue was partitioned between EtOAc and sat. aq. $NaHCO_3$. The organic extract was washed with brine, dried over $Na_2SO_4$, filtered, and concentrated. The residue was purified by column chromatography (silica gel, eluting with 20% EtOAc in $CH_2Cl_2$) to give compound 263 (0.26 g, quantitative yield) as a tan solid. m/z=421/423 (M+1).

Compound 264: A reaction vessel was charged with compound 263 (0.26 g, 50.58 mmol) and dimethoxyethane (20 mL). (2-Morpholinopyridin-4-yl)boronic acid (0.16 g, 0.77 mmol), potassium carbonate (0.25 g, 1.81 mmol), tetrakis(triphenylphosphine)palladium(0) (0.15 g, 0.13 mmol), and water (5 mL) were added. The reaction mixture was purged with nitrogen for 10 min. The reaction vessel was sealed and heated at 90° C. overnight. After cooled to room temperature, the mixture was concentrated. The residue was partitioned between EtOAc and brine. The organic extract was dried with $MgSO_4$, filtered, and concentrated. The residue was purified by column chromatography (silica gel, eluting with 10% MeOH in EtOAc) to give compound 264 (0.196 g, 67% yield) as a yellow solid. m/z=505 (M+1).

Compound 265: Compound 264 (0.194 g, 0.38 mmol) was taken up in THF (8 mL). 3 N aq. HCl (5 mL, 15 mmol) was added. The mixture was stirred at room temperature overnight and then concentrated. The residue was neutralized by addition of sat. aq. $NaHCO_3$ to pH 7. The mixture was extracted with EtOAc. The organic extract was dried with $MgSO_4$, filtered, and concentrated to give compound 265 (0.179 g, quantitative yield) as a white solid. m/z=461 (M+1).

Compound 266: Compound 265 (0.177 g, 0.38 mmol) was mixed with ethyl formate (12 mL, 149 mmol) and treated with sodium methoxide (30 wt. % in MeOH, 0.28 g, 1.55 mmol). The reaction mixture was stirred at room temperature overnight and then treated with sat. aq. $KH_2PO_4$ to adjust pH to 5. The mixture was extracted with EtOAc. The organic extract was dried with $MgSO_4$, filtered, and concentrated to give compound 266 (0.185 g, 99% yield) as an orange solid. m/z=489 (M+1).

Compound 267: A mixture of compound 266 (0.185 g, 0.38 mmol) in EtOH (10 mL) was treated with hydroxylamine hydrochloride (0.12 g, 1.73 mmol). The mixture was heated at 50° C. overnight, cooled to room temperature, and concentrated. The residue was diluted with EtOAc and washed with sat. aq. NaHCO$_3$. The organic extract was dried with MgSO$_4$, filtered, and concentrated. The residue was purified by column chromatography (silica gel, eluting with 5% MeOH in EtOAc) to give compound 267 (0.140 g, 76% yield) as a white solid. m/z=486 (M+1).

Compound 268: A mixture of compound 267 (0.138 g, 0.28 mmol) in MeOH (10 mL) was treated with potassium carbonate (0.16 g, 1.16 mmol). The mixture stirred at room temperature overnight and then concentrated. The residue was partitioned between EtOAc and sat. aq. KH$_2$PO$_4$. The organic extract was dried with MgSO$_4$, filtered, and concentrated to give compound 268 (0.135 g, 98% yield) as a yellow solid. m/z=486 (M+1).

T160: A solution of compound 268 (0.132 g, 0.27 mmol) in anhydrous DMF (3 mL) was cooled to 0° C. under nitrogen. A solution of 1,3-dibromo-5,5-dimethylhydantoin (39 mg, 0.14 mmol) in anhydrous DMF (1 mL) was added. The mixture was stirred at 0° C. for 30 min, and then anhydrous pyridine (0.30 mL, 3.71 mmol) was added. The mixture was stirred at 50° C. for 4 h and at room temperature overnight. The mixture was concentrated. The residue was partitioned between EtOAc and sat. aq. KH$_2$PO$_4$. The organic extract was washed with water, dried with Na$_2$SO$_4$, filtered, and concentrated. The residue was purified by column chromatography (silica gel, eluting with EtOAc) to give compound T160 (58 mg, 45% yield) as a beige solid. m/z=484 (M+1); $^1$H NMR (400 MHz, CDCl$_3$) δ 8.62 (s, 1H), 8.06 (dd, J=0.8, 5.3 Hz, 1H), 7.51 (s, 1H), 7.33 (s, 1H), 6.91 (s, 1H), 6.54 (dd, J=1.3, 5.4 Hz, 1H), 3.94 (s, 3H), 3.82 (m, 4H), 3.50 (m, 4H), 2.52 (m, 3H), 2.09 (m, 2H), 1.82 (m, 1H), 1.48 (s, 3H), 1.30 (d, J=6.8 Hz, 3H).

Compound 269a: A mixture of compound 173 (100 mg, 0.396 mmol) in toluene (5 mL) was heated to 45° C., and cyclopropylamine (45 mg, 0.79 mmol) was added. The reaction mixture was heated at 45° C. for 19 h, cooled to room temperature, and concentrated. The residue was purified by column chromatography (silica gel, eluting with 50% EtOAc in hexanes) to give compound 269a (96 mg, 83% yield) as a viscous yellow oil. m/z=292 (M+1).

Compound 270a: A solution of compound 269a (93 mg, 0.319 mmol) in EtOH (10 mL) was treated with 4-isopropylbenzaldehyde (95 mg, 0.641 mmol) and ammonium acetate (246 mg, 3.19 mmol) sequentially. The reaction mixture was stirred at room temperature for 17 h and then concentrated. The residue was diluted with EtOAc and was washed with sat. aq. NaHCO$_3$. The organic extract was dried with Na$_2$SO$_4$, filtered, and concentrated. The residue was purified by column chromatography (silica gel, eluting with 10% to 100% EtOAc in hexanes) to give compound 270a (147 mg, quantitative yield) as a white glass. m/z=421 (M+1).

Compound 271a: A solution of compound 270a (143 mg, <0.319 mmol) in THF (10 mL) was treated with 3.0 N aq. HCl (1.13 mL, 3.39 mmol). The reaction mixture was stirred at room temperature for 18 h and then concentrated. The residue was partitioned between EtOAc and sat. aq. NaHCO$_3$. The organic extract was washed with brine, dried with Na$_2$SO$_4$, filtered, and concentrated to give compound 271a (123 mg, quantitative yield) as a clear glass, which was used in the next step without further purification. m/z=377 (M+1).

Compound 272a: A solution of compound 271a (122 mg, <0.319 mmol) in ethyl formate (15 mL, 186 mmol) at 0° C. was treated with sodium methoxide (5.4 M in MeOH, 0.60 mL, 3.24 mmol). The reaction mixture was stirred at room temperature for 2 h and then concentrated. The residue was partitioned between EtOAc and sat. aq. KH$_2$PO$_4$. The organic extract was washed with brine, dried with Na$_2$SO$_4$, filtered, and concentrated. The crude product was dissolved in EtOH (15 mL) and treated with 6.0 N aq. HCl (0.54 mL, 3.24 mmol) and hydroxylamine hydrochloride (34 mg, 0.49 mmol) sequentially. The reaction mixture was heated at 60° C. for 18 h and then concentrated. The residue was partitioned between EtOAc and sat. aq. NaHCO$_3$. The organic extract was washed with brine, dried with Na$_2$SO$_4$, filtered, and concentrated to give compound 272a (118 mg, 92% yield) as a glass, which was used in the next step without further purification. m/z=402 (M+1).

Compound 273a: A solution of compound 272a (117 mg, 0.291 mmol) in MeOH (10 mL) was treated with potassium carbonate (81 mg, 0.59 mmol). The reaction mixture was stirred at room temperature for 13 h and then heated 50° C. for 3 h. The solvent was removed in vacuo and the residue was partitioned between EtOAc and sat. aq. KH$_2$PO$_4$. The organic extract was washed with brine, dried with Na$_2$SO$_4$, filtered, and concentrated. The residue was purified by column chromatography (silica gel, eluting with 50% EtOAc in hexanes) to give compound 273a (78 mg, 67% yield) as a clear glass. m/z=402 (M+1).

T161: A solution of 273a (77 mg, 0.19 mmol) in anhydrous DMF (3 mL) was cooled to 0° C. under nitrogen. A solution of 1,3-dibromo-5,5-dimethylhydantoin (30 mg, 0.10 mmol) in anhydrous DMF (1 mL) was added. The mixture was stirred at 0° C. for 1 h and then treated with anhydrous pyridine (0.15 mL, 1.86 mmol). The mixture was heated at 60° C. for 4 hours and then cooled to room temperature. The reaction mixture was diluted with EtOAc and washed with sat. aq. KH$_2$PO$_4$. The organic layer was separated. The aqueous phase was extracted with EtOAc. The combined organic extracts were washed with water and brine, dried with Na$_2$SO$_4$, filtered, and concentrated. The residue was purified by column chromatography (silica gel, eluting with 40% EtOAc in hexanes) to give compound T161 (60 mg, 79% yield) as an orange solid. m/z=400 (M+1); $^1$H NMR (400 MHz, CDCl$_3$) δ 8.60 (s, 1H), 7.61 (m, 2H), 7.28 (m, 2H), 3.21 (tt, J=3.9, 7.0 Hz, 1H), 2.95 (hept, J=7.0 Hz, 1H), 2.86 (ddd, J=1.2, 6.2, 16.5 Hz, 1H), 2.70 (m, 1H), 2.56 (qd, J=6.8, 13.5 Hz, 1H), 2.09 (m, 2H), 1.82 (tdd, J=6.3, 12.8, 19.1 Hz, 1H), 1.43 (s, 3H), 1.31 (d, J=6.8 Hz, 3H), 1.28 (d, J=6.9 Hz, 6H), 0.96 (m, 2H), 0.68 (m, 1H), 0.58 (m, 1H).

Compound 269b: A pressure vessel was charged with compound 173 (500 mg, 1.98 mmol), isopropylamine (0.32 mL, 3.72 mmol) and toluene (10 mL). The vessel was sealed, and the reaction mixture was heated at 100° C. for 20 h. After cooled to room temperature, the solvent was removed in vacuo and the residue was purified by column chromatography (silica gel, eluting with 30% EtOAc in hexanes) to give compound 269b (464 mg, 80% yield) as a yellow viscous oil which solidified upon standing. m/z=294 (M+1).

Compound 270b: A solution of compound 269b (342 mg, 1.16 mmol) in EtOH (30 mL) was treated with 4-isopropylbenzaldehyde (345 mg, 2.33 mmol) and ammonium acetate (894 mg, 11.60 mmol) sequentially. The reaction mixture was stirred at room temperature for 60 h and heated at 60° C. for 5 h. The mixture was concentrated. The residue was diluted with EtOAc and was washed with sat. aq. NaHCO$_3$.

The organic extract was dried with Na₂SO₄, filtered, and concentrated. The residue was purified by column chromatography (silica gel, eluting with 50% EtOAc in hexanes) to give compound 270b (142 mg, 29% yield) as a light yellow glass. m/z=423 (M+1).

Compound 271b: A solution of compound 270b (214 mg, 0.506 mmol) in THF (20 mL) was treated with 3.0 N aq. HCl (1.69 mL, 5.07 mmol). The reaction mixture was stirred at room temperature for 18 h and then concentrated. The residue was partitioned between EtOAc and sat. aq. NaHCO₃. The organic extract was washed with brine, dried with Na₂SO₄, filtered, and concentrated to give compound 271b (176 mg, 92%) as a solid and was used in the next step without further purification. m/z=379 (M+1).

Compound 272b: A solution of compound 271b (176 mg, 0.465 mmol) in ethyl formate (20 mL, 249 mmol) at 0° C. was treated with sodium methoxide (5.4 M in MeOH, 0.86 mL, 4.64 mmol). The reaction mixture was stirred at room temperature for 2 h and then concentrated. The residue was partitioned between EtOAc and sat. aq. $KH_2PO_4$. The organic extract was washed with brine, dried with Na₂SO₄, filtered, and concentrated. The crude product was dissolved in EtOH (20 mL) and treated with 6.0 N aq. HCl (0.78 mL, 4.68 mmol) and hydroxylamine hydrochloride (48 mg, 0.69 mmol) sequentially. The reaction mixture was heated at 60° C. for 3 h and then concentrated. The residue was partitioned between EtOAc and sat. aq. NaHCO₃. The organic extract was washed with brine; dried with Na₂SO₄, filtered, and concentrated to give compound 272b (192 mg, quantitative yield) as a yellow glass, which was used in the next step without further purification. m/z=404 (M+1).

Compound 273b: A solution of compound 272b (191 mg, 0.473 mmol) in MeOH (20 mL) was treated with potassium carbonate (131 mg, 0.946 mmol). The reaction mixture was stirred at 50° C. for 5.5 h. The solvent was removed in vacuo and the residue was partitioned between EtOAc and sat. aq. $KH_2PO_4$. The organic extract was washed with brine, dried with Na₂SO₄, filtered, and concentrated. The residue was purified by column chromatography (silica gel, eluting with 50% EtOAc in hexanes) to give compound 273b (113 mg, 59% yield) as a white glass. m/z=404 (M+1).

T162: A solution of compound 273b (112 mg, 0.277 mmol) in anhydrous DMF (3 mL) was cooled to 0° C. under nitrogen. A solution of 1,3-dibromo-5,5-dimethylhydantoin (43.6 mg, 0.153 mmol) in anhydrous DMF (1 mL) was added. The mixture was stirred at 0° C. for 1 h, and then treated with anhydrous pyridine (0.22 mL, 2.72 mmol). The mixture was heated at 60° C. for 4 hours and then cooled to room temperature. The reaction mixture was diluted with EtOAc and washed with sat. aq. $KH_2PO_4$. The organic layer was separated. The aqueous phase was extracted with EtOAc. The combined organic extracts were washed with water and brine, dried with Na₂SO₄, filtered, and concentrated. The residue was purified by column chromatography (silica gel, eluting with 30% EtOAc in hexanes) to give compound T162 (86 mg, 77% yield) as an orange solid. m/z=402 (M+1); ¹H NMR (400 MHz, CDCl₃) δ 8.63 (s, 1H), 7.39 (m, 2H), 7.31 (m, 2H), 4.57 (hept, J=7.0 Hz, 1H), 2.94 (m, 2H), 2.82 (ddd, J=6.4, 11.1, 15.9 Hz, 1H), 2.56 (qd, J=6.8, 13.5 Hz, 1H), 2.12 (m, 2H), 1.84 (ddt, J=6.2, 11.1, 13.1 Hz, 1H), 1.49 (d, J=6.9 Hz, 3H), 1.44 (s, 3H), 1.39 (d, J=7.0 Hz, 3H), 1.31 (d, J=6.8 Hz, 3H), 1.27 (d, J=6.9 Hz, 6H).

Compound 269c: In a sealable vial, a solution of compound 173 (0.36 g, 1.43 mmol) and methylamine (40 wt. % in water, 0.23 g, 2.96 mmol) in benzene (10 mL) was flushed with N₂. The vial was sealed and heated at 80° C. for 6 h. After cooled to room temperature, the reaction mixture was partitioned between sat. aq. $KH_2PO_4$ (50 mL) and EtOAc (50 mL). The organic extract was washed with brine (50 mL), dried with MgSO₄, filtered, and concentrated. The residue was purified by column chromatography (silica gel, eluting with 50% EtOAc in hexanes) to give compound 269c (0.29 g, 76% yield) as a yellow oil. m/z=266 (M+1).

Compound 270c: In a scalable vial, a solution of compound 269c (0.29 g, 1.09 mmol) and 4-isopropylbenzaldehyde (0.33 g, 2.23 mmol) in EtOH (5 mL) was treated with ammonium acetate (0.84 g, 10.90 mmol). The mixture was flushed with N₂. The vial was sealed and heated at 60° C. overnight. The mixture was concentrated. The residue was diluted with EtOAc (50 mL) and stirred at room temperature under N₂ for 1 h. The mixture was filtered through a pad of Celite®. The filtrate was concentrated. The residue was purified by column chromatography (silica gel, eluting with EtOAc) to give compound 270c (0.40 g, 93% yield) as a light yellow waxy solid. m/z=395 (M+1).

Compound 271c: A solution of compound 270c (0.40 g, 1.01 mmol) and 3 N aq. HCl (3.4 mL, 10.2 mmol) in MeOH (25 mL) was stirred at room temperature under N₂ overnight. The mixture was concentrated. The residue was partitioned between 10% aq. NH₄OH (25 mL) and CHCl₃ (25 mL). The organic extract was washed with brine (25 mL), dried with MgSO₄, filtered, and concentrated to give compound 271c (0.33 g, 93% yield) as an off-white solid. m/z=351 (M+1).

Compound 272c: A solution of compound 271c (0.33 g, 0.94 mmol) in ethyl formate (10 mL, 124 mmol) was treated with sodium methoxide (30 wt. % solution in MeOH, 0.90 mL, 4.80 mmol). The mixture was stirred at room temperature overnight and then concentrated. The residue was partitioned between sat. aq. $KH_2PO_4$ (25 mL) and EtOAc (25 mL). The organic extract was washed with brine (25 mL), dried with MgSO₄, filtered, and concentrated to give compound 272c (0.35 g, 98% yield) as a tan solid. m/z=379 (M+1).

Compound 273c: A solution of compound 272c (0.35 g, 0.92 mmol) and acetic acid (0.53 mL, 9.26 mmol) in EtOH (5 mL) was treated with hydroxylamine hydrochloride (96 mg, 1.38 mmol). The mixture was heated at 60° C. under N₂ for 2 h, stirred at room temperature overnight, and then concentrated. The residue was partitioned between sat. aq. NaHCO₃ (25 mL) and CHCl₃ (25 mL). The organic extract was washed with brine (25 mL), dried with MgSO₄, filtered, and concentrated to give compound 273c (0.33 g, 95% yield) as a yellow solid. m/z=376 (M+1).

Compound 274c: A solution of compound 273c (0.33 g, 0.88 mmol) in MeOH (20 mL) was treated with potassium carbonate (0.61 g, 4.42 mmol). The mixture was stirred at room temperature under N₂ for 16 h and then concentrated. The residue was partitioned between sat. aq. $KH_2PO_4$ (25 mL) and CHCl₃ (25 mL). The organic extract was washed with brine (25 mL); dried with MgSO₄, filtered, and concentrated. The residue was purified by column chromatography (silica gel, eluting with 50% EtOAc in hexanes) to give compound 274c (0.23 g, 70% yield) as light yellow foamy solid. m/z=376 (M+1).

T163: To a stirring solution of compound 274c (0.23 g, 0.61 mmol) in degassed DMF (4 mL) at 0° C. under N₂ was added dropwise a solution of 1,3-dibromo-5,5-dimethylhydantoin (96 mg, 0.34 mmol) in degassed DMF (1 mL). The mixture was stirred at 0° C. for 30 min, and then treated with pyridine (0.50 mL, 6.18 mmol). The mixture was heated at 60° C. for 4 h and then concentrated. The residue was partitioned between sat. aq. $KH_2PO_4$ (25 mL) and CHCl₃ (25 mL). The organic extract was washed with brine (25 mL), dried with MgSO$_4$, filtered, and concentrated. The residue was purified by column chromatography (silica gel, eluting with 50% EtOAc in hexanes) to give compound T163 (130 mg, 57% yield) as a yellow-orange solid. m/z=374 (M+1); $^1$H NMR (400 MHz, CDCl$_3$) δ 8.62 (s, 1H), 7.50 (m, 2H), 7.32 (m, 2H), 3.55 (s, 3H), 2.96 (hept, J=6.9 Hz, 1H), 2.65 (m, 3H), 2.12 (m, 2H), 1.85 (m, 1H), 1.44 (s, 3H), 1.31 (d, J=6.8 Hz, 3H), 1.27 (d, J=6.9 Hz, 6H).

Compound 269d: In a sealable vial, a solution of compound 173 (0.35 g, 1.39 mmol) and 2-methoxyethylamine (0.21 g, 2.80 mmol) in benzene (10 mL) was flushed with N$_2$. The vial was sealed and heated at 80° C. for 4 h. After cooled to room temperature, the reaction mixture was partitioned between sat. aq. KH$_2$PO$_4$ (50 mL) and EtOAc (50 mL). The organic extract was washed with brine (50 mL), dried with MgSO$_4$, filtered, and concentrated. The residue was purified by column chromatography (silica gel, eluting with 25% EtOAc in hexanes) to give compound 269d (0.30 g, 70% yield) as a light yellow oil. m/z=310 (M+1).

Compound 270d: In a sealable vial, a solution of compound 269d (0.30 g, 0.97 mmol) and 4-isopropylbenzaldehyde (0.29 g, 1.96 mmol) in EtOH (5 mL) was treated with ammonium acetate (0.75 g, 9.73 mmol). The mixture was flushed with N$_2$. The vial was sealed and heated at 60° C. overnight. The mixture was concentrated. The residue was diluted with EtOAc (50 mL) and stirred at room temperature under N$_2$ for 1 h. The mixture was filtered through a pad of Celite®. The filtrate was concentrated. The residue was purified by column chromatography (silica gel, eluting with 75% to 100% EtOAc in hexanes) to give compound 270d (0.32 g, 75% yield) as a light yellow waxy solid. m/z=439 (M+1).

Compound 271d: A solution of compound 270d (0.32 g, 0.73 mmol) and 3 N aq. HCl (2.4 mL, 7.2 mmol) in MeOH (25 mL) was stirred at room temperature under N$_2$ overnight. The mixture was concentrated. The residue was partitioned between 10% aq. NH$_4$OH (25 mL) and CHCl$_3$ (25 mL). The organic extract was washed with brine (25 mL), dried with MgSO$_4$, filtered, and concentrated to give compound 271d (0.27 g, 94% yield) as a tan solid. m/z=395 (M+1).

Compound 272d: A solution of compound 271d (0.27 g, 0.68 mmol) in ethyl formate (10 mL, 124 mmol) was treated with sodium methoxide (30 wt. % solution in MeOH, 0.64 mL, 3.41 mmol). The mixture was stirred at room temperature overnight and then concentrated. The residue was partitioned between sat. aq. KH$_2$PO$_4$ (25 mL) and EtOAc (25 mL). The organic extract was washed with brine (25 mL), dried with MgSO$_4$, filtered, and concentrated to give compound 272d (0.31 g, quantitative yield) as a dark yellow-brown oil. m/z=423 (M+1).

Compound 273d: A solution of compound 272d (0.31 g, ≤0.68 mmol) and acetic acid (0.40 mL, 6.99 mmol) in EtOH (5 mL) was treated with hydroxylamine hydrochloride (71 mg, 1.02 mmol). The mixture was heated at 60° C. under N$_2$ for 2 h, stirred at room temperature overnight, and then concentrated. The residue was partitioned between sat. aq. NaHCO$_3$ (25 mL) and CHCl$_3$ (25 mL). The organic extract was washed with brine (25 mL), dried with MgSO$_4$, filtered, and concentrated to give compound 273d (0.23 g, 80% yield) as a yellow-brown solid. m/z=420 (M+1).

Compound 274d: A solution of compound 273d (0.23 g, 0.55 mmol) in MeOH (20 mL) was treated with potassium carbonate (0.38 g, 2.75 mmol). The mixture was stirred at room temperature under N$_2$ for 16 h and then concentrated. The residue was partitioned between sat. aq. KH$_2$PO$_4$ (25 mL) and CHCl$_3$ (25 mL). The organic extract was washed with brine (25 mL), dried with MgSO$_4$, filtered, and concentrated. The residue was purified by column chromatography (silica gel, eluting with 50% EtOAc in hexanes) to give compound 274d (0.13 g, 57% yield) as a light yellow solid. m/z=420 (M+1).

T164: To a stirring solution of compound 274d (0.13 g, 0.31 mmol) in degassed DMF (4 mL) at 0° C. under N$_2$ was added dropwise a solution of 1,3-dibromo-5,5-dimethylhydantoin (53 mg, 0.18 mmol) in degassed DMF (1 mL). The mixture was stirred at 0° C. for 30 min, and then treated with pyridine (0.25 mL, 3.09 mmol). The mixture was heated at 60° C. for 4 h and then concentrated. The residue was partitioned between sat. aq. KH$_2$PO$_4$ (25 mL) and CHCl$_3$ (25 mL). The organic extract was washed with brine (25 mL), dried with MgSO$_4$, filtered, and concentrated. The residue was purified by column chromatography (silica gel, eluting with 50% EtOAc in hexanes) to give compound T164 (100 mg, 77% yield) as an orange solid. m/z=418 (M+1); $^1$H NMR (400 MHz, CDCl$_3$) δ 8.62 (s, 1H), 7.49 (m, 2H), 7.31 (m, 2H), 4.11 (td, J=5.8, 14.8 Hz, 1H), 3.98 (td, J=5.8, 14.8 Hz, 1H), 3.53 (dt, J=2.5, 5.7 Hz, 2H), 3.27 (s, 3H), 2.95 (hept, J=7.0 Hz, 1H), 2.74 (m, 2H), 2.57 (qd, J=6.8, 13.4 Hz, 1H), 2.12 (m, 2H), 1.83 (m, 1H), 1.44 (s, 3H), 1.31 (d, J=6.8 Hz, 3H), 1.27 (d, J=6.9 Hz, 6H).

Compound 269e: In a sealable vial, a solution of compound 173 (0.71 g, 2.81 mmol) and 2-(benzyloxy)-1-etheneamine (0.85 g, 5.62 mmol) in benzene (20 mL) was flushed with N$_2$. The vial was sealed and heated at 80° C. for 4 h. After cooled to room temperature, the reaction mixture was partitioned between sat. aq. KH$_2$PO$_4$ (50 mL) and EtOAc (50 mL). The organic extract was washed with brine (50 mL), dried with MgSO$_4$, filtered, and concentrated. The residue was purified by column chromatography (silica gel, eluting with 25% EtOAc in hexanes) to give compound 269e (0.91 g, 84% yield) as a light yellow oil. m/z=386 (M+1).

Compound 270e: In a scalable vial, a solution of compound 269e (0.91 g, 2.36 mmol) and 4-isopropylbenzaldehyde (0.70 g, 4.72 mmol) in EtOH (10 mL) was treated with ammonium acetate (1.82 g, 23.61 mmol). The mixture was flushed with N$_2$. The vial was sealed and heated at 60° C. overnight. The mixture was concentrated. The residue was diluted with EtOAc (50 mL) and stirred at room temperature under N$_2$ for 1 h. The mixture was filtered through a pad of Celite®. The filtrate was concentrated. The residue was purified by column chromatography (silica gel, eluting with EtOAc) to give compound 270e (1.10 g, 91% yield) as a light yellow oil. m/z=515 (M+1).

Compound 271e: A solution of compound 270e (1.10 g, 2.14 mmol) and 3 N aq. HCl (7.1 mL, 21.3 mmol) in MeOH (100 mL) was stirred at room temperature under N$_2$ overnight. The mixture was concentrated. The residue was partitioned between 10% aq. NH$_4$OH (25 mL) and CHCl$_3$ (25 mL). The organic extract was washed with brine (25 mL), dried with MgSO$_4$, filtered, and concentrated to give compound 271e (0.93 g, 92% yield) as yellow-brown oil. m/z=471 (M+1).

Compound 272e: A solution of compound 271e (0.34 g, 0.72 mmol) in ethyl formate (10 mL, 124 mmol) was treated with sodium methoxide (30 wt. % solution in MeOH, 0.68 mL, 3.62 mmol). The mixture was stirred at room temperature overnight and then concentrated. The residue was partitioned between sat. aq. KH$_2$PO$_4$ (25 mL) and EtOAc (25 mL). The organic extract was washed with brine (25 mL), dried with MgSO$_4$, filtered, and concentrated to give compound 272e (0.34 g, 94% yield) as a light yellow solid. m/z=499 (M+1).

Compound 273e: A solution of compound 272e (0.34 g, 0.68 mmol) and acetic acid (0.40 mL, 6.99 mmol) in EtOH (5 mL) was treated with hydroxylamine hydrochloride (71 mg, 1.02 mmol). The mixture was heated at 60° C. under $N_2$ for 2 h, stirred at room temperature overnight, and then concentrated. The residue was partitioned between sat. aq. $NaHCO_3$ (25 mL) and $CHCl_3$ (25 mL). The organic extract was washed with brine (25 mL), dried with $MgSO_4$, filtered, and concentrated to give compound 273e (0.32 g, 95% yield) as a tan solid. m/z=496 (M+1).

Compound 274e: A solution of compound 273e (0.32 g, 0.64 mmol) in MeOH (20 mL) was treated with potassium carbonate (0.45 g, 3.26 mmol). The mixture was stirred at room temperature under $N_2$ for 16 h and then concentrated. The residue was partitioned between sat. aq. $KH_2PO_4$ (25 mL) and $CHCl_3$ (25 mL). The organic extract was washed with brine (25 mL), dried with $MgSO_4$, filtered, and concentrated. The residue was purified by column chromatography (silica gel, eluting with 50% EtOAc in hexanes) to give compound 274e (0.21 g, 65% yield) as a tan solid. m/z=496 (M+1).

T165: To a stirring solution of compound 274e (0.21 g, 0.42 mmol) in degassed DMF (4 mL) at 0° C. under $N_2$ was added dropwise a solution of 1,3-dibromo-5,5-dimethylhydantoin (73 mg, 0.26 mmol) in degassed DMF (1 mL). The mixture was stirred at 0° C. for 30 min. and then treated with pyridine (0.34 mL, 4.20 mmol). The mixture was heated at 60° C. for 4 h and then concentrated. The residue was partitioned between sat. aq. $KH_2PO_4$ (25 mL) and $CHCl_3$ (25 mL). The organic extract was washed with brine (25 mL), dried with $MgSO_4$, filtered, and concentrated. The residue was purified by column chromatography (silica gel, eluting with 50% EtOAc in hexanes) to give compound T165 (120 mg, 57% yield) as an orange solid. m/z=494 (M+1); $^1H$ NMR (400 MHz, $CDCl_3$) 8.63 (s, 1H), 7.45 (m, 2H), 7.28 (m, 5H), 7.13 (m, 2H), 4.41 (s, 2H), 4.14 (td, J=5.8, 14.8 Hz, 1H), 4.01 (td, J=5.6, 14.7 Hz, 1H), 3.59 (m, 2H), 2.94 (hept, J=6.9 Hz, 1H), 2.72 (m, 1H), 2.59 (m, 2H), 2.05 (m, 2H), 1.78 (qd, J=6.5, 12.9 Hz, 1H), 1.44 (s, 3H), 1.29 (d, J=6.8 Hz, 3H), 1.26 (d, J=6.9 Hz, 6H).

Compound 269f: In a sealable vial, a solution of compound 173 (1.01 g, 4.00 mmol) and benzylamine (0.86 g, 8.02 mmol) in benzene (20 mL) was flushed with $N_2$. The vial was sealed and heated at 80° C. for 4 h. After cooled to room temperature, the reaction mixture was partitioned between sat. aq. $KH_2PO_4$ (50 mL) and EtOAc (50 mL). The organic extract was washed with brine (50 mL), dried with $MgSO_4$, filtered, and concentrated. The residue was purified by column chromatography (silica gel, eluting with 25% EtOAc in hexanes) to give compound 269f (1.10 g, 80% yield) as a light yellow solid. m/z=342 (M+1).

Compound 270f: A solution of compound 269f (1.10 g, 3.22 mmol) and 4-isopropylbenzaldehyde (0.95 g, 6.41 mmol) in EtOH (10 mL) was treated with ammonium acetate (2.48 g, 32.17 mmol). The mixture was stirred at room temperature overnight and then concentrated. The residue was diluted with EtOAc (50 mL) and stirred at room temperature under $N_2$ for 1 h. The mixture was filtered through a pad of Celite®. The filtrate was concentrated. The residue was purified by column chromatography (silica gel, eluting with 50% EtOAc in hexanes) to give compound 270f (1.54 g, quantitative yield) as an off-white solid. m/z=471 (M+1).

Compound 271f: A solution of compound 270f (1.54 g, ≤3.22 mmol) and 3 N aq. HCl (5.5 mL, 16.5 mmol) in MeOH (25 mL) was stirred at room temperature under $N_2$ overnight. The mixture was concentrated. The residue was partitioned between 10% aq. $NH_4OH$ (25 mL) and $CHCl_3$ (25 mL). The organic extract was washed with brine (25 mL), dried with $MgSO_4$, filtered, and concentrated to give compound 271f (1.23 g, 90% yield) as an off-white solid. m/z=427 (M+1).

Compound 272f: A solution of compound 271f (0.50 g, 1.17 mmol) in ethyl formate (10 mL, 124 mmol) was treated with sodium methoxide (30 wt. % solution in MeOH, 1.10 mL, 5.86 mmol). The mixture was stirred at room temperature overnight, and then concentrated. The residue was partitioned between sat. aq. $KH_2PO_4$ (25 mL) and EtOAc (25 mL). The organic extract was washed with brine (25 mL), dried with $MgSO_4$, filtered, and concentrated to give compound 272f (0.61 g, quantitative yield) as a yellow oil. m/z=455 (M+1).

Compound 273f: A solution of compound 272f (0.61 g, ≤1.17 mmol) and acetic acid (0.70 mL, 12.23 mmol) in EtOH (5 mL) was treated with hydroxylamine hydrochloride (0.13 g, 1.87 mmol). The mixture was heated at 60° C. under $N_2$ for 2 h, stirred at room temperature overnight, and then concentrated. The residue was partitioned between sat. aq. $NaHCO_3$ (25 mL) and $CHCl_3$ (25 mL). The organic extract was washed with brine (25 mL), dried with $MgSO_4$, filtered, and concentrated to give compound 273f (0.51 g, 96% yield) as a light yellow solid. m/z=452 (M+1).

Compound 274f: A solution of compound 273f (0.51 g, 1.13 mmol) in MeOH (20 mL) was treated with potassium carbonate (0.78 g, 5.64 mmol). The mixture was stirred at room temperature under $N_2$ for 16 h and then concentrated. The residue was partitioned between sat. aq. $KH_2PO_4$ (25 mL) and $CHCl_3$ (25 mL). The organic extract was washed with brine (25 mL), dried with $MgSO_4$, filtered, and concentrated to give compound 274f (0.53 g, quantitative yield) as alight yellow solid. m/z=452 (M+1).

T166: To a stirring solution of compound 274f (0.15 g, 0.33 mmol) in degassed DMF (4 mL) at 0° C. under $N_2$ was added dropwise a solution of 1,3-dibromo-5,5-dimethylhydantoin (57 mg, 0.20 mmol) in degassed DMF (1 mL). The mixture was stirred at 0° C. for 30 min, and then treated with pyridine (0.27 mL, 3.33 mmol). The mixture was heated at 60° C. for 4 h and then concentrated. The residue was partitioned between sat. aq. $KH_2PO_4$ (25 mL) and $CHCl_3$ (25 mL). The organic extract was washed with brine (25 mL), dried with $MgSO_4$, filtered, and concentrated. The residue was purified by column chromatography (silica gel, eluting with 50% EtOAc in hexanes) to give compound T166 (69 mg, 46% yield) as an orange solid. m/z=450 (M+1); $^1H$ NMR (400 MHz, $CDCl_3$) δ 8.67 (s, 1H), 7.43 (m, 2H), 7.34 (m, 3H), 7.24 (m, 2H), 6.99 (m, 2H), 5.19 (d, J=16.9 Hz, 1H), 5.07 (d, J=16.8 Hz, 1H), 2.91 (hept. J=7.0 Hz, 1H), 2.52 (m, 2H), 2.38 (ddd, J=6.6, 11.0, 16.2 Hz, 1H), 2.07 (m, 2H), 1.77 (ddt, J=6.5, 11.0, 12.9 Hz, 1H), 1.47 (s, 3H), 1.27 (d, J=6.8 Hz, 3H), 1.24 (d, J=6.9 Hz, 6H).

Compound 269g: A solution of compound 173 (0.31 g, 1.23 mmol), and 4-fluorobenzylamine (0.31 g, 2.48 mmol) in benzene (10 mL) was refluxed under $N_2$ overnight. After cooled to room temperature, the reaction mixture was partitioned between sat. aq. $KH_2PO_4$ (50 mL) and EtOAc (50 mL). The organic extract was washed with brine (50 mL), dried with $MgSO_4$, filtered, and concentrated. The residue was purified by column chromatography (silica gel, eluting with 25% EtOAc in hexanes) to give compound 269g (0.36 g, 82% yield) as a viscous yellow oil. m/z=360 (M+1).

Compound 270g: A solution of compound 269g (0.36 g, 1.00 mmol) and 4-isopropylbenzaldehyde (0.30 g, 2.02 mmol) in EtOH (10 mL) was treated with ammonium acetate (0.78 g, 10.12 mmol). The mixture was stirred at room temperature under $N_2$ for 16 h and then concentrated. The residue was diluted with EtOAc (50 mL) and stirred at room temperature under N$_2$ for 1 h. The mixture was filtered through a pad of Celite®. The filtrate was concentrated. The residue was purified by column chromatography (silica gel, eluting with 70% EtOAc in hexanes) to give compound 270g (0.45 g, 92% yield) as an off-white solid. m/z=489 (M+1).

Compound 271g: A solution of compound 270g (0.45 g, 0.92 mmol) and 3 N aq. HCl (3.1 mL, 9.3 mmol) in MeOH (20 mL) was stirred at room temperature under N$_2$ overnight. The mixture was concentrated. The residue was partitioned between 10% aq. NH$_4$OH (25 mL) and CHCl$_3$ (25 mL). The organic extract was washed with brine (25 mL), dried with MgSO$_4$, filtered, and concentrated to give compound 271g (0.37 g, 90% yield) as an off-white solid. m/z=445 (M+1).

Compound 272g: A solution of compound 271g (0.37 g, 0.83 mmol) in ethyl formate (10 mL, 124 mmol) was treated with sodium methoxide (30 wt. % solution in MeOH, 0.80 mL, 4.26 mmol). The mixture was stirred at room temperature overnight and then concentrated. The residue was partitioned between sat. aq. KH$_2$PO$_4$ (25 mL) and EtOAc (25 mL). The organic extract was washed with brine (25 mL), dried with MgSO$_4$, filtered, and concentrated to give compound 272g (0.37 g, 94% yield) as a yellow solid. m/z=473 (M+1).

Compound 273g: A solution of compound 272g (0.37 g, 0.78 mmol) and acetic acid (0.45 mL, 7.86 mmol) in EtOH (5 mL) was treated with hydroxylamine hydrochloride (81 mg, 1.16 mmol). The mixture was heated at 60° C. under N$_2$ for 2 h, stirred at room temperature overnight, and then concentrated. The residue was partitioned between sat. aq. NaHCO$_3$ (25 mL) and CHCl$_3$ (25 mL). The organic extract was washed with brine (25 mL), dried with MgSO$_4$, filtered, and concentrated to give compound 273g (0.35 g, 95% yield) as a light yellow solid. m/z=470 (M+1).

Compound 274g: A solution of compound 273g (0.35 g, 0.74 mmol) in MeOH (10 mL) was treated with potassium carbonate (0.52 g, 3.76 mmol). The mixture was stirred at room temperature under N$_2$ for 16 h and then concentrated. The residue was partitioned between sat. aq. KH$_2$PO$_4$ (25 mL) and CHCl$_3$ (25 mL). The organic extract was washed with brine (25 mL), dried with MgSO$_4$, filtered, and concentrated. The residue was purified by column chromatography (silica gel, eluting with 50% EtOAc in hexanes) to give compound 274g (0.27 g, 77% yield) as a light yellow solid. m/z=470 (M+1).

T167: To a stirring solution of compound 274g (0.27 g, 0.57 mmol) in degassed DMF (4 mL) at 0° C. under N$_2$ was added dropwise a solution of 1,3-dibromo-5,5-dimethylhydantoin (90 mg, 0.31 mmol) in degassed DMF (1 mL). The mixture was stirred at 0° C. for 30 min. and then treated with pyridine (0.46 mL, 5.69 mmol). The mixture was heated at 60° C. for 4 h and then concentrated. The residue was partitioned between sat. aq. KH$_2$PO$_4$ (25 mL) and CHCl$_3$ (25 mL). The organic extract was washed with brine (25 mL), dried with MgSO$_4$, filtered, and concentrated. The residue was purified by column chromatography (silica gel, eluting with 50% EtOAc in hexanes) to give compound T167 (0.14 g, 52% yield) as an orange solid. m/z=468 (M+1): $^1$H NMR (400 MHz, CDCl$_3$) δ 8.65 (s, 1H), 7.41 (m, 2H), 7.26 (m, 2H), 7.04 (m, 2H), 6.96 (m, 2H), 5.16 (d, J=16.7 Hz, 1H), 5.04 (d, J=16.6 Hz, 1H), 2.92 (hept, J=7.0 Hz, 1H), 2.52 (m, 2H), 2.38 (ddd, J=6.6, 11.0, 16.2 Hz, 1H), 2.07 (m, 2H), 1.78 (tdd, J=6.3, 12.9, 19.2 Hz, 1H), 1.46 (s, 3H), 1.28 (d, J=6.8 Hz, 3H), 1.24 (d, J=6.9 Hz, 6H).

Compound 269h: A solution of compound 173 (0.30 g, 1.19 mmol), and 2-fluorobenzylamine (0.30 g, 2.40 mmol) in benzene (10 mL) was refluxed under N$_2$ overnight. After cooled to room temperature, the reaction mixture was partitioned between sat. aq. KH$_2$PO$_4$ (50 mL) and EtOAc (50 mL). The organic extract was washed with brine (50 mL), dried with MgSO$_4$, filtered, and concentrated. The residue was purified by column chromatography (silica gel, eluting with 25% EtOAc in hexanes) to give compound 269h (0.31 g, 72% yield) as a yellow solid. m/z=360 (M+1).

Compound 270h: A solution of compound 269h (0.31 g, 0.86 mmol) and 4-isopropylbenzaldehyde (0.26 g, 1.75 mmol) in EtOH (10 mL) was treated with ammonium acetate (0.67 g, 8.69 mmol). The mixture was stirred at room temperature under N$_2$ for 16 h and then concentrated. The residue was diluted with EtOAc (50 mL) and stirred at room temperature under N$_2$ for 1 h. The mixture was filtered through a pad of Celite®. The filtrate was concentrated. The residue was purified by column chromatography (silica gel, eluting with 70% EtOAc in hexanes) to give compound 270h (0.42 g, 100% yield) as an off-white solid. m/z=489 (M+1).

Compound 271h: A solution of compound 270h (0.42 g, 0.86 mmol) and 3 N aq. HCl (2.9 mL, 8.7 mmol) in MeOH (20 mL) was stirred at room temperature under N$_2$ overnight. The mixture was concentrated. The residue was partitioned between 10% aq. NH$_4$OH (25 mL) and CHCl$_3$ (25 mL). The organic extract was washed with brine (25 mL), dried with MgSO$_4$, filtered, and concentrated to give compound 271h (0.36 g, 94% yield) as an off-white solid. m/z=445 (M+1).

Compound 272h: A solution of compound 271h (0.36 g, 0.81 mmol) in ethyl formate (10 mL, 124 mmol) was treated with sodium methoxide (30 wt. % solution in MeOH, 0.76 mL, 4.05 mmol). The mixture was stirred at room temperature overnight and then concentrated. The residue was partitioned between sat. aq. KH$_2$PO$_4$ (25 mL) and EtOAc (25 mL). The organic extract was washed with brine (25 mL), dried with MgSO$_4$, filtered, and concentrated to give compound 272h (0.37 g, 97% yield) as a yellow solid. m/z=473 (M+1).

Compound 273h: A solution of compound 272h (0.37 g, 0.78 mmol) and acetic acid (0.45 mL, 7.86 mmol) in EtOH (5 mL) was treated with hydroxylamine hydrochloride (81 mg, 1.16 mmol). The mixture was heated at 60° C. under N$_2$ for 2 h, stirred at mom temperature overnight, and then concentrated. The residue was partitioned between sat. aq. NaHCO$_3$ (25 mL) and CHCl$_3$ (25 mL). The organic extract was washed with brine (25 mL), dried with MgSO$_4$, filtered, and concentrated to give compound 273h (0.35 g, 95% yield) as a yellow solid. m/z=470 (M+1).

Compound 274h: A solution of compound 273h (0.35 g, 0.74 mmol) in MeOH (10 mL) was treated with potassium carbonate (0.51 g, 3.69 mmol). The mixture was stirred at room temperature under N$_2$ for 16 h and then concentrated. The residue was partitioned between sat. aq. KH$_2$PO$_4$ (25 mL) and CHCl$_3$ (25 mL). The organic extract was washed with brine (25 mL), dried with MgSO$_4$, filtered, and concentrated. The residue was purified by column chromatography (silica gel, eluting with 50% EtOAc in hexanes) to give compound 274h (0.22 g, 63% yield) as a light yellow solid. m/z=470 (M+1).

T168: To a stirring solution of compound 274h (0.22 g, 0.47 mmol) in degassed DMF (4 mL) at 0° C. under N$_2$ was added dropwise a solution of 1,3-dibromo-5,5-dimethylhydantoin (74 mg, 0.26 mmol) in degassed DMF (1 mL). The mixture was stirred at 0° C. for 30 min, and then treated with pyridine (0.38 mL, 4.70 mmol). The mixture was heated at 60° C. for 4 h and then concentrated. The residue was partitioned between sat. aq. KH$_2$PO$_4$ (25 mL) and CHCl$_3$ (25 mL). The organic extract was washed with brine (25 mL), dried with MgSO$_4$, filtered, and concentrated. The residue was purified by column chromatography (silica gel, eluting with 50% EtOAc in hexanes) to give compound T168 (85 mg, 39% yield) as an orange solid. m/z=468 (M+1); $^1$H NMR (400 MHz, CDCl$_3$) δ 8.66 (s, 1H), 7.41 (m, 2H), 7.29 (m, 1H), 7.25 (m, 2H), 7.10 (m, 2H), 6.71 (dt, J=1.7, 7.8 Hz, 1H), 5.20 (d, J=17.3 Hz, 1H), 5.14 (d, J=17.3 Hz, 1H), 2.92 (hept, J=6.9 Hz, 1H), 2.54 (m, 2H), 2.39 (ddd, J=6.7, 11.0, 16.8 Hz, 1H), 2.08 (m, 2H), 1.79 (m, 1H), 1.47 (s, 3H), 1.28 (d, J=6.8 Hz, 3H), 1.24 (d, J=6.9 Hz, 6H).

Compound 269i: A solution of compound 173 (0.30 g, 1.19 mmol), and 4-chlorobenzylamine (0.34 g, 2.40 mmol) in benzene (10 mL) was refluxed under N$_2$ overnight. After cooled to room temperature, the reaction mixture was partitioned between sat. aq. KH$_2$PO$_4$ (50 mL) and EtOAc (50 mL). The organic extract was washed with brine (50 mL), dried with MgSO$_4$, filtered, and concentrated. The residue was purified by column chromatography (silica gel, eluting with 25% EtOAc in hexanes) to give compound 269i (0.36 g, 80% yield) as a yellow oil. m/z=376 (M+1).

Compound 270i: A solution of compound 269i (0.36 g, 0.96 mmol) and 4-isopropylbenzaldehyde (0.28 g, 1.89 mmol) in EtOH (10 mL) was treated with ammonium acetate (0.74 g, 9.60 mmol). The mixture was stirred at room temperature under N$_2$ for 16 h and then concentrated. The residue was diluted with EtOAc (50 mL) and stirred at room temperature under N$_2$ for 1 h. The mixture was filtered through a pad of Celite®. The filtrate was concentrated. The residue was purified by column chromatography (silica gel, eluting with 70% EtOAc in hexanes) to give compound 270i (0.43 g, 89% yield) as an off-white solid. m/z=505 (M+1).

Compound 271i: A solution of compound 270i (0.43 g, 0.85 mmol) and 3 N aq. HCl (2.9 mL, 8.7 mmol) in MeOH (20 mL) was stirred at room temperature under N$_2$ overnight. The mixture was concentrated. The residue was partitioned between 10% aq. NH$_4$OH (25 mL) and CHCl$_3$ (25 mL). The organic extract was washed with brine (25 mL), dried with MgSO$_4$, filtered, and concentrated to give compound 271i (0.36 g, 92% yield) as an off-white solid. m/z=461 (M+1).

Compound 272i: A solution of compound 271i (0.36 g, 0.78 mmol) in ethyl formate (10 mL, 124 mmol) was treated with sodium methoxide (30 wt. % solution in MeOH, 0.73 mL, 3.89 mmol). The mixture was stirred at room temperature overnight, and then concentrated. The residue was partitioned between sat. aq. KH$_2$PO$_4$ (25 mL) and EtOAc (25 mL). The organic extract was washed with brine (25 mL), dried with MgSO$_4$, filtered, and concentrated to give compound 272i (0.37 g, 97% yield) as a yellow solid. m/z=489 (M+1).

Compound 273i: A solution of compound 272i (0.37 g, 0.76 mmol) and acetic acid (0.45 mL, 7.86 mmol) in EtOH (5 mL) was treated with hydroxylamine hydrochloride (80 mg, 1.16 mmol). The mixture was heated at 60° C. under N$_2$ for 2 h, stirred at room temperature overnight, and then concentrated. The residue was partitioned between sat. aq. NaHCO$_3$ (25 mL) and CHCl$_3$ (25 mL). The organic extract was washed with brine (25 mL), dried with MgSO$_4$, filtered, and concentrated to give compound 273i (0.37 g, quantitative yield) as a yellow solid. m/z=486 (M+1).

Compound 274i: A solution of compound 273i (0.37 g, 0.76 mmol) in MeOH (10 mL) was treated with potassium carbonate (0.53 g, 3.84 mmol). The mixture was stirred at room temperature under N$_2$ for 16 h and then concentrated. The residue was partitioned between sat. aq. KH$_2$PO$_4$ (25 mL) and CHCl$_3$ (25 mL). The organic extract was washed with brine (25 mL), dried with MgSO$_4$, filtered, and concentrated. The residue was purified by column chromatography (silica gel, eluting with 50% EtOAc in hexanes) to give compound 274i (0.26 g, 70% yield) as a light yellow solid. m/z=486 (M+1).

T169: To a stirring solution of compound 274i (0.26 g, 0.53 mmol) in degassed DMF (4 mL) at 0° C. under N$_2$ was added dropwise a solution of 1,3-dibromo-5,5-dimethyl-hydantoin (84 mg, 0.29 mmol) in degassed DMF (1 mL). The mixture was stirred at 0° C. for 30 min, and then treated with pyridine (0.43 mL, 5.32 mmol). The mixture was heated at 60° C. for 4 h and then concentrated. The residue was partitioned between sat. aq. KH$_2$PO$_4$ (25 mL) and CHCl$_3$ (25 mL). The organic extract was washed with brine (25 mL), dried with MgSO$_4$, filtered, and concentrated. The residue was purified by column chromatography (silica gel, eluting with 30% EtOAc in hexanes) to give compound T169 (0.12 g, 46% yield) as an orange solid. m/z=484 (M+1): $^1$H NMR (400 MHz, CDCl$_3$) δ 8.65 (s, 1H), 7.40 (m, 2H), 7.33 (m, 2H), 7.25 (m, 2H), 6.93 (m, 2H), 5.16 (d, J=16.9 Hz, 1H), 5.03 (d, J=16.9 Hz, 1H), 2.92 (hept, J=6.7 Hz, 1H), 2.52 (m, 2H), 2.37 (ddd, J=6.6, 10.9, 16.5 Hz, 1H), 2.07 (m, 2H), 1.77 (m, 1H), 1.46 (s, 3H), 1.27 (d, J=6.8 Hz, 3H), 1.24 (d, J=6.9 Hz, 6H).

Compound 269j: A mixture of compound 173 (225 mg, 0.892 mmol), 2-(aminomethyl)pyridine (0.18 mL, 1.75 mmol), and a catalytic amount of p-toluenesulfonic acid monohydrate in anhydrous toluene (3 mL) was heated in a Biotage microwave synthesizer at 150° C. for 1 h. After cooled to room temperature, the mixture was concentrated, and the residue was purified by column chromatography (silica gel, eluting with EtOAc) to give compound 269j (222 mg, 73% yield) as a yellow viscous oil. m/z=343 (M+1).

Compound 270j: A solution of compound 269j (221 mg, 0.645 mmol) in EtOH (10 mL) was treated with 4-isopropylbenzaldehyde (191 mg, 1.29 mmol) and ammonium acetate (497 mg, 6.45 mmol) sequentially. The reaction mixture was stirred at room temperature for 17 h and then concentrated. The residue was diluted with EtOAc and was washed with sat. aq. NaHCO$_3$. The organic extract was dried with Na$_2$SO$_4$, filtered, and concentrated. The residue was purified by column chromatography (silica gel, eluting with EtOAc) to give compound 270j (273 mg, 90% yield) as a yellow glass. m/z=472 (M+1).

Compound 271j: A solution of compound 270j (321 mg, 0.681 mmol) in THF (30 mL) was treated with 3.0 N aq. HCl (2.27 mL, 6.81 mmol). The reaction mixture was stirred at room temperature for 24 h and then concentrated. The residue was partitioned between EtOAc and sat. aq. NaHCO$_3$. The organic extract was washed with brine, dried with Na$_2$SO$_4$, filtered, and concentrated to give compound 271j (310 mg, quantitative yield) as a yellow glass and was used in the next step without further purification. m/z=428 (M+1).

Compound 273j: A solution of compound 271j (309 mg, ≤0.681 mmol) in ethyl formate (30 mL, 373 mmol) at 0° C. was treated with sodium methoxide (5.4 M in MeOH, 1.33 mL, 7.18 mmol). The reaction mixture was stirred at room temperature for 3 h and then concentrated. The residue was partitioned between EtOAc and sat. aq. KH$_2$PO$_4$. The organic extract was washed with brine, dried with Na$_2$SO$_4$, filtered, and concentrated to give compound 272j. Compound 272j was dissolved in EtOH (30 mL) and treated with 6.0 N aq. HCl (1.20 mL, 7.20 mmol) and hydroxylamine hydrochloride (75 mg, 1.08 mmol) sequentially. The reaction mixture was heated at 60° C. for 4 h and then concentrated. The residue was partitioned between EtOAc and sat. aq. NaHCO$_3$. The organic extract was washed with brine, dried with Na$_2$SO$_4$, filtered, and concentrated to give compound 273j (374 mg, quantitative yield) as a brown viscous oil, which was used in the next step without further purification. m/z=453 (M+1).

Compound 274j: A solution of compound 273j (373 mg, 0.824 mmol) in MeOH (30 mL) was treated with potassium carbonate (228 mg, 1.65 mmol). The reaction mixture was stirred at 50° C. for 6 h. The solvent was removed in vacuo and the residue was partitioned between EtOAc and sat. aq. $KH_2PO_4$. The organic extract was washed with brine, dried with $Na_2SO_4$, filtered, and concentrated. The residue was purified by column chromatography (silica gel, eluting with EtOAc) to give compound 274j (200 mg, 54% yield) as a light yellow glass. m/z=453 (M+1).

T170: A solution of 274j (200 mg, 0.441 mmol) in anhydrous DMF (3 mL) was cooled to 0° C. under nitrogen. A solution of 1,3-dibromo-5,5-dimethylhydantoin (65 mg, 0.23 mmol) in anhydrous DMF (1 mL) was added. The mixture was stirred at 0° C. for 1 h, and then treated with anhydrous pyridine (0.36 mL, 4.45 mmol) was added. The mixture was heated at 60° C. for 4 hours and then cooled to room temperature. The reaction mixture was diluted with EtOAc and washed with sat. aq. $KH_2PO_4$. The organic layer was separated. The aqueous phase was extracted with EtOAc. The combined organic extracts were washed with water and brine, dried with $Na_2SO_4$, filtered, and concentrated. The residue was purified by column chromatography (silica gel, eluting with EtOAc), followed by a second column chromatography (silica gel, eluting with 0% to 2% MeOH in $CH_2Cl_2$) to give partially purified product, which was purified again by preparative TLC (silica gel, eluting with 5% MeOH in $CH_2Cl_2$) to give compound T170 (26 mg, 13% yield) as an orange solid. m/z=451 (M+1): $^1$H NMR (400 MHz, $CDCl_3$) δ 8.66 (s, 1H), 8.60 (ddd, J=0.9, 1.8, 4.9 Hz, 1H), 7.68 (dt, J=1.8, 7.7 Hz, 1H), 7.44 (m, 2H), 7.25 (m, 3H), 6.80 (br d, J=7.9 Hz, 1H), 5.29 (d, J=17.3 Hz, 1H), 5.17 (d, J=17.2 Hz, 1H), 2.91 (hept, J=7.0 Hz, 1H), 2.55 (m, 2H), 2.40 (m, 1H), 2.08 (m, 2H), 1.79 (m, 1H), 1.47 (s, 3H), 1.28 (d. J=6.8 Hz, 3H), 1.23 (d, J=6.9 Hz, 6H).

Compound 269k: A mixture of compound 173 (225 mg, 0.892 mmol), 4-(aminomethyl)pyridine (0.18 mL, 1.75 mmol), and a catalytic amount of p-toluenesulfonic acid monohydrate in anhydrous toluene (3 mL) was heated in a Biotage microwave synthesizer at 150° C. for 1 h. After cooled to room temperature, the mixture was concentrated, and the residue was purified by column chromatography (silica gel, eluting with EtOAc) to give compound 269k (311 mg, quantitative yield) as a yellow viscous oil. m/z=343 (M+1).

Compound 270k: A solution of compound 269k (311 mg, ≤0.892 mmol) in EtOH (15 mL) was treated with 4-isopropylbenzaldehyde (269 mg, 1.82 mmol) and ammonium acetate (700 mg, 9.08 mmol) sequentially. The reaction mixture was stirred at mom temperature for 21 h and then heated at 50° C. for 22 h. The mixture was concentrated. The residue was diluted with EtOAc and was washed with sat. aq. $NaHCO_3$. The organic extract was dried with $Na_2SO_4$, filtered, and concentrated. The residue was purified by column chromatography (silica gel, eluting with 2% MeOH in EtOAc) to give compound 270k (171 mg, 41% yield) as a clear glass. m/z=472 (M+1).

Compound 271k: A solution of compound 270k (221 mg, 0.468 mmol) in THF (20 mL) was treated with 3.0 N aq. HCl (1.56 mL, 4.68 mmol). The reaction mixture was stirred at room temperature for 24 h and then concentrated. The residue was partitioned between EtOAc and sat. aq. $NaHCO_3$. The organic extract was washed with brine, dried with $Na_2SO_4$, filtered, and concentrated to give compound 271k (215 mg, quantitative yield) as a yellow glass and was used in the next step without further purification. m/z=428 (M+1).

Compound 273k: A solution of compound 271k (215 mg, 0.468 mmol) in ethyl formate (25 mL, 311 mmol) at 0° C. was treated with sodium methoxide (5.4 M in MeOH, 0.93 mL, 5.02 mmol). The reaction mixture was stirred at room temperature for 24 h and then concentrated. The residue was partitioned between EtOAc and sat. aq. $KH_2PO_4$. The organic extract was washed with brine, dried with $Na_2SO_4$, filtered, and concentrated to give compound 272k. Compound 272k was dissolved in EtOH (20 mL) and treated with 6.0 N aq. HCl (1.19 mL, 7.14 mmol), and hydroxylamine hydrochloride (52 mg, 0.75 mmol) sequentially. The reaction mixture was heated at 60° C. for 22 h and then concentrated. The residue was partitioned between EtOAc and sat. aq. $NaHCO_3$. The organic extract was washed with brine, dried with $Na_2SO_4$, filtered, and concentrated. The residue was purified by column chromatography (silica gel, eluting with EtOAc) to give compound 273k (142 mg, 67% yield) as a yellow glass. m/z=453 (M+1).

Compound 274k: A solution of compound 273k (141 mg, 0.311 mmol) in MeOH (20 mL) was treated with potassium carbonate (86 mg, 0.623 mmol). The reaction mixture was stirred at room temperature for 16 h and then heated at 50° C. for 6 h. The solvent was removed in vacuo and the residue was partitioned between EtOAc and sat. aq. $KH_2PO_4$. The organic extract was washed with brine, dried with $Na_2SO_4$, filtered, and concentrated. The residue was purified by column chromatography (silica gel, eluting with EtOAc) to give compound 274k (102 mg, 72% yield) as a yellow glass. m/z=453 (M+1).

T171: A solution of 274k (101 mg, 0.223 mmol) in anhydrous DMF (3 mL) was cooled 30 to 0° C. under nitrogen. A solution of 1,3-dibromo-5,5-dimethylhydantoin (35 mg, 0.122 mmol) in anhydrous DMF (1 mL) was added. The mixture was stirred at 0° C. for 1 h and then treated with anhydrous pyridine (0.18 mL, 2.23 mmol) was added. The mixture was heated at 60° C. for 4 hours and then cooled to room temperature. The reaction mixture was diluted with EtOAc and washed with sat. aq. $KH_2PO_4$. The organic layer was separated. The aqueous phase was extracted with EtOAc. The combined organic extracts were washed with water and brine, dried with $Na_2SO_4$, filtered, and concentrated. The residue was purified by column chromatography (silica gel, eluting with 5% MeOH in $CH_2Cl_2$) to give compound T171 (57 mg, 57% yield) as an orange solid. m/z=451 (M+1); $^1$H NMR (400 MHz, $CDCl_3$) δ 8.65 (s, 1H), 8.61 (m, 2H), 7.36 (m, 2H), 7.25 (m, 2H), 6.93 (m, 2H), 5.17 (d, 1H, J=17.5 Hz), 5.07 (d, 1H, J=17.5 Hz), 2.91 (m, 1H), 2.57 (dq, J=13.5, 6.8 Hz, 1H), 2.44 (m, 2H), 2.08 (m, 2H), 1.81 (m, 1H), 1.48 (s, 3H), 1.28 (d, J=6.7 Hz, 3H), 1.23 (d, J=6.9 Hz, 6H).

Compound 275: A mixture of compound 271e (0.59 g, 1.25 mmol) and 10% Pd/C (0.5 g) in EtOH (25 mL) was hydrogenated (balloon pressure) at room temperature for 3 days. The mixture was filtered, and the filtrate was concentrated to give compound 275 (0.38 g, 80% yield) as tan solid. m/z=381 (M+1).

Compound 276: A solution of compound 275 (0.38 g, 1.00 mmol) in ethyl formate (10 mL, 124 mmol) was treated with sodium methoxide (30 wt. % solution in MeOH, 0.94 mL, 5.01 mmol). The mixture was stirred at room temperature overnight and then concentrated. The residue was partitioned between sat. aq. $KH_2PO_4$ (25 mL) and EtOAc (25 mL). The organic extract was washed with brine (25 mL), dried with MgSO$_4$, filtered, and concentrated to give compound 276 (0.37 g, 90% yield) as a dark yellow solid. m/z=409 (M+1).

Compound 277: A solution of compound 276 (0.37 g, 0.91 mmol) and acetic acid (0.52 mL, 9.08 mmol) in EtOH (5 mL) was treated with hydroxylamine hydrochloride (94 mg, 1.35 mmol). The mixture was heated at 60° C. under N$_2$ for 2 h, stirred at room temperature overnight, and then concentrated. The residue was partitioned between sat. aq. NaHCO$_3$ (25 mL) and CHCl$_3$ (25 mL). The organic extract was washed with brine (25 mL), dried with MgSO$_4$, filtered, and concentrated to give compound 277 (0.34 g, 93% yield) as a tan solid. m/z=406 (M+1).

Compound 278: A solution of compound 277 (0.34 g, 0.83 mmol) in MeOH (10 mL) was treated with potassium carbonate (0.54 g, 3.91 mmol). The mixture was stirred at room temperature under N$_2$ for 16 h and then concentrated. The residue was partitioned between sat. aq. KH$_2$PO$_4$ (25 mL) and CHCl$_3$ (25 mL). The organic extract was washed with brine (25 mL), dried with MgSO$_4$, filtered, and concentrated. The residue was purified by column chromatography (silica gel, eluting with 75% EtOAc in hexanes) to give compound 278 (0.16 g, 47% yield) as a light yellow solid. m/z=406 (M+1).

T172: To a stirring solution of compound 278 (0.16 g, 0.39 mmol) in degassed DMF (4 mL) at 0° C. under N$_2$ was added dropwise a solution of 1,3-dibromo-5,5-dimethyl-hydantoin (68 mg, 0.24 mmol) in degassed DMF (1 mL). The mixture was stirred at 0° C. for 30 min, and then treated with pyridine (0.32 mL, 3.96 mmol). The mixture was heated at 60° C. for 4 h and then concentrated. The residue was partitioned between sat. aq. KH$_2$PO$_4$ (25 mL) and CHCl$_3$ (25 mL). The organic extract was washed with brine (25 mL), dried with MgSO$_4$, filtered, and concentrated. The residue was purified by column chromatography (silica gel, eluting with 75% EtOAc in hexanes) to give compound T172 (85 mg, 53% yield) as an orange solid. m/z=404 (M+1): $^1$H NMR (400 MHz, CDCl$_3$) δ 8.61 (s, 1H), 7.49 (m, 2H), 7.31 (m, 2H), 4.13 (td, J=5.9, 14.7 Hz, 1H), 3.99 (td, J=5.7, 14.6 Hz, 1H), 3.79 (m, 2H), 2.95 (hept, J=7.0 Hz, 1H), 2.74 (m, 2H), 2.57 (qd, J=6.8, 13.5 Hz, 1H), 2.12 (m, 2H), 1.84 (qd, J=6.3, 17.3 Hz, 1H), 1.44 (s, 3H), 1.31 (d, J=6.7 Hz, 3H), 1.27 (d, J=6.9 Hz, 6H).

Compound 279: A solution of compound 270f (0.22 g, 0.47 mmol) in EtOAc (20 mL) was treated with 10% Pd/C (0.20 g). The mixture was hydrogenated (balloon pressure) at room temperature for 16 h and filtered. The filtrate was concentrated to give compound 279 (0.18 g, quantitative yield) as an off-white solid. m/z=381 (M+1).

Compound 280: A solution of compound 279 (0.44 g, 1.16 mmol) and 3 N aq. HCl (3.9 mL, 11.7 mmol) in MeOH (20 mL) was stirred at room temperature under N$_2$ overnight. The mixture was concentrated. The residue was partitioned between 10% aq. NH$_4$OH (25 mL) and CHCl$_3$ (25 mL). The organic extract was washed with brine (25 mL), dried with MgSO$_4$, filtered, and concentrated to give compound 280 (0.39 g, 100% yield) as an off-white solid. m/z=337 (M+1).

Compound 281: A solution of compound 280 (0.43 g, 1.28 mmol) in ethyl formate (10 mL, 124 mmol) was treated with sodium methoxide (30 wt. % solution in MeOH, 1.20 mL, 6.46 mmol). The mixture was stirred at room temperature overnight and then concentrated. The residue was partitioned between sat. aq. KH$_2$PO$_4$ (25 mL) and EtOAc (25 mL). The organic extract was washed with brine (25 mL), dried with MgSO$_4$, filtered, and concentrated to give compound 281 (0.36 g, 77% yield) as a yellow solid. m/z=365 (M+1).

Compound 282: A solution of compound 281 (0.36 g, 0.99 mmol) and acetic acid (0.57 mL, 9.96 mmol) in EtOH (5 mL) was treated with hydroxylamine hydrochloride (0.14 g, 2.01 mmol). The mixture was heated at 60° C. under N$_2$ for 2 h, stirred at room temperature overnight, and then concentrated. The residue was partitioned between sat. aq. NaHCO$_3$ (25 mL) and CHCl$_3$ (25 mL). The organic extract was washed with brine (25 mL), dried with MgSO$_4$, filtered, and concentrated to give compound 282 (0.31 g, 86% yield) as a yellow solid. m/z=362 (M+1).

Compound 283: A solution of compound 282 (0.31 g, 0.86 mmol) in MeOH (20 mL) was treated with potassium carbonate (0.60 g, 4.34 mmol). The mixture was stirred at room temperature under N$_2$ for 16 h and then concentrated. The residue was partitioned between sat. aq. KH$_2$PO$_4$ (25 mL) and CHCl$_3$ (25 mL). The organic extract was washed with brine (25 mL), dried with MgSO$_4$, filtered, and concentrated. The residue was purified by column chromatography (silica gel, eluting with 5% MeOH in CHCl$_3$) to give compound 283 (0.19 g, 61% yield) as a light yellow solid. m/z=362 (M+1).

T173: To a stirring solution of compound 283 (0.19 g, 0.52 mmol) in degassed DMF (4 mL) at 0° C. under N$_2$ was added dropwise a solution of 1,3-dibromo-5,5-dimethyl-hydantoin (83 mg, 0.29 mmol) in degassed DMF (1 mL). The mixture was stirred at 0° C. for 30 min, and then treated with pyridine (0.42 mL, 5.19 mmol). The mixture was heated at 60° C. for 4 h and then concentrated. The residue was partitioned between sat. aq. KH$_2$PO$_4$ (25 mL) and CHCl$_3$ (25 mL). The organic extract was washed with brine (25 mL), dried with MgSO$_4$, filtered, and concentrated. The residue was purified by column chromatography (silica gel, eluting with 2.5% MeOH in CHCl$_3$) to give compound T173 (79 mg, 42% yield) as an orange solid. m/z=360 (M+1); $^1$H NMR (400 MHz, CDCl$_3$) δ 8.92 (bs, 1H), 8.63 (s, 1H), 7.68 (m, 2H), 7.28 (m, 2H), 2.93 (m, 1H), 2.76 (m, 2H), 2.57 (dq, J=13.5, 6.8 Hz, 1H), 2.12 (m, 2H), 1.85 (m, 1H), 1.45 (s, 3H), 1.30 (d, J=6.8 Hz, 3H), 1.26 (d, J=6.9 Hz, 6H).

T174: A mixture of compound T173 (48 mg, 0.13 mmol) and sodium acetate (55 mg, 0.67 mmol) in acetic anhydride (2 mL, 21.16 mmol) was stirred at 100° C. under N$_2$ overnight. After cooling to room temperature, the mixture was filtered. The filtrate was concentrated, and the residue was purified by column chromatography (silica gel, eluting with 50% EtOAc in hexanes) to give compound T174 (26 mg, 48% yield) as an orange solid. m/z=402 (M+1); $^1$H NMR (400 MHz, CDCl$_3$) δ 8.54 (s, 1H), 7.43 (m, 2H), 7.34 (m, 2H), 3.01 (m, 2H), 2.84 (ddd, J=6.7, 11.1, 17.9 Hz, 1H), 2.56 (qd, J=6.7, 13.4 Hz, 1H), 2.11 (s, 3H), 2.10 (m, 2H), 1.80 (m, 1H), 1.45 (s, 3H), 1.31 (d, J=6.8 Hz, 3H), 1.28 (d, J=6.9 Hz, 6H).

Compound 285: A mixture of compound 284 (3.0 g, 17.12 mmol), Boc-hydrazide (2.26 g, 17.10 mmol) and glacial acetic acid (1.95 mL, 34.06 mmol) in MeOH (100 mL) was stirred at room temperature for 1 h. Sodium cyanoborohydride (2.15 g, 34.21 mmol) was added. After stirring at room temperature for 21 h, the reaction mixture was diluted with water (250 mL) and extracted with EtOAc (2×100 mL). The combined organic extracts were washed with brine, dried with Na$_2$SO$_4$, filtered, and concentrated to give compound 285 (4.94 g, 99% yield) as a clear viscous oil which solidified upon standing. m/z=292 (M+1).

Compound 286: A mixture of compound 285 (4.94 g, 16.95 mmol) in hydrogen chloride solution (5~6 N in isopropanol, 100 mL) was stirred at 45° C. for 20 h. Upon cooling, the precipitated white solid was collected by filtration, washed with EtOAc, and dried in vacuo at 40° C. to give compound 286 (3.58 g, 80% yield). m/z=192 (M+1).

Compounds 287a and 287b: A solution of compound 101 (114 mg, 0.333 mmol) and 286 (152 mg, 0.667 mmol) in n-butanol (5 mL) was heated at 110° C. for 43 h. After cooled to room temperature, the reaction mixture was partitioned between EtOAc and sat. aq. $KH_2PO_4$. The organic extract was washed with brine, dried with $Na_2SO_4$, filtered, and concentrated. The residue was purified by column chromatography (silica gel, eluting with 20% EtOAc in hexanes) to give compound 287a and 287b (~1/1 mixture, 96 mg, 58% yield). m/z=497 (M+1).

Compounds 288a and 288b: A solution of 287a and 287b (93 mg, 0.187 mmol) in MeOH (20 mL) was treated with potassium carbonate (52 mg, 0.377 mmol). The reaction mixture was stirred at room temperature for 14 h followed by heated at 50° C. for 4 h. The solvent was removed in vacuo and the residue was partitioned between EtOAc and sat. aq. $KH_2PO_4$. The organic extract was washed with brine, dried with $Na_2SO_4$, filtered, and concentrated to give compound 288a and 288b (83 mg, 89% yield) as a yellow glass, which was used in the next step without further purification. m/z=497 (M+1).

T175 (mixture of compounds 289a and 289b): A solution of compound 288a and 288b (83 mg, 0.167 mmol) in toluene (10 mL) under nitrogen was treated with DDQ (49 mg, 0.217 mmol). The reaction mixture was stirred at room temperature for 3 h, and then concentrated. The residue was diluted with EtOAc and washed with sat. aq. $NaHCO_3$ and brine. The organic extract was dried with $Na_2SO_4$, filtered, and concentrated. The residue was purified by column chromatography (silica gel, eluting with 40% EtOAc in hexanes) to give compound T175 (mixture of compound 289a and 289b, 19 mg, 23% yield) as an orange solid. 289a/289b: m/z=495 (M+1); $^1$H NMR (400 MHz, $CDCl_3$) Mixture of regioisomers in 3/1 ratio. Major isomer: δ 8.15 (s, 1H), 7.57 (dt, J=1.9, 7.6 Hz, 1H), 7.26 (m, 3H), 7.11 (ddd, J=1.2, 8.2, 10.6 Hz, 1H), 6.89 (m, 4H), 4.19 (tdd, J=4.1, 7.4, 11.4 Hz, 1H), 3.89 (m, 2H), 3.77 (br d, J=12.9 Hz, 1H), 2.94 (m, 2H), 2.63 (m, 5H), 2.29 (dt, J=1.9, 12.5 Hz, 1H), 2.16 (m, 1H), 2.00 (m, 1H), 1.60 (m, 1H), 1.56 (s, 3H), 1.37 (d, J=6.8 Hz, 3H).

Compound 290: In a sealable vial, a mixture of compound 44 (0.22 g, 0.46 mmol), 3-methyl-5-(4,4,5,5-tetramethyl-1,3,2-dioxaborolan-2-yl)pyridazine (0.10 g, 0.45 mmol), and potassium carbonate (0.19 g, 1.37 mmol) in 1,4-dioxane (4 mL) and DMF (1 mL) was degassed. [1,1'-Bis(diphenylphosphino)ferrocene]dichloropalladium(II) (34 mg, 0.046 mmol) was added. The mixture was degassed again. The vial was sealed and heated at 100° C. for 16 h. After cooled to room temperature, the mixture was diluted with EtOAc (50 mL) and washed with sat. aq. $KH_2PO_4$ (50 mL). The organic extract was washed with brine, dried with $MgSO_4$, filtered, and concentrated. The residue was purified by column chromatography (silica gel, eluting with 5% MeOH in $CHCl_3$) to give compound 290 (0.21 g, 93%) as a light brown solid. m/z=490 (M+1).

T176: To a stirring solution of compound 290 (0.21 g, 0.43 mmol) in degassed DMF (4 mL) at 0° C. under $N_2$ was added dropwise a solution of 1,3-dibromo-5,5-dimethylhydantoin (61 mg, 0.21 mmol) in degassed DMF (1 mL). The mixture was stirred at 0° C. for 30 min, and then treated with pyridine (0.35 mL, 4.33 mmol). The mixture was heated at 60° C. for 4 h and then concentrated. The residue was partitioned between sat. aq. $KH_2PO_4$ (25 mL) and $CHCl_3$ (25 mL). The organic extract was washed with brine (25 mL), dried with $MgSO_4$, filtered, and concentrated. The residue was purified by column chromatography (silica gel, eluting with 5% MeOH in $CHCl_3$) to give compound T176 (0.12 g, 57% yield) as a tan solid. m/z=488 (M+1); $^1$H NMR (400 MHz, $CDCl_3$) δ 9.38 (d, J=2.3 Hz, 1H), 9.23 (d, J=1.4 Hz, 1H), 8.72 (d, J=5.3 Hz, 1H), 7.92 (m, 3H), 7.70 (m, 2H), 7.60 (d, J=2.3 Hz, 1H), 7.54 (s, 1H), 3.42 (dd, J=5.6, 17.3 Hz, 1H), 3.00 (ddd, J=6.9, 11.7, 18.1 Hz, 1H), 2.85 (s, 3H), 2.56 (td, J=6.7, 13.4 Hz, 1H), 2.27 (dt, J=2.1, 12.7 Hz, 1H), 2.18 (dd, J=6.9, 13.8 Hz, 1H), 1.84 (m, 1H), 1.63 (s, 3H), 1.34 (d, J=6.7 Hz, 3H).

Compound 291: In a sealable vial, a mixture of compound 154 (0.21 g, 0.44 mmol), 3-methyl-5-(4,4,5,5-tetramethyl-1,3,2-dioxaborolan-2-yl)pyridazine (0.14 g, 0.64 mmol) and potassium carbonate (0.18 g, 1.30 mmol) in 1,4-dioxane (4 mL) and DMF (1 mL) was degassed. [1,1'-Bis(diphenylphosphino)ferrocene]dichloropalladium(II) (31 mg, 0.042 mmol) was added. The mixture was degassed again. The vial was sealed and heated at 100° C. for 16 h. After cooled to room temperature, the mixture was diluted with EtOAc (50 mL) and washed with sat. aq. $KH_2PO_4$ (50 mL). The organic extract was washed with brine (50 mL), dried with $MgSO_4$, filtered, and concentrated. The residue was purified by column chromatography (silica gel, eluting with 10% MeOH in $CHCl_3$) to give compound 291 (0.13 g, 59% yield) as a brown solid. m/z=506 (M+1).

T177: To a stirring solution of compound 291 (0.13 g, 0.26 mmol) in degassed DMF (4 mL) at 0° C. under $N_2$ was added dropwise a solution of 1,3-dibromo-5,5-dimethylhydantoin (37 mg, 0.13 mmol) in degassed DMF (1 mL). The mixture was stirred at 0° C. for 30 min, and then treated with pyridine (0.21 mL, 2.60 mmol). The mixture was heated at 60° C. for 4 h and then concentrated. The residue was partitioned between sat. aq. $KH_2PO_4$ (25 mL) and $CHCl_3$ (25 mL). The organic extract was washed with brine (25 mL), dried with $MgSO_4$, filtered, and concentrated. The residue was purified by column chromatography (silica gel, eluting with 5% MeOH in $CHCl_3$) to give compound T177 (78 mg, 60% yield) as a light yellow solid. m/z=504 (M+1); $^1$H NMR (400 MHz, $CDCl_3$) δ 9.38 (d, J=2.3 Hz, 1H), 7.89 (m, 2H), 7.70 (m, 4H), 7.59 (m, 2H), 7.12 (m, 2H), 2.93 (m, 2H), 2.85 (s, 3H), 2.57 (qd, J=6.7, 13.4 Hz, 1H), 2.28 (dt, J=2.1, 12.7 Hz, 1H), 2.17 (dd, J=6.4, 13.9 Hz, 1H), 1.84 (ddd, J=6.1, 12.2, 18.8 Hz, 1H), 1.63 (s, 3H), 1.34 (d, J=6.7 Hz, 3H).

Compound 292: In a sealable vial, a mixture of compound 154 (0.85 g, 1.73 mmol), bis(pinacolato)diboron (0.66 g, 2.60 mmol) and potassium acetate (0.51 g, 5.20 mmol) in 1,4-dioxane (17 mL) was degassed. 1,1'-Bis(diphenylphosphino)ferrocene-palladium (II) chloride (0.13 g, 0.18 mmol) was added. The mixture was degassed again. The vial was sealed. The mixture was heated at 100° C. for 16 h. After cooled to room temperature, the mixture was diluted with EtOAc (50 mL) and filtered. The filtrate was washed with sat. aq. $KH_2PO_4$ (50 mL) and sat. aq. NaCl (50 mL). The organic extract was dried with $MgSO_4$, filtered, and concentrated. The residue was purified by column chromatography (silica gel, eluting with 50% EtOAc in hexanes) to give partially purified compound 292 (0.98 g, quantitative yield) as a light yellow solid. m/z=540 (M+1).

Compound 293a: In a sealable vial, a mixture of compound 292 (0.30 g, 0.56 mmol), 3-bromopyridazine (0.11 g, 0.69 mmol) and $K_3PO_4$ (0.35 g, 1.65 mmol) in 1,4-dioxane (4 mL) and DMF (1 mL) was degassed. Tetrakis(triphenylphosphine)palladium (0) (65 mg, 0.056 mmol) was added. The mixture was degassed again. The vial was sealed. The mixture was heated at 100° C. for 16 h and cooled to room temperature. The mixture was diluted with EtOAc (50 mL) and washed with sat. aq. $KH_2PO_4$ (50 mL). The organic extract was washed with sat. aq. NaCl solution (50 mL), dried with MgSO$_4$, filtered, and concentrated. The residue was purified by column chromatography (silica gel, eluting with 10% MeOH in CHCl$_3$) to give compound 293a (0.13 g, 48% yield) as a light yellow solid. m/z=492 (M+1).

T178: To a stirring solution of compound 293a (0.13 g, 0.26 mmol) in degassed DMF (4 mL) at 0° C. under N$_2$ was added dropwise a solution of 1,3-dibromo-5,5-dimethylhydantoin (38 mg, 0.13 mmol) in degassed DMF (1 mL). The mixture was stirred at 0° C. for 30 min, and then pyridine (0.21 mL, 2.60 mmol) was added. The mixture was heated at 60° C. for 4 h and then concentrated. The residue was partitioned between sat. aq. KH$_2$PO$_4$ (25 mL) and EtOAc (25 mL). The organic extract was washed with sat. aq. NaCl solution (25 mL), dried with MgSO$_4$, filtered, and concentrated. The residue was purified by column chromatography (silica gel, eluting with 5% MeOH in CHCl$_3$). The impure product obtained was triturated with Et$_2$O. The solid was collected by filtration and dried under vacuum to give T178 (41 mg, 32% yield) as an off-white solid. m/z=490 (M+1): $^1$H NMR (400 MHz, CDCl$_3$) δ 9.25 (dd, J=1.6, 4.9 Hz, 1H), 8.36 (m, 2H), 7.99 (dd, J=1.6, 8.6 Hz, 1H), 7.70 (m, 4H), 7.64 (dd, J=4.9, 8.6 Hz, 1H), 7.62 (s, 1H), 7.11 (m, 2H), 2.91 (m, 2H), 2.56 (td, J=6.7, 13.4 Hz, 1H), 2.28 (dt, J=2.0, 12.8 Hz, 1H), 2.17 (dd, J=6.3, 13.9 Hz, 1H), 1.83 (m, 1H), 1.63 (s, 3H), 1.34 (d, J=6.7 Hz, 3H).

Compound 293b: In a sealable vial, a mixture of compound 292 (0.28 g, 0.52 mmol), 3-chloro-5-methylpyridazine (83 mg, 0.64 mmol), and K$_3$PO$_4$ (0.33 g, 1.55 mmol) in 1,4-dioxane (4 mL) and DMF (1 mL) was degassed. Tetrakis(triphenylphosphine)palladium(0) (60 mg, 0.052 mmol) was added. The mixture was degassed again. The vial was sealed. The mixture was heated at 90° C. for 2 days. After cooled to room temperature, the mixture was diluted with EtOAc (50 mL) and washed with sat. aq. KH$_2$PO$_4$ (50 mL). The organic extract was washed with sat. aq. NaCl solution (50 mL), dried with MgSO$_4$, filtered, and concentrated. The residue was purified by column chromatography twice (silica gel, eluting with 5% MeOH in CHCl$_3$) to give compound 293b (0.12 g, 46% yield) as an off-white solid. m/z=506 (M+1).

T179: To a stirring solution of compound 293b (0.12 g, 0.24 mmol) in degassed DMF (4 mL) at 0° C. under N$_2$ was added dropwise a solution of 1,3-dibromo-5,5-dimethylhydantoin (34 mg, 0.12 mmol) in degassed DMF (1 mL). The mixture was stirred at 0° C. for 30 min. and then pyridine (0.19 mL, 2.35 mmol) was added. The mixture was heated at 60° C. for 4 h and then concentrated. The residue was partitioned between sat. aq. KH$_2$PO$_4$ (25 mL) and EtOAc (25 mL). The organic extract was washed with sat. aq. NaCl solution (25 mL), dried with MgSO$_4$, filtered, and concentrated. The residue was purified by column chromatography (silica gel, eluting with 2% MeOH in CHCl$_3$) to give partially purified product. The product obtained was triturated with Et$_2$O. The solid was collected by filtration and dried under vacuum to give T179 (51 mg, 43% yield) as an off-white solid. m/z=504 (M+1): $^1$H NMR (400 MHz, CDCl$_3$) δ 9.09 (d, J=2.2 Hz, 1H), 8.34 (m, 2H), 7.79 (m, 1H), 7.69 (m, 4H), 7.61 (s, 1H), 7.12 (m, 2H), 2.95 (ddd, J=1.6, 6.4, 16.0 Hz, 1H), 2.86 (m, 1H), 2.57 (qd, J=6.7, 13.4 Hz, 1H), 2.49 (s, 3H), 2.27 (dt, J=2.0, 12.8 Hz, 1H), 2.16 (dd, J=6.4, 13.8 Hz, 1H), 1.83 (tdd, J=6.3, 12.7, 19.1 Hz, 1H), 1.62 (s, 3H), 1.33 (d, J=6.7 Hz, 3H).

Compound 295: To a stirring solution of compound 294 (1.00 g, 2.35 mmol) in CH$_2$Cl$_2$ (25 mL) at −10° C. under N$_2$ was added dropwise diisobutylaluminum hydride (1.2 M in toluene, 4.9 mL, 5.9 mmol). After stirring for 1 h, the reaction was quenched by dropwise addition of sat. aq. potassium sodium tartrate (25 mL). After stirring for another 1 h, the cold mixture was treated with sat. aq. KH$_2$PO$_4$ (25 mL). The cold bath was removed, and the mixture was stirred at room temperature for 1 h. The organic layer was separated, washed with sat. aq. NaCl (25 mL), dried with MgSO$_4$, filtered, and concentrated to give compound 295 (0.99 g, quantitative yield) as a light yellow liquid.

Compound 296: To a stirring solution of compound 295 (0.99 g, ≤2.35 mmol) in MeOH (25 mL) at 0° C. under N$_2$ was added in one portion sodium borohydride (89 mg, 2.35 mmol). The mixture was stirred at 0° C. for 1 h, at room temperature for 1 h, and then concentrated. The residue was partitioned between sat. aq. KH$_2$PO$_4$ (25 mL) and EtOAc (25 mL). The organic extract was washed with sat. aq. NaCl solution (25 mL), dried with MgSO$_4$, filtered, and concentrated to give compound 2% (0.99 g, quantitative yield) as yellow liquid. m/z=400 (M+1).

Compound 297: A solution of compound 296 (0.99 g, ≤2.35 mmol) and triethylamine (0.41 mL, 2.94 mmol) in CH$_2$Cl$_2$ (20 mL) at 0° C. under N$_2$ was treated with methanesulfonyl chloride (0.33 g, 2.88 mmol). The mixture was stirred at 0° C. for 1 h and then quenched with sat. aq. KH$_2$PO$_4$ (25 mL). The mixture was stirred at room temperature for 1 h. The organic layer was separated, washed with sat. aq. NaCl (25 mL), dried with MgSO$_4$, filtered, and concentrated to give compound 297 (1.03 g, 92% yield) as a red-yellow liquid. m/z=478 (M+1).

Compound 298: A solution of compound 297 (1.03 g, 2.16 mmol) in CH$_3$CN (20 mL) at room temperature under N$_2$ was treated with dropwise addition of tetrabutylammonium fluoride (1.0 M solution in THF, 2.7 mL, 2.7 mmol). After the addition was complete, the mixture was heated at 60° C. for 16 h and then cooled and concentrated. The residue was partitioned between sat. aq. NaHCO$_3$ (50 mL) and EtOAc (50 mL). The organic extract was washed with sat. aq. NaCl (50 mL), dried with MgSO$_4$, filtered, and concentrated. The residue was purified by column chromatography (silica gel, eluting with 20% EtOAc in hexanes) to give compound 298 (0.20 g, 23% yield) as a light yellow liquid. m/z=402 (M+1).

Compound 299: In a sealable vial, a solution of compound 146 (0.22 g, 0.46 mmol) and compound 298 (0.23 g, 0.57 mmol) in 1,4-dioxane (5 mL) was degassed. Tetrakis(triphenylphosphine)palladium(0) (53 mg, 0.046 mmol) was added. The mixture was degassed again. The vial was sealed and heated at 120° C. for 48 h. After cooled to room temperature, the mixture was partitioned between sat. aq. KH$_2$PO$_4$ (50 mL) and EtOAc (50 mL). The organic extract was washed with sat. aq. NaCl (50 mL), dried with MgSO$_4$, filtered, and concentrated. The residue was purified by column chromatography (silica gel, eluting with 5% MeOH in CHCl$_3$) to give partially purified product, which was purified again by column chromatography (silica gel, eluting with 5% MeOH in EtOAc) to give compound 299 (55 mg, 24% yield) as a light yellow solid. m/z=506 (M+1).

T180: To a stirring solution of compound 299 (55 mg, 0.11 mmol) in degassed DMF (4 mL) at 0° C. under N$_2$ was added dropwise a solution of 1,3-dibromo-5,5-dimethylhydantoin (16 mg, 0.056 mmol) in degassed DMF (1 mL). The mixture was stirred at 0° C. for 30 min, and then pyridine (0.10 mL, 1.24 mmol) was added. The mixture was heated at 60° C. for 4 h and then concentrated. The residue was partitioned between sat. aq. KH$_2$PO$_4$ (25 mL) and EtOAc (25 mL). The organic extract was washed with sat. aq. NaCl solution (25 mL), dried with MgSO$_4$, filtered, and concentrated. The residue was purified by column chromatography (silica gel, eluting with 5% MeOH in CHCl$_3$) to give compound T180 (22 mg, 40% yield) as light yellow solid. m/z=504 (M+1); $^1$H NMR (400 MHz, CDCl$_3$) δ 8.97 (br s, 1H), 8.71 (d, J=5.1 Hz, 1H), 8.60 (d, J=4.7 Hz, 1H), 8.07 (td, J=2.0, 8.0 Hz, 1H), 7.91 (m, 2H), 7.77 (br s, 1H), 7.66 (m, 2H), 7.61 (s, 1H), 7.54 (m, 1H), 7.36 (dd, J=4.8, 8.0 Hz, 1H), 5.60 (d, J=46.8 Hz, 2H), 3.00 (dd, J=5.9, 16.2 Hz, 1H), 2.91 (m, 1H), 2.58 (qd, J=6.7, 13.4 Hz, 1H), 2.30 (m, 1H), 2.20 (dd, J=6.3, 13.9 Hz, 1H), 1.85 (tdd, J=6.3, 12.7, 19.0 Hz, 1H), 1.64 (s, 3H), 1.35 (d, J=6.7 Hz, 3H).

Compound 300: In a scalable vial, a solution of compound 154 (0.24 g, 0.49 mmol) and compound 298 (0.20 g, 0.50 mmol) in 1,4-dioxane (5 mL) was degassed. Tetrakis(triphenylphosphine)palladium (56 mg, 0.048 mmol) was added. The mixture was degassed again. The vial was sealed and heated at 120° C. for 16 h. After cooled to room temperature, the mixture was partitioned between sat. aq. KH$_2$PO$_4$ (50 mL) and EtOAc (50 mL). The organic extract was washed with sat. aq. NaCl (50 mL), dried with MgSO$_4$, filtered, and concentrated. The residue was purified by column chromatography (silica gel, eluting with 5% MeOH in CHCl$_3$) to give partially purified product, which was purified again by column chromatography (silica gel, eluting with EtOAc) to give compound 300 (71 mg, 28% yield) as a light yellow solid. m/z=523 (M+1).

T181: To a stirring solution of compound 300 (71 mg, 0.14 mmol) in degassed DMF (4 mL) at 0° C. under N$_2$ was added dropwise a solution of 1,3-dibromo-5,5-dimethylhydantoin (20 mg, 0.070 mmol) in degassed DMF (1 mL). The mixture was stirred at 0° C. for 30 min, and then pyridine (0.11 mL, 1.36 mmol) was added. The mixture was heated at 60° C. for 4 h and then concentrated. The residue was partitioned between sat. aq. KH$_2$PO$_4$ (25 mL) and EtOAc (25 mL). The organic extract was washed with sat. aq. NaCl (25 mL), dried with MgSO$_4$, filtered, and concentrated. The residue was purified by column chromatography (silica gel, eluting with 2% MeOH in CHCl$_3$) to give compound T181 (24 mg, 34% yield) as light yellow solid. m/z=521 (M+1); $^1$H NMR (400 MHz, CDCl$_3$) δ 8.70 (d, J=5.1 Hz, 1H), 7.89 (m, 2H), 7.76 (m, 1H), 7.71 (m, 2H), 7.65 (m, 3H), 7.54 (m, 1H), 7.12 (m, 2H), 5.60 (d, J=46.8 Hz, 2H), 2.95 (dd, J=6.1, 15.9 Hz, 1H), 2.87 (m, 1H), 2.57 (qd, J=6.7, 13.4 Hz, 1H), 2.28 (dt, J=2.0, 12.7 Hz, 1H), 2.17 (dd, J=6.4, 13.8 Hz, 1H), 1.83 (ddd, J=6.4, 12.6, 19.2 Hz, 1H), 1.62 (s, 3H), 1.34 (d, J=6.7 Hz, 3H).

Compound 301: In sealable vial, a solution of compound 156a (0.25 g, 0.57 mmol) in EtOH (20 mL) was treated with hydroxylamine (50 wt. % aq. solution, 0.24 g, 3.63 mmol). The mixture was flushed with N$_2$. The vial was sealed and heated at 80° C. under N$_2$ for 16 h. The mixture was concentrated and dried under vacuum to give compound 301 (0.24 g, 89% yield) as a light yellow solid. m/z=472 (M+1).

Compound 302: A suspension of compound 301 (0.24 g, 0.51 mmol) in 1,4-dioxane (5 mL) was treated with N,N-dimethylacetamide dimethylacetal (90%: 0.23 g, 1.55 mmol). The mixture was heated at 60° C. under N$_2$ for 4 h and then concentrated. The residue was purified by column chromatography (silica gel, eluting with 50% EtOAc in hexanes) to give compound 302 (0.20 g, 79% yield) as an off-white solid. m/z=496 (M+1).

Compound 303: A mixture of compound 302 (0.20 g, 0.40 mmol) and K$_2$CO$_3$ (0.28 g, 2.02 mmol) in MeOH (10 mL) was stirred at room temperature under N$_2$ for 16 h. The mixture was concentrated. The residue was partitioned between sat. aq. KH$_2$PO$_4$ (50 mL) and EtOAc (50 mL). The organic extract was washed with sat. aq. NaCl (50 mL), dried with MgSO$_4$, filtered, and concentrated. The residue was purified by column chromatography (silica gel, eluting with 50% EtOAc in hexanes) to give compound 303 (0.14 g, 70% yield) as a white solid. m/z=496 (M+1).

T182: To a stirring solution of compound 303 (0.14 g, 0.28 mmol) in degassed DMF (4 mL) at 0° C. under N$_2$ was added dropwise a solution of 1,3-dibromo-5,5-dimethylhydantoin (40 mg, 0.14 mmol) in degassed DMF (1 mL). The mixture was stirred at 0° C. for 30 min, and then pyridine (0.23 mL, 2.84 mmol) was added. The mixture was heated at 60° C. for 4 h and then concentrated. The residue was partitioned between sat. aq. KH$_2$PO$_4$ (25 mL) and EtOAc (25 mL). The organic extract was washed with sat. aq. NaCl (25 mL), dried with MgSO$_4$, filtered, and concentrated. The residue was purified by column chromatography (silica gel, eluting with 50% EtOAc in hexanes) to give compound T182 (96 mg, 69% yield) as an off-white solid. m/z=494 (M+1): $^1$H NMR (400 MHz, CDCl$_3$) δ 8.32 (m, 2H), 7.70 (m, 2H), 7.64 (m, 2H), 7.55 (s, 11H), 7.11 (m, 2H), 2.95 (ddd, J=1.2, 6.0, 15.6 Hz, 1H), 2.86 (m, 1H), 2.71 (s, 3H), 2.56 (qd, J=6.7, 13.4 Hz, 1H), 2.26 (dt, J=2.0, 12.6 Hz, 1H), 2.16 (dd, J=6.4, 13.8 Hz, 1H), 1.82 (ddd, J=6.4, 12.6, 19.0 Hz, 1H), 1.61 (s, 3H), 1.33 (d, J=6.7 Hz, 3H).

Compound 304: A mixture of compound 301 (0.14 g, 0.30 mmol) and K$_2$CO$_3$ (0.21 g, 1.52 mmol) in MeOH (10 mL) was stirred at room temperature under N$_2$ for 16 h. The mixture was concentrated. The residue was treated with sat. KH$_2$PO$_4$ solution (25 mL). The precipitated solid was collected by filtration, washed with water, and dried under vacuum to give compound 304 (0.12 g, 86% yield) as an off-white solid. m/z=472 (M+1).

Compound 305: To a stirring solution of compound 304 (0.12 g, 0.25 mmol) in degassed DMF (4 mL) at 0° C. under N$_2$ was added dropwise a solution of 1,3-dibromo-5,5-dimethylhydantoin (36 mg, 0.13 mmol) in degassed DMF (1 mL). The mixture was stirred at 0° C. for 30 min, and then pyridine (0.20 mL, 2.47 mmol) was added. The mixture was heated at 60° C. for 4 h and then concentrated. The residue was partitioned between sat. aq. KH$_2$PO$_4$ (25 mL) and EtOAc (25 mL). The organic extract was washed with sat. aq. NaCl (25 mL), dried with MgSO$_4$, filtered, and concentrated. The residue was purified by column chromatography (silica gel, eluting with 70% EtOAc in hexanes) to give compound 305 (64 mg, 53% yield) as a light yellow solid. m/z=470 (M+1).

T183: A solution of compound 305 (64 mg, 0.14 mmol) in trimethyl orthoformate (3 mL, 27.42 mmol) was heated at 60° C. under N$_2$ for 16 h. The mixture was concentrated, and the residue was partitioned between sat. aq. NaHCO$_3$ (25 mL) and EtOAc (25 mL). The organic extract was washed with sat. aq. NaCl (25 mL), dried with MgSO$_4$, filtered, and concentrated to give a light yellow solid. The crude product was triturated with Et$_2$O. The solid was collected by filtration and dried under vacuum to give compound T183 (31 mg, 46% yield) as an off-white solid. m/z=480 (M+1): $^1$H NMR (400 MHz, CDCl$_3$) δ 8.84 (s, 1H), 8.38 (m, 2H), 7.68 (m, 4H), 7.56 (s, 1H), 7.11 (m, 2H), 2.95 (ddd, J=1.6, 6.4, 16.2 Hz, 1H), 2.86 (m, 1H), 2.56 (td, J=6.7, 13.4 Hz, 1H), 2.27 (dt, J=2.1, 12.7 Hz, 1H), 2.17 (dd. J=6.5, 13.8 Hz, 1H), 1.82 (tdd, J=6.3, 12.6, 19.0 Hz, 1H), 1.62 (s, 3H), 1.33 (d, J=6.7 Hz, 3H).

Compound 306: In scalable vial, a solution of compound 156b (0.25 g, 0.59 mmol) in EtOH (20 mL) was treated with hydroxylamine (50 wt. % aq. solution, 0.12 g, 1.82 mmol). The mixture was flushed with N$_2$. The vial was sealed and heated at 50° C. under N$_2$ for 16 h. The mixture was concentrated and dried under vacuum to give compound 306 (0.28 g, quantitative yield) as a yellow gummy solid. m/z=455 (M+1).

Compound 307: A suspension of compound 306 (0.28 g, 0.59 mmol) in 1,4-dioxane (5 mL) was treated with N,N-dimethylacetamide dimethylacetal (90%; 0.26 g, 1.76 mmol). The mixture was heated at 60° C. under $N_2$ for 2 h and then concentrated. The residue was purified by column chromatography (silica gel, eluting with 5% MeOH in $CHCl_3$) to give compound 307 (0.28 g, 99% yield) as an orange solid. m/z=479 (M+1).

Compound 308: A mixture of compound 307 (0.28 g, 0.58 mmol) and $K_2CO_3$ (0.41 g, 2.97 mmol) in MeOH (10 mL) was stirred at room temperature under $N_2$ for 16 h. The mixture was concentrated. The residue was partitioned between sat. aq. $KH_2PO_4$ (50 mL) and EtOAc (50 mL). The organic extract was washed with sat. aq. NaCl (50 mL), dried with $MgSO_4$, filtered, and concentrated. The residue was purified by column chromatography (silica gel, eluting with 5% MeOH in $CHCl_3$) to give compound 308 (0.18 g, 64% yield) as a light yellow solid. m/z=479 (M+1).

T184: To a stirring solution of compound 308 (0.18 g, 0.37 mmol) in degassed DMF (4 mL) at 0° C. under $N_2$ was added dropwise a solution of 1,3-dibromo-5,5-dimethylhydantoin (54 mg, 0.19 mmol) in degassed DMF (1 mL). The mixture was stirred at 0° C. for 30 min. and then pyridine (0.30 mL, 3.71 mmol) was added. The mixture was heated at 60° C. for 4 h and then concentrated. The residue was partitioned between sat. aq. $KH_2PO_4$ (25 mL) and EtOAc (25 mL). The organic extract was washed with sat. aq. NaCl solution (25 mL), dried with $MgSO_4$, filtered, and concentrated. The residue was purified by column chromatography (silica gel, eluting with 5% MeOH in $CHCl_3$) to give partially purified product. The product was triturated with $Et_2O$. The solid was collected by filtration and dried under vacuum to give compound T184 (77 mg, 43% yield) as an off-white solid. m/z=477 (M+1); $^1$H NMR (400 MHz, $CDCl_3$) δ 8.96 (s, 1H), 8.59 (s, 1H), 8.33 (m, 2H), 8.07 (td, J=1.8, 7.9 Hz, 1H), 7.64 (m, 2H), 7.54 (s, 1H), 7.35 (dd, J=4.8, 8.0 Hz, 1H), 2.99 (ddd, J=1.4, 6.3, 15.9 Hz, 1H), 2.91 (m, 1H), 2.71 (s, 3H), 2.56 (td, J=6.7, 13.4 Hz, 1H), 2.28 (dt, J=2.1, 12.7 Hz, 1H), 2.18 (dd, J=6.4, 13.9 Hz, 1H), 1.84 (tdd, J=6.4, 12.7 Hz, 18.9 Hz, 1H), 1.62 (s, 3H), 1.34 (d, J=6.7 Hz, 3H).

Example 2: Biological Data

A. AREc32 Luciferase Reporter Assay

The AREc32 luciferase reporter assay allows for quantitative assessment of the endogenous activity of the Nrf2 transcription factor in cultured mammalian cells. AREc32 cells are derived from MCF-7 human breast carcinoma cells that were stably transfected with a reporter construct that contains the firefly luciferase gene located downstream of eight copies of the rat GSTA2 antioxidant response element (ARE) sequence (Wang et al., 2006; Concept Life Sciences Integrated Discovery and Development Services Ltd (CL-SIDDS)). Active Nrf2 binds to the ARE sequences and increases expression of the firefly luciferase gene. To assess the Nrf2-activating potential of the test compounds, AREc32 cells were plated in black %-well plates at a density of 20,000 cells per well in triplicate in DMEM+10% FBS+0.8 mg/mL Geneticin and incubated at 37° C. with 5% $CO_2$ in a humidified atmosphere. The next day, cells were treated with DMSO (vehicle) or test compound (concentration ranges of 0.4-200 nM or 3.9-2000 nM) for 19 hours. Luciferase activity was determined using the ONE-Glo Luciferase assay (Promega). The luminescence signal was measured on a BMG Pherastar microplate reader. The mean luminescence value from test compound-treated wells was normalized to that from DMSO-treated wells and was represented as fold-induction. Data were analyzed using GraphPad Prism version 6.00 for Windows, GraphPad Software, La Jolla Calif. USA. A non-linear regression curve with log (agonist) vs. response using a variable slope was used to fit the data. Where applicable, a maximum threshold value of 50-fold over DMSO was set. $EC_{2x}$ values were interpolated from the curve. $EC_{2x}$ corresponds to the concentration of test compound required to increase GST ARE Luciferase reporter activity by 2-fold.

B. RORγ Assay and Cell Viability

The RORγ assay system was purchased from Indigo Biosciences. This nuclear receptor assay utilizes a human cell line that has been engineered to express a hybrid form of the Human RAR-related Orphan Receptor Gamma (RORγ) at high levels. The N-terminal DNA binding domain (DBD) of the native RORγ receptor was substituted with the yeast GAL4-DBD to generate the GAL4-RORγ hybrid nuclear receptor. The reporter cell line is transfected with a plasmid that encodes the beetle luciferase gene under the control of the GAL4 upstream activating sequence (UAS). GAL4 binds to the UAS and increases transcription of downstream target genes. The GAL4-RORγ hybrid is constitutively active; therefore, the principle application of this reporter assay system is to screen test compounds to quantify inverse-agonist activities against human RORγ. Because the ligand binding domain (LBD) of RORγ is identical to the LBD of RORγt, this assay is an accurate surrogate for evaluating activity of experimental ligands against RORγt. To assess the RORγ inverse-agonist activity of the test compounds, reporter cells were plated in white 96-well plates in triplicate and were treated with DMSO (vehicle) or test compound (concentration ranges of 7.8-2000 nM) at 37° C. with 5% $CO_2$ in a humidified atmosphere for 23 hours. After this incubation, luciferin was added to the wells and luciferase activity was determined by measuring the luminescence signal using a BMG Pherastar microplate reader. Viability was determined using the Live Cell Multiplex Assay (Indigo Biosciences). Values from test compound samples were normalized to those from DMSO-treated samples. Data were analyzed using GraphPad Prism version 6.00 for Windows (GraphPad Software, La Jolla Calif. USA). A non-linear regression analysis with log (inhibitor) vs. normalized response using a variable slope was applied to fit the data and determine the $IC_{50}$ values for inhibition of RORγ and cell viability. Inhibition that is closely correlated with reduced viability is considered to be non-specific.

C. IL-17 Release from Differentiated Primary Human T-Cells and Cell Viability

Primary human cryopreserved CD4+ T Cells (Lonza) were thawed according to the manufacturer's recommendations and plated either in Lymphocyte Growth Medium-3 (LGM-3) or X-VIVO 20 media (Lonza) in 96-well tissue culture plates at a density of ~2×10$^5$ cells per well, and allowed to recover for approximately 4 hours at 37° C. with 5% $CO_2$ in a humidified atmosphere. After the recovery step, DMSO (vehicle) or test compound at doses ranging from 2 to 500 nM or 4 to 1000 nM in a three-fold dilution series was added to the cells. Three replicate wells were tested for each treatment condition. Final DMSO concentration in each well was 0.1%. Immediately after treatment, CD4+ T cells were activated by adding Dynabeads Human T-Activator CD3/CD28 (Life Technologies; bead-to-cell ratio of 1:2.5) and differentiated into Th17 cells by adding a mixture of the following cytokines: transforming growth factor-β (TGF-β, 5 ng/mL), IL-6 (20 ng/mL), IL-23 (20 ng/mL), and IL-1β (10 ng/mL). Undifferentiated control cells received only cytokine IL-2 (50 ng/mL). All human recombinant cytokines were purchased from R&D Systems. Following a 45-hour incubation at 37° C. with 5% $CO_2$ in a humidified atmosphere, the plates were centrifuged for 3 minutes at 250×g, and half of the supernatant was transferred to a new plate to be used in the IL-17A assay (see below). Cell viability was assessed in the original plate using the CyQuant Direct Assay (Life Technologies). CyQuant reagent (an amount equal to 10% of remaining media volume) was added to the wells, and the plates were then incubated at 37° C. for 75 min. Fluorescence was read on a SpectraMax M2e spectrophotometer at 480 nm (excitation) and 535 nm (emission) wavelengths. CyQuant values from test compound samples were normalized to those from DMSO-treated samples. The concentration of IL-17A in the supernatant was measured using the Homogeneous Time-Resolved Fluorescence (HTRF) assay (Cisbio Bioassays) according to the manufacturer's protocol. The assay was performed at room temperature in low volume, solid white 384-well plates (Greiner Bio-One). Samples and standards (serially-diluted human recombinant IL-17A (0 to 5,000 pg/mL concentration range; Cisbio Bioassays) were incubated with the anti-human IL-17A antibody conjugates (the HTRF donor and acceptor pair) for 16 hours and fluorescence was measured using a Pherastar FS microplate reader (BMG Labtech) in the HTRF mode (excitation at 337 nm and emission at 665 nm and 620 nm). IL-17A levels were assessed in duplicate aliquots of supernatant from each well resulting in a total of six readings per test condition. The 665 nm/620 nm signal ratio was calculated and the concentration of IL-17A in each sample was determined by interpolation from the standard curve. The amount of IL-17A from test compound treated samples were normalized to that of the vehicle-treated samples, set to 100%. Data were analyzed using GraphPad Prism (GraphPad Software, La Jolla California USA). Concentrations of test compound were transformed by taking the logarithm of each concentration used. The $IC_{50}$ values for compound-mediated reduction in IL-17A levels and cell viability were determined by non-linear regression analysis using the log (inhibitor) vs. normalized response with variable slope equation. Inhibition that is closely correlated with reduced viability is considered to be non-specific.

TABLE 1

Biological Activity Data for Compounds T1-T186 in hIL17, RORγ, and NRF2 GST ARE $EC_{2x}$ assays

| T# | Structure | hIL17 IC50 (μM) | RORγ IC50 (μM) | NRF2 ARE 2-Fold (μM) |
|---|---|---|---|---|
| T1 | 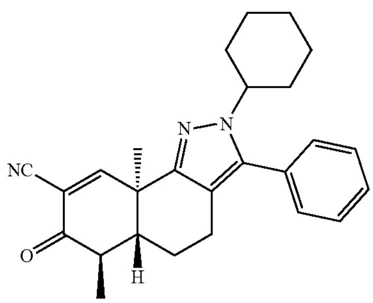 [SMILES: C[C@H]1C(=O)C(C#N)=C[C@@]2(C)c3nn(C4CCCCC4)c(-c4ccccc4)c3CC[C@H]12] | 0.065 | 0.174 | 1.446 |
| T2 | 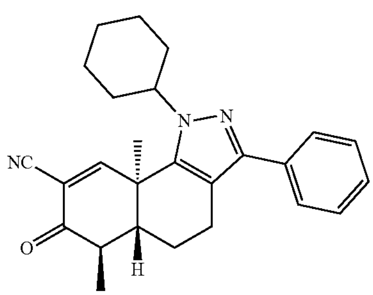 [SMILES: C[C@H]1C(=O)C(C#N)=C[C@@]2(C)c3c(c(-c4ccccc4)nn3C3CCCCC3)CC[C@H]12] | 0.083 | 0.098 | 0.660 |
| T3 | 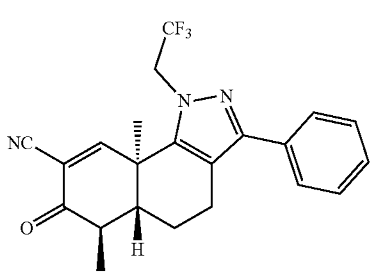 [SMILES: C[C@H]1C(=O)C(C#N)=C[C@@]2(C)c3c(c(-c4ccccc4)nn3CC(F)(F)F)CC[C@H]12] | 0.092 | 0.276 | 1.461 |

TABLE 1-continued

Biological Activity Data for Compounds T1-T186
in hIL17, RORγ, and NRF2 GST ARE EC$_{2x}$ assays

| T# | Structure | hIL17 IC50 (μM) | RORγ IC50 (μM) | NRF2 ARE 2-Fold (μM) |
|---|---|---|---|---|
| T4 | 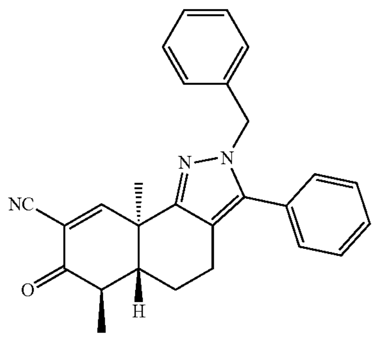 [SMILES: C[C@H]1C(=O)C(C#N)=C[C@@]2(C)c3nn(Cc4ccccc4)c(-c4ccccc4)c3CC[C@H]12] | 0.223 | 0.140 | 0.914 |
| T5 | 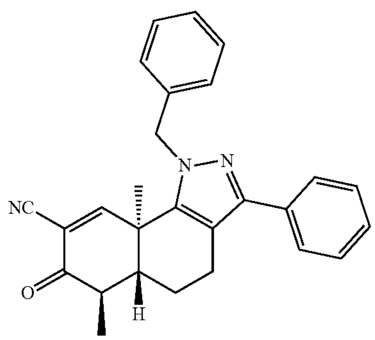 [SMILES: C[C@H]1C(=O)C(C#N)=C[C@@]2(C)c3c(c(-c4ccccc4)nn3Cc3ccccc3)CC[C@H]12] | 0.119 | 0.136 | 0.587 |
| T6 | 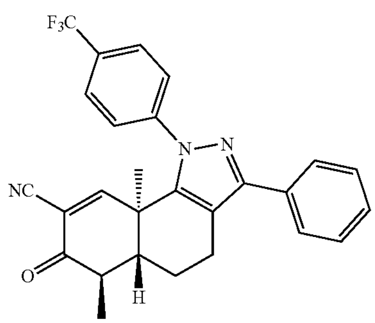 [SMILES: C[C@H]1C(=O)C(C#N)=C[C@@]2(C)c3c(c(-c4ccccc4)nn3-c3ccc(C(F)(F)F)cc3)CC[C@H]12] | 0.035 | 0.091 | 0.242 |
| T7 | 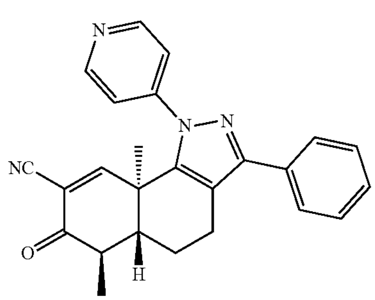 | 0.170 | 0.158 | 0.265 |

TABLE 1-continued

Biological Activity Data for Compounds T1-T186
in hIL17, RORγ, and NRF2 GST ARE EC$_{2x}$ assays

| T# | Structure | hIL17 IC50 (μM) | RORγ IC50 (μM) | NRF2 ARE 2-Fold (μM) |
|---|---|---|---|---|
| T8 | 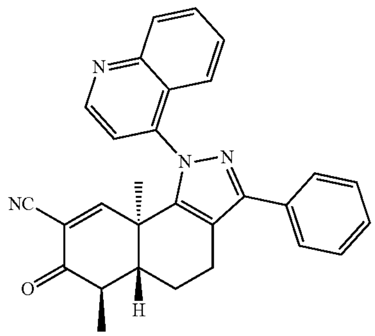 | 0.073 | 0.081 | 0.426 |
| T9 | 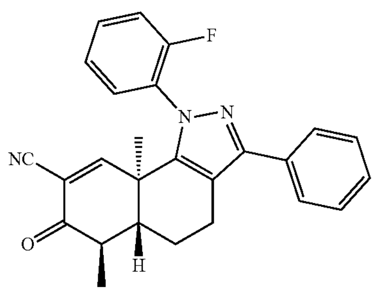 | 0.127 | 0.063 | 0.122 |
| T10 | 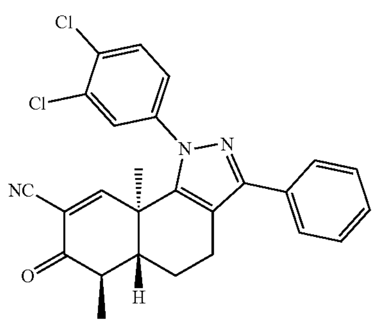 [SMILES: C[C@H]1C(=O)C(C#N)=C[C@@]2(C)c3c(c(-c4ccccc4)nn3-c3ccc(Cl)c(Cl)c3)CC[C@H]12] | 0.078 | 0.088 | 0.260 |
| T11 | 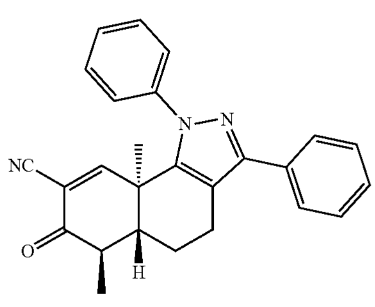 [SMILES: C[C@H]1C(=O)C(C#N)=C[C@@]2(C)c3c(c(-c4ccccc4)nn3-c3ccccc3)CC[C@H]12] | 0.111 | 0.073 | 0.107 |

TABLE 1-continued

Biological Activity Data for Compounds T1-T186
in hIL17, RORγ, and NRF2 GST ARE EC$_{2x}$ assays

| T# | Structure | hIL17 IC50 (μM) | RORγ IC50 (μM) | NRF2 ARE 2-Fold (μM) |
|---|---|---|---|---|
| T12 | 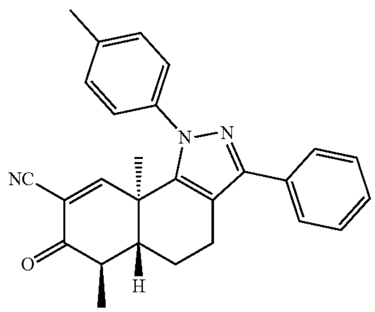 [SMILES: Cc1ccc(-n2nc(-c3ccccc3)c3c2[C@]2(C)C=C(C#N)C(=O)[C@H](C)[C@H]2CC3)cc1] | 0.076 | 0.055 | 0.135 |
| T13 | 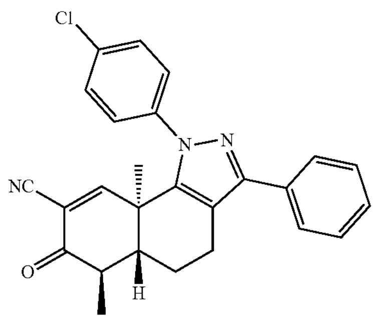 [SMILES: C[C@H]1C(=O)C(C#N)=C[C@@]2(C)c3c(c(-c4ccccc4)nn3-c3ccc(Cl)cc3)CC[C@H]12] | 0.096 | 0.129 | 0.274 |
| T14 | 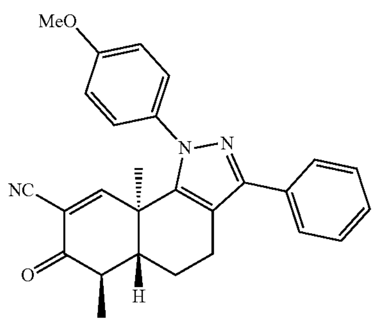 [SMILES: COc1ccc(-n2nc(-c3ccccc3)c3c2[C@]2(C)C=C(C#N)C(=O)[C@H](C)[C@H]2CC3)cc1] | 0.057 | 0.060 | 0.147 |
| T15 | 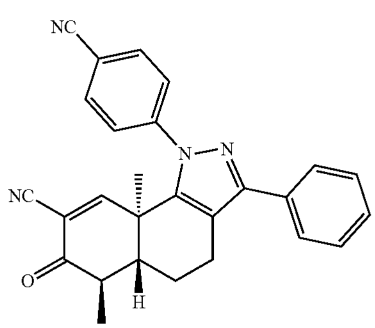 [SMILES: C[C@H]1C(=O)C(C#N)=C[C@@]2(C)c3c(c(-c4ccccc4)nn3-c3ccc(C#N)cc3)CC[C@H]12] | 0.141 | 0.257 | 0.502 |

TABLE 1-continued

Biological Activity Data for Compounds T1-T186
in hIL17, RORγ, and NRF2 GST ARE EC$_{2x}$ assays

| T# | Structure | hIL17 IC50 (μM) | RORγ IC50 (μM) | NRF2 ARE 2-Fold (μM) |
|---|---|---|---|---|
| T16 | 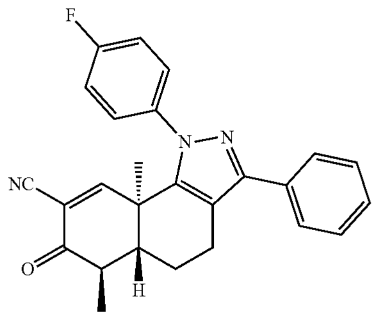 [SMILES: C[C@H]1C(=O)C(C#N)=C[C@@]2(C)c3c(c(-c4ccccc4)nn3-c3ccc(F)cc3)CC[C@H]12] | | 0.248 | 0.292 |
| T17 | 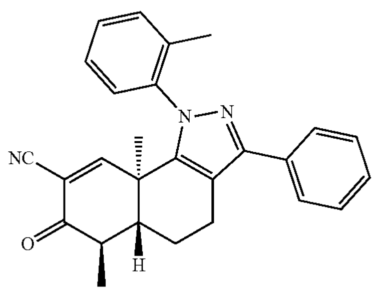 [SMILES: Cc1ccccc1-n1nc(-c2ccccc2)c2c1[C@]1(C)C=C(C#N)C(=O)[C@H](C)[C@H]1CC2] | 0.094 | 0.077 | 0.105 |
| T18 | 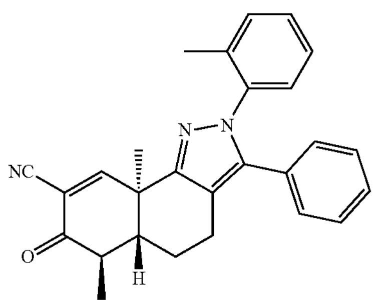 [SMILES: Cc1ccccc1-n1nc2c(c1-c1ccccc1)CC[C@@H]1[C@@H](C)C(=O)C(C#N)=C[C@@]21C] | 0.182 | 0.114 | 0.741 |
| T19 | 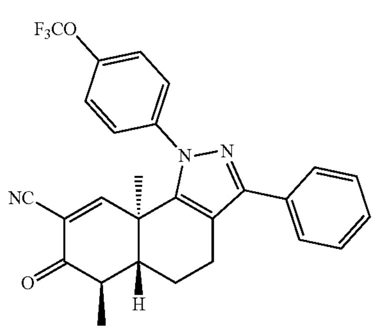 [SMILES: C[C@H]1C(=O)C(C#N)=C[C@@]2(C)c3c(c(-c4ccccc4)nn3-c3ccc(OC(F)(F)F)cc3)CC[C@H]12] | 0.032 | 0.085 | 0.247 |

TABLE 1-continued

Biological Activity Data for Compounds T1-T186
in hIL17, RORγ, and NRF2 GST ARE EC$_{2x}$ assays

| T# | Structure | hIL17 IC50 (μM) | RORγ IC50 (μM) | NRF2 ARE 2-Fold (μM) |
|---|---|---|---|---|
| T20 | 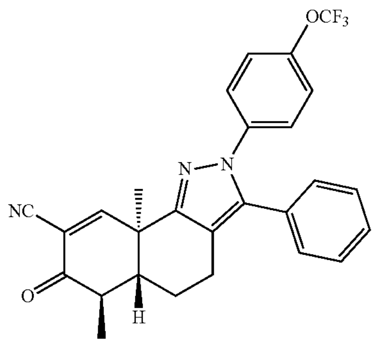 [SMILES: C[C@H]1C(=O)C(C#N)=C[C@@]2(C)c3nn(-c4ccc(OC(F)(F)F)cc4)c(-c4ccccc4)c3CC[C@H]12] | 0.094 | 0.115 | 0.927 |
| T21 | 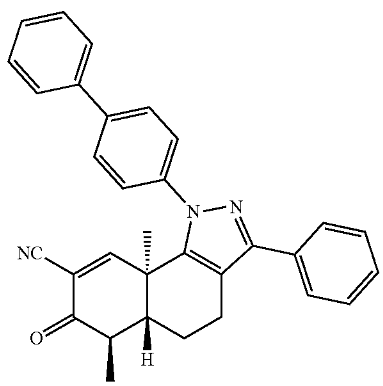 [SMILES: C[C@H]1C(=O)C(C#N)=C[C@@]2(C)c3c(c(-c4ccccc4)nn3-c3ccc(-c4ccccc4)cc3)CC[C@H]12] | 0.019 | 0.080 | 0.161 |
| T22 | 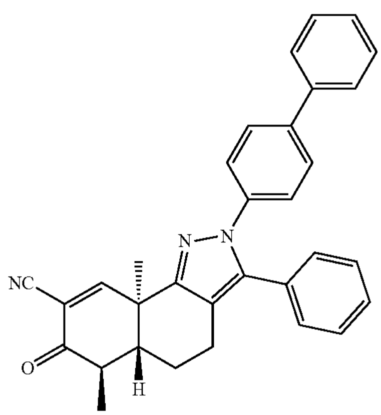 [SMILES: C[C@H]1C(=O)C(C#N)=C[C@@]2(C)c3nn(-c4ccc(-c5ccccc5)cc4)c(-c4ccccc4)c3CC[C@H]12] | 0.056 | 0.175 | 1.047 |
| T23 | 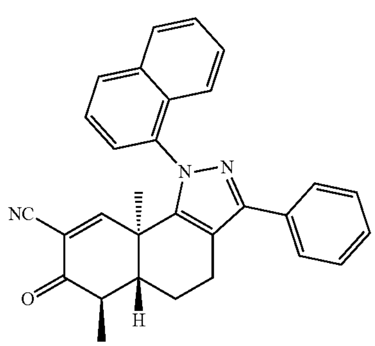 [SMILES: C[C@H]1C(=O)C(C#N)=C[C@@]2(C)c3c(c(-c4ccccc4)nn3-c3cccc4ccccc34)CC[C@H]12] | 0.089 | 0.118 | 0.190 |

TABLE 1-continued

Biological Activity Data for Compounds T1-T186
in hIL17, RORγ, and NRF2 GST ARE EC$_{2x}$ assays

| T# | Structure | hIL17 IC50 (μM) | RORγ IC50 (μM) | NRF2 ARE 2-Fold (μM) |
|---|---|---|---|---|
| T24 | 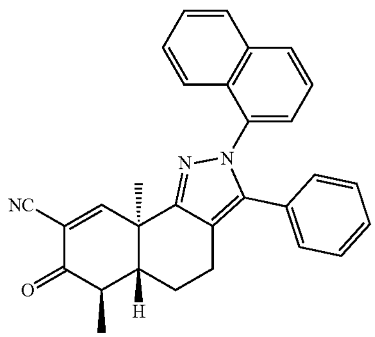 [SMILES: C[C@H]1C(=O)C(C#N)=C[C@@]2(C)c3nn(-c4cccc5ccccc45)c(-c4ccccc4)c3CC[C@H]12] | 0.030 | 0.284 | 0.827 |
| T25 | 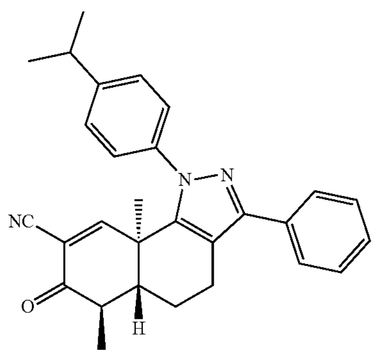 [SMILES: CC(C)c1ccc(-n2nc(-c3ccccc3)c3c2[C@]2(C)C=C(C#N)C(=O)[C@H](C)[C@H]2CC3)cc1] | 0.028 | 0.092 | 0.149 |
| T26 | 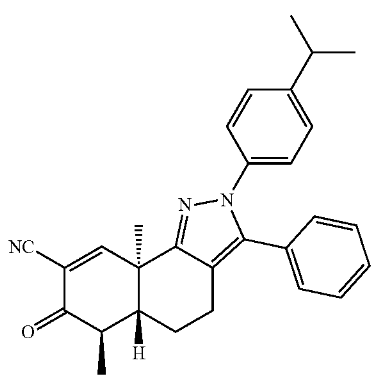 [SMILES: CC(C)c1ccc(-n2nc3c(c2-c2ccccc2)CC[C@@H]2[C@@H](C)C(=O)C(C#N)=C[C@@]32C)cc1] | 0.061 | 0.104 | 0.944 |
| T27 | 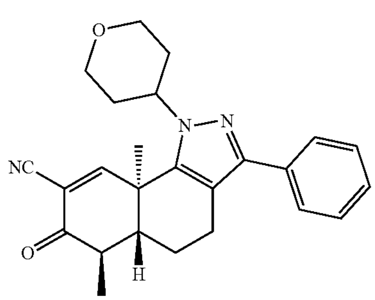 | 0.061 | 0.132 | 0.204 |

TABLE 1-continued

Biological Activity Data for Compounds T1-T186
in hIL17, RORγ, and NRF2 GST ARE EC$_{2x}$ assays

| T# | Structure | hIL17 IC50 (μM) | RORγ IC50 (μM) | NRF2 ARE 2-Fold (μM) |
| --- | --- | --- | --- | --- |
| T28 | 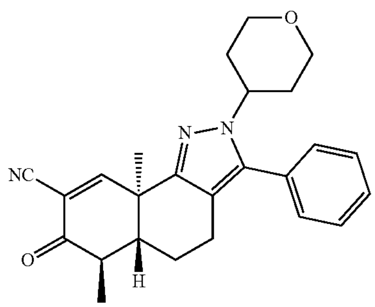 [SMILES: C[C@H]1C(=O)C(C#N)=C[C@@]2(C)c3nn(C4CCOCC4)c(-c4ccccc4)c3CC[C@H]12] | 0.136 | 0.090 | 0.719 |
| T29 | 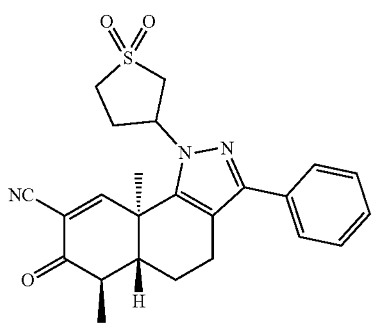 [SMILES: C[C@H]1C(=O)C(C#N)=C[C@@]2(C)c3c(c(-c4ccccc4)nn3C3CCS(=O)(=O)C3)CC[C@H]12] | | 0.470 | 0.837 |
| T30 | 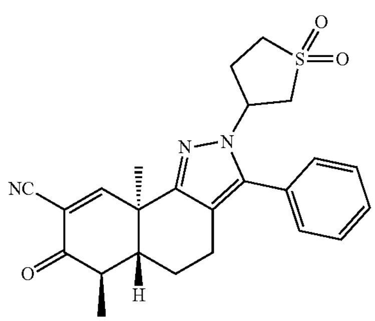 [SMILES: C[C@H]1C(=O)C(C#N)=C[C@@]2(C)c3nn(C4CCS(=O)(=O)C4)c(-c4ccccc4)c3CC[C@H]12] | | 0.143 | 0.462 |
| T31 | 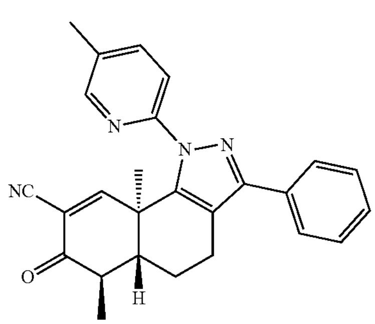 | 0.100 | 0.091 | 0.298 |

TABLE 1-continued

Biological Activity Data for Compounds T1-T186
in hIL17, RORγ, and NRF2 GST ARE EC$_{2x}$ assays

| T# | Structure | hIL17 IC50 (μM) | RORγ IC50 (μM) | NRF2 ARE 2-Fold (μM) |
|----|-----------|-----------------|----------------|----------------------|
| T32 | 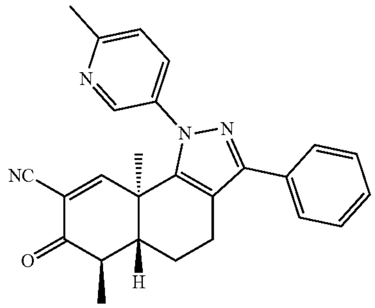 [SMILES: Cc1ccc(-n2nc(-c3ccccc3)c3c2[C@]2(C)C=C(C#N)C(=O)[C@H](C)[C@H]2CC3)cn1] | 0.170 | 0.124 | 0.258 |
| T33 | 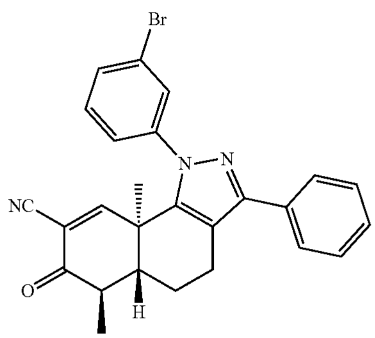 [SMILES: C[C@H]1C(=O)C(C#N)=C[C@@]2(C)c3c(c(-c4ccccc4)nn3-c3cccc(Br)c3)CC[C@H]12] | | 0.089 | 0.290 |
| T34 | 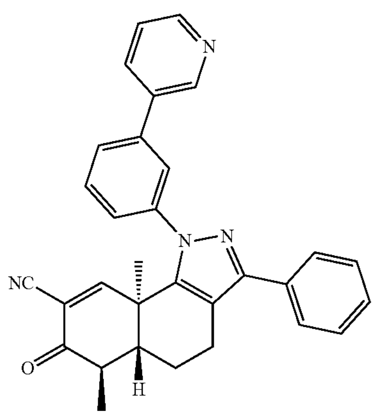 [SMILES: C[C@H]1C(=O)C(C#N)=C[C@@]2(C)c3c(c(-c4ccccc4)nn3-c3cccc(-c4cccnc4)c3)CC[C@H]12] | 0.087 | 0.087 | 0.245 |
| T35 | 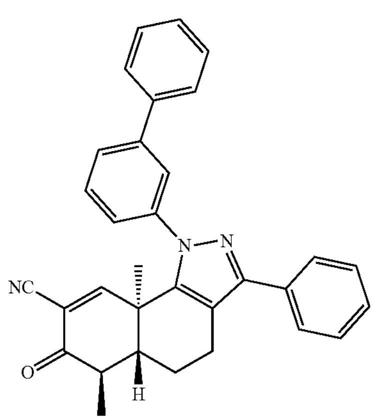 [SMILES: C[C@H]1C(=O)C(C#N)=C[C@@]2(C)c3c(c(-c4ccccc4)nn3-c3cccc(-c4ccccc4)c3)CC[C@H]12] | 0.058 | 0.129 | 0.328 |

TABLE 1-continued

Biological Activity Data for Compounds T1-T186
in hIL17, RORγ, and NRF2 GST ARE EC$_{2x}$ assays

| T# | Structure | hIL17 IC50 (μM) | RORγ IC50 (μM) | NRF2 ARE 2-Fold (μM) |
|---|---|---|---|---|
| T36 | 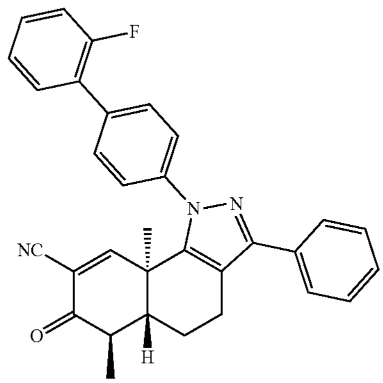 [SMILES: C[C@H]1C(=O)C(C#N)=C[C@@]2(C)c3c(c(-c4ccccc4)nn3-c3ccc(-c4ccccc4F)cc3)CC[C@H]12] | 0.022 | 0.087 | 0.233 |
| T37 | 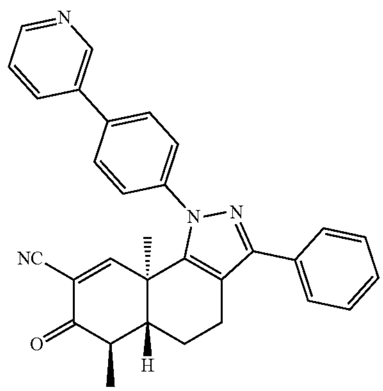 [SMILES: C[C@H]1C(=O)C(C#N)=C[C@@]2(C)c3c(c(-c4ccccc4)nn3-c3ccc(-c4cccnc4)cc3)CC[C@H]12] | 0.024 | 0.032 | 0.167 |
| T38 | 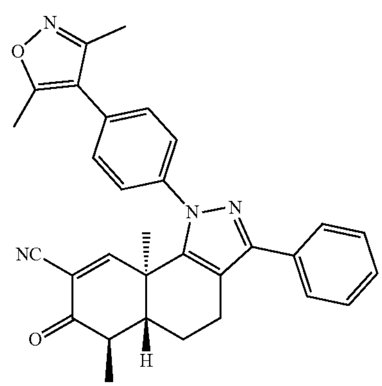 [SMILES: Cc1noc(C)c1-c1ccc(-n2nc(-c3ccccc3)c3c2[C@]2(C)C=C(C#N)C(=O)[C@H](C)[C@H]2CC3)cc1] | 0.037 | 0.046 | 0.215 |
| T39 | 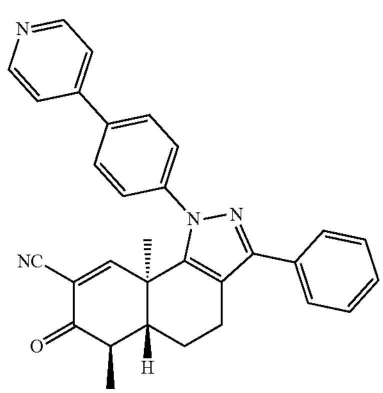 [SMILES: C[C@H]1C(=O)C(C#N)=C[C@@]2(C)c3c(c(-c4ccccc4)nn3-c3ccc(-c4ccncc4)cc3)CC[C@H]12] | 0.031 | 0.025 | 0.139 |

TABLE 1-continued
Biological Activity Data for Compounds T1-T186
in hIL17, RORγ, and NRF2 GST ARE EC$_{2x}$ assays
| T# | Structure | hIL17 IC50 (μM) | RORγ IC50 (μM) | NRF2 ARE 2-Fold (μM) |
|---|---|---|---|---|
| T40 | 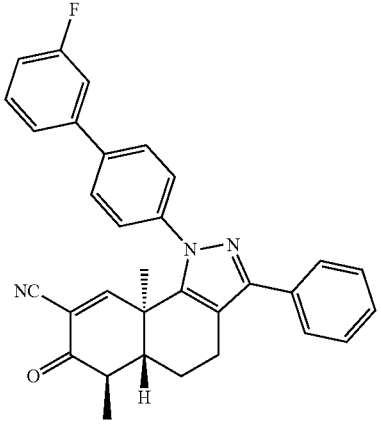 [SMILES: C[C@H]1C(=O)C(C#N)=C[C@@]2(C)c3c(c(-c4ccccc4)nn3-c3ccc(-c4cccc(F)c4)cc3)CC[C@H]12] | 0.023 | 0.080 | 0.238 |
| T41 | 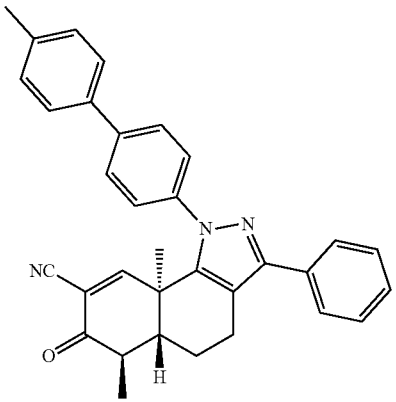 [SMILES: Cc1ccc(-c2ccc(-n3nc(-c4ccccc4)c4c3[C@]3(C)C=C(C#N)C(=O)[C@H](C)[C@H]3CC4)cc2)cc1] | 0.025 | 0.083 | 0.249 |
| T42 | 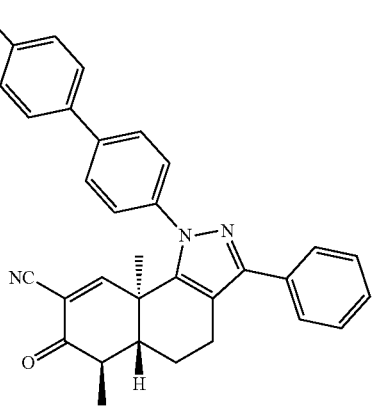 | 0.035 | 0.033 | 0.130 |

TABLE 1-continued

Biological Activity Data for Compounds T1-T186
in hIL17, RORγ, and NRF2 GST ARE EC$_{2x}$ assays

| T# | Structure | hIL17 IC50 (μM) | RORγ IC50 (μM) | NRF2 ARE 2-Fold (μM) |
|---|---|---|---|---|
| T43 | 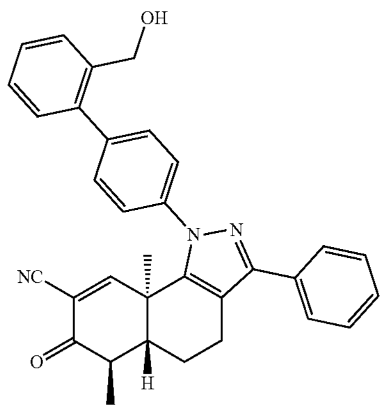 [SMILES: C[C@H]1C(=O)C(C#N)=C[C@@]2(C)c3c(c(-c4ccccc4)nn3-c3ccc(-c4ccccc4CO)cc3)CC[C@H]12] | 0.043 | 0.053 | 0.174 |
| T44 | 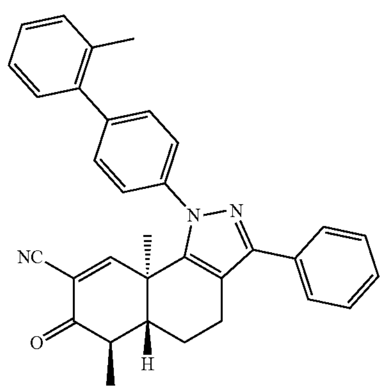 [SMILES: Cc1ccccc1-c1ccc(-n2nc(-c3ccccc3)c3c2[C@]2(C)C=C(C#N)C(=O)[C@H](C)[C@H]2CC3)cc1] | 0.041 | 0.083 | 0.242 |
| T45 | 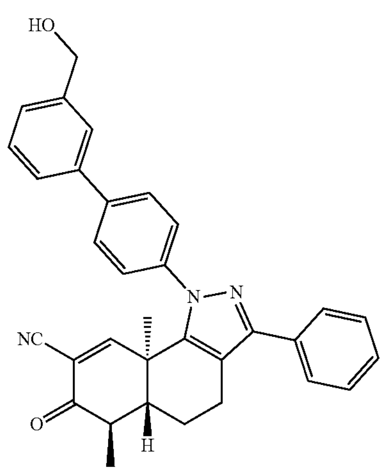 [SMILES: C[C@H]1C(=O)C(C#N)=C[C@@]2(C)c3c(c(-c4ccccc4)nn3-c3ccc(-c4cccc(CO)c4)cc3)CC[C@H]12] | 0.022 | 0.044 | 0.147 |

TABLE 1-continued
Biological Activity Data for Compounds T1-T186
in hIL17, RORγ, and NRF2 GST ARE EC$_{2x}$ assays
| T# | Structure | hIL17 IC50 (μM) | RORγ IC50 (μM) | NRF2 ARE 2-Fold (μM) |
|---|---|---|---|---|
| T46 | 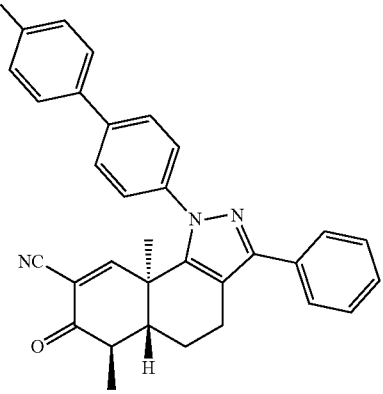 | 0.020 | 0.065 | 0.219 |
| T47 | 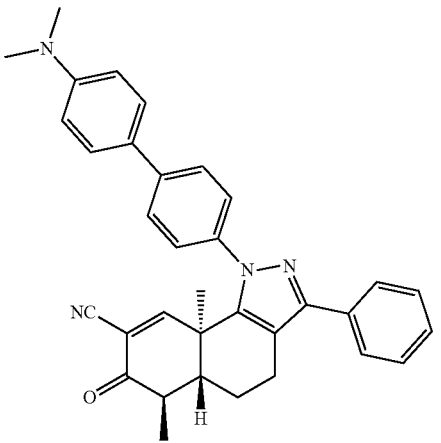 [SMILES: C[C@H]1C(=O)C(C#N)=C[C@@]2(C)c3c(c(-c4ccccc4)nn3-c3ccc(-c4ccc(N(C)C)cc4)cc3)CC[C@H]12] | 0.026 | 0.068 | 0.253 |
| T48 | 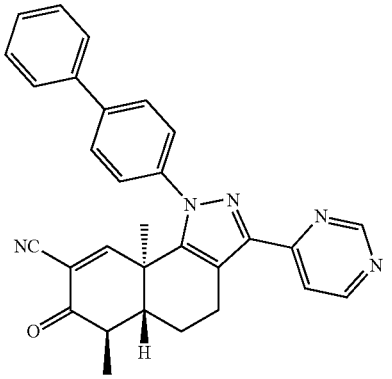 [SMILES: C[C@H]1C(=O)C(C#N)=C[C@@]2(C)c3c(c(-c4ccncn4)nn3-c3ccc(-c4ccccc4)cc3)CC[C@H]12] | 0.030 | 0.045 | 0.187 |

TABLE 1-continued

Biological Activity Data for Compounds T1-T186
in hIL17, RORγ, and NRF2 GST ARE EC$_{2x}$ assays

| T# | Structure | hIL17 IC50 (μM) | RORγ IC50 (μM) | NRF2 ARE 2-Fold (μM) |
|---|---|---|---|---|
| T49 | 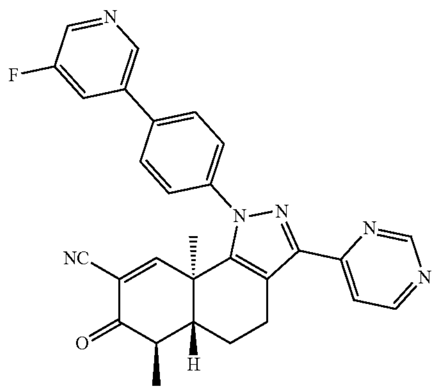 [SMILES: C[C@H]1C(=O)C(C#N)=C[C@@]2(C)c3c(c(-c4ccncn4)nn3-c3ccc(-c4cncc(F)c4)cc3)CC[C@H]12] | 0.052 | 0.059 | 0.392 |
| T50 | 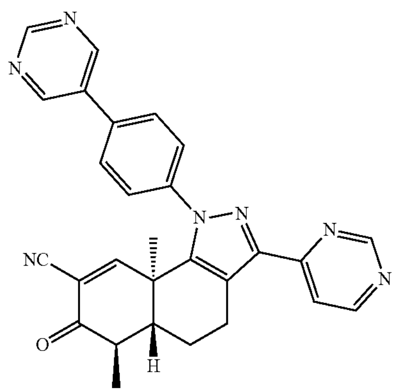 [SMILES: C[C@H]1C(=O)C(C#N)=C[C@@]2(C)c3c(c(-c4ccncn4)nn3-c3ccc(-c4cncnc4)cc3)CC[C@H]12] | 0.326 | 0.115 | 0.977 |
| T51 | 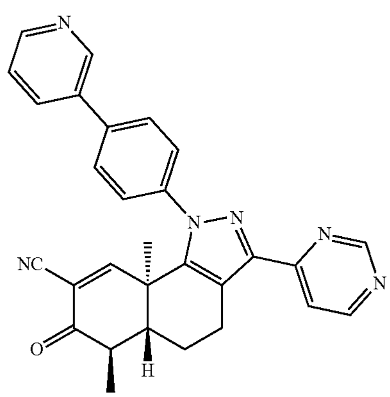 [SMILES: C[C@H]1C(=O)C(C#N)=C[C@@]2(C)c3c(c(-c4ccncn4)nn3-c3ccc(-c4cccnc4)cc3)CC[C@H]12] | 0.091 | 0.048 | 0.501 |
| T52 | 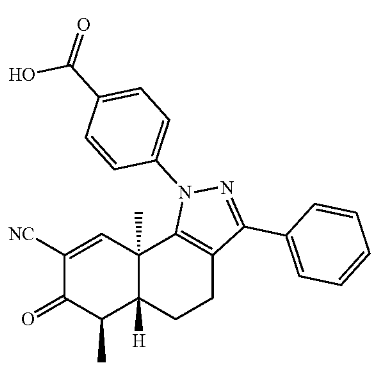 [SMILES: C[C@H]1C(=O)C(C#N)=C[C@@]2(C)c3c(c(-c4ccccc4)nn3-c3ccc(C(=O)O)cc3)CC[C@H]12] | >2.000 | >2.000 | |

TABLE 1-continued

Biological Activity Data for Compounds T1-T186
in hIL17, RORγ, and NRF2 GST ARE EC$_{2x}$ assays

| T# | Structure | hIL17 IC50 (μM) | RORγ IC50 (μM) | NRF2 ARE 2-Fold (μM) |
|---|---|---|---|---|
| T53 | 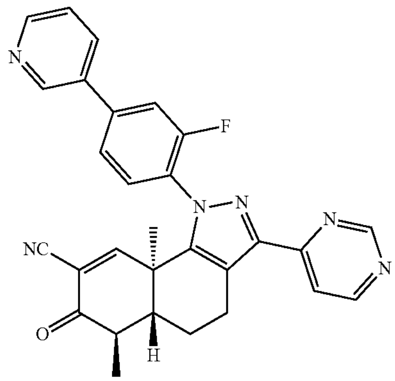 [SMILES: C[C@H]1C(=O)C(C#N)=C[C@@]2(C)c3c(c(-c4ccncn4)nn3-c3ccc(-c4cccnc4)cc3F)CC[C@H]12] | 0.088 | 0.057 | 0.489 |
| T54 | 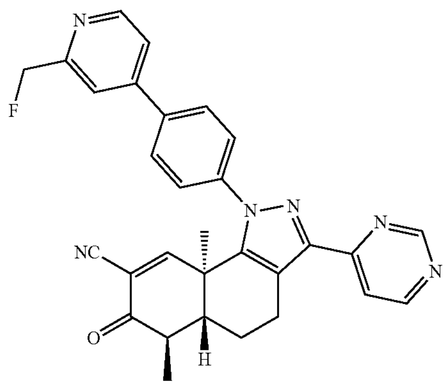 [SMILES: C[C@H]1C(=O)C(C#N)=C[C@@]2(C)c3c(c(-c4ccncn4)nn3-c3ccc(-c4ccnc(CF)c4)cc3)CC[C@H]12] | 0.033 | 0.052 | 0.355 |
| T55 | 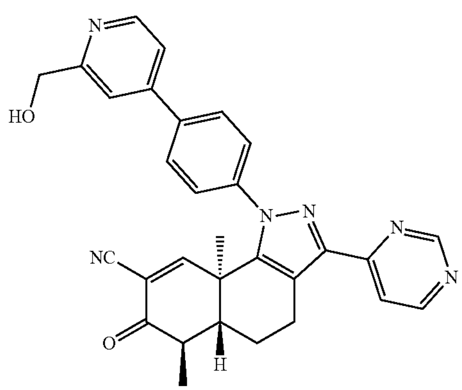 [SMILES: C[C@H]1C(=O)C(C#N)=C[C@@]2(C)c3c(c(-c4ccncn4)nn3-c3ccc(-c4ccnc(CO)c4)cc3)CC[C@H]12] | 0.149 | 0.174 | 0.609 |

TABLE 1-continued
Biological Activity Data for Compounds T1-T186
in hIL17, RORγ, and NRF2 GST ARE EC$_{2x}$ assays
| T# | Structure | hIL17 IC50 (μM) | RORγ IC50 (μM) | NRF2 ARE 2-Fold (μM) |
|----|-----------|-----------------|----------------|----------------------|
| T56 | 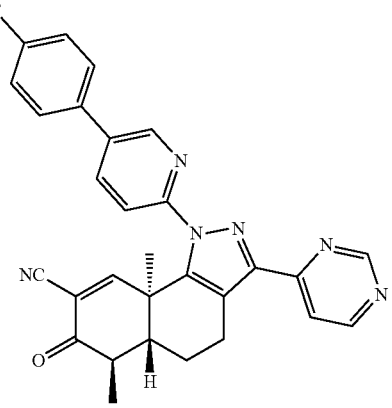 | 0.055 | 0.099 | 0.433 |
| T57 | 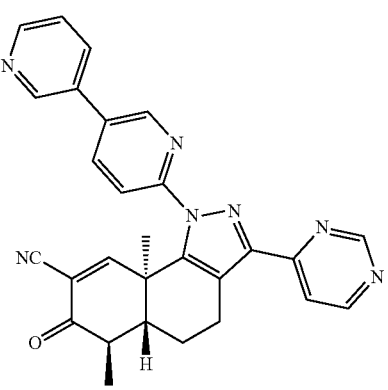 [SMILES: C[C@H]1C(=O)C(C#N)=C[C@@]2(C)c3c(c(-c4ccncn4)nn3-c3ccc(-c4cccnc4)cn3)CC[C@H]12] | 0.067 | 0.096 | 0.403 |
| T58 | 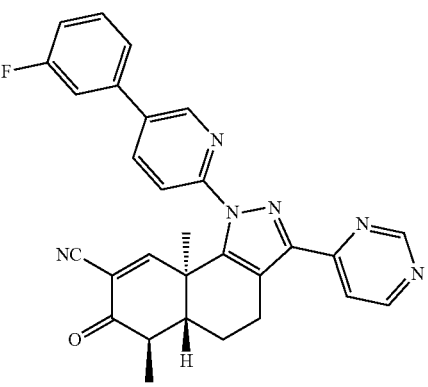 [SMILES: C[C@H]1C(=O)C(C#N)=C[C@@]2(C)c3c(c(-c4ccncn4)nn3-c3ccc(-c4cccc(F)c4)cn3)CC[C@H]12] | 0.043 | 0.128 | 0.355 |

TABLE 1-continued

Biological Activity Data for Compounds T1-T186
in hIL17, RORγ, and NRF2 GST ARE EC$_{2x}$ assays

| T# | Structure | hIL17 IC50 (μM) | RORγ IC50 (μM) | NRF2 ARE 2-Fold (μM) |
|---|---|---|---|---|
| T59 | 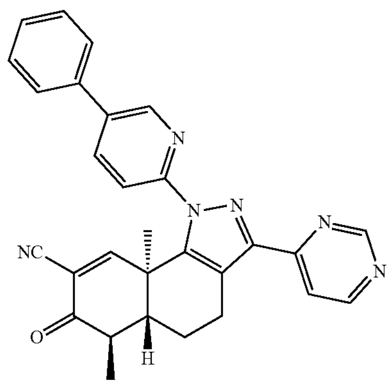 [SMILES: C[C@H]1C(=O)C(C#N)=C[C@@]2(C)c3c(c(-c4ccncn4)nn3-c3ccc(-c4ccccc4)cn3)CC[C@H]12] | 0.099 | 0.113 | 0.449 |
| T60 | 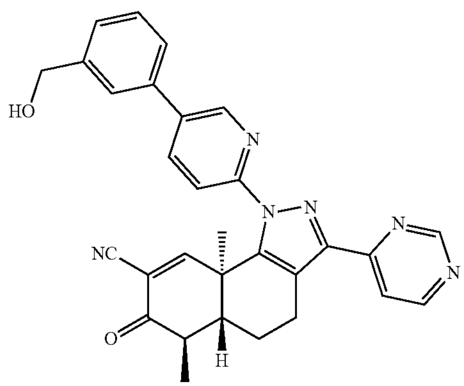 [SMILES: C[C@H]1C(=O)C(C#N)=C[C@@]2(C)c3c(c(-c4ccncn4)nn3-c3ccc(-c4cccc(CO)c4)cn3)CC[C@H]12] | 0.141 | 0.101 | 0.440 |
| T61 | 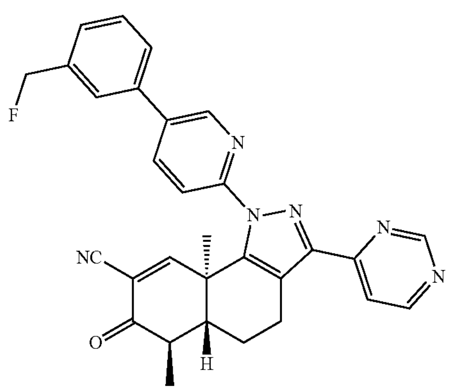 | 0.115 | 0.136 | 0.251 |
| T62 | 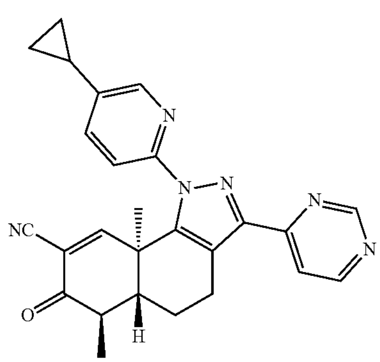 [SMILES: C[C@H]1C(=O)C(C#N)=C[C@@]2(C)c3c(c(-c4ccncn4)nn3-c3ccc(C4CC4)cn3)CC[C@H]12] | | 0.284 | 0.691 |

TABLE 1-continued

Biological Activity Data for Compounds T1-T186 in hIL17, RORγ, and NRF2 GST ARE EC$_{2x}$ assays

| T# | Structure | hIL17 IC50 (μM) | RORγ IC50 (μM) | NRF2 ARE 2-Fold (μM) |
|---|---|---|---|---|
| T63 | 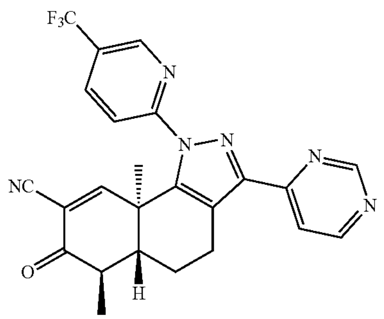 [SMILES: C[C@H]1C(=O)C(C#N)=C[C@@]2(C)c3c(c(-c4ccncn4)nn3-c3ccc(C(F)(F)F)cn3)CC[C@H]12] | 0.151 | 0.201 | 0.725 |
| T64 | 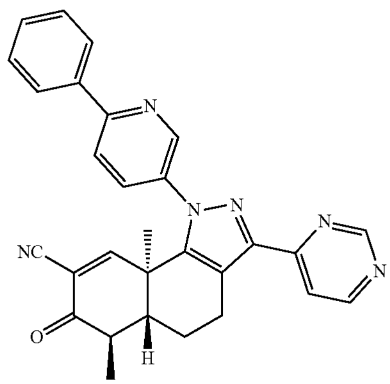 [SMILES: C[C@H]1C(=O)C(C#N)=C[C@@]2(C)c3c(c(-c4ccncn4)nn3-c3ccc(-c4ccccc4)nc3)CC[C@H]12] | 0.144 | 0.122 | 0.636 |
| T65 | 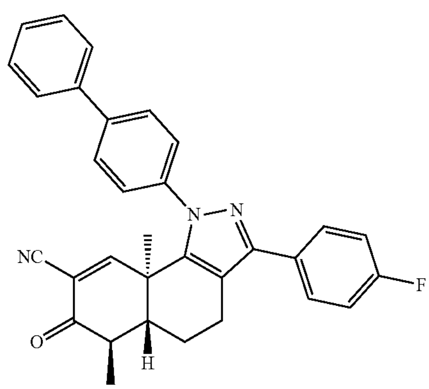 [SMILES: C[C@H]1C(=O)C(C#N)=C[C@@]2(C)c3c(c(-c4ccc(F)cc4)nn3-c3ccc(-c4ccccc4)cc3)CC[C@H]12] | 0.012 | 0.077 | 0.201 |
| T66 | 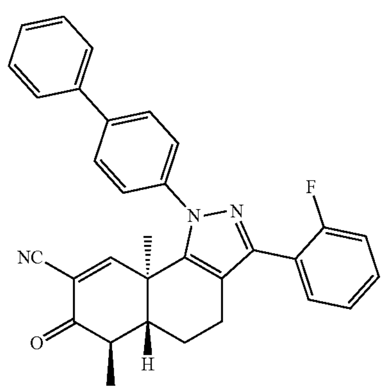 [SMILES: C[C@H]1C(=O)C(C#N)=C[C@@]2(C)c3c(c(-c4ccccc4F)nn3-c3ccc(-c4ccccc4)cc3)CC[C@H]12] | 0.019 | 0.058 | 0.128 |

TABLE 1-continued

Biological Activity Data for Compounds T1-T186
in hIL17, RORγ, and NRF2 GST ARE EC$_{2x}$ assays

| T# | Structure | hIL17 IC50 (μM) | RORγ IC50 (μM) | NRF2 ARE 2-Fold (μM) |
|---|---|---|---|---|
| T67 | 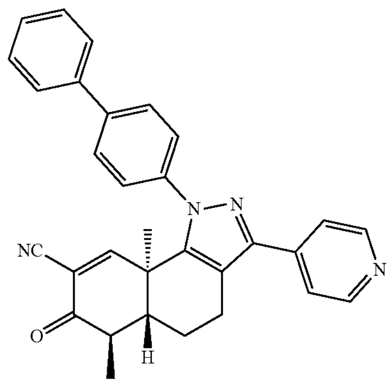 [SMILES: C[C@H]1C(=O)C(C#N)=C[C@@]2(C)c3c(c(-c4ccncc4)nn3-c3ccc(-c4ccccc4)cc3)CC[C@H]12] | 0.026 | 0.049 | 0.269 |
| T68 | 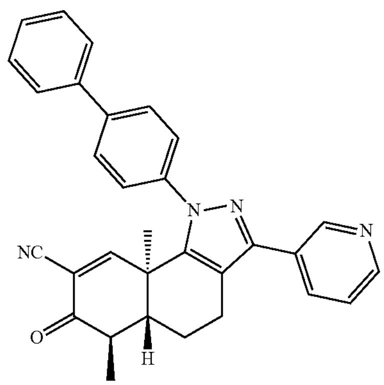 [SMILES: C[C@H]1C(=O)C(C#N)=C[C@@]2(C)c3c(c(-c4cccnc4)nn3-c3ccc(-c4ccccc4)cc3)CC[C@H]12] | 0.027 | 0.036 | 0.248 |
| T69 | 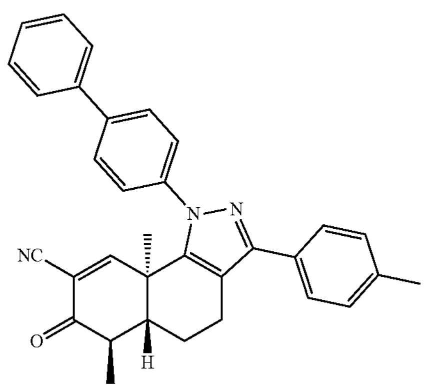 [SMILES: Cc1ccc(-c2nn(-c3ccc(-c4ccccc4)cc3)c3c2CC[C@@H]2[C@@H](C)C(=O)C(C#N)=C[C@@]32C)cc1] | 0.012 | 0.142 | 0.380 |
| T70 | 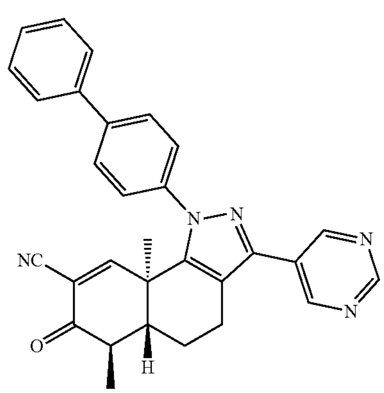 [SMILES: C[C@H]1C(=O)C(C#N)=C[C@@]2(C)c3c(c(-c4cncnc4)nn3-c3ccc(-c4ccccc4)cc3)CC[C@H]12] | 0.058 | 0.075 | 0.472 |

TABLE 1-continued
Biological Activity Data for Compounds T1-T186
in hIL17, RORγ, and NRF2 GST ARE EC$_{2x}$ assays
| T# | Structure | hIL17 IC50 (μM) | RORγ IC50 (μM) | NRF2 ARE 2-Fold (μM) |
|---|---|---|---|---|
| T71 | 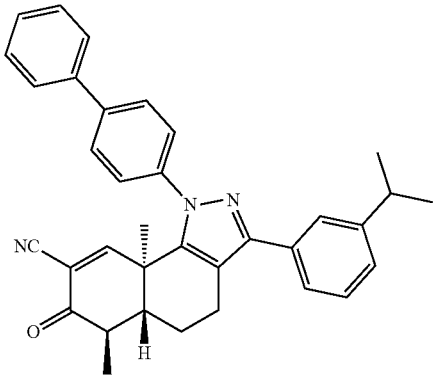 [SMILES: CC(C)c1cccc(-c2nn(-c3ccc(-c4ccccc4)cc3)c3c2CC[C@@H]2[C@@H](C)C(=O)C(C#N)=C[C@@]32C)c1] | 0.009 | 0.294 | 0.257 |
| T72 | 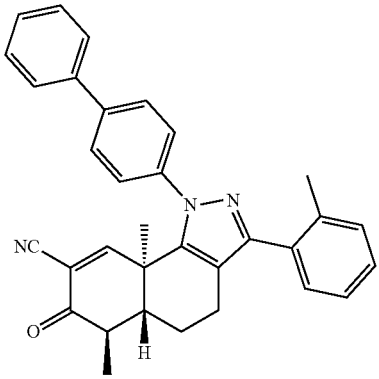 [SMILES: Cc1ccccc1-c1nn(-c2ccc(-c3ccccc3)cc2)c2c1CC[C@@H]1[C@@H](C)C(=O)C(C#N)=C[C@@]21C] | 0.010 | 0.138 | 0.205 |
| T73 | 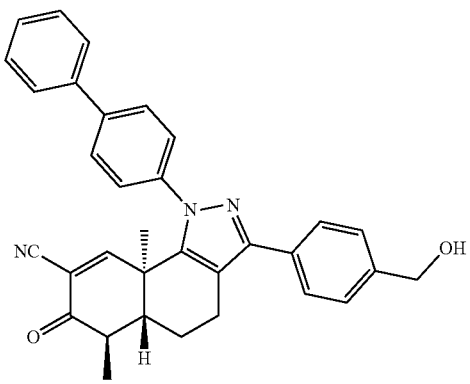 [SMILES: C[C@H]1C(=O)C(C#N)=C[C@@]2(C)c3c(c(-c4ccc(CO)cc4)nn3-c3ccc(-c4ccccc4)cc3)CC[C@H]12] | 0.030 | 0.040 | 0.159 |

TABLE 1-continued

Biological Activity Data for Compounds T1-T186
in hIL17, RORγ, and NRF2 GST ARE EC$_{2x}$ assays

| T# | Structure | hIL17 IC50 (μM) | RORγ IC50 (μM) | NRF2 ARE 2-Fold (μM) |
|---|---|---|---|---|
| T74 | 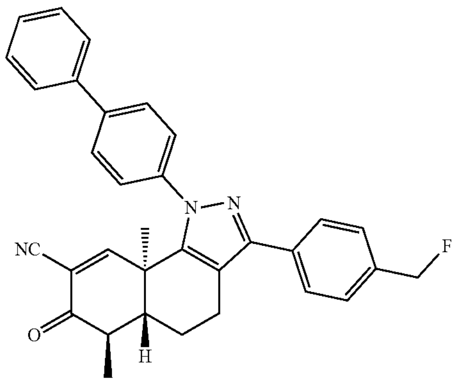 [SMILES: C[C@H]1C(=O)C(C#N)=C[C@@]2(C)c3c(c(-c4ccc(CF)cc4)nn3-c3ccc(-c4ccccc4)cc3)CC[C@H]12] | 0.016 | 0.111 | 0.182 |
| T75 | 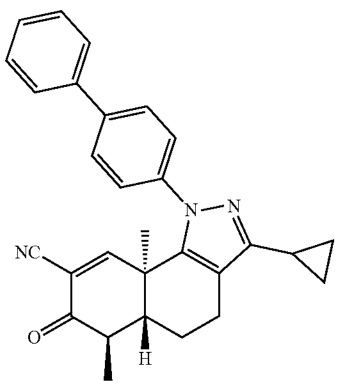 [SMILES: C[C@H]1C(=O)C(C#N)=C[C@@]2(C)c3c(c(C4CC4)nn3-c3ccc(-c4ccccc4)cc3)CC[C@H]12] | 0.130 | 0.068 | 0.248 |
| T76 | 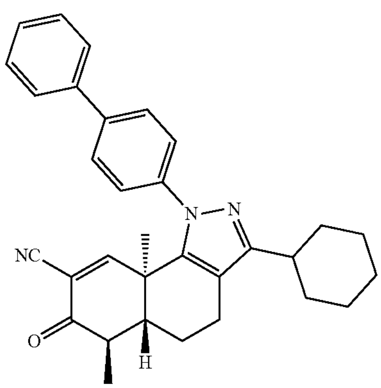 [SMILES: C[C@H]1C(=O)C(C#N)=C[C@@]2(C)c3c(c(C4CCCCC4)nn3-c3ccc(-c4ccccc4)cc3)CC[C@H]12] | 0.030 | 0.073 | 0.465 |
| T77 | 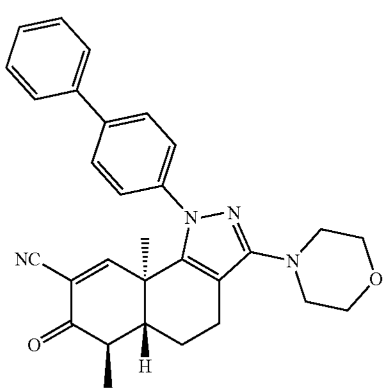 [SMILES: C[C@H]1C(=O)C(C#N)=C[C@@]2(C)c3c(c(N4CCOCC4)nn3-c3ccc(-c4ccccc4)cc3)CC[C@H]12] | 0.068 | 0.111 | 0.908 |

TABLE 1-continued

Biological Activity Data for Compounds T1-T186
in hIL17, RORγ, and NRF2 GST ARE EC$_{2x}$ assays

| T# | Structure | hIL17 IC50 (μM) | RORγ IC50 (μM) | NRF2 ARE 2-Fold (μM) |
|---|---|---|---|---|
| T78 | 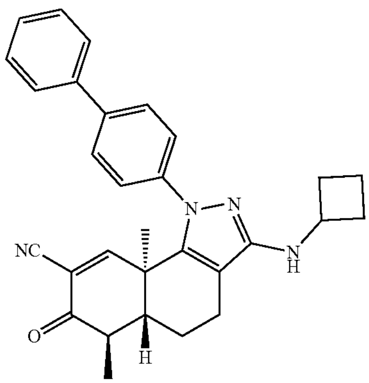 [SMILES: C[C@H]1C(=O)C(C#N)=C[C@@]2(C)c3c(c(NC4CCC4)nn3-c3ccc(-c4ccccc4)cc3)CC[C@H]12] | 0.048 | 0.062 | 0.534 |
| T79 | 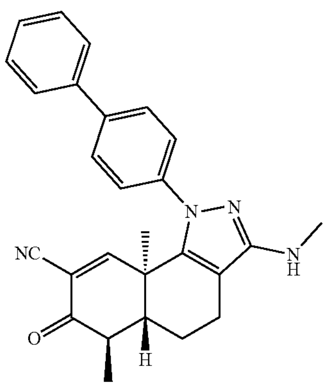 [SMILES: CNc1nn(-c2ccc(-c3ccccc3)cc2)c2c1CC[C@@H]1[C@@H](C)C(=O)C(C#N)=C[C@@]21C] | 0.178 | 0.140 | 1.042 |
| T80 | 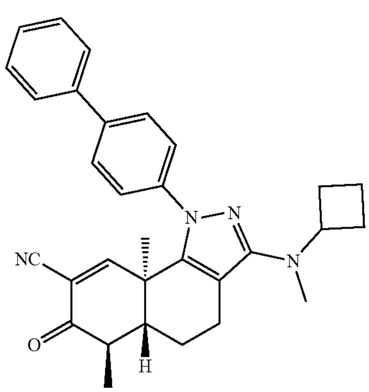 [SMILES: C[C@H]1C(=O)C(C#N)=C[C@@]2(C)c3c(c(N(C)C4CCC4)nn3-c3ccc(-c4ccccc4)cc3)CC[C@H]12] | 0.017 | 0.071 | 0.347 |

TABLE 1-continued
Biological Activity Data for Compounds T1-T186
in hIL17, RORγ, and NRF2 GST ARE EC$_{2x}$ assays
| T# | Structure | hIL17 IC50 (μM) | RORγ IC50 (μM) | NRF2 ARE 2-Fold (μM) |
|---|---|---|---|---|
| T81 | 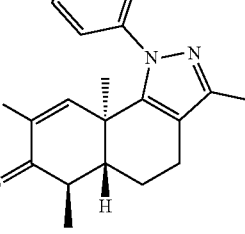 | 0.030 | 0.067 | 0.243 |
| T82 | 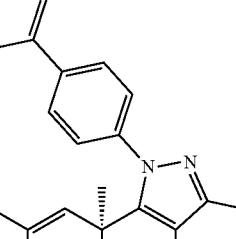 | 0.063 | 0.044 | 0.208 |
| T83 | 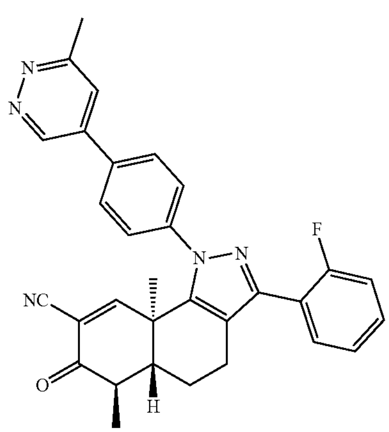 [SMILES: Cc1cc(-c2ccc(-n3nc(-c4ccccc4F)c4c3[C@]3(C)C=C(C#N)C(=O)[C@H](C)[C@H]3CC4)cc2)cnn1] | 0.020 | 0.033 | 0.139 |

TABLE 1-continued

Biological Activity Data for Compounds T1-T186
in hIL17, RORγ, and NRF2 GST ARE EC$_{2x}$ assays

| T# | Structure | hIL17 IC50 (μM) | RORγ IC50 (μM) | NRF2 ARE 2-Fold (μM) |
|---|---|---|---|---|
| T84 | 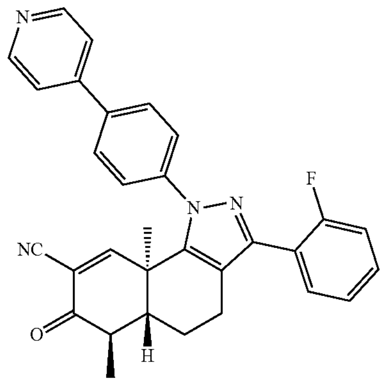 [SMILES: C[C@H]1C(=O)C(C#N)=C[C@@]2(C)c3c(c(-c4ccccc4F)nn3-c3ccc(-c4ccncc4)cc3)CC[C@H]12] | 0.033 | 0.023 | 0.121 |
| T85 | 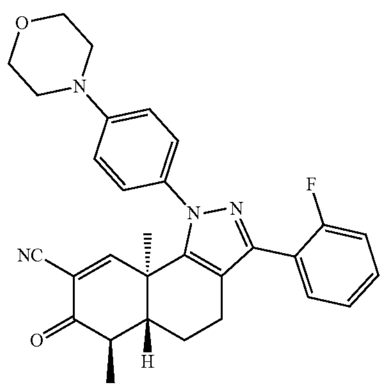 [SMILES: C[C@H]1C(=O)C(C#N)=C[C@@]2(C)c3c(c(-c4ccccc4F)nn3-c3ccc(N4CCOCC4)cc3)CC[C@H]12] | 0.046 | 0.050 | 0.079 |
| T86 | 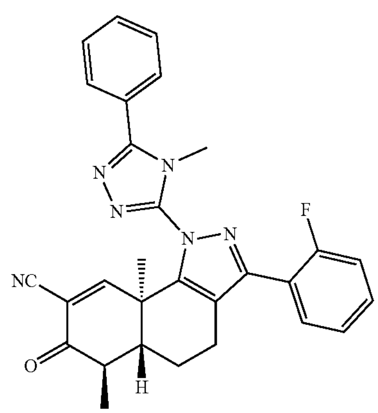 [SMILES: C[C@H]1C(=O)C(C#N)=C[C@@]2(C)c3c(c(-c4ccccc4F)nn3-c3nnc(-c4ccccc4)n3C)CC[C@H]12] | 0.088 | 0.351 | 1.475 |

TABLE 1-continued

Biological Activity Data for Compounds T1-T186
in hIL17, RORγ, and NRF2 GST ARE EC$_{2x}$ assays

| T# | Structure | hIL17 IC50 (μM) | RORγ IC50 (μM) | NRF2 ARE 2-Fold (μM) |
|---|---|---|---|---|
| T87 | 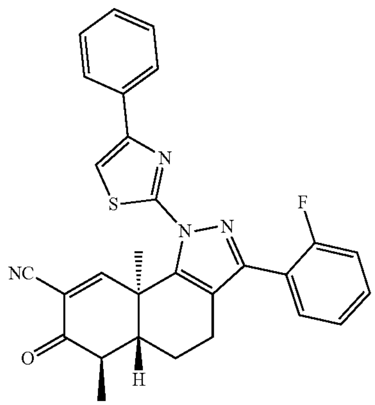 [SMILES: C[C@H]1C(=O)C(C#N)=C[C@@]2(C)c3c(c(-c4ccccc4F)nn3-c3nc(-c4ccccc4)cs3)CC[C@H]12] | 0.027 | 0.685 | 1.262 |
| T88 | 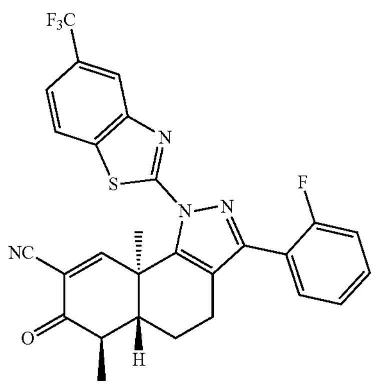 [SMILES: C[C@H]1C(=O)C(C#N)=C[C@@]2(C)c3c(c(-c4ccccc4F)nn3-c3nc4cc(C(F)(F)F)ccc4s3)CC[C@H]12] | 0.011 | 0.219 | 0.743 |
| T89 | 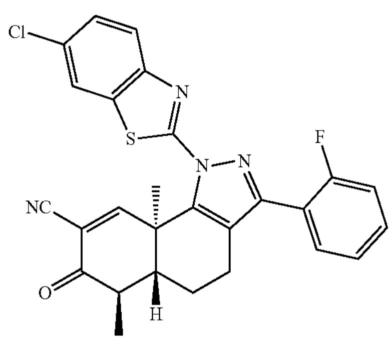 [SMILES: C[C@H]1C(=O)C(C#N)=C[C@@]2(C)c3c(c(-c4ccccc4F)nn3-c3nc4ccc(Cl)cc4s3)CC[C@H]12] | 0.013 | 0.251 | 0.482 |
| T90 | 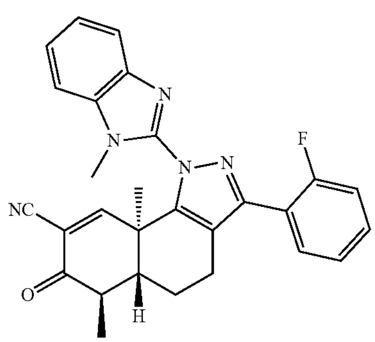 [SMILES: C[C@H]1C(=O)C(C#N)=C[C@@]2(C)c3c(c(-c4ccccc4F)nn3-c3nc4ccccc4n3C)CC[C@H]12] | 0.057 | 0.135 | 1.313 |

TABLE 1-continued

Biological Activity Data for Compounds T1-T186
in hIL17, RORγ, and NRF2 GST ARE EC$_{2x}$ assays

| T# | Structure | hIL17 IC50 (μM) | RORγ IC50 (μM) | NRF2 ARE 2-Fold (μM) |
|---|---|---|---|---|
| T91 | 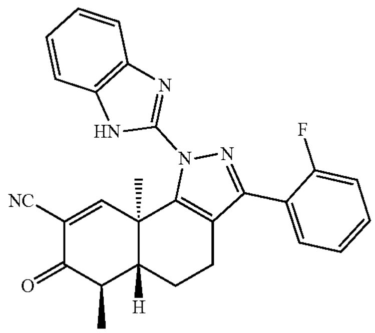 [SMILES: C[C@H]1C(=O)C(C#N)=C[C@@]2(C)c3c(c(-c4ccccc4F)nn3-c3nc4ccccc4[nH]3)CC[C@H]12] | >0.500 | >2.000 | >2.000 |
| T92 | 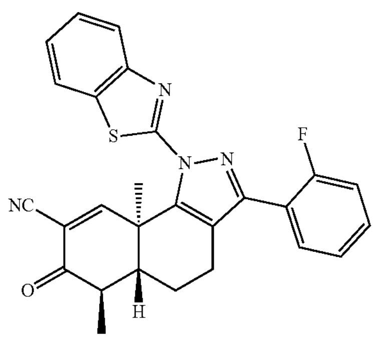 [SMILES: C[C@H]1C(=O)C(C#N)=C[C@@]2(C)c3c(c(-c4ccccc4F)nn3-c3nc4ccccc4s3)CC[C@H]12] | 0.028 | 0.340 | 0.491 |
| T93 | 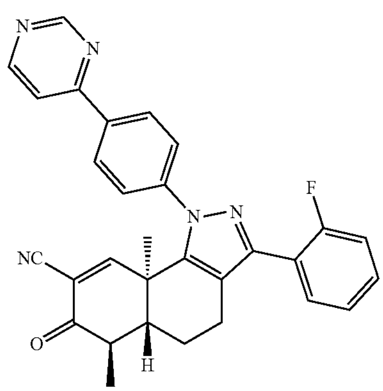 [SMILES: C[C@H]1C(=O)C(C#N)=C[C@@]2(C)c3c(c(-c4ccccc4F)nn3-c3ccc(-c4ccncn4)cc3)CC[C@H]12] | 0.037 | 0.042 | 0.139 |
| T94 | 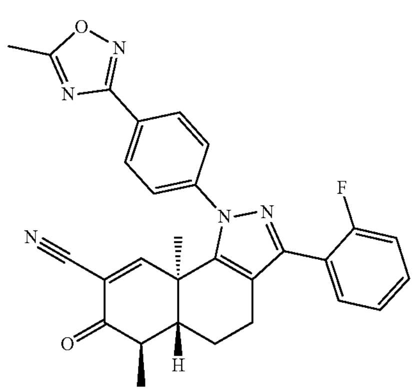 [SMILES: Cc1nc(-c2ccc(-n3nc(-c4ccccc4F)c4c3[C@]3(C)C=C(C#N)C(=O)[C@H](C)[C@H]3CC4)cc2)no1] | 0.024 | 0.065 | 0.146 |

TABLE 1-continued

Biological Activity Data for Compounds T1-T186
in hIL17, RORγ, and NRF2 GST ARE EC$_{2x}$ assays

| T# | Structure | hIL17 IC50 (μM) | RORγ IC50 (μM) | NRF2 ARE 2-Fold (μM) |
|---|---|---|---|---|
| T95 | 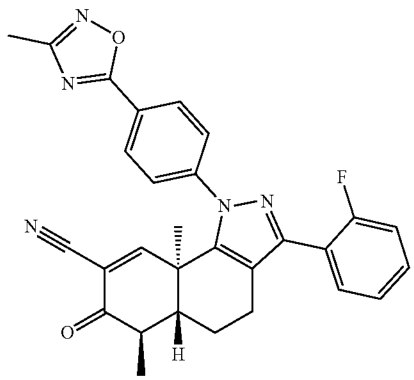 [SMILES: Cc1noc(-c2ccc(-n3nc(-c4ccccc4F)c4c3[C@]3(C)C=C(C#N)C(=O)[C@H](C)[C@H]3CC4)cc2)n1] | 0.040 | 0.062 | 0.185 |
| T96 | 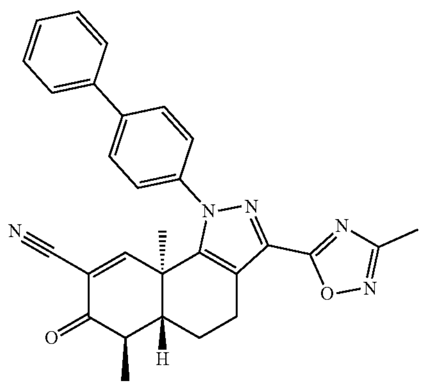 [SMILES: Cc1noc(-c2nn(-c3ccc(-c4ccccc4)cc3)c3c2CC[C@@H]2[C@@H](C)C(=O)C(C#N)=C[C@@]32C)n1] | 0.032 | 0.059 | 0.258 |
| T97 | 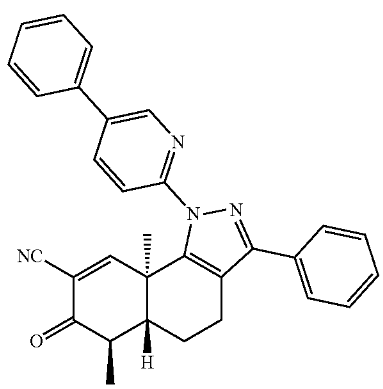 [SMILES: C[C@H]1C(=O)C(C#N)=C[C@@]2(C)c3c(c(-c4ccccc4)nn3-c3ccc(-c4ccccc4)cn3)CC[C@H]12] | 0.038 | 0.107 | 0.597 |
| T98 | 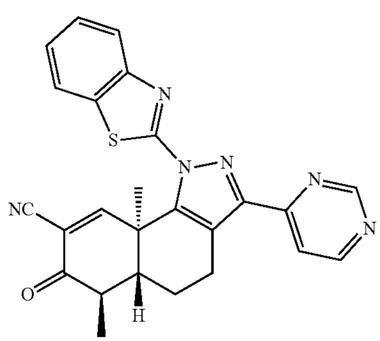 [SMILES: C[C@H]1C(=O)C(C#N)=C[C@@]2(C)c3c(c(-c4ccncn4)nn3-c3nc4ccccc4s3)CC[C@H]12] | 0.078 | 0.289 | 0.275 |

TABLE 1-continued

Biological Activity Data for Compounds T1-T186
in hIL17, RORγ, and NRF2 GST ARE EC$_{2x}$ assays

| T# | Structure | hIL17 IC50 (μM) | RORγ IC50 (μM) | NRF2 ARE 2-Fold (μM) |
|---|---|---|---|---|
| T99 | 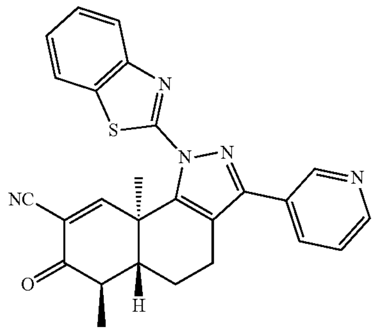 [SMILES: C[C@H]1C(=O)C(C#N)=C[C@@]2(C)c3c(c(-c4cccnc4)nn3-c3nc4ccccc4s3)CC[C@H]12] | 0.087 | 0.449 | 0.329 |
| T100 | 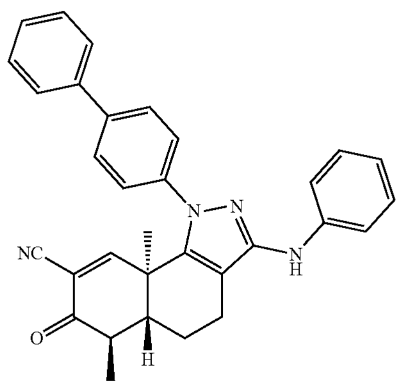 [SMILES: C[C@H]1C(=O)C(C#N)=C[C@@]2(C)c3c(c(Nc4ccccc4)nn3-c3ccc(-c4ccccc4)cc3)CC[C@H]12] | 0.016 | 0.110 | 0.319 |
| T101 | 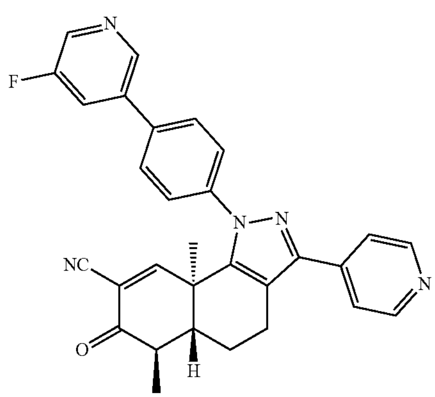 | 0.051 | 0.054 | 0.353 |
| T102 | 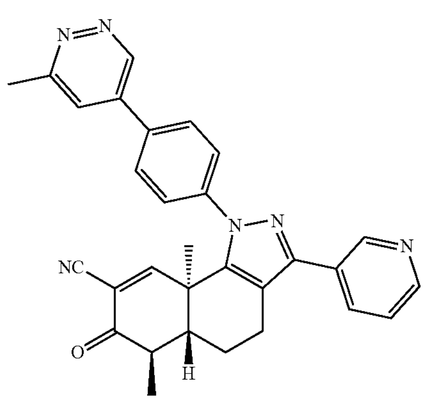 [SMILES: Cc1cc(-c2ccc(-n3nc(-c4cccnc4)c4c3[C@]3(C)C=C(C#N)C(=O)[C@H](C)[C@H]3CC4)cc2)cnn1] | 0.056 | 0.090 | 0.918 |

TABLE 1-continued

Biological Activity Data for Compounds T1-T186
in hIL17, RORγ, and NRF2 GST ARE EC$_{2x}$ assays

| T# | Structure | hIL17 IC50 (μM) | RORγ IC50 (μM) | NRF2 ARE 2-Fold (μM) |
|---|---|---|---|---|
| T103 | 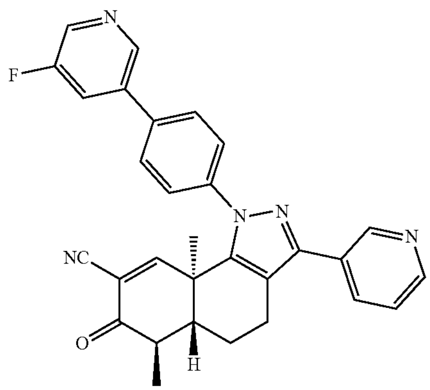 [SMILES: C[C@H]1C(=O)C(C#N)=C[C@@]2(C)c3c(c(-c4cccnc4)nn3-c3ccc(-c4cncc(F)c4)cc3)CC[C@H]12] | 0.031 | 0.047 | 0.365 |
| T104 | 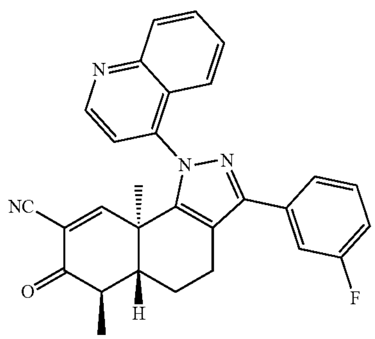 [SMILES: C[C@H]1C(=O)C(C#N)=C[C@@]2(C)c3c(c(-c4cccc(F)c4)nn3-c3ccnc4ccccc34)CC[C@H]12] | 0.062 | 0.208 | 0.638 |
| T105 | 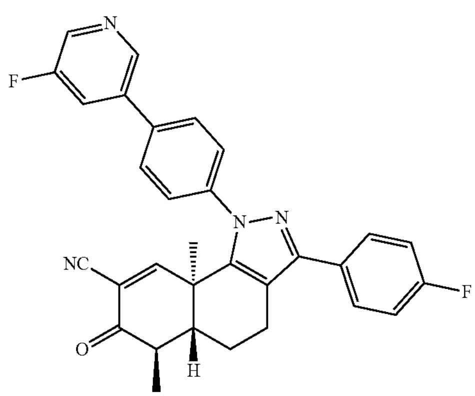 [SMILES: C[C@H]1C(=O)C(C#N)=C[C@@]2(C)c3c(c(-c4ccc(F)cc4)nn3-c3ccc(-c4cncc(F)c4)cc3)CC[C@H]12] | 0.021 | 0.067 | 0.361 |
| T106 | 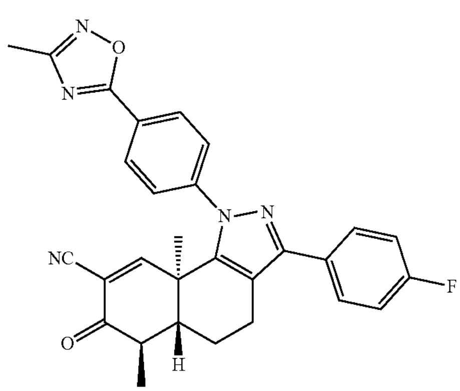 [SMILES: Cc1noc(-c2ccc(-n3nc(-c4ccc(F)cc4)c4c3[C@]3(C)C=C(C#N)C(=O)[C@H](C)[C@H]3CC4)cc2)n1] | 0.027 | 0.083 | 0.290 |

TABLE 1-continued

Biological Activity Data for Compounds T1-T186
in hIL17, RORγ, and NRF2 GST ARE EC$_{2x}$ assays

| T# | Structure | hIL17 IC50 (μM) | RORγ IC50 (μM) | NRF2 ARE 2-Fold (μM) |
|---|---|---|---|---|
| T107 | 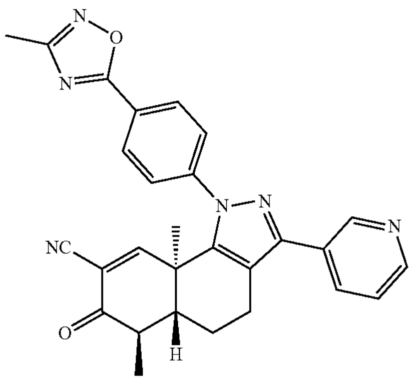 [SMILES: Cc1noc(-c2ccc(-n3nc(-c4cccnc4)c4c3[C@]3(C)C=C(C#N)C(=O)[C@H](C)[C@H]3CC4)cc2)n1] | 0.087 | 0.112 | 0.505 |
| T108 | 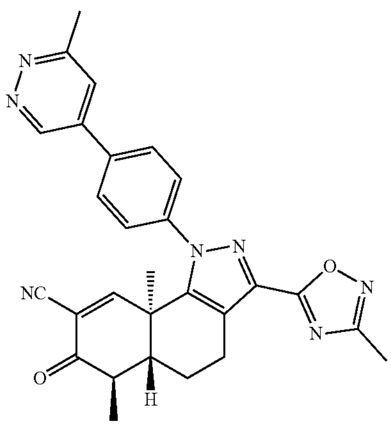 [SMILES: Cc1cc(-c2ccc(-n3nc(-c4nc(C)no4)c4c3[C@]3(C)C=C(C#N)C(=O)[C@H](C)[C@H]3CC4)cc2)cnn1] | 0.223 | 0.154 | 1.245 |
| T109 | 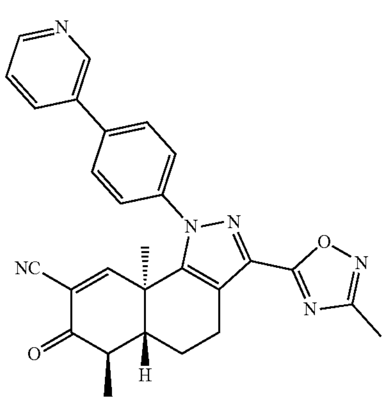 [SMILES: Cc1noc(-c2nn(-c3ccc(-c4cccnc4)cc3)c3c2CC[C@@H]2[C@@H](C)C(=O)C(C#N)=C[C@@]32C)n1] | 0.163 | 0.089 | 0.543 |

TABLE 1-continued

Biological Activity Data for Compounds T1-T186
in hIL17, RORγ, and NRF2 GST ARE EC$_{2x}$ assays

| T# | Structure | hIL17 IC50 (μM) | RORγ IC50 (μM) | NRF2 ARE 2-Fold (μM) |
|---|---|---|---|---|
| T110 | 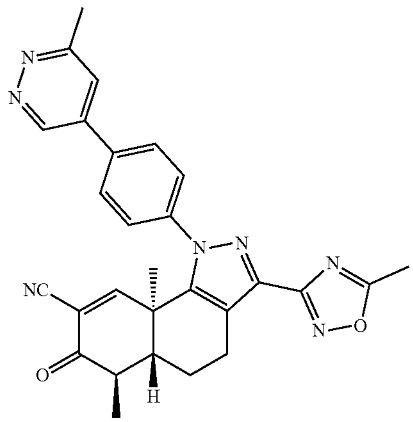 [SMILES: Cc1cc(-c2ccc(-n3nc(-c4noc(C)n4)c4c3[C@]3(C)C=C(C#N)C(=O)[C@H](C)[C@H]3CC4)cc2)cnn1] | 0.126 | 0.193 | 1.309 |
| T111 | 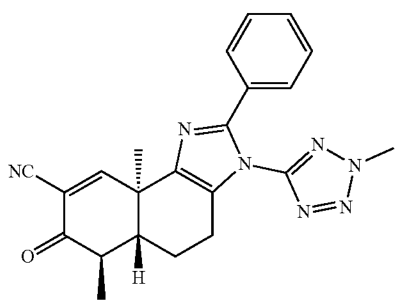 [SMILES: C[C@H]1C(=O)C(C#N)=C[C@@]2(C)c3nc(-c4ccccc4)n(-c4nnn(C)n4)c3CC[C@H]12] | | 0.768 | 0.590 |
| T112 | 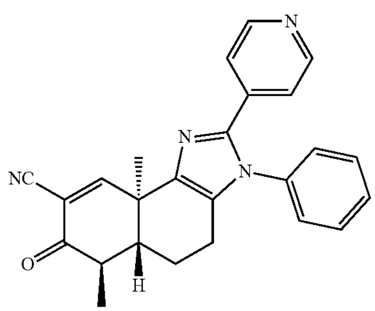 [SMILES: C[C@H]1C(=O)C(C#N)=C[C@@]2(C)c3nc(-c4ccncc4)n(-c4ccccc4)c3CC[C@H]12] | | 0.264 | 0.563 |
| T113 | 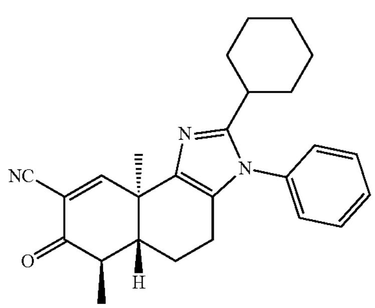 [SMILES: C[C@H]1C(=O)C(C#N)=C[C@@]2(C)c3nc(C4CCCCC4)n(-c4ccccc4)c3CC[C@H]12] | 0.181 | 0.172 | >1.000 |

TABLE 1-continued

Biological Activity Data for Compounds T1-T186
in hIL17, RORγ, and NRF2 GST ARE EC$_{2x}$ assays

| T# | Structure | hIL17 IC50 (μM) | RORγ IC50 (μM) | NRF2 ARE 2-Fold (μM) |
|---|---|---|---|---|
| T114 | 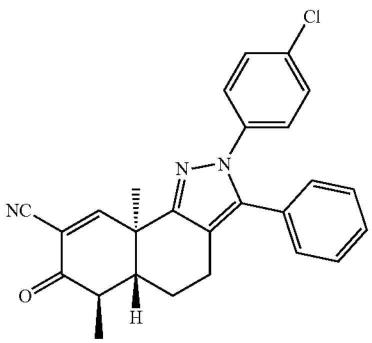 [SMILES: C[C@H]1C(=O)C(C#N)=C[C@@]2(C)c3nn(-c4ccc(Cl)cc4)c(-c4ccccc4)c3CC[C@H]12] | 0.507 | 0.106 | 0.894 |
| T115 | 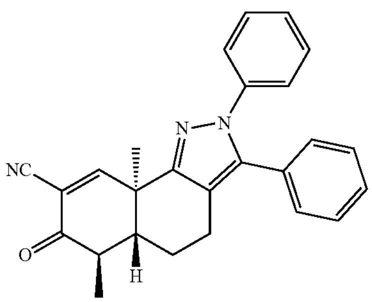 [SMILES: C[C@H]1C(=O)C(C#N)=C[C@@]2(C)c3nn(-c4ccccc4)c(-c4ccccc4)c3CC[C@H]12] | 0.287 | 0.077 | 0.466 |
| T116 | 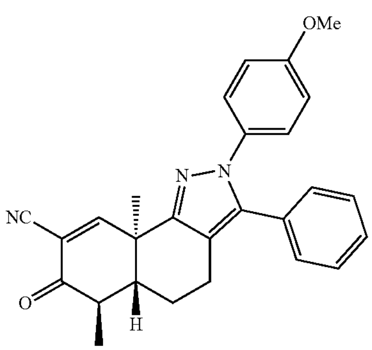 | 0.191 | 0.080 | 0.483 |
| T117 | 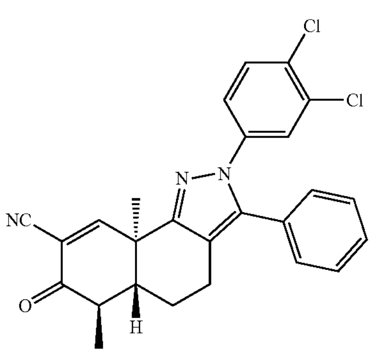 [SMILES: C[C@H]1C(=O)C(C#N)=C[C@@]2(C)c3nn(-c4ccc(Cl)c(Cl)c4)c(-c4ccccc4)c3CC[C@H]12] | 0.107 | 0.114 | 0.834 |

TABLE 1-continued

Biological Activity Data for Compounds T1-T186
in hIL17, RORγ, and NRF2 GST ARE EC$_{2x}$ assays

| T# | Structure | hIL17 IC50 (μM) | RORγ IC50 (μM) | NRF2 ARE 2-Fold (μM) |
| --- | --- | --- | --- | --- |
| T118 | 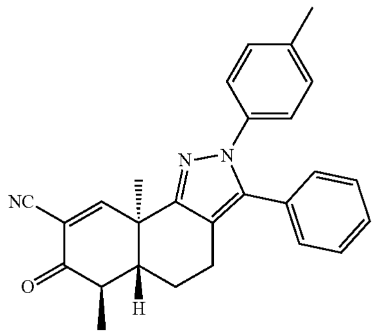 [SMILES: Cc1ccc(-n2nc3c(c2-c2ccccc2)CC[C@@H]2[C@@H](C)C(=O)C(C#N)=C[C@@]32C)cc1] | 0.158 | 0.122 | 0.635 |
| T119 | 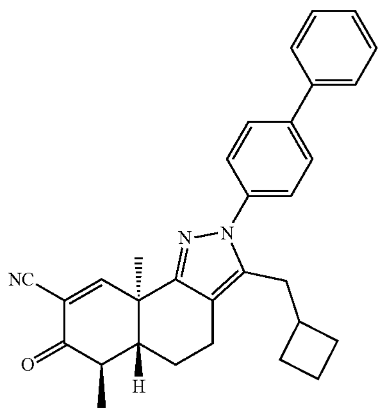 [SMILES: C[C@H]1C(=O)C(C#N)=C[C@@]2(C)c3nn(-c4ccc(-c5ccccc5)cc4)c(CC4CCC4)c3CC[C@H]12] | 0.043 | 0.158 | 1.155 |
| T120 | 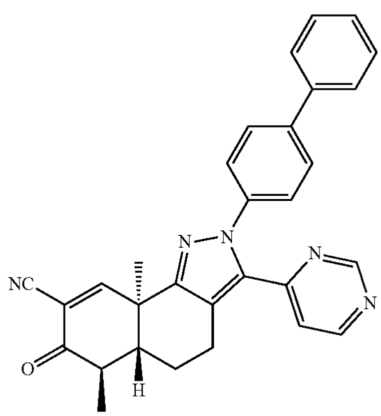 [SMILES: C[C@H]1C(=O)C(C#N)=C[C@@]2(C)c3nn(-c4ccc(-c5ccccc5)cc4)c(-c4ccncn4)c3CC[C@H]12] | 0.054 | 0.092 | 0.908 |
| T121 | 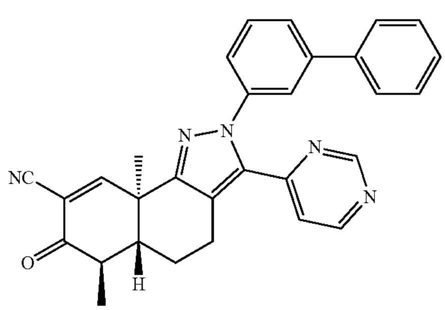 [SMILES: C[C@H]1C(=O)C(C#N)=C[C@@]2(C)c3nn(-c4cccc(-c5ccccc5)c4)c(-c4ccncn4)c3CC[C@H]12] | 0.085 | 0.242 | 1.072 |

TABLE 1-continued

Biological Activity Data for Compounds T1-T186
in hIL17, RORγ, and NRF2 GST ARE EC$_{2x}$ assays

| T# | Structure | hIL17 IC50 (μM) | RORγ IC50 (μM) | NRF2 ARE 2-Fold (μM) |
|---|---|---|---|---|
| T122 | 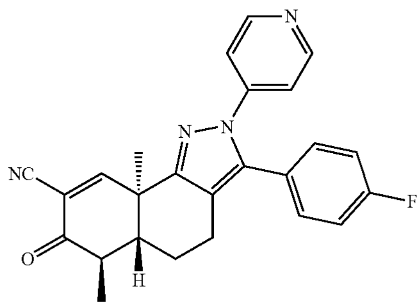 [SMILES: C[C@H]1C(=O)C(C#N)=C[C@@]2(C)c3nn(-c4ccncc4)c(-c4ccc(F)cc4)c3CC[C@H]12] | 0.246 | 0.097 | 0.441 |
| T123 | 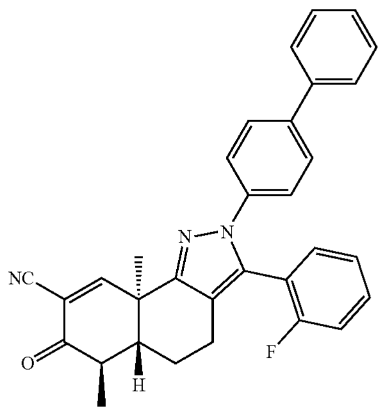 [SMILES: C[C@H]1C(=O)C(C#N)=C[C@@]2(C)c3nn(-c4ccc(-c5ccccc5)cc4)c(-c4ccccc4F)c3CC[C@H]12] | 0.050 | 0.139 | 1.181 |
| T124 | 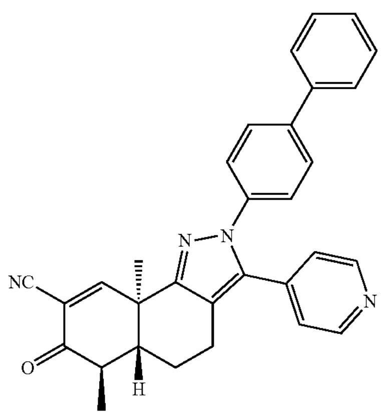 [SMILES: C[C@H]1C(=O)C(C#N)=C[C@@]2(C)c3nn(-c4ccc(-c5ccccc5)cc4)c(-c4ccncc4)c3CC[C@H]12] | 0.077 | 0.123 | 0.651 |
| T125 | 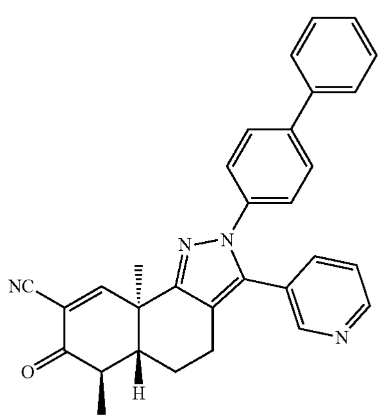 [SMILES: C[C@H]1C(=O)C(C#N)=C[C@@]2(C)c3nn(-c4ccc(-c5ccccc5)cc4)c(-c4cccnc4)c3CC[C@H]12] | 0.086 | 0.137 | 0.877 |

TABLE 1-continued

Biological Activity Data for Compounds T1-T186
in hIL17, RORγ, and NRF2 GST ARE EC$_{2x}$ assays

| T# | Structure | hIL17 IC50 (μM) | RORγ IC50 (μM) | NRF2 ARE 2-Fold (μM) |
|---|---|---|---|---|
| T126 | 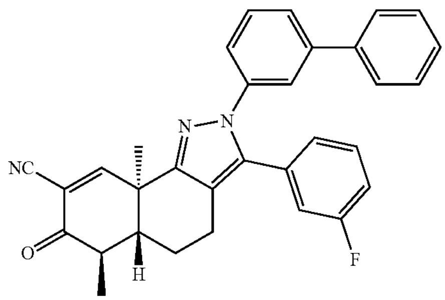 [SMILES: C[C@H]1C(=O)C(C#N)=C[C@@]2(C)c3nn(-c4cccc(-c5ccccc5)c4)c(-c4cccc(F)c4)c3CC[C@H]12] | 0.021 | 0.253 | 1.117 |
| T127 | 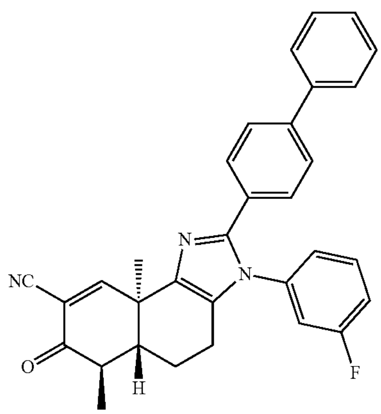 [SMILES: C[C@H]1C(=O)C(C#N)=C[C@@]2(C)c3nc(-c4ccc(-c5ccccc5)cc4)n(-c4cccc(F)c4)c3CC[C@H]12] | 0.062 | 0.267 | 1.119 |
| T128 | 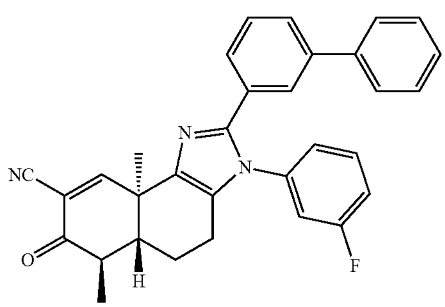 [SMILES: C[C@H]1C(=O)C(C#N)=C[C@@]2(C)c3nc(-c4cccc(-c5ccccc5)c4)n(-c4cccc(F)c4)c3CC[C@H]12] | 0.117 | 0.158 | 0.818 |
| T129 | 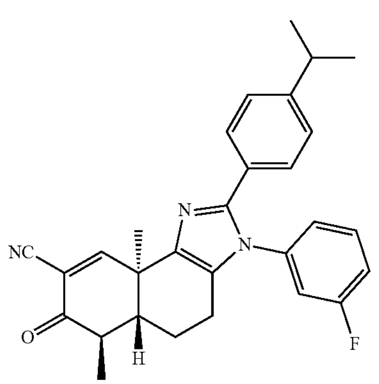 [SMILES: CC(C)c1ccc(-c2nc3c(n2-c2cccc(F)c2)CC[C@@H]2[C@@H](C)C(=O)C(C#N)=C[C@@]32C)cc1] | 0.073 | 0.214 | 1.291 |

TABLE 1-continued

Biological Activity Data for Compounds T1-T186
in hIL17, RORγ, and NRF2 GST ARE EC$_{2x}$ assays

| T# | Structure | hIL17 IC50 (μM) | RORγ IC50 (μM) | NRF2 ARE 2-Fold (μM) |
|---|---|---|---|---|
| T130 | 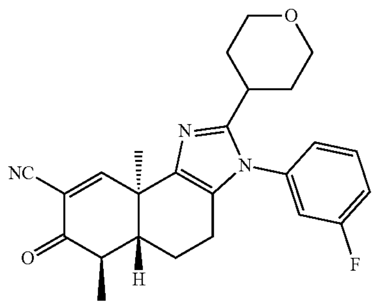 [SMILES: C[C@H]1C(=O)C(C#N)=C[C@@]2(C)c3nc(C4CCOCC4)n(-c4cccc(F)c4)c3CC[C@H]12] | 0.273 | 0.345 | 1.782 |
| T131 | 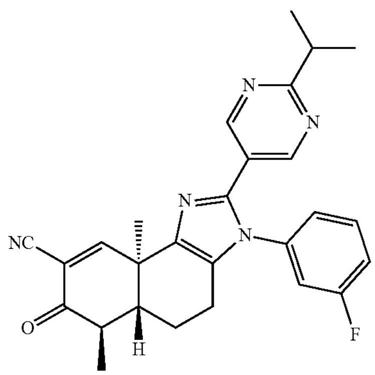 [SMILES: CC(C)c1ncc(-c2nc3c(n2-c2cccc(F)c2)CC[C@@H]2[C@@H](C)C(=O)C(C#N)=C[C@@]32C)cn1] | 0.138 | 0.170 | 0.767 |
| T132 | 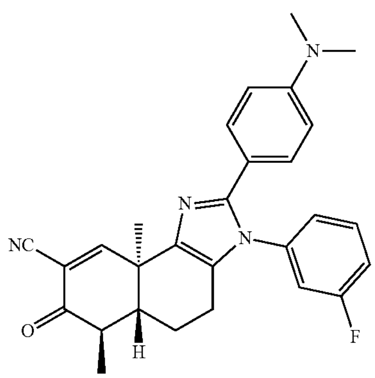 [SMILES: C[C@H]1C(=O)C(C#N)=C[C@@]2(C)c3nc(-c4ccc(N(C)C)cc4)n(-c4cccc(F)c4)c3CC[C@H]12] | 0.114 | 0.110 | 1.025 |
| T133 | 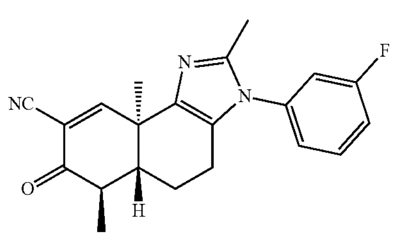 [SMILES: Cc1nc2c(n1-c1cccc(F)c1)CC[C@@H]1[C@@H](C)C(=O)C(C#N)=C[C@@]21C] | 0.247 | 0.225 | 0.767 |

TABLE 1-continued

Biological Activity Data for Compounds T1-T186
in hIL17, RORγ, and NRF2 GST ARE EC$_{2x}$ assays

| T# | Structure | hIL17 IC50 (μM) | RORγ IC50 (μM) | NRF2 ARE 2-Fold (μM) |
|---|---|---|---|---|
| T134 | 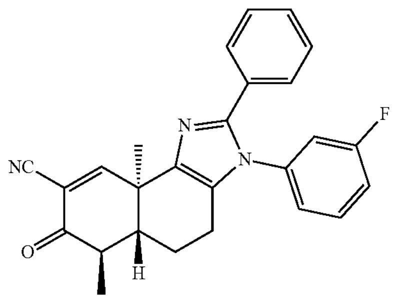 [SMILES: C[C@H]1C(=O)C(C#N)=C[C@@]2(C)c3nc(-c4ccccc4)n(-c4cccc(F)c4)c3CC[C@H]12] | 0.183 | 0.143 | 0.832 |
| T135 | 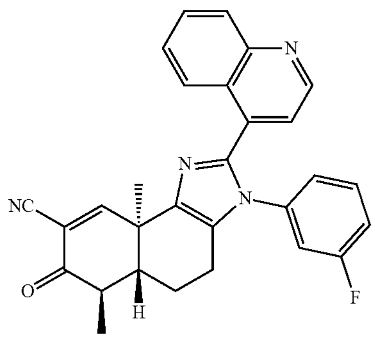 [SMILES: C[C@H]1C(=O)C(C#N)=C[C@@]2(C)c3nc(-c4ccnc5ccccc45)n(-c4cccc(F)c4)c3CC[C@H]12] | 0.160 | 0.141 | 0.896 |
| T136 | 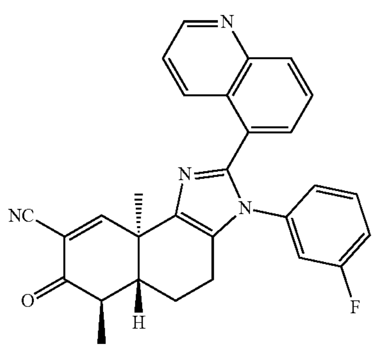 [SMILES: C[C@H]1C(=O)C(C#N)=C[C@@]2(C)c3nc(-c4cccc5ncccc45)n(-c4cccc(F)c4)c3CC[C@H]12] | 0.144 | 0.189 | 0.753 |
| T137 | 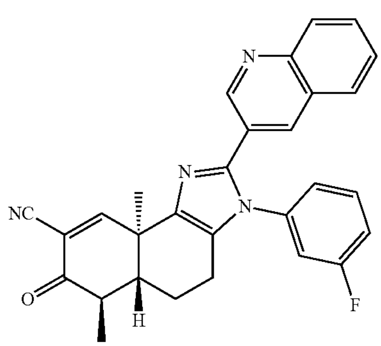 [SMILES: C[C@H]1C(=O)C(C#N)=C[C@@]2(C)c3nc(-c4cnc5ccccc5c4)n(-c4cccc(F)c4)c3CC[C@H]12] | 0.240 | 0.093 | 0.618 |

TABLE 1-continued

Biological Activity Data for Compounds T1-T186 in hIL17, RORγ, and NRF2 GST ARE EC$_{2x}$ assays

| T# | Structure | hIL17 IC50 (μM) | RORγ IC50 (μM) | NRF2 ARE 2-Fold (μM) |
|---|---|---|---|---|
| T138 | 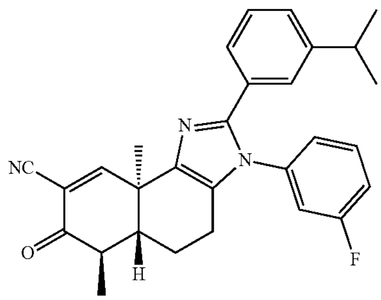 [SMILES: CC(C)c1cccc(-c2nc3c(n2-c2cccc(F)c2)CC[C@@H]2[C@@H](C)C(=O)C(C#N)=C[C@@]32C)c1] | 0.201 | 0.284 | 0.941 |
| T139 | 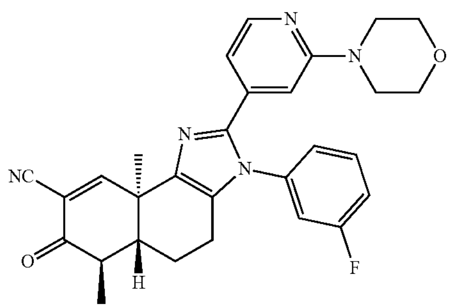 [SMILES: C[C@H]1C(=O)C(C#N)=C[C@@]2(C)c3nc(-c4ccnc(N5CCOCC5)c4)n(-c4cccc(F)c4)c3CC[C@H]12] | 0.128 | 0.112 | 0.660 |
| T140 | 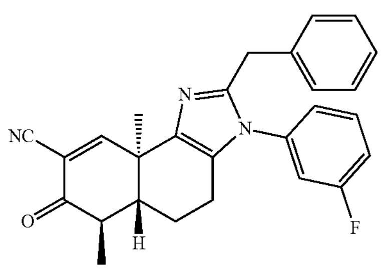 [SMILES: C[C@H]1C(=O)C(C#N)=C[C@@]2(C)c3nc(Cc4ccccc4)n(-c4cccc(F)c4)c3CC[C@H]12] | 0.288 | 0.113 | 1.268 |
| T141 | 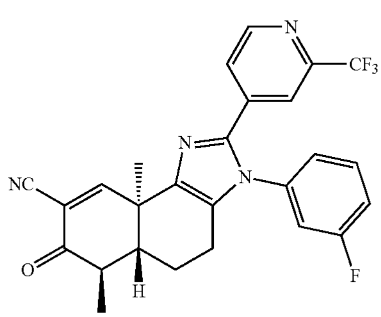 [SMILES: C[C@H]1C(=O)C(C#N)=C[C@@]2(C)c3nc(-c4ccnc(C(F)(F)F)c4)n(-c4cccc(F)c4)c3CC[C@H]12] | 0.194 | 0.146 | 0.892 |

TABLE 1-continued

Biological Activity Data for Compounds T1-T186
in hIL17, RORγ, and NRF2 GST ARE EC$_{2x}$ assays

| T# | Structure | hIL17 IC50 (μM) | RORγ IC50 (μM) | NRF2 ARE 2-Fold (μM) |
|---|---|---|---|---|
| T142 | 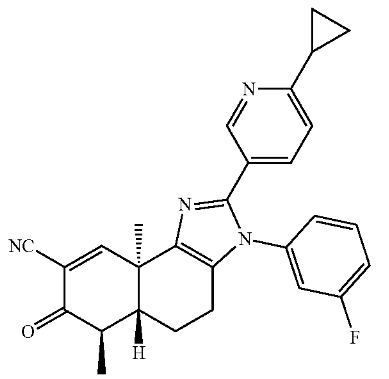 [SMILES: C[C@H]1C(=O)C(C#N)=C[C@@]2(C)c3nc(-c4ccc(C5CC5)nc4)n(-c4cccc(F)c4)c3CC[C@H]12] | 0.156 | 0.076 | 0.861 |
| T143 | 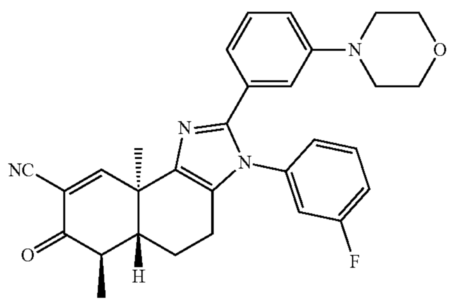 [SMILES: C[C@H]1C(=O)C(C#N)=C[C@@]2(C)c3nc(-c4cccc(N5CCOCC5)c4)n(-c4cccc(F)c4)c3CC[C@H]12] | 0.132 | 0.095 | 0.643 |
| T144 | 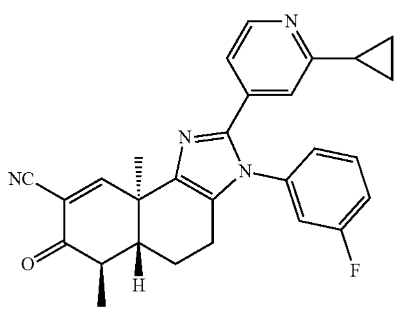 [SMILES: C[C@H]1C(=O)C(C#N)=C[C@@]2(C)c3nc(-c4ccnc(C5CC5)c4)n(-c4cccc(F)c4)c3CC[C@H]12] | 0.207 | 0.173 | 1.122 |
| T145 | 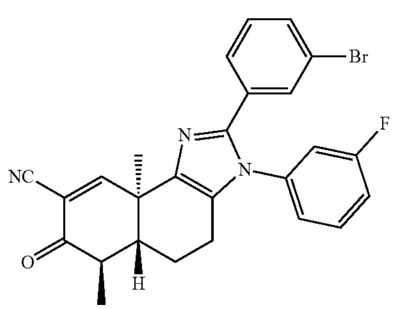 [SMILES: C[C@H]1C(=O)C(C#N)=C[C@@]2(C)c3nc(-c4cccc(Br)c4)n(-c4cccc(F)c4)c3CC[C@H]12] | 0.087 | 0.092 | 0.755 |

TABLE 1-continued
Biological Activity Data for Compounds T1-T186
in hIL17, RORγ, and NRF2 GST ARE EC$_{2x}$ assays
| T# | Structure | hIL17 IC50 (μM) | RORγ IC50 (μM) | NRF2 ARE 2-Fold (μM) |
|---|---|---|---|---|
| T146 | 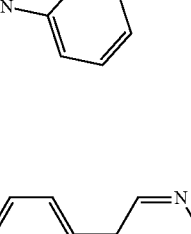 | 0.070 | 0.106 | 0.423 |
| T147 | 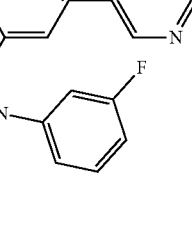 | 0.185 | 0.108 | 0.515 |
| T148 | 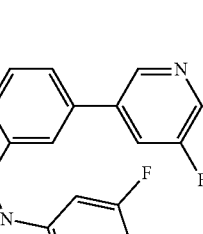 | 0.086 | 0.149 | 0.566 |
| T149 | 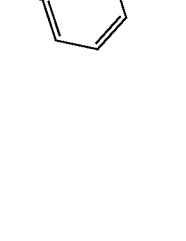 | 0.129 | 0.159 | 0.687 |

TABLE 1-continued

Biological Activity Data for Compounds T1-T186
in hIL17, RORγ, and NRF2 GST ARE EC$_{2x}$ assays

| T# | Structure | hIL17 IC50 (μM) | RORγ IC50 (μM) | NRF2 ARE 2-Fold (μM) |
|---|---|---|---|---|
| T150 | 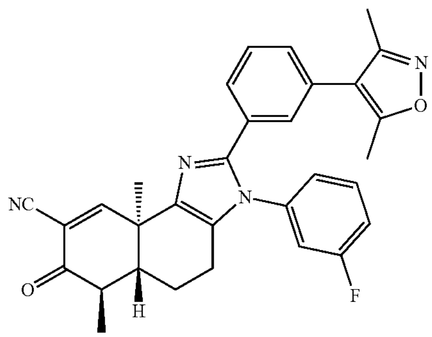 [SMILES: Cc1noc(C)c1-c1cccc(-c2nc3c(n2-c2cccc(F)c2)CC[C@@H]2[C@@H](C)C(=O)C(C#N)=C[C@@]32C)c1] | 0.104 | 0.135 | 0.488 |
| T151 | 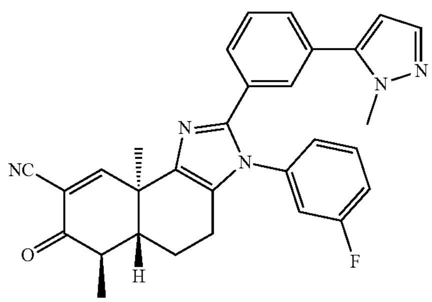 [SMILES: C[C@H]1C(=O)C(C#N)=C[C@@]2(C)c3nc(-c4cccc(-c5ccnn5C)c4)n(-c4cccc(F)c4)c3CC[C@H]12] | 0.154 | 0.234 | 0.749 |
| T152 | 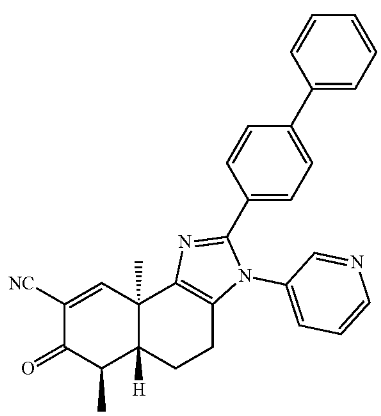 [SMILES: C[C@H]1C(=O)C(C#N)=C[C@@]2(C)c3nc(-c4ccc(-c5ccccc5)cc4)n(-c4cccnc4)c3CC[C@H]12] | 0.131 | 0.188 | 1.164 |
| T153 | 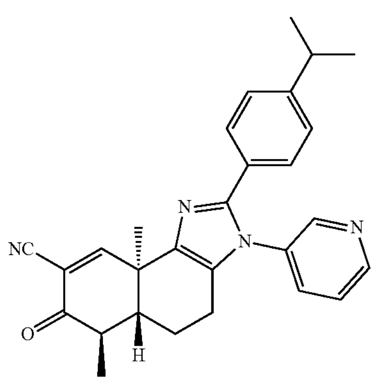 [SMILES: CC(C)c1ccc(-c2nc3c(n2-c2cccnc2)CC[C@@H]2[C@@H](C)C(=O)C(C#N)=C[C@@]32C)cc1] | 0.108 | 0.334 | 1.247 |

TABLE 1-continued

Biological Activity Data for Compounds T1-T186
in hIL17, RORγ, and NRF2 GST ARE EC$_{2x}$ assays

| T# | Structure | hIL17 IC50 (μM) | RORγ IC50 (μM) | NRF2 ARE 2-Fold (μM) |
|---|---|---|---|---|
| T154 | 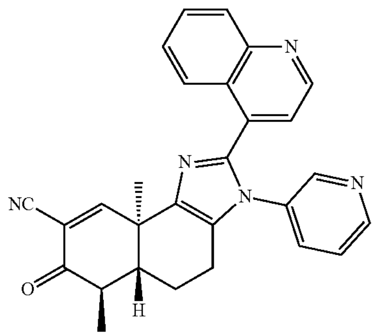 [SMILES: C[C@H]1C(=O)C(C#N)=C[C@@]2(C)c3nc(-c4ccnc5ccccc45)n(-c4cccnc4)c3CC[C@H]12] | 0.415 | 0.572 | 1.969 |
| T155 | 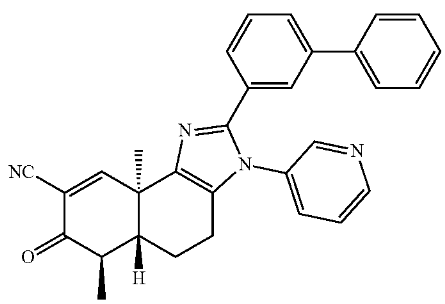 [SMILES: C[C@H]1C(=O)C(C#N)=C[C@@]2(C)c3nc(-c4cccc(-c5ccccc5)c4)n(-c4cccnc4)c3CC[C@H]12] | 0.161 | 0.201 | 0.738 |
| T156 | 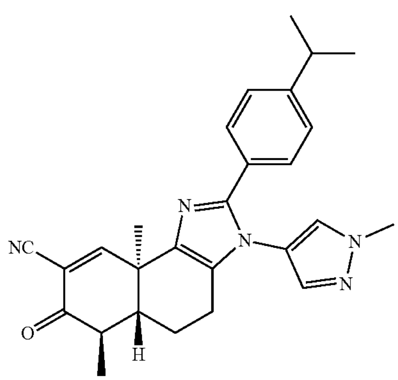 [SMILES: CC(C)c1ccc(-c2nc3c(n2-c2cnn(C)c2)CC[C@@H]2[C@@H](C)C(=O)C(C#N)=C[C@@]32C)cc1] | 0.128 | 0.117 | 1.163 |
| T157 | 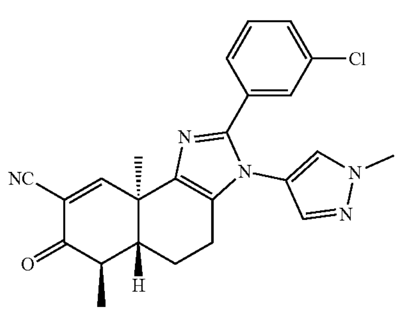 [SMILES: C[C@H]1C(=O)C(C#N)=C[C@@]2(C)c3nc(-c4cccc(Cl)c4)n(-c4cnn(C)c4)c3CC[C@H]12] | 0.322 | 0.103 | 1.280 |

TABLE 1-continued

Biological Activity Data for Compounds T1-T186
in hIL17, RORγ, and NRF2 GST ARE EC$_{2x}$ assays

| T# | Structure | hIL17 IC50 (μM) | RORγ IC50 (μM) | NRF2 ARE 2-Fold (μM) |
|---|---|---|---|---|
| T158 | 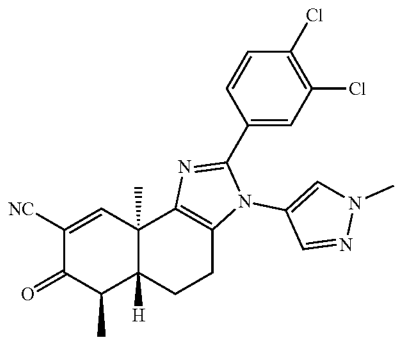 [SMILES: C[C@H]1C(=O)C(C#N)=C[C@@]2(C)c3nc(-c4ccc(Cl)c(Cl)c4)n(-c4cnn(C)c4)c3CC[C@H]12] | 0.240 | 0.124 | 1.093 |
| T159 | 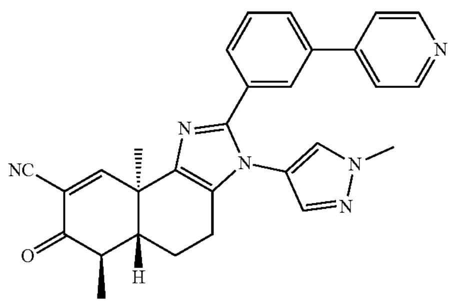 [SMILES: C[C@H]1C(=O)C(C#N)=C[C@@]2(C)c3nc(-c4cccc(-c5ccncc5)c4)n(-c4cnn(C)c4)c3CC[C@H]12] | 0.273 | 0.201 | 1.082 |
| T160 | 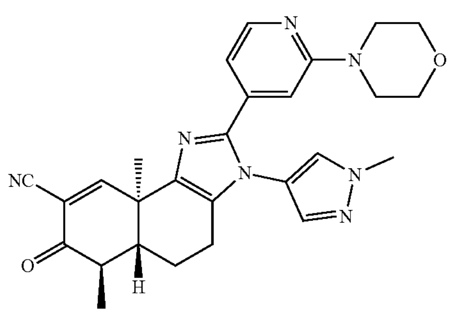 [SMILES: C[C@H]1C(=O)C(C#N)=C[C@@]2(C)c3nc(-c4ccnc(N5CCOCC5)c4)n(-c4cnn(C)c4)c3CC[C@H]12] | 0.468 | 0.562 | >2.000 |
| T161 | 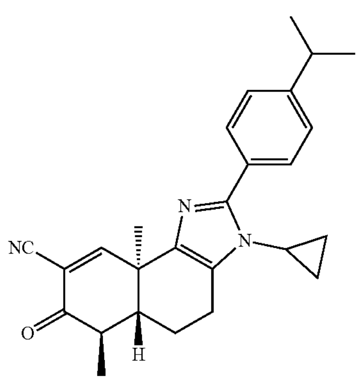 [SMILES: CC(C)c1ccc(-c2nc3c(n2C2CC2)CC[C@@H]2[C@@H](C)C(=O)C(C#N)=C[C@@]32C)cc1] | 0.113 | 0.150 | 1.025 |

TABLE 1-continued

Biological Activity Data for Compounds T1-T186
in hIL17, RORγ, and NRF2 GST ARE EC$_{2x}$ assays

| T# | Structure | hIL17 IC50 (μM) | RORγ IC50 (μM) | NRF2 ARE 2-Fold (μM) |
|---|---|---|---|---|
| T162 | 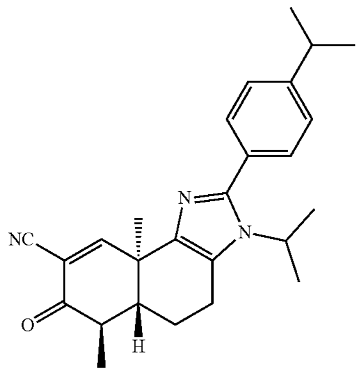 [SMILES: CC(C)c1ccc(-c2nc3c(n2C(C)C)CC[C@@H]2[C@@H](C)C(=O)C(C#N)=C[C@@]32C)cc1] | 0.137 | 0.141 | 1.118 |
| T163 | 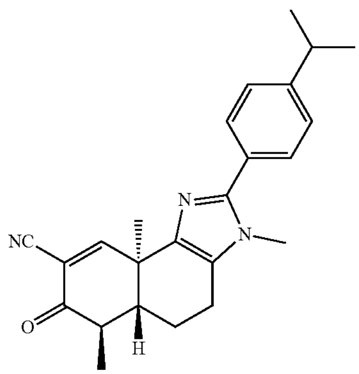 [SMILES: CC(C)c1ccc(-c2nc3c(n2C)CC[C@@H]2[C@@H](C)C(=O)C(C#N)=C[C@@]32C)cc1] | 0.255 | 0.152 | 1.134 |
| T164 | 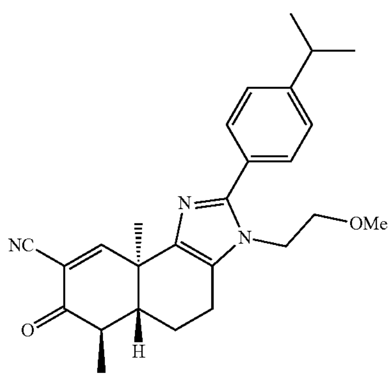 [SMILES: COCCn1c(-c2ccc(C(C)C)cc2)nc2c1CC[C@@H]1[C@@H](C)C(=O)C(C#N)=C[C@@]21C] | 0.158 | 0.237 | >2.000 |
| T165 | 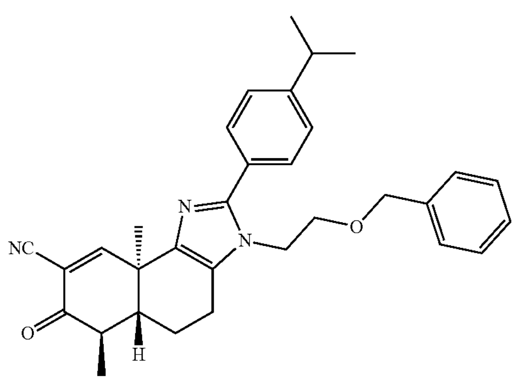 [SMILES: CC(C)c1ccc(-c2nc3c(n2CCOCc2ccccc2)CC[C@@H]2[C@@H](C)C(=O)C(C#N)=C[C@@]32C)cc1] | 0.211 | 0.471 | >2.000 |

TABLE 1-continued

Biological Activity Data for Compounds T1-T186
in hIL17, RORγ, and NRF2 GST ARE EC$_{2x}$ assays

| T# | Structure | hIL17 IC50 (μM) | RORγ IC50 (μM) | NRF2 ARE 2-Fold (μM) |
|---|---|---|---|---|
| T166 | 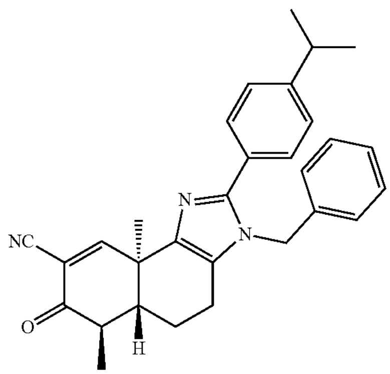 [SMILES: CC(C)c1ccc(-c2nc3c(n2Cc2ccccc2)CC[C@@H]2[C@@H](C)C(=O)C(C#N)=C[C@@]32C)cc1] | 0.063 | 0.228 | 1.679 |
| T167 | 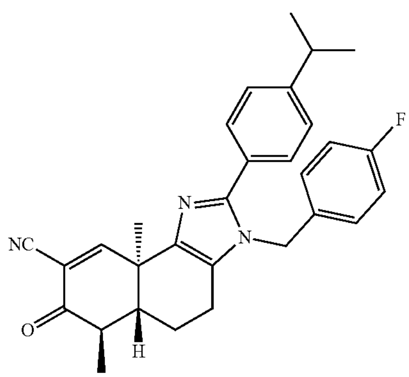 [SMILES: CC(C)c1ccc(-c2nc3c(n2Cc2ccc(F)cc2)CC[C@@H]2[C@@H](C)C(=O)C(C#N)=C[C@@]32C)cc1] | 0.053 | 0.245 | 1.108 |
| T168 | 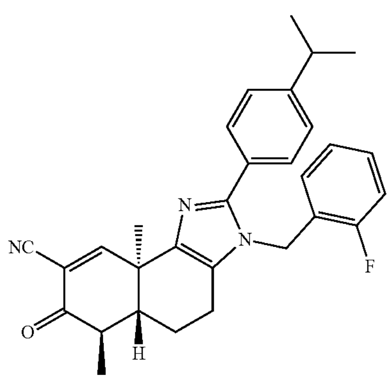 [SMILES: CC(C)c1ccc(-c2nc3c(n2Cc2ccccc2F)CC[C@@H]2[C@@H](C)C(=O)C(C#N)=C[C@@]32C)cc1] | 0.043 | 0.296 | 1.292 |
| T169 | 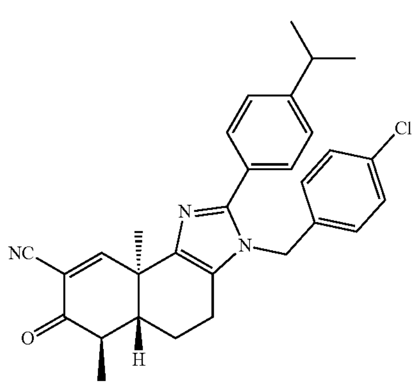 [SMILES: CC(C)c1ccc(-c2nc3c(n2Cc2ccc(Cl)cc2)CC[C@@H]2[C@@H](C)C(=O)C(C#N)=C[C@@]32C)cc1] | 0.033 | 0.371 | 1.009 |

TABLE 1-continued

Biological Activity Data for Compounds T1-T186
in hIL17, RORγ, and NRF2 GST ARE EC$_{2x}$ assays

| T# | Structure | hIL17 IC50 (μM) | RORγ IC50 (μM) | NRF2 ARE 2-Fold (μM) |
|---|---|---|---|---|
| T170 | 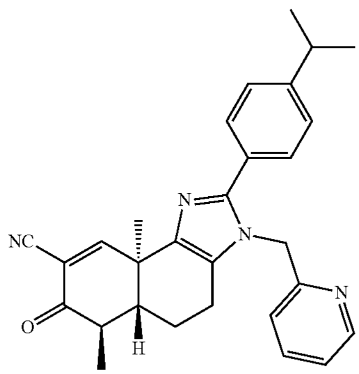 [SMILES: CC(C)c1ccc(-c2nc3c(n2Cc2ccccn2)CC[C@@H]2[C@@H](C)C(=O)C(C#N)=C[C@@]32C)cc1] | 0.072 | 0.103 | 0.602 |
| T171 | 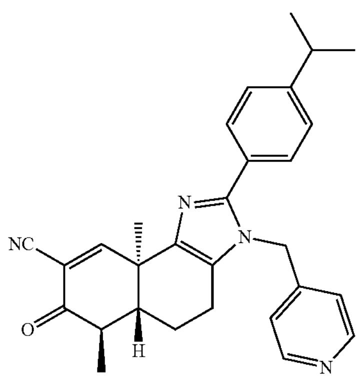 [SMILES: CC(C)c1ccc(-c2nc3c(n2Cc2ccncc2)CC[C@@H]2[C@@H](C)C(=O)C(C#N)=C[C@@]32C)cc1] | 0.157 | 0.260 | 1.015 |
| T172 | 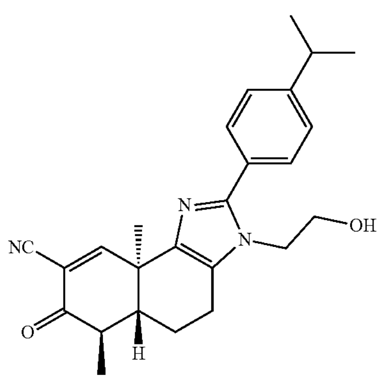 [SMILES: CC(C)c1ccc(-c2nc3c(n2CCO)CC[C@@H]2[C@@H](C)C(=O)C(C#N)=C[C@@]32C)cc1] | >0.500 | 0.178 | >2.000 |
| T173 | 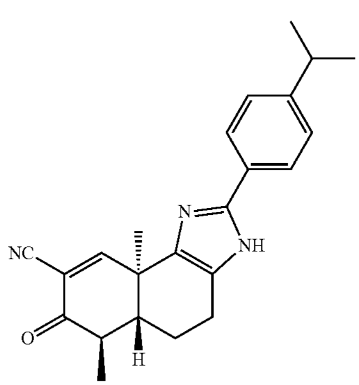 [SMILES: CC(C)c1ccc(-c2nc3c([nH]2)CC[C@@H]2[C@@H](C)C(=O)C(C#N)=C[C@@]32C)cc1] | 0.119 | 1.975 | 0.884 |

TABLE 1-continued

Biological Activity Data for Compounds T1-T186
in hIL17, RORγ, and NRF2 GST ARE EC$_{2x}$ assays

| T# | Structure | hIL17 IC50 (μM) | RORγ IC50 (μM) | NRF2 ARE 2-Fold (μM) |
|---|---|---|---|---|
| T174 | 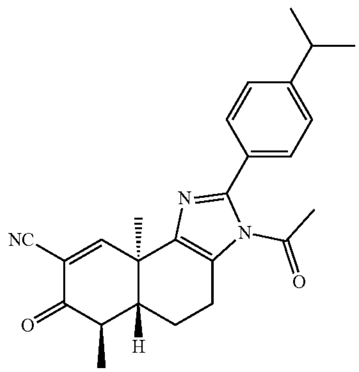 [SMILES: CC(=O)n1c(-c2ccc(C(C)C)cc2)nc2c1CC[C@@H]1[C@@H](C)C(=O)C(C#N)=C[C@@]21C] | 0.368 | 1.600 | 0.923 |
| T175 | 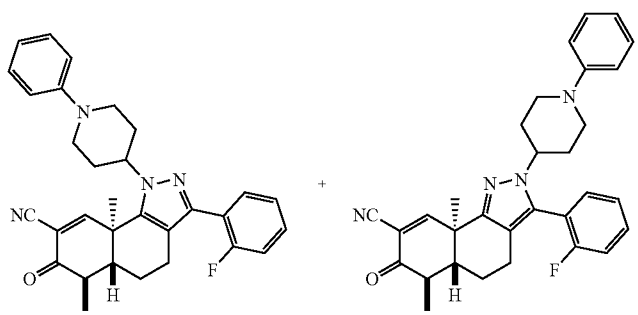 [SMILES: C[C@H]1C(=O)C(C#N)=C[C@@]2(C)c3c(c(-c4ccccc4F)nn3C3CCN(c4ccccc4)CC3)CC[C@H]12 ; C[C@H]1C(=O)C(C#N)=C[C@@]2(C)c3nn(C4CCN(c5ccccc5)CC4)c(-c4ccccc4F)c3CC[C@H]12] | 0.036 | 0.129 | 0.435 |
| T176 | 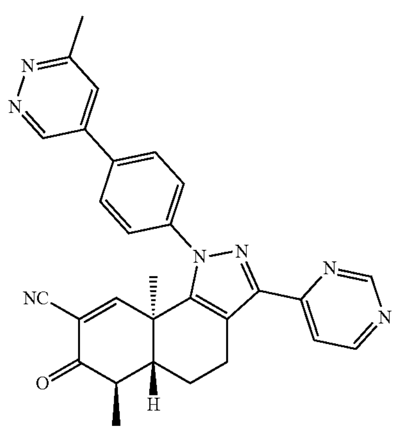 [SMILES: Cc1cc(-c2ccc(-n3nc(-c4ccncn4)c4c3[C@]3(C)C=C(C#N)C(=O)[C@H](C)[C@H]3CC4)cc2)cnn1] | 0.129 | 0.120 | 0.979 |
| T177 | 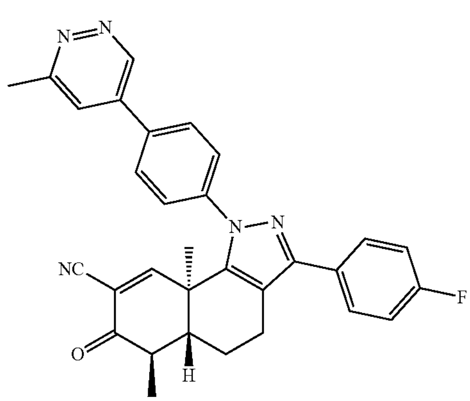 [SMILES: Cc1cc(-c2ccc(-n3nc(-c4ccc(F)cc4)c4c3[C@]3(C)C=C(C#N)C(=O)[C@H](C)[C@H]3CC4)cc2)cnn1] | 0.009 | 0.052 | 0.271 |

TABLE 1-continued

Biological Activity Data for Compounds T1-T186
in hIL17, RORγ, and NRF2 GST ARE EC$_{2x}$ assays

| T# | Structure | hIL17 IC50 (μM) | RORγ IC50 (μM) | NRF2 ARE 2-Fold (μM) |
|---|---|---|---|---|
| T178 | 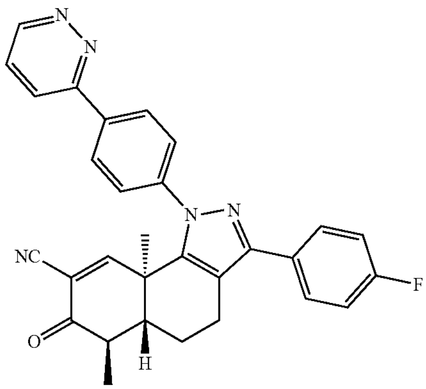 [SMILES: C[C@H]1C(=O)C(C#N)=C[C@@]2(C)c3c(c(-c4ccc(F)cc4)nn3-c3ccc(-c4cccnn4)cc3)CC[C@H]12] | 0.031 | 0.064 | 0.342 |
| T179 | 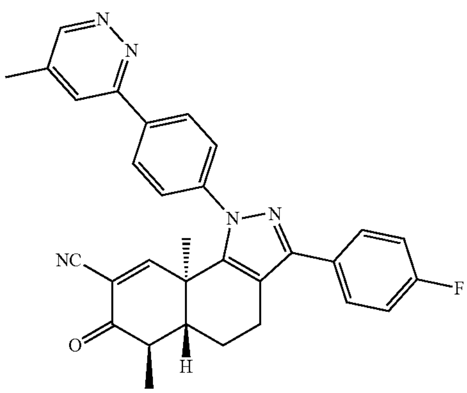 [SMILES: Cc1cnnc(-c2ccc(-n3nc(-c4ccc(F)cc4)c4c3[C@]3(C)C=C(C#N)C(=O)[C@H](C)[C@H]3CC4)cc2)c1] | 0.045 | 0.037 | 0.232 |
| T180 | 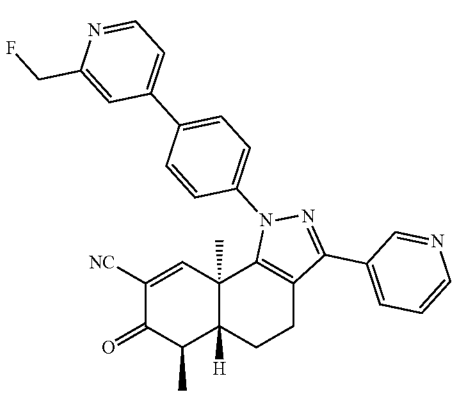 [SMILES: C[C@H]1C(=O)C(C#N)=C[C@@]2(C)c3c(c(-c4cccnc4)nn3-c3ccc(-c4ccnc(CF)c4)cc3)CC[C@H]12] | 0.049 | 0.055 | 0.308 |

TABLE 1-continued

Biological Activity Data for Compounds T1-T186
in hIL17, RORγ, and NRF2 GST ARE EC$_{2x}$ assays

| T# | Structure | hIL17 IC50 (μM) | RORγ IC50 (μM) | NRF2 ARE 2-Fold (μM) |
|---|---|---|---|---|
| T181 | 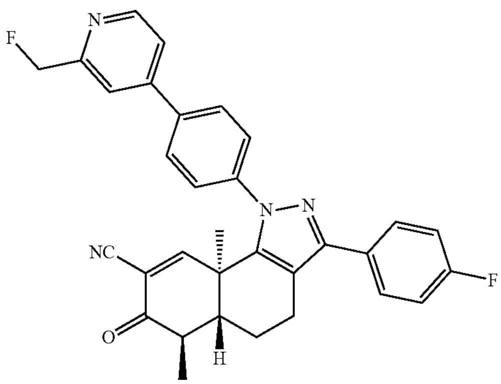 [SMILES: C[C@H]1C(=O)C(C#N)=C[C@@]2(C)c3c(c(-c4ccc(F)cc4)nn3-c3ccc(-c4ccnc(CF)c4)cc3)CC[C@H]12] | 0.024 | 0.060 | 0.250 |
| T182 | 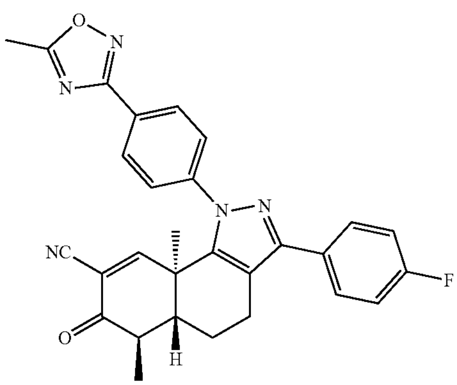 [SMILES: Cc1nc(-c2ccc(-n3nc(-c4ccc(F)cc4)c4c3[C@]3(C)C=C(C#N)C(=O)[C@H](C)[C@H]3CC4)cc2)no1] | 0.032 | 0.096 | 0.249 |
| T183 | 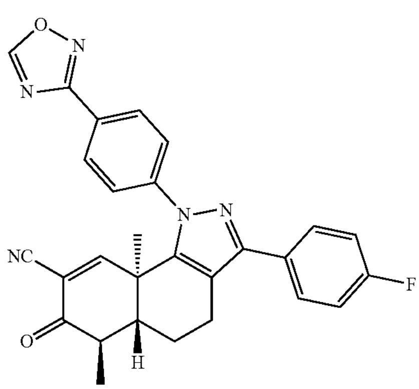 [SMILES: C[C@H]1C(=O)C(C#N)=C[C@@]2(C)c3c(c(-c4ccc(F)cc4)nn3-c3ccc(-c4ncon4)cc3)CC[C@H]12] | 0.068 | 0.113 | 0.526 |
| T184 | 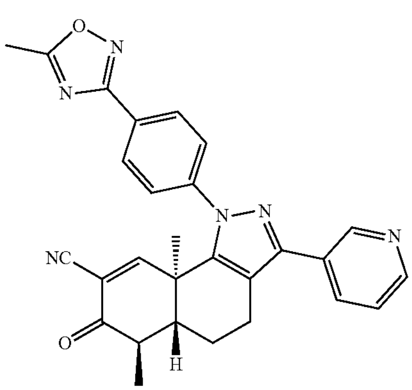 [SMILES: Cc1nc(-c2ccc(-n3nc(-c4cccnc4)c4c3[C@]3(C)C=C(C#N)C(=O)[C@H](C)[C@H]3CC4)cc2)no1] | 0.076 | 0.116 | 0.398 |

TABLE 1-continued

Biological Activity Data for Compounds T1-T186
in hIL17, RORγ, and NRF2 GST ARE $EC_{2x}$ assays

| T# | Structure | hIL17 IC50 (μM) | RORγ IC50 (μM) | NRF2 ARE 2-Fold (μM) |
|---|---|---|---|---|
| T185 | 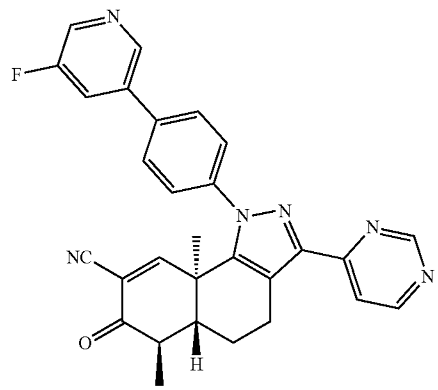 [SMILES: C[C@H]1C(=O)C(C#N)=C[C@@]2(C)c3c(c(-c4ccncn4)nn3-c3ccc(-c4cncc(F)c4)cc3)CC[C@H]12] | >0.500 | 0.625 | >2.000 |
| T186 | 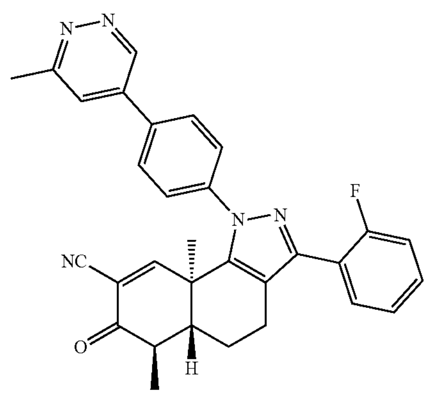 [SMILES: Cc1cc(-c2ccc(-n3nc(-c4ccccc4F)c4c3[C@]3(C)C=C(C#N)C(=O)[C@H](C)[C@H]3CC4)cc2)cnn1] | 0.468 | 0.297 | |

All of the compounds, compositions, and methods disclosed and claimed herein can be made and executed without undue experimentation in light of the present disclosure. While the disclosure may have focused on several embodiments or may have been described in terms of preferred embodiments, it will be apparent to those of skill in the art that variations and modifications may be applied to the compounds, compositions, and methods without departing from the spirit, scope, and concept of the invention. All variations and modifications apparent to those skilled in the art are deemed to the within the spirit, scope, and concept of the invention as defined by the appended claims.

REFERENCES

The following references to the extent that they provide exemplary procedural or other details supplementary to those set forth herein, are specifically incorporated herein by reference.

Anderson, *Practical Process Research &Development—A Guide for Organic Chemists*, $2^{nd}$ ed., Academic Press, New York, 2012.
Bronner, et al., *Expert Opin, Ther. Pat.*, 1:101-112, 2017.
Coltart and Danishefsky, *Org. Lett*, 5:1289, 2003.
Fujiwara, et al., *J. Immunol.*, 193(5):2565-73, 2014.
Gotten, et al., *Nature Reviews Immunology*, 14(9):585-600, 2014.
*Handbook of Pharmaceutical Salts: Properties, and Use*, Stahl and h Eds., Verlag Helvetica Chimica Acta, 2002.
Lu et al., *J. Clin. Invest*, 121(10):4015-29, 2011.
Miosse and Kolls, *Nature Reviews*, 11(10):763-776, 2012.
Reagan-Shaw et al., *FASEB J*, 22(3):659-661, 2008.
Smith, *March's Advanced Organic Chemistry: Reactions, Mechanisms and Structure*, $7^{th}$ Ed, Wiley, 2013.
Waite and Skokos, *International Journal of Inflammation*, 2012:1-10, 2011.
Yang, et al., *Trends in Pharmacological Sciences*, 35(10): 493-500, 2014.

What is claimed is:
1. A compound of the formula:

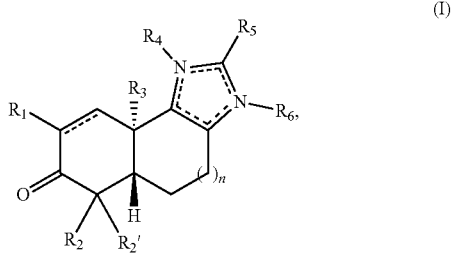

(I)

wherein:
n is 0, 1, or 2;
$R_1$ is cyano, fluoro, —$CF_3$, or —$C(O)R_a$, wherein:
  $R_a$ is hydroxy or amino; or
    alkoxy$_{(C \leq 6)}$, alkylamino$_{(C \leq 6)}$, dialkylamino$_{(C \leq 6)}$, or a substituted version of any of these groups;
$R_2$ is hydrogen; or
  alkyl$_{(C \leq 12)}$, cycloalkyl$_{(C \leq 12)}$, alkenyl$_{(C \leq 12)}$, alkynyl$_{(C \leq 12)}$, aryl$_{(C \leq 18)}$, aralkyl$_{(C \leq 18)}$, heteroaryl$_{(C \leq 18)}$, heteroaralkyl$_{(C \leq 18)}$, or a substituted version of any of these groups;
$R_2'$ is hydrogen;
$R_3$ is alkyl$_{(C \leq 12)}$, alkenyl$_{(C \leq 12)}$, aryl$_{(C \leq 12)}$, aralkyl$_{(C \leq 12)}$, or a substituted version of any of these groups;
$R_4$ and $R_5$ are each independently absent; or
  cycloalkyl$_{(C \leq 12)}$, heterocycloalkyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, -arenediyl$_{(C \leq 12)}$-alkyl$_{(C \leq 12)}$, -arenediyl$_{(C \leq 12)}$-aryl$_{(C \leq 12)}$, -arenediyl$_{(C \leq 12)}$-heteroaryl$_{(C \leq 12)}$, -arenediyl$_{(C \leq 12)}$-heterocycloalkyl$_{(C \leq 12)}$, -arenediyl$_{(C \leq 12)}$-cyclo-alkyl$_{(C \leq 12)}$, -heteroarenediyl$_{(C \leq 12)}$-alkyl$_{(C \leq 12)}$, -heteroarenediyl$_{(C \leq 12)}$-aryl$_{(C \leq 12)}$, -hetero-arenediyl$_{(C \leq 12)}$-heteroaryl$_{(C \leq 12)}$, -heteroarenediyl$_{(C \leq 12)}$-hetero-cycloalkyl$_{(C \leq 12)}$, -heteroarenediyl$_{(C \leq 12)}$-cyclo-alkyl$_{(C \leq 12)}$, -heterocycloalkanediyl$_{(C \leq 12)}$-aryl$_{(C \leq 12)}$, -heterocycloalkanediyl$_{(C \leq 12)}$-heteroaryl$_{(C \leq 12)}$, or a substituted version of any of these groups; or
a group of the formula:

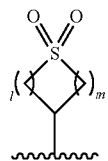

wherein l and m are each 0, 1, 2, or 3;
$R_6$ is absent or amino; or
  alkylamino$_{(C \leq 12)}$, dialkylamino$_{(C \leq 12)}$, cycloalkylamino$_{(C \leq 12)}$, dicycloalkylamino$_{(C \leq 12)}$, alkyl(cycloalkyl)amino$_{(C \leq 12)}$, arylamino$_{(C \leq 12)}$, diarylamino$_{(C \leq 12)}$, alkyl$_{(C \leq 12)}$, cycloalkyl$_{(C \leq 12)}$, -alkanediyl$_{(C \leq 12)}$-cycloalkyl$_{(C \leq 12)}$, -alkanediyl$_{(C \leq 18)}$-aralkoxy$_{(C \leq 18)}$, heterocycloalkyl$_{(C \leq 12)}$, aryl$_{(C \leq 18)}$, -arenediyl$_{(C \leq 12)}$-alkyl$_{(C \leq 12)}$, aralkyl$_{(C \leq 18)}$, -arenediyl$_{(C \leq 18)}$-heterocycloalkyl$_{(C \leq 12)}$, heteroaryl$_{(C \leq 18)}$, -heteroarenediyl$_{(C \leq 12)}$-alkyl$_{(C \leq 12)}$, heteroaralkyl$_{(C \leq 18)}$, acyl$_{(C \leq 12)}$, alkoxy$_{(C \leq 12)}$, or a substituted version of any of these groups;
or a pharmaceutically acceptable salt thereof.

2. The compound of claim 1 further defined as:

(II)

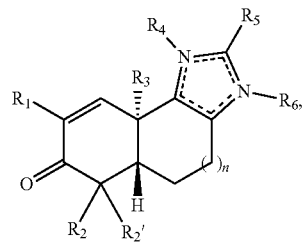

wherein:
n is 0, 1, or 2;
$R_1$ is cyano, fluoro, —$CF_3$, or —$C(O)R_a$, wherein:
  $R_a$ is hydroxy or amino; or
    alkoxy$_{(C \leq 6)}$, alkylamino$_{(C \leq 6)}$, dialkylamino$_{(C \leq 6)}$, or a substituted version of any of these groups;
$R_2$ is hydrogen; or
  alkyl$_{(C \leq 12)}$, cycloalkyl$_{(C \leq 12)}$, alkenyl$_{(C \leq 12)}$, alkynyl$_{(C \leq 12)}$, aryl$_{(C \leq 18)}$, aralkyl$_{(C \leq 18)}$, heteroaryl$_{(C \leq 18)}$, heteroaralkyl$_{(C \leq 18)}$, or a substituted version of any of these groups;
$R_2'$ is hydrogen;
$R_3$ is alkyl$_{(C \leq 12)}$, alkenyl$_{(C \leq 12)}$, aryl$_{(C \leq 12)}$, aralkyl$_{(C \leq 12)}$, or a substituted version of any of these groups;
$R_4$ and $R_5$ are each independently absent; or
  cycloalkyl$_{(C \leq 12)}$, heterocycloalkyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, -arenediyl$_{(C \leq 12)}$-alkyl$_{(C \leq 12)}$, -arenediyl$_{(C \leq 12)}$-aryl$_{(C \leq 12)}$, -arenediyl$_{(C \leq 12)}$-heteroaryl$_{(C \leq 12)}$, -arenediyl$_{(C \leq 12)}$-heterocycloalkyl$_{(C \leq 12)}$, -arenediyl$_{(C \leq 12)}$-cyclo-alkyl$_{(C \leq 12)}$, -heteroarenediyl$_{(C \leq 12)}$-alkyl$_{(C \leq 12)}$, -heteroarenediyl$_{(C \leq 12)}$-aryl$_{(C \leq 12)}$, -hetero-arenediyl$_{(C \leq 12)}$-heteroaryl$_{(C \leq 12)}$, -heteroarenediyl$_{(C \leq 12)}$-hetero-cycloalkyl$_{(C \leq 12)}$, -heteroarenediyl$_{(C \leq 12)}$-cyclo-alkyl$_{(C \leq 12)}$, -heterocycloalkanediyl$_{(C \leq 12)}$-aryl$_{(C \leq 12)}$, -heterocycloalkanediyl$_{(C \leq 12)}$-heteroaryl$_{(C \leq 12)}$, or a substituted version of any of these groups; or
a group of the formula:

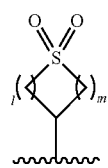

wherein l and m are each 0, 1, 2, or 3;
$R_6$ is absent or amino; or
  alkylamino$_{(C \leq 12)}$, dialkylamino$_{(C \leq 12)}$, cycloalkylamino$_{(C \leq 12)}$, dicycloalkylamino$_{(C \leq 12)}$, alkyl(cycloalkyl)amino$_{(C \leq 12)}$, arylamino$_{(C \leq 12)}$, diarylamino$_{(C \leq 12)}$, alkyl$_{(C \leq 12)}$, cycloalkyl$_{(C \leq 12)}$, -alkanediyl$_{(C \leq 12)}$-cycloalkyl$_{(C \leq 12)}$, -alkanediyl$_{(C \leq 18)}$-aralkoxy$_{(C \leq 18)}$, heterocycloalkyl$_{(C \leq 12)}$, aryl$_{(C \leq 18)}$, -arenediyl$_{(C \leq 12)}$-alkyl$_{(C \leq 12)}$, aralkyl$_{(C \leq 18)}$, -arenediyl$_{(C \leq 18)}$-heterocycloalkyl$_{(C \leq 12)}$, heteroaryl$_{(C \leq 18)}$, -heteroarenediyl$_{(C \leq 12)}$-alkyl$_{(C \leq 12)}$, heteroaralkyl$_{(C \leq 18)}$, acyl$_{(C \leq 12)}$, alkoxy$_{(C \leq 12)}$, or a substituted version of any of these groups;
or a pharmaceutically acceptable salt thereof.

3. The compound of claim 1, further defined as:

(V)

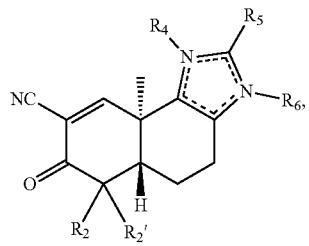

wherein:
R$_2$ independently is hydrogen; or
alkyl$_{(C≤12)}$, cycloalkyl$_{(C≤12)}$, alkenyl$_{(C≤12)}$, alkynyl$_{(C≤12)}$, aryl$_{(C≤18)}$, aralkyl$_{(C≤18)}$, heteroaryl$_{(C≤18)}$, heteroaralkyl$_{(C≤18)}$, or a substituted version of any of these groups;
R$_2$' is hydrogen;
R$_4$ and R$_5$ are each independently absent; or
cycloalkyl$_{(C≤12)}$, heterocycloalkyl$_{(C≤12)}$, aryl$_{(C≤12)}$, aralkyl$_{(C≤12)}$, heteroaryl$_{(C≤12)}$, heteroaralkyl$_{(C≤12)}$, -arenediyl$_{(C≤12)}$-alkyl$_{(C≤12)}$, -arenediyl$_{(C≤12)}$-aryl$_{(C≤12)}$, -arenediyl$_{(C≤12)}$-heteroaryl$_{(C≤12)}$, -arenediyl$_{(C≤12)}$-heterocycloalkyl$_{(C≤12)}$, -arenediyl$_{(C≤12)}$-cyclo-alkyl$_{(C≤12)}$, -heteroarenediyl$_{(C≤12)}$-alkyl$_{(C≤12)}$, -heteroarenediyl$_{(C≤12)}$-aryl$_{(C≤12)}$, -hetero-arenediyl$_{(C≤12)}$-heteroaryl$_{(C≤12)}$, -heteroarenediyl$_{(C≤12)}$-hetero-cycloalkyl$_{(C≤12)}$, -heteroarenediyl$_{(C≤12)}$-cycloalkyl$_{(C≤12)}$, -heterocycloalkanediyl$_{(C≤12)}$-aryl$_{(C≤12)}$, -heterocycloalkanediyl$_{(C≤12)}$-heteroaryl$_{(C≤12)}$, or a substituted version of any of these groups; or
a group of the formula:

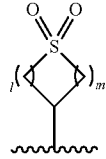

wherein 1 and m are each 0, 1, 2, or 3;
R$_6$ is absent or amino; or
alkylamino$_{(C≤12)}$, dialkylamino$_{(C≤12)}$, cycloalkylamino$_{(C≤12)}$, dicycloalkylamino$_{(C≤12)}$, alkyl(cycloalkyl)amino$_{(C≤12)}$, arylamino$_{(C≤12)}$, diarylamino$_{(C≤12)}$, alkyl$_{(C≤12)}$, cycloalkyl$_{(C≤12)}$, -alkanediyl$_{(C≤12)}$-cycloalkyl$_{(C≤12)}$, -alkanediyl$_{(C≤18)}$-aralkoxy$_{(C≤18)}$, heterocycloalkyl$_{(C≤12)}$, aryl$_{(C≤18)}$, -arenediyl$_{(C≤12)}$-alkyl$_{(C≤12)}$, aralkyl$_{(C≤18)}$, -arenediyl$_{(C≤18)}$-heterocycloalkyl$_{(C≤12)}$, heteroaryl$_{(C≤18)}$, -heteroarenediyl$_{(C≤12)}$-alkyl$_{(C≤12)}$, heteroaralkyl$_{(C≤18)}$, acyl$_{(C≤12)}$, alkoxy$_{(C≤12)}$, or a substituted version of any of these groups;
or a pharmaceutically acceptable salt thereof.
4. The compound of claim 1, further defined as:

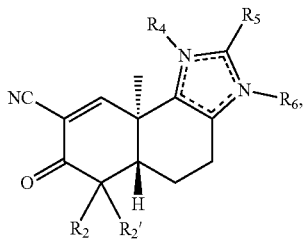

(VII)

wherein:
R$_2$ independently is hydrogen; or
alkyl$_{(C≤12)}$, cycloalkyl$_{(C≤12)}$, alkenyl$_{(C≤12)}$, alkynyl$_{(C≤12)}$, aryl$_{(C≤18)}$, aralkyl$_{(C≤18)}$, heteroaryl$_{(C≤18)}$, heteroaralkyl$_{(C≤18)}$, or a substituted version of any of these groups;
R$_2$' is hydrogen;
R$_4$ and R$_5$ are each independently absent; or
cycloalkyl$_{(C≤12)}$, heterocycloalkyl$_{(C≤12)}$, aryl$_{(C≤12)}$, aralkyl$_{(C≤12)}$, heteroaryl$_{(C≤12)}$, heteroaralkyl$_{(C≤12)}$, -arenediyl$_{(C≤12)}$-alkyl$_{(C≤12)}$, -arenediyl$_{(C≤12)}$-aryl$_{(C≤12)}$, -arenediyl$_{(C≤12)}$-heteroaryl$_{(C≤12)}$, -arenediyl$_{(C≤12)}$-heterocycloalkyl$_{(C≤12)}$, -arenediyl$_{(C≤12)}$-cyclo-alkyl$_{(C≤12)}$, -heteroarenediyl$_{(C≤12)}$-alkyl$_{(C≤12)}$, -heteroarenediyl$_{(C≤12)}$-aryl$_{(C≤12)}$, -hetero-arenediyl$_{(C≤12)}$-heteroaryl$_{(C≤12)}$, -heteroarenediyl$_{(C≤12)}$-hetero-cycloalkyl$_{(C≤12)}$, -heteroarenediyl$_{(C≤12)}$-cycloalkyl$_{(C≤12)}$, -heterocycloalkanediyl$_{(C≤12)}$-aryl$_{(C≤12)}$, -heterocycloalkanediyl$_{(C≤12)}$-heteroaryl$_{(C≤12)}$, or a substituted version of any of these groups; or
a group of the formula:

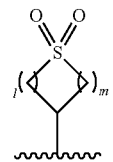

wherein 1 and m are each 0, 1, 2, or 3; and
R$_6$ is absent; or
alkyl$_{(C≤12)}$, cycloalkyl$_{(C≤12)}$, -alkanediyl$_{(C≤12)}$-cycloalkyl$_{(C≤12)}$, -alkane-diyl$_{(C≤18)}$-aralkoxy$_{(C≤18)}$, heterocycloalkyl$_{(C≤12)}$, aryl$_{(C≤18)}$, -arenediyl$_{(C≤12)}$-alkyl$_{(C≤12)}$, aralkyl$_{(C≤18)}$, -arenediyl$_{(C≤18)}$-heterocyclo-alkyl$_{(C≤12)}$, heteroaryl$_{(C≤18)}$, -heteroarenediyl$_{(C≤12)}$-alkyl$_{(C≤12)}$, heteroaralkyl$_{(C≤18)}$, acyl$_{(C≤12)}$, alkoxy$_{(C≤12)}$, or a substituted version of any of these groups;
or a pharmaceutically acceptable salt thereof.
5. The compound of claim 1, further defined as:

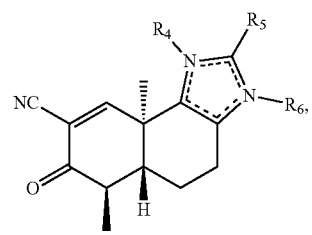

(X)

wherein:
R$_4$ and R$_5$ are each independently absent; or
cycloalkyl$_{(C≤12)}$, heterocycloalkyl$_{(C≤12)}$, aryl$_{(C≤12)}$, aralkyl$_{(C≤12)}$, heteroaryl$_{(C≤12)}$, heteroaralkyl$_{(C≤12)}$, -arenediyl$_{(C≤12)}$-alkyl$_{(C≤12)}$, -arenediyl$_{(C≤12)}$-aryl$_{(C≤12)}$, -arenediyl$_{(C≤12)}$-heteroaryl$_{(C≤12)}$, -arenediyl$_{(C≤12)}$-heterocycloalkyl$_{(C≤12)}$, -arenediyl$_{(C≤12)}$-cyclo-alkyl$_{(C≤12)}$, -heteroarenediyl$_{(C≤12)}$-alkyl$_{(C≤12)}$, -heteroarenediyl$_{(C≤12)}$-aryl$_{(C≤12)}$, -hetero-arenediyl$_{(C≤12)}$-heteroaryl$_{(C≤12)}$, -heteroarenediyl$_{(C≤12)}$-hetero-cycloalkyl$_{(C≤12)}$, -heteroarenediyl$_{(C≤12)}$-cycloalkyl$_{(C≤12)}$, -heterocycloalkanediyl$_{(C≤12)}$-aryl$_{(C≤12)}$, -heterocycloalkanediyl$_{(C≤12)}$-heteroaryl$_{(C≤12)}$, or a substituted version of any of these groups; or a group of the formula:

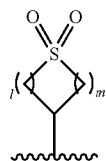

wherein 1 and m are each 0, 1, 2, or 3; and $R_6$ is absent; or alkyl$_{(C\leq12)}$, cycloalkyl$_{(C\leq12)}$, -alkanediyl$_{(C\leq12)}$-cycloalkyl$_{(C\leq12)}$, -alkane-diyl$_{(C\leq18)}$-aralkoxy$_{(C\leq18)}$, heterocycloalkyl$_{(C\leq12)}$, aryl$_{(C\leq18)}$, -arenediyl$_{(C\leq12)}$-alkyl$_{(C\leq12)}$, aralkyl$_{(C\leq18)}$, -arenediyl$_{(C\leq18)}$-heterocyclo-alkyl$_{(C\leq12)}$, heteroaryl$_{(C\leq18)}$, -heteroarenediyl$_{(C\leq12)}$-alkyl$_{(C\leq12)}$, heteroaralkyl$_{(C\leq18)}$, acyl$_{(C\leq12)}$, alkoxy$_{(C\leq12)}$, or a substituted version of any of these groups;

or a pharmaceutically acceptable salt thereof.

6. The compound of claim 1, wherein $R_3$ is alkyl$_{(C\leq12)}$ or substituted alkyl$_{(C\leq12)}$ or $R_1$ is cyano.

7. The compound of claim 1, wherein $R_2$ is hydrogen, alkyl$_{(C\leq12)}$, or substituted alkyl$_{(C\leq12)}$.

8. The compound of claim 1, wherein $R_4$ is aryl$_{(C\leq12)}$, substituted aryl$_{(C\leq12)}$, -arenediyl$_{(C\leq12)}$-aryl$_{(C\leq12)}$, or substituted -arenediyl$_{(C\leq12)}$-aryl$_{(C\leq12)}$.

9. The compound of claim 1, wherein $R_4$ is -arenediyl$_{(C\leq12)}$-heterocycloalkyl$_{(C\leq12)}$ or substituted -arenediyl$_{(C\leq12)}$-heterocycloalkyl$_{(C\leq12)}$.

10. The compound of claim 1, wherein $R_4$ is heteroaryl$_{(C\leq12)}$, substituted heteroaryl$_{(C\leq12)}$, -arenediyl$_{(C\leq12)}$-heteroaryl$_{(C\leq12)}$, substituted -arenediyl$_{(C\leq12)}$-heteroaryl$_{(C\leq12)}$, -heteroarenediyl$_{(C\leq12)}$-aryl$_{(C\leq12)}$, substituted -heteroarenediyl$_{(C\leq12)}$-aryl$_{(C\leq12)}$, -heteroarenediyl$_{(C\leq12)}$-heteroaryl$_{(C\leq12)}$, or substituted -heteroarenediyl$_{(C\leq12)}$-heteroaryl$_{(C\leq12)}$.

11. The compound of claim 1, wherein $R_5$ is aryl$_{(C\leq12)}$, substituted aryl$_{(C\leq12)}$, -arenediyl$_{(C\leq12)}$-aryl$_{(C\leq12)}$, or substituted -arenediyl$_{(C\leq12)}$-aryl$_{(C\leq12)}$.

12. The compound of claim 1, wherein $R_5$ is -arenediyl$_{(C\leq12)}$-heterocycloalkyl$_{(C\leq12)}$ or substituted -arenediyl$_{(C\leq12)}$-heterocycloalkyl$_{(C\leq12)}$.

13. The compound of claim 1, wherein $R_5$ is heteroaryl$_{(C\leq12)}$, substituted heteroaryl$_{(C\leq12)}$, -arenediyl$_{(C\leq12)}$-heteroaryl$_{(C\leq12)}$, substituted -arenediyl$_{(C\leq12)}$-heteroaryl$_{(C\leq12)}$, -heteroarenediyl$_{(C\leq12)}$-aryl$_{(C\leq12)}$, substituted -heteroarenediyl$_{(C\leq12)}$-aryl$_{(C\leq12)}$, -heteroarenediyl$_{(C\leq12)}$-heteroaryl$_{(C\leq12)}$, or substituted -heteroarenediyl$_{(C\leq12)}$-heteroaryl$_{(C\leq12)}$.

14. The compound of claim 1, wherein $R_5$ is -heteroarenediyl$_{(C\leq12)}$-heterocycloalkyl$_{(C\leq12)}$ or substituted -heteroarenediyl$_{(C\leq12)}$-heterocycloalkyl$_{(C\leq12)}$.

15. The compound of claim 1, wherein $R_6$ is aryl$_{(C\leq18)}$, substituted aryl$_{(C\leq18)}$, heteroaryl$_{(C\leq18)}$, or substituted heteroaryl$_{(C\leq18)}$.

16. The compound of claim 1 further defined as:

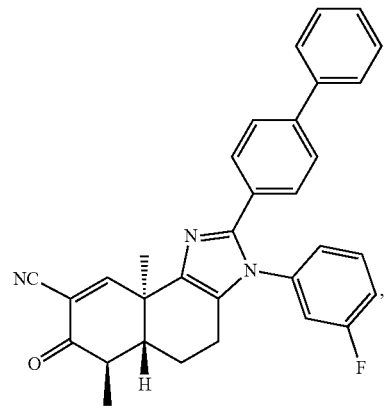

,

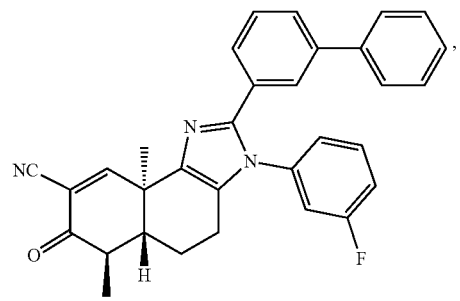

,

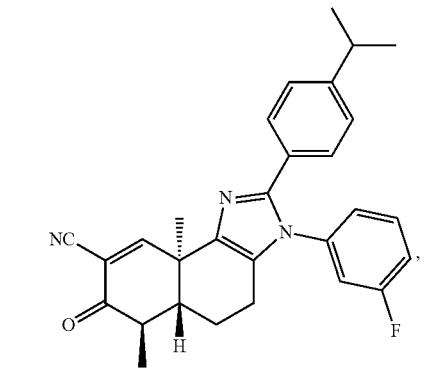

,

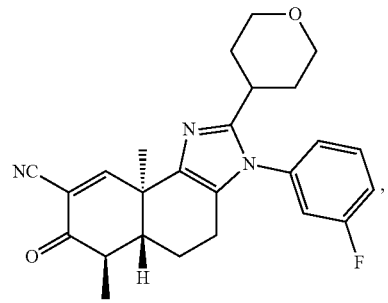

,

471
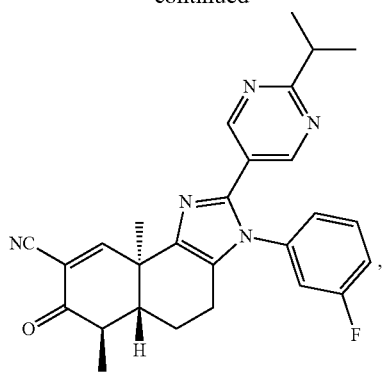
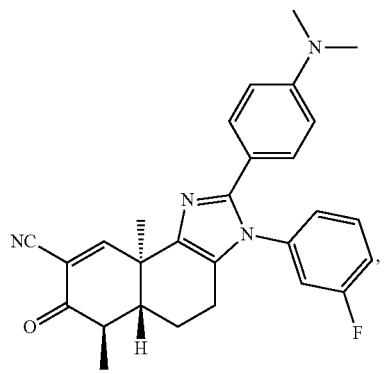
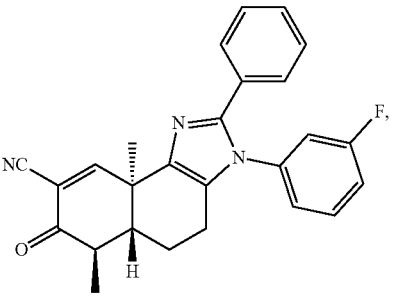
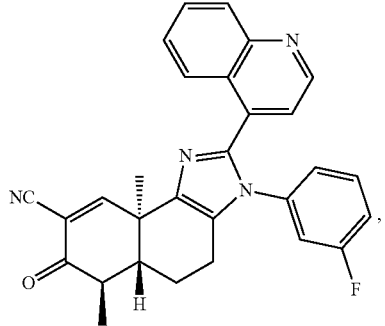
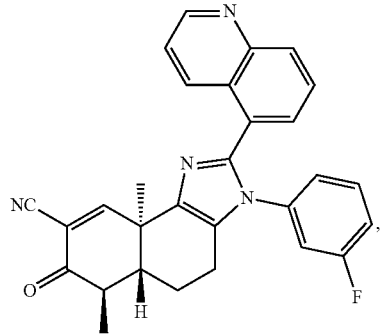
472
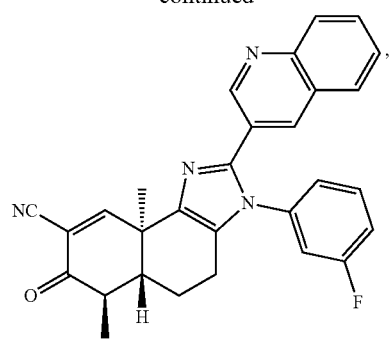
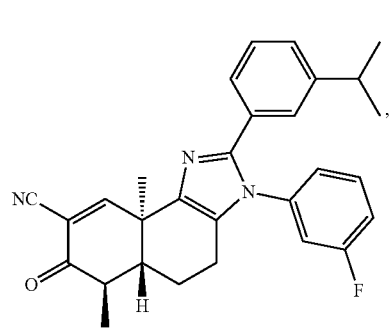
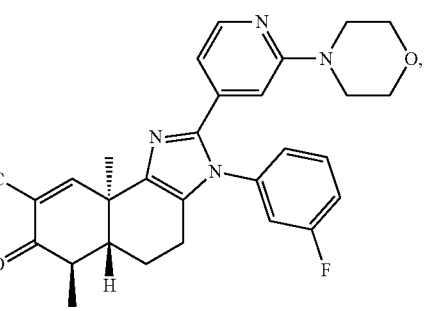
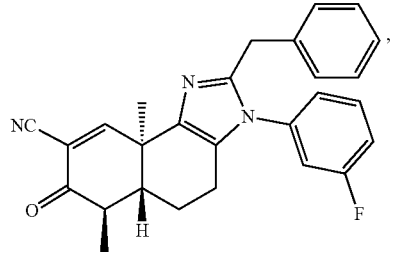
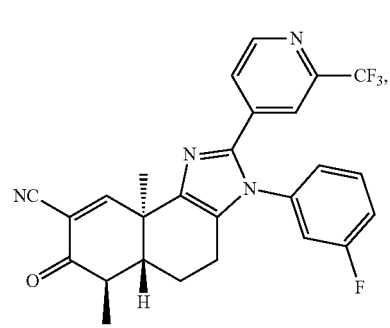

473
-continued
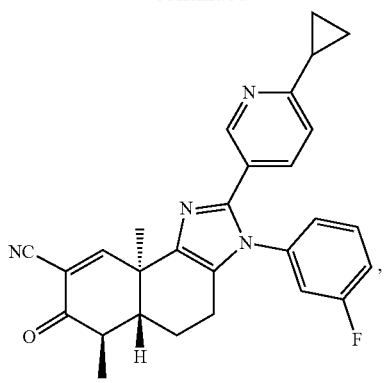
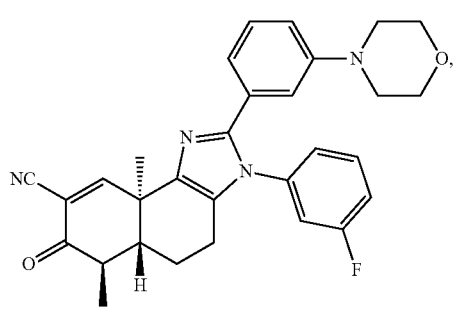
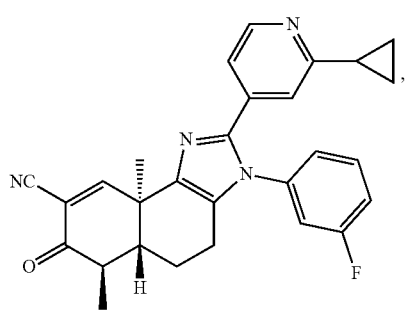
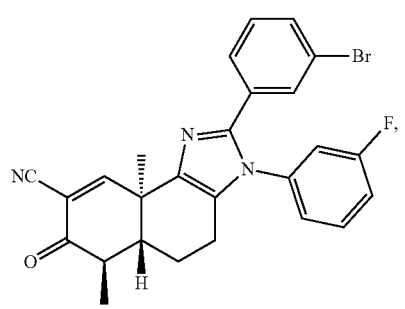
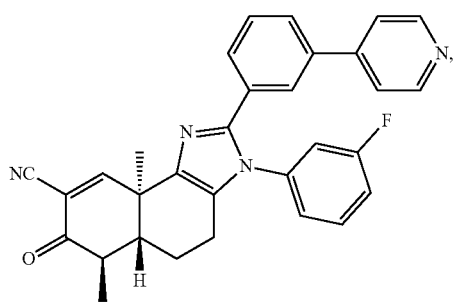
474
-continued
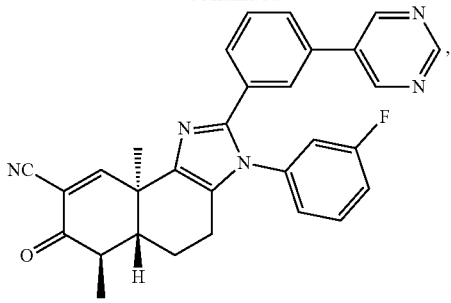
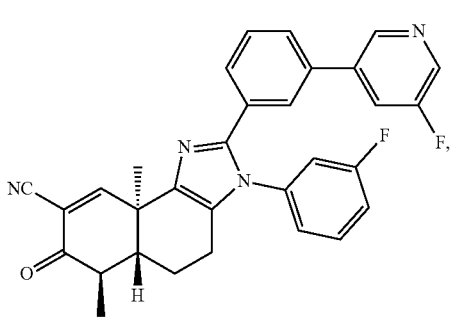
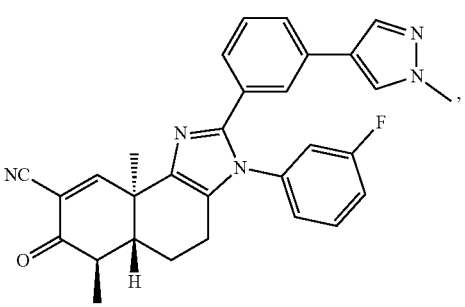
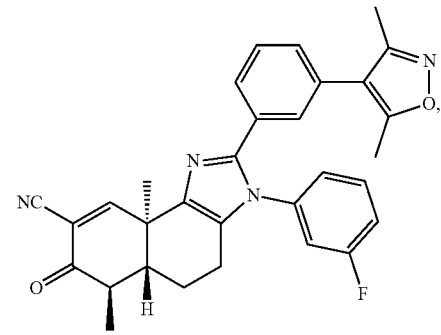
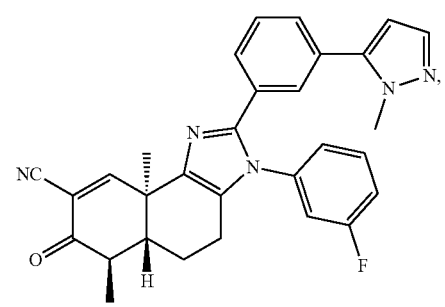

475
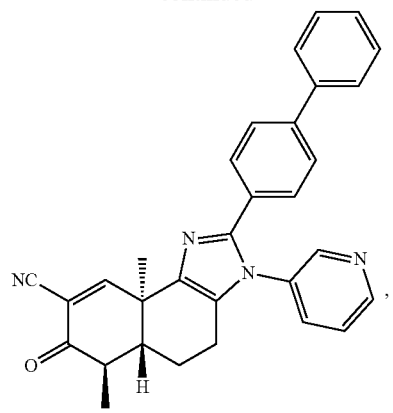
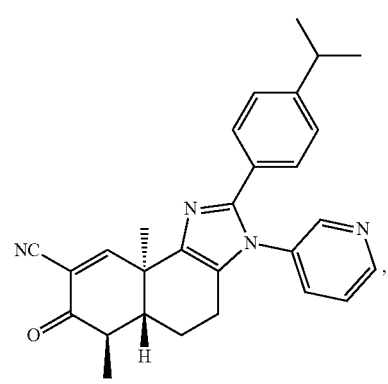
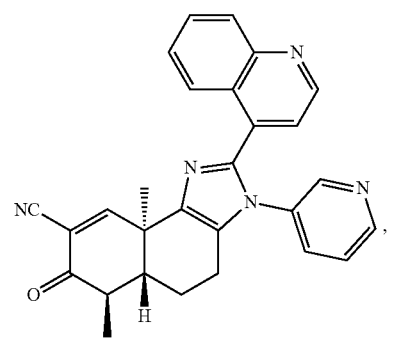
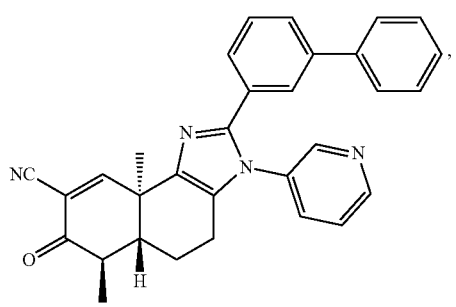
476
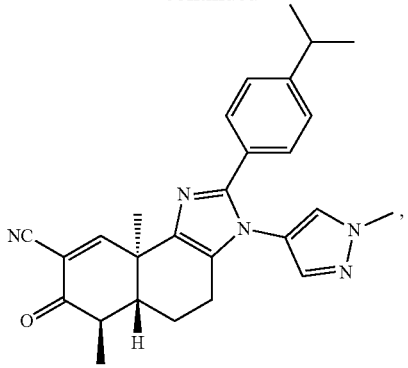
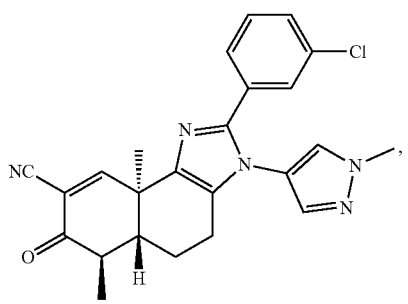
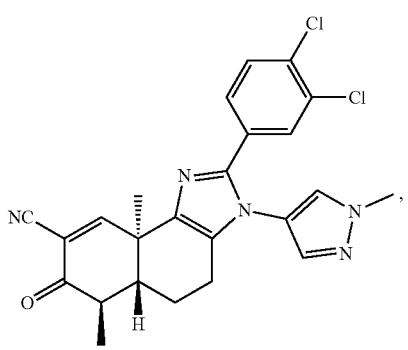
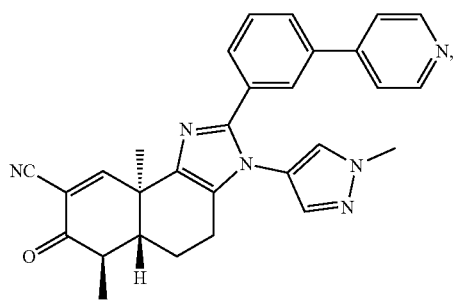
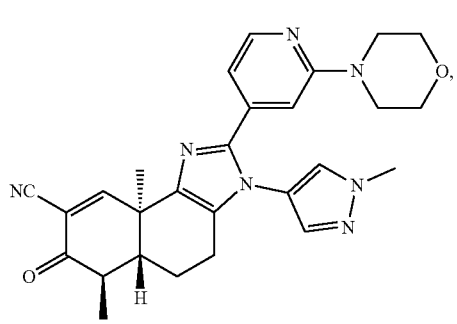

477
-continued
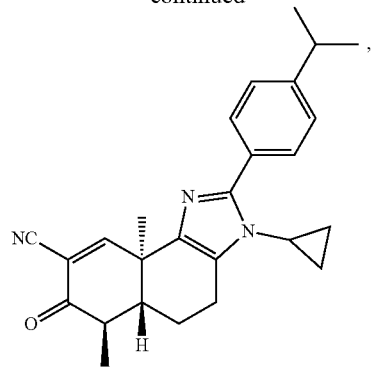
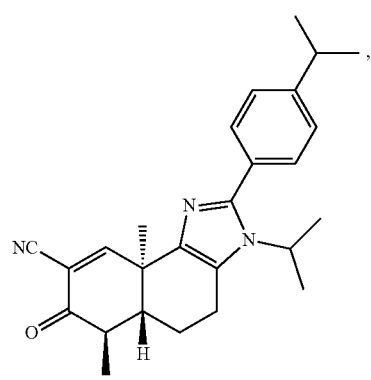
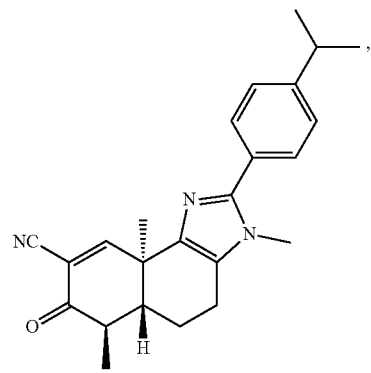
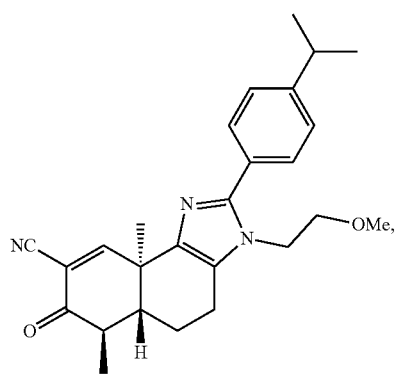
478
-continued
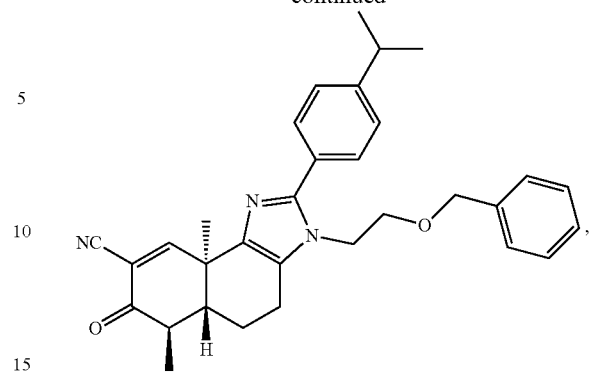
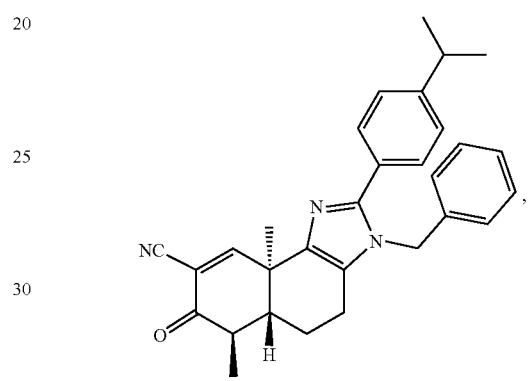
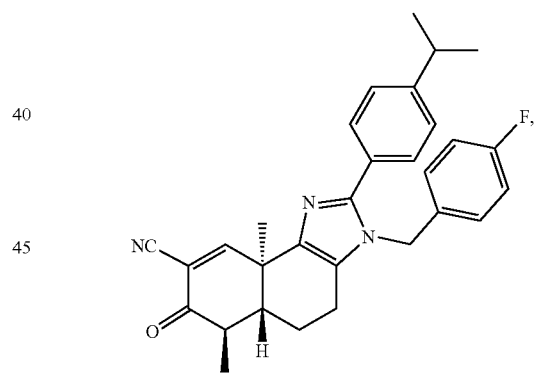
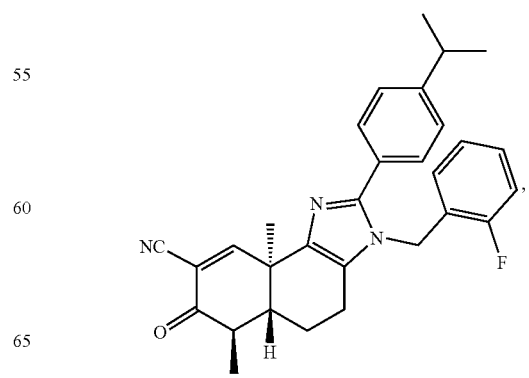

479
-continued
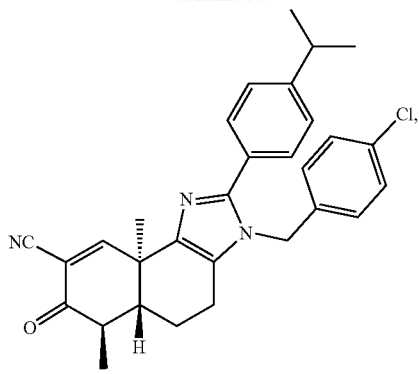
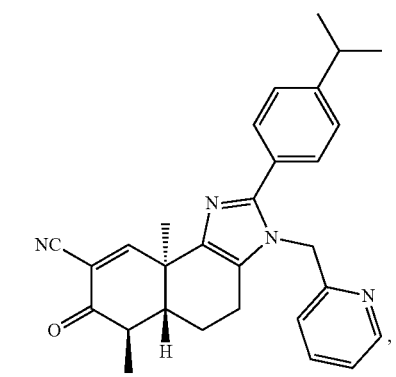
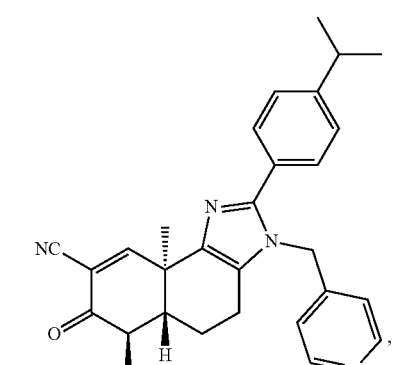
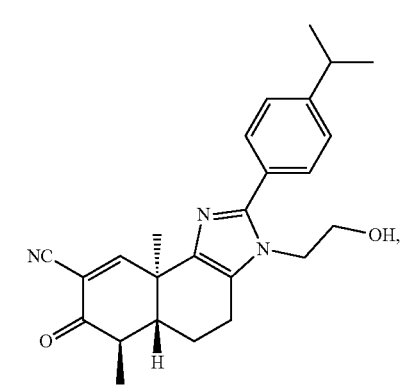
480
-continued
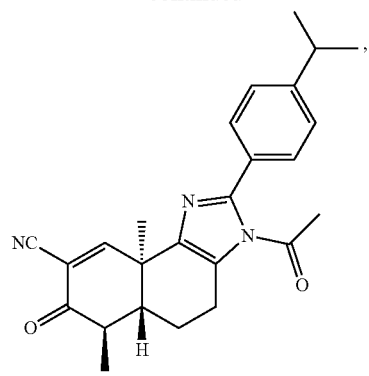
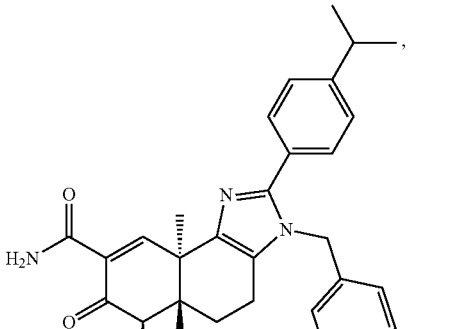
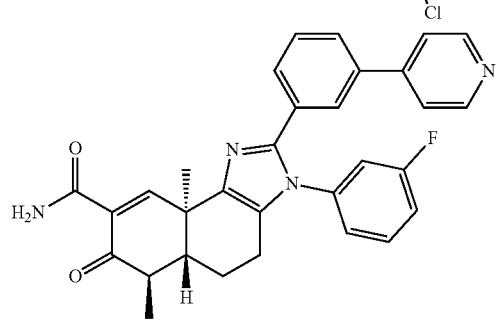
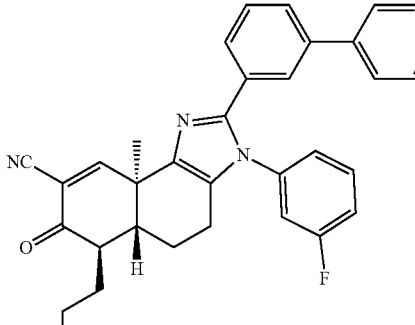
or a pharmaceutically acceptable salt of any of the above formulas.
17. A pharmaceutical composition comprising:
   (a) a compound of claim 1; and
   (b) an excipient.
18. The compound of claim 1, wherein $R_6$ is cycloalkyl$_{(C \leq 12)}$, substituted cycloalkyl$_{(C \leq 12)}$, heterocycloalkyl$_{(C \leq 12)}$, or substituted heterocycloalkyl$_{(C \leq 12)}$.

19. A compound of the formula:

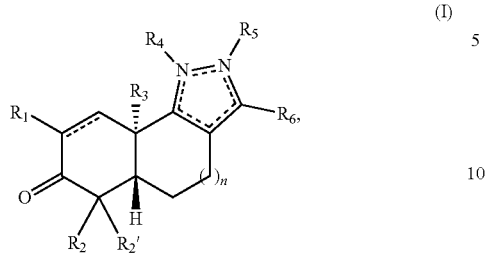
(I)

wherein:
n is 0, 1, or 2;
$R_1$ is cyano, fluoro, —$CF_3$, or —$C(O)R_a$, wherein:
$R_a$ is hydroxy or amino; or
alkoxy$_{(C \leq 6)}$, alkylamino$_{(C \leq 6)}$, dialkylamino$_{(C \leq 6)}$, or a substituted version of any of these groups;
$R_2$ is hydrogen; or
alkyl$_{(C \leq 12)}$, cycloalkyl$_{(C \leq 12)}$, alkenyl$_{(C \leq 12)}$, alkynyl$_{(C \leq 12)}$, aryl$_{(C \leq 18)}$, aralkyl$_{(C \leq 18)}$, heteroaryl$_{(C \leq 18)}$, heteroaralkyl$_{(C \leq 18)}$, or a substituted version of any of these groups;
$R_2'$ is hydrogen;
$R_3$ is alkyl$_{(C \leq 12)}$, alkenyl$_{(C \leq 12)}$, aryl$_{(C \leq 12)}$, aralkyl$_{(C \leq 12)}$, or a substituted version of any of these groups;
$R_4$ and $R_5$ are each independently absent; or
cycloalkyl$_{(C \leq 12)}$, heterocycloalkyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, -arenediyl$_{(C \leq 12)}$-alkyl$_{(C \leq 12)}$, -arenediyl$_{(C \leq 12)}$-aryl$_{(C \leq 12)}$, -arenediyl$_{(C \leq 12)}$-heteroaryl$_{(C \leq 12)}$, -arenediyl$_{(C \leq 12)}$-heterocycloalkyl$_{(C \leq 12)}$, -arenediyl$_{(C \leq 12)}$-cyclo-alkyl$_{(C \leq 12)}$, -heteroarenediyl$_{(C \leq 12)}$-alkyl$_{(C \leq 12)}$, -heteroarenediyl$_{(C \leq 12)}$-aryl$_{(C \leq 12)}$, -hetero-arenediyl$_{(C \leq 12)}$-heteroaryl$_{(C \leq 12)}$, -heteroarenediyl$_{(C \leq 12)}$-hetero-cycloalkyl$_{(C \leq 12)}$, -heteroarenediyl$_{(C \leq 12)}$-cyclo-alkyl$_{(C \leq 12)}$, -heterocycloalkanediyl$_{(C \leq 12)}$-aryl$_{(C \leq 12)}$, -heterocycloalkanediyl$_{(C \leq 12)}$-heteroaryl$_{(C \leq 12)}$, or a substituted version of any of these groups; or
a group of the formula:

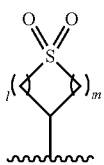

wherein 1 and m are each 0, 1, 2, or 3;
$R_6$ is absent or amino; or
alkylamino$_{(C \leq 12)}$, dialkylamino$_{(C \leq 12)}$, cycloalkylamino$_{(C \leq 12)}$, dicycloalkylamino$_{(C \leq 12)}$, alkyl(cycloalkyl)amino$_{(C \leq 12)}$, arylamino$_{(C \leq 12)}$, diarylamino$_{(C \leq 12)}$, alkyl$_{(C \leq 12)}$, cycloalkyl$_{(C \leq 12)}$, -alkanediyl$_{(C \leq 12)}$-cycloalkyl$_{(C \leq 12)}$, -alkanediyl$_{(C \leq 18)}$-aralkoxy$_{(C \leq 18)}$, heterocycloalkyl$_{(C \leq 12)}$, aryl$_{(C \leq 18)}$, -arenediyl$_{(C \leq 12)}$-alkyl$_{(C \leq 12)}$, aralkyl$_{(C \leq 18)}$, -arenediyl$_{(C \leq 18)}$-heterocycloalkyl$_{(C \leq 12)}$, heteroaryl$_{(C \leq 18)}$, -heteroarenediyl$_{(C \leq 12)}$-alkyl$_{(C \leq 12)}$, heteroaralkyl$_{(C \leq 18)}$, acyl$_{(C \leq 12)}$, alkoxy$_{(C \leq 12)}$, or a substituted version of any of these groups;
or a pharmaceutically acceptable salt thereof.

20. The compound of claim 19 further defined as:

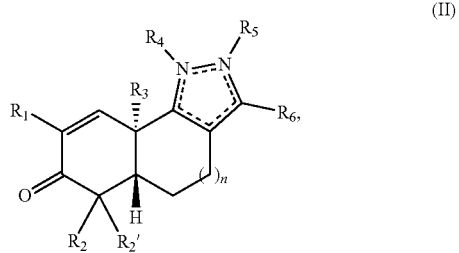
(II)

wherein:
n is 0, 1, or 2;
$R_1$ is cyano, fluoro, —$CF_3$, or —$C(O)R_a$, wherein:
$R_a$ is hydroxy or amino; or
alkoxy$_{(C \leq 6)}$, alkylamino$_{(C \leq 6)}$, dialkylamino$_{(C \leq 6)}$, or a substituted version of any of these groups;
$R_2$ is hydrogen; or
alkyl$_{(C \leq 12)}$, cycloalkyl$_{(C \leq 12)}$, alkenyl$_{(C \leq 12)}$, alkynyl$_{(C \leq 12)}$, aryl$_{(C \leq 18)}$, aralkyl$_{(C \leq 18)}$, heteroaryl$_{(C \leq 18)}$, heteroaralkyl$_{(C \leq 18)}$, or a substituted version of any of these groups;
$R_2'$ is hydrogen;
$R_3$ is alkyl$_{(C \leq 12)}$, alkenyl$_{(C \leq 12)}$, aryl$_{(C \leq 12)}$, aralkyl$_{(C \leq 12)}$, or a substituted version of any of these groups;
$R_4$ and $R_5$ are each independently absent; or
cycloalkyl$_{(C \leq 12)}$, heterocycloalkyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, -arenediyl$_{(C \leq 12)}$-alkyl$_{(C \leq 12)}$, -arenediyl$_{(C \leq 12)}$-aryl$_{(C \leq 12)}$, -arenediyl$_{(C \leq 12)}$-heteroaryl$_{(C \leq 12)}$, -arenediyl$_{(C \leq 12)}$-heterocycloalkyl$_{(C \leq 12)}$, -arenediyl$_{(C \leq 12)}$-cyclo-alkyl$_{(C \leq 12)}$, -heteroarenediyl$_{(C \leq 12)}$-alkyl$_{(C \leq 12)}$, -heteroarenediyl$_{(C \leq 12)}$-aryl$_{(C \leq 12)}$, -hetero-arenediyl$_{(C \leq 12)}$-heteroaryl$_{(C \leq 12)}$, -heteroarenediyl$_{(C \leq 12)}$-hetero-cycloalkyl$_{(C \leq 12)}$, -heteroarenediyl$_{(C \leq 12)}$-cycloalkyl$_{(C \leq 12)}$, -heterocycloalkanediyl$_{(C \leq 12)}$-aryl$_{(C \leq 12)}$, -heterocycloalkanediyl$_{(C \leq 12)}$-heteroaryl$_{(C \leq 12)}$, or a substituted version of any of these groups; or
a group of the formula:

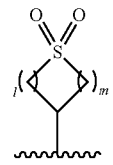

wherein 1 and m are each 0, 1, 2, or 3;
$R_6$ is absent or amino; or
alkylamino$_{(C \leq 12)}$, dialkylamino$_{(C \leq 12)}$, cycloalkylamino$_{(C \leq 12)}$, dicycloalkylamino$_{(C \leq 12)}$, alkyl(cycloalkyl)amino$_{(C \leq 12)}$, arylamino$_{(C \leq 12)}$, diarylamino$_{(C \leq 12)}$, alkyl$_{(C \leq 12)}$, cycloalkyl$_{(C \leq 12)}$, -alkanediyl$_{(C \leq 12)}$-cycloalkyl$_{(C \leq 12)}$, -alkanediyl$_{(C \leq 18)}$-aralkoxy$_{(C \leq 18)}$, heterocycloalkyl$_{(C \leq 12)}$, aryl$_{(C \leq 18)}$, -arenediyl$_{(C \leq 12)}$-alkyl$_{(C \leq 12)}$, aralkyl$_{(C \leq 18)}$, -arenediyl$_{(C \leq 18)}$-heterocycloalkyl$_{(C \leq 12)}$, heteroaryl$_{(C \leq 18)}$, -heteroarenediyl$_{(C \leq 12)}$-alkyl$_{(C \leq 12)}$, heteroaralkyl$_{(C \leq 18)}$, acyl$_{(C \leq 12)}$, alkoxy$_{(C \leq 12)}$, or a substituted version of any of these groups;
or a pharmaceutically acceptable salt thereof.

21. The compound of claim 19, further defined as:

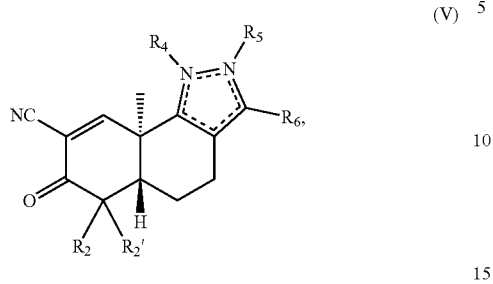

(V)

wherein:

R$_2$ is hydrogen; or cycloalkyl$_{(C\leq12)}$, alkenyl$_{(C\leq12)}$, alkynyl$_{(C\leq12)}$, aryl$_{(C\leq18)}$, aralkyl$_{(C\leq18)}$, heteroaryl$_{(C\leq18)}$, heteroaralkyl$_{(C\leq18)}$, or a substituted version of any of these groups;

R$_2$' is hydrogen;

R$_4$ and R$_5$ are each independently absent; or cycloalkyl$_{(C\leq12)}$, heterocycloalkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, -arenediyl$_{(C\leq12)}$-alkyl$_{(C\leq12)}$, -arenediyl$_{(C\leq12)}$-aryl$_{(C\leq12)}$, -arenediyl$_{(C\leq12)}$-heteroaryl$_{(C\leq12)}$, -arenediyl$_{(C\leq12)}$-heterocycloalkyl$_{(C\leq12)}$, -arenediyl$_{(C\leq12)}$-cyclo-alkyl$_{(C\leq12)}$, -heteroarenediyl$_{(C\leq12)}$-alkyl$_{(C\leq12)}$, -heteroarenediyl$_{(C\leq12)}$-aryl$_{(C\leq12)}$, -hetero-arenediyl$_{(C\leq12)}$-heteroaryl$_{(C\leq12)}$, -heteroarenediyl$_{(C\leq12)}$-hetero-cycloalkyl$_{(C\leq12)}$, -heteroarenediyl$_{(C\leq12)}$-cyclo-alkyl$_{(C\leq12)}$, -heterocycloalkanediyl$_{(C\leq12)}$-aryl$_{(C\leq12)}$, -heterocycloalkanediyl$_{(C\leq12)}$-heteroaryl$_{(C\leq12)}$, or a substituted version of any of these groups; or a group of the formula:

wherein 1 and m are each 0, 1, 2, or 3;

R$_6$ is absent or amino; or alkylamino$_{(C\leq12)}$, dialkylamino$_{(C\leq12)}$, cycloalkylamino$_{(C\leq12)}$, dicycloalkylamino$_{(C\leq12)}$, alkyl(cycloalkyl)amino$_{(C\leq12)}$, arylamino$_{(C\leq12)}$, diarylamino$_{(C\leq12)}$, alkyl$_{(C\leq12)}$, cycloalkyl$_{(C\leq12)}$, -alkanediyl$_{(C\leq12)}$-cycloalkyl$_{(C\leq12)}$, -alkanediyl$_{(C\leq18)}$-aralkoxy$_{(C\leq18)}$, heterocycloalkyl$_{(C\leq12)}$, aryl$_{(C\leq18)}$, -arenediyl$_{(C\leq12)}$-alkyl$_{(C\leq12)}$, aralkyl$_{(C\leq18)}$, -arenediyl$_{(C\leq18)}$-heterocycloalkyl$_{(C\leq12)}$, heteroaryl$_{(C\leq18)}$, -heteroarenediyl$_{(C\leq12)}$-alkyl$_{(C\leq12)}$, heteroaralkyl$_{(C\leq18)}$, acyl$_{(C\leq12)}$, alkoxy$_{(C\leq12)}$, or a substituted version of any of these groups;

or a pharmaceutically acceptable salt thereof.

22. The compound of claim 19, further defined as:

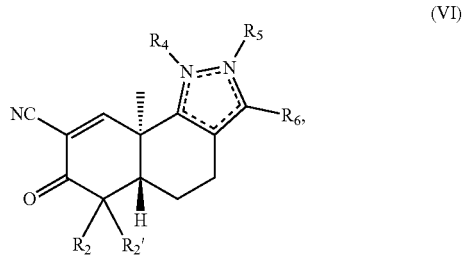

(VI)

wherein:

R$_2$ is hydrogen; or alkyl$_{(C\leq12)}$, cycloalkyl$_{(C\leq12)}$, alkenyl$_{(C\leq12)}$, alkynyl$_{(C\leq12)}$, aryl$_{(C\leq18)}$, aralkyl$_{(C\leq18)}$, heteroaryl$_{(C\leq18)}$, heteroaralkyl$_{(C\leq18)}$, or a substituted version of any of these groups;

R$_2$' is hydrogen;

R$_4$ and R$_5$ are each independently absent; or cycloalkyl$_{(C\leq12)}$, heterocycloalkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, -arenediyl$_{(C\leq12)}$-alkyl$_{(C\leq12)}$, -arenediyl$_{(C\leq12)}$-aryl$_{(C\leq12)}$, -arenediyl$_{(C\leq12)}$-heteroaryl$_{(C\leq12)}$, -arenediyl$_{(C\leq12)}$-heterocycloalkyl$_{(C\leq12)}$, -arenediyl$_{(C\leq12)}$-cyclo-alkyl$_{(C\leq12)}$, -heteroarenediyl$_{(C\leq12)}$-alkyl$_{(C\leq12)}$, -heteroarenediyl$_{(C\leq12)}$-aryl$_{(C\leq12)}$, -hetero-arenediyl$_{(C\leq12)}$-heteroaryl$_{(C\leq12)}$, -heteroarenediyl$_{(C\leq12)}$-hetero-cycloalkyl$_{(C\leq12)}$, -heteroarenediyl$_{(C\leq12)}$-cyclo-alkyl$_{(C\leq12)}$, -heterocycloalkanediyl$_{(C\leq12)}$-aryl$_{(C\leq12)}$, -heterocycloalkanediyl$_{(C\leq12)}$-heteroaryl$_{(C\leq12)}$, or a substituted version of any of these groups; or a group of the formula:

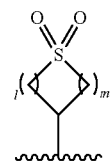

wherein 1 and m are each 0, 1, 2, or 3; and

R$_6$ is absent; or alkylamino$_{(C\leq12)}$, dialkylamino$_{(C\leq12)}$, cycloalkylamino$_{(C\leq12)}$, dicycloalkylamino$_{(C\leq12)}$, alkyl(cycloalkyl)amino$_{(C\leq12)}$, arylamino$_{(C\leq12)}$, diarylamino$_{(C\leq12)}$, alkyl$_{(C\leq12)}$, cycloalkyl$_{(C\leq12)}$, -alkanediyl$_{(C\leq12)}$-cycloalkyl$_{(C\leq12)}$, -alkanediyl$_{(C\leq18)}$-aralkoxy$_{(C\leq18)}$, heterocycloalkyl$_{(C\leq12)}$, aryl$_{(C\leq18)}$, -arenediyl$_{(C\leq12)}$-alkyl$_{(C\leq12)}$, aralkyl$_{(C\leq18)}$, -arenediyl$_{(C\leq18)}$-heterocycloalkyl$_{(C\leq12)}$, heteroaryl$_{(C\leq18)}$, -heteroarenediyl$_{(C\leq12)}$-alkyl$_{(C\leq12)}$, heteroaralkyl$_{(C\leq18)}$, acyl$_{(C\leq12)}$, alkoxy$_{(C\leq12)}$, or a substituted version of any of these groups;

or a pharmaceutically acceptable salt thereof.

23. The compound of claim 19, further defined as:

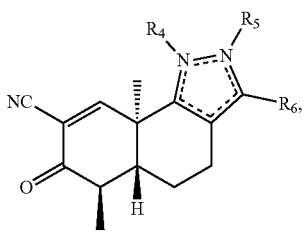

(IX)

wherein:
R$_4$ and R$_5$ are each independently absent; or
cycloalkyl$_{(C\leq12)}$, heterocycloalkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, -arenediyl$_{(C\leq12)}$-alkyl$_{(C\leq12)}$, -arenediyl$_{(C\leq12)}$-aryl$_{(C\leq12)}$, -arenediyl$_{(C\leq12)}$-heteroaryl$_{(C\leq12)}$, -arenediyl$_{(C\leq12)}$-heterocycloalkyl$_{(C\leq12)}$, -arenediyl$_{(C\leq12)}$-cyclo-alkyl$_{(C\leq12)}$, -heteroarenediyl$_{(C\leq12)}$-alkyl$_{(C\leq12)}$, -heteroarenediyl$_{(C\leq12)}$-aryl$_{(C\leq12)}$, -hetero-arenediyl$_{(C\leq12)}$-heteroaryl$_{(C\leq12)}$, -heteroarenediyl$_{(C\leq12)}$-hetero-cycloalkyl$_{(C\leq12)}$, -heteroarenediyl$_{(C\leq12)}$-cycloalkyl$_{(C\leq12)}$, -heterocycloalkanediyl$_{(C\leq12)}$-aryl$_{(C\leq12)}$, -heterocycloalkanediyl$_{(C\leq12)}$-heteroaryl$_{(C\leq12)}$, or a substituted version of any of these groups; or
a group of the formula:

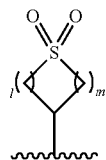

wherein l and m are each 0, 1, 2, or 3; and
R$_6$ is absent; or
alkylamino$_{(C\leq12)}$, dialkylamino$_{(C\leq12)}$, cycloalkylamino$_{(C\leq12)}$, dicycloalkylamino$_{(C\leq12)}$, alkyl(cycloalkyl)amino$_{(C\leq12)}$, arylamino$_{(C\leq12)}$, diarylamino$_{(C\leq12)}$, alkyl$_{(C\leq12)}$, cycloalkyl$_{(C\leq12)}$, -alkanediyl$_{(C\leq12)}$-cycloalkyl$_{(C\leq12)}$, -alkanediyl$_{(C\leq18)}$-aralkoxy$_{(C\leq18)}$, heterocycloalkyl$_{(C\leq12)}$, aryl$_{(C\leq18)}$, -arenediyl$_{(C\leq18)}$-alkyl$_{(C\leq12)}$, aralkyl$_{(C\leq18)}$, -arenediyl$_{(C\leq18)}$-heterocycloalkyl$_{(C\leq12)}$, heteroaryl$_{(C\leq18)}$, -heteroarenediyl$_{(C\leq12)}$-alkyl$_{(C\leq12)}$, heteroaralkyl$_{(C\leq18)}$, acyl$_{(C\leq12)}$, alkoxy$_{(C\leq12)}$, or a substituted version of any of these groups;
or a pharmaceutically acceptable salt thereof.

24. The compound of claim 19, wherein R$_3$ is alkyl$_{(C\leq12)}$ or substituted alkyl$_{(C\leq12)}$ or R$_1$ is cyano.

25. The compound of claim 19, wherein R$_2$ is hydrogen, alkyl$_{(C\leq12)}$, or substituted alkyl$_{(C\leq12)}$.

26. The compound of claim 19, wherein R$_4$ is aryl$_{(C\leq12)}$, substituted aryl$_{(C\leq12)}$, -arenediyl$_{(C\leq12)}$-aryl$_{(C\leq12)}$, or substituted -arenediyl$_{(C\leq12)}$-aryl$_{(C\leq12)}$.

27. The compound of claim 19, wherein R$_4$ is -arenediyl$_{(C\leq12)}$-heterocycloalkyl$_{(C\leq12)}$ or substituted -arenediyl$_{(C\leq12)}$-heterocycloalkyl$_{(C\leq12)}$.

28. The compound of claim 19, wherein R$_4$ is heteroaryl$_{(C\leq12)}$, substituted heteroaryl$_{(C\leq12)}$, -arenediyl$_{(C\leq12)}$-heteroaryl$_{(C\leq12)}$, substituted -arenediyl$_{(C\leq12)}$-heteroaryl$_{(C\leq12)}$, -heteroarenediyl$_{(C\leq12)}$-aryl$_{(C\leq12)}$, substituted -heteroarenediyl$_{(C\leq12)}$-aryl$_{(C\leq12)}$, -heteroarenediyl$_{(C\leq12)}$-heteroaryl$_{(C\leq12)}$, or substituted -heteroarenediyl$_{(C\leq12)}$-heteroaryl$_{(C\leq12)}$.

29. The compound of claim 19, wherein R$_5$ is aryl$_{(C\leq12)}$, substituted aryl$_{(C\leq12)}$, -arenediyl$_{(C\leq12)}$-aryl$_{(C\leq12)}$, or substituted -arenediyl$_{(C\leq12)}$-aryl$_{(C\leq12)}$.

30. The compound of claim 19, wherein R$_5$ is -arenediyl$_{(C\leq12)}$-heterocycloalkyl$_{(C\leq12)}$ or substituted -arenediyl$_{(C\leq12)}$-heterocycloalkyl$_{(C\leq12)}$.

31. The compound of claim 19, wherein R$_5$ is heteroaryl$_{(C\leq12)}$, substituted heteroaryl$_{(C\leq12)}$, -arenediyl$_{(C\leq12)}$-heteroaryl$_{(C\leq12)}$, substituted -arenediyl$_{(C\leq12)}$-heteroaryl$_{(C\leq12)}$, -heteroarenediyl$_{(C\leq12)}$-aryl$_{(C\leq12)}$, substituted -heteroarenediyl$_{(C\leq12)}$-aryl$_{(C\leq12)}$, -heteroarenediyl$_{(C\leq12)}$-heteroaryl$_{(C\leq12)}$, or substituted -heteroarenediyl$_{(C\leq12)}$-heteroaryl$_{(C\leq12)}$.

32. The compound of claim 19, wherein R$_5$ is -heteroarenediyl$_{(C\leq12)}$-heterocycloalkyl$_{(C\leq12)}$ or substituted -heteroarenediyl$_{(C\leq12)}$-heterocycloalkyl$_{(C\leq12)}$.

33. The compound of claim 19, wherein R$_6$ is aryl$_{(C\leq18)}$, substituted aryl$_{(C\leq18)}$, heteroaryl$_{(C\leq18)}$, or substituted heteroaryl$_{(C\leq18)}$.

34. The compound of claim 19, wherein R$_6$ is cycloalkyl$_{(C\leq12)}$, substituted cycloalkyl$_{(C\leq12)}$, heterocycloalkyl$_{(C\leq12)}$, or substituted heterocycloalkyl$_{(C\leq12)}$.

35. The compound of claim 19, wherein R$_6$ is alkylamino$_{(C\leq12)}$, substituted alkylamino$_{(C\leq12)}$, cycloalkylamino$_{(C\leq12)}$, substituted cycloalkylamino$_{(C\leq12)}$, alkyl(cycloalkyl)amino$_{(C\leq12)}$, or substituted alkyl(cycloalkyl)amino$_{(C\leq12)}$.

36. The compound of claim 19 further defined as:

487
-continued
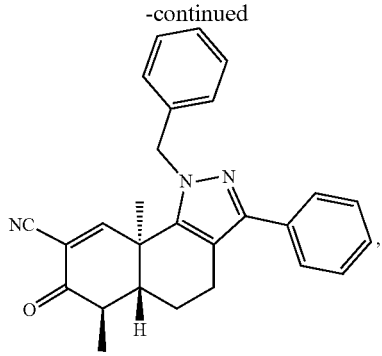
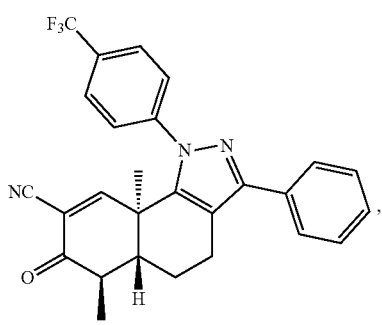
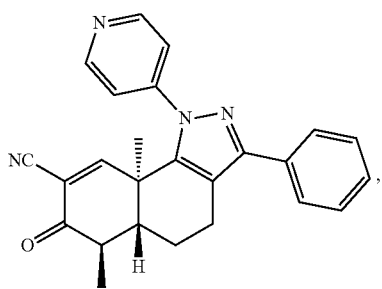
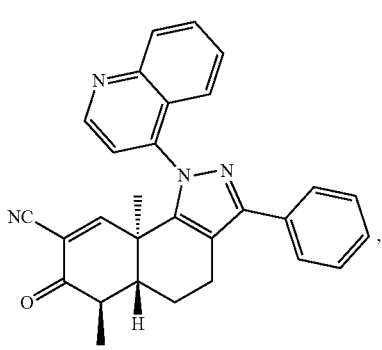
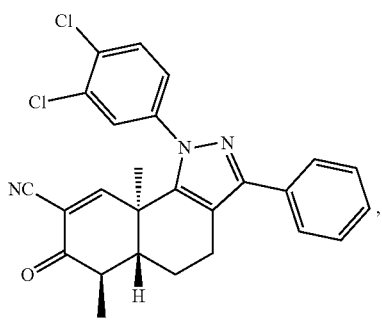
488
-continued
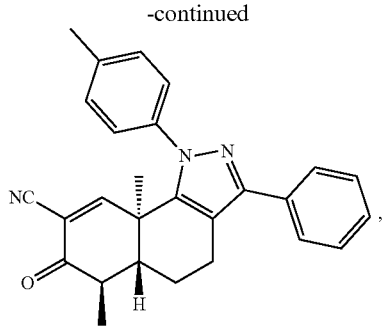
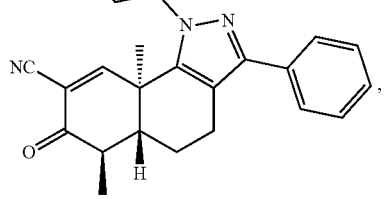
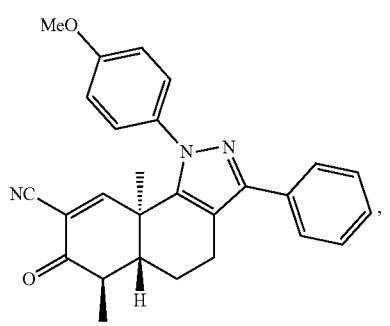
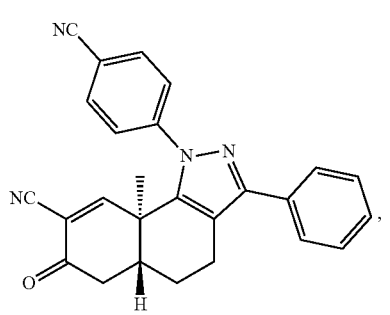
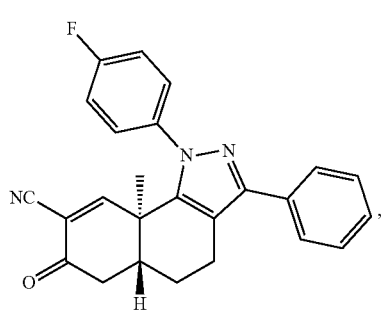

-continued
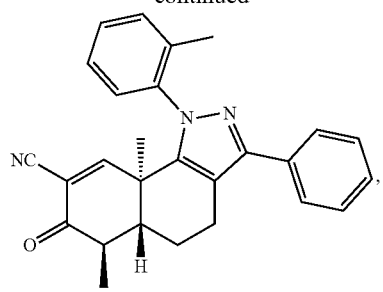
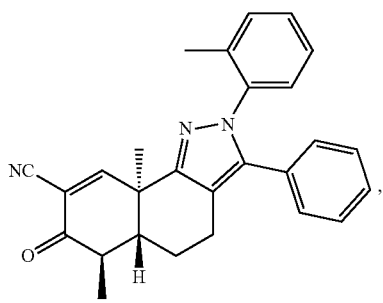
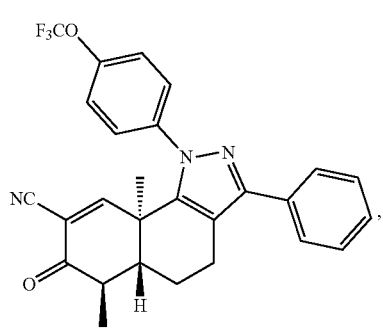
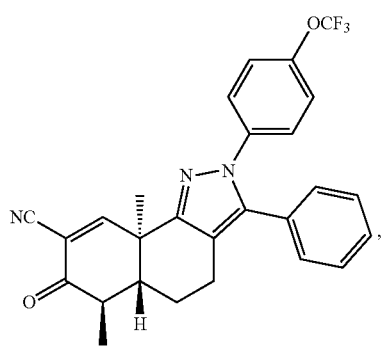
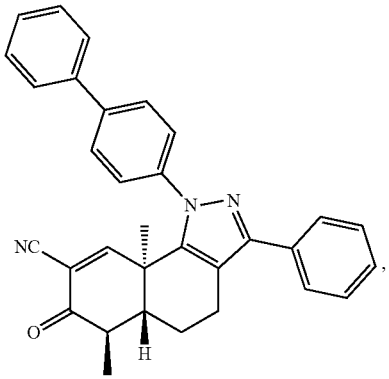
-continued
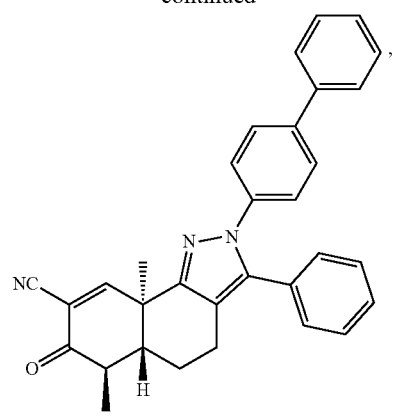
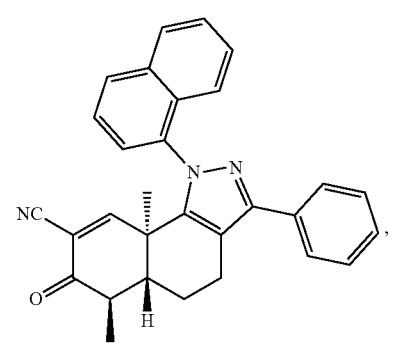
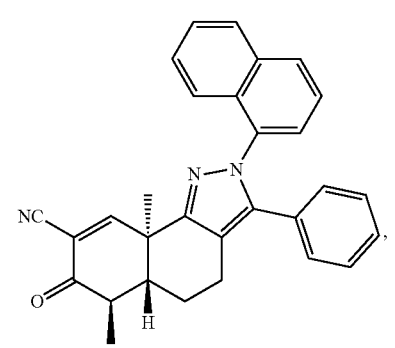
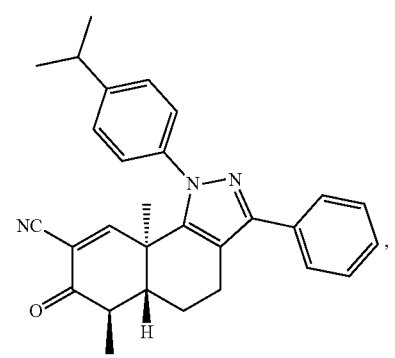

491
-continued
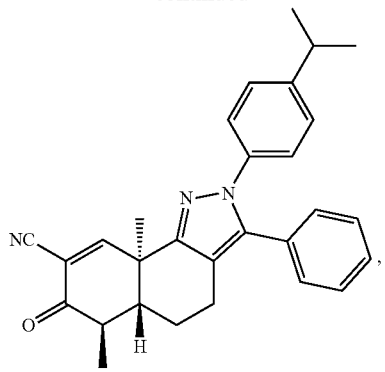
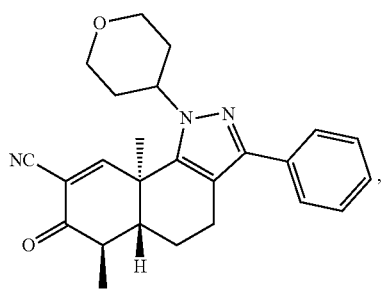
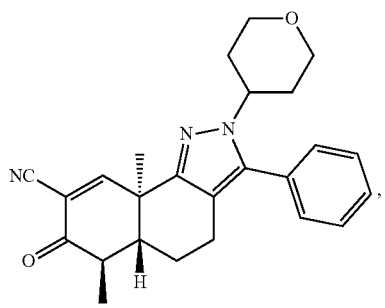
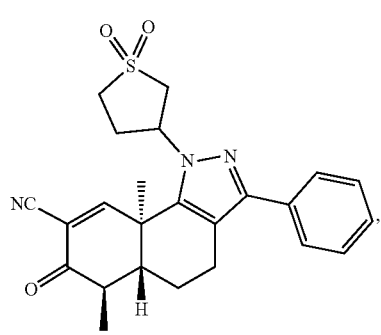
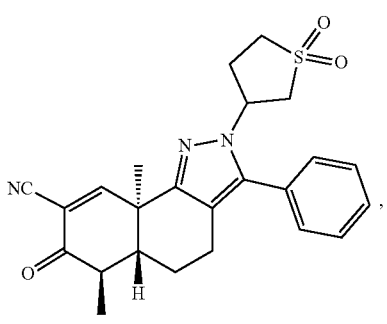
492
-continued
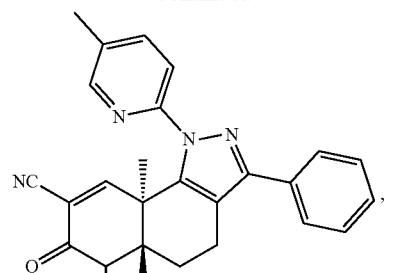

493
-continued
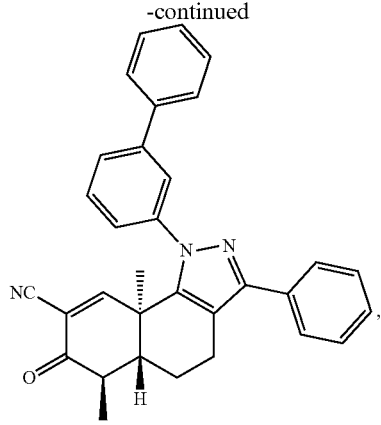
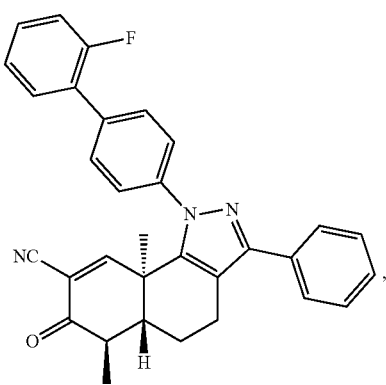
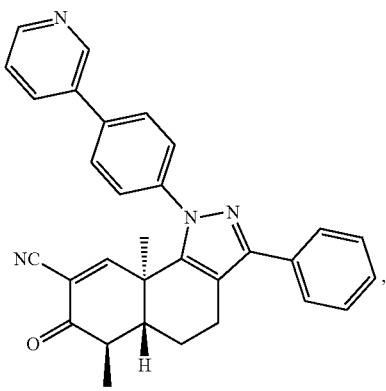
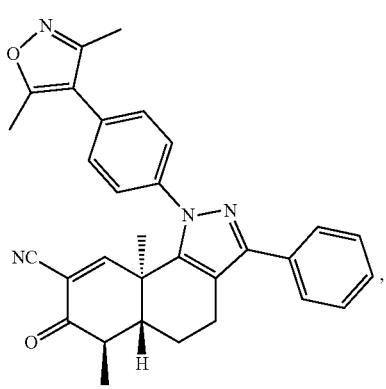
494
-continued
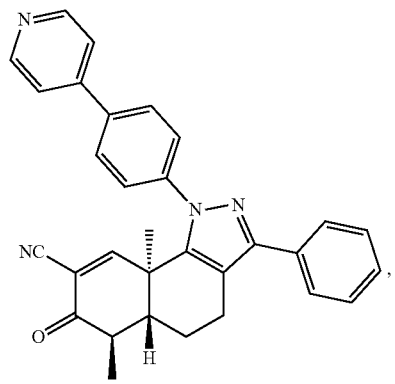
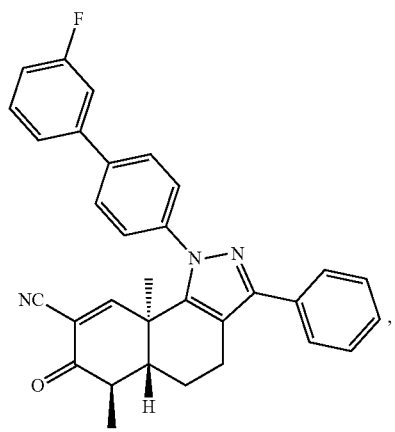
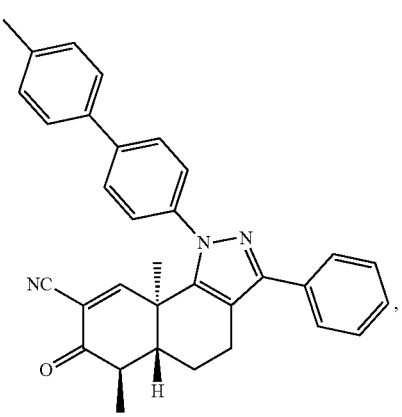
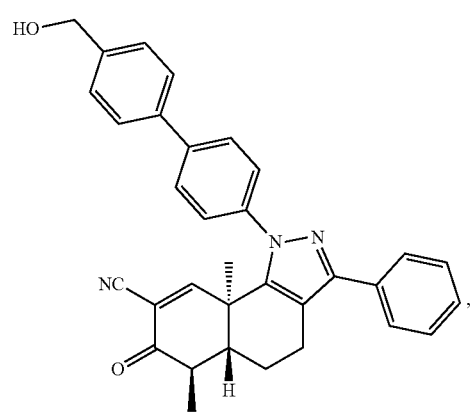

495
-continued
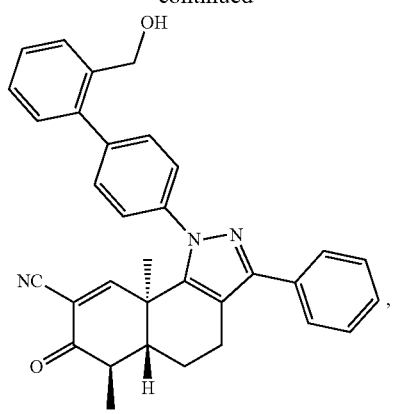
496
-continued
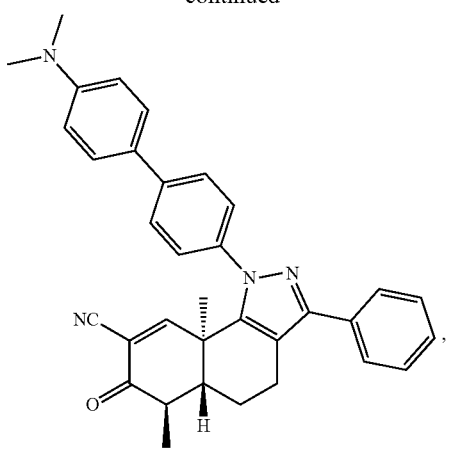
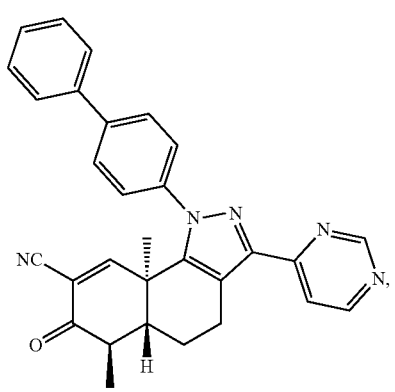
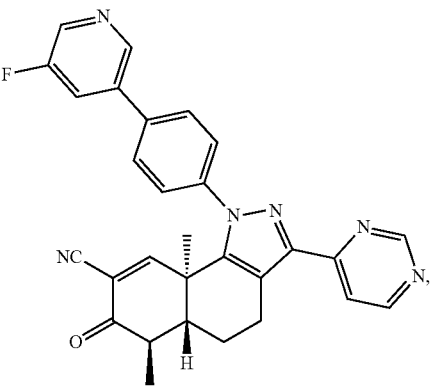
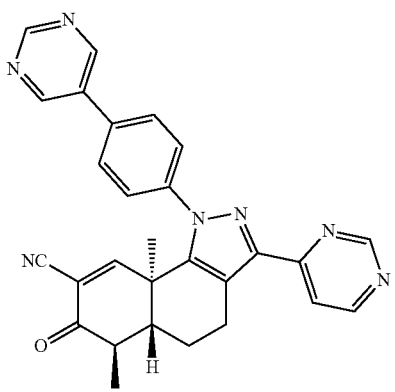

497
-continued
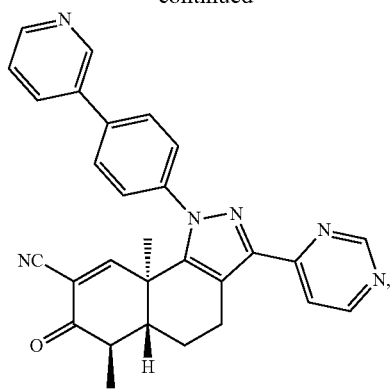
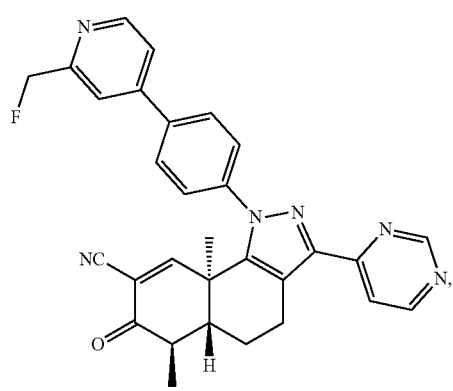
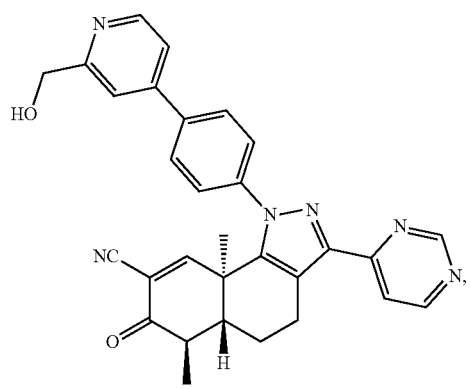
498
-continued
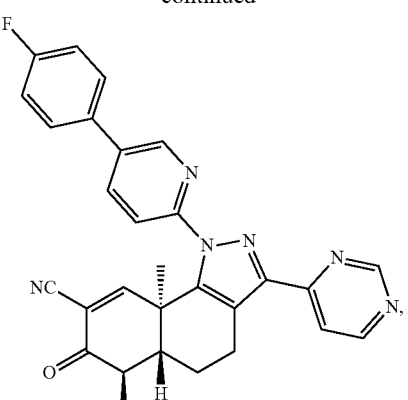
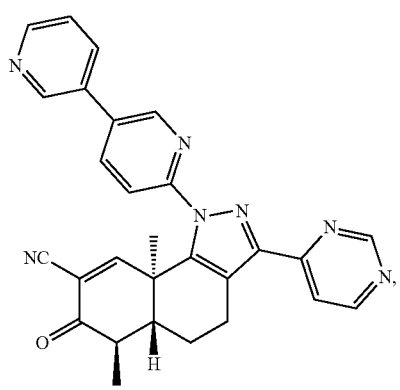
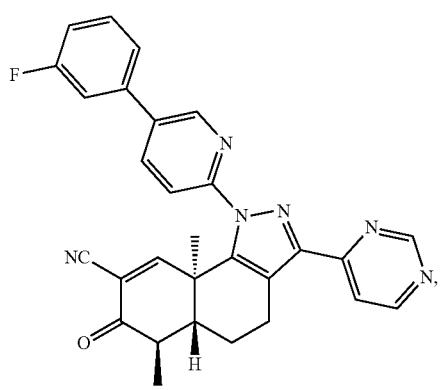
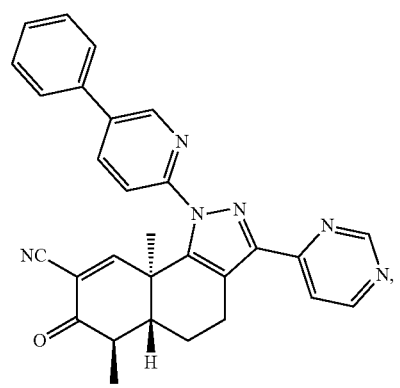

499
-continued
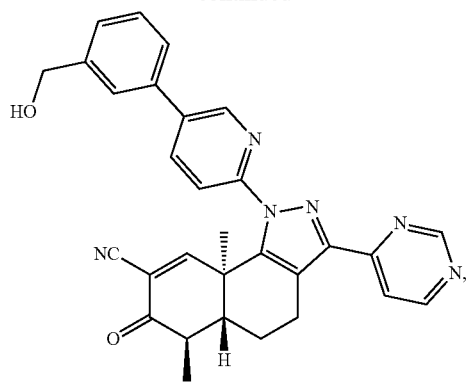
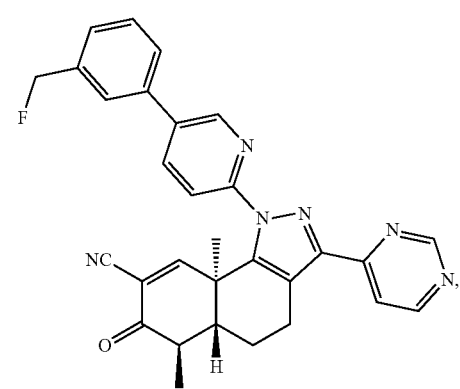
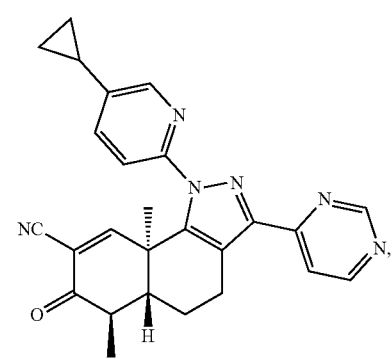
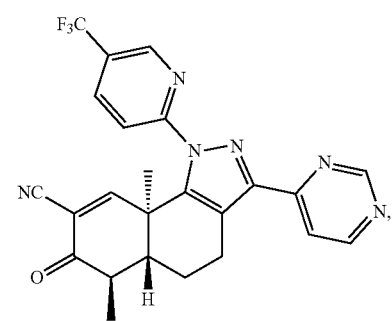
500
-continued
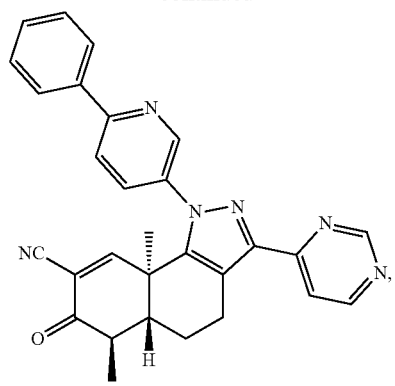
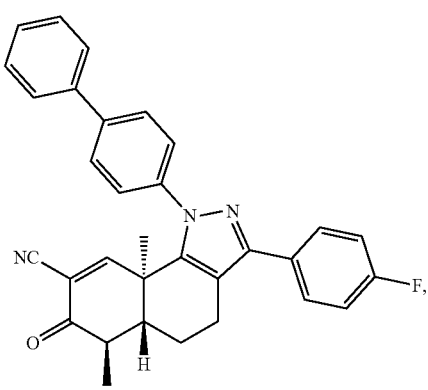
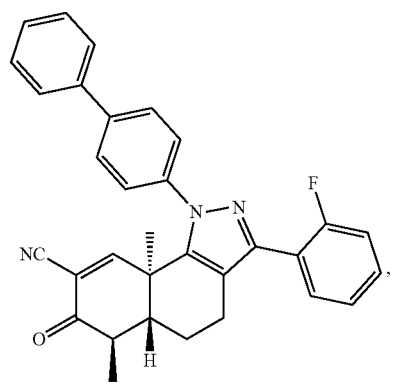
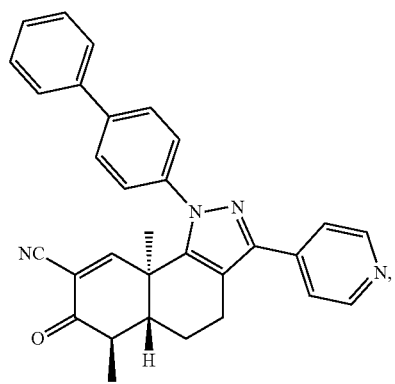

501
-continued
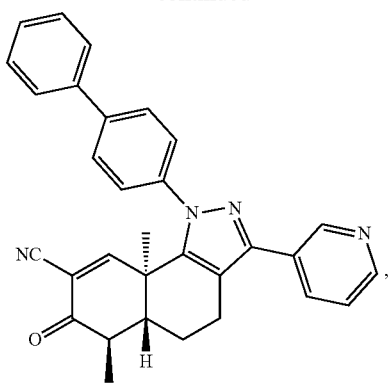
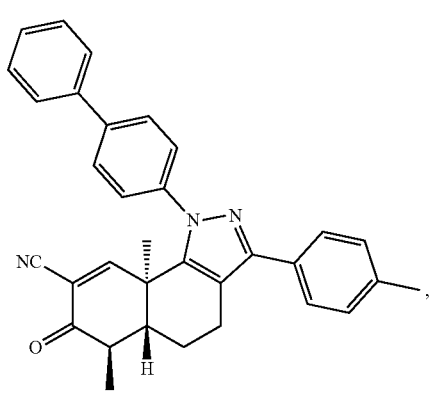
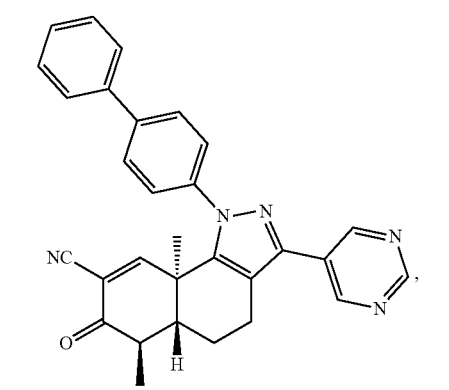
502
-continued
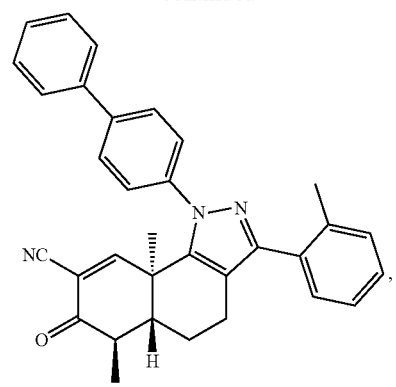
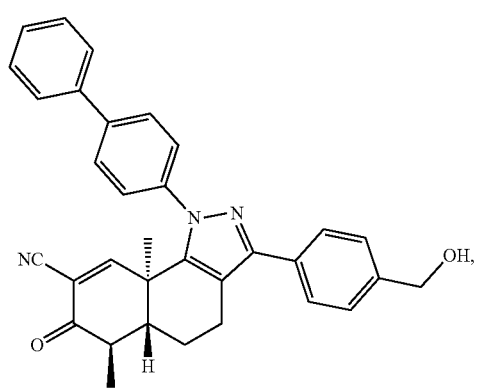
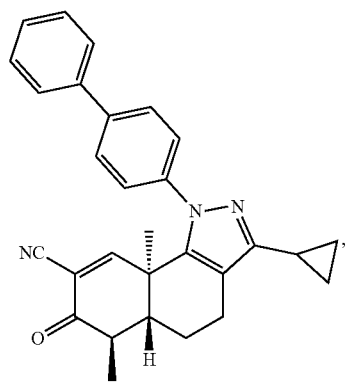

503
-continued
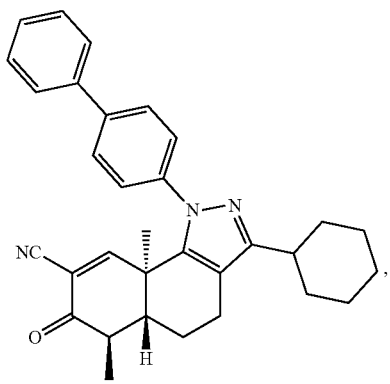
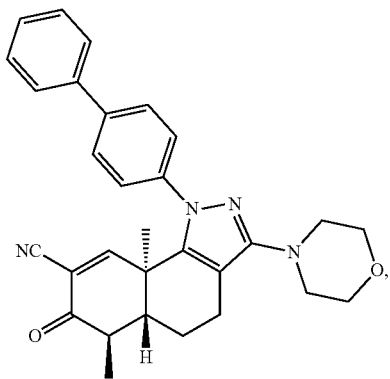
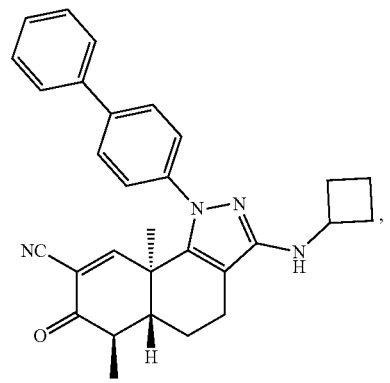
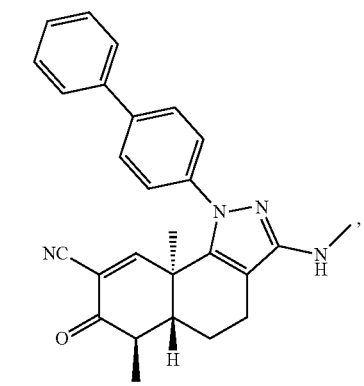
504
-continued
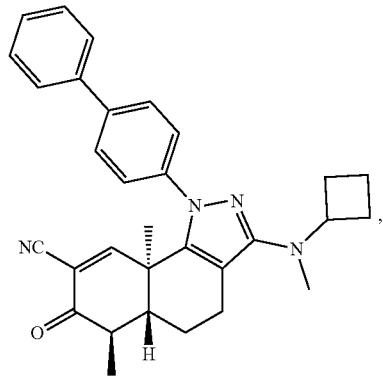
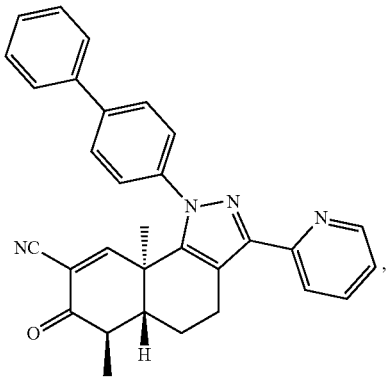
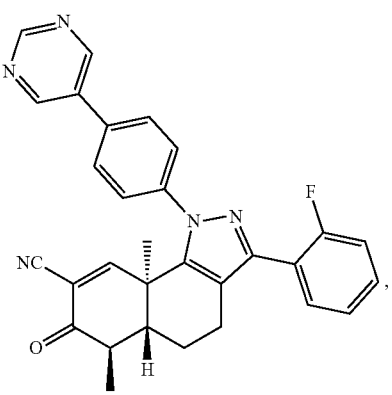
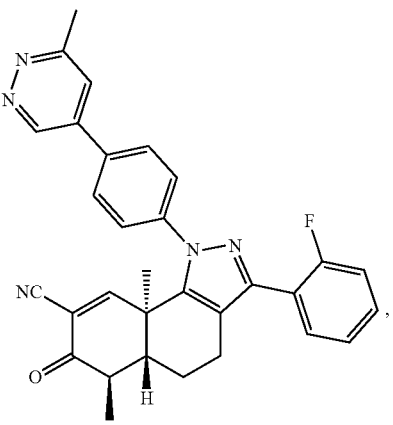

505
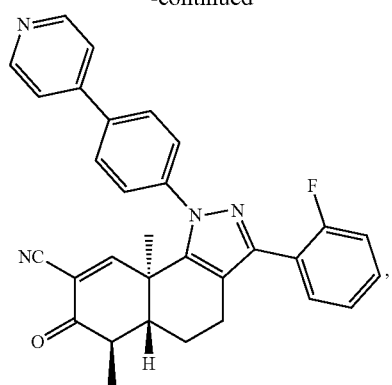
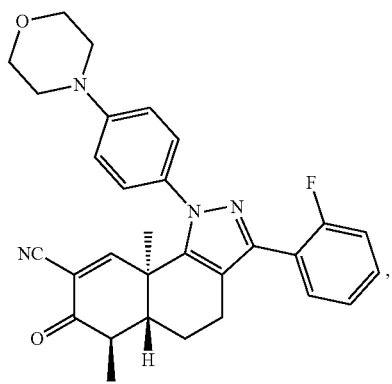
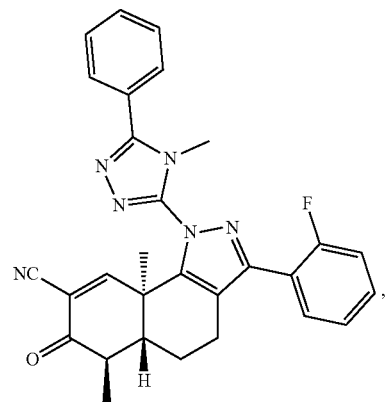
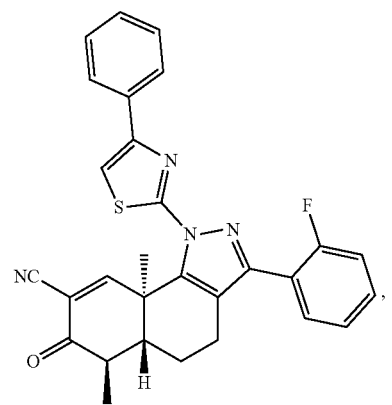
506
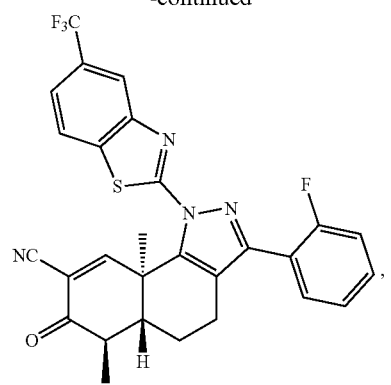
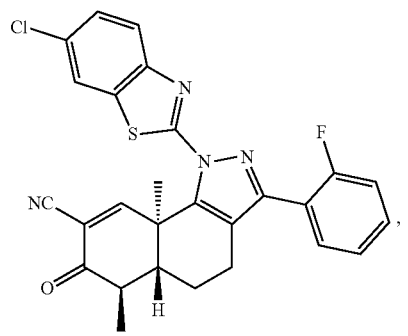
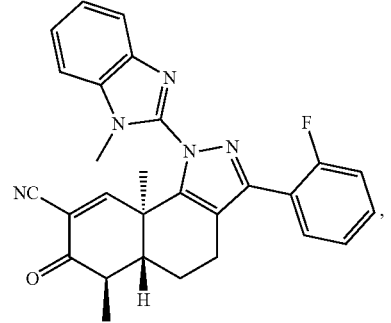
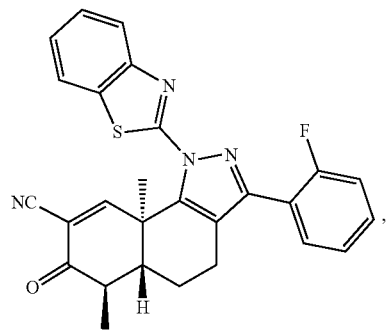

507
-continued
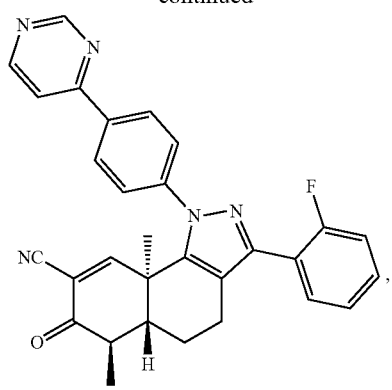
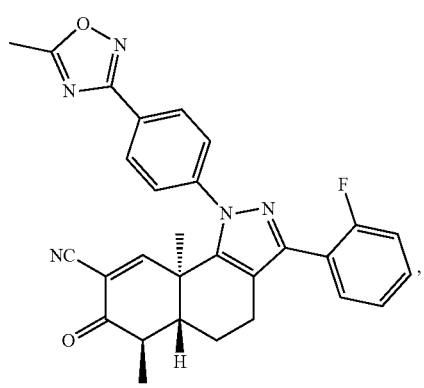
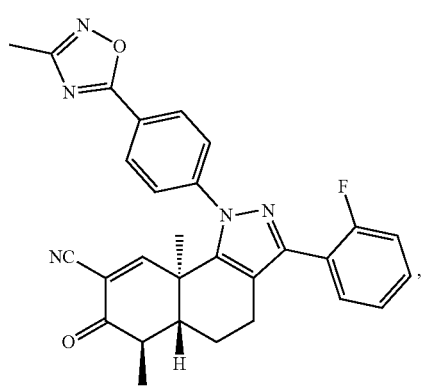
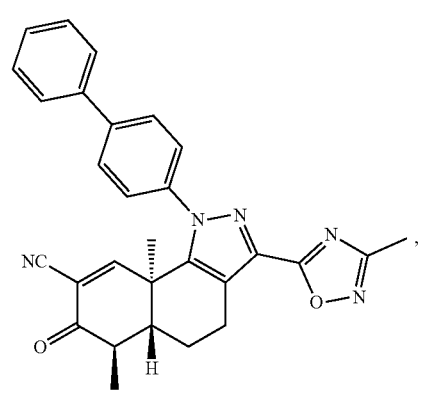
508
-continued
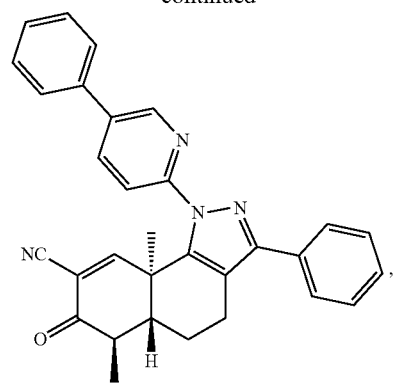
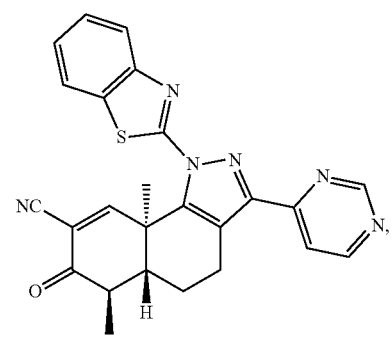
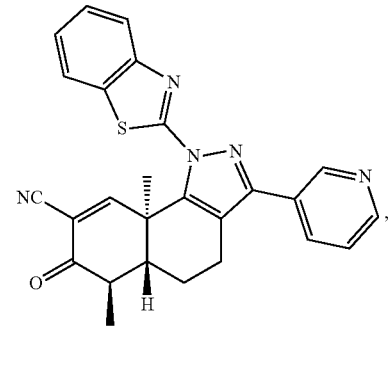
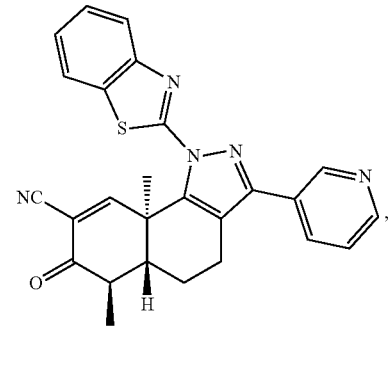

509
-continued
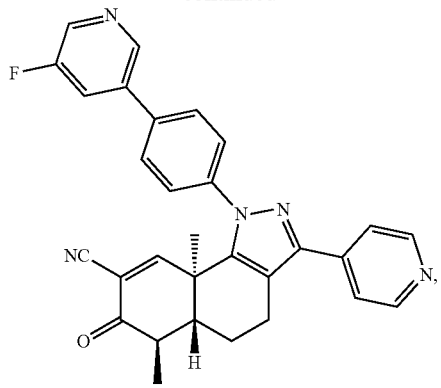
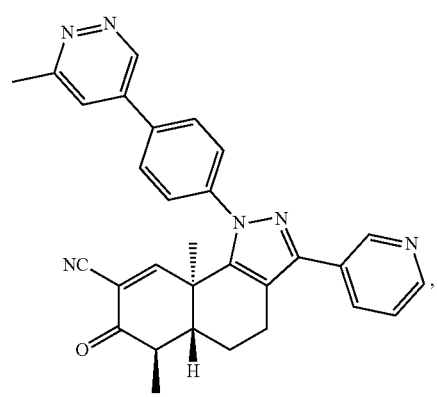
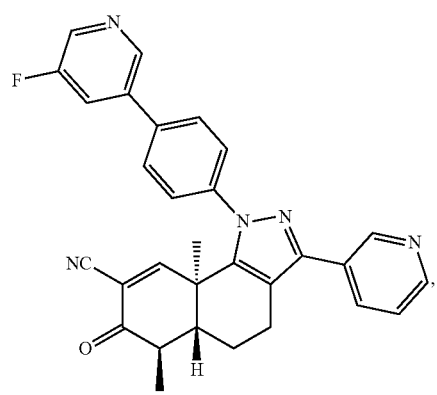
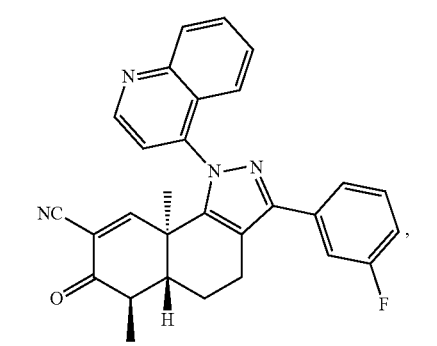
510
-continued
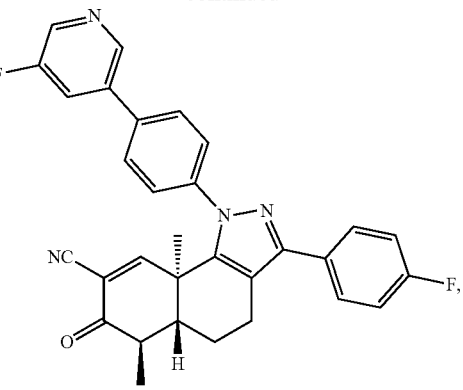
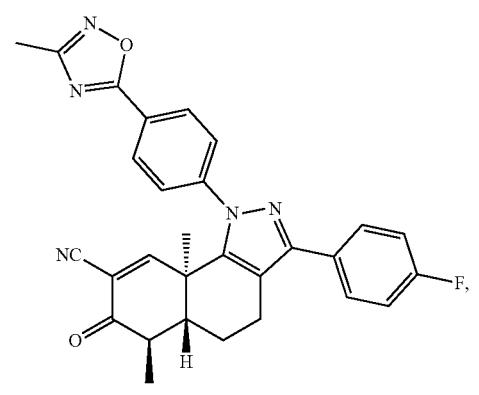
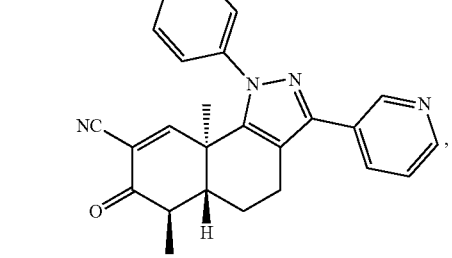
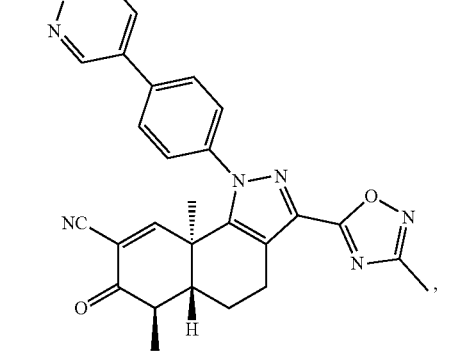

511
-continued
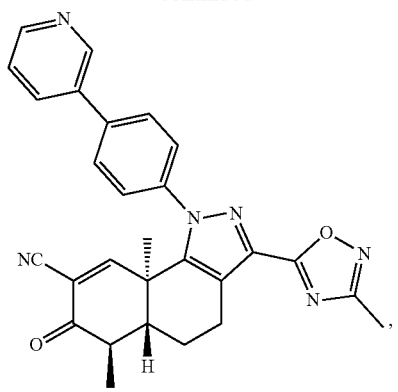
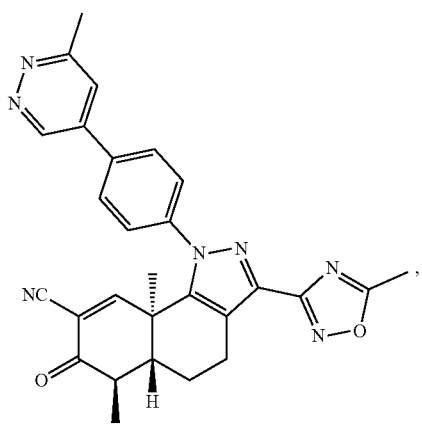
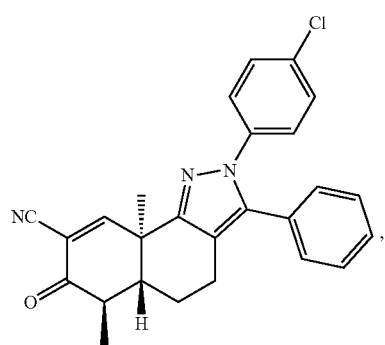
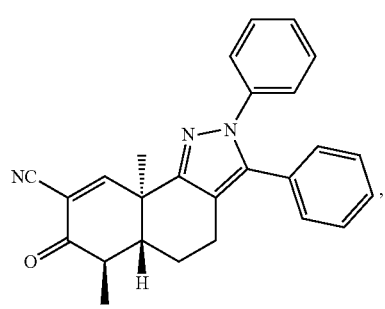
512
-continued
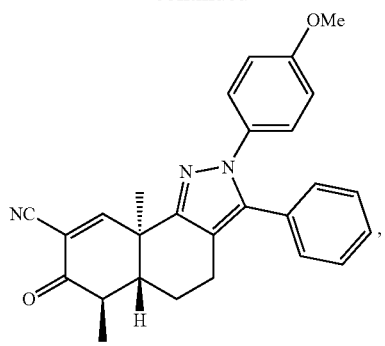
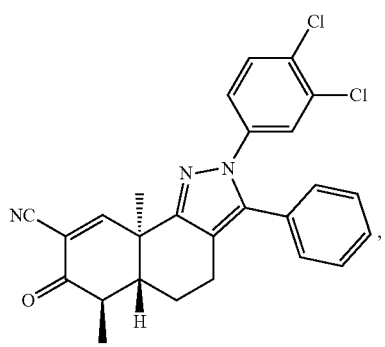
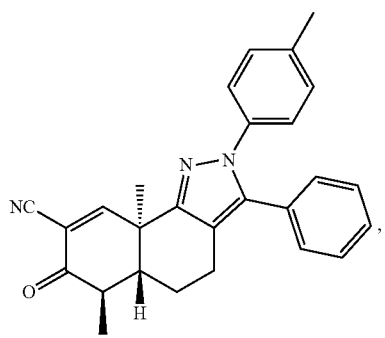
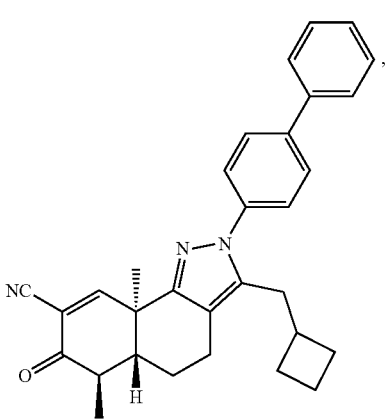

513
-continued
514
-continued
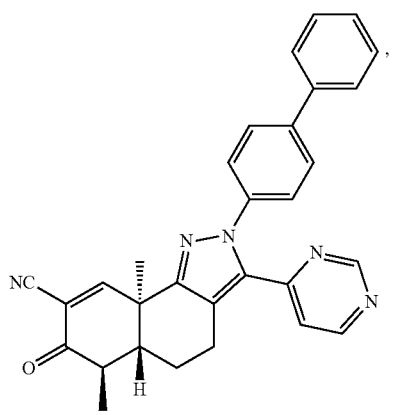
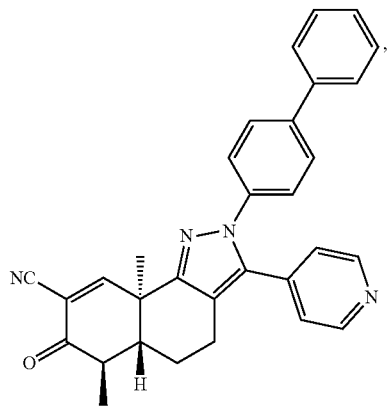

515 -continued 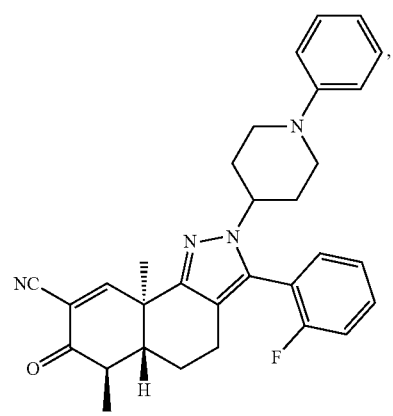
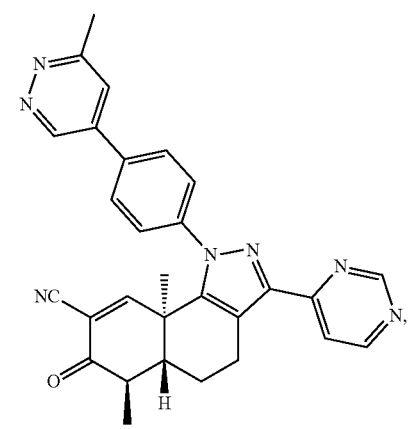
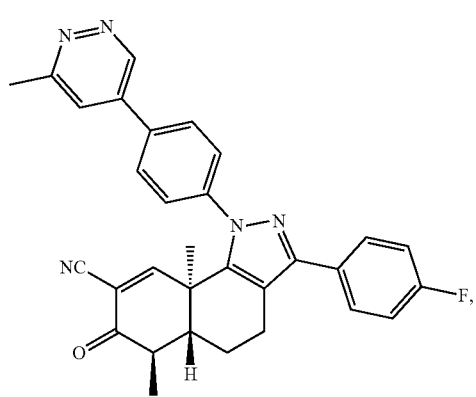
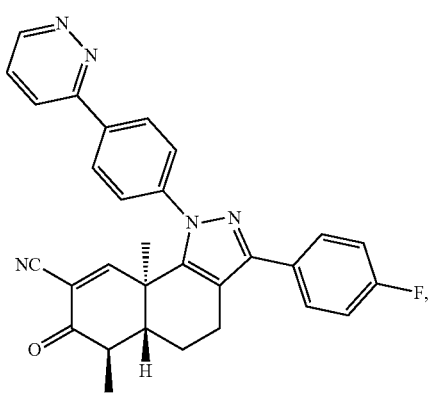
516 -continued 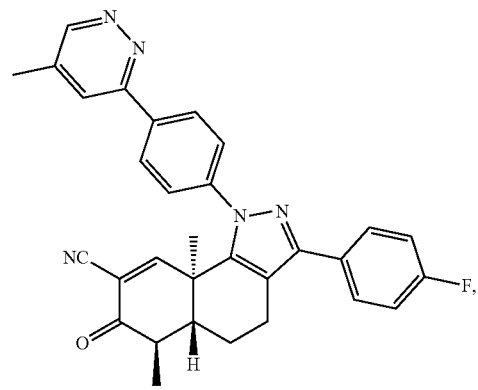
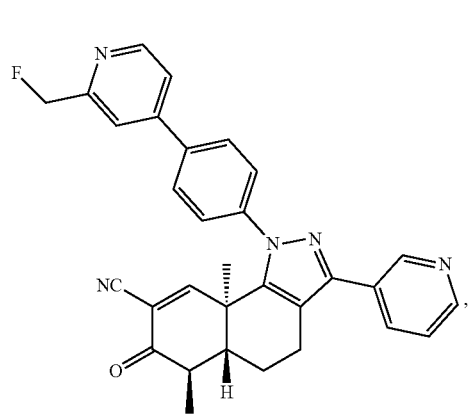
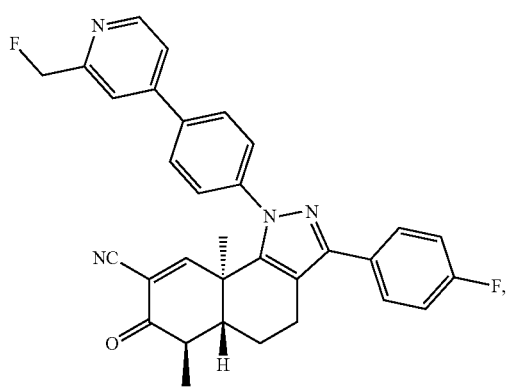
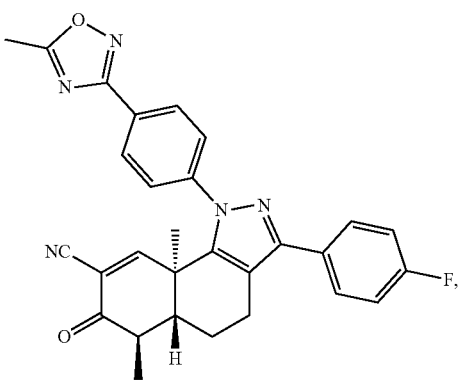

517
-continued
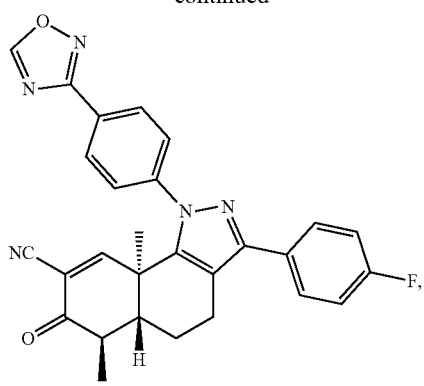
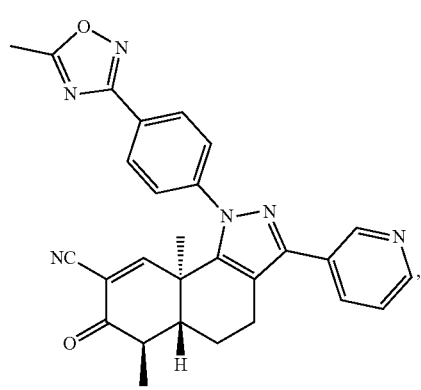
518
-continued
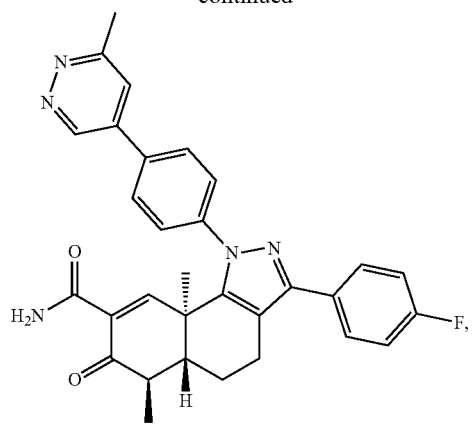
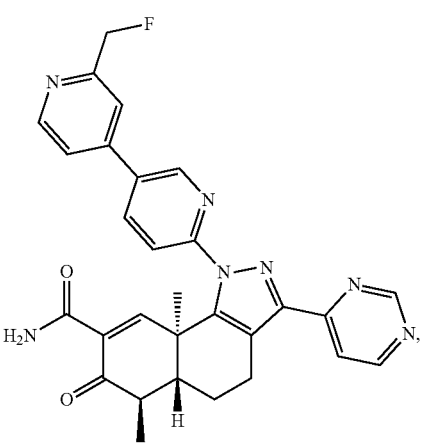
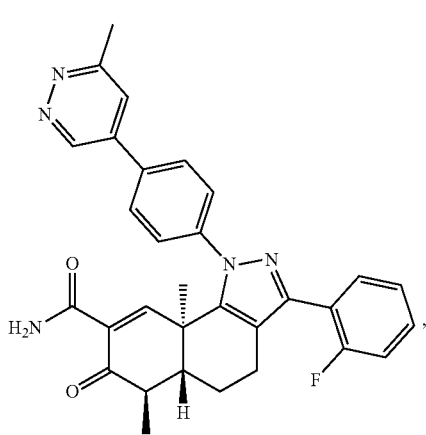
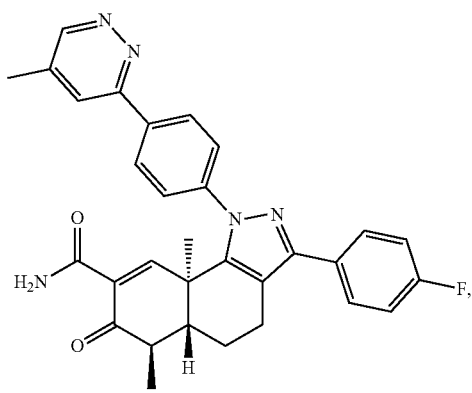

519
-continued
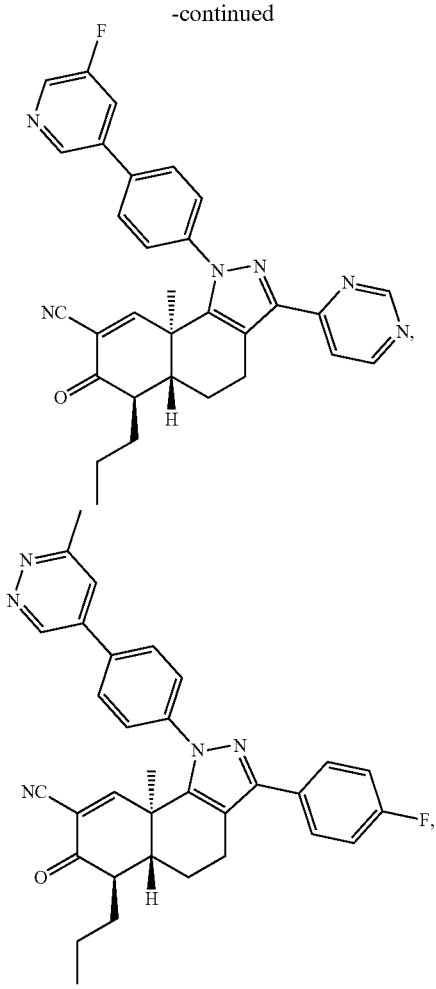
520
-continued
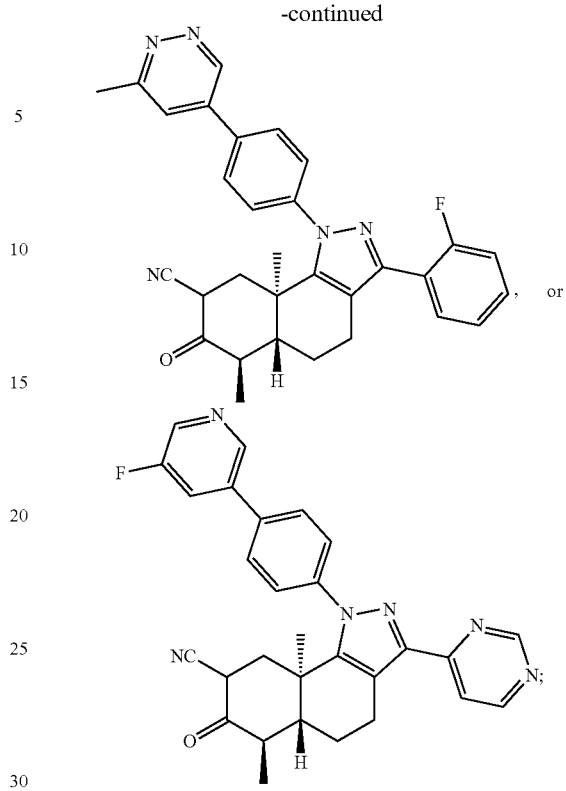
or a pharmaceutically acceptable salt of any of the above formulas.
37. A pharmaceutical composition comprising:
(a) a compound of claim 19; and
(b) an excipient.
* * * * *